(12) United States Patent
Hasvold et al.

(10) Patent No.: US 7,456,169 B2
(45) Date of Patent: Nov. 25, 2008

(54) HETEROCYCLIC KINASE INHIBITORS

(75) Inventors: Lisa A. Hasvold, Grayslake, IL (US); Laura Hexamer, Gurnee, IL (US); Gaoquan Li, Madison, WI (US); Nan-Horng Lin, Vernon Hills, IL (US); Hing Sham, South San Francisco, CA (US); Thomas J. Sowin, Wadsworth, IL (US); Gerard M. Sullivan, Labe Villa, IL (US); Le Wang, Mundelein, IL (US); Ping Xia, St. Louis, MO (US)

(73) Assignee: Abbott Laboratories Inc., Abbott Park, IL (US)

( * ) Notice: Subject to any disclaimer, the term of this patent is extended or adjusted under 35 U.S.C. 154(b) by 174 days.

(21) Appl. No.: 11/466,638

(22) Filed: Aug. 23, 2006

(65) Prior Publication Data

US 2007/0254867 A1 Nov. 1, 2007

Related U.S. Application Data

(63) Continuation-in-part of application No. 10/785,120, filed on Feb. 25, 2004, now abandoned.

(60) Provisional application No. 60/450,476, filed on Feb. 27, 2003.

(51) Int. Cl.
 C07D 413/00 (2006.01)
 A61K 31/5513 (2006.01)

(52) U.S. Cl. ..................... 514/220; 540/495

(58) Field of Classification Search ............ 514/211.04, 514/220; 540/488, 495
 See application file for complete search history.

(56) References Cited

U.S. PATENT DOCUMENTS

| | | | |
|---|---|---|---|
| 3,150,125 | A | 9/1964 | Schmutz et al. |
| 6,291,504 | B1 | 9/2001 | Nugiel et al. |
| 6,297,238 | B1 | 10/2001 | Doyle et al. |
| 6,407,103 | B2 | 6/2002 | Nugiel et al. |
| 6,462,036 | B1 | 10/2002 | Doyle et al. |
| 2001/0027195 | A1 | 10/2001 | Nugiel et al. |

FOREIGN PATENT DOCUMENTS

| | | |
|---|---|---|
| WO | 99/54308 | 10/1999 |
| WO | 00/27822 | 5/2000 |
| WO | 01/87846 | 11/2001 |
| WO | 02/44174 | 6/2002 |
| WO | 02/46182 | 6/2002 |
| WO | 03/004491 | 1/2003 |
| WO | 03/007883 | 1/2003 |
| WO | 03/033499 | 4/2003 |
| WO | 03/070236 | 8/2003 |

OTHER PUBLICATIONS

Deosta, et al. "Synthesis, charactreization, and biological evaluation of a novel class of N-(arylethyl)-N-alkyl-2-(1-pyrrolidinyl)ethylamines: Structural requirements and binding affinity at the receptor", J. Med. Chem., 35:38-47 (1992).
Harris, et al., "Improved functional group compatibility in the palladium-catalyzed synthesis of aryl amines", Org. Ltrs., 4(17):2885-2888 (2002).
Hunziker, et al., Arznelmittel-Forschung, 13:324-328 (1963) Abstract.
Kuenzle, et al., Helvetica Chimia Acta, 52(3):622-628 (1969) Abstract.
Lemek, et al., "Synthesis of selectively deuterated nitrobenzene derivatives", Tetrahedron, 57:4753-4757 (2001).
Nugiel, et al., "Indenopyrazoles as novel cyclin dependent kinase (CDK) inhibitors", J. Med. Chem., 44:1334-1336 (2001).
Nugiel, et al., "Synthesis and evaluation of indenopyrazoles as cyclin-dependent kinase inhibitors. 2. Probing the indeno ring substituent pattern", J. Med. Chem., 45:5224-5232 (2002).
Yue, et al., "Synthesis and evaluation of indenopyrazoles as cyclin-dependent kinase inhibitors. 3. Structure activity relationships at C3", J. Med. Chem., 45:5233-5248 (2002).

*Primary Examiner*—Bruck Kifle
(74) *Attorney, Agent, or Firm*—B. Gregory Donner

(57) ABSTRACT

Compounds having the formula

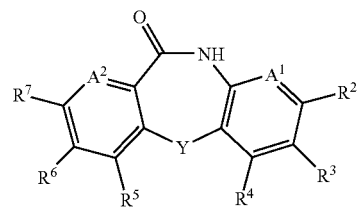

are useful for inhibiting protein kinases. Also disclosed are methods of making the compounds, compositions containing the compounds, and methods of treatment using the compounds.

2 Claims, No Drawings

HETEROCYCLIC KINASE INHIBITORS

This application is a continuation-in-part of U.S. patent application Ser. No. 10/785,120, filed Feb. 25, 2004 now abandoned, which claims priority from U.S. Provisional Patent Application Ser. No. 60/450,476, filed Feb. 27, 2003, which is hereby incorporated by reference.

TECHNICAL FIELD

The present invention relates to substituted tricyclic heterocycles which are useful for inhibiting protein kinases, methods of making the compounds, compositions containing the compounds, and methods of treatment using the compounds.

BACKGROUND OF THE INVENTION

Protein kinases have been clearly shown to be important in the progression of many disease states that are induced by the inappropriate proliferation of cells. These kinases are often found to be up-regulated in many hyperproliferative states such as cancer. These kinases may be important in cell signaling, where their inappropriate activation induces cells to proliferate (e.g., EGFR, ERBB2, VEGFR, FGFR, PDGFR, c-Met, IGF-1R, RET, TIE2). Alternatively, they may be involved in signal transduction within cells (e.g., c-Src, PKC, Akt, PKA, c-Abl, PDK-1). Often these signal transduction genes are recognized proto-oncogenes. Many of these kinases control cell cycle progression near the G1-S transition (e.g., Cdk2, Cdk4), at the G2-M transition (e.g., Wee1, Myt1, Chk1, Cdc2) or at the spindle checkpoint (Plk, Aurora1 or 2, Bub1 or 3). Furthermore, kinases are intimately linked to the DNA damage response (e.g., ATM, ATR, Chk1, Chk2). Deregulation of these cellular functions: cell signaling, signal transduction, cell cycle control, and DNA repair, are all hallmarks of hyperproliferative diseases, particularly cancer. It is therefore likely that pharmacological modulation of one or more kinases would be useful in slowing or stopping disease progression in these diseases.

SUMMARY OF THE INVENTION

In its principle embodiment the present invention provides a compound of formula (I)

or a therapeutically acceptable salt thereof, wherein
$A^1$ is selected from the group consisting of $CR^1$ and N;
$A^2$ is selected from the group consisting of $CR^8$, and N;
$R^1$ and $R^8$ are independently selected from the group consisting of hydrogen, alkoxy, alkyl, amino, aminoalkyl, cyano, halo, hydroxy, hydroxyalkyl, and nitro;
$R^2$, $R^3$, $R^4$, and $R^5$ are independently selected from the group consisting of hydrogen, alkenyl, alkoxy, alkoxyalkoxy, alkoxyalkoxyalkoxy, alkoxyalkyl, alkoxycarbonyl, alkoxycarbonylalkyl, alkyl, alkylcarbonyl, alkylcarbonylalkyl, alkylsulfonylamino, amino, aminoalkoxy, aminoalkyl, aminocarbonyl, aminocarbonylalkyl, aminosulfonyl, aryl, arylalkoxy, arylalkoxyalkyl, arylalkyl, arylalkylcarbonyl, arylcarbonylalkyl, aryloxyalkyl, carboxy, carboxyalkyl, cyano, cyanoalkyl, cycloalkyl, cycloalkylalkyl, halo, haloalkoxy, haloalkyl, heterocyclyl, heterocyclylalkoxy, heterocyclylalkyl, heterocyclylcarbonylalkyl, heterocyclyloxyalkyl, hydroxy, hydroxyalkoxy, hydroxyalkyl, nitro, nitroalkyl, and $-(CR^9R^{10})_mC(O)NR^{11}R^{12}$;
one of $R^6$ and $R^7$ is hydrogen and the other is selected from the group consisting of hydrogen, aryl, cycloalkyl, halo, heterocyclyl, and $-XR^{13}$;
$R^9$ and $R^{10}$ are independently selected from the group consisting of hydrogen, alkenyl, alkyl, aminoalkyl, and hydroxyalkyl; or
$R^9$ and $R^{10}$, together with the carbon atom to which they are attached, form a cycloalkyl group;
$R^{11}$ and $R^{12}$ are each independently selected from the group consisting of hydrogen, alkenyl, alkoxyalkyl, alkyl, amino, aminoalkyl, aryl, arylalkyl, cyanoalkyl, cycloalkyl, cycloalkylalkyl, haloalkyl, heterocyclyl, heterocyclylalkyl, hydroxyalkyl, $-NR^cR^d$, $(NR^cR^d)$alkyl, and $(NR^cR^d)$carbonylalkyl; or
$R^{11}$ and $R^{12}$, together with the nitrogen atom to which they are attached, form a heterocyclyl ring selected from the group consisting of azetidinyl, diazepanyl, imidazolidinyl, morpholinyl, piperazinyl, piperidinyl, pyrrolidinyl and thiomorpholinyl, which can each be optionally substituted with one, two, or three substituents independently selected from the group consisting of alkoxy, alkoxycarbonyl, alkenyl, alkyl, alkylcarbonyl, aryl, carboxy, carboxyalkyl, and heterocyclyl, heterocyclylalkyl, hydroxy, hydroxyalkyl, $-NR^cR^d$, $(NR^cR^d)$alkyl, and $(NR^cR^d)$carbonyl, wherein $R^c$ and $R^d$ are each independently selected from the group consisting of hydrogen, alkoxycarbonyl, alkyl, alkylcarbonyl, alkylsulfonyl, aryl, arylsulfonyl, heterocyclyl, heterocyclcarbonyl, heterocyclylsulfonyl, and formyl;
$R^{13}$ is selected from the group consisting of aryl, cycloalkyl, and heterocyclyl;
X is selected from the group consisting of $-O-$, $-NR^{14}-$, $-C(O)-$, $-S-$, $-SO_2-$, $-(CH_2)_n-$, $-C(O)NR^{14}-$, $-NR^{14}C(O)-$, $-SO_2NR^{14}-$, $-NR^{14}SO_2-$, $-O(CH_2)_m-$, $-(CH_2)_mO-$, $-CH=CH-$ and $-C\equiv C-$; wherein $R^{14}$ is selected from the group consisting of hydrogen, alkenyl, alkyl, aminoalkyl, and hydroxyalkyl;
Y is selected from the group consisting of $NR^{15}$ and O;
wherein $R^{15}$ is selected from the group consisting of hydrogen, alkoxycarbonyl, alkyl, alkylcarbonyl, arylalkyl, cycloalkyl, and cycloalkylalkyl;
m is 0-3; and
n is 1-3.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen; and
$R^6$ is as defined in formula (I).

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of alkoxycarbonyl and alkoxycarbonylalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of amino and aryl; and
$R^6$ is as defined in formula (I).

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of carboxy, carboxyalkyl, cyano, nitro, and heterocyclyl; and
$R^6$ is as defined in formula (I).

In another embodiment, the present invention provides a compound of formula (I) wherein
$A^1$ is $CR^1$;
$A^2$ is $CR^8$;
Y is $NR^{15}$; and
$R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 0;
one of $R^{11}$ and $R^{12}$ is hydrogen and the other is heterocyclylalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$; and
$R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 0;
one of $R^{11}$ and $R^{12}$ is hydrogen and the other is selected from the group consisting of amino, aminoalkyl, arylalkyl, and hydroxyalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 0;
$R^{11}$ and $R^{12}$, together with the nitrogen atom to which they are attached, form a heterocyclyl ring selected from the group consisting of diazepanyl, imidazolidinyl, morpholinyl, piperazinyl, piperidinyl, and pyrrolidinyl, which can each be optionally substituted with one, two, or three substituents independently selected from the group consisting of alkoxy, alkoxycarbonyl, alkenyl, alkyl, alkylcarbonyl, aryl, carboxy, carboxy, heterocyclyl, heterocyclylalkyl, hydroxy, and hydroxyalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$; and
$R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 1;
one of $R^{11}$ and $R^{12}$ is selected from the group consisting of hydrogen and alkyl and the other is heterocyclylalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$; and $R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 1;
one of $R^{11}$ and $R^{12}$ is selected from the group consisting of hydrogen and alkyl and the other is selected from the group consisting of alkoxyalkyl and hydroxyalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$; and
$R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 1;
one of $R^{11}$ and $R^{12}$ is selected from the group consisting of hydrogen and alkyl and the other is selected from the group consisting of alkyl, aminoalkyl, aryl, aryalkyl, and heterocyclyl; and
$R^6$ is as defined in formula (I).

In another embodiment, the present invention provides a compound of formula (I) wherein
$A^1$ is $CR^1$;
$A^2$ is $CR^8$;
Y is $NR^{15}$; and
$R^1$, $R^3$, $R^4$, $R^5$, $R^7$, $R^8$, and $R^{15}$ are hydrogen;
$R^2$ is $-(CR^9R^{10})_m C(O)NR^{11}R^{12}$;
m is 1;
$R^{11}$ and $R^{12}$, together with the nitrogen atom to which they are attached, form a heterocyclyl ring selected from the group consisting of diazepanyl, imidazolidinyl, morpholinyl, piperazinyl, piperidinyl, and pyrrolidinyl, which can each be optionally substituted with one, two, or three substituents independently selected from the group consisting of alkoxy, alkoxycarbonyl, alkenyl, alkyl, alkylcarbonyl, aryl, carboxy, carboxy, heterocyclyl, heterocyclylalkyl, hydroxy, and hydroxyalkyl; and
$R^6$ is as defined in formula (I).

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is $-(CR^9R^{10})_m C(O)NR^9R^{10}$;
m is 1; and
$R^{11}$ is hydrogen;
$R^{12}$ is aryl wherein the aryl is phenyl optionally substituted with 1 morpholinyl group;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
$R^c$ and $R^d$ are independently selected from the group consisting of hydrogen, alkyl, and alkylcarbonyl.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is —$(CR^9R^{10})_m C(O)NR^{11}R^{12}$;
 m is 1; and
 $R^{11}$ is hydrogen;
 $R^{12}$ is aryl wherein the aryl is phenyl optionally substituted with 1 morpholinyl group; and
 $R^6$ is aryl wherein the aryl is phenyl substituted in the three position with methoxy and substituted in the four position with a heterocyclyl group.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is —$(CR^9R^{10})_m C(O)NR^{11}R^{12}$;
 m is 1; and
 $R^{11}$ is hydrogen;
 $R^{12}$ is aryl wherein the aryl is phenyl optionally substituted with 1 morpholinyl group; and
 $R^6$ is heterocyclyl.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^5$, $R^7$, $R^8$, and $R^{15}$ are hydrogen;
 $R^2$ is —$(CR^9R^{10})_m C(O)NR^{11}R^{12}$;
 m is 1; and
 $R^{11}$ is hydrogen;
 $R^{12}$ is aryl wherein the aryl is phenyl optionally substituted with 1 morpholinyl group; and
 $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is hydroxyalkyl;
 $R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
 $R^c$ and $R^d$ are independently selected from the group consisting of hydrogen, alkyl, and alkylcarbonyl.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is hydroxyalkyl; and $R^6$ is aryl wherein the aryl is phenyl substituted in the three position with methoxy and substituted in the four position with a heterocyclyl group.

In another embodiment, the present invention provides a compound of formula (I) wherein
 $A^1$ is $CR^1$;
 $A^2$ is $CR^8$;
 Y is $NR^{15}$; and
 $R^1$, $R^3$, $R^4$, $R^5$, $R^7$, $R^8$, and $R^{15}$ are hydrogen;
 $R^2$ is hydroxyalkyl; and
 $R^6$ is heterocyclyl.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is hydroxyalkyl; and
 $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is alkoxy;
 $R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
 $R^c$ and $R^d$ are independently selected from the group consisting of hydrogen, alkyl, and alkylcarbonyl.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is alkoxy; and
 $R^6$ is aryl wherein the aryl is phenyl substituted in the three position with methoxy and substituted in the four position with a heterocyclyl group.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is alkoxy; and
 $R^6$ is heterocyclyl.

In another embodiment, the present invention provides a compound of formula (I) wherein
 $A^1$ is $CR^1$;
 $A^2$ is $CR^8$;
 Y is $NR^{15}$;
 $R^1$, $R^3$, $R^4$, $R^5$, $R^7$, $R^8$, and $R^{15}$ are hydrogen;
 $R^2$ is alkoxy; and
 $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is arylalkoxy;
R$^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ are independently selected from the group consisting of hydrogen, alkyl, and alkylcarbonyl.

In another embodiment, the present invention provides a compound of formula (I) wherein
In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is arylalkoxy; and
R$^6$ is aryl wherein the aryl is phenyl substituted in the three position with methoxy and substituted in the four position with a heterocyclyl group.

In another embodiment, the present invention provides a compound of formula (I) wherein
A$^1$ is CR$^1$;
A$^2$ is CR$^8$;
Y is NR$^{15}$; and
R$^1$, R$^3$, R$^4$, R$^5$, R$^7$, R$^8$, and R$^{15}$ are hydrogen;
R$^2$ is arylalkoxy; and
R$^6$ is heterocyclyl.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is arylalkoxy; and
R$^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is aryloxyalkyl wherein the aryl is phenyl substituted with 1 morpholinyl group;
R$^6$ is aryl wherein the aryl is phenyl substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ are independently selected from the group consisting of hydrogen, alkyl, and alkylcarbonyl.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is aryloxyalkyl wherein the aryl is phenyl substituted with 1 morpholinyl group; and
R$^6$ is aryl wherein the aryl is phenyl substituted in the three position with methoxy and substituted in the four position with a heterocyclyl group.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is aryloxyalkyl wherein the aryl is phenyl substituted with 1 morpholinyl group; and
R$^6$ is heterocyclyl.

In another embodiment, the present invention provides a compound of formula (I) wherein
A$^1$ is CR$^1$;
A$^2$ is CR$^8$;
Y is NR$^{15}$;
R$^1$, R$^3$, R$^5$, R$^7$, R$^8$, and R$^{15}$ are hydrogen;
R$^2$ is aryloxyalkyl wherein the aryl is phenyl substituted with 1 morpholinyl group; and
R$^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is heterocyclyloxyalkyl;
R$^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ are independently selected from the group consisting of hydrogen, alkyl, and alkylcarbonyl.

In another embodiment, the present invention provides a compound of formula (I) wherein
A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is heterocyclyloxyalkyl; and
R$^6$ is aryl wherein the aryl is phenyl substituted in the three position with methoxy and substituted in the four position with a heterocyclyl group.

In another embodiment, the present invention provides a compound of formula (I) wherein A¹ is CR¹;
A² is CR⁸;
Y is NR¹⁵;
R¹, R³, R⁴, R⁵, R⁷, R⁸, and R¹⁵ are hydrogen;
R² is heterocyclyloxyalkyl; and
R⁶ is heterocyclyl.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclyloxyalkyl; and
R⁶ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH₂, halo, methoxy or hydroxy.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclyloxyalkyl wherein the heterocyclyl is pyridinyl optionally substituted with 1 substituent selected from alkyl, cyano, halo, or hydroxy;
R⁶ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR^c R^d, NH₂SO₂—, or NH₂CO—; and
R^c and R^d are independently selected from the group consisting of hydrogen, alkyl, and alkylcarbonyl.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclyloxyalkyl wherein the heterocyclyl is pyridinyl optionally substituted with 1 substituent selected from alkyl, cyano, halo, or hydroxy; and
R⁶ is aryl wherein the aryl is phenyl substituted in the three position with methoxy and substituted in the four position with a heterocyclyl group.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclyloxyalkyl wherein the heterocyclyl is pyridinyl optionally substituted with 1 substituent selected from alkyl, cyano, halo, or hydroxy; and
R⁶ is heterocyclyl.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclyloxyalkyl wherein the heterocyclyl is pyridinyl optionally substituted with 1 substituent selected from alkyl, cyano, halo, or hydroxy; and
R⁶ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted 1 substituent selected from with alkyl, —NH₂, halo, methoxy or hydroxy.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclylalkyl;
R⁶ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR^c R^d, NH₂SO₂—, or NH₂CO—; and
R^c and R^d are independently selected from the group consisting of hydrogen, alkyl, and alkylcarbonyl.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclylalkyl; and
R⁶ is aryl wherein the aryl is phenyl substituted in the three position with methoxy and substituted in the four position with a heterocyclyl group.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclylalkyl; and
R⁶ is heterocyclyl.

In another embodiment, the present invention provides a compound of formula (I) wherein
A¹ is CR¹;
A² is CR⁸;
Y is NR¹⁵;
R¹, R³, R⁴, R⁵, R⁷, R⁸, and R¹⁵ are hydrogen;
R² is heterocyclylalkyl; and
R⁶ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH₂, halo, methoxy or hydroxy.

In another embodiment, the present invention provides a compound of formula (I) wherein
A¹ is CR¹;
A² is CR⁸;
Y is NR¹⁵;
R¹, R², R³, R⁵, R⁷, R⁸, and R¹⁵ are hydrogen;
R³ is —(CR⁹R¹⁰)ₘC(O)NR¹¹R¹²;
m is 1; and
R¹¹ is hydrogen;
R¹² is aryl wherein the aryl is phenyl optionally substituted with 1 morpholinyl group;

$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^cR^d$, $NH_2SO_2$—, or $NH_2CO$—; and $R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is —$(CR^9R^{10})_mC(O)NR^{11}R^{12}$;
m is 1; and
$R^{11}$ is hydrogen;
$R^{12}$ is aryl wherein the aryl is phenyl optionally substituted with 1 morpholinyl group; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is —$(CR^9R^{10})_mC(O)NR^{11}R^{12}$;
m is 1; and
$R^{11}$ is hydrogen;
$R^{12}$ is aryl wherein the aryl is phenyl optionally substituted with 1 morpholinyl group; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^3$, $R^5$, $R^7$, $R^8$, and $R^{15}$ are hydrogen;
$R^3$ is —$(CR^9R^{10})_mC(O)NR^{11}R^{12}$;
m is 1; and
$R^{11}$ is hydrogen;
$R^{12}$ is aryl wherein the aryl is phenyl optionally substituted with 1 morpholinyl group; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
$A^1$ is $CR^1$;
$A^2$ is $CR^8$;
Y is $NR^{15}$;
$R^1R^2$, $R^4$, $R^5$, $R^7$, $R^8$, and $R^{15}$ are hydrogen;
$R^3$ is hydroxyalkyl;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, heterocyclyl, heterocyclylalkyl, heterocyclylalkoxy, heterocyclylsulfonyl-NH—, hydroxy, hydroxyalkyl, hydroxyalkoxy, hydroxyalkoxyalkoxyalkoxyl, nitro, —$NR^cR^d$, $NH_2SO_2$—, or $NH_2CO$—; and $R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is hydroxyalkyl; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is hydroxyalkyl; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is hydroxyalkyl; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
$A^1$ is $CR^1$;
$A^2$ is $CR^8$;
Y is $NR^{15}$; and
$R^1$, $R^2$, $R^4$, $R^5$, $R^7$, $R^8$, and $R^{15}$ are hydrogen;
$R^3$ is alkoxy;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, heterocyclyl, heterocyclylalkyl, heterocyclylalkoxy, heterocyclylsulfonyl-NH—, hydroxy, hydroxyalkyl, hydroxyalkoxy, hydroxyalkoxyalkoxyalkoxyl, nitro, —$NR^cR^d$, $NH_2SO_2$—, or $NH_2CO$—;

$R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is alkoxy; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;

Y is NR$^{15}$;
R$^1$, R$^2$, R$^4$, R$^5$, R$^7$, R$^8$, and R$^{15}$ are hydrogen;
R$^3$ is alkoxy; and
R$^6$ is heterocyclyl.

In another embodiment, the present invention provides a compound of formula (I) wherein
A$^1$ is CR$^1$;
A$^2$ is CR$^8$;
Y is NR$^{15}$;
R$^1$, R$^2$, R$^4$, R$^5$, R$^7$, R$^8$, and R$^{15}$ are hydrogen;
R$^3$ is alkoxy; and
R$^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
A$^1$ is CR$^8$;
A$^2$ is CR$^8$;
Y is NR$^{15}$;
R$^1$, R$^3$, R$^4$, R$^5$, R$^7$, R$^8$, and R$^{15}$ are hydrogen;
R$^3$ is aryloxyalkyl wherein the aryl is phenyl optionally substituted with 1 morpholinyl group;
R$^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ dare independently selected from the group consisting of hydrogen, alkyl, and alkylcarbonyl.

In another embodiment, the present invention provides a compound of formula (I) wherein
A$^1$ is CR$^8$;
A$^2$ is CR$^8$;
Y is NR$^{15}$; R$^1$, R$^3$, R$^4$, R$^5$, R$^7$, R$^8$, and R$^{15}$ are hydrogen;
R$^3$ is aryloxyalkyl wherein the aryl is phenyl optionally substituted with 1 morpholinyl group; and
R$^6$ is aryl wherein the aryl is phenyl substituted in the three position with methoxy and substituted in the four position with a heterocyclyl group.

In another embodiment, the present invention provides a compound of formula (I) wherein
A$^1$ is CR$^1$;
A$^2$ is CR$^8$;
Y is NR$^{15}$;
R$^1$, R$^2$, R$^4$, R$^5$, R$^7$, R$^8$, and R$^{15}$ are hydrogen;
R$^3$ is aryloxyalkyl wherein the aryl is phenyl optionally substituted with 1 morpholinyl group; and
R$^6$ is heterocyclyl.

In another embodiment, the present invention provides a compound of formula (I) wherein
A$^1$ is CR$^1$;
A$^2$ is CR$^8$;
Y is NR$^{15}$;
R$^1$, R$^2$, R$^4$, R$^5$, R$^7$, R$^8$, and R$^{15}$ are hydrogen;
R$^3$ is aryloxyalkyl wherein the aryl is phenyl optionally substituted with 1 morpholinyl group; and
R$^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
A$^1$ is CR$^1$;
A$^2$ is CR$^8$;
Y is NR$^{15}$;
R$^1$, R$^2$, R$^4$, R$^5$, R$^7$, R$^8$, and R$^{15}$ are hydrogen;
R$^3$ is arylalkoxy;
R$^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ are independently selected from the group consisting of hydrogen, alkyl, and alkylcarbonyl.

In another embodiment, the present invention provides a compound of formula (I) wherein
A$^1$ is CR$^1$;
A$^2$ is CR$^8$;
Y is NR$^{15}$;
R$^1$, R$^2$, R$^4$, R$^5$, R$^7$, R$^8$, and R$^{15}$ are hydrogen;
R$^3$ is arylalkoxy; and
R$^6$ is aryl wherein the aryl is phenyl substituted in the three position with methoxy and substituted in the four position with a heterocyclyl group.

In another embodiment, the present invention provides a compound of formula (I) wherein
A$^1$ is CR$^1$;
A$^2$ is CR$^8$;
Y is NR$^{15}$;
R$^1$R$^2$, R$^4$, R$^5$, R$^7$, R$^8$, and R$^{15}$ are hydrogen;
R$^3$ is arylalkoxy; and
R$^6$ is heterocyclyl.

In another embodiment, the present invention provides a compound of formula (I) wherein
A$^1$ is CR$^1$;
A$^2$ is CR$^8$;
Y is NR$^{15}$;
R$^1$R$^2$, R$^4$, R$^5$, R$^7$, R$^8$, and R$^{15}$ are hydrogen;
R$^3$ is arylalkoxy; and
R$^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
A$^1$ is CR$^1$;
A$^2$ is CR$^8$;
Y is NR$^{15}$;
R$^1$, R$^2$, R$^4$, R$^5$, R$^7$, R$^8$, and R$^{15}$ are hydrogen;
R$^3$ is heterocyclyloxyalkyl;
R$^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ are independently selected from the group consisting of hydrogen, alkyl, and alkylcarbonyl.

In another embodiment, the present invention provides a compound of formula (I) wherein $A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is heterocyclyloxyalkyl; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is heterocyclyloxyalkyl; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is heterocyclyloxyalkyl; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is heterocyclylalkyl;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
$R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is heterocyclylalkyl; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1 R^2$, $R^4$, $R^5$, $R^7$, $R^8$, and $R^{15}$ are hydrogen;
$R^3$ is heterocyclylalkyl; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is heterocyclylalkyl; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is —$(CR^9R^{10})_m C(O)NR^{11}R^{12}$;
$R^3$ is —$(CR^9R^{10})_m C(O)NR^{11}R^{12}$;
m is 1; and
$R^{11}$ is hydrogen;
$R^{12}$ is aryl wherein the aryl is phenyl optionally substituted with 1 morpholinyl group;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
$R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is —$(CR^9R^{10})_m C(O)NR^9R^{10}$;
$R^3$ is —$(CR^9R^{10})_m C(O)NR^{11}R^{12}$;
m is 1; and
$R^{11}$ is hydrogen;
$R^{12}$ is aryl wherein the aryl is phenyl optionally substituted with 1 morpholinyl group; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is —$(CR^9R^{10})_m C(O)NR^9R^{10}$;
$R^3$ is —$(CR^9R^{10})_m C(O)NR^{11}R^{12}$;
m is 1; and
$R^{11}$ is hydrogen;
$R^{12}$ is aryl wherein the aryl is phenyl optionally substituted with 1 morpholinyl group; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is —$(CR^9R^{10})_m C(O)NR^9R^{10}$;
$R^3$ is —$(CR^9R^{10})_m C(O)NR^{11}R^{12}$;
m is 1; and $R^{11}$ is hydrogen;

$R^{12}$ is aryl wherein the aryl is phenyl optionally substituted with 1 morpholinyl group; and $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is hydroxyalkyl;
$R^3$ is hydroxyalkyl;

$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and R$^c$ and R$^d$ are independently selected from the group consisting of hydrogen, alkyl, and alkylcarbonyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is hydroxyalkyl;
$R^3$ is hydroxyalkyl; and $R^6$ is aryl wherein the aryl is phenyl substituted in the three position with methoxy and substituted in the four position with a heterocyclyl group.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is hydroxyalkyl;
$R^3$ is hydroxyalkyl; and
$R^6$ is heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is hydroxyalkyl;
$R^3$ is hydroxyalkyl; and $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with 1 morpholinyl group;

$R^3$ is aryloxyalkyl wherein the aryl is phenyl optionally substituted with 1 morpholinyl group;

$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and R$^c$ and R$^d$ are independently selected from the group consisting of hydrogen, alkyl, and alkylcarbonyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is aryloxyalkyl wherein the aryl is phenyl optionally substituted with 1 morpholinyl group;
$R^3$ is aryloxyalkyl wherein the aryl is phenyl optionally substituted with 1 morpholinyl group; and $R^6$ is aryl wherein the aryl is phenyl substituted in the three position with methoxy and substituted in the four position with a heterocyclyl group.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is aryloxyalkyl wherein the aryl is phenyl optionally substituted with 1 morpholinyl group;
$R^3$ is aryloxyalkyl wherein the aryl is phenyl optionally substituted with 1 morpholinyl group; and
$R^6$ is heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with 1 morpholinyl group;
$R^3$ is aryloxyalkyl wherein the aryl is phenyl optionally substituted with 1 morpholinyl group; and $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;
$R^3$ is heterocyclyloxyalkyl;

$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and $R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;
$R^3$ is heterocyclyloxyalkyl; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;
$R^3$ is heterocyclyloxyalkyl; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;
$R^3$ is heterocyclyloxyalkyl; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is alkoxy;
$R^3$ is alkoxy;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
$R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is alkoxy;
$R^3$ is alkoxy;
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is alkoxy;
$R^3$ is alkoxy; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is alkoxy;
$R^3$ is alkoxy; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —$NH_2$, halo, methoxy or hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is arylalkoxy;
$R^3$ is arylalkoxy;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —$NR^c R^d$, $NH_2SO_2$—, or $NH_2CO$—; and
$R^c$ and $R^d$ are independently selected from the group consisting of hydrogen, alkyl, and alkylcarbonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is arylalkoxy;
$R^3$ is arylalkoxy; and
$R^6$ is aryl wherein the aryl is phenyl substituted in the three position with methoxy and substituted in the four position with a heterocyclyl group.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is arylalkoxy;
$R^3$ is arylalkoxy; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is arylalkoxy;
$R^3$ is arylalkoxy; and $R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
$A^1$ is CR$^1$;
$A^2$ is CR$^8$;
Y is NR$^{15}$;
$R^1$, $R^4$, $R^5$, $R^7$, $R^8$, and $R^{15}$ are hydrogen;
$R^2$ is heterocyclylalkyl;
$R^3$ is heterocyclylalkyl;
$R^6$ is aryl wherein the aryl is phenyl substituted in the three position with methoxy and substituted in the four or five position with alkoxy, alkoxyalkoxy, alkoxycarbonyl, alkoxycarbonylalkenyl, alkylcarbonyl, alkylsulfonyl, aminoalkyl, aminoalkoxy, arylalkoxy, arylalkyl, cyano, cyanoalkyl, cyanoalkoxy, halo, haloalkenyl, hydroxy, hydroxyalkyl, hydroxyalkoxy, hydroxyalkoxyalkoxyalkoxyl, nitro, —NR$^c$R$^d$, NH$_2$SO$_2$—, or NH$_2$CO—; and
R$^c$ and R$^d$ are independently selected from the group consisting of hydrogen, alkyl, and alkylcarbonyl.

In another embodiment, the present invention provides a compound of formula (I) wherein
$A^1$ is CR$^1$;
$A^2$ is CR$^8$;
Y is NR$^{15}$;
$R^1$, $R^4$, $R^5$, $R^7$, $R^8$, and $R^{15}$ are hydrogen;
$R^2$ is heterocyclylalkyl;
$R^3$ is heterocyclylalkyl; and
$R^6$ is aryl wherein the aryl is phenyl substituted in the three position with methoxy and substituted in the four position with heterocyclyl, heterocyclylalkyl, heterocyclylalkoxy, heterocyclylsulfonyl-NH— wherein the heterocyclyl.

In another embodiment, the present invention provides a compound of formula (I) wherein
$A^1$ is CR$^1$;
$A^2$ is CR$^8$;
Y is NR$^{15}$;
$R^1$, $R^4$, $R^5$, $R^7$, $R^3$, and $R^{15}$ are hydrogen;
$R^2$ is heterocyclylalkyl;
$R^3$ is heterocyclylalkyl; and
$R^6$ is heterocyclyl.

In another embodiment, the present invention provides a compound of formula (I) wherein
$A^1$ is CR$^1$;
$A^2$ is CR$^8$;
Y is NR$^{15}$;
$R^1$, $R^4$, $R^5$, $R^7$, $R^8$, and $R^{15}$ are hydrogen;
$R^2$ is heterocyclylalkyl;
$R^3$ is heterocyclylalkyl; and
$R^6$ is heterocyclyl wherein the heterocyclyl is pyrazinyl, pyridazinyl, pyridinyl, or pyrimidinyl wherein the pyrazinyl, pyridazinyl, pyridinyl, or pyrimidinyl is optionally substituted with 1 substituent selected from alkyl, —NH$_2$, halo, methoxy or hydroxy.

In another embodiment, the present invention provides a compound of formula (I) wherein
$A^1$ is CR$^1$;
$A^2$ is CR$^8$;
Y is NR$^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1 or 2;

$R^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
$R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and
R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
$A^1$ is CR$^1$;
$A^2$ is CR$^8$;
Y is NR$^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
$R^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1 or 2;
$R^9$ and $R^{10}$ are independently selected from the group consisting of hydrogen and alkyl;
$R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1 or 2;
R$^9$ and R$^{10}$ are independently selected from the group consisting of hydrogen and alkyl; R$^{11}$ is hydrogen;
R$^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

R$^6$ is aryl wherein the aryl is phenyl substituted with methoxy and heterocyclylalkoxy, wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1 or 2;
R$^9$ and R$^{10}$ are independently selected from the group consisting of hydrogen and alkyl; R$^{11}$ is hydrogen;
R$^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

R$^6$ is aryl wherein the aryl is phenyl substituted with methoxy and heterocyclyloxy, wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy, wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy, wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy, wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy, wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyl wherein the heterocyclyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl wherein the heterocyclyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyl wherein the heterocyclyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclyl wherein the heterocyclyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl wherein the heterocyclyl of the heterocyclylalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkyl wherein the heterocyclyl of the heterocyclylalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen; R$^2$ is heterocyclylalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, ($NR^cR^d$)alkyl, ($NR^cR^d$)alkoxy, and ($NR^cR^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl wherein the heterocyclyl of the heterocyclylalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, ($NR^cR^d$)alkyl, ($NR^cR^d$)alkoxy, and ($NR^cR^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, ($NR^cR^d$)alkyl, ($NR^cR^d$)alkoxy, and ($NR^cR^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$; $A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, ($NR^cR^d$)alkyl, ($NR^cR^d$)alkoxy, and ($NR^cR^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$; Y is $NR^{15}$;
$R^1$, $R^4$, $R^5$, $R^7$, $R^8$, and $R^{15}$ are hydrogen;
$R^2$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyloxyalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$; R$^1$, R$^4$, R$^5$, R$^7$, R$^8$, and R$^{15}$ are hydrogen;
R$^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$; Y is $NR^{15}$;
$R^1$, $R^4$, $R^5$, $R^7$, $R^3$, and $R^{15}$ are hydrogen;
$R^2$ is heterocyclyloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkoxy;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^3$, and R$^{15}$ are hydrogen;
R$^2$ is heterocyclylalkoxy wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkoxy;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkoxy wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is heterocyclylalkoxy wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$; R$^1$, R$^4$, R$^5$, R$^7$, R$^8$, and R$^{15}$ are hydrogen;
R$^2$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen; R$^2$ is aminoalkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is aminoalkyl wherein R$^a$ and R$^b$ are independently selected from the group consisting of hydrogen, alkyl, alkylcarbony, (NR$^c$R$^d$)alkyl, alkylsulfonyl, and arylsulfonyl, wherein R$^c$ and R$^d$ are independently selected from the group consisting of hydrogen, and alkyl;
R$^3$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$; $A^2$ is $CR^8$;

Y is $NR^{15}$;

$R^1$, $R^4$, $R^5$, $R^7$, $R^8$, and $R^{15}$ are hydrogen;

$R^2$ is aminoalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is aminoalkyl wherein $R^a$ and $R^b$ are independently selected from the group consisting of hydrogen, alkyl, alkylcarbony, $(NR^cR^d)$alkyl, alkylsulfonyl, and arylsulfonyl, wherein $R^c$ and $R^d$ are independently selected from the group consisting of hydrogen and alkyl; $R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is aminoalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is aminoalkyl wherein $R^a$ and $R^b$ are independently selected from the group consisting of hydrogen, alkyl, alkylcarbony, $(NR^cR^d)$alkyl, alkylsulfonyl, and arylsulfonyl, wherein Re and $R^d$ are independently selected from the group consisting of hydrogen and alkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is aminoalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aminoalkyl wherein $R^a$ and $R^b$ are independently selected from the group consisting of hydrogen, alkyl, alkylcarbony, $(NR^cR^d)$alkyl, alkylsulfonyl, and arylsulfonyl, wherein $R^c$ and $R^d$ are independently selected from the group consisting of hydrogen and alkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1 or 2;
$R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclyl;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclyl wherein the heterocyclyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl $R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclylalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclylalkyl wherein the heterocyclyl of the heterocyclylalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclyloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclylalkoxy;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is heterocyclylalkoxy wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aminoalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is aminoalkyl wherein $R^a$ and $R^b$ are independently selected from the group consisting of hydrogen, alkyl, alkylcarbony, $(NR^cR^d)$alkyl, alkylsulfonyl, and arylsulfonyl, wherein $R^c$ and $R^d$ are independently selected from the group consisting of hydrogen and alkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —$NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1 or 2;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; $R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$; $R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$; Y is $NR^{15}$;
$R^1$, $R^4$, $R^5$, $R^7$, $R^8$, and $R^{15}$ are hydrogen;
$R^2$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl wherein the heterocyclyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl wherein the heterocyclyl of the heterocyclylalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aminoalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$, wherein $R^c$ and $R^d$ are independently selected from the group consisting of hydrogen, alkyl, alkylcarbonyl, and heterocyclyl, wherein the heterocyclyl is pyridinyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aminoalkyl wherein $R^a$ and $R^b$ are independently selected from the group consisting of hydrogen, alkyl, alkylcarbony, $(NR^cR^d)$alkyl, alkylsulfonyl, and arylsulfonyl, wherein $R^c$ and $R^d$ are independently selected from the group consisting of hydrogen and alkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$, wherein $R^c$ and $R^d$ are independently selected from the group consisting of hydrogen, alkyl, alkylcarbonyl, and heterocyclyl, wherein the heterocyclyl is pyridinyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of alkoxy, alkoxycarbonylalkyl, alkyl, carboxyalkyl, hydroxyalkyl, and —$(CR^9R^{10})_mC(O)NR^{11}R^{12}$;
m is 1 or 2;
$R^9$ and $R^{10}$ are independently selected from the group consisting of hydrogen and alkyl; $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of alkoxy, alkoxycarbonylalkyl, alkyl, carboxyalkyl, hydroxyalkyl, and —$(CR^9R^{10})_mC(O)NR^{11}R^{12}$;
m is 1 or 2;
$R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of alkoxy, alkoxycarbonylalkyl, alkyl, carboxyalkyl, hydroxyalkyl, and —$(CR^9R^{10})_mC(O)NR^{11}R^{12}$;
m is 1 or 2;
$R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with methoxy and heterocyclylalkoxy, wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of alkoxy, alkoxycarbonylalkyl, alkyl, carboxyalkyl, hydroxyalkyl, and —$(CR^9R^{10})_mC(O)NR^{11}R^{12}$;
m is 1 or 2;
$R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with methoxy and heterocyclyloxy, wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl;
$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl;
$R^6$ is aryl wherein the aryl is phenyl substituted with methoxy and heterocyclylalkoxy, wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^6$ is aryl wherein the aryl is phenyl substituted with methoxy and heterocyclylalkoxy, wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; R$^3$ is aryloxyalkyl;
R$^6$ is aryl wherein the aryl is phenyl substituted with methoxy and heterocyclyloxy, wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
R$^6$ is aryl wherein the aryl is phenyl substituted with methoxy and heterocyclyloxy, wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; R$^3$ is heterocyclyl;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen; R$^2$ is selected from the group consisting of hydrogen, alkoxy, alkoxycarbonylalkyl, alkyl, carboxyalkyl, hydroxyalkyl, and —(CR$^9$R$^{10}$)$_m$ C(O)NR$^{11}$R$^{12}$;
R$^3$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; $R^3$ is heterocyclyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; $R^3$ is heterocyclyl;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;

Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^3$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^3$ is heterocyclylalkyl;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^3$ is heterocyclylalkyl wherein the heterocyclyl of the heterocyclylalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

$R^3$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;

$A^2$ is $CR^8$;

Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; $R^3$ is heterocyclylalkyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl wherein the heterocyclyl of the heterocyclylalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl wherein the heterocyclyl of the heterocyclylalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl wherein the heterocyclyl of the heterocyclylalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl;
$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

R⁶ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^3$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

R⁶ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; R$^3$ is heterocyclyloxyalkyl;

R⁶ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

R⁶ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; R$^3$ is heterocyclyloxyalkyl;

R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^3$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;

R$^3$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkoxy;

R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy wherein the heterocyclyl of the heterocyclylalkoxy is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy wherein the heterocyclyl of the heterocyclylalkoxy is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^c R^d$, $(NR^cR^d)$alkyl, $(NR^cR^d)$alkoxy, and $(NR^cR^d)$carbonyl, wherein the alkyl of the heterocyclylalkyl is optionally substituted with one substituent selected from the group consisting of alkoxy and hydroxy; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl, wherein the alkyl of the heterocyclylalkyl is optionally substituted with one substituent selected from the group consisting of alkoxy and hydroxy; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
  $A^1$ is CR$^1$;
  $A^2$ is CR$^8$;
  Y is NR$^{15}$;
  $R^1$, $R^4$, $R^5$, $R^7$, $R^8$, and $R^{15}$ are hydrogen;
  $R^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
  $R^3$ is heterocyclylalkoxy;
  $R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
  $A^1$ is CR$^1$;
  $A^2$ is CR$^8$;
  Y is NR$^{15}$;
  $R^1$, $R^4$, $R^5$, $R^7$, $R^8$, and $R^{15}$ are hydrogen;
  $R^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
  $R^3$ is heterocyclylalkoxy wherein the heterocyclyl of the heterocyclylalkoxy is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
  $A^1$ is CR$^1$;
  $A^2$ is CR$^8$;
  Y is NR$^{15}$;
  $R^1$, $R^4$, $R^5$, $R^7$, $R^8$, and $R^{15}$ are hydrogen;
  $R^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
  $R^3$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
  $A^1$ is CR$^1$;
  $A^2$ is CR$^8$;
  Y is NR$^{15}$;
  $R^1$, $R^4$, $R^5$, $R^7$, $R^8$, and $R^{15}$ are hydrogen;
  $R^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$; $R^3$ is heterocyclylalkoxy;
  $R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkoxy wherein the heterocyclyl of the heterocyclylalkoxy is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is aminoalkyl;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is aminoalkyl wherein R$^a$ and R$^b$ are independently selected from the group consisting of hydrogen, alkyl, alkylcarbony, and (NR$^c$R$^d$)alkyl, wherein R$^c$ and R$^d$ are independently selected from the group consisting of hydrogen and alkyl;
R$^6$ is aryl wherein the aryl is phenyl substituted with methoxy and heterocyclyl wherein the heterocyclyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —NR$^c$R$^d$, (NR$^c$R$^d$)alkyl, (NR$^c$R$^d$)alkoxy, and (NR$^c$R$^d$)carbonyl; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl wherein $R^a$ and $R^b$ are independently selected from the group consisting of hydrogen, alkyl, alkylcarbony, and $(NR^cR^d)$alkyl, wherein Re and $R^d$ are independently selected from the group consisting of hydrogen and alkyl;

$R^6$ is aryl wherein the aryl is phenyl substituted with methoxy and heterocyclylalkyl wherein the heterocyclyl of the heterocyclylalkyl is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl; and $R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl wherein $R^a$ and $R^b$ are independently selected from the group consisting of hydrogen, alkyl, alkylcarbony, and $(NR^cR^d)$alkyl, wherein Re and $R^d$ are independently selected from the group consisting of hydrogen and alkyl; and $R^6$ is aryl wherein the aryl is phenyl substituted with methoxy and heterocyclylalkoxy wherein the heterocyclyl of the heterocyclylalkoxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl; and $R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, —$NR^cR^d$, $(NR^cR^d)$alkyl, $(NR^cR^d)$alkoxy, and $(NR^cR^d)$carbonyl; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is aminoalkyl wherein $R^a$ and $R^b$ are independently selected from the group consisting of hydrogen, alkyl, alkylcarbony, and $(NR^cR^d)$alkyl, wherein $R^c$ and $R^d$ are independently selected from the group consisting of hydrogen and alkyl; and
$R^6$ is aryl wherein the aryl is phenyl substituted with methoxy and heterocyclyloxy wherein the heterocyclyl of the heterocyclyloxy is selected from the group consisting of dihydropyridinyl, dioxolanyl, furyl, imidazolyl, isoxazolyl, morpholinyl, oxadiazolyl, oxazolyl, oxazolidinyl, piperazinyl, piperidinyl, pyrrolidinyl, pyrrolyl, pyrazolyl, pyridinyl, tetrahydrofuranyl, tetrahydropyranyl, thiadiazolyl, thiazolyl, and thienyl, wherein the heterocyclyl is optionally substituted with one, two, or three substituents selected from the group consisting of alkoxy, alkoxycarbonyl, alkyl, cyano, cycloalkyl, halo, haloalkoxy, haloalkyl, hydroxy, oxo, $-NR^cR^d$, $(NR^cR^d)$alkyl, $(NR^cR^d)$alkoxy, and $(NR^cR^d)$carbonyl; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
m is 1 or 2;
$R^9$ and $R^{10}$ are independently selected from the group consisting of hydrogen and alkyl; $R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; $R^3$ is aryloxyalkyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; $R^3$ is heterocyclyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl;

R$^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl wherein the heterocyclyl of the heterocyclylalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
R$^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A$^1$ is CR$^1$;
A$^2$ is CR$^8$;
Y is NR$^{15}$; R$^1$, R$^4$, R$^5$, R$^7$, R$^8$, and R$^{15}$ are hydrogen;
R$^2$ is selected from the group consisting of hydrogen, alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$; Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclylalkoxy;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclylalkoxy wherein the heterocyclyl of the heterocyclylalkoxy is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;
$R^6$ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, $-NR^cR^d$, $(NR^cR^d)$alkyl, $(NR^cR^d)$alkoxy, $(NR^cR^d)$carbonyl, and nitro; and
$R^c$ and $R^d$ are independently selected from the group consisting of hydrogen, alkyl, alkylcarbonyl, phenyl, pyridinyl, and thienyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;

R³ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

R⁶ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A¹ is CR¹;
A² is CR⁸;
Y is NR¹⁵;
R¹, R⁴, R⁵, R⁷, R⁸, and R¹⁵ are hydrogen;
R² is selected from the group consisting of hydrogen, alkoxy, alkoxycarbonylalkyl, alkyl, carboxyalkyl, hydroxyalkyl, and —(CR⁹R¹⁰)$_m$C(O)NR¹¹R¹²;
R³ is aminoalkyl;
R⁶ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A¹ is CR¹;
A² is CR⁸;
Y is NR¹⁵;
R¹, R⁴, R⁵, R⁷, R⁸, and R¹⁵ are hydrogen;
R² is selected from the group consisting of hydrogen, alkoxy, alkoxycarbonylalkyl, alkyl, carboxyalkyl, hydroxyalkyl, and —(CR⁹R¹⁰)$_m$C(O)NR¹¹R¹²;
R³ is aminoalkyl wherein R$^a$ and R$^b$ are independently selected from the group consisting of hydrogen, alkyl, alkylcarbony, and (NR$^c$R$^d$)alkyl, wherein Re and R$^d$ are independently selected from the group consisting of hydrogen and alkyl;
R⁶ is aryl wherein the aryl is phenyl substituted with one substituent selected from the group consisting of halo and methoxy, and optionally one substituent selected from the group consisting of alkoxy, alkoxyalkoxy, alkoxyalkoxyalkoxy, alkoxycarbonyl, alkyl, alkylcarbonyl, cyano, cyanoalkoxy, cyanoalkyl, halo, haloalkoxy, haloalkyl, hydroxy, hydroxyalkoxy, hydroxyalkyl, —NR$^c$R$^d$, (NR$^c$R$^d$)alkyl, (NR$^c$R$^d$)alkoxy, (NR$^c$R$^d$)carbonyl, and nitro; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A¹ is CR¹;
A² is CR⁸;
Y is NR¹⁵;
R¹, R⁴, R⁵, R⁷, R⁸, and R¹⁵ are hydrogen;
R² is selected from the group consisting of hydrogen, alkoxy, alkoxycarbonylalkyl, alkyl, carboxyalkyl, hydroxyalkyl, and —(CR⁹R¹⁰)$_m$C(O)NR¹¹R¹²;
R³ is selected from the group consisting of hydrogen, alkoxy, alkoxycarbonylalkyl, alkyl, carboxyalkyl, hydroxyalkyl, and —(CR⁹R¹⁰)$_m$C(O)NR¹¹R¹²;
m is 1 or 2;
R⁹ and R¹⁰ are independently selected from the group consisting of hydrogen and alkyl; R¹¹ is hydrogen;
R¹² is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

R⁶ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and NR$^c$R$^d$; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A¹ is CR¹;
A² is CR⁸;
Y is NR¹⁵;
R¹, R⁴, R⁵, R⁷, R⁸, and R¹⁵ are hydrogen;
R² is selected from the group consisting of hydrogen, alkoxy, alkoxycarbonylalkyl, alkyl, carboxyalkyl, hydroxyalkyl, and —(CR⁹R¹⁰)$_m$C(O)NR¹¹R¹²;
R³ is aryloxyalkyl;
R⁶ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and NR$^c$R$^d$; and R$^c$ and R$^d$ are independently selected from the group consisting of hydrogen, alkyl, alkylcarbonyl, phenyl, pyridinyl, and thienyl.

In another embodiment, the present invention provides a compound of formula (I) wherein A¹ is CR¹;
A² is CR⁸;
Y is NR¹⁵;
R¹, R⁴, R⁵, R⁷, R³, and R¹⁵ are hydrogen;
R² is selected from the group consisting of hydrogen, alkoxy, alkoxycarbonylalkyl, alkyl, carboxyalkyl, hydroxyalkyl, and —(CR⁹R¹⁰)$_m$C(O)NR¹¹R¹²;

$R^3$ is aryloxyalkyl wherein the aryl of the aryloxyalkyl is phenyl optionally substituted with one or two substituents selected from the group consisting of alkoxy, alkyl, cyano, cyanoalkyl, halo, haloalkoxy, haloalkyl, hydroxy, and heterocyclyl, wherein the heterocyclyl is selected from the group consisting of morpholinyl, oxazolyl, piperazinyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl, wherein the heterocyclyl is optionally substituted with one or two substituents selected from the group consisting of alkoxy, alkyl, and alkylcarbonyl;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyl;
$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyl wherein the heterocyclyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclyl, wherein the heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclylalkyl;
$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is heterocyclylalkyl wherein the heterocyclyl of the heterocyclylalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is heterocyclylalkyl, wherein the heterocyclyl of the heterocyclylalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is heterocyclyloxyalkyl;
$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is heterocyclyloxyalkyl wherein the heterocyclyl of the heterocyclyloxyalkyl is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is heterocyclyloxyalkyl, wherein the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is heterocyclylalkoxy;
$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy wherein the heterocyclyl of the heterocyclylalkoxy is selected from the group consisting of dihydropyridinyl, morpholinyl, imidazolyl, piperazinyl, piperidinyl, pyridinyl, pyrrolidinyl, and quinolinyl, wherein the heterocyclyl is optionally substituted with alkoxy, alkoxycarbonyl, alkyl, alkylcarbonyl, cyano, halo, haloalkoxy, haloalkyl, hydroxy, and oxo;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is heterocyclylalkoxy, wherein the heterocyclyl of the heterocyclylalkoxy is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl, wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$; and $R^c$ and $R^d$ are independently selected from the group consisting of hydrogen, alkyl, alkylcarbonyl, phenyl, pyridinyl, and thienyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl; and $R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$, wherein Re and $R^d$ are independently selected from the group consisting of hydrogen, alkyl, alkylcarbonyl, and heterocyclyl, wherein the heterocyclyl is pyridinyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is aminoalkyl wherein $R^a$ and $R^b$ are independently selected from the group consisting of hydrogen, alkyl, alkylcarbony, and ($NR^cR^d$)alkyl, wherein Re and $R^d$ are independently selected from the group consisting of hydrogen and alkyl; and $R^6$ is aryl wherein the aryl is phenyl substituted with methoxy and one substituent selected from the group consisting of aryl, arylalkyl, and arylalkoxy, wherein the aryl, the aryl of the arylalkyl, and the aryl of the arylalkoxy is phenyl optionally substituted with one or two substituents selected from the group consisting of alkoxy, alkoxycarbonyl, alkyl, alkylcarbonyl, cyano, cycloalkyl, halo, haloalkoxy, haloalkyl, hydroxy, and $NR^cR^d$, wherein Re and $R^d$ are independently selected from the group consisting of hydrogen, alkyl, alkylcarbonyl, and heterocyclyl, wherein the heterocyclyl is pyridinyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and
$R^{11}$ is hydrogen;
$R^{12}$ is aryl; and
$R^6$ is heterocyclyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $—(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $—(CR^9R^{10})_mC(O)NR^{11}R^{12}$;

m is 1; and $R^{11}$ is hydrogen;

$R^{12}$ is aryl; and $R_6$ is heterocyclyl wherein the heterocyclyl is optionally substituted with arylalkyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $—(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $—(CR^9R^{10})_mC(O)NR^{11}R^{12}$;

m is 1; and $R^{11}$ is hydrogen;

$R^{12}$ is aryl; and $R_6$ is heterocyclyl wherein the heterocyclyl is optionally substituted with aryloxyalkyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and $—(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and $R^{11}$ is hydrogen;

$R^{12}$ is aryl; and $R^6$ is heterocyclyl wherein the heterocyclyl is optionally substituted with heterocyclylalkyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and $R^{11}$ is hydrogen;

$R^{12}$ is aryl; and $R_6$ is heterocyclyl wherein the heterocyclyl is optionally substituted with a second heterocyclyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

m is 1; and $R^{11}$ is hydrogen;

$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is aryloxyalkyl; and $R^6$ is heterocyclyl.

In another embodiment, the present invention provides a compound of formula (I) wherein $A^1$ is $CR^1$;

$A^2$ is $CR^8$;

Y is $NR^{15}$;

$R^1$, $R^3$, $R^4$, $R^5$, $R^7$, $R^8$, and $R^{15}$ are hydrogen;

$R^2$ is aryloxyalkyl; and $R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, aralkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and $R^c$ and $R^d$ are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl; and
$R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R^6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl; and
$R^6$ is heterocyclyl optionally substituted with arylalkyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl; and
$R^6$ is heterocyclyl optionally substituted with aryloxyalkyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl; and
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl; and
$R_6$ is heterocyclyl optionally substituted with heterocyclylalkyl.

In another embodiment, the present invention provides a compound of formula (I) wherein
$A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl; and $R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl; and
$R^6$ is heterocyclyl optionally substituted with a second heterocyclyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein $A^1$ is $CR^1$;
$A^2$ is $CR^8$; Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl;
$R_6$ is heterocyclyl. In another embodiment, the present invention provides a compound of formula (I) wherein $A^1$ is $CR^1$;
$A^2$ is $CR^8$;
Y is $NR^{15}$; $R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, (NR$^c$R$^d$)alkyl, (NR$^c$R$^d$)carbonylalkyl, and (NR$^c$R$^d$)sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is selected from the group consisting of heterocyclyl, heterocyclylalkoxy, heterocyclylalkyl, and heterocyclyloxyalkyl;
R$_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
R$_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is selected from the group consisting of heterocyclyl, heterocyclylalkoxy, heterocyclylalkyl, and heterocyclyloxyalkyl;
R$_6$ is heterocyclyl optionally substituted with arylalkyl.

In another embodiment, the present invention provides a compound of formula (I) wherein A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
R$_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein A$^1$ is CR$^1$;
A$^2$ is CR$^8$;
Y is NR$^{15}$;
R$^1$, R$^3$, R$^4$, R$^5$, R$^7$, R$^8$, and R$^{15}$ are hydrogen;
R$^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R^6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl;
$R_6$ is heterocyclyl optionally substituted with aryloxyalkyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl;
$R^6$ is heterocyclyl optionally substituted with a second heterocyclyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl;

$R_6$ is heterocyclyl optionally substituted with heterocyclylalkyl.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein $A^1$ is $CR^1$;
$A^2$ is $CR^8$;
Y is $NR^{15}$;
$R^1$, $R^3$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein
  $A^1$ is $CR^1$;
  $A^2$ is $CR^8$;
  Y is $NR^{15}$;
  $R^1$, $R^3$, $R^4$, $R^5$, $R^7$, $R^8$, and $R^{15}$ are hydrogen;
  $R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
  $R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein
  $A^1$ is $CR^1$;
  $A^2$ is $CR^8$;
  Y is $NR^{15}$;
  $R^1$, $R^2$, $R^4$, $R^5$, $R^7$, $R^8$, and $R^{15}$ are hydrogen;
  $R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
  m is 1; and
  $R^{11}$ is hydrogen;
  $R^{12}$ is aryl; and
  $R_6$ is heterocyclyl.

In another embodiment, the present invention provides a compound of formula (I) wherein
  $A^1$ is $CR^1$;
  $A^2$ is $CR^8$;
  Y is $NR^{15}$;
  $R^1$, $R^2$, $R^4$, $R^5$, $R^7$, $R^8$, and $R^{15}$ are hydrogen;
  $R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
  m is 1; and
  $R^{11}$ is hydrogen;
  $R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, ($NR^cR^d$)alkyl, ($NR^cR^d$)carbonylalkyl, and ($NR^cR^d$)sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
  $A^1$ is $CR^1$;
  $A^2$ is $CR^8$;
  Y is $NR^{15}$;
  $R^1$, $R^2$, $R^4$, $R^5$, $R^7$, $R^8$, and $R^{15}$ are hydrogen;
  $R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
  m is 1; and
  $R^{11}$ is hydrogen;
  $R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
  $A^1$ is $CR^1$;
  $A^2$ is $CR^8$;
  Y is $NR^{15}$;
  $R^1$, $R^2$, $R^4$, $R^5$, $R^7$, $R^8$, and $R^{15}$ are hydrogen;
  $R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
  m is 1; and
  $R^{11}$ is hydrogen;
  $R^{12}$ is aryl; and
  $R_6$ is heterocyclyl wherein the heterocyclyl is optionally substituted with arylalkyl.

In another embodiment, the present invention provides a compound of formula (I) wherein
  $A^1$ is $CR^1$;
  $A^2$ is $CR^8$;
  Y is $NR^{15}$;
  $R^1$, $R^2$, $R^4$, $R^5$, $R^7$, $R^8$, and $R^{15}$ are hydrogen;
  $R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
  m is 1; and
  $R^{11}$ is hydrogen;
  $R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl; and
$R_6$ is heterocyclyl wherein the heterocyclyl is optionally substituted with aryloxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl; and
$R_6$ is heterocyclyl wherein the heterocyclyl is optionally substituted with heterocyclylalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R^6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl; and
$R_6$ is heterocyclyl wherein the heterocyclyl is optionally substituted with a second heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
m is 1; and
$R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$ In another embodiment, the present invention provides a compound of formula (I) wherein
$A^1$ is $CR^1$;
$A^2$ is $CR^8$;
Y is $NR^{15}$;
$R^1R^2$, $R^4$, $R^5$, $R^7$, $R^8$, and $R^{15}$ are hydrogen;
$R^3$ is aryloxyalkyl; and
$R^6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl; and
$R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1R^2$, $R^4$, $R^5$, $R^7$, $R^8$, and $R^{15}$ are hydrogen;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl; and
$R_6$ is heterocyclyl optionally substituted with arylalkyl.

In another embodiment, the present invention provides a compound of formula (I) wherein
$A^1$ is $CR^1$;
$A^2$ is $CR^8$;
Y is $NR^{15}$;
$R^1R^2$, $R^4$, $R^5$, $R^7$, $R^8$, and $R^{15}$ are hydrogen;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein
$A^1$ is $CR^1$;
$A^2$ is $CR^8$;
Y is $NR^{15}$;
$R^1 R^2$, $R^4$, $R^5$, $R^7$, $R^8$, and $R^{15}$ are hydrogen;
$R^3$ is aryloxyalkyl; and
$R_6$ is heterocyclyl optionally substituted with aryloxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl; and
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl; and
$R_6$ is heterocyclyl optionally substituted with heterocyclylalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl; and
$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl; and
$R_6$ is heterocyclyl optionally substituted with a second heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein
$A^1$ is $CR^1$;
$A^2$ is $CR^8$;
Y is $NR^{15}$;
$R^1 R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;
$R_6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;
$R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;
$R_6$ is heterocyclyl optionally substituted with arylalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;
$R_6$ is heterocyclyl optionally substituted with aryloxyalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;
$R_6$ is heterocyclyl optionally substituted with a second heterocyclyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;
$R_6$ is heterocyclyl optionally substituted with heterocyclylalkyl.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$ In another embodiment, the present invention provides a compound of formula (I) wherein $A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein $A^1$ is $CR^1$;
$A^2$ is $CR^8$;
Y is $NR^{15}$;
$R^1$, $R^2$, $R^4$, $R^5$, $R^7$, $R^8$, and $R^{15}$ are hydrogen;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of alkoxy, alkoxycarbonylalkyl, alkyl, carboxyalkyl, hydroxyalkyl, and —$(CR^9R^{10})_m C(O)NR^{11}R^{12}$;
$R^3$ is selected from the group consisting of alkoxy, alkoxycarbonylalkyl, alkyl, carboxyalkyl, hydroxyalkyl, and —$(CR^9R^{10})_m C(O)NR^{11}R^{12}$;
m is 1; and
$R^{11}$ is hydrogen;
$R^{12}$ is aryl; and
$R_6$ is heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of alkoxy, alkoxycarbonylalkyl, alkyl, carboxyalkyl, hydroxyalkyl, and —$(CR^9R^{10})_m C(O)NR^{11}R^{12}$;
$R^3$ is selected from the group consisting of alkoxy, alkoxycarbonylalkyl, alkyl, carboxyalkyl, hydroxyalkyl, and —$(CR^9R^{10})_m C(O)NR^{11}R^{12}$;
m is 1; and
$R^{11}$ is hydrogen;
$R^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;

R$_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, (NR$^c$R$^d$)alkyl, (NR$^c$R$^d$)carbonylalkyl, and (NR$^c$R$^d$)sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1; and
R$^{11}$ is hydrogen;
R$^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and R$_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1; and
R$^{11}$ is hydrogen;
R$^{12}$ is aryl wherein the aryl; and
R$_6$ is heterocyclyl is optionally substituted with arylalkyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1; and
R$^{11}$ is hydrogen;
R$^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and R$_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^8$, and R$^{15}$ are hydrogen;
R$^2$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1; and
R$^{11}$ is hydrogen;
R$^{12}$ is aryl; and
R$_6$ is heterocyclyl optionally substituted with aryloxyalkyl.

In another embodiment, the present invention provides a compound of formula (I) wherein A$^1$ is CR$^1$;
A$^2$ is CR$^8$;
Y is NR$^{15}$;
R$^1$, R$^4$, R$^5$, R$^7$, R$^3$, and R$^{15}$ are hydrogen;
R$^2$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
R$^3$ is selected from the group consisting of alkoxy, alkoxycarbonylalkyl, alkyl, carboxyalkyl, hydroxyalkyl, and —(CR$^9$R$^{10}$)$_m$C(O)NR$^{11}$R$^{12}$;
m is 1; and
R$^{11}$ is hydrogen;
R$^{12}$ is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and R$_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein A¹ is CR¹;
A² is CR⁸;
Y is NR¹⁵;
R¹, R⁴, R⁵, R⁷, R⁸, and R¹⁵ are hydrogen;
R² is selected from the group consisting of alkoxy, alkoxycarbonylalkyl, alkyl, carboxyalkyl, hydroxyalkyl, and —(CR⁹R¹⁰)$_m$C(O)NR¹¹R¹²;
R³ is selected from the group consisting of alkoxy, alkoxycarbonylalkyl, alkyl, carboxyalkyl, hydroxyalkyl, and —(CR⁹R¹⁰)$_m$C(O)NR¹¹R¹²;
m is 1; and
R¹¹ is hydrogen;
R¹² is aryl; and
R₆ is heterocyclyl optionally substituted with heterocyclylalkyl.

In another embodiment, the present invention provides a compound of formula (I) wherein
A¹ is CR¹;
A² is CR⁸;
Y is NR¹⁵;
R¹, R⁴, R⁵, R⁷, R⁸, and R¹⁵ are hydrogen;
R² is selected from the group consisting of alkoxy, alkoxycarbonylalkyl, alkyl, carboxyalkyl, hydroxyalkyl, and —(CR⁹R¹⁰)$_m$C(O)NR¹¹R¹²;
R³ is selected from the group consisting of alkoxy, alkoxycarbonylalkyl, alkyl, carboxyalkyl, hydroxyalkyl, and —(CR⁹R¹⁰)$_m$C(O)NR¹¹R¹²;
m is 1; and
R¹¹ is hydrogen;
R¹² is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
R₆ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
A¹ is CR¹;
A² is CR⁸;
Y is NR¹⁵;
R¹, R⁴, R⁵, R⁷, R³, and R¹⁵ are hydrogen;
R² is selected from the group consisting of alkoxy, alkoxycarbonylalkyl, alkyl, carboxyalkyl, hydroxyalkyl, and —(CR⁹R¹⁰)$_m$C(O)NR¹¹R¹²;
R³ is selected from the group consisting of alkoxy, alkoxycarbonylalkyl, alkyl, carboxyalkyl, hydroxyalkyl, and —(CR⁹R¹⁰)$_m$C(O)NR¹¹R¹²;
m is 1; and
R¹¹ is hydrogen;
R¹² is aryl; and
R₆ is heterocyclyl optionally substituted with a second heterocyclyl.

In another embodiment, the present invention provides a compound of formula (I) wherein
A¹ is CR¹;
A² is CR⁸;
Y is NR¹⁵;
R¹, R⁴, R⁵, R⁷, R⁸, and R¹⁵ are hydrogen;
R² is selected from the group consisting of alkoxy, alkoxycarbonylalkyl, alkyl, carboxyalkyl, hydroxyalkyl, and —(CR⁹R¹⁰)$_m$C(O)NR¹¹R¹²;
R³ is selected from the group consisting of alkoxy, alkoxycarbonylalkyl, alkyl, carboxyalkyl, hydroxyalkyl, and —(CR⁹R¹⁰)$_m$C(O)NR¹¹R¹²;
m is 1; and
R¹¹ is hydrogen;
R¹² is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
R₆ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
A¹ is CR¹;
A² is CR⁸;
Y is NR¹⁵;
R¹, R⁴, R⁵, R⁷, R⁸, and R¹⁵ are hydrogen;
R² is selected from the group consisting of alkoxy, alkoxycarbonylalkyl, alkyl, carboxyalkyl, hydroxyalkyl, and —(CR⁹R¹⁰)$_m$C(O)NR¹¹R¹²;
R³ is selected from the group consisting of alkoxy, alkoxycarbonylalkyl, alkyl, carboxyalkyl, hydroxyalkyl, and —(CR⁹R¹⁰)$_m$C(O)NR¹¹R¹²;
m is 1; and
R¹¹ is hydrogen;
R¹² is aryl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
R₆ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and NH₂

In another embodiment, the present invention provides a compound of formula (I) wherein
A¹ is CR¹;
A² is CR⁸;
Y is NR¹⁵;
R¹, R⁴, R⁵, R⁷, R⁸, and R¹⁵ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; $R^3$ is aryloxyalkyl; and $R_6$ is heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; $R^3$ is aryloxyalkyl;

$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, ($NR^cR^d$)alkyl, ($NR^cR^d$)carbonylalkyl, and ($NR^cR^d$)sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;

$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, ($NR^cR^d$)alkyl, ($NR^cR^d$)carbonylalkyl, and ($NR^cR^d$)sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; $R^3$ is aryloxyalkyl; and $R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl; and
$R_6$ is heterocyclyl optionally substituted with arylalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and $R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl; and
$R_6$ is heterocyclyl optionally substituted with aryloxyalkyl.

In another embodiment, the present invention provides a compound of formula (I) wherein
$A^1$ is $CR^1$;
$A^2$ is $CR^8$;
Y is $NR^{15}$;
$R^1, R^4, R^5, R^7, R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl; and
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1, R^4, R^5, R^7, R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl; and
$R_6$ is heterocyclyl optionally substituted with heterocyclylalkyl.

In another embodiment, the present invention provides a compound of formula (I) wherein
$A^1$ is $CR^1$;
$A^2$ is $CR^8$;
Y is $NR^{15}$;
$R^1, R^4, R^5, R^7, R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl; and
$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1, R^4, R^5, R^7, R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl; and
$R^6$ is heterocyclyl optionally substituted with a second heterocyclyl.

In another embodiment, the present invention provides a compound of formula (I) wherein
$A^1$ is $CR^1$;
$A^2$ is $CR^8$;
Y is $NR^{15}$;
$R^1, R^4, R^5, R^7, R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1, R^4, R^5, R^7, R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl; and
$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein
$A^1$ is $CR^1$;
$A^2$ is $CR^8$;
Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl;

$R_6$ is heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl;

$R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;

$R^1$, $R^4$, $R^5$, $R^7$, $R^3$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl;

$R_6$ is heterocyclyl optionally substituted with arylalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R^6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl;

$R_6$ is heterocyclyl optionally substituted with aryloxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of heterocyclyl, heterocyclylalkoxy, heterocyclylalkyl, and heterocyclyloxyalkyl;

$R_6$ is heterocyclyl optionally substituted with a second heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;

$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_m C(O)NR^{11}R^{12}$;

$R^3$ is selected from the group consisting of heterocyclyl, heterocyclylalkoxy, heterocyclylalkyl, and heterocyclyloxyalkyl;

$R_6$ is heterocyclyl optionally substituted with heterocyclylalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_m C(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_m C(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;

$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_m C(O)NR^{11}R^{12}$;

$R^3$ is selected from the group consisting of heterocyclyl, heterocyclylalkoxy, heterocyclylalkyl, and heterocyclyloxyalkyl;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;

$R^2$ is selected from the group consisting of hydrogen, alkoxy, alkoxycarbonylalkyl, alkyl, carboxyalkyl, hydroxyalkyl, and —$(CR^9R^{10})_m C(O)NR^{11}R^{12}$;

$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;

$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$ In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R^3$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$ In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl optionally substituted with arylalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl optionally substituted with aryloxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl optionally substituted with heterocyclylalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, and thiomorpholinyl, triazolyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl optionally substituted with a second heterocyclyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;

$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and $R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is aryloxyalkyl wherein the aryl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$ In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$;
$R_6$ is heterocyclyl wherein the heterocyclyl is pyrrolo[2,3-c]pyridinyl optionally substituted with one, two, or three substituents independently selected from the group consisting of alkenyl, alkoxyalkyl, alkyl, alkylsulfonylalkyl, alkynyl, arylalkyl, aryloxyalkyl, arylsulfonyl, cyanoalkyl, cycloalkyl, cycloalkylalkyl, heterocyclyl, heterocyclylalkyl, hydroxyalkyl, $(NR^cR^d)$alkyl, $(NR^cR^d)$carbonylalkyl, and $(NR^cR^d)$sulfonylalkyl; and
Rc and Rd are independently selected from the group consisting of hydrogen, alkyl, alkylcarbonyl, arylcarbonyl, alkylsulfonyl, and arylsulfonyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with one, two, or three substituents independently selected from the group consisting of alkoxyalkyl, alkyl, alkylsulfonylalkyl, alkynyl, cyanoalkyl, cycloalkyl, cycloalkylalkyl, and hydroxyalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl optionally substituted with arylalkyl.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein $A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with arylalkyl, wherein the aryl of the arylalkyl is phenyl optionally substituted with one, two, three, four, or five substituents independently selected from the group consisting of alkoxy, alkyl, cyano, halo, haloalkoxy, haloalkyl, and hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl optionally substituted with aryloxyalkyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with aryloxyalkyl, wherein the aryl of the aryloxyalkyl is phenyl optionally substituted with one or two substituents selected from the group consisting of alkoxy, alkyl, cyano, halo, haloalkoxy, haloalkyl, hydroxy, and heterocyclyl, wherein the heterocyclyl is selected from the group consisting of morpholinyl, oxazolyl, piperidinyl, pyrrolidinyl, pyrrolyl, furyl, imidazolyl, isoxazolyl, oxadiazolyl, thiadiazolyl, thiazolyl, thienyl, thiomorpholinyl, and triazolyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl optionally substituted with a second heterocyclyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and $-(CR^9R^{10})_mC(O)NR^{11}R^{12}$; and
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R_6$ is heterocyclyl wherein the heterocyclyl is pyrrolo[2,3-c]pyridinyl optionally substituted with a second heterocyclyl wherein the second heterocyclyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the second heterocyclyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R_6$ is heterocyclyl optionally substituted with heterocyclylalkyl.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrrolidinyl, pyrrolyl, and quinolinyl, wherein the heterocyclyl is optionally substituted with one, two or three substituents independently selected from the group consisting of alkoxy, alkoxyalkoxy, alkoxycarbonyl, alkyl, alkylcarbonyl, cyano, cycloalkyl, cycloalkylalkyl, halo, haloalkoxy, haloalkyl, hydroxy, hydroxyalkyl, oxo, nitro, aryl, arylalkyl, and arylcarbonyl, wherein the aryl, the aryl of the arylalkyl, and the aryl of the arylcarbonyl is phenyl optionally substituted with one or two substituents selected from the group consisting of alkoxy, alkoxycarbonyl, alkyl, alkylcarbonyl, cyano, halo, haloalkoxy, haloalkyl, hydroxy, hydroxyalkyl, and nitro;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^8$, and $R^{15}$ are hydrogen;
$R^2$ is selected from the group consisting of heterocyclyl, heterocyclylalkoxy, heterocyclylalkyl, and heterocyclyloxyalkyl, wherein the heterocyclyl, the heterocyclyl of the heterocyclylalkoxy, the heterocyclyl of the heterocyclylalkyl, and the heterocyclyl of the heterocyclyloxyalkyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl, wherein the heterocyclyl is substituted with a second heterocyclyl wherein the second heterocyclyl is selected from the group consisting of dihydropyridinyl, morpholinyl, imidazolyl, piperazinyl, piperidinyl, pyrazolyl, pyridinyl, pyrimidinyl, pyrrolidinyl, pyrrolyl, and quinolinyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R_6$ is heterocyclyl wherein the heterocyclyl is pyrrolo[2,3-c]pyridinyl optionally substituted with heterocyclylalkyl, wherein the heterocyclyl of the heterocyclylalkyl is selected from the group consisting of imidazolyl, isoxazolyl, morpholinyl, piperidinyl, pyrazinyl, pyrrolidinyl, pyridinyl, tetrahydrofuranyl, tetrahydropyranyl, thiazolyl, and thienyl, wherein the heterocyclyl of the heterocyclylalkyl is optionally substituted with one or two substituents selected from the group consisting of alkyl, halo, haloalkoxy, haloalkyl, oxo, and hydroxy.

In another embodiment, the present invention provides a compound of formula (I) wherein
$A^1$ is $CR^1$;
$A^2$ is $CR^8$;
Y is $NR^{15}$;
$R^1$, $R^4$, $R^5$, $R^7$, $R^3$, and $R^{15}$ are hydrogen;
$R^2$ is selected from the group consisting of heterocyclyl, heterocyclylalkoxy, heterocyclylalkyl, and heterocyclyloxyalkyl;
$R^3$ is selected from the group consisting of hydrogen, alkoxy, alkoxycarbonylalkyl, alkyl, carboxyalkyl, hydroxyalkyl, and —$(CR^9R^{10})_mC(O)NR^{11}R^{12}$; and
$R_6$ is heterocyclyl wherein the heterocyclyl is selected from the group consisting of benzimidazolyl, imidazo[1,5-a]pyridinyl, isoquinolinyl, and thieno[2,3-c]pyridinyl, wherein the heterocyclyl is optionally substituted with one or two substituents independently selected from the group consisting of alkoxy, alkyl, cyano, halo, haloalkoxy, haloalkyl, hydroxy, and $NH_2$.

In another embodiment the present invention provides a pharmaceutical composition comprising a compound of formula (I), or a therapeutically acceptable salt thereof, in combination with a therapeutically acceptable carrier.

In another embodiment the present invention provides a method for inhibiting protein kinases in a patient in recognized need of such treatment comprising administering to the patient a therapeutically acceptable amount of a compound of formula (I), or a therapeutically acceptable salt thereof.

In another embodiment the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

As used in the present specification the following terms have the meanings indicated:

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkoxy," as used herein, refers to an alkoxy group attached to the parent molecular moiety through an alkoxy group, wherein the alkoxyalkoxy group may be substituted with at least one hydroxy group.

The term "alkoxyalkoxyalkyl," as used herein, refers to an alkoxyalkoxy group attached to the parent molecular moiety through an alkoxy group, wherein the alkoxyalkoxyalkoxy group may be substituted with at least one hydroxy group.

The term "alkoxyalkyl," as used herein, refers to an alkoxy group attached to the parent molecular moiety through an alkyl group.

The term "alkoxycarbonyl," as used herein, refers to an alkoxy group attached to the parent molecular moiety through a carbonyl group.

The term "alkoxycarbonylalkenyl," as used herein, refers to an alkoxycarbonyl group attached to the parent molecular moiety through an alkenyl group.

The term "alkoxycarbonylalkyl," as used herein, refers to an alkoxycarbonyl group attached to the parent molecular moiety through an alkyl group.

The term "alkoxysulfonyl," as used herein, refers to an alkoxy group attached to the parent molecular moiety through a sulfonyl group.

The term "alkoxysulfonylalkyl," as used herein, refers to an alkoxysulfonyl group attached to the parent molecular moiety through an alkyl group.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylcarbonylalkyl," as used herein, refers to an alkylcarbonyl group attached to the parent molecular moiety through an alkyl group.

The term "alkylsulfonyl," as used herein, refers to an alkyl group attached to the parent molecular moiety through a sulfonyl group.

The term "alkylsulfonylalkyl," as used herein, refers to an alkylsulfonyl group attached to the parent molecular moiety through an alkyl group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino," as used herein, refers to $-NR^aR^b$, wherein $R^a$ and $R^b$ are independently selected from the group consisting of hydrogen, alkoxyalkylcarbonyl, alkoxycarbonyl, alkyl, alkylcarbonyl, alkylsulfonyl, aryl, arylalkyl, arylalkylcarbonyl, arylalkylsulfonyl, arylsulfonyl, arylsulfonylalkyl, arylsulfonylalkylcarbonyl, cycloalkyl, cycloalkylalkyl, cycloalkylcarbonyl, haloalkylsulfonyl, heterocyclyl, heterocyclylalkylcarbonyl, heterocyclylalkylsulfonyl, heterocyclylcarbonyl, heterocyclylsulfonyl, $-NR^cR^d$, $(NR^cR^d)$alkyl, $(NR^cR^d)$alkylcarbonyl, $(NR^cR^d)$alkylsulfonyl, $(NR^cR^d)$carbonyl, $(NR^cR^d)$carbonylalkyl, and $(NR^cR^d)$carbonylalkylcarbonyl, wherein the aryl groups of the present invention can be optionally substituted with one, two, three, four, or five substituents independently selected from the group consisting of alkoxy, alkoxyalkyl, alkoxycarbonyl, alkyl, alkylcarbonyl, alkylsulfonyl, a second aryl group, arylalkyl, arylsulfonyl, carboxy, cyano, halo, heterocyclyl, heterocyclylalkyl, hydroxy, nitro, and oxo, wherein the second aryl group, the aryl part of the arylalkyl and the arylsulfonyl, the heterocyclyl, and the heterocyclyl part of the heterocyclylalkyl can be optionally substituted with one, two, three, four, or five substituents independently selected from the group consisting of alkoxy, alkoxyalkyl, alkoxycarbonyl, alkyl, alkylcarbonyl, carboxy, cyano, halo, haloalkoxy, haloalkyl, hydroxy, nitro, and oxo. Representative examples of amino include, but are not limited to, $-NH_2$, methylamino, dimethylamino, diethylamino, ethylmethylamino, (4-aminobutanoyl)amino, (3-aminopropanoyl)amino, [(2S)-2-amino-4-methylpentanoyl]amino, [(2R)-2-amino-4-methylpentanoyl]amino, (2-amino-4-methylpentanoyl)amino, [(dimethylamino)acetyl]amino, [(1-methyl-1H-imidazol-5-yl)acetyl]amino, (1H-imidazol-4-ylacetyl)amino, thien-3-ylcarbonylamino, thien-2-ylcarbonylamino, (1H-pyrrol-3-ylcarbonyl)amino, (1H-pyrrol-2-ylcarbonyl)amino, [(2,5-dimethyl-1H-pyrrol-3-yl)carbonyl]amino, (1,3-thiazol-4-ylcarbonyl)amino, (1H-pyrazol-5-ylcarbonyl)amino, (1H-pyrazol-4-ylcarbonyl)amino, isonicotinoylamino, (3-pyrrolidin-1-ylpropanoyl)amino, (3-piperidin-1-ylpropanoyl)amino, (3-morpholin-4-ylpropanoyl)amino, [3-(phenylsulfonyl)propanoyl]amino, ({[(4-methylphenyl)sulfonyl]amino}acetyl)amino, (pyridin-2-ylcarbonyl)amino, (pyridin-3-ylcarbonyl)amino, (pyridin-3-ylacetyl)amino, [(4-methylpiperazin-1-yl)acetyl]amino, {[(2S)-5-oxopyrrolidin-2-yl]carbonyl}amino, {[(2R)-5-oxopyrrolidin-2-yl]carbonyl}amino, [(2-furoylamino)acetyl]amino, [(2S)-2-hydroxy-2-phenylethanoyl]amino, [(2R)-2-hydroxy-2-phenylethanoyl]amino, [(2-hydroxy-2-phenylethanoyl]amino, (3-piperidin-1-ylpropanoyl)amino, [(3-chloropropyl)sulfonyl]amino, (benzylsulfonyl)amino, [(2,2,2-trifluoroethyl)sulfonyl]amino, [(1-methyl-1H-imidazol-4-yl)sulfonyl]amino, [(3-morpholin-4-ylpropyl)sulfonyl]amino, [(3-piperidin-1-ylpropyl)sulfonyl]amino, ([3-(diethylamino)propyl]sulfonyl)amino, {[3-(dimethylamino)propyl]sulfonyl}amino, [(chloromethyl)sulfonyl]amino, (4-morpholin-4-ylbenzoyl)amino, (tetrahydro-2H-pyran-4- ylcarbonyl)amino, cis [(4-hydroxycyclohexyl)carbonyl] amino, and [2-(dimethylamino)ethyl](methyl)amino. The term "aminoalkoxy," as used herein, refers to an amino group attached to the parent molecular moiety through an alkoxy group.

The term "aminoalkyl," as used herein, refers to an amino group attached to the parent molecular moiety through an alkyl group.

The term "aminocarbonyl," as used herein, refers to an amino group attached to the parent molecular moiety through a carbonyl group.

The term "aminocarbonylalkyl," as used herein, refers to an aminocarbonyl group attached to the parent molecular moiety through an alkyl group.

The term "aminosulfonyl," as used herein, refers to an amino group attached to the parent molecular moiety through a sulfonyl group.

The term "aminosulfonylalkyl," as used herein, refers to an aminosulfonyl group, attached to the parent molecular moiety through an alkyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl.

The aryl groups of the present invention can be optionally substituted with one, two, three, four, or five substituents independently selected from the group consisting of alkoxy, alkoxyalkoxy, alkoxyalkoxyalkoxy, alkoxyalkyl, alkoxycarbonyl, alkoxycarbonylalkenyl, alkoxycarbonylalkyl, alkoxysulfonyl, alkyl, alkylcarbonyl, alkylsulfonyl, amino, aminocarbonyl, aminosulfonyl, a second aryl group, arylalkyl, arylalkoxy, aryloxy, arylsulfonyl, carboxy, cyano, cyanoalkoxy, cyanoalkyl, formyl, halo, haloalkoxy, haloalkenyl, haloalkyl, heterocyclyl, heterocyclylalkoxy, heterocyclylalkyl, heterocyclyloxy, heterocyclyloxyalkyl, heterocyclylsulfonyl, hydroxy, hydroxyalkyl, hydroxyalkoxy, nitro, —NR$^c$R$^d$, (NR$^c$R$^d$)alkyl, (NR$^c$R$^d$)alkoxy, (NR$^c$R$^d$)carbonyl, and oxo, wherein the second aryl group, the aryl part of the arylalkyl, arylalkoxy, aryloxy and arylsulfonyl, the heterocyclyl, and the heterocyclyl part of the heterocyclylalkoxy, heterocyclylalkyl, heterocyclyloxy, heterocyclyloxyalkyl, and heterocyclylsulfonyl can be optionally substituted with one, two, three, four, or five substituents independently selected from the group consisting of alkoxy, alkoxyalkyl, alkoxycarbonyl, alkyl, alkylcarbonyl, carboxy, cyano, halo, haloalkoxy, haloalkyl, hydroxy, nitro, and oxo.

The term "arylalkoxy," as used herein, refers to an aryl group attached to the parent molecular moiety through an alkoxy group.

The term "arylalkyl," as used herein, refers to an aryl group attached to the parent molecular moiety through an alkyl group. The alkyl portion of the arylalkyl group may be substituted with at least one substituent selected from the group consisting of alkoxy and hydroxy. Representative examples of arylalkyl include, but are not limited to, benzyl, 2-phenylethyl, 2-hydroxy-4-phenylbutyl, (2R)-2-hydroxy-4-phenylbutyl, and (2S)-2-hydroxy-4-phenylbutyl.

The term "arylalkylsulfonyl," as used herein, refers to an arylalkyl group attached to the parent molecular moiety through a sulfonyl group.

The term "aryloxy," as used herein, refers to an aryl group attached to the parent molecular moiety through an oxygen atom.

The term "aryloxyalkyl," as used herein, refers to an aryloxy group attached to the parent molecular moiety through an alkyl group. The alkyl of the aryloxyalkyl group may be substituted with a substituent selected from the group consisting of alkoxy, hydroxy and —NR$^c$R$^d$.

The term "arylsulfonyl," as used herein, refers to an aryl group attached to the parent molecular moiety through a sulfonyl group.

The term "arylsulfonylalkyl," as used herein, refers to an arylsulfonyl group attached to the parent molecular moiety through an alkyl group.

The term "arylsulfonylalkylcarbonyl," as used herein, refers to an arylsulfonylalkyl group attached to the parent molecular moiety through a carbonyl group.

The term "carbonyl," as used herein, refers to —C(O)—.

The term "carboxy," as used herein, refers to —CO$_2$H.

The term "carboxyalkyl," as used herein, refers to a carboxy group attached to the parent molecular moiety through an alkyl group.

The term "cyano," as used herein, refers to —CN.

The term "cyanoalkoxy," as used herein, refers to a cyano group attached to the parent molecular moiety through an alkoxy group.

The term "cyanoalkyl," as used herein, refers to a cyano group attached to the parent molecular moiety through an alkyl group.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to twelve carbon atoms. Examples of cycloalkyl groups include, but are not limited to, cyclopropyl, cyclopentyl, bicyclo[3.1.1]heptyl, and adamantyl. The cycloalkyl groups of the present invention can be optionally substituted with one, two, three, or four substituents independently selected from the group consisting of alkoxy, alkoxyalkyl, alkoxycarbonyl, alkyl, alkylcarbonyl, alkylsulfonyl, —NR$^c$R$^d$, (NR$^c$R$^d$)alkyl, (NR$^c$R$^d$)carbonyl, a second aryl group, arylalkyl, arylsulfonyl, carboxy, cyano, halo, heterocyclyl, heterocyclylalkyl, hydroxy, hydroxyalkyl, nitro, and oxo, wherein the second aryl group, the aryl part of the arylalkyl and the arylsulfonyl, the heterocyclyl, and the heterocyclyl part of the heterocyclylalkyl can be optionally substituted with one, two, three, four, or five substituents independently selected from the group consisting of alkoxy, alkoxyalkyl, alkoxycarbonyl, alkyl, alkylcarbonyl, carboxy, cyano, halo, haloalkoxy, haloalkyl, hydroxy, nitro, and oxo.

The term "cycloalkylalkyl," as used herein, refers to a cycloalkyl group attached to the parent molecular moiety through an alkyl group.

The term "cycloalkylcarbonyl," as used herein, refers to a cycloalkyl group attached to the parent molecular moiety through a carbonyl group.

The term "formyl," as used herein, means a —CHO group.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkenyl," as used herein, refers to an alkenyl group substituted by one, two, three, or four halogen atoms.

The term "haloalkylsulfonyl," as used herein, refers to a haloalkyl group attached to the parent molecular moiety through a sulfonyl group.

The term "heterocyclyl," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, as defined herein, a monocyclic cycloalkyl group, as defined herein, or another monocyclic heterocyclyl group, as defined herein; and tricyclic groups in which a bicyclic system is fused to a phenyl group, a monocyclic cycloalkenyl group, as defined herein, a monocyclic cycloalkyl group, as defined herein, or another monocyclic heterocyclyl group. The heterocyclyl groups of the present invention can be attached to the parent molecular moiety through a carbon atom or a nitrogen atom in the group. Examples of heterocyclyl groups include, but are not limited to, 1H-benzimidazolyl, benzofuranyl, 1,3-benzodioxole benzothienyl, 1,3-dioxolane, furyl, imidazolyl, imidazopyridinyl, indolinyl, indolyl, isoquinolinyl, isothiazolyl, isoxazolyl, morpholinyl, 1,2,4-oxadiazole, 1,3,4-oxadiazole, oxazolyl, 1,3-oxazolidinyl, 6-oxo-1,6-dihydropyridinyl, 4-oxo-pyridinyl, 2-oxo-tetrahydrofuran, piperazinyl, piperidinyl, pyrazinyl, pyrazolyl, pyridinyl, pyrimidinyl, pyrrolidinyl, pyrrolopyridinyl, pyrrolyl, quinolinyl, tetrahydrofuran, tetrahydropyranyl, 1,2,3-thiadiazole, 1,2,4-thiadiazole, 1,3,4-thiadiazole, thiazolyl, thienyl, thienopyridinyl, thiomorpholinyl, and the like.

The heterocyclyl groups of the present invention can be optionally substituted with one, two, three, four, or five substituents independently selected from the group consisting of alkoxy, alkoxyalkyl, alkoxycarbonyl, alkoxycarbonylalkyl, alkoxysulfonylalkyl, alkyl, alkylcarbonyl, alkylsulfonyl, alkylsulfonylalkyl, alkynyl, amino, aminocarbonyl, aminosulfonyl, aryl, arylalkoxy, arylalkyl, aryloxyalkyl, arylsulfonyl, arylsulfonylalkyl, carboxy, carboxyalkyl, cyano, cyanoalkyl, cycloalkyl, cycloalkylalkyl, halo, haloalkoxy, haloalkyl, a second heterocyclyl group, heterocyclylalkyl, hydroxy, hydroxyalkyl, nitro, —$NR^cR^d$, ($NR^cR^d$)alkyl, ($NR^c R^d$)carbonyl and oxo, wherein the aryl, the aryl part of the arylalkoxy, arylalkyl, aryloxyalkyl and arylsulfonyl, the second heterocyclyl group, and the heterocyclyl part of the heterocyclylalkyl can be optionally substituted with one, two, three, four, or five substituents independently selected from the group consisting of alkoxy, alkoxyalkyl, alkoxycarbonyl, alkyl, alkylcarbonyl, carboxy, cyano, halo, haloalkoxy, haloalkyl, hydroxy, methylenedioxy, nitro, and oxo. Representative examples of a substituted heterocyclyl include, but are not limited to, isothiazolidine 1,1-dioxide, 2-oxopyridin-1 (2H)-yl, 5-fluoro-2-oxopyridin-1 (2H)-yl, 6-oxopyridazin-1 (6H)-yl, 3-methyl-2-oxopyridin-1 (2H)-yl, 4-methyl-2-oxopyridin-1 (2H)-yl, 5-chloro-2-oxopyridin-1 (2H)-yl, 1-oxoisoquinolin-2 (1H)-yl, 2-oxo-5-(trifluoromethyl) pyridin-1(2H)-yl, 3-methoxy-2-oxopyridin-1 (2H)-yl, 1,4-dioxa-8-azaspiro[4.5]decane, 2-oxopyrrolidin-1-yl, 2-oxo-1,3-oxazolidin-5-yl, and 2,2-dimethyl-1,3-dioxolan-4-yl.

The term "heterocyclylalkoxy," as used herein, refers to a heterocyclyl group attached to the parent molecular group through an alkoxy group.

The term "heterocyclylalkyl," as used herein, refers to a heterocyclyl group attached to the parent molecular group through an alkyl group. The alkyl of the heterocyclylalkyl group may be substituted with at least one substituent selected from the group consisting of alkoxy and hydroxy.

The term "heterocyclylalkylcarbonyl," as used herein, refers to a heterocyclylalkyl group attached to the parent molecular group through a carbonyl group.

The term "heterocyclylcarbonylalkyl," as used herein, refers to a heterocyclylcarbonyl group attached to the parent molecular group through an alkyl group.

The term "heterocyclylalkylsulfonyl," as used herein, refers to a heterocyclylalkyl group attached to the parent molecular group through a sulfonyl group.

The term "heterocyclylcarbonyl," as used herein, refers to a heterocyclyl group attached to the parent molecular group through a carbonyl group.

The term "heterocyclyloxy," as used herein, refers to a heterocyclyl group attached to the parent molecular group through an oxygen atom.

The term "heterocyclyloxyalkyl," as used herein, refers to a heterocyclyloxy group attached to the parent molecular group through an alkyl group.

The term "heterocyclylsulfonyl," as used herein, refers to a heterocyclyl group attached to the parent molecular group through a sulfonyl group.

The term "hydroxy," as used herein, refers to —OH.

The term "hydroxyalkyl," as used herein, refers to an alkyl group substituted by at least one hydroxy group. The alkyl part of the hydroxyalkyl group can be optionally substituted with an aryl group.

The term "hydroxyalkoxy," as used herein, refers to an alkoxy group substituted by at least one hydroxy group. The hydroxyalkoxy group can be optionally substituted with a —$SO_3H$ group.

The term "methylenedioxy" as used herein, refers to a —$OCH_2O$— group wherein the oxygen atoms of the methylenedioxy are attached to the parent molecular moiety through two adjacent carbon atoms on a phenyl group or the oxygen atoms of the methylenedioxy are attached to the same single carbon atom on a heterocycle including, but not limited to, azetidinyl, piperindinyl, pyrrolidinyl, and azepanyl.

The term "—$NR^cR^d$" as used herein, refers to two groups, $R^c$ and $R^d$, which are appended to the parent molecular moiety through a nitrogen atom. $R^c$ and $R^d$ are each independently hydrogen, alkoxycarbonyl, alkyl, alkylcarbonyl, alkylsulfonyl, aryl, arylsulfonyl, heterocyclyl, heterocyclcarbonyl, heterocyclylsulfonyl, or formyl. Representative examples of —$NR^cR^d$ include, but are not limited to, —$NH_2$, methylamino, acetylamino, dimethylamino, and acetylmethylamino.

The term "($NR^cR^d$)alkoxyl" as used herein, refers to a —$NR^cR^d$ group, as defined herein, appended to the parent molecular moiety through an alkoxy group, as defined herein.

The term "($NR^cR^d$)alkyl" as used herein, refers to a —$NR^c R^d$ group, as defined herein, appended to the parent molecular moiety through an alkyl group, as defined herein. Representative examples of ($NR^cR^d$)alkyl include, but are not limited to, aminomethyl, (methylamino)methyl, 2-(dimethylamino) ethyl, and (ethylmethylamino)carbonyl.

The term "(NR$^c$R$^d$)carbonyl" as used herein, refers to a —NR$^c$R$^d$ group, as defined herein, appended to the parent molecular moiety through a carbonyl group, as defined herein.

The term "(NR$^c$R$^d$)alkylcarbonyl" as used herein, refers to a (NR$^c$R$^d$)alkyl group, as defined herein, appended to the parent molecular moiety through a carbonyl group, as defined herein. Representative examples of (NR$^c$R$^d$)alkylcarbonyl include, but are not limited to, (4-aminobutanoyl)amino, (3-aminopropanoyl)amino, [(2S)-2-amino-4-methylpentanoyl]amino, and [(dimethylamino)acetyl]amino. The term "(NR$^c$R$^d$)carbonyl" as used herein, refers to a —NR$^c$R$^d$ group, as defined herein, appended to the parent molecular moiety through a carbonyl group, as defined herein. Representative examples of (NR$^c$R$^d$)carbonyl include, but are not limited to, aminocarbonyl, (methylamino)carbonyl, (dimethylamino)carbonyl, and (ethylmethylamino)carbonyl.

The term "(NR$^c$R$^d$)carbonylalkyl" as used herein, refers to a (NR$^c$R$^d$)carbonyl group, as defined herein, appended to the parent molecular moiety through an alkyl group, as defined herein.

The term "(NR$^c$R$^d$)carbonylalkylcarbonyl" as used herein, refers to a (NR$^c$R$^d$)carbonylalkyl group, as defined herein, appended to the parent molecular moiety through a carbonyl group, as defined herein.

The term "nitro," as used herein, refers to —NO$_2$.

The term "nitroalkyl," as used herein, refers to a nitro group attached to the parent molecular moiety through an alkyl group.

The term "oxo," as used herein, refers to (=O).

The term "sulfonyl," as used herein, refers to —SO$_2$—.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit protein kinases. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

In accordance with methods of treatment of the present invention, the compounds can be administered alone or in combination with other anticancer agents, or in combination with other chemotherapeutic methods such as radiation. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, rectally, parenterally, intracisternally, intravaginally, intraperitoneally, topically (as by powders, ointments, drops or transdermal patch), bucally, as an oral or nasal spray, or locally, as in a prosthesis placed within the body, such as stents, grafts, catheters and balloons particularly within vasculature. The term "parenteral," as used herein, refers to modes of administration which include intravenous, intraarterial, intramuscular, intraperitoneal, intrasternal, subcutaneous and intraarticular injection, infusion, and placement, such as for example, in the body particularly the vasculature.

The pharmaceutical compositions of the present invention comprise a compound of the present invention and a pharmaceutically acceptable carrier or excipient, which may be administered orally, rectally, parenterally, intracisternally, intravaginally, intraperitoneally, topically (as by powders, ointments, drops or transdermal patch), bucally, as an oral or nasal spray, or locally, as in a prosthesis placed within the body, such as stents, grafts, catheters and balloons particularly within vasculature. The phrase "pharmaceutically acceptable carrier" means a non-toxic, semi-solid or liquid filler, diluent, encapsulating material or formulation auxiliary of any type.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The anticancer effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

The Chk1 enzymatic assay was carried out using recombinant Chk1 kinase domain protein covering amino acids from residue 1 to 289 and a polyhistidine tag at the C-terminal end. Human cdc25c peptide substrate contained a sequence from amino acid residue 204 to 225. The reaction mixture contained 25 mM of HEPES at pH 7.4, 10 mM $MgCl_2$, 0.08 mM Triton X-100, 0.5 mM DTT, 5 $\mu$M ATP, 4 nM 33P ATP, 5 $\mu$M cdc25c peptide substrate, and 6.3 nM of the recombinant Chk1 protein. Compound vehicle DMSO was maintained at 2% in the final reaction. After 30 minutes at room temperature, the reaction was stopped by addition of equal volume of 4M NaCl and 0.1M EDTA, pH 8. A 40 $\mu$L aliquot of the reaction was added to a well in a Flash Plate (NEN Life Science Products, Boston, Mass.) containing 160 $\mu$L of phosphate-buffered saline (PBS) without calcium chloride and magnesium chloride and incubated at room temperature for 10 minutes. The plate was then washed 3 times in PBS with 0.05% of Tween-20 and counted in a Packard TopCount counter (Packard BioScience Company, Meriden, Conn.).

Compounds of the present invention inhibited Chk1 at $IC_{50}$ values between about 0.2 nM and about 280 µM. Preferred compounds inhibited Chk1 at $IC_{50}$ values between about 0.2 nM and about 80 nM. Most preferred compounds inhibited Chk1 at $IC_{50}$ values between about 0.2 nM and about 30 nM. Thus, the compounds of the invention are useful in treating disorders which are caused or exacerbated by increased protein kinase levels.

The compounds of the invention, including but not limited to those specified in the examples, possess the ability to inhibit protein kinases. As protein kinase inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Synthetic Methods

Abbreviations which have been used in the descriptions of the scheme and the examples that follow are: Me for methyl, Et for ethyl, LHMDS for lithium bis(trimethylsilyl)amide, HATU for O—(-7-Azabenzotriazol-1-yl)-N,N,N',N',-tetramethyluronium hexafluorophosphate, PPh$_3$ for triphenylphosphine, PCy$_3$ for tricyclohexylphosphine, dba for dibenzylideneacetone, CyMAP for 2-dicyclohexyl phosphino-2'-(N, N-dimethylsmino)biphenyl, EDC for 1-(3-dimethylaminopropyl)-3-ethylcarbodiimide hydrochloride, 1,3-dicyclohexylcarbodiimide, HOBt for 1-hydroxybenzotriazole, DMSO for dimethylsulfoxide, DME for 1,2-dimethoxyethane, THF for tetrahydrofuran, DMF for N,N-dimethylformamide, TFA for trifluoracetic acid, DPPF for diphenylphosphinoferrocene, OAc for acetate, TMS for trimethylsilyl, DMA for dimethylacetamide, and DIEA for diisopropylethylamine.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $A^1$, $A^2$, X, Y, Z, and $R^1$-$R^7$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

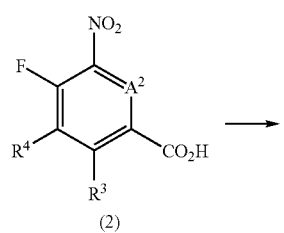

(2)

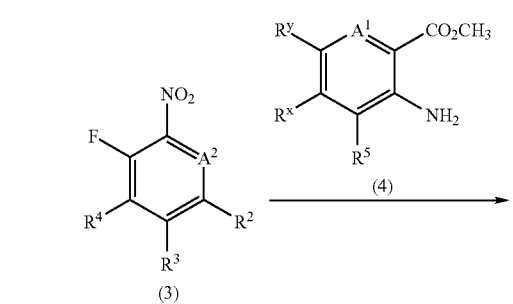

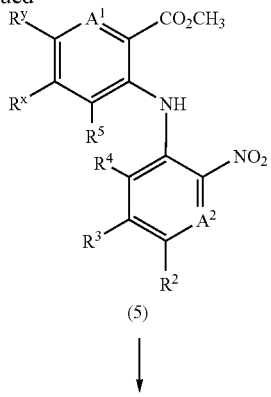

(5)

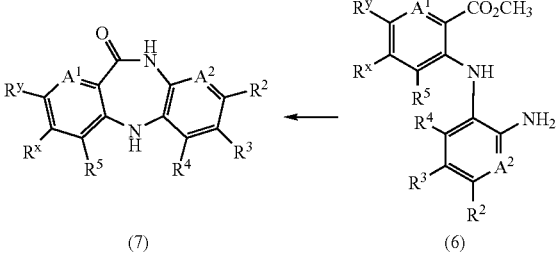

(7) (6)

Scheme 1 shows the synthesis of compounds of formula (7) (compounds of formula (I) wherein Y is $NR^{15}$ wherein $R^{15}$ is H). Compounds of formula (2) can be esterified using conditions known to those of ordinary skill in the art to provide compounds of formula (3) where $R^2$ is alkoxycarbonyl. Alternatively, compounds of formula (2) can be treated sequentially with thionyl chloride, trimethylsilyldiazomethane, and silver (I) benzoate in triethylamine to provide compounds of formula (3) where $R^2$ is alkoxycarbonylalkyl. Compounds of formula (3) can be treated with compounds of formula (4) (where one of $R^x$ and $R^y$ is halogen and the other is hydrogen) in the presence of a base such as $K_2CO_3$, $Na_2CO_3$, or $Cs_2CO_3$ in a polar solvent such as N,N-dimethylacetamide to provide compounds of formula (5). Reduction of the nitro group using conditions known to those of ordinary skill in the art (for example, Pt/C in the presence of hydrogen in an alcoholic solvent system such as ethanol and ethyl acetate) provides compounds of formula (6) which can be cyclized in the presence of a strong acid such as concentrated HCl to provide compounds of formula (7).

Scheme 2

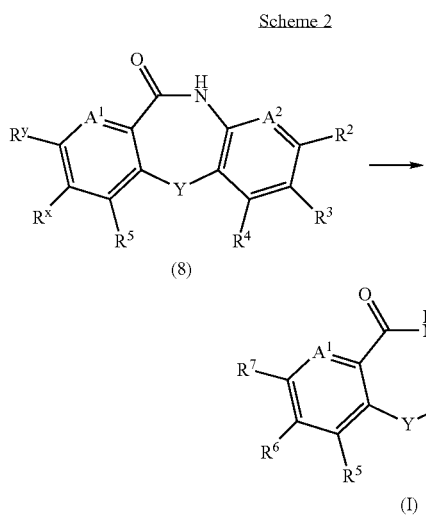

The conversion of compounds of formula (8) to compounds of formula (I) is shown in Scheme 2. Compounds of formula (I) where one of $R^6$ and $R^7$ is hydrogen and the other is aryl or heterocyclyl can be prepared by coupling compounds of formula (8) where one of $R^x$ and $R^y$ is Cl, Br, or I to an appropriately substituted organometallic reagent (such as an organoborane or an organostannane) in the presence of a palladium catalyst (such as Pd(PPh$_3$)$_4$, Pd(PCy$_3$)$_2$Cl$_2$, or Pd$_2$(dba)$_3$ with CyMAP) and optionally in the presence of a base (when the organometallic reagent is an organoborane) such as Cs$_2$CO$_3$ or CsF.

Alternatively, compounds of formula (I) where one of $R^6$ and $R^7$ is hydrogen and the other is —$XR^{13}$ (where X is —O— or —NR$^{14}$— and $R^{13}$ is aryl or heterocyclyl) can be prepared by treating compounds of formula (8) where one of $R^x$ and $R^y$ is Cl, Br, or I with the appropriately substituted alcohol or amine in the presence of a base such as Cs$_2$CO$_3$ or CsF and a palladium catalyst such as Pd$_2$(dba)$_3$ with CyMAP or Pd(PCy$_3$)$_2$Cl$_2$.

Compounds of formula (I) where $R^2$ is alkoxycarbonyl or alkoxycarbonylalkyl can be saponified using conditions known to those of ordinary skill in the art, then reacted with an appropriately substituted amine in the presence of a coupling agent such as EDC, DCC, HOBt, and mixtures thereof, to provide compounds of formula (I) where $R^2$ is aminocarbonyl or aminocarbonylalkyl.

Compounds of formula (I) where $R^2$ is Br or Cl can be coupled to an appropriately substituted organometallic reagent as described above to provide compounds of formula (I) where $R^2$ is aryl or heterocyclyl.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names consistent with ACD nomenclature.

Methyl 4-chloro-2-iodobenzoate was prepared from the corresponding carboxylic acid by methods known to those of ordinary skill in the art.

EXAMPLE 1 methyl 3-chloro-11-oxo-10,11-dihydro-5H-dibenzo[b,e][1,4]diazepine-8-carboxylate

EXAMPLE 1A methyl 2-{[2-amino-4-(methoxycarbonyl)phenyl]amino}-4-chlorobenzoate A mixture of methyl 4-chloro-2-iodobenzoate (0.593 g, 2 mmol), methyl 3,4-diaminobenzoate (0.332 g, 2 mmol), copper (0.126 g, 2 mmol), and K$_2$CO$_3$ (0.276 g, 2 mmol) in chlorobenzene (40 mL) was heated to reflux for 20 hours, cooled to room temperature, diluted with ethyl acetate, and filtered through diatomaceous earth (Celite®). The solution was washed with water and brine, dried (MgSO$_4$), filtered, and concentrated under vacuum. The residue was purified by flash column chromatography on silica gel with 7:3 hexanes/ethyl acetate to provide 0.453 g (68%) of the desired product. MS (DCI) m/e 334 (M+H)$^+$, 352 (M+NH$_4$)$^+$; $^1$H NMR (300 MHz, DMSO-d$_6$) δ 8.99 (s, 1H), 7.89 (d, J=8.5 Hz, 1H), 7.47 (d, J=1.0 Hz, 1H), 7.21 (m, 2H), 6.80 (dd, J=8.5, 2.0 Hz, 1H), 6.65 (d, J=2.1 Hz, 1H), 5.30 (s, 2H), 3.86 (s, 3H), 3.82 (s, 3H).

EXAMPLE 1B methyl 3-chloro-11-oxo-10,11-dihydro-5H-dibenzo[b,e][1,4]diazepine-8-carboxylate A solution of Example 1A (0.43 g, 1.28 mmol) in 37% HCl (20 mL) and methanol (50 mL) was heated to reflux for 20 hours, cooled to room temperature, and filtered. The filter cake was washed with 1:1H$_2$O/methanol and dried in a vacuum oven at 65° C. to provide 0.34 g (87%) of the desired product. MS (DCI) m/e 303 (M+H)$^+$, 320 (M+NH$_4$)$^+$; $^1$H NMR (300 MHz, DMSO-d$_6$) δ 10.04 (s, 1H), 8.50 (s, 1H), 7.72 (d, J=8.5 Hz, 1H), 7.55-7.60 (m, 2H), 7.08 (d, J=2 Hz, 1H), 7.03 (d, J=8.1 Hz, 1H), 6.96 (dd, J=8.5, 2 Hz, 1H), 3.80 (s, 3H).

EXAMPLE 2

8-bromo-3-chloro-5,10-dihydro-11H-dibenzo[b,e][1,4]diazepin-11-one

EXAMPLE 2A methyl 2-[(4-bromo-2-nitrophenyl)amino]-4-chlorobenzoate

A mixture of methyl 4-chloro-2-iodobenzoate (5.93 g, 20 mmol), 4-bromo-2-nitroaniline (4.34 g, 20 mmol), copper (1.26 g, 20 mmol), and K$_2$CO$_3$ (2.76 g, 20 mmol) in chlorobenzene (300 mL) was heated to reflux for 2 days, cooled to room temperature, diluted with ethyl acetate, and filtered through diatomaceous earth (Celite®). The solution was washed with water and brine, dried (MgSO$_4$), filtered, and concentrated under vacuum. The residue was purified by flash column chromatography on silica gel with 9:1 hexanes/ethyl acetate to provide 6.86 g (89%) of the desired product. MS (DCI) m/e 386 (M+H)⁺, 403 (M+NH₄)⁺; $^1$H NMR (300 MHz, DMSO-d₆) δ 10.83 (s, 1H), 8.28 (d, J=2.4 Hz, 1H), 7.97 (d, J=8.5 Hz, 1H), 7.82 (dd, J=9.1, 2.4 Hz, 1H), 7.63 (d, J=9.1 Hz, 1H), 7.52 (d, J=2.1 Hz, 1H), 7.17 (dd, J=8.5, 2 Hz, 1H), 3.87 (s, 3H).

EXAMPLE 2B 8-bromo-3-chloro-5,10-dihydro-11H-dibenzo[b,e][1,4]diazepin-11-one A mixture of Example 2A (6.0 g, 15.6 mmol) and SnCl₂.2H₂O (10.54 g, 46.8 mmol) in 37% HCl (200 mL) and methanol (300 mL) was heated to reflux for 20 hours, cooled to room temperature, and filtered. The filter cake was washed with 1:1 H₂O/methanol and dried in a vacuum oven at 65° C. to provide 4.6 g (91%) of the desired product. MS (DCI) m/e 324 (M+H)⁺, 341 (M+NH₄)⁺; $^1$H NMR (300 MHz, DMSO-d₆) δ 9.98 (s, 1H), 8.18 (s, 1H), 7.69 (d, J=8.5 Hz, 1H), 7.12-7.16 (m, 2H), 7.05 (d, J=2 Hz, 1H), 6.95 (dd, J=8.4, 2 Hz, 1H), 6.91 (d, J=9.1 Hz, 1H).

EXAMPLE 3

3-chloro-8-nitro-5,10-dihydro-11H-dibenzo[b,e][1,4]diazepin-11-one

EXAMPLE 3A methyl 2-[(2-amino-4-nitrophenyl)amino]-4-chlorobenzoate

The desired product was prepared by substituting 2-amino-4-nitrophenylamine for methyl 3,4-diaminobenzoate in Example 1A. MS (DCI) m/e 322 (M+H)⁺, 339 (M+NH₄)⁺; $^1$H NMR (300 MHz, DMSO-d₆) δ 9.08 (s, 1H), 7.92 (d, J=8.5 Hz, 1H), 7.67 (d, J=2.8 Hz, 1H), 7.47 (dd, J=8.5, 2.4 Hz, 1H), 7.33 (d, J=8.8 Hz, 1H), 6.90 (dd, J=8.5, 2.0 Hz, 1H), 6.86 (d, J=2.0 Hz, 1H), 5.65 (s, 2H), 3.87 (s, 3H).

EXAMPLE 3B 3-chloro-8-nitro-5,10-dihydro-11H-dibenzo[b,e][1,4]diazepin-11-one The desired product was prepared by substituting Example 3A for Example 1A in Example 1B. MS (DCI) m/e 290 (M+H)⁺, 307 (M+NH₄)⁺; $^1$H NMR (400 MHz, DMSO-d₆) δ 10.16 (s, 1H), 8.84 (s, 1H), 7.84-7.87 (m, 2H), 7.76 (d, J=8.6 Hz, 1H), 7.08-7.11 (m, 2H), 6.99 (dd, J=8.3, 1.7 Hz, 1H).

EXAMPLE 4

3-chloro-11-oxo-10,11-dihydro-5H-dibenzo[b,e][1,4]diazepine-8-carbonitrile

EXAMPLE 4A methyl 2-[(2-amino-4-cyanophenyl)amino]-4-chlorobenzoate

The desired product was prepared by substituting 3,4-diaminobenzonitrile for methyl 3,4-diaminobenzoate in Example 1A. MS (DCI) m/e 302 (M+H)⁺, 319 (M+NH₄)⁺; $^1$H NMR (500 MHz, DMSO-d₆) δ 8.99 (s, 1H), 7.89 (d, J=8.8 Hz, 1H), 7.26 (d, J=8.1 Hz, 1H), 7.13 (d, J=1.9 Hz, 1H), 7.00 (dd, J=7.8, 1.9 Hz, 1H), 6.83 (dd, J=8.7, 2.0 Hz, 1H), 6.67 (d, J=1.9 Hz, 1H), 5.47 (s, 2H), 3.86 (s, 3H).

EXAMPLE 4B 3-chloro-11-oxo-10,11-dihydro-5H-dibenzo[b,e][1,4]diazepine-8-carbonitrile The desired product was prepared by substituting Example 4A for Example 1A in Example 1B. MS (DCI) m/e 290 (M+H)⁺, 307 (M+NH₄)⁺; $^1$H NMR (400 MHz, DMSO-d₆) δ 10.06 (s, 1H), 8.61 (s, 1H), 7.73 (d, J=8.6 Hz, 1H), 7.40 (dd, J=8.6, 1.8 Hz, 1H), 7.30 (d, J=1.8 Hz, 1H), 7.07 (d, J=2.4 Hz, 1H), 7.06 (d, J=3.6 Hz, 1H), 6.98 (dd, J=8.3, 1.9 Hz, 1H).

EXAMPLE 5

3-chloro-8-(trifluoromethyl)-5,10-dihydro-11H-dibenzo[b,e][1,4]diazepin-11-one

EXAMPLE 5A methyl 4-chloro-2-{[2-nitro-4-(trifluoromethyl)phenyl]amino}benzoate The desired product was prepared by substituting 2-nitro-4-(trifluoromethyl)aniline for methyl 3,4-diaminobenzoate in Example 1A. MS (DCI) m/e 375 (M+H)⁺, 392 (M+NH₄)⁺; $^1$H NMR (300 MHz, DMSO-d₆) δ 11.05 (s, 1H), 8.42 (d, J=2.0 Hz, 1H), 8.00 (d, J=8.8 Hz, 1H), 7.93 (dd, J=9.1, 2.3 Hz, 1H), 7.75 (d, J=8.8 Hz, 1H), 7.67 (d, J=2.0 Hz, 1H), 7.30 (dd, J=8.5, 2.1 Hz, 1H), 5.47 (s, 2H), 3.88 (s, 3H).

EXAMPLE 5B

2-{[2-amino-4-(trifluoromethyl)phenyl]amino}-4-chlorobenzoic acid

The desired product was prepared by substituting Example 5A for Example 2A in Example 2B. MS (DCI) m/e 331 (M+H)⁺; $^1$H NMR (500 MHz, DMSO-d₆) δ 9.29 (s, 1H), 7.89 (d, J=8.4 Hz, 1H), 7.32 (d, J=8.1 Hz, 1H), 7.24 (d, J=1.6 Hz, 1H), 7.00 (dd, J=8.1, 1.3 Hz, 1H), 6.78 (dd, J=8.7, 2.1 Hz, 1H), 6.62 (d, J=1.9 Hz, 1H).

EXAMPLE 5C 3-chloro-8-(trifluoromethyl)-5,10-dihydro-11H-dibenzo[b,e][1,4]diazepin-11-one A mixture of Example 5B (0.3 g, 0.91 mmol) and TsOH.H₂O (0.35 g, 1.82 mmol) in toluene (50 mL) was heated to reflux for 20 hours using a Dean-Stark trap to remove water. The reaction was cooled to room temperature, concentrated under vacuum, diluted with ethyl acetate, washed with saturated NaHCO₃ and brine, dried (MgSO₄), filtered, and concentrated under vacuum. The residue was purified by flash column chromatography on silica gel with 7:3 hexanes/ethyl acetate to provide 0.21 g (81%) of the desired product. MS (DCI) m/e 313 (M+H)⁺, 330 (M+NH₄)⁺; $^1$H NMR (300 MHz, DMSO-d₆) δ 10.08 (s, 1H), 8.48 (s, 1H), 7.72 (d, J=8.4 Hz, 1H), 7.29-7.35 (m, 2H), 7.12 (d, J=8.1 Hz, 1H), 7.08 (d, J=2.0 Hz, 1H), 6.97 (dd, J=8.5, 2.1 Hz, 1H).

EXAMPLE 6 methyl (3-chloro-11-oxo-10,11-dihydro-5H-dibenzo[b,e][1,4]diazepin-8-yl)acetate

EXAMPLE 6A methyl (4-amino-3-nitrophenyl)acetate

Concentrated nitric acid (10 mL, >69% pure) was added to acetic anhydride (100 mL) cooled to −10° C. The solution was treated portionwise with N-[4-(cyanomethyl)phenyl]acetamide (5.0 g, 28.7 mmol) at a rate which maintained an internal temperature below −5° C. The solution was stirred for 1 hour while warming to room temperature. The solution was poured into an ice/water mixture and extracted several times with ethyl acetate. The combined extracts were washed with 10% $Na_2CO_3$ and brine, dried ($MgSO_4$), filtered, and concentrated under vacuum. The residue was purified by flash column chromatography on silica gel with 1:1 hexanes/ethyl acetate to provide 4.82 g (77%) of N-[4-(cyanomethyl)-2-nitrophenyl]acetamide.

A mixture of N-[4-(cyanomethyl)-2-nitrophenyl]acetamide (4.8 g), concentrated HCl (100 mL), and water (300 mL) was heated to reflux for two days, cooled to room temperature, and concentrated to near dryness under vacuum. The concentrate was treated with methanol (300 mL) and concentrated $H_2SO_4$ (30 mL), heated to reflux overnight, and concentrated under vacuum to remove the methanol. The residue was partitioned between ethyl acetate and water and the organic layers were combined, washed with saturated $NaHCO_3$ and brine, dried ($MgSO_4$), and concentrated under vacuum. The residue was purified by flash column chromatography on silica gel with 7:3 hexanes/ethyl acetate to provide 4.1 g (89%) of the desired product. MS (DCI) m/e 211 $(M+H)^+$, 228 $(M+NH_4)^+$; $^1$H NMR (300 MHz, DMSO-$d_6$) δ 7.88 (d, J=2 Hz, 1H), 7.39 (s, 2H), 7.30 (dd, J=8.5, 2 Hz, 1H), 6.97 (d, J=8.4 Hz, 1H), 3.61 (s, 3H).

EXAMPLE 6B methyl 4-chloro-2-{[4-(2-methoxy-2-oxoethyl)-2-nitrophenyl]amino}benzoate The desired product was prepared by substituting methyl (4-amino-3-nitrophenyl)acetate for 4-bromo-2-nitroaniline in Example 2A. MS (DCI) m/e 379 $(M+H)^+$, 396 $(M+NH_4)^+$; $^1$H NMR (300 MHz, DMSO-$d_6$) δ 10.84 (s, 1H), 8.10 (d, J=2.1 Hz, 1H), 7.96 (d, J=8.5, Hz, 1H), 7.67 (d, J=8.5 Hz, 1H), 7.60 (dd, J=8.8, 2.0 Hz, 1H), 7.46 (d, J=2.1 Hz, 1H), 7.11 (dd, J=8.5, 2 Hz, 1H), 3.69 (s, 3H), 3.81 (s, 2H), 3.65 (s, 3H).

EXAMPLE 6C methyl 2-{[2-amino-4-(2-methoxy-2-oxoethyl)phenyl]amino}-4-chlorobenzoate A mixture of Example 6B (0.73 g, 1.93 mmol), 5% Pt/C, methanol (15 mL) and ethyl acetate (15 mL) was equipped with a balloon of hydrogen gas and stirred at room temperature. After uptake of the hydrogen was complete, the solution was filtered through diatomaceous earth (Celite®). The filtrate was concentrated under vacuum and the residue was purified by flash column chromatography on silica gel with 7:3 hexanes/ethyl acetate to provide 0.64 g (95%) of the desired product. MS (DCI) m/e 349 $(M+H)^+$, 366 $(M+NH_4)^+$; $^1$H NMR (500 MHz, DMSO-$d_6$) δ 8.81 (s, 1H), 7.85 (d, J=8.5 Hz, 1H), 6.96 (d, J=8.1 Hz, 1H), 6.69-6.72 (m, 2H), 6.50 (dd, J=7.8, 1.8 Hz, 1H), 6.40 (d, J=2.1 Hz, 1H), 5.00 (s, 2H), 3.86 (s, 3H), 3.63 (s, 3H), 3.55 (s, 2H).

EXAMPLE 6D methyl (3-chloro-11-oxo-10,11-dihydro-5H-dibenzo[b,e][1,4]diazepin-8-yl)acetate The desired product was prepared by substituting Example 6C for Example 5B in Example 5C. MS (DCI) m/e 317 $(M+H)^+$, 334 $(M+NH_4)^+$; $^1$H NMR (500 MHz, DMSO-$d_6$) δ 9.88 (s, 1H), 8.03 (s, 1H), 7.68 (d, J=8.7 Hz, 1H), 7.06 (d, J=2.2 Hz, 1H), 6.91-6.93 (m, 2H), 6.86-6.87 (m, 2H), 3.60 (s, 3H), 3.54 (s, 2H).

EXAMPLE 7

8-amino-3-chloro-5,10-dihydro-11H-dibenzo[b,e][1,4]diazepin-11-one

EXAMPLE 7A methyl 2-[(2-amino-4-nitrophenyl)amino]-4-chlorobenzoate

The desired product was prepared by substituting 4-nitro-1,2-benzenediamine for methyl 3,4-diaminobenzoate in Example 1A.

EXAMPLE 7B methyl 4-chloro-2-[(2,4-diaminophenyl)amino]benzoate

The desired product was prepared by substituting Example 7A for Example 6B in Example 6C. MS (DCI) m/e 292 $(M+H)^+$; $^1$H NMR (300 MHz, DMSO-$d_6$) δ 8.58 (s, 1H), 7.80 (d, J=8.8 Hz, 1H), 6.63 (d, J=2.1 Hz, 1H), 6.60 (d, J=2.4 Hz, 1H), 6.34 (d, J=2.1 Hz, 1H), 6.03 (d, J=2.2 Hz, 1H), 5.89 (dd, J=8.1, 2.5 Hz, 1H), 4.84 (s, 2H), 4.63 (s, 2H), 3.84 (s, 3H).

EXAMPLE 7C 8-amino-3-chloro-5,10-dihydro-11H-dibenzo[b,e][1,4]diazepin-11-one The desired product was prepared by substituting Example 7B for Example 5B in Example 5C. MS (DCI) m/e 259 (M)+, 277 $(M+NH_4)^+$; $^1$H NMR (500 MHz, DMSO-$d_6$) δ 9.69 (s, 1H), 7.64 (d, J=8.4 Hz, 1H), 7.56 (s, 1H), 7.00 (d, J=1.9 Hz, 1H), 6.85 (dd, J=8.4, 1.9 Hz, 1H), 6.65 (d, J=8.1 Hz, 1H), 6.20-6.21 (m, 2H), 4.81 (s, 2H).

EXAMPLE 8

3-chloro-8-hydroxy-5,10-dihydro-11H-dibenzo[b,e][1,4]diazepin-11-one

EXAMPLE 8A methyl 2-{[4-(benzyloxy)-2-nitrophenyl]amino}-4-chlorobenzoate

The desired product was prepared by substituting 4-(benzyloxy)-2-nitroaniline for 4-bromo-2-nitroaniline in Example 2A. MS (DCI) m/e 413 $(M+H)^+$, 430 $(M+NH_4)^+$; $^1$H NMR (300 MHz, DMSO-$d_6$) δ 10.53 (s, 1H), 7.93 (d, J=8.4 Hz, 1H), 7.73 (d, J=3.1 Hz, 1H), 7.67 (d, J=9.2 Hz, 1H), 7.36-7.51 (m, 6H), 7.23 (d, J=2.0 Hz, 1H), 7.00 (dd, J=8.5, 2.0 Hz, 1H), 5.21 (s, 2H), 3.89 (s, 3H).

EXAMPLE 8B methyl 2-{[2-amino-4-(benzyloxy)phenyl]amino}-4-chlorobenzoate

The desired product was prepared by substituting Example 8A for Example 6B in Example 6C. MS (DCI) m/e 383 (M+H)$^+$; $^1$H NMR (500 MHz, DMSO-$d_6$) δ 8.70 (s, 1H), 7.83 (d, J=8.8 Hz, 1H), 7.33-7.46 (m, 5H), 6.90 (d, J=8.4 Hz, 1H), 6.67 (dd, J=8.8, 2.2 Hz, 1H), 6.47 (d, J=2.8 Hz, 1H), 6.33 (d, J=2.2 Hz, 1H), 6.27 (dd, J=8.5, 2.8 Hz, 1H), 5.04 (s, 2H), 5.01 (s, 2H), 3.85 (s, 3H).

EXAMPLE 8C 3-chloro-8-hydroxy-5,10-dihydro-11H-dibenzo[b,e][1,4]diazepin-11-one The desired product was prepared by substituting Example 8B for Example 5B in Example 5C. MS (DCI) m/e 260 (M)+, 278 (M+NH$_4$)$^+$; $^1$H NMR (500 MHz, DMSO-$d_6$) δ 9.79 (s, 1H), 9.15 (s, 1H), 7.56 (s, 1H), 7.71 (s, 1H), 7.65 (d, J=8.4 Hz, 1H), 7.03 (d, J=2.2 Hz, 1H), 6.87 (dd, J=8.4, 2.2 Hz, 1H), 6.77 (d, J=8.7 Hz, 1H), 6.44 (d, J=2.5 Hz, 1H), 6.38 (dd, J=8.4, 2.5 Hz, 1H).

EXAMPLE 9

3-bromo-5,10-dihydro-11H-dibenzo[b,e][1,4]diazepin-11-one

A mixture of 4-bromo-2-chlorobenzoic acid (2.35 g, 10 mmol), 1,2-benzenediamine (1.08 g, 10 mmol) and copper (0.63 g, 10 mmol) in chlorobenzene (150 mL) was heated to reflux for 48 hours and filtered. The filter cake was washed with ethyl acetate several times. The combined filtrates were concentrated under vacuum and the residue was purified by flash column chromatography on silica gel with 8:2 hexanes/ethyl acetate to provide 1.20 g (22%) of the desired product. MS (DCI) m/e 289 (M+H)$^+$, 307 (M+NH$_4$)$^+$; $^1$H NMR (500 MHz, DMSO-$d_6$) δ 9.90 (s, 1H), 8.02 (s, 1H), 7.62 (d, J=8.4 Hz, 1H), 7.24 (d, J=1.8 Hz, 1H), 7.06 (dd, J=8.4, 1.8 Hz, 1H), 6.92-6.95 (m, 5H).

EXAMPLE 10

3-(4-hydroxy-3-methoxyphenyl)-5,10-dihydro-11H-dibenzo[b,e][1,4]diazepin-11-one

A mixture of Example 9 (116 mg, 0.4 mmol), 2-methoxy-4-(4,4,5,5-tetramethyl-1,3,2-dioxaborolan-2-yl)phenol (150 mg, 0.6 mmol), Pd(PPh$_3$)$_4$ (23 mg, 0.02 mmol), and CsF (121 mg, 0.8 mmol) in DME (20 mL) and methanol (10 mL) was heated to reflux for 16 hours, cooled to room temperature, and partitioned between ethyl acetate and water. The organic layer was washed with brine, dried (MgSO$_4$), filtered, and concentrated under vacuum. The residue was purified by flash column chromatography on silica gel with 1:1 hexanes/ethyl acetate to provide 0.108 g (81%) of the desired product. MS (DCI) m/e 333 (M+H)$^+$, 350 (M+NH$_4$)$^+$; $^1$H NMR (500 MHz, DMSO-$d_6$) δ 9.90 (s, 1H), 8.02 (s, 1H), 7.62 (d, J=8.4 Hz, 1H), 7.24 (d, J=1.8 Hz, 1H), 7.15-7.18 (m, 2H), 7.08 (dd, J=8.1, 1.5 Hz, 1H), 6.97-7.02 (m, 5H), 3.86 (s, 3H).

EXAMPLE 11

3-(11-oxo-10,11-dihydro-5H-dibenzo[b,e][1,4]diazepin-3-yl)benzonitrile

The desired product was prepared by substituting 3-cyanophenylboronic acid for 2-methoxy-4-(4,4,5,5-tetramethyl-1,3,2-dioxaborolan-2-yl)phenol in Example 10. MS (DCI) m/e 312 (M+H)$^+$, 329 (M+NH$_4$)$^+$; $^1$H NMR (500 MHz, DMSO-$d_6$) δ 9.86 (s, 1H), 8.10 (s, 1H), 7.98 (d, J=8.4 Hz, 1H), 7.94 (s, 1H), 7.88 (d, J=7.8 Hz, 1H), 7.79 (d, J=8.1 Hz, 1H), 7.71 (t, J=7.8 Hz, 1H), 7.34 (d, J=1.9 Hz, 1H), 7.26 (dd, J=8.1, 1.9 Hz, 1H), 6.90-7.02 (m, 4H).

EXAMPLE 12 methyl 3-(4-hydroxy-3-methoxyphenyl)-11-oxo-10,11-dihydro-5H-dibenzo[b,e][1,4]diazepine-8-carboxylate A mixture of Example 1B (92 mg, 0.3 mmol), 2-methoxy-4-(4,4,5,5-tetramethyl-1,3,2-dioxaborolan-2-yl)phenol (112 mg, 0.45 mmol), Pd(PCy$_3$)$_2$Cl$_2$ (11 mg, 0.015 mmol), and CsF (144 mg, 0.9 mmol) in DME (20 mL) and methanol (10 mL) was heated to reflux for 16 hours, cooled to room temperature, and partitioned between ethyl acetate and water. The organic layer was washed with brine, dried (MgSO$_4$), filtered, and concentrated under vacuum. The residue was purified by flash column chromatography on silica gel with 1:1 hexanes/ethyl acetate to provide 95 mg (81%) of the desired product. MS (DCI) m/e 391 (M+H)$^+$; $^1$H NMR (500 MHz, DMSO-$d_6$) δ 9.88 (s, 1H), 9.26 (s, 1H), 8.36 (s, 1H), 7.75 (d, J=8.1 Hz, 1H), 7.60 (d, J=2.2 Hz, 1H), 7.55 (dd, J=8.1, 1.9 Hz, 1H), 7.24 (d, J=2.1 Hz, 1H), 7.17-7.19 (m, 2H), 7.06-7.09 (m, 2H), 6.87 (d, J=8.1 Hz, 1H), 3.86 (s, 3H), 3.80 (s, 3H).

EXAMPLE 13

3-(4-hydroxy-3-methoxyphenyl)-11-oxo-10,11-dihydro-5H-dibenzo[b,e][1,4]diazepine-8-carboxylic acid A mixture of Example 12 (80 mg, 0.2 mmol) and LiOH (24 mL, 1 mmol) in methanol (10 mL), THF (10 mL), and water (10 mL) was heated to reflux overnight, cooled to room temperature, and adjusted to pH <5 with concentrated HCl. The solid was collected by filtration to provide 55 mg of the desired product. MS (DCI) m/e 377 (M+H)$^+$; $^1$H NMR (300 MHz, DMSO-$d_6$) δ 12.65 (s, 1H), 9.89 (s, 1H), 9.28 (s, 1H), 8.33 (s, 1H), 7.75 (d, J=8.1 Hz, 1H), 7.57 (d, J=1.7 Hz, 1H), 7.52 (dd, J=8.1, 1.6 Hz, 1H), 7.24 (d, J=1.7 Hz, 1H), 7.17-7.20 (m, 2H), 7.04-7.10 (m, 2H), 6.88 (d, J=8.1 Hz, 1H), 3.86 (s, 3H).

EXAMPLE 14

3-(4-hydroxy-3-methoxyphenyl)-11-oxoN[3-(1-pyrrolidinyl)propyl]-10,11-dihydro-5H-dibenzo[b,e][1,4]diazepine-8-carboxamide A mixture of Example 13 (55 mg, 0.15 mmol), 3-pyrrolidin-1-ylpropylamine (58 mg, 0.45 mmol), EDC (143 mg, 0.75 mmol), HOBt (101 mg, 75 mmol), and triethylamine hydrochloride (103 mg, 0.75 mmol) in DMF (5 mL) was heated to 65° C. for 16 hours, cooled to room temperature, poured into water, and extracted with 3:1 dichloromethane/isopropyl alcohol. The combined extracts were washed with brine, dried (MgSO$_4$), filtered, and concentrated under vacuum. The residue was purified by HPLC to provide 45 mg of the desired product as the trifluoroacetate salt. MS (DCI) m/e 487 (M+H)$^+$; $^1$H NMR (500 MHz, DMSO-d$_6$) δ 9.82 (s, 1H), 8.36 (t, J=5.6 Hz, 1H), 8.21 (s, 1H), 7.74 (d, J=8.1 Hz, 1H), 7.46 (d, J=1.8 Hz, 1H), 7.41 (dd, J=8.1, 1.9 Hz, 1H), 7.26 (d, J=1.6 Hz, 1H), 7.18 (d, J=2.2 Hz, 1H), 7.16 (d, J=1.6 Hz, 1H), 7.09 (dd, J=8.4, 2.2 Hz, 1H), 7.04 (d, J=8.4 Hz, 1H), 6.88 (d, J=8.1 Hz, 1H), 3.86 (s, 3H), 3.25-3.29 (m, 2H), 2.55 (br m, 6H), 1.68-1.72 (m, 6H).

EXAMPLE 15

N-[3-(dimethylamino)propyl]-3-(4-hydroxy-3-methoxyphenyl)-11-oxo-10,11-dihydro-5H-dibenzo[b,e][1,4]diazepine-8-carboxamide The desired product was prepared by substituting N,N-dimethyl-1,3-propanediamine for 3-pyrrolidin-1-ylpropylamine in Example 14. MS (DCI) m/e 461 (M+H)$^+$; $^1$H NMR (500 MHz, DMSO-d$_6$) (TFA salt) δ 9.82 (s, 1H), 9.24 (br s, 1H), 8.26 (t, J=5.6 Hz, 1H), 8.15 (s, 1H), 7.73 (d, J=8.2 Hz, 1H), 7.45 (d, J=1.9 Hz, 1H), 7.41 (dd, J=8.1, 1.9 Hz, 1H), 7.23 (d, J=1.6 Hz, 1H), 7.18 (d, J=2.1 Hz, 1H), 7.16 (d, J=1.9 Hz, 1H), 7.07 (dd, J=8.1, 2.1 Hz, 1H), 7.02 (d, J=8.1 Hz, 1H), 6.87 (d, J=8.5 Hz, 1H), 3.86 (s, 3H), 3.21-3.25 (m, 2H), 2.25 (t, J=7.2 Hz, 2H), 2.13 (s, 6H), 1.62 (m, 2H).

EXAMPLE 16

3-(4-hydroxy-3-methoxyphenyl)N[3-(4-morpholinyl)propyl]-11-oxo-10,11-dihydro-5H-dibenzo[b,e][1,4]diazepine-8-carboxamide The desired product was prepared by substituting 3-(4-morpholinyl)propylamine for 3-pyrrolidin-1-ylpropylamine in Example 14. MS (DCI) m/e 502 (M+H)$^+$; $^1$H NMR (500 MHz, DMSO-d$_6$) (TFA salt) δ 9.84 (s, 1H), 9.65 (br s, 1H), 9.25 (br s, 1H), 8.41 (t, J=5.7 Hz, 1H), 8.21 (s, 1H), 7.73 (d, J=8.1 Hz, 1H), 7.47 (d, J=2.1 Hz, 1H), 7.44 (dd, J=8.1, 2.1 Hz, 1H), 7.24 (d, J=1.6 Hz, 1H), 7.17-7.19 (m, 2H), 7.08 (dd, J=8.1, 1.9 Hz, 1H), 7.04 (d, J=8.1 Hz, 1H), 6.87 (d, J=8.1 Hz, 1H), 3.97-4.00 (m, 2H), 3.90 (s, 3H), 3.61-3.66 (m, 2H), 3.42-3.48 (m, 4H), 3.05-3.14 (m, 4H), 1.86-1.92 (m, 2H).

EXAMPLE 17

3-(4-hydroxy-3-methoxyphenyl)-11-oxoN[3-(2-oxo-1-pyrrolidinyl)propyl]-10,11-dihydro-5H-dibenzo[b,e][1,4]diazepine-8-carboxamide The desired product was prepared by substituting 1-(3-aminopropyl)-2-pyrrolidinone for 3-pyrrolidin-1-ylpropylamine in Example 14. MS (DCI) m/e 501 (M+H)$^+$; $^1$H NMR (500 MHz, DMSO-d$_6$) (TFA salt) δ 9.84 (s, 1H), 9.65 (br s, 1H), 9.29 (br s, 1H), 8.24 (t, J=5.2 Hz, 1H), 8.18 (s, 1H), 7.74 (d, J=8.2 Hz, 1H), 7.42-7.47 (m, 2H), 7.24 (s, 1H), 7.17 (m, 1H), 7.09 (dd, J=8.3, 1.8 Hz, 1H), 7.43 (d, J=8.0 Hz, 1H), 6.80 (d, J=7.9 Hz, 1H), 3.86 (s, 3H), 3.17-3.23 (m, 6H), 2.20-2.24 (m, 2H), 1.89-1.94 (m, 2H), 1.63-1.71 (m, 2H).

EXAMPLE 18

N-(2-hydroxyethyl)-3-(4-hydroxy-3-methoxyphenyl)-11-oxo-10,11-dihydro-5H-dibenzo[b,e][1,4]diazepine-8-carboxamide The desired product was prepared by substituting 2-aminoethanol for 3-pyrrolidin-1-ylpropylamine in Example 14. MS (DCI) m/e 420 (M+H)$^+$; $^1$H NMR (500 MHz, DMSO-d$_6$) δ 9.82 (s, 1H), 9.25 (s, 1H), 8.16-8.18 (m, 2H), 7.43 (d, J=8.4 Hz, 1H), 7.47 (d, J=1.9 Hz, 1H), 7.45 (dd, J=8.4, 2.1 Hz, 1H), 7.23 (d, J=1.5 Hz, 1H), 7.16-7.18 (m, 2H), 7.08 (dd, J=8.3, 1.8 Hz, 1H), 7.01 (d, J=8.1 Hz, 1H), 6.87 (d, J=8.5 Hz, 1H), 4.67 (t, J=5.6 Hz, 1H), 3.86 (s, 3H), 3.47-3.50 (m, 2H), 3.27-3.30 (m, 2H).

EXAMPLE 19

N-(2,3-dihydroxypropyl)-3-(4-hydroxy-3-methoxyphenyl)-11-oxo-10,11-dihydro-5H-dibenzo[b,e][1,4]diazepine-8-carboxamide The desired product was prepared by substituting 3-amino-1,2-propanediol for 3-pyrrolidin-1-ylpropylamine in Example 14. MS (DCI) m/e 450 (M+H)$^+$; $^1$H NMR (500 MHz, DMSO-d$_6$) δ 9.82 (s, 1H), 9.25 (s, 1H), 8.17 (s, 1H), 8.12 (t, J=5.6 Hz, 1H), 7.43 (d, J=8.1 Hz, 1H), 7.44-7.48 (m, 2H), 7.24 (d, J=1.6 Hz, 1H), 7.16-7.18 (m, 2H), 7.08 (dd, J=8.1, 1.9 Hz, 1H), 7.02 (d, J=8.1 Hz, 1H), 6.87 (d, J=8.1 Hz, 1H), 4.75 (t, J=2.5 Hz, 1H), 4.53 (t, J=5.6 Hz, 1H), 3.86 (s, 3H), 3.60 (m, 1H), 3.32-3.34 (m, 2H), 3.14-3.20 (m, 2H).

EXAMPLE 20

N-[2-(acetylamino)ethyl]-3-(4-hydroxy-3-methoxyphenyl)-11-oxo-10,11-dihydro-5H-dibenzo[b,e][1,4]diazepine-8-carboxamide The desired product was prepared by substituting N-(2-aminoethyl)acetamide for 3-pyrrolidin-1-ylpropylamine in Example 14. MS (DCI) m/e 461 (M+H)$^+$; $^1$H NMR (500 MHz, DMSO-d$_6$) δ 9.84 (s, 1H), 9.25 (br s, 1H), 8.28 (t, J=5.5 Hz, 1H), 8.17 (s, 1H), 7.92 (t, J=5.2 Hz, 1H), 7.23 (d, J=8.3 Hz, 1H), 7.47 (d, J=1.8 Hz, 1H), 7.42, (dd, J=8.3, 1.9 Hz, 1H), 7.24 (d, J=1.9 Hz, 1H), 7.16-7.18 (m, 2H), 7.08 (dd, J=8.3, 2.1 Hz, 1H), 7.02 (d, J=8.3 Hz, 1H), 6.87 (d, J=8.0 Hz, 1H), 3.86 (s, 3H), 3.24-3.27 (m, 2H), 3.15-3.20 (m, 2H), 1.80 (s, 3H).

EXAMPLE 21

3-(4-hydroxy-3-methoxyphenyl)-8-[(3-hydroxy-1-pyrrolidinyl)carbonyl]-5,10-dihydro-11H-dibenzo[b,e][1,4]diazepin-11-one The desired product was prepared by substituting 3-pyrrolidinol for 3-pyrrolidin-1-ylpropylamine in Example 14. MS (DCI) m/e 446 (M+H)$^+$; $^1$H NMR (500 MHz, DMSO-d$_6$) 6 9.83 (s, 1H), 9.25 (br s, 1H), 8.12 (s, 1H), 7.74 (d, J=8.3 Hz, 1H), 7.24 (d, J=1.5 Hz, 1H), 7.13-7.18 (m, 4H), 7.08 (dd, J=8.3, 2.2 Hz, 1H), 7.01 (d, J=8.3 Hz, 1H), 6.87 (d, J=8.3 Hz, 1H), 4.27 (m, 1H), 3.86 (s, 3H), 3.40-3.61-3.27 (m, 4H), 1.79 (m, 2H).

EXAMPLE 22

3-(4-hydroxy-3-methoxyphenyl)-8-{[(2S)-2-(hydroxymethyl)-1-pyrrolidinyl]carbonyl}-5,10-dihydro-11H-dibenzo[b,e][1,4]diazepin-11-one The desired product was prepared by substituting (2S)-2-pyrrolidinylmethanol for 3-pyrrolidin-1-ylpropylamine in Example 14. MS (DCI) m/e 460 (M+H)$^+$; $^1$H NMR (500 MHz, DMSO-d$_6$) δ 9.80 (s, 1H), 9.25 (br s, 1H), 8.10 (s, 1H), 7.73 (d, J=8.3 Hz, 1H), 7.24 (d, J=1.6 Hz, 1H), 7.18 (d, J=2.1 Hz, 1H), 7.07 7.16 (m, 3H), 7.01 (d, J=8.3 Hz, 1H), 6.87 (d, J=8.0 Hz, 1H), 3.34-3.44 (m, 5H), 3.86 (s, 3H), 1.84-1.92 (m, 4H).

EXAMPLE 23

3-(4-hydroxy-3-methoxyphenyl)-8-{[2-(hydroxymethyl)-1-piperidinyl]carbonyl}-5,10-dihydro-11H-dibenzo[b,e][1,4]diazepin-11-one The desired product was prepared by substituting 2-piperidinylmethanol for 3-pyrrolidin-1-ylpropylamine in Example 14. MS (DCI) m/e 474 (M+H)$^+$; $^1$H NMR (500 MHz, DMSO-d$_6$) δ 9.84 (s, 1H), 9.29 (br s, 1H), 8.08 (s, 1H), 7.72 (d, J=8.3 Hz, 1H), 7.25 (d, J=1.5 Hz, 1H), 7.16-7.21 (m, 2H), 7.09 (m, 1H), 6.98-7.03 (m, 2H), 6.88 (d, J=8.0 Hz, 1H), 4.35 (m, 1H), 3.86 (s, 3H), 3.28-3.34 (m, 4H), 1.48-1.80 (m, 6H).

EXAMPLE 24 ethyl 1-{[3-(4-hydroxy-3-methoxyphenyl)-11-oxo-10,11-dihydro-5H-dibenzo[b,e][1,4]diazepin-8-yl]carbonyl}-2-piperidinecarboxylate The desired product was prepared by substituting ethyl 2-piperidinecarboxylate for 3-pyrrolidin-1-ylpropylamine in Example 14. MS (DCI) m/e 516 (M+H)$^+$; $^1$H NMR (500 MHz, DMSO-d$_6$) δ 9.89 (s, 1H), 9.28 (s, 1H), 8.14 (s, 1H), 7.73-7.74 (d, J=8.2 Hz, 1H), 7.24 (d, J=1.2 Hz, 1H), 7.17-7.19 (m, 2H), 7.07-7.09 (dd, J=8.2, 2.1 Hz, 1H), 6.95-7.05 (m, 3H), 6.88 (d, J=8.2 Hz, 1H), 4.16 (br s, 2H), 3.86 (s, 3H), 3.61 (m, 1H), 1.29-1.79 (m, 11H).

EXAMPLE 25 ethyl 1-{[3-(4-hydroxy-3-methoxyphenyl)-11-oxo-10,11-dihydro-5H-dibenzo[b,e][1,4]diazepin-8-yl]carbonyl}-3-piperidinecarboxylate The desired product was prepared by substituting ethyl 3-piperidinecarboxylate for 3-pyrrolidin-1-ylpropylamine in Example 14. MS (DCI) m/e 516 (M+H)$^+$; $^1$H NMR (500 MHz, DMSO-d$_6$,) δ 9.88 (s, 1H), 9.28 (s, 1H), 8.12 (s, 1H), 7.73-7.74 (d, J=8.2 Hz, 1H), 7.24 (d, J=1.5 Hz, 1H), 7.16-7.18 (m, 2H), 7.08-7.09 (dd, J=8.2, 2.1 Hz, 1H), 6.99-7.04 (b, 3H), 6.88 (d, J=8.2 Hz, 1H), 4.06 (b, 2H), 3.86 (s, 3H), 3.06-3.11 (m, 1H), 2.50-2.54 (m, 2H), 1.06-1.96 (m, 11H).

EXAMPLE 26 ethyl 1-{[3-(4-hydroxy-3-methoxyphenyl)-11-oxo-10,11-dihydro-5H-dibenzo[b,e][1,4]diazepin-8-yl]carbonyl}-4-piperidinecarboxylate The desired product was prepared by substituting ethyl 4-piperidinecarboxylate for 3-pyrrolidin-1-ylpropylamine in Example 14. MS (DCI) m/e 516 (M+H)$^+$; $^1$H NMR (DMSO-d$_6$, 500 MHz) δ 9.86 (s, 1H), 9.28 (br s, 1H), 8.13 (s, 1H), 7.74 (d, J=8.2 Hz, 1H), 7.24 (d, J=1.5 Hz, 1H), 7.17-7.19 (m, 2H), 7.08 (dd, J=8.2, 1.8 Hz, 1H), 6.99-7.04 (m, 3H), 6.88 (d, J=8.2 Hz, 1H), 4.08 (q, J=7.0 Hz, 2H), 3.71 (m, 2H), 3.86 (s, 3H), 2.98 (m, 2H), 2.63 (m, 1H), 1.85 (m, 2H), 1.47-1.55 (m, 2H), 1.19 (t, J=7.0 Hz, 3H).

EXAMPLE 27

3-(4-hydroxy-3-methoxyphenyl)-8-[(3-hydroxy-1-piperidinyl)carbonyl]-5,10-dihydro-11H-dibenzo[b,e][1,4]diazepin-11-one The desired product was prepared by substituting 3-piperidinol for 3-pyrrolidin-1-ylpropylamine in Example 14. MS (DCI) m/e 460 (M+H)$^+$; $^1$H NMR (500 MHz, DMSO-d$_6$) δ 9.85 (s, 1H), 9.28 (s, 1H), 8.11 (s, 1H), 7.73 (d, J=8.2 Hz, 1H), 7.24 (d, J=1.5 Hz, 1H), 7.17-7.19 (m, 2H), 7.08 (dd, J=8.2, 1.5 Hz, 1H), 6.98-7.04 (m, 3H), 6.88 (d, J=8.2 Hz, 1H), 3.86 (s, 3H), 3.48 (m, 1H), 2.98 (m, 2H), 1.38-1.84 (m, 6H).

EXAMPLE 28

3-(4-hydroxy-3-methoxyphenyl)-11-oxoN(3-pyridinylmethyl)-10,11-dihydro-5H-dibenzo[b,e][1,4]diazepine-8-carboxamide The desired product was prepared by substituting 3-pyridinylmethylamine for 3-pyrrolidin-1-ylpropylamine in Example 14. MS (DCI) m/e 467 (M+H)$^+$; $^1$H NMR (500 MHz, DMSO-d$_6$) (TFA salt) δ 9.88 (s, 1H), 8.99 (t, J=5.8 Hz, 1H), 8.73 (s, 1H), 8.67 (d, J=4.9 Hz, 1H), 8.25 (s, 1H), 8.15 (d, J=7.9 Hz, 1H), 7.73-7.75 (m, 2H), 7.51 (s, 1H), 7.49 (d, J=1.8 Hz, 1H), 7.25 (d, J=1.5 Hz, 1H), 7.17-7.19 (m, 2H), 7.09 (dd, J=8.2, 2.1 Hz, 1H), 7.07 (d, J=8.5 Hz, 1H), 6.88 (d, J=7.9 Hz, 1H), 4.55 (d, J=5.5 Hz, 2H), 3.86 (s, 3H).

EXAMPLE 29

3-(4-hydroxy-3-methoxyphenyl)N[4-(methylsulfonyl)benzyl]-11-oxo-10,11-dihydro-5H-dibenzo[b,e][1,4]diazepine-8-carboxamide The desired product was prepared by substituting 1-[4-(methylsulfonyl)phenyl]methanamine for 3-pyrrolidin-1-ylpropylamine in Example 14. MS (DCI) m/e 545 (M+H)$^+$; $^1$H NMR (500 MHz, DMSO-d$_6$) δ 9.84 (s, 1H), 9.25 (s, 1H), 8.94 (t, J=5.9 Hz, 1H), 8.20 (s, 1H), 7.88 (d, J=8.1 Hz, 1H), 7.74 (d, J=8.4 Hz, 1H), 7.55 (d, J=8.4 Hz, 1H), 7.50-7.52 (m, 2H), 7.24 (d, J=1.6 Hz, 1H), 7.18 (m, 2H), 7.09 (dd, J=8.1, 2.2 Hz, 1H), 7.05 (d, J=8.1 Hz, 1H), 6.88 (d, J=8.1 Hz, 1H), 4.53 (d, J=5.9 Hz, 2H), 3.86 (s, 3H), 3.18 (s, 3H).

EXAMPLE 30

N-(2-fluorobenzyl)-3-(4-hydroxy-3-methoxyphenyl)-11-oxo-10,11-dihydro-5H-dibenzo[b,e][1,4]diazepine-8-carboxamide The desired product was prepared by substituting 2-fluorobenzylamine for 3-pyrrolidin-1-ylpropylamine in Example 14. MS (DCI) m/e 484 (M+H)$^+$; $^1$H NMR (500 MHz, DMSO-d$_6$) δ 9.83 (s, 1H), 9.25 (s, 1H), 8.78 (t, J=5.8 Hz, 1H), 8.19 (s, 1H), 7.74 (d, J=8.1 Hz, 1H), 7.49-7.51 (m, 2H), 7.28-7.36 (m, 2H), 7.24 (s, 1H), 7.14-7.18 (m, 3H), 7.08 (dd, J=8.3, 2.0 Hz, 1H), 7.04 (d, J=8.1 Hz, 1H), 6.88 (d, J=8.1 Hz, 1H), 4.45 (d, J=5.9 Hz, 2H), 3.86 (s, 3H).

EXAMPLE 31

3-(4-hydroxy-3-methoxyphenyl)N(2-methoxybenzyl)-11-oxo-10,11-dihydro-5H-dibenzo[b,e][1,4]diazepine-8-carboxamide The desired product was prepared by substituting 2-methoxybenzylamine for 3-pyrrolidin-1-ylpropylamine in Example 14. MS (DCI) m/e 496 (M+H)$^+$; $^1$H NMR (500 MHz, DMSO-d$_6$) δ 9.84 (s, 1H), 9.25 (s, 1H), 8.90 (t, J=5.9 Hz, 1H), 8.20 (s, 1H), 7.93 (s, 1H), 7.91 (s, 1H), 7.74 (d, J=8.1 Hz, 1H), 7.50-7.52 (m, 2H), 7.44 (s, 1H), 7.42 (s, 1H), 7.24 (d, J=1.6 Hz, 1H), 7.14-7.18 (m, 2H), 7.08 (dd, J=8.3, 2.0 Hz, 1H), 7.05 (d, J=8.1 Hz, 1H), 6.88 (d, J=8.1 Hz, 1H), 4.51 (d, J=5.9 Hz, 2H), 3.86 (s, 3H), 3.84 (s, 3H).

EXAMPLE 32

3-(4-hydroxy-3-methoxyphenyl)-11-oxoN(2-pyridinylmethyl)-10,11-dihydro-5H-dibenzo[b,e][1,4]diazepine-8-carboxamide The desired product was prepared by substituting 2-pyridinylmethylamine for 3-pyrrolidin-1-ylpropylamine in Example 14. MS (DCI) m/e 467 (M+H)$^+$; $^1$H NMR (500 MHz, DMSO-$d_6$) (TFA salt) δ 9.86 (s, 1H), 8.98 (t, J=5.8 Hz, 1H), 8.64 (d, J=4.7 Hz, 1H), 8.23 (s, 1H), 8.06 (m, 1H), 7.75 (d, J=8.4 Hz, 1H), 7.52-7.56 (m, 3H), 7.25 (d, J=1.6 Hz, 1H), 7.17-7.19 (m, 2H), 7.06-7.10 (m, 2H), 6.88 (d, J=8.1 Hz, 1H), 4.62 (d, J=5.6 Hz, 2H), 3.86 (s, 3H).

EXAMPLE 33

3-(4-hydroxy-3-methoxyphenyl)-11-oxoN(4-pyridinylmethyl)-10,11-dihydro-5H-dibenzo[b,e][1,4]diazepine-8-carboxamide The desired product was prepared by substituting 4-pyridinylmethylamine for 3-pyrrolidin-1-ylpropylamine in Example 14. MS (DCI) m/e 467 (M+H)$^+$; $^1$H NMR (500 MHz, DMSO-$d_6$) (TFA salt) δ 9.86 (s, 1H), 9.05 (t, J=5.9 Hz, 1H), 8.73 (d, J=6.2 Hz, 1H), 8.24 (s, 1H), 7.71-7.76 (m, 2H), 7.54 (d, J=1.9 Hz, 1H), 7.53 (s, 1H), 7.25 (d, J=1.6 Hz, 1H), 7.17-7.19 (m, 2H), 7.06-7.10 (m, 2H), 6.88 (d, J=8.1 Hz, 1H), 4.62 (d, J=5.6 Hz, 2H), 3.86 (s, 3H).

EXAMPLE 34

3-(4-hydroxy-3-methoxyphenyl)N[2-(4-methoxyphenyl)ethyl]-11-oxo-10,11-dihydro-5H-dibenzo[b,e][1,4]diazepine-8-carboxamide The desired product was prepared by substituting 2-(2-methoxyphenyl)ethylamine for 3-pyrrolidin-1-ylpropylamine in Example 14. MS (DCI) m/e 510 (M+H)$^+$; $^1$H NMR (500 MHz, DMSO-$d_6$) δ 9.84 (s, 1H), 9.25 (t, J=5.9 Hz, 1H), 8.29 (d, J=5.6 Hz, 1H), 8.16 (s, 1H), 7.74 (d, J=8.1 Hz, 1H), 7.46 (d, J=1.9 Hz, 1H), 7.41 (dd, J=8.4, 1.9 Hz, 1H), 7.24 (d, J=1.6 Hz, 1H), 7.17-7.18 (m, 2H), 7.12-7.15 (m, 2H), 7.08 (dd, J=8.3, 2.0 Hz, 1H), 7.02 (d, J=8.2 Hz, 1H), 6.88 (d, J=8.1 Hz, 1H), 6.83-6.86 (m, 2H), 3.86 (s, 3H), 3.71 (s, 3H), 3.38-3.42 (m, 2H), 2.75 (t, J=7.3 Hz, 2H).

EXAMPLE 35

1-{[3-(4-hydroxy-3-methoxyphenyl)-11-oxo-10,11-dihydro-5H-dibenzo[b,e][1,4]diazepin-8-yl]carbonyl}-2-piperidinecarboxylic acid The desired product was prepared by substituting Example 24 for Example 12 in Example 13. MS (ESI) m/e 486 (M−H)$^-$; $^1$H NMR (500 MHz, DMSO-$d_6$,) δ 12.90 (br s, 1H), 9.85 (s, 1H), 9.24 (s, 1H), 8.10 (s, 1H), 7.73 (d, J=8.1 Hz, 1H), 7.24 (s, 1H), 7.16-7.18 (m, 1H), 7.08 (dd, J=8.3, 2.0 Hz, 1H), 6.92-7.05 (m, 3H), 6.87 (d, J=8.1 Hz, 1H), 5.11 (m, 1H), 3.86 (s, 3H), 3.59 (m, 1H), 3.16 (m, 1H), 1.30-2.16 (m, 6H).

EXAMPLE 36

1-{[3-(4-hydroxy-3-methoxyphenyl)-11-oxo-10,11-dihydro-5H-dibenzo[b,e][1,4]diazepin-8-yl]carbonyl}-3-piperidinecarboxylic acid The desired product was prepared by substituting Example 25 for Example 12 in Example 13. MS (ESI) m/e 486 (M−H)$^-$; $^1$H NMR (500 MHz, DMSO-$d_6$) δ 12.36 (s, 1H), 9.84 (s, 1H), 9.24 (s, 1H), 8.10 (s, 1H), 7.73 (d, J=8.4 Hz, 1H), 7.24 (d, J=1.6 Hz, 1H), 7.16-7.18 (m, 2H), 7.08 (dd, J=8.3, 2.0 Hz, 1H), 6.98-7.04 (m, 3H), 6.88 (d, J=8.4 Hz, 1H), 3.86 (s, 3H), 2.90-3.02 (m, 2H), 2.43 (m, 1H), 1.98 (m, 1H), 1.41-1.63 (m, 3H).

EXAMPLE 37

1-{[3-(4-hydroxy-3-methoxyphenyl)-11-oxo-10,11-dihydro-5H-dibenzo[b,e][1,4]diazepin-8-yl]carbonyl}-4-piperidinecarboxylic acid The desired product was prepared by substituting Example 26 for Example 12 in Example 13. MS (ESI) m/e 486 (M−H)$^-$; $^1$H NMR (500 MHz, DMSO-$d_6$) δ 12.25 (s, 1H), 9.83 (s, 1H), 9.24 (s, 1H), 8.10 (s, 1H), 7.73 (d, J=8.1 Hz, 1H), 7.24 (d, J=1.6 Hz, 1H), 7.16-7.18 (m, 2H), 7.08 (dd, J=8.1, 2.2 Hz, 1H), 6.98-7.04 (m, 3H), 6.88 (d, J=8.1 Hz, 1H), 3.86 (s, 3H), 2.90-3.02 (m, 2H), 2.45-2.54 (m, 3H), 1.80-1.86 (m, 2H), 1.46-1.34 (m, 2H).

EXAMPLE 38 tert-butyl 2-{[3-(4-hydroxy-3-methoxyphenyl)-11-oxo-10,11-dihydro-5H-dibenzo[b,e][1,4]diazepin-8-yl]carbonyl}hydrazinecarboxylate The desired product was prepared by substituting tert-butyl hydrazinecarboxylate for 3-pyrrolidin-1-ylpropylamine in Example 14. MS (DCI) m/e 491 (M+H)$^+$; $^1$H NMR (500 MHz, DMSO-$d_6$) δ 9.75 (br s, 1H), 9.64 (s, 1H), 8.55 (s, 1H), 7.99 (s, 1H), 7.50 (d, J=8.3 Hz, 1H), 7.19-7.23 (m, 2H), 7.00 (d, J=1.53 Hz, 1H), 6.98-6.95 (m, 2H), 6.84 (dd, J=8.3, 2.2 Hz, 1H), 6.80 (d, J=8.3 Hz, 1H), 6.64 (d, J=8.3 Hz, 1H), 3.82 (s, 3H), 1.18 (s, 9H).

EXAMPLE 39

3-(4-hydroxy-3-methoxyphenyl)-11-oxo-10,11-dihydro-5H-dibenzo[b,e][1,4]diazepine-8-carbonitrile The desired product was prepared by substituting Example 4 for Example 1B in Example 12. MS (DCI) m/e 357 (M+H)$^+$, 375 (M+NH$_4$)$^+$; $^1$H NMR (500 MHz, DMSO-$d_6$) δ 9.92 (s, 1H), 9.27 (s, 1H), 8.50 (s, 1H), 7.77 (d, J=8.1 Hz, 1H), 7.39 (dd, J=8.4, 1.9 Hz, 1H), 7.30 (d, J=1.9 Hz, 1H), 7.18-7.23 (m, 3H), 7.08-7.11 (m, 2H), 6.84 (d, J=8.1 Hz, 1H), 3.86 (s, 3H).

EXAMPLE 40

3-(4-hydroxy-3-methoxyphenyl)-8-nitro-5,10-dihydro-11H-dibenzo[b,e][1,4]diazepin-11-one The desired product was prepared by substituting Example 3 for Example 1B in Example 12. MS (DCI) m/e 378 (M+H)$^+$, 395 (M+NH$_4$)$^+$; $^1$H NMR (500 MHz, DMSO-$d_6$) δ 10.03 (s, 1H), 9.29 (s, 1H), 8.77 (s, 1H), 7.83-7.87 (m, 2H), 7.80 (d, J=8.3 Hz, 1H), 7.19-7.25 (m, 3H), 7.08-7.13 (m, 2H), 6.89 (d, J=8.3 Hz, 1H), 3.86 (s, 3H).

EXAMPLE 41

8-amino-3-(4-hydroxy-3-methoxyphenyl)-5,10-dihydro-11H-dibenzo[b,e][1,4]diazepin-11-one The desired product was prepared by substituting Example 7C for Example 1B in Example 12. MS (DCI) m/e 347 (M+H)$^+$; $^1$H NMR (500 MHz, DMSO-d$_6$) (HCl salt) δ 9.99 (s, 1H), 9.26 (br s, 1H), 8.07 (s, 1H), 7.73 (d, J=8.1 Hz, 1H), 7.26 (d, J=1.6 Hz, 1H), 7.16-7.18 (m, 2H), 7.07-7.08 (m, 2H), 6.87-6.93 (m, 3H), 3.86 (s, 3H).

EXAMPLE 42

N-[3-(4-hydroxy-3-methoxyphenyl)-11-oxo-10,11-dihydro-5H-dibenzo[b,e][1,4]diazepin-8-yl]methanesulfonamide

EXAMPLE 42A

N-(3-chloro-11-oxo-10,11-dihydro-5H-dibenzo[b,e][1,4]diazepin-8-yl)methanesulfonamide A mixture of Example 7C (30 mg, 0.11 mmol) and CH$_3$SO$_2$Cl (13 mg, 0.112 mmol) in pyridine (4 mL) was stirred overnight at room temperature. The excess pyridine was removed under reduced pressure and the residue was washed with hexanes and filtered. The filter cake was dried in a vacuum oven to provide the desired product. MS (DCI) m/e 338 (M+H)$^+$, 355 (M+NH$_4$)$^+$.

EXAMPLE 42B

N-[3-(4-hydroxy-3-methoxyphenyl)-11-oxo-10,11-dihydro-5H-dibenzo[b,e][1,4]diazepin-8-yl]methanesulfonamide The desired product was prepared by substituting Example 42A for Example 1B in Example 12. MS (DCI) m/e 426 (M+H)$^+$; $^1$H NMR (500 MHz, DMSO-d$_6$) δ 9.81 (s, 1H), 9.46 (s, 1H), 9.22 (br s, 1H), 7.84 (s, 1H), 7.71 (d, J=8.1 Hz, 1H), 7.22 (d, J=1.6 Hz, 1H), 7.14-7.17 (m, 2H), 7.07 (dd, J=8.3, 2.0 Hz, 1H), 6.97 (d, J=8.4 Hz, 1H), 6.91 (d, J=2.5 Hz, 1H), 6.87 (d, J=8.1 Hz, 1H), 6.80 (dd, J=8.4, 2.2 Hz, 1H), 3.86 (s, 3H), 2.92 (s, 3H).

EXAMPLE 43

N-[3-(3-methoxy-4-nitrophenyl)-11-oxo-10,11-dihydro-5H-dibenzo[b,e][1,4]diazepin-8-yl]methanesulfonamide The desired product was prepared by substituting Example 43A and 2-(3-methoxy-4-nitrophenyl)-4,4,5,5-tetramethyl-1,3,2-dioxaborolane for Example 1B and 2-methoxy-4-(4,4,5,5-tetramethyl-1,3,2-dioxaborolan-2-yl)phenol, respectively, in Example 12. MS (DCI) m/e 454 (M+H)$^+$, 472 (M+NH$_4$)$^+$; $^1$H NMR (500 MHz, DMSO-d$_6$) δ 9.93 (s, 1H), 9.48 (s, 1H), 8.00 (d, J=8.4 Hz, 1H), 7.97 (s, 1H), 7.79 (d, J=8.1 Hz, 1H), 7.50 (d, J=1.3 Hz, 1H), 7.32-7.34 (m, 2H), 7.29 (dd, J=8.1, 1.6 Hz, 1H), 6.97 (d, J=8.4 Hz, 1H), 6.92 (d, J=2.2 Hz, 1H), 6.81 (dd, J=8.4, 2.2 Hz, 1H), 4.02 (s, 3H), 2.91 (s, 3H).

EXAMPLE 44

N-[3-(4-hydroxy-3-methoxyphenyl)-11-oxo-10,11-dihydro-5H-dibenzo[b,e][1,4]diazepin-8-yl]acetamide

EXAMPLE 44A

N-(3-chloro-11-oxo-10,11-dihydro-5H-dibenzo[b,e][1,4]diazepin-8-yl)acetamide A solution of Example 7C (100 mg, 0.38 mmol) in pyridine (10 mL) at 0° C. was treated with acetyl chloride (32 mg, 0.40 mmol), stirred overnight, and concentrated. The residue was purified by flash column chromatography on silica gel with ethyl acetate to provide 64 mg (56%) of the desired product. MS (DCI) m/e 302 (M+H)$^+$, 319 (M+NH$_4$)$^+$; $^1$H NMR (500 MHz, DMSO-d$_6$) δ 9.93 (s, 1H), 9.81 (s, 1H), 7.93 (s, 1H), 7.67 (d, J=8.4 Hz, 1H), 7.25 (d, J=1.9 Hz, 1H), 7.16 (dd, J=8.4, 2.2 Hz, 1H), 7.05 (d, J=1.9 Hz, 1H), 6.90 (dd, J=8.4, 1.9 Hz, 1H), 6.88 (d, J=8.7 Hz, 1H), 1.99 (s, 3H).

EXAMPLE 44B

N-[3-(4-hydroxy-3-methoxyphenyl)-11-oxo-10,11-dihydro-5H-dibenzo[b,e][1,4]diazepin-8-yl]acetamide The desired product was prepared by substituting Example 44A for Example 1B in Example 12. MS (DCI) m/e 390 (M+H)$^+$; $^1$H NMR (500 MHz, DMSO-d$_6$) δ 9.80 (s, 1H), 9.78 (s, 1H), 9.22 (s, 1H), 7.75 (s, 1H), 7.70 (d, J=8.1 Hz, 1H), 7.21-7.24 (m, 2H), 7.12-7.17 (m, 3H), 7.07 (m, 1H), 6.91 (d, J=8.7 Hz, 1H), 6.87 (d, J=8.1 Hz, 1H), 3.85 (s, 3H), 1.99 (s, 2H).

EXAMPLE 45

N-[3-(3-methoxy-4-nitrophenyl)-11-oxo-10,11-dihydro-5H-dibenzo[b,e][1,4]diazepin-8-yl]acetamide The desired product was prepared by substituting Example 44A and 2-(3-methoxy-4-nitrophenyl)-4,4,5,5-tetramethyl-1,3,2-dioxaborolane for Example 1B and 2-methoxy-4-(4,4,5,5-tetramethyl-1,3,2-dioxaborolan-2-yl)phenol, respectively, in Example 12. MS (DCI) m/e 419 (M+H)$^+$; $^1$H NMR (500 MHz, DMSO-d$_6$) δ 9.93 (s, 1H), 9.81 (s, 1H), 8.00 (d, J=8.4 Hz, 1H), 7.89 (s, 1H), 7.79 (d, J=8.1 Hz, 1H), 7.52 (d, J=1.6 Hz, 1H), 7.35-7.37 (m, 2H), 7.26-7.30 (m, 2H), 7.16 (dd, J=8.4, 2.2 Hz, 1H), 6.93 (d, J=8.4 Hz, 1H), 4.03 (s, 3H), 2.00 (s, 3H).

EXAMPLE 46

8-(3-aminophenyl)-3-(4-hydroxy-3-methoxyphenyl)-5,10-dihydro-11H-dibenzo[b,e][1,4]diazepin-11-one

EXAMPLE 46A

8-(3-aminophenyl)-3-chloro-5,10-dihydro-11H-dibenzo[b,e][1,4]diazepin-11-one The desired product was prepared by substituting Example 2 and 3-(4,4,5,5-tetramethyl-1,3,2-dioxaborolan-2-yl)phenylamine for Example 1B and 2-methoxy-4-(4,4,5,5-tetramethyl-1,3,2-dioxaborolan-2-yl)phenol, respectively, in Example 12. MS (DCI) m/e 335 (M+H)$^+$, 353 (M+NH$_4$)$^+$; $^1$H NMR (500 MHz, DMSO-$d_6$) δ 9.94 (s, 1H), 8.13 (s, 1H), 7.72 (d, J=8.4 Hz, 1H), 7.17-7.19 (m, 2H), 7.06-7.09 (m, 2H), 7.01 (d, J=8.11 Hz, 1H), 6.93 (dd, J=8.6, 2.0 Hz, 1H), 6.73 (d, J=1.9 Hz, 1H), 6.66 (d, J=7.8 Hz, 1H), 6.52 (dd, J=7.5, 1.9 Hz, 1H), 5.11 (s, 2H).

EXAMPLE 46B 8-(3-aminophenyl)-3-(4-hydroxy-3-methoxyphenyl)-5,10-dihydro-11H-dibenzo[b,e][1,4]diazepin-11-one The desired product was prepared by substituting Example 46A for Example 1B in Example 12. MS (DCI) m/e 424 (M+H)$^+$; $^1$H NMR (500 MHz, DMSO-$d_6$,) δ 9.91 (s, 1H), 9.24 (s, 1H), 7.97 (s, 1H), 7.74 (d, J=8.1 Hz, 1H), 7.25 (d, J=1.3 Hz, 1H), 7.03-7.19 (m, 7H), 6.88 (d, J=8.11 Hz, 1H), 6.73 (s, 1H), 6.67, (d, J=7.8 Hz, 1H), 6.62 (dd, J=8.0, 1.4 Hz, 1H), 5.10 (s, 2H), 3.86 (s, 3H).

EXAMPLE 47

3-(4-hydroxy-3-methoxyphenyl)-8-(3-hydroxyphenyl)-5,10-dihydro-11H-dibenzo[b,e][1,4]diazepin-11-one

EXAMPLE 47A 3-chloro-8-(3-hydroxyphenyl)-5,10-dihydro-11H-dibenzo[b,e][1,4]diazepin-11-one The desired product was prepared by substituting Example 2 and 3-(4,4,5,5-tetramethyl-1,3,2-dioxaborolan-2-yl)phenol for Example 1B and 2-methoxy-4-(4,4,5,5-tetramethyl-1,3,2-dioxaborolan-2-yl)phenol, respectively, in Example 12. MS (DCI) m/e 336 (M+H)$^+$, 354 (M+NH$_4$)$^+$; $^1$H NMR (500 MHz, DMSO-$d_6$) δ 9.95 (s, 1H), 9.49 (s, 1H), 8.17 (s, 1H), 7.72 (d, J=8.3 Hz, 1H), 7.20-7.24 (m, 3H), 7.09 (d, J=2.2 Hz, 1H), 7.03 (d, J=8.11 Hz, 1H), 6.91-6.97 (m, 3H), 6.73, (dd, J=8.0, 1.5 Hz, 1H).

EXAMPLE 47B 3-(4-hydroxy-3-methoxyphenyl)-8-(3-hydroxyphenyl)-5,10-dihydro-11H-dibenzo[b,e][1,4]diazepin-11-one The desired product was prepared by substituting Example 47A for Example 1B in Example 12. MS (DCI) m/e 425 (M+H)$^+$; $^1$H NMR (500 MHz, DMSO-$d_6$) δ 9.81 (s, 1H), 9.46 (s, 1H), 9.24 (s, 1H), 8.00 (s, 1H), 7.75 (d, J=8.1 Hz, 1H), 7.15-7.25 (m, 7H), 7.09 (dd, J=8.3, 2.0 Hz, 1H), 7.06 (d, J=8.11 Hz, 1H), 6.96 (d, J=7.8 Hz, 1H), 6.92 (s, 1H), 6.88 (d, J=8.1 Hz, 1H), 6.72 (dd, J=8.0, 2.0 Hz, 1H), 3.87 (s, 3H).

EXAMPLE 48

3-(4-hydroxy-3-methoxyphenyl)-8-(3-pyridinyl)-5,10-dihydro-11H-dibenzo[b,e][1,4]diazepin-11-one

EXAMPLE 48A 3-chloro-8-(3-pyridinyl)-5,10-dihydro-11H-dibenzo[b,e][1,4]diazepin-11-one The desired product was prepared by substituting Example 2 and diethyl 3-pyridinylboronate for Example 1B and 2-methoxy-4-(4,4,5,5-tetramethyl-1,3,2-dioxaborolan-2-yl) phenol, respectively, in Example 12. MS (DCI) m/e 322 (M+H)$^+$; $^1$H NMR (500 MHz, DMSO-$d_6$) δ 9.95 (s, 1H), 8.78 (d, J=2.2 Hz, 1H), 8.53 (dd, J=4.7, 1.3 Hz, 1H), 8.24 (s, 1H), 7.94 (m, 1H), 7.72 (d, J=8.6 Hz, 1H), 7.46 (dd, J=7.5, 4.8 Hz, 1H), 7.31-7.36 (m, 2H), 7.09 (m, 1H), 6.95 (dd, J=8.1, 2.0 Hz, 1H).

EXAMPLE 48B 3-(4-hydroxy-3-methoxyphenyl)-8-(3-pyridinyl)-5,10-dihydro-11H-dibenzo[b,e][1,4]diazepin-11-one The desired product was prepared by substituting Example 48A for Example 1B in Example 12. MS (DCI) m/e 410 (M+H)$^+$; $^1$H NMR (500 MHz, DMSO-$d_6$) δ 9.81 (s, 1H), 9.25 (s, 1H), 8.79 (d, J=1.9 Hz, 1H), 8.25 (d, J=3.4 Hz, 1H), 8.09 (s, 1H), 7.95 (dd, J=6.2, 2.2 Hz, 1H), 7.76 (d, J=8.4 Hz, 1H), 7.46 (dd, J=7.9, 4.9 Hz, 1H), 7.32-7.35 (m, 2H), 7.26 (d, J=1.6 Hz, 1H), 7.16-7.19 (m, 2H), 7.12 (d, J=8.1 Hz, 1H), 7.10 (dd, J=8.3, 2.0 Hz, 1H), 6.88 (d, J=8.1 Hz, 1H), 3.87 (s, 3H).

EXAMPLE 49

3-(4-hydroxy-3-methoxyphenyl)-8-(1H-pyrrol-2-yl)-5,10-dihydro-11H-dibenzo[b,e][1,4]diazepin-11-one

EXAMPLE 49A 3-chloro-8-(1H-pyrrol-2-yl)-5,10-dihydro-11H-dibenzo[b,e][1,4]diazepin-11-one The desired product was prepared by substituting Example 2 and 1-(tert-butoxycarbonyl)-1H-pyrrol-2-ylboronic acid for Example 9 and 2-methoxy-4-(4,4,5,5-tetramethyl-1,3,2-dioxaborolan-2-yl)phenol, respectively, in Example 10 MS (DCI) m/e 310 (M+H)$^+$, 327 (M+NH$_4$)$^+$; $^1$H NMR (500 MHz, DMSO-$d_6$) δ 11.10 (s, 1H), 9.87 (s, 1H), 8.05 (s, 1H), 7.70 (d, J=8.3 Hz, 1H), 7.18-7.22 (m, 2H), 7.07 (d, J=2.2 Hz, 1H), 6.91-6.96 (m, 2H), 6.79 (m, 1H), 6.29 (t, J=3.7 Hz, 1H), 6.08 (m, 1H).

EXAMPLE 49B 3-(4-hydroxy-3-methoxyphenyl)-8-(1H-pyrrol-2-yl)-5,10-dihydro-11H-dibenzo[b,e][1,4]diazepin-11-one The desired product was prepared by substituting Example 49A for Example 1B in Example 12. MS (DCI) m/e 398 (M+H)$^+$; $^1$H NMR (500 MHz, DMSO-$d_6$) δ 11.09 (s, 1H), 9.74 (s, 1H), 9.24 (br s, 1H), 7.89 (s, 1H), 7.73 (d, J=6.9 Hz, 1H), 7.08-7.24 (m, 6H), 6.99 (d, J=6.6 Hz, 1H) 6.88 (d, J=6.9 Hz, 1H), 6.78 (s, 1H), 6.29 (s, 1H), 6.08 (s, 1H), 3.86 (s, 3H).

EXAMPLE 50

3-(3-methoxy-4-nitrophenyl)-8-(1H-pyrrol-2-yl)-5,10-dihydro-11H-dibenzo[b,e][1,4]diazepin-11-one The desired product was prepared by substituting Example 49A and 2-(3-methoxy-4-nitrophenyl)-4,4,5,5-tetramethyl-1,3,2-dioxaborolane for Example 1B and 2-methoxy-4-(4,4,5,5-tetramethyl-1,3,2-dioxaborolan-2-yl)phenol, respectively, in Example 12. MS (DCI) m/e 427 (M+H)$^+$, 444 (M+NH$_4$)$^+$; $^1$H NMR (500 MHz, DMSO-$d_6$) δ 11.10 (s, 1H), 9.87 (s, 1H), 8.00-8.02 (m, 2H), 7.82 (d, J=8.3 Hz, 1H), 7.53 (s, 1H), 7.34-7.36 (m, 2H), 7.30 (dd, J=8.3, 1.5 Hz, 1H), 7.20-7.22 (m, 2H), 7.00 (d, J=8.9 Hz, 1H), 6.79 (d, J=1.2 Hz, 1H), 6.29 (s, 1H), 6.08 (d, J=2.8 Hz, 1H), 4.04 (s, 3H).

EXAMPLE 51 methyl [3-(3-methoxy-4-nitrophenyl)-11-oxo-10,11-dihydro-5H-dibenzo[b,e][1,4]diazepin-8-yl]acetate The desired product was prepared by substituting Example 6D and 2-(3-methoxy-4-nitrophenyl)-4,4,5,5-tetramethyl-1,3,2-dioxaborolane for Example 1B and 2-methoxy-4-(4,4,5,5-tetramethyl-1,3,2-dioxaborolan-2-yl)phenol, respectively, in Example 12. MS (ESI) m/e 432 (M−H)⁻; ¹H NMR (500 MHz, DMSO-$d_6$) δ 9.87 (s, 1H), 7.98-8.01 (m, 2H), 7.78 (d, J=8.4 Hz, 1H), 7.51 (d, J=1.6 Hz, 1H), 7.30-7.34 (m, 2H), 7.29 (dd, J=8.3, 1.7 Hz, 1H), 6.96 (d, J=7.8 Hz, 1H), 6.85-6.87 (m, 2H), 4.02 (s, 3H), 3.59 (s, 3H), 3.53 (s, 2H).

EXAMPLE 52 methyl [3-(4-hydroxy-3-methoxyphenyl)-11-oxo-10,11-dihydro-5H-dibenzo[b,e][1,4]diazepin-8-yl]acetate The desired product was prepared by substituting Example 6D for Example 1B in Example 12. MS (DCI) m/e 404 (M+H)⁺; ¹H NMR (500 MHz, DMSO-$d_6$) δ 9.74 (s, 1H), 9.23 (s, 1H), 7.86 (s, 2H), 7.71 (d, J=8.1 Hz, 1H), 7.23 (d, J=1.6 Hz, 1H), 7.17 (d, J=1.9 Hz, 1H), 7.15 (dd, J=8.4, 1.6 Hz, 1H), 7.07 (dd, J=8.3, 2.0 Hz, 1H), 6.95 (d, J=7.8 Hz, 1H), 6.84-6.88 (m, 3H), 3.86 (s, 3H), 3.60 (s, 3H), 3.53 (s, 2H).

EXAMPLE 53 methyl [3-(3-methoxyphenyl)-11-oxo-10,11-dihydro-5H-dibenzo[b,e][1,4]diazepin-8-yl]acetate The desired product was prepared by substituting Example 6D and 3-methoxyphenylboronic acid for Example 1B and 2-methoxy-4-(4,4,5,5-tetramethyl-1,3,2-dioxaborolan-2-yl)phenol, respectively, in Example 12. MS (ESI) m/e 387 (M−H)⁻; ¹H NMR (300 MHz, DMSO-$d_6$) δ 9.83 (s, 1H), 7.92 (s, 1H), 7.75 (d, J=8.14 Hz, 1H), 7.39 (d, J=7.80 Hz, 1H), 7.29 (d, J=1.70 Hz, 1H), 7.15-7.22 (m, 3H), 6.94-7.01 (m, 2H), 6.84-6.87 (m, 2H), 3.83 (s, 3H), 3.60 (s, 3H), 3.54 (s, 2H).

EXAMPLE 54 methyl [3-(4-chloro-3-methoxyphenyl)-11-oxo-10,11-dihydro-5H-dibenzo[b,e][1,4]diazepin-8-yl]acetate

EXAMPLE 54A methyl [11-oxo-3-(4,4,5,5-tetramethyl-1,3,2-dioxaborolan-2-yl)-10,11-dihydro-5H-dibenzo[b,e][1,4]diazepin-8-yl]acetate A mixture of CyMAP ligand (23 mg, 0.058 mmol) and Pd₂(dba)₃ (11 mg, 0.012 mmol) in dioxane (2.0 mL) purged with nitrogen was stirred at room temperature under nitrogen for 30 minutes, treated with Example 6D (93 mg, 0.29 mmol), bis(pinacolato)diboron (85 mg, 0.33 mmol), and potassium acetate (47 mg, 0.47 mmol), stirred at 85° C. under nitrogen overnight, cooled to room temperature, diluted with ethyl acetate, filtered through diatomaceous earth (Celite®), and concentrated under vacuum. The residue was dissolved in dichloromethane (2.5 mL), treated with hexanes (10.0 mL), concentrated to a final volume of about 5-6 mL, and filtered. The filter cake provided 99 mg (83%) of the desired product. MS (DCI/NH₃) m/e 409 (M+H)⁺.

EXAMPLE 54B methyl [3-(4-chloro-3-methoxyphenyl)-11-oxo-10,11-dihydro-5H-dibenzo[b,e][1,4]diazepin-8-yl]acetate The desired product was prepared by substituting Example 54A and 2-chloro-5-iodoanisole for 2-methoxy-4-(4,4,5,5-tetramethyl-1,3,2-dioxaborolan-2-yl)phenol and Example 1B, respectively, in Example 10. MS (DCI) m/e 423 (M+H)⁺, 440 (M+NH₄)⁺; ¹H NMR (500 MHz, DMSO-$d_6$) δ 9.83 (s, 1H), 7.94 (s, 1H), 7.77 (d, J=8.0 Hz, 1H), 7.53 (d, J=8.3 Hz, 1H), 7.29 (d, J=1.7 Hz, 1H), 7.34 (d, J=1.8 Hz, 1H), 7.30 (d, J=1.8 Hz, 1H), 7.19-7.24 (m, 2H), 6.96 (d, J=8.0 Hz, 1H), 6.84-6.87 (m, 2H), 3.96 (s, 3H), 3.60 (s, 3H), 3.54 (s, 2H).

EXAMPLE 55

3-(3-methoxy-4-nitrophenyl)-5,10-dihydro-11H-dibenzo[b,e][1,4]diazepin-11-one

The desired product was prepared by substituting 2-(3-methoxy-4-nitrophenyl)-4,4,5,5-tetramethyl-1,3,2-dioxaborolane for 2-methoxy-4-(4,4,5,5-tetramethyl-1,3,2-dioxaborolan-2-yl)phenol in Example 10. MS (DCI) m/e 362 (M+H)⁺, 379 (M+NH₄)⁺; ¹H NMR (500 MHz, DMSO-$d_6$) δ 9.88 (s, 1H), 8.00-8.02 (m, 2H), 7.80 (d, J=8.0 Hz, 1H), 7.53 (d, J=1.8 Hz, 1H), 7.33-7.36 (m, 2H), 7.30 (dd, J=8.1, 1.7 Hz, 1H), 6.90-7.03 (m, 4H), 4.03 (s, 3H).

EXAMPLE 56

3-(4-chloro-3-methoxyphenyl)-5,10-dihydro-11H-dibenzo[b,e][1,4]diazepin-11-one

EXAMPLE 56A 3-(4,4,5,5-tetramethyl-1,3,2-dioxaborolan-2-yl)-5,10-dihydro-11H-dibenzo[b,e][1,4]diazepin-11-one A mixture of tri(cyclohexyl)phosphine (336 mg, 1.2 mmol) and Pd₂(dba)₃ (230 mg, 0.25 mmol) in dioxane (60 mL) purged with nitrogen was stirred at room temperature under nitrogen for 30 minutes, treated with Example 9 (2.89 g, 10 mmol), bis(pinacolato)diboron (2.8 g, 11 mmol), and potassium acetate (1.47 g, 15 mmol) stirred at 85° C. under nitrogen overnight, cooled to room temperature, diluted with ethyl acetate, and poured into water. The organic layer was washed with brine, dried (MgSO₄), filtered, and concentrated under vacuum. The residue was purified by flash column chromatography on silica gel with 3:2 hexanes/ethyl acetate to provide 3.1 g (92%) of the desired product. MS (DCI) m/e 337 (M+H)⁺, 354 (M+NH₄)⁺; ¹H NMR (500 MHz, DMSO-$d_6$) δ 9.86 (s, 1H), 7.82 (s, 1H), 7.68 (d, J=7.8 Hz, 1H), 7.42 (s, 1H), 7.16 (dd, J=7.8, 0.9 Hz, 1H), 7.02 (dd, J=7.8, 1.6 Hz, 1H), 6.88-6.98 (m, 3H), 1.30 (s, 12H).

EXAMPLE 56B

3-(4-chloro-3-methoxyphenyl)-5,10-dihydro-11H-dibenzo[b,e][1,4]diazepin-11-one The desired product was prepared by substituting Example 56A and 2-chloro-5-iodoanisole for 2-methoxy-4-(4,4,5,5-tetramethyl-1,3,2-dioxaborolan-2-yl)phenol and Example 9, respectively, in Example 10. MS (DCI) m/e 362 (M+H)+, 379 (M+NH4)+; $^1$H NMR (500 MHz, DMSO-d$_6$) δ 9.84 (s, 1H), 7.95 (s, 1H), 7.78 (d, J=8.0 Hz, 1H), 7.53 (d, J=8.0 Hz, 1H), 7.34 (d, J=1.8 Hz, 1H), 7.31 (m, 1H), 7.20-7.25 (m, 2H), 6.89-7.03 (m, 2H), 3.96 (s, 3H).

EXAMPLE 57

3-(4-bromo-3-methoxyphenyl)-5,10-dihydro-11H-dibenzo[b,e][1,4]diazepin-11-one

EXAMPLE 57A

4-bromo-3-methoxyaniline

The desired product was prepared by substituting 2-bromo-5-nitroanisole for Example 6B in Example 6C. MS (ESI) m/e 203 (M+H)+; $^1$H NMR (300 MHz, DMSO-d$_6$) δ 7.09 (d, J=8.48 Hz, 1H), 6.30 (d, J=2.37 Hz, 1H), 6.09 (dd, J=8.48, 2.37 Hz, 1H), 5.28 (s, 2H), 3.72 (s, 3H).

EXAMPLE 57B

1-bromo-4-iodo-2-methoxybenzene

Example 57A (102 mg, 0.50 mmol) was treated with concentrated HCl (10 mL), cooled to 0° C., treated with a solution of NaNO$_2$ (45 mg, 0.65 mmol) in H$_2$O (5 mL), stirred at 0° C. for 1 hour, treated with a solution of KI (249 mg, 1.5 mmol) in H$_2$O (5 mL), stirred overnight while warming to room temperature, and extracted with ethyl acetate. The extract was washed with H$_2$O and 10% Na$_2$S$_2$O$_3$, dried (MgSO$_4$), filtered, and concentrated to provide 147 mg (94%) of the desired product. MS (ESI) m/e 332 (M+20)+; $^1$H NMR (300 MHz, DMSO-d$_6$) δ 7.39 (d, J=1.87 Hz, 1H), 7.34 (d, J=8.11 Hz, 1H), 7.24 (dd, J=8.11, 1.87 Hz, 1H), 3.86 (s, 3H).

EXAMPLE 57C

3-(4-bromo-3-methoxyphenyl)-5,10-dihydro-11H-dibenzo[b,e][1,4]diazepin-11-one The desired product was prepared by substituting Example 56A and Example 57B for 2-methoxy-4-(4,4,5,5-tetramethyl-1,3,2-dioxaborolan-2-yl)phenol and Example 9, respectively, in Example 10. MS (ESI) m/e 393 (M–H)−; $^1$H NMR (500 MHz, DMSO-d$_6$) δ 9.83 (s, 1H), 7.95 (s, 1H), 7.77 (d, J=8.11 Hz, 1H), 7.68 (d, J=8.11 Hz, 1H), 7.31 (d, J=1.56 Hz, 1H), 7.30 (d, J=1.87 Hz, 1H), 7.23 (dd, J=8.27, 1.72 Hz, 1H), 7.14 (dd, J=8.11, 1.87 Hz, 1H), 6.89-7.02 (m, 4H), 3.95 (s, 3H).

EXAMPLE 58 methyl [3-(4-bromo-3-methoxyphenyl)-11-oxo-10,11-dihydro-5H-dibenzo[b,e][1,4]diazepin-8-yl]acetate The desired product was prepared by substituting Example 54A and Example 57B for 2-methoxy-4-(4,4,5,5-tetramethyl-1,3,2-dioxaborolan-2-yl)phenol and Example 9, respectively, in Example 10. MS (ESI) m/e 465 (M–H)−; $^1$H NMR (300 MHz, DMSO-d$_6$) δ 9.85 (s, 1H), 7.95 (s, 1H), 7.76 (d, J=8.11 Hz, 1H), 7.68 (d, J=8.5 Hz, 1H), 7.29-7.30 (m, 2H), 7.30 (d, J=1.87 Hz, 1H), 7.23 (dd, J=8.4, 1.7 Hz, 1H), 7.14 (dd, J=8.1, 2.0 Hz, 1H), 6.95 (m, 1H), 6.83-6.87 (m, 2H), 3.95 (s, 3H), 3.59 (s, 3H), 3.54 (s, 2H).

EXAMPLE 59

3-(4-acetyl-3-methoxyphenyl)-5,10-dihydro-11H-dibenzo[b,e][1,4]diazepin-11-one

EXAMPLE 59A

4-chloro-1-iodo-2-methoxybenzene

The desired product was prepared by substituting 2-amino-5-chloroanisole for Example 57A in Example 57B. MS (ESI) m/e 288 (M+20)+; $^1$H NMR (300 MHz, DMSO-d$_6$) δ 7.76 (d, J=8.48 Hz, 1H), 7.09 (d, J=2.03 Hz, 1H), 6.84 (dd, J=8.31, 2.20 Hz, 1H), 3.85 (s, 3H).

EXAMPLE 59B

1-(4-chloro-2-methoxyphenyl)ethanone

A solution of Example 59A (2.68 g, 10 mmol) in DMF (40 mL) was treated with triethylamine (1.53 mL, 11 mmol), n-butyl vinyl ether (6.5 mL, 50 mmol), DPPF (554 mg, 1 mmol) and Pd(OAc)$_2$ (112 mg, 0.5 mmol), purged with nitrogen, heated to 80° C. for 6 hours, cooled to room temperature, and partitioned between ethyl acetate and water. The aqueous layer was extracted with ethyl acetate, and the combined organic layers were washed with water and brine, dried (MgSO$_4$), filtered, and concentrated under vacuum. The residue was purified by flash column chromatography on silica gel with 4:1 hexanes/ethyl acetate to provide 1.20 g (65%) of the desired product. MS (ESI) m/e 185 (M+H)+; $^1$H NMR (300 MHz, DMSO-d$_6$) δ 7.60 (d, J=8.14 Hz, 1H), 7.27 (d, J=1.70 Hz, 1H), 7.09 (dd, J=8.31, 1.86 Hz, 1H), 3.92 (s, 3H).

EXAMPLE 59C

3-(4-acetyl-3-methoxyphenyl)-5,10-dihydro-11H-dibenzo[b,e][1,4]diazepin-11-one A mixture of Example 56A (67 mg, 0.2 mmol), Example 59B (37 mg, 0.2 mmol), CyMAP ligand (11.8 mg, 0.03 mmol), Pd(OAc)$_2$ (4.9 mg, 0.002 mmol), and CsF (91 mg, 0.6 mmol) in DME (8 mL) and methanol (4 mL) was heated to reflux overnight, cooled to room temperature, and partitioned between water and ethyl acetate. The aqueous layer was extracted with ethyl acetate and the combined organic layers were washed with brine, dried (MgSO$_4$), filtered, and concentrated under vacuum. The residue was purified by flash column chromatography on silica gel with 1:1 hexanes/ethyl acetate to provide 0.036 g (50%) of the desired product. MS (ESI) m/e 359 (M+H)+; $^1$H NMR (300 MHz, DMSO-d$_6$) δ 9.88 (s, 1H), 7.99 (s, 1H), 7.79 (d, J=8.14 Hz, 1H), 7.70 (d, J=8.14 Hz, 1H), 7.27-7.36 (m, 3H), 6.91-7.01 (m, 5H), 4.00 (s, 3H), 2.56 (s, 3H).

EXAMPLE 60

2-methoxy-4-(11-oxo-10,11-dihydro-5H-dibenzo[b,e][1,4]diazepin-3-yl)benzonitrile

EXAMPLE 60A 4-chloro-2-methoxybenzonitrile

A mixture of Example 59A (2.68 g, 10 mmol), $Zn(CN)_2$ (0.654 g, 5.5 mmol), and $Pd(PPh_3)_4$ (0.577 g, 0.5 mmol) in DMF (15 mL) was stirred at 90° C. for 6 hours and cooled to room temperature. The reaction mixture was poured into water (500 mL) and extracted with ethyl acetate several times. The combined extracts were washed with water and brine, dried ($MgSO_4$), filtered, and concentrated under vacuum. The residue was purified by flash column chromatography on silica gel with 9:1 hexanes/ethyl acetate to provide 1.34 g (90%) of the desired product. MS (DCI) m/e 168 $(M+H)^+$; $^1H$ NMR (300 MHz, $CDCl_3$) δ 7.49 (d, J=8.1 Hz, 1H), 6.97-7.03 (m, 2H).

EXAMPLE 60B 2-methoxy-4-(11-oxo-10,11-dihydro-5H-dibenzo[b,e][1,4]diazepin-3-yl)benzonitrile The desired product was prepared by substituting Example 60A for Example 59B in Example 59C. MS (DCI) m/e 342 $(M+H)^+$, 359 $(M+NH_4)^+$; $^1H$ NMR (500 MHz, DMSO-$d_6$) δ 9.88 (s, 1H), 7.98 (s, 1H), 7.84 (d, J=7.8 Hz, 1H), 7.80 (d, J=8.1 Hz, 1H), 7.42 (s, 1H), 7.33-7.35 (m, 2H), 7.29 (dd, J=8.1, 1.6 Hz, 1H), 6.90-7.02 (m, 4H), 4.02 (s, 3H).

EXAMPLE 61 methyl [3-(4-cyano-3-methoxyphenyl)-11-oxo-10,11-dihydro-5H-dibenzo[b,e][1,4]diazepin-8-yl]acetate The desired product was prepared by substituting Example 54A and Example 60A for Example 56A and Example 59B, respectively, in Example 59C. MS (DCI) m/e 414 $(M+H)^+$, 431 $(M+NH_4)^+$; $^1H$ NMR (500 MHz, DMSO-$d_6$) δ 9.87 (s, 1H), 7.97 (s, 1H), 7.83 (d, J=7.8 Hz, 1H), 7.79 (d, J=8.1 Hz, 1H), 7.42 (s, 1H), 7.32-7.34 (m, 2H), 7.29 (dd, J=8.3, 1.7 Hz, 1H), 6.96 (d, J=8.1 Hz, 1H), 6.95-6.97 (m, 2H), 4.02 (s, 3H), 3.60 (s, 3H), 3.54 (s, 2H).

EXAMPLE 62 methyl 2-methoxy-4-(11-oxo-10,11-dihydro-5H-dibenzo[b,e][1,4]diazepin-3-yl)benzoate The desired product was prepared by substituting methyl 4-chloro-2-methoxybenzoate for Example 59B in Example 59C. MS (DCI) m/e 375 $(M+H)^+$, 392 $(M+NH_4)^+$; $^1H$ NMR (500 MHz, DMSO-$d_6$) δ 9.85 (s, 1H), 7.97 (s, 1H), 7.76-7.80 (m, 2H), 7.34-7.36 (m, 2H), 7.28 (d, J=1.6 Hz, 1H), 7.27 (d, J=1.6 Hz, 1H), 6.91-7.03 (m, 4H), 3.93 (s, 3H), 3.81 (s, 3H).

EXAMPLE 63

2-methoxy-4-(11-oxo-10,11-dihydro-5H-dibenzo[b,e][1,4]diazepin-3-yl)benzoic acid The desired product was prepared by substituting Example 62 for Example 12 in Example 13. MS (DCI) m/e 361 $(M+H)^+$, 378 $(M+NH_4)^+$; $^1H$ NMR (500 MHz, DMSO-$d_6$) δ 9.85 (s, 1H), 7.97 (s, 1H), 7.79 (d, J=8.1 Hz, 1H), 7.75 (d, J=7.8 Hz, 1H), 7.24-7.28 (m, 2H), 6.91-7.03 (m, 4H), 3.92 (s, 3H).

EXAMPLE 64

N-(δ 4-dihydroxybenzyl)-2-methoxy-4-(11-oxo-10,11-dihydro-5H-dibenzo[b,e][1,4]diazepin-3-yl)benzamide The desired product was prepared by substituting Example 63 and 4-(aminomethyl)-1,2-benzenediol for Example 13 and 3-pyrrolidin-1-ylpropylamine, respectively, in Example 14. MS (ESI) m/e 483 $(M+H)^+$; $^1H$ NMR (400 MHz, DMSO-$d_6$) δ 9.84 (s, 1H), 8.79 (s, 1H), 8.54 (t, J=5.98 Hz, 1H), 7.97 (s, 1H), 7.87 (d, J=7.98 Hz, 1H), 7.79 (d, J=7.98 Hz, 1H), 7.35 (d, J=1.53 Hz, 1H), 7.34 (d, J=1.23 Hz, 1H), 7.30 (dd, J=7.98, 1.53 Hz, 1H), 7.27 (dd, J=8.29, 1.53 Hz, 1H), 6.89-7.03 (m, 4H), 6.75 (d, J=1.84 Hz, 1H), 6.67 (m, 1H), 6.59 (dd, J=7.98, 1.84 Hz, 1H), 4.34 (d, J=5.83 Hz, 2H), 3.99 (s, 3H).

EXAMPLE 65

2-methoxy-4-(11-oxo-10,11-dihydro-5H-dibenzo[b,e][1,4]diazepin-3-yl)benzamide

The desired product was prepared by substituting 4-chloro-2-methoxybenzamide for Example 59B in Example 59C. MS (DCI) m/e 360 $(M+H)^+$, 377 $(M+NH_4)^+$; $^1H$ NMR (500 MHz, DMSO-$d_6$) δ 9.89 (s, 1H), 8.00 (s, 1H), 7.91 (d, J=8.1 Hz, 1H), 7.79 (d, J=8.0 Hz, 1H), 7.70 (s, 1H), 7.60 (d, J=1.2 Hz, 1H), 7.36 (d, J=1.8 Hz, 1H), 7.33 (s, 1H), 6.89-7.04 (m, 4H), 4.00 (s, 3H).

EXAMPLE 66 methyl [3-(5-methoxy-2-methyl-4-nitrophenyl)-11-oxo-10,11-dihydro-5H-dibenzo[b,e][1,4]diazepin-8-yl]acetate

EXAMPLE 66A 1-chloro-5-methoxy-2-methyl-4-nitrobenzene

Acetic anhydride (10 mL) at −10° C. was treated with concentrated nitric acid (>69% pure, 1 mL) and then treated portionwise with 2-chloro-4-methoxy-1-methylbenzene (0.78 g, 5 mmol) at a rate that maintained the internal temperature lower than −5° C. The solution was stirred for additional one hour while warming to room temperature, poured into an ice and water mixture, and extracted with ethyl acetate several times. The organic layers were combined, washed with 10% $Na_2CO_3$ and brine, dried ($MgSO_4$), and concentrated under vacuum. The residue was purified by flash column chromatography on silica gel eluting with 9:1 hexanes/ethyl acetate to provide 0.75 g (71%) of the desired product. MS (DCI) m/e 219 $(M+NH_4)^+$; $^1H$ NMR ($CDCl_3$, 300 MHz) δ 7.78 (s, 1H), 7.09 (s, 1H), 3.94 (s, 3H), 2.35 (s, 3H).

EXAMPLE 66B methyl [3-(5-methoxy-2-methyl-4-nitrophenyl)-11-oxo-10,11-dihydro-5H-dibenzo[b,e][1,4]diazepin-8-yl]acetate The desired product was prepared by substituting Example 66A and Example 54A for Example 59B and Example 56A, respectively, in Example 59C. MS (DCI) m/e 447 $(M+H)^+$; $^1H$ NMR (500 MHz, DMSO-$d_6$) δ 9.87 (s, 1H), 7.95 (s, 1H), 7.86 (s, 1H), 7.77 (d, J=8.0 Hz, 1H), 7.16 (s, 1H), 7.00 (d, J=1.5 Hz, 1H), 6.92-6.95 (m, 2H), 6.85-6.88 (m, 2H), 3.91 (s, 3H), 3.60 (s, 3H), 3.54 (s, 2H), 2.21 (s, 3H).

EXAMPLE 67 methyl [3-(4-cyano-5-methoxy-2-methylphenyl)-11-oxo-10,11-dihydro-5H-dibenzo[b,e][1,4]diazepin-8-yl]acetate

EXAMPLE 67A 1-chloro-4-iodo-5-methoxy-2-methylbenzene

The desired product was prepared by substituting 4-chloro-2-methoxy-5-methylaniline for Example 57A in Example 57B. MS (DCI) m/e 283 (M+H)$^+$; $^1$H NMR (300 MHz, CDCl$_3$) δ 7.62 (s, 1H), 6.80 (s, 1H), 3.85 (s, 3H), 2.27 (s, 3H).

EXAMPLE 67B 4-chloro-2-methoxy-5-methylbenzonitrile

The desired product was prepared by substituting Example 67A for Example 59A in Example 60A. MS (DCI) m/e 199 (M+NH$_4$)$^+$; $^1$H NMR (300 MHz, CDCl$_3$) δ 7.40 (s, 1H), 6.98 (s, 1H), 3.91 (s, 3H), 2.31 (s, 3H).

EXAMPLE 67C methyl [3-(4-cyano-5-methoxy-2-methylphenyl)-11-oxo-10,11-dihydro-5H-dibenzo[b,e][1,4]diazepin-8-yl]acetate The desired product was prepared by substituting Example 54A and Example 67B for Example 56A and Example 59B, respectively, in Example 59C. MS (DCI) m/e 428 (M+H)$^+$; $^1$H NMR (500 MHz, DMSO-d$_6$) δ 9.86 (s, 1H), 7.93 (s, 1H), 7.76 (d, J=8.1 Hz, 1H), 7.68 (s, 1H), 7.05 (s, 1H), 6.99 (d, J=1.6 Hz, 1H), 6.96 (d, J=8.1 Hz, 1H), 6.90-6.94 (m, 2H), 6.85-6.87 (m, 2H), 3.90 (s, 3H), 3.60 (s, 3H), 3.54 (s, 2H), 2.17 (s, 3H).

EXAMPLE 68

3-(2-methoxy-4-pyridinyl)-5,10-dihydro-11H-dibenzo[b,e][1,4]diazepin-11-one

EXAMPLE 68A 2-fluoro-3-iodopyridine

A −40° C. solution of diethylamine (12.4 g, 125 mmol) in THF (100 mL) was treated dropwise with 1.6 M n-butyllithiumi in hexane (79 mL, 125 mmol), stirred at 0° C. briefly, cooled to −78° C., treated with a solution of 2-fluororpyridine (9.71 g, 100 mmol) in THF (80 mL), stirred at −78° C. for 2 hours, treated with a solution of iodine (34.48 g, 120 mmol) in THF (100 mL), and stirred overnight while gradually warming to room temperature. The reaction mixture was poured into water (1 L) and extracted with diethyl ether several times. The combined extracts were washed with water, Na$_2$S$_2$O$_3$, and brine, dried (MgSO$_4$), filtered, and concentrated under vacuum. The residue was purified by flash column chromatography on silica gel eluting with 25:1 hexanes/ethyl acetate to provide 15.9 g (71%) of the desired product.

EXAMPLE 68B 2-fluoro-4-iodopyridine

A −40° C. solution of diethylamine (5.51 g, 55.5 mmol) in THF (80 mL) was treated dropwise with 2.5 M n-butyllithium in hexane (22.2 mL, 55.5 mmol), stirred at 0° C. briefly, cooled to −78° C., treated with a solution of Example 68A (9.9 g, 44.4 mmol) in THF (80 mL), stirred at −78° C. for 2 hours, treated with water (3.6 g, 200 mmol), stirred for 5 minutes, then poured into water (500 mL), and extracted with diethyl ether several times. The combined extracts were washed water and brine, dried (MgSO$_4$), filtered and concentrated under vacuum. The residue was purified by flash column chromatography on silica gel eluting with 25:1 hexanes/ethyl acetate to provide 9.5 g (96%) of the desired product.

EXAMPLE 68C 3-(2-fluoro-4-pyridinyl)-5,10-dihydro-11H-dibenzo[b,e][1,4]diazepin-11-one The desired product was prepared by substituting Example 68B and Example 56A for Example 9 and 2-methoxy-4-(4,4,5,5-tetramethyl-1,3,2-dioxaborolan-2-yl)phenol, respectively, in Example 10. MS (DCI) m/e 428 (M+H)$^+$; $^1$H NMR (500 MHz, DMSO-d$_6$) δ 9.92 (s, 1H), 8.35 (d, J=5.3 Hz, 1H), 8.00 (s, 1H), 7.82 (d, J=8.1 Hz, 1H), 7.60-7.62 (m, 1H), 7.44 (s, 1H), 7.42 (s, 1H), 7.34 (dd, J=8.1, 1.9 Hz, 1H), 6.91-7.03 (m, 4H).

EXAMPLE 68D 3-(2-methoxy-4-pyridinyl)-5,10-dihydro-11H-dibenzo[b,e][1,4]diazepin-11-one A mixture of sodium (14 mg, 0.6 mmol) in methanol (5 mL) was treated with Example 68C (46 mg, 0.15 mmol), heated to reflux until a homogeneous solution formed, and concentrated. The residue was diluted with water (10 mL), adjusted to pH 5 with 10% HCl, and extracted with ethyl acetate several times. The combined extracts were washed with brine, dried (MgSO$_4$), filtered, and concentrated under vacuum. The residue was purified by flash column chromatography on silica gel eluting with 3:2 hexanes/ethyl acetate to provide 35 mg (74%) of the desired product. MS (DCI) m/e 318 (M+H)$^+$; $^1$H NMR (500 MHz, DMSO-d$_6$) δ 9.89 (s, 1H), 8.26 (d, J=5.5 Hz, 1H), 7.97 (s, 1H), 7.79 (d, J=8.3 Hz, 1H), 7.38 (d, J=1.8 Hz, 1H), 7.27 (dd, J=8.3, 1.7 Hz, 1H), 7.24 (dd, J=5.5, 1.5 Hz, 1H), 6.90-7.03 (m, 5H).

EXAMPLE 69

3-(2-methoxy-4-pyridinyl)-11-oxoN[3-(1-pyrrolidinyl)propyl]-10,11-dihydro-5H-dibenzo[b,e][1,4]diazepine-8-carboxamide

EXAMPLE 69A 2-fluoro-4-(4,4,5,5-tetramethyl-1,3,2-dioxaborolan-2-yl)pyridine

A −78° C. solution of Example 68B (3.35 g, 15 mmol) diethyl ether (100 mL) was treated dropwise with 2.5 M n-butyllithium (7.2 mL, 18 mmol), stirred for 2 hours at −78° C., treated with tributyl borate (4.14 g, 18 mmol), stirred at −78° C. for one hour and warmed to room temperature over 2 hours. The solution was treated with pinacol (2.30 g, 19.5 mmol) and acetic acid (0.9 g, 15 mmol), stirred overnight, and filtered through diatomaceous earth (Celite®). The pad was washed with diethyl ether several times and the filtrate was concentrated to a volume of 50 mL. The mixture was diluted with ethyl acetate, washed with water and brine, dried (MgSO$_4$), filtered, and concentrated under vacuum. The residue was purified by flash column chromatography on silica gel eluting with 25:1 hexanes/ethyl acetate to provide 2.34 g (70%) of the desired product. MS (DCI) m/e 224 (M+H)$^+$; $^1$H NMR (300 MHz, CDCl$_3$,) δ 8.24 (d, J=5.1 Hz, 1H), 7.50 (dd, J=4.8, 2.7 Hz, 1H), 7.23 (d, J=2.4 Hz, 1H), 1.36 (s, 12H).

EXAMPLE 69B methyl 3-(2-fluoro-4-pyridinyl)-11-oxo-10,11-dihydro-5H-dibenzo[b,e][1,4]diazepine-8-carboxylate The desired product was prepared by substituting Example 69A and Example 1B for Example 56A and Example 59B, respectively, in Example 59C. MS (DCI) m/e 364 (M+H)$^+$, 381 (M+NH$_4$)$^+$; $^1$H NMR (500 MHz, DMSO-d$_6$) δ 10.05 (s, 1H), 8.48 (s, 1H), 8.36 (d, J=5.3 Hz, 1H), 7.85 (d, J=8.1 Hz, 1H), 7.62 (m, 2H), 7.57 (dd, J=8.3, 2.0 Hz, 1H), 7.45 (s, 1H), 7.24 (t, J=2.3 Hz, 1H), 7.37 (dd, J=8.1, 1.9 Hz, 1H), 7.08 (d, J=8.4 Hz, 1H), 3.61 (s, 3H).

EXAMPLE 69C 3-(2-fluoro-4-pyridinyl)-11-oxo-10,11-dihydro-5H-dibenzo[b,e][1,4]diazepine-8-carboxylic acid A mixture of Example 69B (60 mg, 0.17 mmol) and LiOH (20 mg, 0.85 mmol) in water (5 mL) and THF (5 mL) was heated to reflux until a homogeneous solution formed, adjusted to pH 5 with 10% HCl, and extracted with ethyl acetate several times. The combined extracts were washed with brine, dried (CaCl$_2$), filtered, and concentrated under vacuum to provide 47 mg (80%) of the desired product. MS (DCI) m/e 349 (M)$^+$; $^1$H NMR (500 MHz, DMSO-d$_6$) δ 10.03 (s, 1H), 8.42 (s, 1H), 8.36 (d, J=5.3 Hz, 1H), 7.85 (d, J=8.4 Hz, 1H), 7.62 (d, J=5.3 Hz, 1H), 7.60 (d, J=1.6 Hz, 1H), 7.55 (dd, J=8.4, 1.9 Hz, 1H), 7.45 (s, 1H), 7.24 (d, J=1.6 Hz, 1H), 7.37 (dd, J=8.1, 1.9 Hz, 1H), 7.05 (d, J=8.4 Hz, 1H).

EXAMPLE 69D 3-(2-fluoro-4-pyridinyl)-11-oxoN[3-(1-pyrrolidinyl)propyl]-10,11-dihydro-5H-dibenzo[b,e][1,4]diazepine-8-carboxamide The desired product was prepared by substituting Example 69C for Example 13 in Example 14. MS (DCI) m/e 460 (M+H)$^+$; $^1$H NMR (500 MHz, DMSO-d$_6$, TFA salt) δ 10.01 (s, 1H), 9.47 (s, 1H), 8.41 (t, J=5.6 Hz, 1H), 8.36 (d, J=5.3 Hz, 1H), 8.33 (s, 1H), 7.83 (d, J=7.3 Hz, 1H), 7.62 (d, J=5.3 Hz, 1H), 7.42-7.50 (m, 4H), 7.37 (d, J=8.3, 1.7 Hz, 1H), 7.04 (d, J=8.4 Hz, 1H), 3.53-3.56 (m, 2H), 3.28-3.31 (m, 2H), 3.14-3.17 (m, 2H), 2.96-3.00 (m, 2H), 1.99-2.02 (m, 2H), 1.84-1.88 (m, 4H).

EXAMPLE 69E 3-(2-methoxy-4-pyridinyl)-11-oxoN[3-(1-pyrrolidinyl)propyl]-10,11-dihydro-5H-dibenzo[b,e][1,4]diazepine-8-carboxamide The desired product was prepared by substituting Example 69D for Example 68C in Example 68D. MS (DCI) m/e 472 (M+H)$^+$; $^1$H NMR (500 MHz, DMSO-d$_6$) δ 9.95 (s, 1H), 8.33 (t, J=5.5 Hz, 1H), 8.25-8.27 (m, 2H), 7.80 (d, J=8.1 Hz, 1H), 7.47 (d, J=1.9 Hz, 1H), 7.42 (dd, J=8.3, 2.0 Hz, 1H), 7.37 (d, J=1.9 Hz, 1H), 7.29 (dd, J=8.3, 1.7 Hz, 1H), 7.24 (dd, J=5.3, 1.6 Hz, 1H), 7.01-7.04 (m, 2H), 3.91 (s, 3H), 3.24-3.28 (m, 2H), 2.41-2.44 (m, 6H), 1.65-1.68 (m, 6H).

EXAMPLE 70

11-oxo-3-(2-oxo-1,2-dihydro-4-pyridinyl)N[3-(1-pyrrolidinyl)propyl]-10,11-dihydro-5H-dibenzo[b,e][1,4]diazepine-8-carboxamide A solution of Example 69D (TFA salt, 150 mg) in acetic acid (25 mL) and water (5 mL) was heated to 100° C. for 16 hours, cooled to room temperature, and concentrated under vacuum. The residue was purified by preparative HPLC to provide 120 mg of the desired product as the TFA salt. MS (DCI) m/e 458 (M+H)$^+$; $^1$H NMR (500 MHz, DMSO-d$_6$) δ 11.12 (br s, 1H), 9.98 (s, 1H), 9.56 (s, 1H), 8.42 (s, 1H), 8.28 (d, J=2.8 Hz, 1H), 7.79 (dd, J=8.1, 2.9 Hz, 1H), 7.45-7.50 (m, 3H), 7.31 (s, 1H), 7.21 (dd, J=8.3, 1.9 Hz, 1H), 7.04 (dd, J=8.3, 2.8 Hz, 1H), 6.54 (s, 1H), 6.41-6.43 (m, 1H), 3.54-3.58 (m, 2H), 3.30-3.32 (m, 2H), 3.15-3.17 (m, 2H), 2.97-3.04 (m, 2H), 2.01 (m, 2H), 1.86-1.87 (m, 4H).

EXAMPLE 71 methyl [3-(2-fluoro-5-methyl-4-pyridinyl)-11-oxo-10,11-dihydro-5H-dibenzo[b,e][1,4]diazepin-8-yl]acetate

EXAMPLE 71A 2-fluoro-3-iodo-5-methylpyridine

The desired product was prepared by substituting 2-fluoro-5-methylpyridine for 2-fluoropyridine in Example 68A. MS (DCI) m/e 238 (M+H)$^+$.

EXAMPLE 71B 2-fluoro-4-iodo-5-methylpyridine

The desired product was prepared by substituting Example 71A for Example 69A in Example 69B. MS (DCI) m/e 238 (M+H)$^+$.

EXAMPLE 71C 2-fluoro-5-methyl-4-(4,4,5,5,-tetramethyl-1,3,2-dioxaborolan-2-yl)pyridine The desired product was prepared by substituting Example 71B for Example 68B in Example 69A. MS (DCI) m/e 237 (M)$^+$; $^1$H NMR (300 MHz, CDCl$_3$) δ 8.00 (s, 1H), 7.22 (d, J=2.2 Hz, 1H), 2.44 (s, 3H), 1.36 (s, 12H).

EXAMPLE 71D methyl [3-(2-fluoro-5-methyl-4-pyridinyl)-11-oxo-10,11-dihydro-5H-dibenzo[b,e][1,4]diazepin-8-yl]acetate The desired product was prepared by substituting Example 71C and Example 6D for Example 56A and Example 59B, respectively, in Example 59C. MS (DCI) m/e 392 (M+H)$^+$, 409 (M+NH$_4$)$^+$; $^1$H NMR (500 MHz, DMSO-d$_6$) δ 9.90 (s, 1H), 8.18 (s, 1H), 7.96 (s, 1H), 7.78 (d, J=8.0 Hz, 1H), 7.08 (d, J=1.8 Hz, 1H), 7.03 (d, J=1.2 Hz, 1H), 6.92-6.97 (m, 2H), 6.85-6.88 (m, 2H), 3.60 (s, 3H), 3.54 (s, 2H), 2.22 (s, 3H).

EXAMPLE 72 methyl [3-(2-methoxy-5-methyl-4-pyridinyl)-11-oxo-10,11-dihydro-5H-dibenzo[b,e][1,4]diazepin-8-yl]acetate A mixture of sodium (18 mg, 0.8 mmol) in methanol (5 mL) was treated with Example 71D (30 mg, 0.077 mmol), heated to reflux for 24 hours, and concentrated under vacuum. The residue was diluted with water (10 mL), adjusted to pH 5 with 10% HCl, and extracted with ethyl acetate several times. The combined extracts were washed with brine, dried (MgSO$_4$), filtered, and concentrated under vacuum. The residue was treated with excess 2.0M TMSCHN$_2$ in hexanes and concentrated to provide the desired product. MS (DCI) m/e 404 (M+H)$^+$; $^1$H NMR (500 MHz, DMSO-d$_6$) δ 9.86 (s, 1H), 8.08 (d, J=5.5 Hz, 1H), 7.92 (s, 1H), 7.74 (d, J=8.0 Hz, 1H), 6.98 (s, 1H), 6.84-6.93 (m, 4H), 6.64 (s, 1H), 3.84 (s, 3H), 3.59 (s, 3H), 3.53 (s, 2H), 2.13 (s, 3H).

EXAMPLE 73

[3-(3-methoxy-4-nitrophenyl)-11-oxo-10,11-dihydro-5H-dibenzo[b,e][1,4]diazepin-8-yl]acetic acid The desired product was prepared by substituting Example 51 for Example 12 in Example 13. MS (ESI) m/e 418 (M–H)$^-$; $^1$H NMR (300 MHz, DMSO-d$_6$) δ 12.28 (s, 1H), 9.90 (s, 1H), 8.00-8.03 (m, 2H), 7.80 (d, J=8.1 Hz, 1H), 7.52 (d, J=1.7 Hz, 1H), 7.29-7.36 (m, 3H), 6.96 (m, 1H), 6.84-6.87 (m, 2H), 4.03 (s, 3H), 3.43 (s, 2H).

EXAMPLE 74

2-[3-(3-methoxy-4-nitrophenyl)-11-oxo-10,11-dihydro-5H-dibenzo[b,e][1,4]diazepin-8-yl]N[3-(1-pyrrolidinyl)propyl]acetamide The desired product was prepared by substituting Example 73 for Example 13 in Example 14. MS (ESI) m/e 528 (M–H)$^-$; $^1$H NMR (400 MHz, DMSO-d$_6$) δ 9.93 (s, 1H), 8.12 (t, 1H), 8.02 (d, 1H), 8.00 (s, 1H), 7.80 (d, 1H), 7.52 (d, 1H), 7.35 (t, 1H), 7.33 (t, 1H), 7.30 (d, 1H), 6.95 (d, 1H), 6.86-6.88 (m, 2H), 4.03 (s, 3H), 3.48 (b, 2H), 3.29 (s, 2h), 3.07-3.12 (q, 2H), 3.00-3.06 (m, 2H), 2.86-2.95 (m, 2H), 1.91-1.99 (m, 2H), 1.70-1.84 (m, 4H).

EXAMPLE 75

N-[2-(dimethylamino)ethyl]-2-[3-(3-methoxy-4-nitrophenyl)-11-oxo-10,11-dihydro-5H-dibenzo[b,e][1,4]diazepin-8-yl]Nmethylacetamide The desired product was prepared by substituting Example 73 and N-[2-(dimethylamino)ethyl]Nmethylamine for Example 13 and 3-pyrrolidin-1-ylpropylamine, respectively, in Example 14. MS (ESI) m/e 502 (M–H)$^-$; $^1$H NMR (500 MHz, DMSO-d$_6$) δ 9.86 (s, 1H), 8.01 (d, J=8.11 Hz, 2H), 7.95 (s, 1H), 7.79 (d, J=8.11 Hz, 1H), 7.52 (d, J=1.56 Hz, 1H), 7.33-7.35 (m, 2H), 7.30 (dd, J=8.11, 1.56 Hz, 1H), 6.95 (d, J=8.11 Hz, 1H), 6.84 (d, J=2.18 Hz, 1H), 6.82 (d, J=8.11 Hz, 1H), 4.03 (s, 3H), 3.56 (s, 1H), 3.54 (s, 1H), 3.35 (t, J=6.86 Hz, 2H), 2.96 (s, 2H), 2.81 (s, 1H), 2.32 (t, J=6.86 Hz, 2H), 2.14 (d, J=2.50 Hz, 6H).

EXAMPLE 76

8-[2-(3-hydroxy-1-piperidinyl)-2-oxoethyl]-3-(3-methoxy-4-nitrophenyl)-5,10-dihydro-11H-dibenzo[b,e][1,4]diazepin-11-one The desired product was prepared by substituting Example 73 and 3-piperidinol for Example 13 and 3-pyrrolidin-1-yl-propylamine, respectively, in Example 14. MS (ESI) m/e 501 (M–H)$^-$; $^1$H NMR (500 MHz, DMSO-d$_6$) δ 9.87 (d, J=2.81 Hz, 1H), 8.01 (d, J=8.42 Hz, 2H), 7.96 (s, 1H), 7.80 (d, J=8.42 Hz, 1H), 7.52 (d, J=1.56 Hz, 1H), 7.33-7.35 (m, 2H), 7.29 (dd, J=8.11, 1.56 Hz, 1H), 6.95 (d, J=7.80 Hz, 1H), 6.80-6.85 (m, 2H), 4.79-4.84 (m, 2H), 4.03 (s, 3H), 3.42 (m, 4H), 2.93-3.07 (m, 2H), 1.80 (m, 1H), 1.62 (m, 1H), 1.39 (m, 1H), 1.23 (m, 1H).

EXAMPLE 77

3-(3-methoxy-4-nitrophenyl)-8-[2-(4-methyl-1,4-diazepan-1-yl)-2-oxoethyl]-5,10-dihydro-11H-dibenzo[b,e][1,4]diazepin-11-one The desired product was prepared by substituting Example 73 and 1-methyl-1,4-diazepane for Example 13 and 3-pyrrolidin-1-ylpropylamine, respectively, in Example 14. MS (ESI) m/e 514 (M–H)$^-$; $^1$H NMR (500 MHz, DMSO-d$_6$) δ 9.89 (s, 1H), 8.01 (d, J=8.14 Hz, 1H), 7.98 (s, 1H), 7.79 (d, J=8.14 Hz, 1H), 7.52 (d, J=1.36 Hz, 1H), 7.28-7.36 (m, 3H), 6.95 (d, J=8.14 Hz, 1H), 6.81-6.85 (m, 2H), 4.03 (s, 3H), 3.56 (s, 2H), 3.38-3.53 (m, 6H), 2.54 (m, 1H), 2.47 (m, 1H), 2.25 (d, J=4.41 Hz, 3H), 1.71-1.80 (m, 2H).

EXAMPLE 78

2-[3-(3-methoxy-4-nitrophenyl)-11-oxo-10,11-dihydro-5H-dibenzo[b,e][1,4]diazepin-8-yl]-N,N-dimethylacetamide The desired product was prepared by substituting Example 73 and N,N-dimethylamine for Example 13 and 3-pyrrolidin-1-ylpropylamine, respectively, in Example 14. MS (ESI) m/e 445 (M–H)$^-$; $^1$H NMR (300 MHz, DMSO-d$_6$) δ 9.88 (s, 1H), 8.01 (d, J=8.48 Hz, 1H), 7.97 (s, 1H), 7.79 (d, J=8.14 Hz, 1H), 7.52 (d, J=1.70 Hz, 1H), 7.32-7.36 (m, 2H), 7.28-7.32 (dd, J=8.14, 1.70 Hz, 1H) 6.95 (d, J=7.80 Hz, 1H), 6.80-6.85 (m, 2H), 4.03 (s, 3H), 3.55 (s, 2H), 2.97 (s, 3H), 2.81 (s, 3H).

EXAMPLE 79

8-[2-(4-hydroxy-1-piperidinyl)-2-oxoethyl]-3-(3-methoxy-4-nitrophenyl)-5,10-dihydro-11H-dibenzo[b,e][1,4]diazepin-11-one The desired product was prepared by substituting Example 73 and 4-piperidinol for Example 13 and 3-pyrrolidin-1-yl-propylamine, respectively, in Example 14. MS (ESI) m/e 501 (M–H)$^-$; $^1$H NMR (500 MHz, DMSO-d$_6$) δ 9.87 (s, 1H), 8.01 (d, J=8.42 Hz, 1H), 7.96 (s, 1H), 7.80 (d, J=8.11 Hz, 1H), 7.52 (d, J=1.56 Hz, 1H), 7.34-7.35 (m, 2H), 7.29 (dd, J=8.27, 1.72 Hz, 1H), 6.94 (d, J=7.80 Hz, 1H), 6.81-6.84 (m, 2H), 4.67 (s, 1H), 4.03 (s, 3H), 3.88-3.91 (m, 1H), 3.63-3.69 (m, 2H), 3.56 (s, 2H), 3.10-3.15 (m, 1H), 2.96-3.01 (m, 1H), 1.61-1.67 (m, 2H), 1.15-1.24 (m, 2H).

Example 80 to Example 118 were Prepared Using the Following Procedure

Syntheses were performed using a PE Biosystems (Applied Biosystems) Solaris 530 organic synthesizer. Each of the round bottom flasks was charged with 81 mg of polymer-supported (PS)-DCC resin (loading 1.24 mmol/g) supplied by Argonaut Technologies. The reaction block was then assembled and placed on the Solaris 530. The amine monomers (0.6 mmol) were each dissolved in 3 mL of DMA. Example 73 (MW 419.11) was dissolved in 40 mL of DMA (747 mg, 1.78 mmol). Solutions of HOBt (409 g, 3.0 mmol) in 68 mL of DMA and DIEA (1.580 mL in 68 mL DMA) were placed on the instrument. The Solaris was primed with DMA then into each of the 48 vials containing PS-DCC resin was added 0.75 mL of the Example 73 solution (0.033 mmol) followed by 0.75 mL of HOBt solution (1 equivalent), 0.209 mL of each amine solution (1.25 equivalents) and 0.75 mL of DIEA solution (3 equivalents). The reactions were heated to 55° C. overnight and transferred with methanol to 20 mL vials containing 39 mg MP-Carbonate resin (2.55 mmol/g, 3 equivalents). The MP-Carbonate resin was filtered and the reactions were concentrated to dryness. The residues were dissolved in 1:1 DMSO/methanol and purified by reverse phase HPLC using 10:100 acetonitrile/0.1% aqueous TFA.

EXAMPLE 80

2-[3-(3-methoxy-4-nitrophenyl)-11-oxo-10,11-dihydro-5H-dibenzo[b,e][1,4]diazepin-8-yl]N[2-(2-pyridinyl)ethyl]acetamide The desired product was prepared using 2-(2-pyridinyl)ethylamine. MS (ESI) 524 (M+H)$^+$; $^1$H NMR (DMSO-d$_6$) □ 9.86 (s, 1H), 8.61 (d, J=4.7 Hz, 1H), 8.02 (m, 3H), 7.95 (s, 1H), 7.81 (d, J=8.1 Hz, 1H), 7.51 (m, 3H), 7.34 (m, 2H), 7.30 (dd, J=8.3, 1.7 Hz, 1H), 6.92 (d, J=8.1 Hz, 1H), 6.80 (m, 2H), 4.03 (s, 3H), 3.43 (m, 2H), 3.23 (s, 2H), 2.98 (m, 2H).

EXAMPLE 81

2-[3-(3-methoxy-4-nitrophenyl)-11-oxo-10,11-dihydro-5H-dibenzo[b,e][1,4]diazepin-8-yl]NF 2-(3-pyridinyl)ethyl]acetamide The desired product was prepared using 2-(3-pyridinyl)ethylamine. MS (ESI) 524 (M+H)$^+$; $^1$H NMR (DMSO-d$_6$) □ 9.86 (s, 1H), 8.63 (s, 1H), 8.58 (d, J=5.0 Hz, 1H), 8.03 (m, 3H), 7.95 (s, 1H), 7.81 (d, J=8.1 Hz, 1H), 7.62 (m, 1H), 7.52 (s, 1H), 7.34 (m, 2H), 7.30 (dd, J=8.3, 1.7 Hz, 1H), 6.93 (d, J=8.1 Hz, 1H), 6.80 (m, 2H), 4.03 (s, 3H), 3.34 (m, 2H), 3.24 (s, 2H), 2.83 (m, 2H).

EXAMPLE 82

2-[3-(3-Methoxy-4-nitro-phenyl)-11-oxo-10,11-dihydro-5H-dibenzo[b,e][1,4]diazepin-8-yl]N(4-pyridin-2-yl-ethyl)-acetamide The desired product was prepared using 2-(4-pyridinyl)ethylamine. MS (ESI) 524 (M+H)$^+$; $^1$H NMR (DMSO-d$_6$) □ 9.87 (s, 1H), 8.65 (d, J=5.3 Hz, 2H), 8.05 (br t, J=5.6 Hz, 1H), 8.01 (d, J=8.4 Hz, 1H), 7.95 (s, 1H), 7.81 (d, J=8.4 Hz, 1H), 7.64 (m, 2H), 7.52 (s, 1H), 7.34 (m, 2H), 7.30 (dd, J=8.1, 1.9 Hz, 1H), 6.93 (d, J=8.1 Hz, 1H), 6.80 (m, 2H), 4.03 (s, 3H), 3.34 (m, 2H), 3.24 (s, 2H), 2.83 (m, 2H).

EXAMPLE 83

2-[3-(3-methoxy-4-nitrophenyl)-11-oxo-10,11-dihydro-5H-dibenzo[b,e][1,4]diazepin-8-yl]N3-quinolinylacetamide The desired product was prepared using 3-quinolinamine. MS (ESI) 546 (M+H)$^+$; $^1$H NMR (DMSO-d$_6$) □ 10.60 (s, 1H), 9.91 (s, 1H), 8.93 (d, J=2.5 Hz, 1H), 8.68 (d, J=2.2 Hz, 1H), 8.01 (m, 2H), 7.96 (d, J=8.1 Hz, 1H), 7.90 (d, J=7.8 Hz, 1H), 7.80 (d, J=8.1 Hz, 1H), 7.64 (m, 1H), 7.57 (m, 1H), 7.53 (d, J=1.6 Hz, 1H), 7.35 (m, 2H), 7.30 (dd, J=8.1, 1.6 Hz, 1H), 6.99 (m, 3H), 4.03 (s, 3H), 3.62 (s, 2H).

EXAMPLE 84

2-[3-(3-methoxy-4-nitrophenyl)-11-oxo-10,11-dihydro-5H-dibenzo[b,e][1,4]diazepin-8-yl]N6-quinolinylacetamide The desired product was prepared using 6-quinolinamine. MS (ESI) 544 (M−H)$^-$; $^1$H NMR (DMSO-d$_6$) □ 10.53 (s, 1H), 9.92 (s, 1H), 8.87 (d, J=3.1 Hz, 1H), 8.45 (m, 2H), 8.02 (m, 3H), 7.89 (dd, J=9.4, 2.2 Hz, 1H), 7.80 (d, J=8.1 Hz, 1H), 7.61 (dd, J=8.4, 4.4 Hz, 1H), 7.52 (d, J=1.6 Hz, 1H), 7.35 (m, 2H), 7.30 (dd, J=8.3, 1.7 Hz, 1H), 6.98 (m, 3H), 4.03 (s, 3H), 3.61 (s, 2H).

EXAMPLE 85

2-[3-(3-methoxy-4-nitrophenyl)-11-oxo-10,11-dihydro-5H-dibenzo[b,e][1,4]diazepin-8-yl]N[4-(4-morpholinyl)phenyl]acetamide The desired product was prepared using 4-(4-morpholinyl)aniline. MS (ESI) 580 (M+H)$^+$; $^1$H NMR (DMSO-d$_6$) □ 9.90 (s, 1H), 9.87 (s, 1H), 8.01 (d, J=8.4 Hz, 1H), 7.96 (s, 1H), 7.80 (d, J=8.1 Hz, 1H), 7.52 (d, J=1.2 Hz, 1H), 7.44 (d, J=9.0 Hz, 2H), 7.35 (m, 2H), 7.30 (dd, J=8.3, 1.7 Hz, 1H), 6.95 (m, 3H), 6.88 (d, J=9.0 Hz, 2H), 4.03 (s, 3H), 3.72 (m, 4H), 3.48 (s, 2H), 3.03 (m, 4H).

EXAMPLE 86

N-[(1S)-1-(hydroxymethyl)-2-methylpropyl]-2-[3-(3-methoxy-4-nitrophenyl)-11-oxo-10,11-dihydro-5H-dibenzo[b,e][1,4]diazepin-8-yl]acetamide The desired product was prepared using (2S)-2-amino-3-methyl-1-butanol. MS (ESI) 505 (M+H)$^+$; $^1$H NMR (DMSO-d$_6$) □ 9.88 (s, 1H), 8.01 (d, J=8.4 Hz, 1H), 7.93 (s, 1H), 7.81 (d, J=8.1 Hz, 1H), 7.60 (d, J=8.7 Hz, 1H), 7.52 (d, J=1.2 Hz, 1H), 7.34 (m, 2H), 7.30 (dd, J=8.3, 1.7 Hz, 1H), 6.93 (m, 1H), 6.87 (m, 2H), 4.50 (br s, 1H), 4.03 (s, 3H), 3.53 (m, 1H), 3.35 (m, 2H), 3.25 (s, 2H), 1.81 (m, 1H), 0.83 (d, J=7.5 Hz, 3H), 0.79 (d, J=7.5 Hz, 3H).

EXAMPLE 87

N-[(1R)-1-(hydroxymethyl)-2-methylpropyl]-2-[3-(3-methoxy-4-nitrophenyl)-11-oxo-10,11-dihydro-5H-dibenzo[b,e][1,4]diazepin-8-yl]acetamide The desired product was prepared using (2R)-2-amino-3-methyl-1-butanol. MS (ESI) 505 (M+H)$^+$; $^1$H NMR (DMSO-d$_6$) □ 9.88 (s, 1H), 8.01 (d, J=8.4 Hz, 1H), 7.93 (s, 1H), 7.81 (d, J=8.1 Hz, 1H), 7.60 (d, J=8.7 Hz, 1H), 7.52 (d, J=1.2 Hz, 1H), 7.34 (m, 2H), 7.30 (dd, J=8.3, 1.7 Hz, 1H), 6.93 (m, 1H), 6.87 (m, 2H), 4.50 (br s, 1H), 4.03 (s, 3H), 3.53 (m, 1H), 3.35 (m, 2H), 3.25 (s, 2H), 1.81 (m, 1H), 0.83 (d, J=7.5 Hz, 3H), 0.79 (d, J=7.5 Hz, 3H).

EXAMPLE 88

N-(3-ethoxypropyl)-2-[3-(3-methoxy-4-nitrophenyl)-11-oxo-10,11-dihydro-5H-dibenzo[b,e][1,4]diazepin-8-yl]acetamide The desired product was prepared using 3-ethoxypropylamine. MS (ESI) 505 (M+H)$^+$; $^1$H NMR (DMSO-d$_6$) □ 9.88 (s, 1H), 8.01 (d, J=8.4 Hz, 1H), 7.93 (s, 1H), 7.88 (br t, J=5.3 Hz, 1H), 7.80 (d, J=8.1 Hz, 1H), 7.52 (d, J=1.6 Hz, 1H), 7.34 (m, 2H), 7.30 (dd, J=8.3, 1.7 Hz, 1H), 6.93 (d, J=8.1 Hz, 1H), 6.85 (m, 2H), 4.03 (s, 3H), 3.35 (m, 4H), 3.25 (s, 2H), 3.01 (q, J=7.5 Hz, 2H), 1.60 (m, 2H), 1.06 (t, J=7.5 Hz, 3H).

EXAMPLE 89

N-[2-(diethylamino)ethyl]-2-[3-(3-methoxy-4-nitrophenyl)-11-oxo-10,11-dihydro-5H-dibenzo[b,e][1,4]diazepin-8-yl]acetamide The desired product was prepared using N-(2-aminoethyl)-N,N-diethylamine. MS (ESI) 518 (M+H)$^+$; $^1$H NMR (DMSO-d$_6$) □ 9.88 (s, 1H), 9.12 (v br s, 1H), 8.26 (br t, J=5.6 Hz, 1H), 8.01 (d, J=8.4 Hz, 1H), 7.98 (s, 1H), 7.80 (d, J=8.1 Hz, 1H), 7.52 (d, J=1.6 Hz, 1H), 7.34 (m, 2H), 7.30 (dd, J=8.3, 1.7 Hz, 1H), 6.95 (d, J=8.1 Hz, 1H), 6.87 (m, 2H), 4.03 (s, 3H), 3.32 (s, 2H), 3.10 (m, 6H), 1.15 (t, J=7.3 Hz, 6H).

EXAMPLE 90

N-[(1R)-1-(hydroxymethyl)-3-methylbutyl]-2-[3-(3-methoxy-4-nitrophenyl)-11-oxo-10,11-dihydro-5H-dibenzo[b,e][1,4]diazepin-8-yl]acetamide The desired product was prepared using (2R)-2-amino-4-methyl-1-pentanol. MS (ESI) 519 (M+H)$^+$; $^1$H NMR (DMSO-d$_6$) □ 9.88 (s, 1H), 8.01 (d, J=8.4 Hz, 1H), 7.93 (s, 1H), 7.81 (d, J=8.1 Hz, 1H), 7.63 (d, J=8.4 Hz, 1H), 7.52 (d, J=1.6 Hz, 1H), 7.34 (m, 2H), 7.30 (dd, J=8.3, 1.7 Hz, 1H), 6.93 (d, J=8.1 Hz 1H), 6.87 (m, 2H), 4.57 (br s, 1H), 4.03 (s, 3H), 3.74 (m, 1H), 3.22 (m, 2H), 3.26 (s, 2H), 1.55 (m, 1H), 1.27 (m, 2), 0.84 (d, J=6.9 Hz, 3H), 0.79 (d, J=6.9 Hz, 3H).

EXAMPLE 91

N-[(1S)-1-(hydroxymethyl)-3-methylbutyl]-2-[3-(3-methoxy-4-nitrophenyl)-11-oxo-10,11-dihydro-5H-dibenzo[b,e][1,4]diazepin-8-yl]acetamide The desired product was prepared using (2S)-2-amino-4-methyl-1-pentanol. MS (ESI) 519 (M+H)$^+$; $^1$H NMR (DMSO-d$_6$) □ 9.88 (s, 1H), 8.01 (d, J=8.4 Hz, 1H), 7.93 (s, 1H), 7.81 (d, J=8.1 Hz, 1H), 7.63 (d, J=8.4 Hz, 1H), 7.52 (d, J=1.6 Hz, 1H), 7.34 (m, 2H), 7.30 (dd, J=8.3, 1.7 Hz, 1H), 6.93 (d, J=8.1 Hz 1H), 6.87 (m, 2H), 4.57 (br s, 1H), 4.03 (s, 3H), 3.74 (m, 1H), 3.22 (m, 2H), 3.26 (s, 2H), 1.55 (m, 1H), 1.27 (m, 2), 0.84 (d, J=6.9 Hz, 3H), 0.79 (d, J=6.9 Hz, 3H).

EXAMPLE 92

N-[3-(1H-imidazol-1-yl)propyl]-2-[3-(3-methoxy-4-nitrophenyl)-11-oxo-10,11-dihydro-5H-dibenzo[b,e][1,4]diazepin-8-yl]acetamide The desired product was prepared using 3-(1H-imidazol-1-yl)propylamine. MS (ESI) 527 (M+H)$^+$; $^1$H NMR (DMSO-d$_6$) □ 14.35 (v br s, 1H), 9.88 (s, 1H), 9.05 (s, 1H), 8.07 (br t, J=5.8 Hz, 1H), 8.01 (d, J=8.4 Hz, 1H), 7.96 (s, 1H), 7.80 (d, J=8.1 Hz, 1H), 7.75 (s, 1H), 7.67 (s, 1H), 7.52 (d, J=1.6 Hz, 1H), 7.34 (m, 2H), 7.30 (dd, J=8.3, 1.7 Hz, 1H), 6.93 (d, J=7.8 Hz, 1H), 6.85 (m, 2H), 4.17 (m, 2H), 4.03 (s, 3H), 3.29 (s, 2H), 3.03 (m, 2H), 1.94 (m, 2H).

EXAMPLE 93

N-(3-hydroxypropyl)-2-[3-(3-methoxy-4-nitrophenyl)-11-oxo-10,11-dihydro-5H-dibenzo[b,e][1,4]diazepin-8-yl]acetamide The desired product was prepared using 3-amino-1-propanol. MS (ESI) 477 (M+H)$^+$; $^1$H NMR (DMSO-d$_6$) □ 9.88 (s, 1H), 8.01 (d, J=8.4 Hz, 1H), 7.94 (s, 1H), 7.90 (br t, J=5.5 Hz, 1H), 7.80 (d, J=8.4 Hz, 1H), 7.52 (d, J=1.6 Hz, 1H), 7.34 (m, 2H), 7.30 (dd, J=8.3, 1.7 Hz, 1H), 6.93 (d, J=7.8 Hz, 1H), 6.85 (m, 2H), 4.37 (br s, 1H), 4.03 (s, 3H), 3.39 (m, 2H), 3.25 (s, 2H), 3.08 (m, 2H), 1.54 (m, 2H).

EXAMPLE 94

N-[3-(diethylamino)propyl]-2-[3-(3-methoxy-4-nitrophenyl)-11-oxo-10,11-dihydro-5H-dibenzo[b,e][1,4]diazepin-8-yl]acetamide The desired product was prepared using N-(3-aminopropyl)-N,N-diethylamine. MS (ESI) 532 (M+H)$^+$; $^1$H NMR (DMSO-d$_6$) □ 9.88 (s, 1H), 9.00 (v br s, 1H), 8.12 (br t, J=5.8 Hz, 1H), 8.01 (d, J=8.4 Hz, 1H), 7.96 (s, 1H), 7.80 (d, J=8.1 Hz, 1H), 7.52 (d, J=1.6 Hz, 1H), 7.34 (m, 2H), 7.30 (dd, J=8.3, 1.7 Hz, 1H), 6.95 (d, J=7.8 Hz, 1H), 6.87 (m, 2H), 4.03 (s, 3H), 3.28 (s, 2H), 3.12 (m, 2H), 3.05 (m, 4H), 2.95 (m, 2H), 1.72 (m, 2H), 1.10 (t, J=7.3 Hz, 6H).

EXAMPLE 95

N-[(1S)-2-hydroxy-1-phenylethyl]-2-[3-(3-methoxy-4-nitrophenyl)-11-oxo-10,11-dihydro-5H-dibenzo[b,e][1,4]diazepin-8-yl]acetamide The desired product was prepared using (2S)-2-amino-2-phenylethanol. MS (ESI) 539 (M+H)$^+$; $^1$H NMR (DMSO-d$_6$) □ 9.87 (s, 1H), 8.35 (d, J=8.1 Hz, 1H), 8.01 (d, J=8.4 Hz, 1H), 7.94 (s, 1H), 7.80 (d, J=8.1 Hz, 1H), 7.52 (d, J=1.2 Hz, 1H), 7.34 (m, 2H), 7.27 (m, 5H), 7.20 (m, 1H), 6.93 (d, J=7.8 Hz, 1H), 6.87 (m, 2H), 4.80 (m, 2H), 4.03 (s, 3H), 3.55 (d, J=6.2 Hz, 2H), 3.38 (s, 2H).

EXAMPLE 96

N-[(1R)-2-hydroxy-1-phenylethyl]-2-[3-(3-methoxy-4-nitrophenyl)-11-oxo-10,11-dihydro-5H-dibenzo[b,e][14]diazepin-8-yl]acetamide The desired product was prepared using (2R)-2-amino-2-phenylethanol. MS (ESI) 539 (M+H)$^+$; $^1$H NMR (DMSO-d$_6$) □ 9.87 (s, 1H), 8.35 (d, J=8.1 Hz, 1H), 8.01 (d, J=8.4 Hz, 1H), 7.94 (s, 1H), 7.80 (d, J=8.1 Hz, 1H), 7.52 (d, J=1.2 Hz, 1H), 7.34 (m, 2H), 7.27 (m, 5H), 7.20 (m, 1H), 6.93 (d, J=7.8 Hz, 1H), 6.87 (m, 2H), 4.80 (m, 2H), 4.03 (s, 3H), 3.55 (d, J=6.2 Hz, 2H), 3.38 (s, 2H).

EXAMPLE 97

N-(3,4-difluorobenzyl)-2-[3-(3-methoxy-4-nitrophenyl)-11-oxo-10,11-dihydro-5H-dibenzo[b,e][1,4]diazepin-8-yl]acetamide The desired product was prepared using 3,4-difluorobenzylamine. MS (ESI) 545 (M+H)+; $^1$H NMR (DMSO-d$_6$) □ 9.88 (s, 1H), 8.48 (br t, J=5.9 Hz, 1H), 8.01 (d, J=8.4 Hz, 1H), 7.96 (s, 1H), 7.80 (d, J=8.1 Hz, 1H), 7.52 (d, J=1.6 Hz, 1H), 7.35 (m, 3H), 7.30 (dd, J=8.3, 1.7 Hz, 1H), 7.24 (m, 1H), 7.06 (br m, 1H), 6.94 (d, J=7.8 Hz, 1H), 6.88 (m, 2H), 4.23 (d, J=5.9 Hz, 2H), 4.03 (s, 3H), 3.36 (s, 2H).

EXAMPLE 98

N-(4-hydroxybutyl)-2-[3-(3-methoxy-4-nitrophenyl)-11-oxo-10,11-dihydro-5H-dibenzo[b,e][1,4]diazepin-8-yl]acetamide The desired product was prepared using 4-amino-1-butanol. MS (ESI) 491 (M+H)+; $^1$H NMR (DMSO-d$_6$) □ 9.88 (s, 1H), 8.01 (d, J=8.4 Hz, 1H), 7.94 (s, 1H), 7.90 (br t, J=5.8 Hz, 1H), 7.80 (d, J=8.1 Hz, 1H), 7.52 (d, J=1.6 Hz, 1H), 7.34 (m, 2H), 7.30 (dd, J=8.3, 1.7 Hz, 1H), 6.93 (d, J=7.8 Hz, 1H), 6.85 (m, 2H), 4.37 (br t, J=6.2 Hz, 1H), 4.03 (s, 3H), 3.37 (m, 2H), 3.26 (s, 2H), 3.02 (m, 2H), 1.40 (m, 4H).

EXAMPLE 99

N-(1-benzyl-4-piperidinyl)-2-[3-(3-methoxy-4-nitrophenyl)-11-oxo-10,11-dihydro-5H-dibenzo[b,e][1,4]diazepin-8-yl]acetamide The desired product was prepared using 1-benzyl-4-piperidinamine. MS (ESI) 592 (M+H)+; $^1$H NMR (DMSO-d$_6$) □ 9.88 (s, 1H), 9.46 (br s, 1H), 8.05 (d, J=7.5 Hz, 1H), 8.01 (d, J=8.4 Hz, 1H), 7.95 (s, 1H), 7.80 (d, J=8.1 Hz, 1H), 7.50 (m, 6H), 7.34 (m, 2H), 7.30 (dd, J=8.3, 1.7 Hz, 1H), 6.93 (d, J=7.8 Hz, 1H), 6.85 (m, 2H), 4.27 (d, J=5.0 Hz, 2H), 4.03 (s, 3H), 3.72 (m, 1H), 3.27 (s, 2H), 3.04 (m, 2H), 1.90 (m, 2H), 1.60 (m, 2H).

EXAMPLE 100

N-[4-(dimethylamino)butyl]-2-[3-(3-methoxy-4-nitrophenyl)-11-oxo-10,11-dihydro-5H-dibenzo[b,e][1,4]diazepin-8-yl]acetamide The desired product was prepared using N-(4-aminobutyl)-N,N-dimethylamine. MS (ESI) 518 (M+H)+; $^1$H NMR (DMSO-d$_6$) □ 9.88 (s, 1H), 9.28 (v br s, 1H), 8.01 (m, 2H), 7.96 (s, 1H), 7.80 (d, J=8.1 Hz, 1H), 7.52 (d, J=1.6 Hz, 1H), 7.34 (m, 2H), 7.30 (dd, J=8.3, 1.7 Hz, 1H), 6.95 (d, J=7.8 Hz, 1H), 6.87 (m, 2H), 4.03 (s, 3H), 3.27 (s, 2H), 3.05 (m, 4H), 2.72 (s, 3H), 2.70 (s, 3H), 1.54 (m, 2H), 1.40 (m, 2H).

EXAMPLE 101

N-{2-[4-(aminosulfonyl)phenyl]ethyl}-2-[3-(3-methoxy-4-nitrophenyl)-11-oxo-10,11-dihydro-5H-dibenzo[b,e][1,4]diazepin-8-yl]acetamide The desired product was prepared using 4-(2-aminoethyl)benzenesulfonamide. MS (ESI) 602 (M+H)+; $^1$H NMR (DMSO-d$_6$) □ 9.88 (s, 1H), 8.05 (br t, J=5.5 Hz, 1H), 8.01 (d, J=8.4 Hz, 1H), 7.94 (s, 1H), 7.80 (d, J=8.1 Hz, 1H), 7.73 (d, 2H), 7.52 (d, J=1.6 Hz, 1H), 7.36 (m, 4H), 7.30 (dd, J=8.1, 1.6 Hz, 1H), 7.25 (s, 2H), 6.94 (d, J=8.1 Hz, 1H), 6.87 (s, 1H), 6.82 (dd, J=8.1, 1.6 Hz, 1H), 4.03 (s, 3H), 3.25 (s, 2H), 2.78 (m, 2H).

EXAMPLE 102

N-(2-hydroxyethyl)-2-[3-(3-methoxy-4-nitrophenyl)-11-oxo-10,11-dihydro-5H-dibenzo[b,e][1,4]diazepin-8-yl]Npropylacetamide The desired product was prepared using 2-(propylamino)ethanol. MS (ESI) 505 (M+H)+; $^1$H NMR (DMSO-d$_6$) □ 9.88 (s, 1H), 8.01 (d, J=8.4 Hz, 1H), 7.95 and 7.93 (both s, total 1H), 7.80 (d, J=8.1 Hz, 1H), 7.52 (d, J=1.2 Hz, 1H), 7.34 (m, 2H), 7.30 (dd, J=8.1, 1.6 Hz, 1H), 6.93 (d, J=7.8 Hz, 1H), 6.83 (m, 2H), 4.80 and 4.60 (both v br s, total 1H), 4.03 (s, 3H), 3.59 and 3.53 (both s, total 2H), 3.50 and 3.45 (both m, total 2H), 3.20 (m, 1H), 1.45 (m, 2H), 0.83 and 0.79 (both t, J=7.3 Hz, total 3H).

EXAMPLE 103

8-[2-(4-ethyl-1-piperazinyl)-2-oxoethyl]-3-(3-methoxy-4-nitrophenyl)-5,10-dihydro-11H-dibenzo[b,e][1,4]diazepin-11-one The desired product was prepared using 1-ethylpiperazine. MS (ESI) 516 (M+H)+.

EXAMPLE 104

8-{2-[4-(2-hydroxyethyl)-1-piperazinyl]-2-oxoethyl}-3-(3-methoxy-4-nitrophenyl)-5,10-dihydro-11H-dibenzo[b,e][1,4]diazepin-11-one The desired product was prepared using 2-(1-piperazinyl)ethanol. MS (ESI) 532 (M+H)+.

EXAMPLE 105

2-[3-(3-methoxy-4-nitrophenyl)-11-oxo-10,11-dihydro-5H-dibenzo[b,e][1,4]diazepin-8-yl]NmethylN[2-(2-pyridinyl)ethyl]acetamide The desired product was prepared using N-methylN[2-(2-pyridinyl)ethyl]amine. MS (ESI) 538 (M+H)+; $^1$H NMR (DMSO-d$_6$) □ 9.85 (s, 1H), 8.65 (m, 1H), 8.09, 8.02, 8.00, 7.95 (m, d, d, m, J (for the d)=2.5 Hz, total 3H), 7.80 (m, 1H), 7.60 (m, 1H), 7.52 (s, 1H), 7.48 (m, 1H), 7.35 (m, 2H), 7.30 (m, 1H), 6.93 (d, J=8.1 Hz, 1H), 6.76 (m, 1H), 6.72 (m, 1H), 4.04 (s, 3H), 3.67, (m, 2H), 3.49 and 3.42 (both s, total 2H), 3.05 (m, 2H), 2.97 and 2.82 (both s, total 3H).

EXAMPLE 106

3-(3-methoxy-4-nitrophenyl)-8-[2-oxo-2-(4-phenyl-1-piperazinyl)ethyl]-5,10-dihydro-11H-dibenzo[b,e][1,4]diazepin-11-one The desired product was prepared using 1-phenylpiperazine. MS (ESI) 564 (M+H)$^+$; $^1$H NMR (DMSO-d$_6$) □ 9.88 (s, 1H), 8.01 (d, J=8.4 Hz, 1H), 7.92 (s, 1H), 7.80 (d, J=8.4 Hz, 1H), 7.52 (d, J=1.2 Hz, 1H), 7.35 (m, 2H), 7.30 (dd, J=8.1, 1.6 Hz, 1H), 7.20 (m, 2H), 6.94 (m, 3H), 6.85 (m, 2H), 6.79 (m, 1H), 4.03 (s, 3H), 3.64 (s, 2H), 3.60 (m, 4H), 3.08 (m, 4H).

EXAMPLE 107

3-(3-methoxy-4-nitrophenyl)-8-{2-oxo-2-[4-(2-pyridinyl)-1-piperazinyl]ethyl}-5,10-dihydro-11H-dibenzo[b,e][1,4]diazepin-11-one The desired product was prepared using 1-(2-pyridinyl)piperazine. MS (ESI) 565 (M+H)$^+$; $^1$H NMR (DMSO-d$_6$) □ 9.88 (s, 1H), 8.17 (m, 1H), 8.01 (d, J=8.4 Hz, 1H), 7.97 (s, 1H), 7.80 (d, J=8.1 Hz, 1H), 7.73 (b rm, 1H), 7.52 (s, 1H), 7.35 (m, 2H), 7.30 (dd, J=8.1, 1.6 Hz, 1H), 7.15 (br m, 1H), 6.96 (d, J=8.7 Hz, 1H), 6.85 (m 2H), 6.78 (br m, 1H), 4.03 (s, 3H), 3.65 (s, 2H), 3.62 (br s, 4H), 3.54 (br m, 4H).

EXAMPLE 108

2-[3-(3-methoxy-4-nitrophenyl)-11-oxo-10,11-dihydro-5H-dibenzo[b,e][1,4]diazepin-8-yl]N(3-pyridinylmethyl)acetamide The desired product was prepared using 3-pyridinylmethylamine. MS (ESI) 510 (M+H)$^+$; $^1$H NMR (DMSO-d$_6$) □ 9.88 (s, 1H), 8.58 (m, 3H), 8.01 (d, J=8.4 Hz, 1H), 7.97 (s, 1H), 7.94 (m, 1H), 7.80 (d, J=8.1 Hz, 1H), 7.61 (m, 1H), 7.52 (s, 1H), 7.34 (m, 2H), 7.30 (dd, J=8.1, 1.9 Hz, 1H), 6.93 (d, J=7.8 Hz, 1H), 6.85 (m, 2H), 4.34 (d, J=5.9 Hz, 2H), 4.03 (s, 3H), 3.36 (s, 2H).

EXAMPLE 109

2-[3-(3-methoxy-4-nitrophenyl)-11-oxo-10,11-dihydro-5H-dibenzo[b,e][1,4]diazepin-8-yl]N(4-pyridinylmethyl)acetamide The desired product was prepared using 4-pyridinylmethylamine. MS (ESI) 510 (M+H)$^+$; $^1$H NMR (DMSO-d$_6$) □ 9.89 (s, 1H), 8.66 (m, 3H), 8.01 (d, J=8.4 Hz, 1H), 7.98 (s, 1H), 7.81 (d, J=8.1 Hz, 1H), 7.58 (d, J=5.6 Hz, 2H), 7.52 (s, 1H), 7.34 (m, 2H), 7.30 (dd, J=8.3, 1.7 Hz, 1H), 6.96 (d, J=8.1 Hz, 1H), 6.90 (m, 2H), 4.42 (d, J=5.6 Hz, 2H), 4.03 (s, 3H), 3.43 (s, 2H).

EXAMPLE 110

2-[3-(3-methoxy-4-nitrophenyl)-11-oxo-10,11-dihydro-5H-dibenzo[b,e][1,4]diazepin-8-yl]N(2-pyridinylmethyl)acetamide The desired product was prepared using 2-pyridinylmethylamine. MS (ESI) 510 (M+H)$^+$; $^1$H NMR (DMSO-d$_6$) □ 9.88 (s, 1H), 8.58 (m, 2H), 8.01 (d, J=8.4 Hz, 1H), 7.97 (s, 1H), 7.93 (m, 1H), 7.81 (d, J=8.1 Hz, 1H), 7.52 (s, 1H), 7.41 (m, 2H), 7.34 (m, 2H), 7.30 (dd, J=8.1, 1.6 Hz, 1H), 6.96 (d, J=8.1 Hz, 1H), 6.90 (m, 2H), 4.41 (d, J=5.6 Hz, 2H), 4.03 (s, 3H), 3.41 (s, 2H).

EXAMPLE 111

N-[2-(dimethylamino)ethyl]-2-[3-(3-methoxy-4-nitrophenyl)-11-oxo-10,11-dihydro-5H-dibenzo[b,e][14]diazepin-8-yl]acetamide The desired product was prepared using N-(2-aminoethyl)-N,N-dimethylamine. MS (ESI) 490 (M+H)$^+$; $^1$H NMR (DMSO-d$_6$) □ 9.88 (s, 1H), 9.28 (v br s, 1H), 8.18 (br t, J=5.6 Hz, 1H), 8.01 (d, J=8.4 Hz, 1H), 7.96 (s, 1H), 7.80 (d, J=8.1 Hz, 1H), 7.52 (d, J=1.2 Hz, 1H), 7.34 (m, 2H), 7.30 (dd, J=8.1, 1.6 Hz, 1H), 6.95 (d, J=7.8 Hz, 1H), 6.87 (m, 2H), 4.03 (s, 3H), 3.32 (s, 2H), 3.12 (v br m, 2H), 2.78 (s, 6H).

EXAMPLE 112

N-[3-(dimethylamino)propyl]-2-[3-(3-methoxy-4-nitrophenyl)-11-oxo-10,11-dihydro-5H-dibenzo[b,e][1,4]diazepin-8-yl]acetamide The desired product was prepared using N-(3-aminopropyl)-N,N-dimethylamine. MS (ESI) 504 (M+H)$^+$; $^1$H NMR (DMSO-d$_6$) □ 9.88 (s, 1H), 9.30 (v br s, 1H), 8.10 (br t, J=5.6 Hz, 1H), 8.01 (d, J=8.4 Hz, 1H), 7.96 (s, 1H), 7.80 (d, J=8.1 Hz, 1H), 7.52 (d, J=1.6 Hz, 1H), 7.34 (m, 2H), 7.30 (dd, J=8.1, 1.6 Hz, 1H), 6.95 (d, J=7.8 Hz, 1H), 6.87 (m, 2H), 4.03 (s, 3H), 3.28 (s, 2H), 3.09 (m, 2H), 2.98 (m, 2H), 2.74 (s, 3H), 2.73 (s, 3H), 1.74 (m, 2H).

EXAMPLE 113

2-[3-(3-methoxy-4-nitrophenyl)-11-oxo-10,11-dihydro-5H-dibenzo[b,e][1,4]diazepin-8-yl]N[2-(1-pyrrolidinyl)ethyl]acetamide The desired product was prepared using 2-(1-pyrrolidinyl)ethylamine. MS (ESI) 516 (M+H)$^+$; $^1$H NMR (DMSO-d$_6$) □ 9.88 (s, 1H), 9.50 (v br s, 1H), 8.19 (br t, J=5.8 Hz, 1H), 8.01 (d, J=8.4 Hz, 1H), 7.96 (s, 1H), 7.80 (d, J=8.4 Hz, 1H), 7.52 (d, J=1.6 Hz, 1H), 7.34 (m, 2H), 7.30 (dd, J=8.3, 1.7 Hz, 1H), 6.95 (d, J=7.8 Hz, 1H), 6.87 (m, 2H), 4.03 (s, 3H), 3.55 (m, 2H), 3.32 (s, 2H), 3.18 (m, 2H), 2.97 (m, 2H), 1.97 (m, 2H), 1.83 (m, 2H).

EXAMPLE 114

2-[3-(3-methoxy-4-nitrophenyl)-11-oxo-10,11-dihydro-5H-dibenzo[b,e][1,4]diazepin-8-yl]N[2-(1-piperidinyl) ethyl]acetamide The desired product was prepared using 2-(1-piperidinyl)ethylamine. MS (ESI) 530 (M+H)$^+$; $^1$H NMR (DMSO-d$_6$) □ 9.88 (s, 1H), 9.08 (v br s, 1H), 8.21 (br t, J=5.6 Hz, 1H), 8.01 (d, J=8.4 Hz, 1H), 7.96 (s, 1H), 7.80 (d, J=8.1 Hz, 1H), 7.52 (d, J=1.6 Hz, 1H), 7.34 (m, 2H), 7.30 (dd, J=8.1, 1.9 Hz, 1H), 6.95 (d, J=7.8 Hz, 1H), 6.87 (m, 2H), 4.03 (s, 3H), 3.32 (s, 2H), 3.08 (m, 2H), 2.85 (m, 2H), 1.76 (m, 2H), 1.60 (m, 3H), 1.33 (m, 1H).

EXAMPLE 115

2-[3-(3-methoxy-4-nitrophenyl)-11-oxo-10,11-dihydro-5H-dibenzo[b,e][1,4]diazepin-8-yl]N[3-(1-piperidinyl)propyl]acetamide The desired product was prepared using 3-(1-piperidinyl)propylamine. MS (ESI) 544 (M+H)$^+$; $^1$H NMR (DMSO-d$_6$) □ 9.88 (s, 1H), 8.93 (v br s, 1H), 8.11 (br t, J=5.8 Hz, 1H), 8.01 (d, J=8.4 Hz, 1H), 7.96 (s, 1H), 7.80 (d, J=8.1 Hz, 1H), 7.52 (d, J=1.2 Hz, 1H), 7.34 (m, 2H), 7.30 (dd, J=8.3, 1.7 Hz, 1H), 6.95 (d, J=8.1 Hz, 1H), 6.87 (m, 2H), 4.03 (s, 3H), 3.28 (s, 2H), 3.10 (m, 2H), 2.94 (m, 2H), 2.78 (m, 2H), 1.75 (m, 4H), 1.60 (m, 3H), 1.33 (m, 1H).

EXAMPLE 116

2-[3-(3-methoxy-4-nitrophenyl)-11-oxo-10,11-dihydro-5H-dibenzo[b,e][1,4]diazepin-8-yl]N[2-(4-morpholinyl)ethyl]acetamide The desired product was prepared using 2-(4-morpholinyl)ethylamine. MS (ESI) 532 (M+H)$^+$; $^1$H NMR (DMSO-d$_6$) □ 9.88 (s, 1H), 9.69 (v br s, 1H), 8.20 (v br s, 1H), 8.01 (d, J=8.4 Hz, 1H), 7.96 (s, 1H), 7.80 (d, J=8.4 Hz, 1H), 7.52 (d, J=1.6 Hz, 1H), 7.34 (m, 2H), 7.30 (dd, J=8.3, 1.7 Hz, 1H), 6.95 (d, J=8.4 Hz, 1H), 6.87 (m, 2H), 4.03 (s, 3H), 3.95 (br m, 2H), 3.63 (br m, 2H), 3.32 (s, 2H), 3.15 (br m, 3H).

EXAMPLE 117

2-[3-(3-methoxy-4-nitrophenyl)-11-oxo-10,11-dihydro-5H-dibenzo[b,e][1,4]diazepin-8-yl]N[3-(4-morpholinyl)propyl]acetamide The desired product was prepared using 3-(4-morpholinyl)propylamine. MS (ESI) 546 (M+H)$^+$; $^1$H NMR (DMSO-d$_6$) □ 9.88 (s, 1H), 9.55 (v br s, 1H), 8.12 (br t, J=5.8 Hz, 1H), 8.01 (d, J=8.4 Hz, 1H), 7.96 (s, 1H), 7.80 (d, J=8.1 Hz, 1H), 7.52 (d, J=1.6 Hz, 1H), 7.34 (m, 2H), 7.30 (dd, J=8.3, 1.7 Hz, 1H), 6.95 (d, J=7.8 Hz, 1H), 6.87 (m, 2H), 4.03 (s, 3H), 3.95 (m, 2H), 3.60 (br t, 2H), 3.29 (s, 2H), 3.10 (m, 2H), 3.03 (m, 2H), 1.76 (m, 2H).

EXAMPLE 118

2-[3-(3-methoxy-4-nitrophenyl)-11-oxo-10,11-dihydro-5H-dibenzo[b,e][1,4]diazepin-8-yl]N[2-(4-methyl-1-piperazinyl)ethyl]acetamide The desired product was prepared using 2-(4-methyl-1-piperazinyl)ethanamine. MS (ESI) 545 (M+H)$^+$.

EXAMPLE 119

8-{2-[(2S)-2-(hydroxymethyl)-1-pyrrolidinyl]-2-oxoethyl}-3-(3-methoxy-4-nitrophenyl)-5,10-dihydro-11H-dibenzo[b,e][1,4]diazepin-11-one The desired product was prepared by substituting Example 73 and (2S)-2-pyrrolidinylmethanol
for Example 13 and 3-pyrrolidin-1-ylpropylamine,

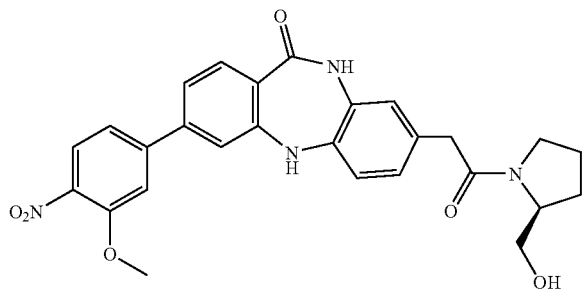

respectively, in Example 14. MS (ESI) m/e 503 (M+H)$^+$; $^1$H NMR (DMSO-d$_6$, 300 MHz): □ 9.89 (s, 1H), 8.01 (d, J=8.14 Hz, 1H), 7.97 (s, 1H), 7.79 (d, J=8.14 Hz, 1H), 7.52 (d, J=1.36 Hz, 1H), 7.29-7.36 (m, 3H), 6.94 (d, J=8.14 Hz, 1H), 6.81-6.86 (m, 2H), 4.03 (s, 3H), 3.90-3.98 (m, 1H), 3.48 (s, 2H), 3.21-3.30 (m, 4H), 1.74-1.91 (m, 4H); MS m/e (ESI) 503 (M-H)$^+$.

EXAMPLE 120

8-amino-3-(3-methoxy-4-nitrophenyl)-5,10-dihydro-11H-dibenzo[b,e][1,4]diazepin-11-one The desired product was prepared by substituting Example 7C and 2-(3-methoxy-4-nitrophenyl)-4,4,5,5-tetramethyl-1,3,2-dioxaborolane for Example 1B and 2-methoxy-4-(4,4,5,5-tetramethyl-1,3,2-dioxaborolan-2-yl)phenol, respectively, in Example 12. MS (DSI) m/e 377 (M+H)$^+$; $^1$H NMR (500 MHz, DMSO-d$_6$, TFA salt) δ 9.91 (s, 1H), 7.94 (d, J=8.3 Hz, 1H), 7.87 (s, 1H), 7.73 (d, J=8.0 Hz, 1H), 7.45 (s, 1H), 7.27-7.28 (m, 2H), 7.23 (d, J=8.0 Hz, 1H), 6.88 (d, J=8.0 Hz, 1H), 6.58-6.61 (m, 2H), 3.96 (s, 3H).

EXAMPLE 121

N-[3-(3-methoxy-4-nitrophenyl)-11-oxo-10,11-dihydro-5H-dibenzo[b,e][1,4]diazepin-8-yl]urea A mixture Example 120 (56 mg, 0.15 mmol) and NaOCN (17 mg, 0.263 mmol) in 4 mL of acetic acid and 0.8 mL of H$_2$O was stirred at room temperature for 12 hours. The solvents were removed and the residue was purified by preparative HPLC. MS (DCI) m/e 420 (M+H)$^+$; $^1$H NMR (500 MHz, DMSO-d$_6$) δ 9.86 (s, 1H), 8.36 (s, 1H), 8.00 (d, J=8.42 Hz, 1H), 7.78-7.80 (m, 2H), 7.52 (d, J=1.56 Hz, 1H), 7.73-7.75 (m, 2H), 7.28 (dd, J=8.27, 1.72 Hz, 1H), 7.01-7.05 (m, 2H), 6.88 (d, J=8.42 Hz, 1H), 5.74 (s, 2H), 4.03 (s, 3H).

EXAMPLE 122

2-(dimethylamino)N[3-(3-methoxy-4-nitrophenyl)-11-oxo-10,11-dihydro-5H-dibenzo[b,e][1,4]diazepin-8-yl]acetamide A mixture of Example 120 (38 mg, 0.10 mmol), dimethylaminoacetic acid (17 mg, 0.12 mmol), HATU (46 mg, 0.12 mmol) and Et$_3$N (0.1 g) in 1 mL of DMF was stirred overnight. The reaction mixture was partitioned between H$_2$O and ethyl acetate, and the organic layer was separated, washed with brine, dried, filtered, and concentrated under vacuum. The residue was purified by preparative HPLC to give the desired product. MS (DCI) m/e 462 (M+H)$^+$; $^1$H NMR (500 MHz, DMSO-d$_6$) δ 10.68 (s, 1H), 10.03 (s, 1H), 8.10 (s, 1H), 8.01 (d, J=8.59 Hz, 1H), 7.80 (d, J=8.29 Hz, 1H), 7.53 (d, J=1.23 Hz, 1H), 7.43 (s, 1H), 7.21-7.36 (m, 4H), 7.03 (d, J=8.59 Hz, 1H), 4.11 (s, 2H), 4.03 (s, 3H), 2.86 (s, 6H).

EXAMPLE 123

(2S)-2-aminoN[3-(3-methoxy-4-nitrophenyl)-11-oxo-10,11-dihydro-5H-dibenzo[b,e][1,4]diazepin-8-yl]-4-methylpentanamide A mixture of Example 120 (56 mg, 0.10 mmol), L-2-tert-butoxycarbonylamino-4-methyl-pentanoic acid (39 mg, 0.17 mmol), HATU (65 mg, 0.17 mmol) and Et$_3$N (0.1 g) in 2 mL of DMF was stirred overnight. The reaction mixture was partitioned between H₂O and ethyl acetate, and the organic layer was separated, washed with brine, dried, filtered, and concentrated under vacuum. The residue was purified by flash column chromatography on silica gel with 1:1 hexanes/ethyl acetate to provide 72 mg (81%) of {1-[3-(3-methoxy-4-nitrophenyl)-11-oxo-10,11-dihydro-5H-dibenzo[b,e][1,4]diazepin-8-ylcarbamoyl]-3-methyl-butyl}-carbamic acid tert-butyl ester, which was treated with 2 mL of TFA and 2 mL of $CH_2Cl_2$. The solvents were removed under vacuum and the residue was purified with preparative HPLC to give the title product. MS (DCI) m/e 490 (M+H)⁺; ¹H NMR (500 MHz, DMSO-d₆) δ 10.42 (s, 1H), 10.02 (s, 1H), 8.00-8.03 (m, 2H), 7.80 (d, J=8.11 Hz, 1H), 7.53 (s, 1H), 7.30-7.38 (m, 4H), 7.22 (d, J=8.42 Hz, 1H), 7.00 (d, J=8.74 Hz, 1H), 4.04 (s, 3H), 3.89 (m, 1H), 1.63-1.67 (m, 3H), 0.93 (t, J=6.24 Hz, 6H).

EXAMPLE 124

4-AminoN[3-(3-methoxy-4-nitrophenyl)-11-oxo-10,11-dihydro-5H-dibenzo[b,e][1,4]diazepin-8-yl]butyramide The title compound was prepared by substituting 4-tert-butoxycarbonylamino-butyric acid for (L) 2-tert-butoxycarbonylamino-4-methyl-pentanoic acid in Example 123. MS (DCI) m/e 462 (M+H)⁺; ¹H NMR (500 MHz, DMSO-d₆) δ 9.96 (s, 1H), 9.89 (s, 1H), 8.00 (d, J=8.42 Hz, 1H), 7.94 (s, 1H), 7.75-7.81 (m, 3H), 7.62 (s, 1H), 7.28-7.36 (m, 4H), 7.18 (d, J=8.11 Hz, 1H), 6.95 (d, J=8.73 Hz, 1H), 4.03 (s, 3H), 2.83-2.86 (m, 2H), 2.39 (t, J=6.2 Hz, 2H), 1.84 (m, 2H).

EXAMPLE 125

3-AminoN[3-(3-methoxy-4-nitrophenyl)-11-oxo-10,11-dihydro-5H-dibenzo[b,e][1,4]diazepin-8-yl]propionamide The title compound was prepared by substituting 3-tert-butoxycarbonylamino-propionic acid for (L) 2-tert-butoxycarbonylamino-4-methyl-pentanoic acid in Example 123. MS (DCI) m/e 448 (M+H)⁺; ¹H NMR (500 MHz, DMSO-d₆) δ 10.05 (s, 1H), 9.99 (s, 1H), 8.00 (d, J=8.42 Hz, 1H), 7.96 (s, 1H), 7.75-7.81 (m, 3H), 7.52 (s, 1H), 7.34-7.36 (m, 2H), 7.30 (dd, J=8.11, 1.25 Hz, 1H), 7.21-7.24 (m, 2H), 6.96 (d, J=8.73 Hz, 1H), 4.03 (s, 3H), 3.08 (t, J=6.40 Hz, 2H), 2.67 (t, J=6.71 Hz, 2H).

EXAMPLE 126

N-[3-(3-Methoxy-4-nitrophenyl)-11-oxo-10,11-dihydro-5H-dibenzo[b,e][1,4]diazepin-8-yl]-2-(3-methyl-3H-imidazol-4-yl)acetamide The title compound was prepared by substituting (3-methyl-3H-imidazol-4-yl)-acetic acid for dimethylaminoacetic acid in Example 122. MS (DCI) m/e 499 (M+H)⁺; ¹H NMR (500 MHz, DMSO-d₆) δ 10.17 (s, 1H), 9.99 (s, 1H), 8.87 (s, 1H), 8.00 (d, J=8.42 Hz, 1H), 7.96 (s, 1H), 7.80 (d, J=8.11 Hz, 1H), 7.52 (d, J=1.56 Hz, 1H), 7.49 (s, 1H), 7.20-7.35 (m, 5H), 6.96 (d, J=8.74 Hz, 1H), 4.03 (s, 3H), 3.83 (s, 3H), 3.80 (s, 2H).

EXAMPLE 127

2-(3H-Imidazol-4-yl)N[3-(3-methoxy-4-nitrophenyl)-11-oxo-10,11-dihydro-5H-dibenzo[b,e][1,4]diazepin-8-yl]acetamide The title compound was prepared by substituting (3H-imidazol-4-yl)-acetic acid for dimethylaminoacetic acid in Example 122. MS (DCI) m/e 485 (M+H)⁺; ¹H NMR (500 MHz, DMSO-d₆) δ 10.18 (s, 1H), 9.99 (s, 1H), 8.98 (s, 1H), 8.00 (d, J=8.42 Hz, 1H), 7.96 (s, 1H), 7.80 (d, J=8.11 Hz, 1H), 7.52 (d, J=1.56 Hz, 1H), 7.49 (s, 1H), 7.20-7.35 (m, 6H), 6.96 (d, J=8.73 Hz, 1H), 4.03 (s, 3H), 3.83 (s, 2H).

EXAMPLE 128

N-[3-(3-methoxy-4-nitrophenyl)-11-oxo-10,11-dihydro-5H-dibenzo[b,e][1,4]diazepin-8-yl]thiophene-3-carboxamide The title compound was prepared by substituting thiophene-3-carboxylic acid for dimethylaminoacetic acid in Example 122. MS (DCI) m/e 487 (M+H)⁺; ¹H NMR (300 MHz, DMSO-d₆) δ 9.98 (s, 1H), 9.97 (s, 1H), 8.30 (m, 1H), 8.01 (d, J=8.42 Hz, 1H), 7.81 (d, J=8.11 Hz, 1H), 7.60-7.64 (m, 2H), 7.53 (d, J=1.87 Hz, 1H), 7.44 (d, J=2.18 Hz, 1H), 7.34-7.36 (m, 2H), 7.29-7.31 (m, 2H), 6.99 (d, J=8.42 Hz, 1H), 4.04 (s, 3H).

EXAMPLE 129

N-[3-(3-methoxy-4-nitrophenyl)-11-oxo-10,11-dihydro-5H-dibenzo[b,e][1,4]diazepin-8-yl]-1H-pyrrole-2-carboxamide The title compound was prepared by substituting 1H-pyrrole-2-carboxylic acid for dimethylaminoacetic acid in Example 122. MS (DCI) m/e 470 (M+H)⁺; ¹H NMR (300 MHz, DMSO-d₆) δ 11.57 (s, 1H), 9.97 (s, 1H), 9.96 (s, 1H), 8.01 (d, J=8.42 Hz, 1H), 7.93 (s, 1H), 7.80 (d, J=8.11 Hz, 1H), 7.53 (d, J=1.56 Hz, 1H), 7.44 (d, J=2.18 Hz, 1H), 7.34-7.36 (m, 2H), 7.26-7.31 (m, 2H), 6.93-7.02 (m, 3H), 6.15 (m, 1H), 4.04 (s, 3H).

EXAMPLE 130

N-[3-(3-methoxy-4-nitrophenyl)-11-oxo-10,11-dihydro-5H-dibenzo[b,e][1,4]diazepin-8-yl]-2,5-dimethyl-1H-pyrrole-3-carboxamide The title compound was prepared by substituting 2,5-dimethyl-1H-pyrrole-3-carboxylic acid for dimethylaminoacetic acid in Example 122. MS (DCI) m/e 498 (M+H)⁺; ¹H NMR (300 MHz, DMSO-d₆) δ 10.77 (s, 1H), 9.88 (s, 1H), 9.09 (s, 1H), 8.00 (d, J=8.42 Hz, 1H), 7.86 (s, 1H), 7.80 (m, 1H), 7.52 (d, J=1.87 Hz, 1H), 7.47 (d, J=2.18 Hz, 1H), 7.34-7.36 (m, 2H), 7.29 (dd, J=8.11, 1.56 Hz, 1H), 7.24 (dd, J=8.58, 2.34 Hz, 1H), 6.92 (d, J=8.73 Hz, 1H), 6.30 (d, J=1.87 Hz, 1H), 4.03 (s, 3H), 2.38 (s, 3H), 2.13 (s, 3H).

EXAMPLE 131

N-[3-(3-methoxy-4-nitrophenyl)-11-oxo-10,11-dihydro-5H-dibenzo[b,e][1,4]diazepin-8-yl]-1,3-thiazole-4-carboxamide The title compound was prepared by substituting 1,3-thiazole-4-carboxylic acid for dimethylaminoacetic acid in Example 122. MS (DCI) m/e 488 (M+H)⁺; ¹H NMR (300

MHz, DMSO-d$_6$) δ 10.20 (s, 1H), 9.87 (s, 1H), 9.25 (s, 1H), 8.46 (s, 1H), 7.98-8.02 (m, 2H), 7.81 (d, J=8.11 Hz, 1H), 7.53-7.56 (m, 2H), 7.34-7.38 (m, 3H), 7.30 (dd, J=8.11, 1.87 Hz, 1H), 6.99 (d, J=8.42 Hz, 1H), 4.04 (s, 3H).

EXAMPLE 132

N-[3-(3-methoxy-4-nitrophenyl)-11-oxo-10,11-dihydro-5H-dibenzo[b,e][1,4]diazepin-8-yl]-1H-pyrazole-5-carboxamide The title compound was prepared by substituting 1H-pyrazole-5-carboxylic acid for dimethylaminoacetic acid in Example 122. MS (DCI) m/e 471 (M+H)$^+$; $^1$H NMR (300 MHz, DMSO-d$_6$) δ 13.35 (s, 1H), 9.87 (s, 1H), 9.85 (s, 1H), 8.02 (d, J=8.11 Hz, 1H), 7.81 (d, J=8.11 Hz, 1H), 7.53-7.56 (m, 3H), 7.31-7.36 (m, 5H), 7.30 (dd, J=8.11, 1.87 Hz, 1H), 6.99 (d, J=8.42 Hz, 1H), 4.04 (s, 3H).

EXAMPLE 133

N-[3-(3-methoxy-4-nitrophenyl)-11-oxo-10,11-dihydro-5H-dibenzo[b,e][1,4]diazepin-8-yl]-1H-pyrazole-4-carboxamide The title compound was prepared by substituting 1H-pyrazole-4-carboxylic acid for dimethylaminoacetic acid in Example 122. MS (DCI) m/e 471 (M+H)$^+$; $^1$H NMR (300 MHz, DMSO-d$_6$) δ 9.97 (s, 1H), 9.72 (s, 1H), 8.01 (d, J=8.42 Hz, 1H), 7.93 (s, 1H), 7.80 (d, J=8.11 Hz, 1H), 7.53 (d, J=1.56 Hz, 1H), 7.40 (d, J=2.50 Hz, 1H), 7.34-7.36 (m, 2H), 7.30 (dd, J=8.11, 1.56 Hz, 1H), 7.26 (dd, J=8.42, 2.18 Hz, 1H), 6.99 (d, J=8.73 Hz, 1H), 4.04 (s, 3H).

EXAMPLE 134

N-[3-(3-methoxy-4-nitrophenyl)-11-oxo-10,11-dihydro-5H-dibenzo[b,e][1,4]diazepin-8-yl]isonicotinamide The title compound was prepared by substituting isonicotinic acid for dimethylaminoacetic acid in Example 122. MS (DCI) m/e 482 (M+H)$^+$; $^1$H NMR (300 MHz, DMSO-d$_6$) δ 10.43 (s, 1H), 10.91 (s, 1H), 8.78 (d, J=5.93 Hz, 1H), 8.01-8.02 (m, 2H), 7.81-7.84 (m, 3H), 7.53 (d, J=1.56 Hz, 1H), 7.48 (d, J=2.18 Hz, 1H), 7.30-7.36 (m, 5H), 7.01 (d, J=8.42 Hz, 1H), 4.04 (s, 3H).

EXAMPLE 135

N-[3-(3-methoxy-4-nitrophenyl)-11-oxo-10,11-dihydro-5H-dibenzo[b,e][1,4]diazepin-8-yl]-3-pyrrolidin-1-ylpropanamide The title compound was prepared by substituting 3-pyrrolidin-1-ylpropionic acid for dimethylaminoacetic acid in Example 122. MS (DCI) m/e 502 (M+H)$^+$; $^1$H NMR (300 MHz, DMSO-d$_6$) δδ 10.06 (s, 1H), 9.99 (s, 1H), 8.00 (d, J=8.59 Hz, 1H), 7.95 (s, 1H), 7.80 (d, J=8.11 Hz, 1H), 7.52 (d, J=1.23 Hz, 1H), 7.31-7.34 (m, 3H), 7.21-7.23 (m, 2H), 6.96 (d, J=8.42 Hz, 1H), 4.03 (s, 3H), 3.42-3.54 (m, 4H), 3.06 (m, 2H), 2.77 (t, J=7.02 Hz, 2H), 2.01-2.03 (m, 2H), 1.85-1.87 (m, 2H).

EXAMPLE 136

N-[3-(3-methoxy-4-nitrophenyl)-11-oxo-10,11-dihydro-5H-dibenzo[b,e][1,4]diazepin-8-yl]-3-piperidin-1-ylpropanamide The title compound was prepared by substituting 3-piperidin-1-ylpropionic acid for dimethylaminoacetic acid in Example 122. MS (DCI) m/e 516 (M+H)$^+$; $^1$H NMR (300 MHz, DMSO-d$_6$) δ 10.06 (s, 1H), 9.99 (s, 1H), 8.00 (d, J=8.59 Hz, 1H), 7.95 (s, 1H), 7.80 (d, J=8.11 Hz, 1H), 7.52 (d, J=1.56 Hz, 1H), 7.33-7.35 (m, 2H), 7.30 (dd, J=8.27, 1.72 Hz, 1H), 7.24 (d, J=2.18 Hz, 1H), 7.21 (dd, J=8.42, 2.18 Hz, 1H), 6.96 (d, J=8.42 Hz, 1H), 4.03 (s, 3H), 3.42-3.54 (m, 4H), 2.92-2.94 (m, 2H), 2.78 (t, J=7.02 Hz, 2H), 2.61-2.63 (m, 2H), 1.81-1.83 (m, 2H), 1.64-1.66 (m, 2H).

EXAMPLE 137

N-[3-(3-methoxy-4-nitrophenyl)-11-oxo-10,11-dihydro-5H-dibenzo[b,e][1,4]diazepin-8-yl]-3-morpholin-4-ylpropanamide The title compound was prepared by substituting 3-morpholin-4-ylpropionic acid for dimethylaminoacetic acid in Example 122. MS (DCI) m/e 518 (M+H)$^+$; $^1$H NMR (300 MHz, DMSO-d$_6$) δ 10.06 (s, 1H), 9.99 (s, 1H), 8.00 (d, J=8.59 Hz, 1H), 7.95 (s, 1H), 7.80 (d, J=8.11 Hz, 1H), 7.52 (d, J=1.56 Hz, 1H), 7.33-7.35 (m, 2H), 7.30 (dd, J=8.27, 1.72 Hz, 1H), 7.24 (d, J=2.18 Hz, 1H), 7.21 (dd, J=8.42, 2.18 Hz, 1H), 6.96 (d, J=8.42 Hz, 1H), 3.98-4.03 (m, 7H), 3.64-3.67 (m, 2H), 3.42-3.44 (m, 2H), 3.10-3.12 (m, 2H), 2.79-2.81 (m, 2H).

EXAMPLE 138

(2R)-2-hydroxyN[3-(3-methoxy-4-nitrophenyl)-11-oxo-10,11-dihydro-5H-dibenzo[b,e][1,4]diazepin-8-yl]-4-phenylbutanamide The title compound was prepared by substituting (2R)-2-hydroxy-4-phenylbutanoic acid for dimethylaminoacetic acid in Example 122. MS (DCI) m/e 539 (M+H)$^+$; $^1$H NMR (300 MHz, DMSO-d$_6$) δ 9.91 (s, 1H), 9.56 (s, 1H), 8.01 (d, J=8.42 Hz, 1H), 7.92 (s, 1H), 7.80 (d, J=8.11 Hz, 1H), 7.52 (d, J=1.56 Hz, 1H), 7.42 (d, J=2.18 Hz, 1H), 7.34-7.35 (m, 2H), 7.17-7.34 (m, 6H), 6.94 (d, J=8.42 Hz, 1H), 5.78 (d, =5.78 Hz, 1H), 4.03 (s, 3H), 3.98-4.01 (m, 1H), 3.27-3.29 (m, 2H), 2.69-2.70 (m, 2H).

EXAMPLE 139

N-[3-(3-methoxy-4-nitrophenyl)-11-oxo-10,11-dihydro-5H-dibenzo[b,e][1,4]diazepin-8-yl]-3-(phenylsulfonyl)propanamide The title compound was prepared by substituting 3-(phenylsulfonyl)propanoic acid for dimethylaminoacetic acid in Example 122. MS (DCI) m/e 573 (M+H)$^+$; $^1$H NMR (300 MHz, DMSO-d$_6$) δ 9.93-9.94 (m, 2H), 8.00 (d, J=8.42 Hz, 1H), 7.90-7.92 (m, 3H), 7.74-7.80 (m, 2H), 7.65-7.68 (m, 2H), 7.52 (d, J=1.56 Hz, 1H), 7.33-7.35 (m, 2H), 7.29 (dd, J=8.11, 1.56 Hz, 1H), 7.19 (d, J=2.18 Hz, 1H), 7.11 (dd, J=8.74, 2.18 Hz, 1H), 6.91 (d, J=8.42 Hz, 1H), 4.03 (s, 3H), 3.57-3.60 (m, 2H), 2.64-2.66 (m, 2H).

EXAMPLE 140

N-[3-(3-methoxy-4-nitrophenyl)-11-oxo-10,11-dihydro-5H-dibenzo[b,e][1,4]diazepin-8-yl]-2-{[(4-methylphenyl)sulfonyl]amino}acetamide The title compound was prepared by substituting {[(4-methylphenyl)sulfonyl]amino}acetic acid for dimethylaminoacetic acid in Example 122. MS (DCI) m/e 588 (M+H)$^+$; $^1$H NMR (300 MHz, DMSO-d$_6$) δ 9.95 (s, 1H), 9.77 (s, 1H), 8.00 (d, J=8.42 Hz, 1H), 7.92 (s, 1H), 7.69-7.80 (m, 2H), 7.53 (d, J=1.87 Hz, 1H), 7.33-7.37 (m, 5H), 7.29 (dd, J=8.27, 1.72 Hz, 1H), 7.17 (d, J=2.18 Hz, 1H), 7.08-7.09 (m, 1H), 6.92 (d, J=8.73 Hz, 1H), 4.03 (s, 3H), 3.60 (s, 2H), 2.35 (s, 2H).

EXAMPLE 141

N-[3-(3-methoxy-4-nitrophenyl)-11-oxo-10,11-dihydro-5H-dibenzo[b,e][1,4]diazepin-8-yl]pyridine-2-carboxamide The title compound was prepared by substituting pyridine-2-carboxylic acid for dimethylaminoacetic acid in Example 122. MS (DCI) m/e 482 (M+H)$^+$; $^1$H NMR (300 MHz, DMSO-d$_6$) δ 10.49 (s, 1H), 9.98 (s, 1H), 8.72 (d, J=4.68 Hz, 1H), 8.14 (d, J=7.80 Hz, 1H), 8.00-8.06 (m, 4H), 7.81 (d, J=8.42 Hz, 1H), 7.67 (m, 1H), 7.62 (d, J=2.18 Hz, 1H), 7.53 (d, J=1.56 Hz, 1H), 7.43 (dd, J=8.58, 2.73 Hz, 1H), 7.35-7.36 (m, 2H), 7.30 (dd, J=8.11, 1.87 Hz, 1H), 7.01 (d, J=8.74 Hz, 1H), 4.04 (s, 3H).

EXAMPLE 142

N-[3-(3-methoxy-4-nitrophenyl)-11-oxo-10,11-dihydro-5H-dibenzo[b,e][1,4]diazepin-8-yl]nicotinamide The title compound was prepared by substituting nicotinic acid for dimethylaminoacetic acid in Example 122. MS (DCI) m/e 482 (M+H)$^+$; $^1$H NMR (300 MHz, DMSO-d$_6$) δ 10.37 (s, 1H), 10.01 (s, 1H), 9.08 (s, 1H), 8.75 (dd, J=4.84, 1.72 Hz, 1H), 8.26-8.28 (m, 1H), 8.00-8.02 (m, 2H), 7.81 (d, J=8.11 Hz, 1H), 7.53-7.57 (m, 2H), 7.48 (d, J=2.18 Hz, 1H), 7.30-7.37 (m, 4H), 7.01 (d, J=8.42 Hz, 1H), 4.04 (s, 3H).

EXAMPLE 143

N-[3-(3-methoxy-4-nitrophenyl)-11-oxo-10,11-dihydro-5H-dibenzo[b,e][1,4]diazepin-8-yl]-2-pyridin-3-ylacetamide The title compound was prepared by substituting pyridin-3-yl-acetic acid for dimethylaminoacetic acid in Example 122. MS (DCI) m/e 496 (M+H)$^+$; $^1$H NMR (300 MHz, DMSO-d$_6$) δ 10.11 (s, 1H), 9.95 (s, 1H), 8.66 (s, 1H), 8.61 (d, J=4.06, Hz, 1H), 8.00-8.04 (m, 2H), 7.93 (s, 1H), 7.79 (d, J=8.11 Hz, 1H), 7.62 (dd, J=7.96, 5.15 Hz, 1H), 7.52 (d, J=1.56 Hz, 1H), 7.33-7.35 (m, 2H), 7.26-7.30 (m, 2H), 7.20 (dd, J=8.74, 2.18 Hz, 1H), 6.95 (d, J=8.74 Hz, 1H), 4.04 (s, 3H), 3.78 (s, 2H).

EXAMPLE 144

N-[3-(3-methoxy-4-nitrophenyl)-11-oxo-10,11-dihydro-5H-dibenzo[b,e][1,4]diazepin-8-yl]-2-(4-methylpiperazin-1-yl)acetamide The title compound was prepared by substituting (4-methyl-piperazin-1-yl)acetic acid for dimethylaminoacetic acid in Example 122. MS (DCI) m/e 517 (M+H)$^+$; $^1$H NMR (300 MHz, DMSO-d$_6$) δ 9.95 (s, 1H), 7.96-8.02 (m, 2H), 7.80 (dd, J=8.11, 2.50 Hz, 1H), 7.25 (d, J=1.56 Hz, 1H), 7.29-7.35 (m, 4H), 7.18 (dd, J=8.58, 2.03 Hz, 1H), 6.96 (m, 1H), 6.71 (m, 1H), 4.03 (s, 3H), 2.89-3.55 (m, 13H).

EXAMPLE 145

3-ethoxyN[3-(3-methoxy-4-nitrophenyl)-11-oxo-10,11-dihydro-5H-dibenzo[b,e][1,4]diazepin-8-yl]propanamide The title compound was prepared by substituting 3-ethoxy-propionic acid for dimethylaminoacetic acid in Example 122. MS (DCI) m/e 517 (M+H)$^+$; $^1$H NMR (500 MHz, DMSO-d$_6$) δ 9.94 (s, 1H), 9.82 (s, 1H), 8.00 (d, J=8.29 Hz, 1H), 7.91 (s, 1H), 7.80 (d, J=7.98 Hz, 1H), 7.52 (d, J=1.56 Hz, 1H), 7.33-7.35 (m, 2H), 7.28-7.30 (m, 2H), 7.18 (dd, J=8.59, 1.59 Hz, 1H), 6.93 (d, J=8.59 Hz, 1H), 4.03 (s, 3H), 3.63 (t, J=6.29 Hz, 2H), 3.42 (q, J=7.06 Hz, 2H), 2.48-2.52 (m, 2H), 1.09 (t, J=7.06 Hz, 1H).

EXAMPLE 146

(2R)N[3-(3-methoxy-4-nitrophenyl)-11-oxo-10,11-dihydro-5H-dibenzo[b,e][1,4]diazepin-8-yl]-5-oxopyrrolidine-2-carboxamide The title compound was prepared by substituting (R) 5-oxo-pyrrolidine-2-carboxylic acid for dimethylaminoacetic acid in Example 122. MS (DCI) m/e 488 (M+H)$^+$; $^1$H NMR (300 MHz, DMSO-d$_6$) δ 9.97 (s, 1H), 9.93 (s, 1H), 8.01 (d, J=8.42 Hz, 1H), 7.94 (s, 1H), 7.84 (s, 1H), 7.80 (d, J=8.42 Hz, 1H), 7.52 (d, J=1.56 Hz, 1H), 7.34-7.35 (m, 2H), 7.28-7.30 (m, 2H), 7.22 (dd, J=8.73, 2.18 Hz, 1H), 6.95 (d, J=8.74 Hz, 1H), 4.16 (m, 1H), 4.03 (s, 3H), 1.95-2.32 (m, 4H).

EXAMPLE 147

4-methoxyN[3-(3-methoxy-4-nitrophenyl)-11-oxo-10,11-dihydro-5H-dibenzo[b,e][1,4]diazepin-8-yl]cyclohexanecarboxamide The title compound was prepared by substituting 4-methoxy-cyclohexanecarboxylic acid for dimethylaminoacetic acid in Example 122. MS (DCI) m/e 517 (M+H)$^+$; $^1$H NMR (300 MHz, DMSO-d$_6$) δ 9.90 (s, 1H), 9.74 (s, 1H), 8.00 (d, J=8.42 Hz, 1H), 7.89 (s, 1H), 7.79 (d, J=8.42 Hz, 1H), 7.52 (d, J=1.56 Hz, 1H), 7.33-7.35 (m, 2H), 7.28-7.31 (m, 2H), 7.17 (d, J=8.73 Hz, 1H), 6.91 (d, J=8.73 Hz, 1H), 4.03 (s, 3H), 3.21-3.24 (m, 4H), 0.95-2.26 (m, 8H).

EXAMPLE 148

(2R)-2-methoxyN[3-(3-methoxy-4-nitrophenyl)-11-oxo-10,11-dihydro-5H-dibenzo[b,e][14]diazepin-8-yl]-2-phenylacetamide The title compound was prepared by substituting (R) methoxy-phenyl-acetic acid for dimethylaminoacetic acid in Example 122. MS (DCI) m/e 525 (M+H)$^+$; $^1$H NMR (300 MHz, DMSO-d$_6$) δ 9.93 (s, 1H), 9.89 (s, 1H), 8.00 (d, J=8.42 Hz, 1H), 7.93 (s, 1H), 7.79 (d, J=8.11 Hz, 1H), 7.52 (s, 1H), 7.45-7.47 (m, 2H), 7.33-7.39 (m, 6H), 7.29 (dd, J=8.11, 1.56 Hz, 1H), 7.22 (dd, J=8.73, 2.18 Hz, 1H), 6.94 (d, J=8.42 Hz, 1H), 4.81 (s, 1H), 4.03 (s, 3H), 3.55 (s, 3H).

EXAMPLE 149

(2S)-2-methoxyN[3-(3-methoxy-4-nitrophenyl)-11-oxo-10,11-dihydro-5H-dibenzo[b,e][1,4]diazepin-8-yl]-2-phenylacetamide The title compound was prepared by substituting (R) methoxy-phenyl-acetic acid for dimethylaminoacetic acid in Example 122. MS (DCI) m/e 525 (M+H)$^+$; $^1$H NMR (300 MHz, DMSO-d$_6$) δ 9.93 (s, 1H), 9.89 (s, 1H), 8.00 (d, J=8.42 Hz, 1H), 7.93 (s, 1H), 7.79 (d, J=8.11 Hz, 1H), 7.52 (s, 1H), 7.45-7.47 (m, 2H), 7.33-7.39 (m, 6H), 7.29 (dd, J=8.11, 1.56 Hz, 1H), 7.22 (dd, J=8.73, 2.18 Hz, 1H), 6.94 (d, J=8.42 Hz, 1H), 4.81 (s, 1H), 4.03 (s, 3H), 3.55 (s, 3H).

EXAMPLE 150

N-(2-{[3-(3-methoxy-4-nitrophenyl)-11-oxo-10,11-dihydro-5H-dibenzo[b,e][1,4]diazepin-8-yl]amino}-2-oxoethyl)-2-furamide The title compound was prepared by substituting [(furan-2-carbonyl)-amino]-acetic acid for dimethylaminoacetic acid in Example 122. MS (DCI) m/e 528 (M+H)$^+$; $^1$H NMR (300 MHz, DMSO-d$_6$) δ 9.97 (s, 1H), 9.93 (s, 1H), 8.55 (t, J=5.93 Hz, 1H), 8.01 (d, J=8.42 Hz, 1H), 7.93 (s, 1H), 7.79 (d, J=8.11 Hz, 1H), 7.53 (d, J=1.56 Hz, 1H), 7.32-7.35 (m, 2H), 7.26-7.30 (m, 2H), 7.19 (dd, J=8.42, 2.18 Hz, 1H), 7.14 (d, J=2.18 Hz, 1H), 6.95 (d, J=8.73 Hz, 1H), 6.64 (dd, J=3.43, 1.56 Hz, 1H), 4.81 (s, 1H), 4.03 (s, 3H), 3.98 (d, J=5.93 Hz, 2H).

EXAMPLE 151

1-acetylN[3-(3-methoxy-4-nitrophenyl)-11-oxo-10,11-dihydro-5H-dibenzo[b,e][1,4]diazepin-8-yl]piperidine-4-carboxamide The title compound was prepared by substituting 1-acetyl-piperidine-4-carboxylic acid for dimethylaminoacetic acid in Example 122. MS (DCI) m/e 530 (M+H)$^+$; $^1$H NMR (300 MHz, DMSO-d$_6$) δ 9.92 (s, 1H), 9.81 (s, 1H), 8.01 (d, J=8.42 Hz, 1H), 7.91 (s, 1H), 7.79 (d, J=8.11 Hz, 1H), 7.53 (d, J=1.56 Hz, 1H), 7.33-7.35 (m, 2H), 7.27-7.30 (m, 2H), 7.19 (dd, J=8.73, 2.18 Hz, 1H), 6.93 (d, J=8.42 Hz, 1H), 4.38 (m, 1H), 4.03 (s, 3H), 3.84 (m, 1H), 3.05 (m, 1H), 2.50-2.56 (m, 2H), 2.00 (s, 3H), 2.72.78 (m, 2H), 1.56-1.57 (m, 1H), 1.43 (m, 1H).

EXAMPLE 152

N-[3-(3-methoxy-4-nitrophenyl)-11-oxo-10,11-dihydro-5H-dibenzo[b,e][1,4]diazepin-8-yl]-N'-phenyl-pentanediamide The title compound was prepared by substituting 5-anilino-5-oxopentanoic acid for dimethylaminoacetic acid in Example 122. MS (DCI) m/e 566 (M+H)$^+$; $^1$H NMR (300 MHz, DMSO-d$_6$) δ 9.93 (s, 1H), 9.86 (s, 1H), 9.80 (s, 1H), 8.01 (d, J=8.42 Hz, 1H), 7.90 (s, 1H), 7.80 (d, J=8.11 Hz, 1H), 7.59 (d, J=7.70 Hz, 2H), 7.52 (d, J=1.56 Hz, 1H), 7.33-7.35 (m, 2H), 7.26-7.30 (m, 4H), 7.18-7.20 (m, 1H), 7.01 (t, J=7.33 Hz, 1H), 6.93 (d, J=8.42 Hz, 1H), 4.03 (s, 3H), 2.32-2.37 (m, 4H), 1.87-1.90 (m, 2H).

EXAMPLE 153

N-[3-(3-methoxy-4-nitrophenyl)-11-oxo-10,11-dihydro-5H-dibenzo[b,e][1,4]diazepin-8-yl]-2-[4-(methylsulfonyl)phenyl]acetamide The title compound was prepared by substituting (4-methanesulfonyl-phenyl)-acetic acid for dimethylaminoacetic acid in Example 122. MS (DCI) m/e 573 (M+H)$^+$; $^1$H NMR (300 MHz, DMSO-d$_6$) δ 10.14 (s, 1H), 9.94 (s, 1H), 8.00 (d, J=8.42 Hz, 1H), 7.93 (s, 1H), 7.88 (d, J=8.42 Hz, 2H), 7.79 (d, J=8.42 Hz, 1H), 7.59 (d, J=8.11 Hz, 2H), 7.52 (d, J=1.56 Hz, 1H), 7.33-7.35 (m, 2H), 7.26-7.30 (m, 2H), 7.19 (dd, J=8.73, 2.18 Hz, 1H), 6.93 (d, J=8.73 Hz, 1H), 4.03 (s, 3H), 3.75 (s, 2H), 3.19 (s, 3H).

EXAMPLE 154

(2S)N[3-(3-methoxy-4-nitrophenyl)-11-oxo-10,11-dihydro-5H-dibenzo[b,e][14]diazepin-8-yl]-5-oxopyrrolidine-2-carboxamide The title compound was prepared by substituting (S) 5-oxo-pyrrolidine-2-carboxylic acid for dimethylaminoacetic acid in Example 122. MS (DCI) m/e 488 (M+H)$^+$; $^1$H NMR (300 MHz, DMSO-d$_6$) δ 9.97 (s, 1H), 9.93 (s, 1H), 8.01 (d, J=8.42 Hz, 1H), 7.94 (s, 1H), 7.84 (s, 1H), 7.80 (d, J=8.42 Hz, 1H), 7.52 (d, J=1.56 Hz, 1H), 7.34-7.35 (m, 2H), 7.28-7.30 (m, 2H), 7.22 (dd, J=8.73, 2.18 Hz, 1H), 6.95 (d, J=8.74 Hz, 1H), 4.15 (m, 1H), 4.03 (s, 3H), 1.95-2.32 (m, 4H).

EXAMPLE 155

4-(8-amino-11-oxo-10,11-dihydro-5H-dibenzo[b,e][1,4]diazepin-3-yl)-2-methoxybenzonitrile

EXAMPLE 155A 8-amino-3-(4,4,5,5-tetramethyl-1,3,2-dioxaborolan-2-yl)-5,10-dihydro-11H-dibenzo[b,e][1,4]diazepin-11-one The title compound was prepared by substituting Example 7C for Example 6D in Example 54A. MS (DCI) m/e 352 (M+H)$^+$.

EXAMPLE 155B 4-(8-amino-11-oxo-10,11-dihydro-5H-dibenzo[b,e][1,4]diazepin-3-yl)-2-methoxybenzonitrile The title compound was prepared by substituting Example 155A and 4-iodo-2-methoxy-benzonitrile for 2-methoxy-4-(4,4,5,5-tetramethyl-1,3,2-dioxaborolan-2-yl)phenol and Example 9, respectively, in Example 10. MS (DCI) m/e 357 (M+H)$^+$; $^1$H NMR (500 MHz, DMSO-d$_6$) δ 9.94 (s, 1H), 7.87 (s, 1H), 7.84 (d, J=8.11 Hz, 1H), 7.80 (d, J=8.11 Hz, 1H), 7.42 (s, 1H), 7.32-7.34 (m, 1H), 7.28 (d, J=8.11 Hz, 1H), 6.92 (d, J=8.42 Hz, 1H), 6.60-6.64 (m, 2H), 4.02 (s, 3H).

EXAMPLE 156

(2S)N [3-(4-cyano-3-methoxyphenyl)-11-oxo-10,11-dihydro-5H-dibenzo[b,e][1,4]diazepin-8-yl]-2-methoxy-2-phenylacetamide The title compound was prepared by substituting Example 155B and (2S)-methoxy(phenyl)acetic acid for Example 120 and dimethylaminoacetic acid, respectively, in Example 122.

MS (DCI) m/e 505 (M+H)+; 1H NMR (500 MHz, DMSO-d6) δ 9.93 (s, 1H), 9.88 (s, 1H), 7.91 (s, 1H), 7.83 (d, J=8.11 Hz, 1H), 7.78 (d, J=8.11 Hz, 1H), 7.47 (d, J=7.18 Hz, 1H), 7.42 (s, 1H), 7.31-7.39 (m, 6H), 7.27 (dd, J=8.27, 1.72 Hz, 1H), 7.22 (dd, J=8.58, 2.34 Hz, 1H), 6.93 (d, J=8.74 Hz, 1H), 4.81 (s, 1H), 4.02 (s, 3H), 3.35 (s, 3H).

EXAMPLE 157

N-[3-(4-cyano-3-methoxyphenyl)-11-oxo-10,11-dihydro-5H-dibenzo[b,e][1,4]diazepin-8-yl]-3-piperidin-1-ylpropanamide The title compound was prepared by substituting Example 155B and 3-piperidin-1-ylpropionic acid for Example 120 and dimethylaminoacetic acid, respectively, in Example 122. MS (DCI) m/e 496 (M+H)+; 1H NMR (500 MHz, DMSO-d6) δ 10.01 (s, 1H), 9.94 (s, 1H), 7.89 (s, 1H), 7.83 (d, J=8.11 Hz, 1H), 7.79 (d, J=8.11 Hz, 1H), 7.42 (s, 1H), 7.32-7.34 (m, 2H), 7.27 (dd, J=8.27, 1.40 Hz, 1H), 7.24 (d, J=1.87 Hz, 1H), 7.19 (dd, J=8.58, 2.03 Hz, 1H), 6.93 (d, J=8.42 Hz, 1H), 4.02 (s, 3H), 2.56-2.58 (m, 2H), 2.35-2.43 (m, 6H), 1.50-1.52 (m, 4H), 1.38-1.40 (m, 2H).

EXAMPLE 158

N-[3-(4-cyano-3-methoxyphenyl)-11-oxo-10,11-dihydro-5H-dibenzo[b,e][1,4]diazepin-8-yl]methanesulfonamide The title compound was prepared by substituting Example 155B for Example 7C in Example 42A. MS (DCI) m/e 435 (M+H)+; 1H NMR (500 MHz, DMSO-d6) δ 9.94 (s, 1H), 9.49 (s, 1H), 7.96 (s, 1H), 7.84 (d, J=7.98 Hz, 1H), 7.79 (d, J=7.98 Hz, 1H), 7.42 (s, 1H), 7.28-7.34 (m, 3H), 6.98 (d, J=8.59 Hz, 1H), 6.93 (d, J=1.84 Hz, 1H), 6.82 (m, 1H), 4.02 (s, 3H), 2.92 (s, 3H).

EXAMPLE 159

8-amino-3-(4-chloro-3-methoxyphenyl)-5,10-dihydro-11H-dibenzo[b,e][1,4]diazepin-11-one The title compound was prepared by substituting Example 155A and 1-chloro-4-iodo-2-methoxy-benzene for 2-methoxy-4-(4,4,5,5-tetramethyl-1,3,2-dioxaborolan-2-yl)phenol and Example 9, respectively, in Example 10. MS (DCI) m/e 366 (M+H)+; 1H NMR (500 MHz, DMSO-d6) δ 9.95 (s, 1H), 7.92 (s, 1H), 7.77 (d, J=7.98 Hz, 1H), 7.53 (d, J=8.24 Hz, 1H), 7.34 (d, J=1.56 Hz, 1H), 7.29 (s, 1H), 7.19-7.24 (m, 2H), 6.96 (d, J=8.29 Hz, 1H), 6.68-6.72 (m, 2H), 3.96 (s, 3H).

EXAMPLE 160

N-[3-(4-chloro-3-methoxyphenyl)-11-oxo-10,11-dihydro-5H-dibenzo[b,e][1,4]diazepin-8-yl]-3-piperidin-1-ylpropanamide The title compound was prepared by substituting Example 159 and 3-piperidin-1-ylpropionic acid for Example 120 and dimethylaminoacetic acid, respectively, in Example 122. MS (DCI) m/e 506 (M+H)+; 1H NMR (500 MHz, DMSO-d6) δ 10.10 (s, 1H), 9.89 (s, 1H), 7.85 (s, 1H), 7.76 (d, J=8.29 Hz, 1H), 7.34 (d, J=1.53 Hz, 1H), 7.28 (s, 1H), 7.17-7.23 (m, 5H), 6.92 (d, J=8.29 Hz, 1H), 3.96 (s, 3H), 2.57 (m, 2H), 2.35-2.42 (m, 6H), 1.49-1.51 (m, 4H), 1.38-1.40 (m, 2H).

EXAMPLE 161

3-(3-methoxy-4-nitrophenyl)-8-(2-oxopyrrolidin-1-yl)-5,10-dihydro-11H-dibenzo[b,e][1,4]diazepin-11-one

EXAMPLE 161A 4-chloroN(3-chloro-11-oxo-10,11-dihydro-5H-dibenzo[b,e][1,4]diazepin-8-yl)butanamide The title compound was prepared by substituting 4-chlorobutyryl chloride for CH3SO2Cl in Example 42A. MS (DCI) m/e 365 (M+H)+; 1H NMR (500 MHz, DMSO-d6) δ 9.95 (s, 1H), 9.88 (s, 1H), 7.95 (s, 1H), 7.67 (d, J=8.48 Hz, 1H), 7.27 (d, J=2.03 Hz, 1H), 7.18 (dd, J=8.48, 2.37 Hz, 1H), 7.05 (d, J=2.03 Hz, 1H), 6.87-6.93 (m, 2H), 3.68 (t, J=6.61 Hz, 2H), 2.43 (t, J=7.29 Hz, 2H), 1.97-2.05 (m, 2H).

EXAMPLE 161B 3-chloro-8-(2-oxopyrrolidin-1-yl)-5,10-dihydro-11H-dibenzo[b,e][1,4]diazepin-11-one Sodium (0.138 g, 6 mmol) was dissolved in 15 mL of anhydrous EtOH at 0° C. To this solution was added Example 161A. The solution was stirred overnight, and the precipitate was collected by filtration to give 0.154 g of the title compound. MS (DCI) m/e 328 (M+H)+; 1H NMR (500 MHz, DMSO-d6) δ 9.93 (s, 1H), 8.06 (s, 1H), 7.72 (d, J=8.48 Hz, 1H), 7.37 (d, J=2.50 Hz, 1H), 7.28 (dd, J=8.73, 2.50 Hz, 1H), 7.09 (d, J=1.87 Hz, 1H), 6.98 (d, J=8.73 Hz, 1H), 6.95 (dd, J=8.42, 1.87 Hz, 1H), 3.77 (t, J=7.02 Hz, 2H), 2.49 (t, J=7.95 Hz, 2H), 2.04-2.10 (m, 2H).

EXAMPLE 161C 3-(3-methoxy-4-nitrophenyl)-8-(2-oxopyrrolidin-1-yl)-5,10-dihydro-11H-dibenzo[b,e][1,4]diazepin-11-one The title compound was prepared by substituting Example 161B and Example 266G for Example 59B and Example 56A, respectively, in Example 59C. MS (DCI) m/e 445 (M+H)+; 1H NMR (500 MHz, DMSO-d6) δ 9.90 (s, 1H), 8.00-8.02 (m, 2H), 7.81 (d, J=8.29 Hz, 1H), 7.63 (d, J=1.53 Hz, 1H), 7.32-7.35 (m, 3H), 7.28-7.31 (m, 1H), 7.25 (dd, J=8.75, 2.30 Hz, 1H), 7.00 (d, J=8.90 Hz, 1H), 4.03 (s, 3H), 3.74 (t, J=6.90 Hz, 2H), 2.46 (t, J=8.13 Hz, 2H), 2.01-2.08 (m, 2H).

EXAMPLE 162

3-(3-methoxy-4-nitrophenyl)-8-(2-oxopiperidin-1-yl)-5,10-dihydro-11H-dibenzo[b,e][1,4]diazepin-11-one

EXAMPLE 162A 5-chloroN(3-chloro-11-oxo-10,11-dihydro-5H-dibenzo[b,e][1,4]diazepin-8-yl)pentanamide The title compound was prepared by substituting 5-chloropentanoyl chloride for CH3SO2Cl in Example 42A. MS (DCI) m/e 379 (M+H)+; 1H NMR (500 MHz, DMSO-d6) δ 9.93 (s, 1H), 9.80 (s, 1H), 7.94 (s, 1H), 7.68 (d, J=8.73 Hz, 1H), 7.28 (d, J=1.87 Hz, 1H), 7.18 (dd, J=8.58, 2.03 Hz, 1H), 7.06 (d, J=1.87 Hz, 1H), 6.88-6.92 (m, 2H), 3.62-3.67 (m, 2H), 2.24-2.32 (m, 2H), 1.61-1.76 (m, 4H).

EXAMPLE 162B 3-chloro-8-(2-oxopiperidin-1-yl)-5,10-dihydro-11H-dibenzo[b,e][1,4]diazepin-11-one Sodium (0.200 g, 8.7 mmol) was dissolved in 25 mL of anhydrous EtOH at 0° C. To this solution was added Example 162A. The solution was heated under reflux for 1 hour. The solution was cooled to room temperature and the precipitate was collected by filtration to give 0.196 g of the title compound. MS (DCI) m/e 342 (M+H)$^+$; $^1$H NMR (500 MHz, DMSO-d$_6$) δ 9.88 (s, 1H), 8.07 (s, 1H), 7.67 (d, J=8.42 Hz, 1H), 7.07 (d, J=1.87 Hz, 1H), 6.92-6.96 (m, 2H), 6.85-6.88 (m, 2H), 3.50 (t, J=5.61 Hz, 2H), 2.35 (t, J=6.24 Hz, 2H), 1.81-1.86 (m, 4H).

EXAMPLE 162C 3-(3-methoxy-4-nitrophenyl)-8-(2-oxopiperidin-1-yl)-5,10-dihydro-11H-dibenzo[b,e][1,4]diazepin-11-one The title compound was prepared by substituting Example 162B and Example 266G for Example 59B and Example 56A, respectively, in Example 59C. MS (DCI) m/e 459 (M+H)$^+$; $^1$H NMR (500 MHz, DMSO-d$_6$) δ 9.88 (s, 1H), 8.05 (s, 1H), 8.01 (d, J=8.29 Hz, 1H), 7.81 (d, J=7.98 Hz, 1H), 7.53 (s, 1H), 7.30-7.36 (m, 3H), 7.00 (m, 1H), 6.86-6.88 (m, 2H), 4.03 (s, 3H), 3.51 (t, J=5.37 Hz, 2H), 2.36 (t, J=6.14 Hz, 2H), 1.79-1.83 (m, 4H).

EXAMPLE 163

3-(4-chloro-3-methoxyphenyl)-8-(2-oxopyrrolidin-1-yl)-5,10-dihydro-11H-dibenzo[b,e][1,4]diazepin-11-one

EXAMPLE 163A 4-chloroN[3-(4-chloro-3-methoxyphenyl)-11-oxo-10,11-dihydro-5H-dibenzo[b,e][1,4]diazepin-8-yl]butanamide The title compound was prepared by substituting Example 159 and 5-chloro-pentanoyl chloride for Example 7C and CH$_3$SO$_2$Cl, respectively, in Example 42A. MS (DCI) m/e 471 (M+H)$^+$; $^1$H NMR (500 MHz, DMSO-d$_6$) δ 9.88 (s, 1H), 9.85 (s, 1H), 7.85 (s, 1H), 7.76 (d, J=8.11 Hz, 1H), 7.52 (d, J=8.42 Hz, 1H), 7.34 (s, 1H), 7.28 (d, J=4.37 Hz, 1H), 7.17-7.23 (m, 5H), 6.93 (d, J=8.73 Hz, 1H), 3.62-3.67 (m, 2H), 2.24-2.32 (m, 2H), 1.61-1.76 (m, 2H).

EXAMPLE 163B 3-(4-chloro-3-methoxyphenyl)-8-(2-oxopyrrolidin-1-yl)-5,10-dihydro-11H-dibenzo [b,e][1,4]diazepin-11-one The title compound was prepared by substituting Example 163A for Example 162A in Example 162B. MS (DCI) m/e 434 (M+H)$^+$; $^1$H NMR (500 MHz, DMSO-d$_6$) δ 9.84 (s, 1H), 7.94 (s, 1H), 7.77 (d, J=8.29 Hz, 1H), 7.53 (d, J=8.29 Hz, 1H), 7.32-7.35 (m, 2H), 7.29 (d, J=1.84 Hz, 1H), 7.20-7.25 (m, 3H), 6.99 (d, J=8.59 Hz, 1H), 3.96 (s, 3H), 3.74 (t, J=6.90 Hz, 2H), 2.46 (t, J=8.13 Hz, 2H), 2.00-2.08 (m, 2H).

EXAMPLE 164

3-chloroN[3-(4-chloro-3-methoxyphenyl)-11-oxo-10,11-dihydro-5H-dibenzo[b,e][1,4]diazepin-8-yl]propane-1-sulfonamide The title compound was prepared by substituting Example 159 and 3-chloro-propane-1-sulfonyl chloride for Example 7C and CH$_3$SO$_2$Cl, respectively, in Example 42A. MS (DCI) m/e 507 (M+H)$^+$; $^1$H NMR (500 MHz, DMSO-d$_6$) δ 9.91 (s, 1H), 9.66 (s, 1H), 7.92 (s, 1H), 7.76 (d, J=8.29 Hz, 1H), 7.53 (d, J=8.29 Hz, 1H), 7.33 (d, J=1.84, Hz, 1H), 7.29 (d, J=1.84 Hz, 1H), 7.19-7.24 (m, 2H), 6.97 (d, J=8.29 Hz, 1H), 6.93 (d, J=2.76 Hz, 1H), 6.82 (dd, J=8.59, 2.59 Hz, 1H), 3.96 (s, 3H), 3.71 (t, J=6.60 Hz, 2H), 3.13-3.17 (m, 2H), 2.08-2.12 (m, 2H).

EXAMPLE 165

N-[3-(4-chloro-3-methoxyphenyl)-11-oxo-10,11-dihydro-5H-dibenzo[b,e][1,4]diazepin-8-yl]-1-phenylmethanesulfonamide The title compound was prepared by substituting Example 159 and phenyl-methanesulfonyl chloride for Example 7C and CH$_3$SO$_2$Cl, respectively, in Example 42A. MS (DCI) m/e 521 (M+H)$^+$; $^1$H NMR (500 MHz, DMSO-d$_6$) δ 9.93 (s, 1H), 9.64 (s, 1H), 7.92 (s, 1H), 7.78 (d, J=8.29 Hz, 1H), 7.53 (d, J=8.29 Hz, 1H), 7.33-7.37 (m, 4H), 7.20-7.30 (m, 5H), 6.96-6.99 (m, 2H), 6.80 (dd, J=8.59, 2.45 Hz, 1H), 4.38 (s, 2H), 3.96 (s, 3H).

EXAMPLE 166

3-(4-chloro-3-methoxyphenyl)-8-(11-dioxidoisothiazolidin-2-yl)-5,10-dihydro-11H-dibenzo[b,e][1,4]diazepin-11-one The title compound was prepared by substituting Example 164 for Example 162A in Example 162B. MS (DCI) m/e 470 (M+H)$^+$; $^1$H NMR (500 MHz, DMSO-d$_6$) δ 9.91 (s, 1H), 7.97 (s, 1H), 7.77 (d, J=7.93 Hz, 1H), 7.53 (d, J=8.24 Hz, 1H), 7.34 (d, J=1.83, 1H), 7.30 (d, J=1.22 Hz, 1H), 7.20-7.25 (m, 2H), 7.02 (d, J=8.54, Hz, 1H), 6.91 (d, J=2.44 Hz, 1H), 6.87 (dd, J=8.54, 2.44 Hz, 1H), 3.96 (s, 3H), 3.63 (t, J=6.56 Hz, 2H), 3.46 (t, J=7.48 Hz, 2H), 2.35-2.40 (m, 2H).

EXAMPLE 167

2,2,2-trifluoroN[3-(3-methoxy-4-nitrophenyl)-11-oxo-10,11-dihydro-5H-dibenzo[b,e][1,4]diazepin-8-yl]ethanesulfonamide The title compound was prepared by substituting Example 120 and 2,2,2-trifluoro-ethanesulfonyl chloride for Example 7C and CH$_3$SO$_2$Cl, respectively, in Example 42A. MS (DCI) m/e 523 (M+H)$^+$; $^1$H NMR (500 MHz, DMSO-d$_6$) δ 9.91 (s, 1H), 7.98-8.02 (m, 2H), 7.80 (d, J=8.11 Hz, 1H), 7.52 (s, 1H), 7.29-7.35 (m, 4H), 6.97 (d, J=8.42 Hz, 1H), 6.91 (s, 1H), 6.81 (d, J=8.42 Hz, 1H), 4.31-4.33 (m, 2H), 4.03 (s, 3H).

EXAMPLE 168

N-[3-(3-methoxy-4-nitrophenyl)-11-oxo-10,11-dihydro-5H-dibenzo[b,e][1,4]diazepin-8-yl]-1-methyl-1H-imidazole-4-sulfonamide The title compound was prepared by substituting Example 120 and 1-methyl-1H-imidazole-4-sulfonyl chloride for Example 7C and $CH_3SO_2Cl$, respectively, in Example 42A. MS (DCI) m/e 521 (M+H)$^+$; $^1$H NMR (500 MHz, DMSO-$d_6$) δ 9.99 (s, 1H), 9.91 (s, 1H), 8.00 (d, J=8.42 Hz, 1H), 7.87 (s, 1H), 7.75-7.78 (m, 2H), 7.71 (s, 1H), 7.51 (J=1.56 Hz, 1H), 7.31-7.35 (m, 2H), 7.28 (dd, J=8.11, 1.87 Hz, 1H), 6.84-6.86 (m, 2H), 6.73 (d, J=8.58, 2.34 Hz, 1H), 4.02 (s, 3H), 3.64 (s, 3H).

EXAMPLE 169

N-[3-(3-methoxy-4-nitrophenyl)-11-oxo-10,11-dihydro-5H-dibenzo[b,e][1,4]diazepin-8-yl]-1-phenylmethanesulfonamide The title compound was prepared by substituting Example 120 and phenylmethanesulfonyl chloride for Example 7C and $CH_3SO_2Cl$, respectively, in Example 42A. MS (DCI) m/e 531 (M+H)$^+$; $^1$H NMR (500 MHz, DMSO-$d_6$) δ 9.97 (s, 1H), 9.64 (s, 1H), 8.01 (d, J=8.29 Hz, 1H), 7.97 (s, 1H), 7.81 (d, J=8.29 Hz, 1H), 7.53 (d, J=1.84 Hz, 1H), 7.27-7.38 (m, 8H), 6.97-6.99 (m, 2H), 6.80 (dd, J=8.29, 2.46 Hz, 1H), 4.38 (s, 2H), 4.03 (s, 3H).

EXAMPLE 170

3-chloroN[3-(3-methoxy-4-nitrophenyl)-11-oxo-10,11-dihydro-5H-dibenzo[b,e][1,4]diazepin-8-yl]propane-1-sulfonamide The title compound was prepared by substituting Example 120 and 3-chloropropane-1-sulfonyl chloride for Example 7C and $CH_3SO_2Cl$, respectively, in Example 42A. MS (DCI) m/e 517 (M+H)$^+$; $^1$H NMR (500 MHz, DMSO-$d_6$) δ 9.98 (s, 1H), 9.70 (s, 1H), 8.01-8.02 (m, 2H), 7.80 (d, J=8.24 Hz, 1H), 7.52 (s, 1H), 7.30-7.35 (m, 3H), 6.98 (d, J=8.24 Hz, 1H), 6.94 (d, J=2.14 Hz, 1H), 6.83 (dd, J=8.54, 2.44 Hz, 1H), 4.03 (s, 3H), 3.71 (t, J=3.71 Hz, 2H), 3.13-3.15 (m, 2H), 2.06-2.13 (m, 2H).

EXAMPLE 171

8-(11-dioxidoisothiazolidin-2-yl)-3-(3-methoxy-4-nitrophenyl)-5,10-dihydro-11H-dibenzo[b,e][1,4]diazepin-11-one The title compound was prepared by substituting Example 170 for Example 162A in Example 162B. MS (DCI) m/e 481 (M+H)$^+$; $^1$H NMR (500 MHz, DMSO-$d_6$) δ 9.93 (s, 1H), 8.00-8.02 (m, 2H), 7.81 (d, J=8.42 Hz, 1H), 7.53 (d, J=1.56 Hz, 1H), 7.34-7.35 (m, 2H), 7.30 (dd, J=8.26, 1.72 Hz, 1H), 7.02 (d, J=8.42, Hz, 1H), 6.92 (d, J=2.18 Hz, 1H), 6.88 (dd, J=8.42, 2.50 Hz, 1H), 4.03 (s, 3H), 3.63 (t, J=6.39 Hz, 2H), 3.46 (t, J=7.49 Hz, 2H), 2.34-2.41 (m, 2H).

EXAMPLE 172

N-[3-(3-methoxy-4-nitrophenyl)-11-oxo-10,11-dihydro-5H-dibenzo[b,e][1,4]diazepin-8-yl]-3-morpholin-4-ylpropane-1-sulfonamide A mixture of Example 170 (10.0 mg, 0.0168 mmol), morpholine (9.0 mmg, 0.112 mmol) in 5 mL of toluene and 1 mL of dioxane was heated under reflux overnight. The solvents were removed under reduced pressure, and residue was purified by preparative HPLC ($CH_3CN$/0.1% TFA in $H_2O$) to give the title compound. MS (DCI) m/e 568 (M+H)$^+$; $^1$H NMR (500 MHz, DMSO-$d_6$) δ 9.97 (s, 1H), 9.72 (s, 1H), 8.01-8.03 (m, 2H), 7.81 (d, J=8.42 Hz, 1H), 7.51 (d, J=1.56 Hz, 1H), 7.30-7.38 (m, 3H), 7.00 (d, J=8.42, Hz, 1H), 6.94 (d, J=2.50, Hz, 1H), 6.84 (dd, J=8.58, 2.34 Hz, 1H), 4.03 (s, 3H), 3.88-3.92 (m, 2H), 3.63-3.70 (m, 4H), 3.00-3.20 (m, 6H), 2.03-2.05 (m, 2H).

EXAMPLE 173

N-[3-(3-methoxy-4-nitrophenyl)-11-oxo-10,11-dihydro-5H-dibenzo[b,e][1,4]diazepin-8-yl]-3-piperidin-1-ylpropane-1-sulfonamide The title compound was prepared by substituting piperidine for morpholine in Example 172. MS (DCI) m/e 566 (M+H)$^+$; $^1$H NMR (500 MHz, DMSO-$d_6$) δ 9.97 (s, 1H), 9.71 (s, 1H), 9.07 (br, 1H), 8.01-8.03 (m, 2H), 7.80 (d, J=8.11 Hz, 1H), 7.51 (s, 1H), 7.31-7.38 (m, 3H), 7.00 (d, J=8.42, Hz, 1H), 6.95 (d, J=2.18, Hz, 1H), 6.84 (dd, J=8.73, 2.18 Hz, 1H), 4.03 (s, 3H), 3.12-3.15 (m, 4H), 2.79-2.84 (m, 2H), 1.99-2.05 (m, 2H), 1.75-1.78 (m, 2H), 1.33-1.60 (m, 4H).

EXAMPLE 174

3-(diethylamino)N[3-(3-methoxy-4-nitrophenyl)-11-oxo-10,11-dihydro-5H-dibenzo[b,e][1,4]diazepin-8-yl]propane-1-sulfonamide The title compound was prepared by substituting diethylamine for morpholine in Example 172. MS (DCI) m/e 554 (M+H)$^+$; $^1$H NMR (500 MHz, DMSO-$d_6$) δ 9.98 (s, 1H), 9.72 (s, 1H), 9.15 (br, 1H), 8.00-8.02 (m, 2H), 7.80 (d, J=7.98 Hz, 1H), 7.52 (d, J=1.84 Hz, 1H), 7.30-7.36 (m, 3H), 7.00 (d, J=8.59, Hz, 1H), 6.95 (d, J=2.45, Hz, 1H), 6.84 (dd, J=8.44, 2.30 Hz, 1H), 4.03 (s, 3H), 3.06-3.17 (m, 8H), 1.96-2.01 (m, 2H), 1.15 (t, J=7.36 Hz, 6H).

EXAMPLE 175

3-(dimethylamino)N[3-(3-methoxy-4-nitrophenyl)-11-oxo-10,11-dihydro-5H-dibenzo[b,e][1,4]diazepin-8-yl]propane-1-sulfonamide The title compound was prepared by substituting dimethylamine for morpholine in Example 172. MS (DCI) m/e 526 (M+H)$^+$; $^1$H NMR (500 MHz, DMSO-$d_6$) δ 9.97 (s, 1H), 9.72 (s, 1H), 9.43 (br, 1H), 8.00-8.02 (m, 2H), 7.80 (d, J=8.29 Hz, 1H), 7.52 (d, J=1.84 Hz, 1H), 7.30-7.36 (m, 3H), 7.00 (d, J=8.59, Hz, 1H), 6.94 (d, J=2.46, Hz, 1H), 6.84 (dd, J=8.59, 2.46 Hz, 1H), 4.03 (s, 3H), 3.06-3.17 (m, 4H), 1.96-2.03 (m, 2H).

EXAMPLE 176

1-chloroN[3-(3-methoxy-4-nitrophenyl)-11-oxo-10,11-dihydro-5H-dibenzo[b,e][1,4]diazepin-8-yl]methanesulfonamide The title compound was prepared by substituting Example 120 and chloro-methanesulfonyl chloride for Example 7C and $CH_3SO_2Cl$, respectively, in Example 42A. MS (DCI) m/e 489 (M+H)⁺; ¹H NMR (500 MHz, DMSO-d₆) δ 10.18 (s, 1H), 9.94 (s, 1H), 8.00-8.02 (m, 2H), 7.80 (d, J=8.11 Hz, 1H), 7.52 (d, J=1.56 Hz, 1H), 7.30-7.35 (m, 3H), 6.99 (d, J=8.42 Hz, 1H), 6.95 (d, J=2.18 Hz, 1H), 6.85 (dd, J=8.58, 2.34 Hz, 1H), 4.91 (s, 2H), 4.03 (s, 3H).

EXAMPLE 177

N-[3-(3-methoxy-4-nitrophenyl)-11-oxo-10,11-dihydro-5H-dibenzo[b,e][1,4]diazepin-8-yl]-4-morpholin-4-ylbenzamide The title compound was prepared by substituting 4-morpholin-4-ylbenzoic acid for dimethylaminoacetic acid in Example 122. MS (DCI) m/e 566 (M+H)⁺; ¹H NMR (500 MHz, DMSO-d₆) δ 9.96 (s, 1H), 9.88 (s, 1H), 8.01 (d, J=8.42 Hz, 1H), 7.94 (s, 1H), 7.86 (d, J=8.73 Hz, 2H), 7.81 (d, J=8.11 Hz, 1H), 7.53 (d, J=1.56 Hz, 1H), 7.48 (d, J=2.50 Hz, 1H), 7.34-7.36 (m, 2H), 7.28-7.32 (m 2H), 7.01 (d, J=9.04 Hz, 2H), 6.97 (d, J=8.42 Hz, 1H), 4.04 (s, 3H), 3.74-3.76 (m, 4H), 3.24-3.27 (m, 4H).

EXAMPLE 178

7-amino-3-(3-methoxy-4-nitrophenyl)-5,10-dihydro-11H-dibenzo[b,e][1,4]diazepin-11-one

EXAMPLE 178A methyl 2-[(5-amino-2-nitrophenyl)amino]-4-chlorobenzoate

The title compound was prepared by substituting 4-nitrobenzene-1,3-diamine for 4-bromo-2-nitroaniline in Example 2A. MS (DCI) m/e 322 (M+H)⁺; ¹H NMR (300 MHz, DMSO-d₆) δ 11.11 (s, 1H), 7.97 (s, 1H), 7.94 (s, 1H), 7.61 (d, J=2.03 Hz, 1H), 7.16 (dd, J=8.48, 2.03 Hz, 1H), 6.70 (s, 2H), 6.61 (d, J=2.37 Hz, 1H), 6.28 (dd, J=9.32, 2.20 Hz, 1H), 3.87 (s, 3H).

EXAMPLE 178B methyl 4-chloro-2-[(2,5-diaminophenyl)amino]benzoate

The title compound was prepared by substituting Example 178A for Example 6B in Example 6C. MS (DCI) m/e 292 (M+H)⁺; ¹H NMR (300 MHz, DMSO-d₆) δ 8.83 (s, 1H), 7.84 (d, J=8.48 Hz, 1H), 6.69 (dd, J=8.65, 2.20 Hz, 1H), 6.61 (d, J=8.81 Hz, 1H), 6.57 (d, J=2.03 Hz, 1H), 6.35-6.38 (m, 2H), 4.41 (s, 3H), 4.11 (s, 3H), 3.85 (s, 3H).

EXAMPLE 178C 7-amino-3-chloro-5,10-dihydro-11H-dibenzo[b,e][1,4]diazepin-11-one The title compound was prepared by substituting Example 178B for Example 5B in Example 5C. MS (DCI) m/e 260 (M+H)⁺; ¹H NMR (300 MHz, DMSO-d₆) δ 9.52 (s, 1H), 7.75 (s, 1H), 7.63 (d, J=8.48 Hz, 1H), 7.06 (d, J=2.03 Hz, 1H), 6.90 (dd, J=8.31, 2.20 Hz, 1H), 6.63 (d, J=8.48 Hz, 1H), 6.13-6.20 (m, 2H), 4.94 (s, 2H).

EXAMPLE 178D 7-amino-3-(3-methoxy-4-nitrophenyl)-5,10-dihydro-11H-dibenzo[b,e][1,4]diazepin-11-one The title compound was prepared by substituting Example 178C and Example 266G for Example 1B and 2-methoxy-4-(4,4,5,5-tetramethyl-1,3,2-dioxaborolan-2-yl)phenol, respectively, in Example 12. MS (DCI) m/e 377 (M+H)⁺; ¹H NMR (300 MHz, DMSO-d₆) δ 9.51 (s, 1H), 8.01 (d, J=8.42 Hz, 1H), 7.77 (d, J=8.11 Hz, 1H), 7.69 (s, 1H), 7.51 (d, J=1.87 Hz, 1H), 7.36 (d, J=1.87 Hz, 1H), 7.33 (dd, J=8.42, 1.87 Hz, 1H), 7.29 (dd, J=8.11, 1.87 Hz, 1H), 6.66 (d, J=8.42 Hz, 1H), 6.25 (d, J=2.18 Hz, 1H), 6.16 (dd, J=8.42, 2.50 Hz, 1H), 4.90 (s, 2H), 4.03 (s, 3H).

EXAMPLE 179

3-chloroN[3-(3-methoxy-4-nitrophenyl)-11-oxo-10,11-dihydro-5H-dibenzo[b,e][1,4]diazepin-7-yl]propane-1-sulfonamide The title compound was prepared by substituting Example 178D and 3-chloro-propane-1-sulfonyl chloride for Example 7C and CH₃SO₂Cl, respectively, in Example 42A. MS (DCI) m/e 517 (M+H)⁺; ¹H NMR (500 MHz, DMSO-d₆) δ 9.84 (s, 1H), 9.75 (s, 1H), 8.14 (s, 1H), 8.01 (d, J=8.42 Hz, 1H), 7.81 (d, J=8.11 Hz, 1H), 7.52 (d, J=1.56 Hz, 1H), 7.40 (d, J=1.56 Hz, 1H), 7.34 (dd, J=8.42, 1.87 Hz, 1H), 7.31 (dd, J=8.26, 1.72 Hz, 1H), 6.99 (d, J=2.18 Hz, 1H), 6.93 (d, J=8.73 Hz, 1H), 6.76 (dd, J=8.58, 2.34 Hz, 1H), 4.04 (s, 3H), 3.72 (t, J=6.55 Hz, 2H), 3.14-3.20 (m, 2H), 2.08-2.13 (m, 2H).

EXAMPLE 180

N-[3-(3-methoxy-4-nitrophenyl)-11-oxo-10,11-dihydro-5H-dibenzo[b,e][1,4]diazepin-7-yl]-1-phenyl-methanesulfonamide The title compound was prepared by substituting Example 178D and phenyl-methanesulfonyl chloride for Example 7C and CH₃SO₂Cl, respectively, in Example 42A. MS (DCI) m/e 531 (M+H)⁺; ¹H NMR (500 MHz, DMSO-d₆) δ 9.76 (s, 1H), 9.65 (s, 1H), 8.06 (s, 1H), 7.95 (d, J=8.42 Hz, 1H), 7.75 (d, J=8.11 Hz, 1H), 7.46 (s, 1H), 7.35 (d, J=1.56 Hz, 1H), 7.20-7.29 (m, 7H), 6.93 (d, J=2.18, Hz, 1H), 6.86 (d, J=8.42 Hz, 1H), 6.67 (dd, J=8.42, 2.18 Hz, 1H), 4.34 (s, 2H), 3.97 (3, 2H).

EXAMPLE 181

1-(4-chlorophenyl)N[3-(3-methoxy-4-nitrophenyl)-11-oxo-10,11-dihydro-5H-dibenzo[b,e][1,4]diazepin-7-yl]methanesulfonamide The title compound was prepared by substituting Example 178D and 4-chlorophenylmethanesulfonyl chloride for Example 7C and CH₃SO₂Cl, respectively, in Example 42A. MS (DCI) m/e 566 (M+H)⁺; ¹H NMR (500 MHz, DMSO-d₆) δ 9.76 (s, 1H), 9.65 (s, 1H), 8.05 (s, 1H), 7.95 (d, J=8.42 Hz, 1H), 7.74 (d, J=8.11 Hz, 1H), 7.46 (s, 1H), 7.21-7.35 (m, 6H), 6.90 (d, J=2.18, Hz, 1H), 6.85 (d, J=8.42 Hz, 1H), 6.56 (dd, J=8.58, 2.34 Hz, 1H), 4.38 (s, 2H), 3.97 (s, 3H).

EXAMPLE 182

N-[3-(3-methoxy-4-nitrophenyl)-11-oxo-10,11-dihydro-5H-dibenzo[b,e][1,4]diazepin-7-yl]-1-methyl-1H-imidazole-4-sulfonamide The title compound was prepared by substituting Example 178D and 1-methyl-1H-imidazole-4-sulfonyl chloride for Example 7C and $CH_3SO_2Cl$, respectively, in Example 42A. MS (DCI) m/e 521 (M+H)$^+$; $^1$H NMR (500 MHz, DMSO-$d_6$) δ 10.04 (s, 1H), 9.75 (s, 1H), 8.00-8.03 (m, 3H), 7.77-7.80 (m, 1H), 7.71-7.74 (m, 2H), 7.51 (d, J=1.56 Hz, 1H), 7.39 (m, 1H), 7.34 (dd, J=8.42, 1.56 Hz, 1H), 7.30 (dd, J=8.11, 1.87 Hz, 1H), 6.87 (d, J=2.50, Hz, 1H), 6.79 (d, J=8.73 Hz, 1H), 6.68 (dd, J=8.58, 2.34 Hz, 1H), 4.04 (s, 3H), 3.97 (s, 3H).

EXAMPLE 183

N-[3-(3-methoxy-4-nitrophenyl)-11-oxo-10,11-dihydro-5H-dibenzo[b,e][1,4]diazepin-7-yl]methanesulfonamide The title compound was prepared by substituting Example 178D for Example 7C in Example 42A. MS (DCI) m/e 521 (M+H)$^+$; $^1$H NMR (500 MHz, DMSO-$d_6$) δ 9.64 (s, 1H), 9.57 (s, 1H), 8.12 (s, 1H), 8.01 (d, J=8.11 Hz, 1H), 7.80 (d, J=8.42 Hz, 1H), 7.52 (d, J=1.56 Hz, 1H), 7.40 (d, J=1.87 Hz, 1H), 7.35 (dd, J=8.42, 1.87 Hz, 1H), 7.32 (dd, J=8.11, 1.87 Hz, 1H), 6.98 (d, J=2.18, Hz, 1H), 6.93 (d, J=8.73 Hz, 1H), 6.75 (dd, J=8.58, 2.34 Hz, 1H), 4.04 (s, 3H), 2.95 (s, 3H).

EXAMPLE 184

N-[3-(3-methoxy-4-nitrophenyl)-11-oxo-10,11-dihydro-5H-dibenzo[b,e][1,4]diazepin-7-yl]-3-morpholin-4-ylpropane-1-sulfonamide The title compound was prepared by substituting Example 179 for Example 170 in Example 172. MS (DCI) m/e 568 (M+H)$^+$; $^1$H NMR (500 MHz, DMSO-$d_6$) δ 9.86 (s, 1H), 9.77 (s, 1H), 8.12 (s, 1H), 8.01 (d, J=8.42 Hz, 1H), 7.80 (d, J=8.11 Hz, 1H), 7.51 (s, 1H), 7.39 (d, J=1.56 Hz, 1H), 7.31-7.34 (m, 2H), 6.98 (d, J=2.18, Hz, 1H), 6.92 (d, J=8.42 Hz, 1H), 6.75 (dd, J=8.42, 2.18 Hz, 1H), 4.02 (s, 3H), 3.96-3.98 (m, 2H), 3.58 (m, 2H), 3.13-3.17 (m, 8H), 3.00-3.02 (m, 2H), 2.02-2.04 (m, 2H).

EXAMPLE 185

N-[3-(3-methoxy-4-nitrophenyl)-11-oxo-10,11-dihydro-5H-dibenzo[b,e][1,4]diazepin-7-yl]-3-piperidin-1-ylpropane-1-sulfonamide The title compound was prepared by substituting Example 179 and piperidine for Example 170 and morpholine, respectively, in Example 172. MS (DCI) m/e 566 (M+H)$^+$; $^1$H NMR (500 MHz, DMSO-$d_6$) δ 9.80 (s, 1H), 9.71 (s, 1H), 9.04 (br, 1H), 8.08 (s, 1H), 7.95 (d, J=8.42 Hz, 1H), 7.74 (d, J=8.11 Hz, 1H), 7.45 (d, J=1.56 Hz, 1H), 7.34 (d, J=1.56 Hz, 1H), 7.23-7.28 (m, 2H), 6.93 (d, J=2.18 Hz, 1H), 6.87 (d, J=8.73 Hz, 1H), 6.70 (dd, J=8.58, 2.34 Hz, 1H), 3.97 (s, 3H), 3.02-3.10 (m, 4H), 2.73-2.78 (m, 2H), 1.95-1.99 (m, 2H), 1.67-1.71 (m, 2H), 1.26-1.55 (m, 4H).

EXAMPLE 186

3-(diethylamino)N[3-(3-methoxy-4-nitrophenyl)-11-oxo-10,11-dihydro-5H-dibenzo[b,e][1,4]diazepin-7-yl]propane-1-sulfonamide The title compound was prepared by substituting Example 179 and diethylamine for Example 170 and morpholine, respectively, in Example 172. MS (DCI) m/e 554 (M+H)$^+$; $^1$H NMR (500 MHz, DMSO-$d_6$) δ 9.86 (s, 1H), 9.77 (s, 1H), 9.11 (br, 1H), 8.13 (s, 1H), 8.01 (d, J=8.42 Hz, 1H), 7.80 (d, J=8.11 Hz, 1H), 7.51 (d, J=1.56 Hz, 1H), 7.40 (d, J=1.56 Hz, 1H), 7.31-7.34 (m, 2H), 6.99 (d, J=2.50 Hz, 1H), 6.92 (d, J=8.73 Hz, 1H), 6.76 (dd, J=8.58, 2.34 Hz, 1H), 4.02 (s, 3H), 3.05-3.18 (m, 10H), 1.95-2.01 (m, 2H), 1.13 (t, J=71.7 Hz, 6H).

EXAMPLE 187

3-(dimethylamino)N[3-(3-methoxy-4-nitrophenyl)-11-oxo-10,11-dihydro-5H-dibenzo[b,e][1,4]diazepin-7-yl]propane-1-sulfonamide The title compound was prepared by substituting Example 179 and dimethylamine for Example 170 and morpholine, respectively, in Example 172. MS (DCI) m/e 526 (M+H)$^+$; $^1$H NMR (500 MHz, DMSO-$d_6$) δ 9.82 (s, 1H), 9.53 (s, 1H), 9.12 (br, 1H), 7.88 (s, 1H), 7.77 (d, J=8.42 Hz, 1H), 7.56 (d, J=8.11 Hz, 1H), 7.27 (d, J=1.56 Hz, 1H), 7.15 (d, J=1.56 Hz, 1H), 7.06-7.10 (m, 2H), 6.74 (d, J=2.18 Hz, 1H), 6.68 (d, J=8.73 Hz, 1H), 6.61 (dd, J=8.42, 2.50 Hz, 1H), 3.78 (s, 3H), 2.82-2.92 (m, 4H), 2.49 (s, 6H), 1.74-1.79 (m, 2H).

EXAMPLE 188

N-[3-(3-methoxy-4-nitrophenyl)-11-oxo-10,11-dihydro-5H-dibenzo[b,e][1,4]diazepin-7-yl]tetrahydro-2H-pyran-4-carboxamide The title compound was prepared by substituting Example 179 and tetrahydro-2H-pyran-4-carboxylic acid for Example 120 and dimethylaminoacetic acid, respectively, in Example 122. MS (DCI) m/e 489 (M+H)$^+$; $^1$H NMR (500 MHz, DMSO-$d_6$) δ 9.80 (s, 1H), 9.79 (s, 1H), 8.00-8.02 (m, 2H), 7.79 (d, J=8.11 Hz, 1H), 7.60 (d, J=1.87 Hz, 1H), 7.52 (d, J=1.25 Hz, 1H), 7.35 (dd, J=8.42, 1.56 Hz, 1H), 7.31 (dd, J=8.11, 1.56 Hz, 1H), 6.93-6.95 (m, 1H), 6.88 (d, J=8.42 Hz, 1H), 4.04 (s, 3H), 3.87-3.91 (m, 2H), 3.30-3.36 (m, 2H), 2.26 (m, 1H), 1.63-1.68 (m, 4H).

EXAMPLE 189

8-(1-hydroxy-1-methylethyl)-3-(3-methoxy-4-nitrophenyl)-5,10-dihydro-11H-dibenzo[b,e][1,4]diazepin-11-one

EXAMPLE 189A 3-chloro-8-(1-hydroxy-1-methylethyl)-5,10-dihydro-11H-dibenzo[b,e][1,4]diazepin-11-one Example 1B (0.180 g, 0.60 mmol) in 20 mL of THF was treated dropwise with 3.0M MeMgBr (1.6 mL, 4.8 mmol) at room temperature. The reaction mixture was stirred overnight. The reaction was quenched carefully with MeOH, and the mixture was poured into water. To this solution was added 5 mL of concentrated HCl solution, and the mixture was extracted by ethyl acetate several times. The combined organic layers were washed with brine, dried (MgSO4), filtered, and concentrated under vacuum. The residue was purified by flash column chromatography on silica gel eluting with 3:7 hexanes/ethyl acetate to provide 0.108 g (60%) of the title compound. MS (DCI) m/e 303 (M+H)$^+$; $^1$H NMR (500 MHz, DMSO-d$_6$) δ 9.56 (s, 1H), 7.72 (s, 1H), 7.42 (d, J=8.29 Hz, 1H), 6.97 (d, J=1.53 Hz, 1H), 6.82 (d, J=1.84 Hz, 1H), 6.80 (dd, J=8.29, 1.84 Hz, 1H), 6.64-6.68 (m, 2H), 4.65 (s, 1H), 1.12 (s, 6H).

EXAMPLE 189B 8-(1-hydroxy-1-methylethyl)-3-(3-methoxy-4-nitrophenyl)-5,10-dihydro-11H-dibenzo[b,e][1,4]diazepin-11-one The desired product was prepared by substituting Example 189A and Example 266G for Example 1B and 2-methoxy-4-(4,4,5,5-tetramethyl-1,3,2-dioxaborolan-2-yl)phenol, respectively, in Example 12. MS (DCI) m/e 420 (M+H)$^+$; $^1$H NMR (500 MHz, DMSO-d$_6$) δ 9.80 (s, 1H), 8.00 (d, J=7.98 Hz, 1H), 7.91 (s, 1H), 7.79 (d, J=7.98 Hz, 1H), 7.51 (s, 1H), 7.21-7.34 (m, 2H), 7.12 (s, 1H), 7.03 (d, J=7.98 Hz, 1H), 6.93 (d, J=7.98 Hz, 1H), 4.88 (s, 1H), 4.02 (s, 3H), 1.36 (s, 6H).

EXAMPLE 190

8-(1-ethyl-1-hydroxypropyl)-3-(3-methoxy-4-nitrophenyl)-5,10-dihydro-11H-dibenzo[b,e][1,4]diazepin-11-one

EXAMPLE 190A 3-chloro-8-(1-ethyl-1-hydroxypropyl)-5,10-dihydro-11H-dibenzo[b,e][1,4]diazepin-11-one The title compound was prepared by substituting EtMgBr for MeMgBr in Example 189A. MS (DCI) m/e 331 (M+H)$^+$; $^1$H NMR (500 MHz, DMSO-d$_6$) δ 9.80 (s, 1H), 7.96 (s, 1H), 7.68 (d, J=8.48 Hz, 1H), 7.07 (d, J=2.03 Hz, 1H), 7.02 (d, J=1.70 Hz, 1H), 6.92 (d, J=2.03 Hz, 1H), 6.87-6.90 (m, 2H), 4.43 (s, 1H), 1.60-1.70 (m, 4H), 0.61-0.66 (m, 6H).

EXAMPLE 190B 8-(1-ethyl-1-hydroxypropyl)-3-(3-methoxy-4-nitrophenyl)-5,10-dihydro-11H-dibenzo[b,e][1,4]diazepin-11-one The desired product was prepared by substituting Example 190A and Example 266G for Example 1B and 2-methoxy-4-(4,4,5,5-tetramethyl-1,3,2-dioxaborolan-2-yl)phenol, respectively, in Example 12. MS (DCI) m/e 448 (M+H)$^+$; $^1$H NMR (500 MHz, DMSO-d$_6$) δ 9.78 (s, 1H), 8.00 (d, J=8.29 Hz, 1H), 7.89 (s, 1H), 7.78 (d, J=8.29 Hz, 1H), 7.51 (d, J=1.84 Hz, 1H), 7.32-7.34 (m, 2H), 7.27 (dd, J=8.13, 1.69 Hz, 1H), 7.02 (s, 1H), 6.93 (m, 2H), 4.39 (s, 1H), 4.02 (s, 3H), 1.62-1.65 (m, 4H), 0.63 (t, J=7.36 Hz, 6H).

EXAMPLE 191

8-(1-hydroxy-1-methylethyl)-3-(pyridin-4-ylamino)-5,10-dihydro-11H-dibenzo[b,e][1,4]diazepin-11-one A mixture of Example 189A (60 mg, 0.20 mmol), 4-aminopyridine (26 mg, 0.24 mmol), Pd$_2$(dba)$_3$ (9.2 mg, 0.01 mmol), CyMAP (11.8 mg, 0.03 mmol), and Cs$_2$CO$_3$ (78 mg, 0.24 mmol) in 2 mL of dioxane was heated at 85° C. overnight. After the reaction mixture cooled to room temperature, it was partitioned between EtOAc and water. The aqueous layer was extracted with EtOAc three times. The combined organic layers were washed with brine, dried (MgSO$_4$), filtered, and concentrated under vacuum. The residue was purified by flash column chromatography on silica gel with 100:5:1 EtOAc/MeOH/NH$_4$OH to provide 54 mg (75%) of the desired product. MS (DCI) m/e 361 (M+H)$^+$; $^1$H NMR (500 MHz, DMSO-d$_6$) δ 9.49 (s, 1H), 9.01 (s, 1H), 8.29 (d, J=4.68 Hz, 1H), 7.79 (s, 1H), 7.64 (d, J=8.73 Hz, 1H), 7.09 (d, J=1.87 Hz, 1H), 6.99-7.03 (m, 3H), 6.86-6.89 (m, 2H), 6.63 (dd, J=8.58, 2.03 Hz, 1H), 4.68 (s, 1H), 1.36 (m, 6H).

EXAMPLE 192

3-[(2-chloropyridin-4-yl)amino]-8-(1-hydroxy-1-methylethyl)-5,10-dihydro-11H-dibenzo[b,e][1,4]diazepin-11-one The desired product was prepared by substituting 2-chloro-4-aminopyridine for 4-aminopyridine in Example 191. MS (DCI) m/e 395 (M+H)$^+$; $^1$H NMR (500 MHz, DMSO-d$_6$) δ 9.55 (s, 1H), 9.26 (s, 1H), 8.07 (d, J=4.99 Hz, 1H), 7.84 (s, 1H), 7.66 (d, J=8.42 Hz, 1H), 7.09 (s, 1H), 6.98-7.01 (m, 3H), 6.85-6.89 (m, 2H), 6.64 (d, J=8.11 Hz, 1H), 4.86 (s, 1H), 1.35 (m, 6H).

EXAMPLE 193

4-{[8-(1-hydroxy-1-methylethyl)-11-oxo-10,11-dihydro-5H-dibenzo[b,e][1,4]diazepin-3-yl]amino}pyridine-2-carbonitrile

EXAMPLE 193A 4-aminopyridine-2-carbonitrile

A mixture of 2-chloro-pyridin-4-ylamine (0.642 g, 5 mmol), Zn(CN)$_2$ (0.323 g, 2.75 mmol) and Pd(PPh$_3$)$_4$ (0.288 g, 0.025 mmol) in 5 mL of DMF was heated at 145° C. for 20 hours. After the reaction mixture cooled to room temperature, it was partitioned between ethyl acetate and H$_2$O. The aqueous layer was extracted with additional ethyl acetate. The combined organic layers were washed with brine, dried (MgSO$_4$), filtered, and concentrated under vacuum. The residue was purified by flash column chromatography on silica gel with 9:1 hexanes/ethyl acetate to provide 0.29 g (20%) of the desired product. MS (DCI) m/e 120 (M+H)$^+$; $^1$H NMR (300 MHz, DMSO-d$_6$) δ 8.08 (d, J=5.76 Hz, 1H), 6.94 (d, J=2.34 Hz, 1H), 6.68 (dd, J=5.76, 2.37 Hz, 1H), 6.59 (s, 2H).

EXAMPLE 193B

4-{[8-(1-hydroxy-1-methylethyl)-11-oxo-10,11-dihydro-5H-dibenzo[b,e][1,4]diazepin-3-yl]amino}pyridine-2-carbonitrile The desired product was prepared by substituting Example 193A for 4-aminopyridine in Example 191. MS (DCI) m/e 386 (M+H)$^+$; $^1$H NMR (500 MHz, DMSO-d$_6$) δ 9.57 (s, 1H), 9.45 (s, 1H), 8.36 (d, J=5.61 Hz, 1H), 7.83 (s, 1H), 7.67 (d, J=8.42 Hz, 1H), 7.48 (d, J=2.18 Hz, 1H), 7.22 (dd, J=5.77, 2.34 Hz, 1H), 7.09 (d, =1.56 HZ, 1H), 7.00-7.01 (m, 1H), 6.86-6.88 (m, 2H), 6.66 (dd, J=8.73, 1.87 Hz, 1H), 4.86 (s, 1H), 1.35 (s, 6H).

EXAMPLE 194

8-(1-hydroxy-1-methylethyl)-3-(pyrimidin-4-ylamino)-5,10-dihydro-11H-dibenzo[b,e][1,4]diazepin-11-one The desired product was prepared by substituting pyrimidin-4-ylamine for 4-aminopyridine in Example 191. MS (DCI) m/e 362 (M+H)$^+$; $^1$H NMR (500 MHz, DMSO-d$_6$) δ 9.74 (s, 1H), 9.54 (s, 1H), 8.71 (s, 1H), 8.34 (d, J=4.60 Hz, 1H), 7.85 (s, 1H), 7.65 (d, J=8.29 Hz, 1H), 7.49 (s, 1H), 6.94-7.09 (m, 4H), 6.88 (d, J=4.91 Hz, 1H), 4.87 (s, 1H), 1.37 (s, 6H).

EXAMPLE 195

8-(1-hydroxy-1-methylethyl)-3-[(2,3,5,6-tetrafluoropyridin-4-yl)amino]-5,10-dihydro-11H-dibenzo[b,e][1,4]diazepin-11-one The desired product was prepared by substituting 2,3,5,6-tetrafluoro-pyridin-4-ylamine for 4-aminopyridine in Example 191. MS (DCI) m/e 433 (M+H)$^+$; $^1$H NMR (500 MHz, DMSO-d$_6$) δ 9.60 (s, 1H), 9.58 (s, 1H), 7.78 (s, 1H), 7.62 (d, J=8.42 Hz, 1H), 7.09 (d, J=1.87 Hz, 1H), 7.00 (dd, J=8.42, 1.87 Hz, 1H), 6.67 (d, J=8.42 Hz, 1H), 6.00-6.-3 (m, 2H), 4.88 (s, 1H), 1.36 (s, 6H).

EXAMPLE 196

8-(1-ethyl-1-hydroxypropyl)-3-(pyridin-4-ylamino)-5,10-dihydro-11H-dibenzo[b,e][1,4]diazepin-11-one The desired product was prepared by substituting Example 190A for Example 189A in Example 191. MS (DCI) m/e 389 (M+H)$^+$; $^1$H NMR (500 MHz, DMSO-d$_6$) δ 9.47 (s, 1H), 9.01 (s, 1H), 8.28 (s, 1H), 7.77 (s, 1H), 7.62 (d, J=1.52 Hz, 1H), 6.99-7.03 (m, 2H), 6.89 (m, 2H), 6.62 (d, J=7.98 Hz, 1H), 4.38 (s, 1H), 1.61-1.64 (m, 4H), 0.64 (s, 6H).

EXAMPLE 197

3-[(2-aminopyrimidin-4-yl)amino]-8-(1-hydroxy-1-methylethyl)-5,10-dihydro-11H-dibenzo[b,e][1,4]diazepin-11-one The desired product was prepared by substituting pyrimidine-2,4-diamine for 4-aminopyridine in Example 191. MS (DCI) m/e 377 (M+H)$^+$; $^1$H NMR (500 MHz, DMSO-d$_6$) δ 9.47 (s, 1H), 9.30 (s, 1H), 7.87 (d, J=5.61 Hz, 1H), 7.75 (d, J=1.56 Hz, 1H), 7.58 (d, J=8.42 Hz, 1H), 7.53 (s, 1H), 7.03-7.08 (m, 2H), 7.01 (dd, J=8.26, 1.72 Hz, 1H), 6.89 (d, J=8.11 Hz, 1H), 6.23 (s, 2H), 6.07 (d, J=5.93 Hz, 1H), 4.86 (s, 1H), 1.35 (s, 6H).

EXAMPLE 198

3-[(2-chloropyridin-4-yl)amino]-8-(1-ethyl-1-hydroxypropyl)-5,10-dihydro-11H-dibenzo[b,e][1,4]diazepin-11-one The desired product was prepared by substituting Example 190A and 2-chloro-4-aminopyridine for Example 189A and 4-aminopyridine, respectively, in Example 191. MS (DCI) m/e 423 (M+H)$^+$; $^1$H NMR (500 MHz, DMSO-d$_6$) δ 9.53 (s, 1H), 9.26 (s, 1H), 8.07 (d, J=5.93 Hz, 1H), 7.83 (s, 1H), 7.66 (d, J=8.42 Hz, 1H), 6.98-7.01 (m, 3H), 6.86-6.89 (m, 3H), 6.63 (dd, J=8.73, 2.18 Hz, 1H), 4.37 (s, 1H), 1.62-1.64 (m, 4H), 0.63 (t, J=7.33 Hz, 6H).

EXAMPLE 199

8-(1-hydroxy-1-methylethyl)-3-[(2,3,6-trifluoropyridin-4-yl)amino]-5,10-dihydro-11H-dibenzo[b,e][1,4]diazepin-11-one

EXAMPLE 199A 2,3,6-trifluoropyridin-4-amine

A mixture of 3-chloro-2,5,6-trifluoro-pyridin-4-ylamine (1.82 g, 10 mmol), 5% Pd/C (0.5 g), and Et$_3$N (3.04 g, 30 mmol) in 50 mL of MeOH was equipped with a balloon of hydrogen gas and stirred at room temperature overnight. The solution was filtered through diatomaceous earth (Celite®). The filtrate was concentrated under vacuum and the residue was partitioned between ethyl acetate and H$_2$O. The aqueous layer was extracted with additional ethyl acetate, and the combined organic layers were washed with brine, dried (MgSO$_4$), filtered and concentrated under vacuum. The residue was purified by flash column chromatography on silica gel with 7:3 hexanes/ethyl acetate to provide 1.33 g (90%) of the desired product. MS (DCI) m/e 149 (M+H)$^+$.

EXAMPLE 199B 8-(1-hydroxy-1-methylethyl)-3-[(2,3,6-trifluoropyridin-4-yl)amino]-5,10-dihydro-11H-dibenzo[b,e][1,4]diazepin-11-one The desired product was prepared by substituting Example 199A for 4-aminopyridine in Example 191. MS (DCI) m/e 423 (M+H)$^+$; $^1$H NMR (500 MHz, DMSO-d$_6$) δ 9.62 (s, 1H), 9.54 (s, 1H), 7.86 (s, 1H), 7.69 (d, J=8.73 Hz, 1H), 7.10 (d, J=1.87 Hz, 1H), 6.88-6.91 (m, 3H), 6.77-6.80 (m, 2H), 4.99 (s, 1H), 1.36 (s, 6H).

EXAMPLE 200

3-({2-[(2-chloropyridin-4-yl)amino]pyridin-4-yl}amino)-8-(1-hydroxy-1-methylethyl)-5,10-dihydro-11H-dibenzo[b,e][1,4]diazepin-11-one The desired product was isolated as a second product in Example 192. MS (DCI) m/e 487 (M+H)$^+$; $^1$H NMR (500 MHz, DMSO-d$_6$) δ 9.59 (s, 1H), 9.49 (s, 1H), 8.97 (s, 1H), 8.04 (m, 2H), 7.97 (s, 1H), 7.79 (s, 1H), 7.65 (d, J=8.42 Hz, 1H), 7.41 (s, J=4.99 Hz, 1H), 7.08 (s, 1H), 6.99 (d, J=8.11 Hz, 1H), 6.89 (d, J=8.11 Hz, 1H), 6.82 (s, 1H), 6.61-6.66 (m, 3H), 4.86 (s, 1H), 1.35 (s, 6H).

EXAMPLE 201 methyl 2-methyl-2-{11-oxo-3-[(2,3,6-trifluoropyridin-4-yl)amino]-10,11-dihydro-5H-dibenzo[b,e][1,4]diazepin-8-yl}propanoate The desired product was prepared by substituting Example 199A and Example 266F for 4-aminopyridine and Example 189A, respectively, in Example 191. MS (DCI) m/e 487 (M+H)$^+$; $^1$H NMR (500 MHz, DMSO-d$_6$) δ 9.67 (s, 1H), 9.58 (s, 1H), 7.97 (s, 1H), 7.70 (d, J=8.54 Hz, 1H), 6.89-6.95 (m, 4H), 6.82 (d, J=4.27 Hz, 1H), 6.79 (dd, J=8.54, 2.14 Hz, 1H), 3.58 (s, 3H), 1.44 (s, 6H).

EXAMPLE 202

2-methylN(4-morpholin-4-ylphenyl)-2-{11-oxo-3-[(2,3,6-trifluoropyridin-4-yl)amino]-10,11-dihydro-5H-dibenzo[b,e][1,4]diazepin-8-yl}propanamide

EXAMPLE 202A 2-(3-chloro-11-oxo-10,11-dihydro-5H-dibenzo[b,e][1,4]diazepin-8-yl)-2-methylpropanoic acid The desired product was prepared by substituting Example 266F for Example 12 in Example 13. MS m/e (DCI) 331 (M+H)$^+$.

EXAMPLE 202B 2-(3-chloro-11-oxo-10,11-dihydro-5H-dibenzo[b,e][1,4]diazepin-8-yl)-2-methylN(4-morpholin-4-ylphenyl)propanamide The desired product was prepared by substituting Example 202A and 4-(4-morpholino)aniline for dimethylaminoacetic acid and Example 120, respectively, in Example 122. MS m/e (DCI) 490 (M+H)$^+$.

EXAMPLE 202C 2-methylN(4-morpholin-4-ylphenyl)-2-{11-oxo-3-[(2,3,6-trifluoropyridin-4-yl)amino]-10,11-dihydro-5H-dibenzo[b,e][1,4]diazepin-8-yl}propanamide The desired product was prepared by substituting Example 202B and Example 199A for Example 189A and 4-aminopyridine, respectively, in Example 191. MS (DCI) m/e 603 (M+H)$^+$; $^1$H NMR (500 MHz, DMSO-d$_6$) δ 9.67 (s, 1H), 9.53 (s, 1H), 8.77 (s, 1H), 7.91 (s, 1H), 7.68 (d, J=8.59 Hz, 1H), 7.41 (s, 1H), 7.59 (s, 1H), 7.01 (s, 1H), 6.90-6.92 (m, 3H), 6.45-6.84 (m, 4H), 3.69-3.71 (m, 4H), 2.99-3.01 (m, 4H), 1.47 (s, 6H).

EXAMPLE 203

2-{3-[(2,6-difluoropyridin-4-yl)amino]-11-oxo-10,11-dihydro-5H-dibenzo[b,e][1,4]diazepin-8-yl}-2-methylN(4-morpholin-4-ylphenyl)propanamide

EXAMPLE 203A 2,6-Difluoro-pyridin-4-ylamine

The title compound was prepared by substituting 3,5-dichloro-2,6-difluoro-pyridin-4-ylamine for 3-chloro-2,5,6-trifluoro-pyridin-4-ylamine in Example 199A. MS (DCI) m/e 183 (M+H)$^+$; $^1$H NMR (500 MHz, DMSO-d$_6$) δ 6.84 (s, 2H), 6.03 (s, 2H).

EXAMPLE 203B

2-{3-[(2,6-difluoropyridin-4-yl)amino]-11-oxo-10,11-dihydro-5H-dibenzo[b,e][1,4]diazepin-8-yl}-2-methylN(4-morpholin-4-ylphenyl)propanamide The desired product was prepared by substituting Example 202B and Example 203A for Example 189A and 4-aminopyridine, respectively, in Example 191. MS (DCI) m/e 585 (M+H)$^+$; $^1$H NMR (500 MHz, DMSO-d$_6$) δ 9.65 (s, 1H), 9.64 (s, 1H), 8.77 (s, 1H), 7.91 (s, 1H), 7.67 (d, J=8.42 Hz, 1H), 7.40 (d, J=9.04 Hz, 2H), 6.88-6.91 (m, 3H), 6.82 (d, J=9.04 Hz, 2H), 6.66 (dd, J=8.42, 1.87 Hz, 1H), 6.55 (s, 2H), 3.69-3.71 (m, 4H), 2.99-3.01 (m, 4H), 1.47 (s, 6H).

EXAMPLE 204

3-[(2,6-difluoropyridin-4-yl)amino]-8-(2-hydroxyethyl)-5,10-dihydro-11H-dibenzo[b,e][1,4]diazepin-11-one

EXAMPLE 204A 3-chloro-8-(2-hydroxyethyl)-5,10-dihydro-11H-dibenzo[b,e][1,4]diazepin-11-one A mixture of Example 6D (6.32 g, 20 mmol) in 100 mL of THF was treated with 1.0 M LiAlH$_4$ in THF (35 mL, 35 mmol) at 0° C. The reaction mixture was stirred for additional 30 min., quenched with MeOH, and concentrated under vacuum. The residue was partitioned between ethyl acetate and pH=3 water. The aqueous layer was extracted with additional ethyl acetate twice. The combined organic layers were washed with brine, dried (MgSO$_4$), filtered, and concentrated under vacuum. The residue was purified by flash column chromatography on silica gel with 1:9 hexanes/ethyl acetate to provide 5.18 g (90%) of the desired product. MS (DCI) m/e 289 and 291 (M+H)$^+$; $^1$H NMR (300 MHz, DMSO-d$_6$) δ 9.83 (s, 1H), 7.96 (s, 1H), 7.67 (d, J=8.5 Hz, 1H), 7.06 (d, J=2.0 Hz, 1H), 6.91 (dd, J=8.5, 2.0 Hz, 1H), 6.81-6.84 (m, 3H), 4.59 (t, J=6.0 Hz, 1H), 3.51-3.53 (m, 2H), 2.58 (t, J=6.9 Hz, 2H).

EXAMPLE 204B

3-[(2,6-difluoropyridin-4-yl)amino]-8-(2-hydroxyethyl)-5,10-dihydro-11H-dibenzo[b,e][1,4]diazepin-11-one The desired product was prepared by substituting Example 204A and Example 203A for Example 189A and 4-aminopyridine, respectively, in Example 191. MS (DCI) m/e 383 (M+H)$^+$; $^1$H NMR (500 MHz, DMSO-d$_6$) δ 9.57 (s, 1H), 9.51 (s, 1H), 7.75 (s, 1H), 7.59 (d, J=8.73 Hz, 1H), 6.77-6.80 (m, 2H), 6.69-6.71 (m, 2H), 6.59 (d, J=8.42 Hz, 1H), 6.47 (s, 2H), 4.49 (t, J=4.99 Hz, 1H), 3.41-3.45 (m, 2H), 2.49 (t, J=7.02 Hz, 2H).

EXAMPLE 205

2-{3-[(2,6-difluoropyridin-4-yl)amino]-11-oxo-10,11-dihydro-5H-dibenzo[b,e][1,4]diazepin-8-yl}-2-methylpropanoic acid

EXAMPLE 205A methyl 2-{3-[(2,6-difluoropyridin-4-yl)amino]-11-oxo-10,11-dihydro-5H-dibenzo[b,e][1,4]diazepin-8-yl}-2-methylpropanoate The desired product was prepared by substituting Example 266F and Example 203A for Example 189A and 4-aminopyridine, respectively, in Example 191. MS (DCI) m/e 439 (M+H)$^+$; $^1$H NMR (500 MHz, DMSO-d$_6$) δ 9.67 (s, 1H), 9.62 (s, 1H), 7.95 (s, 1H), 7.70 (d, J=8.42 Hz, 1H), 6.88-6.95 (m, 4H), 6.68 (dd, J=8.42, 2.18 Hz, 1H), 6.57 (s, 2H), 3.58 (s, 3H), 1.44 (s, 6H).

EXAMPLE 205B

2-{3-[(2,6-difluoropyridin-4-yl)amino]-11-oxo-10,11-dihydro-5H-dibenzo[b,e][1,4]diazepin-8-yl}-2-methylpropanoic acid A mixture of Example 205A (0.52 g, 1.18 mmol) and LiOH (0.144 g, 6.0 mmol) in 20 mL of THF and 20 mL of $H_2O$ was heated under reflux overnight. After the solution cooled to room temperature, the solution was neutralized with 10% HCl, and extracted with ethyl acetate. The organic layer was washed with brine, dried (MgSO4), filtrated and concentrated under vacuum to give the title compound. MS (DCI) m/e 425 $(M+H)^+$; $^1H$ NMR (500 MHz, DMSO-$d_6$) δ 12.27 (br, 1H), 9.72 (s, 1H), 9.68 (s, 1H), 7.98 (s, 1H), 7.75 (d, J=8.73 Hz, 1H), 7.06 (s, 1H), 6.96-6.99 (m, 3H), 6.74 (dd, J=8.73, 2.18 Hz, 1H), 6.62 (s, 2H), 1.46 (s, 6H).

EXAMPLE 206

3-[(2,6-difluoropyridin-4-yl)amino]-7-morpholin-4-yl-5,10-dihydro-11H-dibenzo[b,e][1,4]diazepin-11-one The desired product was prepared by substituting Example 450B and Example 203A for Example 189A and 4-aminopyridine, in Example 191. MS (DCI) m/e 439 $(M+H)^+$; $^1H$ NMR (500 MHz, DMSO-$d_6$) δ 9.65 (s, 1H), 9.49 (s, 1H), 7.79 (s, 1H), 6.83 (d, J=8.73 Hz, 1H), 6.89 (dd, J=8.58, 2.03 Hz, 1H), 6.53-6.57 (m, 4H), 6.57 (s, 2H), 3.71-3.73 (m, 4H), 2.98-3.00 (m, 4H).

EXAMPLE 207

7-morpholin-4-yl-3-[(2,3,6-trifluoropyridin-4-yl)amino]-5,10-dihydro-11H-dibenzo[b,e][1,4]diazepin-11-one The desired product was prepared by substituting Example 450B and Example 199A for Example 189A and 4-aminopyridine, in Example 191. MS (DCI) m/e 442 $(M+H)^+$; $^1H$ NMR (500 MHz, DMSO-$d_6$) δ 9.53 (s, 1H), 9.52 (s, 1H), 7.79 (s, 1H), 7.68 (d, J=8.73 Hz, 1H), 6.90 (d, J=1.87 Hz, 1H), 6.78-6.84 (m, 3H), 6.53-6.55 (m, 2H), 3.71-3.73 (m, 4H), 2.98-3.00 (m, 4H).

EXAMPLE 208

3-[(2,6-difluoropyridin-4-yl)amino]-8-(2-hydroxy-2-methylpropyl)-5,10-dihydro-11H-dibenzo[b,e][1,4]diazepin-11-one

EXAMPLE 208A 3-chloro-8-(2-hydroxy-2-methylpropyl)-5,10-dihydro-11H-dibenzo[b,e][1,4]diazepin-11-one The title compound was prepared by substituting Example 6D for Example 1B in Example 189A. MS (DCI) m/e 317 $(M+H)^+$; $^1H$ NMR (500 MHz, DMSO-$d_6$) δ 9.79 (s, 1H), 7.92 (s, 1H), 7.66 (d, J=8.42 Hz, 1H), 7.05 (d, J=1.87 Hz, 1H), 6.89 (d, J=8.42, 1.87 Hz, 1H), 6.78-6.85 (m, 3H), 4.21 (s, 1H), 2.49 (s, 2H), 1.01 (s, 6H).

EXAMPLE 208B

3-[(2,6-difluoropyridin-4-yl)amino]-8-(2-hydroxy-2-methylpropyl)-5,10-dihydro-11H-dibenzo[b,e][1,4]diazepin-11-one The title compound was prepared by substituting Example 208A and Example 203A for Example 189A and 4-aminopyridine, respectively, in Example 191. MS (DCI) m/e 411 $(M+H)^+$; $^1H$ NMR (500 MHz, DMSO-$d_6$) δ 9.63 (s, 1H), 9.56 (s, 1H), 7.85 (s, 1H), 7.66 (d, J=8.42 Hz, 1H), 6.89 (s, 1H), 6.80 (d, J=7.17 Hz, 2H), 6.69 (d, J=7.80 Hz, 1H), 6.65 (d, J=8.42 Hz, 1H), 6.54 (s, 2H), 4.24 (s, 1H), 2.49 (s, 2H), 1.02 (s, 6H).

EXAMPLE 209 methyl [11-oxo-3-(pyridin-4-ylamino)-10,11-dihydro-5H-dibenzo[b,e][14]diazepin-8-yl]acetate The title compound was prepared by substituting Example 6D for Example 189A in Example 191. MS (DCI) m/e 375 $(M+H)^+$; $^1H$ NMR (500 MHz, DMSO-$d_6$) δ 10.50 (s, 1H), 9.74 (s, 1H), 8.31 (s, 1H), 8.29 (s, 1H), 7.98 (s, 1H), 7.70 (d, J=8.42 Hz, 1H), 7.17 (d, J=7.49 Hz, 2H), 6.89 (d, J=2.18 Hz, 1H), 6.86 (d, J=7.80 Hz, 1H), 6.77-6.80 (m, 3H), 3.53 (s, 3H), 3.47 (s, 2H).

EXAMPLE 210 methyl {3-[(2-chloropyridin-4-yl)amino]-11-oxo-10,11-dihydro-5H-dibenzo[b,e][1,4]diazepin-8-yl}acetate The title compound was prepared by substituting Example 6D and 2-chloro-4-aminopyridine for Example 189A and 4-aminopyridine, respectively, in Example 191. MS (DCI) m/e 409 $(M+H)^+$; $^1H$ NMR (500 MHz, DMSO-$d_6$) δ 9.63 (s, 1H), 9.31 (s, 1H), 8.09 (d, J=6.14 Hz, 1H), 7.93 (s, 1H), 7.67 (d, J=8.59 Hz, 1H), 7.00-7.01 (m, 2H), 6.82-6.92 (m, 4H), 6.66 (d, J=8.90 Hz, 1H), 3.60 (s, 3H), 3.52 (s, 2H).

EXAMPLE 211 methyl {3-[(2-methylpyridin-4-yl)amino]-11-oxo-10,11-dihydro-5H-dibenzo[b,e][1,4]diazepin-8-yl}acetate The title compound was prepared by substituting Example 6D and 2-methyl-4-aminopyridine for Example 189A and 4-aminopyridine, respectively, in Example 191. MS (DCI) m/e 389 $(M+H)^+$; $^1H$ NMR (500 MHz, DMSO-$d_6$) δ 10.81 (s, 1H), 9.80 (s, 1H), 8.26 (d, J=7.37 Hz, 1H), 8.04 (s, 1H), 7.01-7.09 (m, 2H), 6.93-6.94 (m, 2H), 6.82-6.87 (m, 4H), 3.50 (s, 3H), 3.54 (s, 2H).

EXAMPLE 212

3-[(2-chloropyridin-4-yl)amino]-5,10-dihydro-11H-dibenzo[b,e][1,4]diazepin-11-one The title compound was prepared by substituting Example 9 and 2-chloro-4-aminopyridine for Example 189A and 4-aminopyridine, respectively, in Example 191. MS (DCI) m/e 334 $(M+H)^+$; $^1H$ NMR (500 MHz, DMSO-$d_6$) δ 9.64 (s, 1H), 9.29 (s, 1H), 8.09 (d, J=6.14 Hz, 1H), 7.93 (s, 1H), 7.69 (d, J=8.70 Hz, 1H), 6.88-7.01 (m, 7H), 6.67 (dd, J=8.59, 2.15, 1H).

EXAMPLE 213

8-acetyl-3-[(2-chloropyridin-4-yl)amino]-5,10-dihydro-11H-dibenzo[b,e][1,4]diazepin-11-one

EXAMPLE 213A 8-acetyl-3-chloro-5,10-dihydro-11H-dibenzo[b,e][1,4]diazepin-11-one The title compound was isolated as a minor product in Example 189A. MS (DCI) m/e 287 (M+H)$^+$; $^1$H NMR (500 MHz, DMSO-d$_6$) δ 9.98 (s, 1H), 8.51 (s, 1H), 7.73 (d, J=8.59 Hz, 1H), 7.57-7.61 (m, 2H), 7.08 (d, J=1.84 Hz, 1H), 7.04 (d, J=8.29 Hz, 2H), 6.96 (dd, J=8.59, 2.15 Hz, 1H), 2.45 (s, 3H).

EXAMPLE 213B 8-acetyl-3-[(2-chloropyridin-4-yl)amino]-5,10-dihydro-11H-dibenzo[b,e][1,4]diazepin-11-one The title compound was prepared by substituting Example 213A and 2-chloro-4-pyridine for Example 189A and 4-aminopyridine, respectively, in Example 191. MS (DCI) m/e 378 (M+H)$^+$; $^1$H NMR (500 MHz, DMSO-d$_6$) δ 10.00 (s, 1H), 8.59 (s, 2H), 8.49 (s, 1H), 7.86 (d, J=8.11 Hz, 1H), 7.57-7.58 (m, 2H), 7.45 (d, J=5.61 Hz, 2H), 6.94-6.94 (m, 4H), 2.06 (s, 3H).

EXAMPLE 214

{3-[(2-chloropyridin-4-yl)amino]-1-oxo-10,11-dihydro-5H-dibenzo[b,e][1,4]diazepin-8-yl}acetic acid The title compound was prepared by substituting Example 210 for Example 12 in Example 13. MS (DCI) m/e 395 (M+H)$^+$; $^1$H NMR (500 MHz, DMSO-d$_6$) δ 9.69 (s, 1H), 9.65 (s, 1H), 8.11 (d, J=5.93 Hz, 1H), 7.98 (s, 1H), 7.69 (d, J=8.73 Hz, 1H), 7.05-7.06 (m, 2H), 6.91-6.94 (m, 2H), 6.83-6.85 (m, 2H), 6.70 (dd, J=8.58, 2.03 Hz, 1H), 3.42 (s, 2H).

EXAMPLE 215

3-[(2-chloropyridin-4-yl)amino]-8-isopropenyl-5,10-dihydro-11H-dibenzo[b,e][1,4]diazepin-11-one The title compound was isolated as a minor product in Example 192. MS (DCI) m/e 377 (M+H)$^+$; $^1$H NMR (500 MHz, DMSO-d$_6$) δ 9.77 (s, 1H), 9.50 (s, 1H), 8.12-8.13 (m, 2H), 7.71 (d, J=8.42 Hz, 1H), 7.07-7.13 (m, 3H), 6.91-6.97 (m, 3H), 6.70 (dd, J=8.42, 1.87 Hz, 1H), 5.29 (s, 1H), 4.99 (s, 1H), 2.03 (s, 3H).

EXAMPLE 216

2-{3-[(2-chloropyridin-4-yl)amino]-11-oxo-10,11-dihydro-5H-dibenzo[b,e][1,4]diazepin-8-yl}N(4-morpholin-4-ylphenyl)acetamide The title compound was prepared by substituting Example 214 and 4-morpholin-4-ylphenylamine for dimethylaminoacetic acid and Example 120, respectively, in Example 122. MS (DCI) m/e 556 (M+H)$^+$; $^1$H NMR (500 MHz, DMSO-d$_6$) δ 9.89 (s, 1H), 9.65 (s, 1H), 9.32 (s, 1H), 8.08 (d, J=6.55 Hz, 1H), 7.89 (s, 1H), 7.67 (d, J=8.42 Hz, 1H), 7.45 (d, J=9.05 Hz, 2H), 6.99-7.01 (m, 2H), 6.86-6.92 (m, 5H), 6.65 (dd, J=8.58, 2.03 Hz, 1H), 3.72-3.74 (m, 4H), 3.45 (s, 2H), 3.04-3.06 (m, 4H).

EXAMPLE 217

3-[(2-chloropyridin-4-yl)amino]-8-(2-hydroxy-2-methylpropyl)-5,10-dihydro-11H-dibenzo[b,e][1,4]diazepin-11-one The title compound was prepared by substituting Example 208A and 2-chloro-4-aminopyridine for Example 189A and 4-aminopyridine, respectively, in Example 191. MS (DCI) m/e 409 (M+H)$^+$; $^1$H NMR (500 MHz, DMSO-d$_6$) δ 9.59 (s, 1H), 9.30 (s, 1H), 8.09 (d, J=3.05 Hz, 1H), 7.86 (s, 1H), 7.67 (d, J=7.93 Hz, 1H), 7.00 (s, 2H), 6.79-7.87 (m, 4H), 6.65 (d, J=7.63, Hz, 1H), 4.25 (s, 1H), 2.12 (s, 2H), 1.04 (s, 6H).

EXAMPLE 218

2-{3-[(2-chloropyridin-4-yl)amino]-1-oxo-10,11-dihydro-5H-dibenzo[b,e][1,4]diazepin-8-yl}-2-methylN(4-morpholin-4-ylphenyl)propanamide The title compound was prepared by substituting Example 202B and 2-chloro-4-aminopyridine for Example 189A and 4-aminopyridine, respectively, in Example 191. MS (DCI) m/e 584 (M+H)$^+$; $^1$H NMR (500 MHz, DMSO-d$_6$) δ 9.62 (s, 1H), 9.32 (s, 1H), 8.82 (s, 1H), 8.08 (d, J=6.55 Hz, 1H), 7.92 (s, 1H), 7.67 (d, J=8.59 Hz, 1H), 7.44 (d, J=8.90 Hz, 2H), 6.99-7.02 (m, 3H), 6.86-6.92 (m, 5H), 6.65 (dd, J=8.59, 2.15 Hz, 1H), 3.72-3.74 (m, 4H), 3.04-3.07 (m, 4H), 1.48 (s, 6H).

EXAMPLE 219

3-[(2-chloropyridin-4-yl)amino]-8-(2-oxopyrrolidin-1-yl)-5,10-dihydro-11H-dibenzo[b,e][1,4]diazepin-11-one The title compound was prepared by substituting Example 161B and 2-chloro-4-aminopyridine for Example 189A and 4-aminopyridine, respectively, in Example 191. MS (DCI) m/e 420 (M+H)$^+$; $^1$H NMR (500 MHz, DMSO-d$_6$) δ 9.69 (s, 1H), 9.61 (s, 1H), 8.14 (s, 1H), 8.02 (s, 1H), 7.73 (d, J=8.11 Hz, 1H), 7.34 (s, 1H), 7.25 (s, 1H), 6.92-7.08 (m, 4H), 6.72 (d, J=8.11 Hz, 1H), 3.71-3.77 (m, 2H), 3.51-3.53 (m, 2H), 2.05-2.07 (m, 2H).

EXAMPLE 220 methyl {3-[(2-chloropyridin-4-yl)amino]-11-oxo-10,11-dihydro-5H-dibenzo[b,e][1,4]diazepin-7-yl}acetate The title compound was prepared by substituting Example 388D and 2-chloro-4-aminopyridine for Example 189A and 4-aminopyridine, respectively, in Example 191. MS (DCI) m/e 409 (M+H)$^+$; $^1$H NMR (500 MHz, DMSO-d$_6$) δ 9.63 (s, 1H), 9.31 (s, 1H), 8.14 (s, 1H), 8.08-8.10 (m, 1H), 7.95 (s, 1H), 7.67 (d, J=8.59 Hz, 1H), 7.00-7.02 (m, 2H), 6.88-6.89 (m, 3H), 6.78 (dd, J=8.29, 1.84 Hz, 1H), 6.66 (dd, J=8.59, 2.15 Hz, 1H), 3.60 (s, 3H), 3.54 (s, 2H).

EXAMPLE 221

8-[2-(pyridin-2-yloxy)ethyl]-3-[(2,3,6-trifluoropyridin-4-yl)amino]-5,10-dihydro-11H-dibenzo[b,e][1,4]diazepin-11-one

EXAMPLE 221A 3-chloro-8-[2-(pyridin-2-yloxy)ethyl]-5,10-dihydro-11H-dibenzo[b,e][1,4]diazepin-11-one A mixture of Example 204A (150 mg, 0.52 mmol), pyridin-2 (1H)-one (96 mg, 1.0 mmol), PPh$_3$ (180 mg, 0.68 mmol) and di-tert-butyl azodicarboxylate (160 mg, 0.68 mmol) in 10 mL of THF was stirred overnight. The reaction mixture was purified by flash column chromatography on silica gel with 7:3 hexanes/ethyl acetate to provide 72 mg of the desired product. The column was then washed with 100:3:1 EtOAc/MeOH/NH$_4$OH to give 79 mg of 3-chloro-8-[2-(2-oxo-2H-pyridin-1-yl)-ethyl]-5,10-dihydro-dibenzo[b,e][1,4]diazepin-11-one. MS (DCI) m/e 366 (M+H)$^+$; $^1$H NMR (500 MHz, DMSO-d$_6$) δ 9.83 (s, 1H), 8.13-8.14 (m, 1H), 7.97 (s, 1H), 7.65-7.68 (m, 2H), 7.05 (d, J=1.84 Hz, 1H), 6.89-6.95 (m, 5H), 6.76 (d, J=8.42 Hz, 1H), 4.38 (t, J=6.86 Hz, 2H), 2.99 (t, J=6.86 Hz, 2H).

EXAMPLE 221B

8-[2-(pyridin-2-yloxy)ethyl]-3-[(2,3,6-trifluoropyridin-4-yl)amino]-5,10-dihydro-11H-dibenzo[b,e][1,4]diazepin-11-one The title compound was prepared by substituting Example 221A and Example 203A for Example 189A and 4-aminopyridine, respectively, in Example 191. MS (DCI) m/e 478 (M+H)$^+$; $^1$H NMR (500 MHz, DMSO-d$_6$) δ 9.67 (s, 1H), 9.55 (s, 1H), 8.14-8.15 (m, 1H), 7.89 (s, 1H), 7.66-7.70 (m, 2H), 6.94-6.97 (m, 1H), 6.87-6.91 (m, 4H), 6.77-6.81 (m, 3H), 4.39 (t, J=6.75 Hz, 2H), 2.89 (t, J=6.90 Hz, 2H).

EXAMPLE 222

8-(2-hydroxy-2-methylpropyl)-3-[(2,3,5-trifluorophenyl)amino]-5,10-dihydro-11H-dibenzo[b,e][1,4]diazepin-11-one The title compound was prepared by substituting Example 208A and Example 203A for Example 189A and 4-aminopyridine, respectively, in Example 191. MS (DCI) m/e 428 (M+H)$^+$; $^1$H NMR (500 MHz, DMSO-d$_6$) δ 9.68 (s, 1H), 9.59 (s, 1H), 7.87 (s, 1H), 7.74 (d, J=8.42 Hz, 1H), 6.97 (s, 1H), 6.91 (d, J=8.11 Hz, 1H), 6.82-6.86 (m, 4H), 4.27 (s, 1H), 2.65 (s, 2H), 1.08 (s, 6H).

EXAMPLE 223

3-[(3,5-difluorophenyl)amino]-7-(3-hydroxy-3-methylbutyl)-8-methoxy-5,10-dihydro-11H-dibenzo[b,e][1,4]diazepin-11-one

EXAMPLE 223A

N-(3-bromo-4-methoxyphenyl)acetamide

A mixture of 2-bromo-1-methoxy-4-nitro-benzene (5.7 g, 24.6 mmol) and SnCl$_2$.2H$_2$O (16.6 g, 73.7 mmol) in 100 mL of MeOH and 50 mL of concentrated HCl was heated under reflux overnight. After the solution cooled to room temperature, it was extracted with EtOAc several times. The combined organic layers were washed with brine, dried (MgSO$_4$), filtered, and concentrated under vacuum. The residue was diluted with 100 mL of CH$_2$Cl$_2$, and treated with excess Ac$_2$O and Et$_3$N at 0° C. The solution was stirred at room temperature overnight, and washed with brine, dried (MgSO$_4$), filtered, and concentrated under vacuum to give the title compound. MS (DCI) m/e 245 (M+H)$^+$.

EXAMPLE 223B

N-(5-bromo-4-methoxy-2-nitrophenyl)acetamide

Concentrated nitric acid (10 mL, >69% pure) was added to acetic anhydride (50 mL) cooled to −10 IC. The solution was treated portionwise with Example 223A (5.08 g, 20.8 mmol) at a rate which maintained an internal temperature below −5° C. The solution was stirred for 1 hour while warming to room temperature. The solution was poured into an ice/water mixture and extracted several times with ethyl acetate. The combined extracts were washed with 10% Na$_2$CO$_3$ and brine, dried (MgSO$_4$), filtered, and concentrated under vacuum. The residue was purified by flash column chromatography on silica gel with 3:7 hexanes/ethyl acetate to provide 5.88 g (97%) of the title compound. MS (DCI) m/e 290 (M+H)$^+$; $^1$H NMR (500 MHz, DMSO-d$_6$) δ 10.11 (s, 1H), 7.87 (s, 1H), 7.61 (s, 1H), 3.93 (s, 3H), 2.04 (s, 3H).

EXAMPLE 223C 5-bromo-4-methoxy-2-nitroaniline

Example 223B (5.4 g, 18.7 mmol) in 400 mL of MeOH and 10 mL of concentrated H$_2$SO$_4$ was heated under reflux for 4 hours. The solvent was removed under vacuum, and the residue was partitioned between EtOAc and H$_2$O. The organic layer was separated, washed with brine, dried (MgSO$_4$), filtrated and concentrated under vacuum to 4.4 g of the desired product. MS (DCI) m/e 248 (M+H)$^+$; $^1$H NMR (500 MHz, DMSO-d$_6$) δ 7.48 (s, 1H), 7.39 (s, 1H), 3.81 (s, 3H).

EXAMPLE 223D methyl 2-[(5-bromo-4-methoxy-2-nitrophenyl)amino]-4-chlorobenzoate The title compound was prepared by substituting Example 223C for methyl 3,4-diaminobenzoate in Example 1A. MS (DCI) m/e 248 (M+H)$^+$; $^1$H NMR (500 MHz, DMSO-d$_6$) δ 10.50 (s, 1H), 7.91-7.95 (m, 2H), 7.74 (s, 1H), 7.32 (d, J=2.03 Hz, 1H), 7.05 (dd, J=8.48, 2.03 Hz, 1H), 3.95 (s, 3H), 3.88 (s, 3H).

EXAMPLE 223E methyl 2-[(2-amino-5-bromo-4-methoxyphenyl)amino]-4-chlorobenzoate The title compound was prepared by substituting Example 223D for Example 6B in Example 6C. MS (DCI) m/e 248 (M+H)$^+$; $^1$H NMR (500 MHz, DMSO-d$_6$) δ 8.71 (s, 1H), 7.84 (d, J=8.42 Hz, 1H), 7.15 (s, 1H), 6.70 (dd, J=8.58, 2.03 Hz, 1H), 6.56 (s, 1H), 6.28 (d, J=2.18 Hz, 1H), 5.22 (s, 2H), 3.85 (s, 3H), 3.79 (s, 3H).

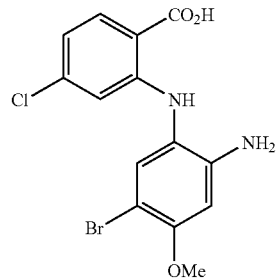

EXAMPLE 223F

2-[(2-amino-5-bromo-4-methoxyphenyl)amino]-4-chlorobenzoic acid

The title compound was prepared by substituting Example 223E for Example 12 in Example 13. MS (DCI) m/e 372 (M+H)$^+$.

EXAMPLE 223G 7-bromo-3-chloro-8-methoxy-5,10-dihydro-11H-dibenzo[b,e][1,4]diazepin-11-one A mixture of Example 223F (0.35 g, 0.94 mmol), HATU (0.430 g, 1.13 mmol), and excess Et$_3$N in 4 mL of DMF was stirred overnight. The reaction mixture was partitioned between EtOAc and H$_2$O. The organic layer was washed with brine, dried (MgSO$_4$), filtrated and concentrated to give 0.34 g of the title compound. MS (DCI) m/e 248 (M+H)$^+$; $^1$H NMR (500 MHz, DMSO-d$_6$) δ 9.89 (s, 1H), 7.90 (s, 1H), 7.67 (d, J=8.42 Hz, 1H), 7.19 (s, 1H), 7.00 (d, J=1.87 Hz, 1H), 6.93 (dd, J=8.42, 2.18 Hz, 1H), 6.75 (s, 1H), 5.22 (s, 2H), 3.73 (s, 3H).

EXAMPLE 223H methyl 3-(3-chloro-8-methoxy-11-oxo-10,11-dihydro-5H-dibenzo[b,e][1,4]diazepin-7-yl)acrylate A mixture of Example 223G (71 mg, 0.2 mmol), methyl acrylate (64 mg, 0.8 mmol), Pd(dppf)Cl$_2$ (33 mg, 0.04 mmol) and 1 mL Et$_3$N in 3 mL of DMF was heated at 110° C. overnight. The reaction mixture was diluted with EtOAc when it was still warm, and poured onto water. The organic layer was separated, washed with brine, dried (MgSO$_4$), filtered and concentrated. The residue was triturated with 20 mL of 1:1 EtOH/Aceton to give 60 mg of the title compound. MS (DCI) m/e 359 (M+H)$^+$; $^1$H NMR (500 MHz, DMSO-d$_6$) δ 10.04 (s, 1H), 7.91 (s, 1H), 7.86-7.75 (m, 2H), 7.25 (s, 1H), 7.03 (d, J=1.53 Hz, 1H), 6.93 (dd, J=8.59, 1.84 Hz, 1H), 6.75 (s, 1H), 6.35 (d, J=15.96 Hz, 1H), 3.78 (s, 3H), 3.77 (s, 3H).

EXAMPLE 223I methyl 3-(3-chloro-8-methoxy-11-oxo-10,11-dihydro-5H-dibenzo[b,e][1,4]diazepin-7-yl)propanoate The title compound was prepared by substituting Example 223H for Example 6B in Example 6C. MS (DCI) m/e 361 (M+H)$^+$; $^1$H NMR (500 MHz, DMSO-d$_6$) δ 9.74 (s, 1H), 7.78 (s, 1H), 7.66 (d, J=8.42 Hz, 1H), 7.03 (d, J=1.87 Hz, 1H), 6.89 (dd, J=8.58, 2.03 Hz, 1H), 6.76 (s, 1H), 6.62 (s, 1H), 3.69 (s, 3H), 3.58 (s, 3H), 2.68-2.71 (m, 2H), 2.49-2.52 (m, 2H).

EXAMPLE 223J 3-chloro-7-(3-hydroxy-3-methylbutyl)-8-methoxy-5,10-dihydro-11H-dibenzo[b,e][1,4]diazepin-11-one The title compound was prepared by substituting Example 223I for Example 1B in Example 189A. MS (DCI) m/e 361 (M+H)$^+$; $^1$H NMR (500 MHz, DMSO-d$_6$) δ 9.74 (s, 1H), 7.76 (s, 1H), 7.66 (d, J=8.24 Hz, 1H), 7.02 (d, J=2.14 Hz, 1H), 6.89 (dd, J=8.39, 1.98 Hz, 1H), 6.76 (s, 1H), 6.59 (s, 1H), 4.20 (s, 1H), 3.68 (s, 3H), 2.45-2.48 (m, 2H), 1.51-1.55 (m, 2H), 1.12 (s, 6H).

EXAMPLE 223K

3-[(3,5-difluorophenyl)amino]-7-(3-hydroxy-3-methylbutyl)-8-methoxy-5,10-dihydro-11H-dibenzo[b,e][1,4]diazepin-11-one The title compound was prepared by substituting Example 223J and Example 203A for Example 189A and 4-aminopyridine in Example 191. MS (DCI) m/e 455 (M+H)$^+$; $^1$H NMR (500 MHz, DMSO-d$_6$) δ 9.67 (s, 1H), 9.52 (s, 1H), 7.67 (m, 2H), 6.87 (m, 1H), 6.76 (m, 1H), 6.56-6.59 (m, 4H), 4.20 (s, 1H), 3.68 (s, 3H), 2.45-2.48 (m, 2H), 1.51-1.55 (m, 2H), 1.12 (s, 6H).

EXAMPLE 224

7-(3-hydroxy-3-methylbutyl)-8-methoxy-3-(3-methoxy-4-nitrophenyl)-5,10-dihydro-11H-dibenzo[b,e][1,4]diazepin-11-one The title compound was prepared by substituting Example 223J and Example 266G for Example 59B and Example 56A, respectively, in Example 59C. MS (DCI) m/e 478 (M+H)$^+$; $^1$H NMR (500 MHz, DMSO-d$_6$) δ 9.74 (s, 1H), 7.76 (s, 1H), 7.66 (d, J=8.24 Hz, 1H), 7.02 (d, J=2.14 Hz, 1H), 6.89 (dd, J=8.39, 1.98 Hz, 1H), 6.76 (s, 1H), 6.59 (s, 1H), 4.20 (s, 1H), 3.68 (s, 3H), 2.45-2.48 (m, 2H), 1.51-1.55 (m, 2H), 1.12 (s, 6H).

EXAMPLE 225

3-[(2,6-difluoropyridin-4-yl)amino]-7-(3-hydroxypropyl)-8-methoxy-5,10-dihydro-11H-dibenzo[b,e][1,4]diazepin-11-one

EXAMPLE 225A 3-chloro-7-(3-hydroxypropyl)-8-methoxy-5,10-dihydro-11H-dibenzo[b,e][1,4]diazepin-11-one The title compound was prepared by substituting Example 223I for Example 6D in Example 204A. MS (DCI) m/e 333 (M+H)$^+$; $^1$H NMR (500 MHz, DMSO-d$_6$) δ 9.71 (s, 1H), 7.75 (s, 1H), 7.66 (d, J=8.73 Hz, 1H), 7.02 (d, J=1.87 Hz, 1H), 6.89 (dd, J=8.42, 2.18 Hz, 1H), 6.75 (s, 1H), 6.60 (s, 1H), 4.39 (t, J=5.15 Hz, 1H), 3.68 (s, 3H), 2.37-2.41 (m, 2H), 2.44-2.50 (m, 2H), 1.59-1.65 (m, 2H).

EXAMPLE 225B

3-[(2,6-difluoropyridin-4-yl)amino]-7-(3-hydroxypropyl)-8-methoxy-5,10-dihydro-11H-dibenzo[b,e][1,4]diazepin-11-one The title compound was prepared by substituting Example 225A and Example 203A for Example 189A and 4-aminopyridine in Example 191A. MS (DCI) m/e 427 (M+H)$^+$; $^1$H NMR (500 MHz, DMSO-d$_6$) δ 9.67 (s, 1H), 9.53 (s, 1H), 7.62-7.68 (m, 2H), 6.87 (s, 1H), 6.75 (s, 1H), 6.67 (d, J=7.93 Hz, 1H), 6.60 (s, 1H), 6.57 (s, 2H), 4.42 (t, J=5.15 Hz, 1H), 3.68 (s, 3H), 3.37-3.41 (m, 2H), 2.44-2.50 (m, 2H), 1.59-1.65 (m, 2H).

EXAMPLE 226

7-(3-hydroxypropyl)-8-methoxy-3-(3-methoxy-4-nitrophenyl)-5,10-dihydro-11H-dibenzo[b,e][1,4]diazepin-11-one The title compound was prepared by substituting Example 225A and Example 266G for Example 59B and Example 56A, respectively, in Example 59C. MS (DCI) m/e 450 (M+H)$^+$; $^1$H NMR (500 MHz, DMSO-d$_6$) δ 9.72 (s, 1H), 8.00 (d, J=8.42 Hz, 1H), 7.78 (d, J=8.42 Hz, 1H), 7.52 (d, J=1.56 Hz, 1H), 7.32-7.35 (m, 2H), 7.27 (dd, J=8.26, 1.72 Hz, 1H), 6.81 (s, 1H), 6.62 (s, 1H), 4.40 (t, J=5.15 Hz, 1H), 3.68 (s, 3H), 3.38-3.42 (m, 2H), 2.44-2.50 (m, 2H), 1.61-1.64 (m, 2H).

EXAMPLE 227

3-[(2,6-difluoropyridin-4-yl)amino]-8-(3-hydroxy-3-methylbutyl)-5,10-dihydro-11H-dibenzo[b,e][1,4]diazepin-11-one

EXAMPLE 227A methyl 3-[4-(acetylamino)phenyl]propanoate 3-(4-Aminophenyl)propionic acid (5.0 g, 30 mmol) in 100 mL of CH$_2$Cl$_2$ and 5 mL of MeOH was treated with 2.0 M TMSCHN$_2$ in hexane dropwise (40 mL, 80 mmol). After bubbling ceased, the solvents were removed under vacuum. The residue was diluted with CH$_2$Cl$_2$, and treated with excess Ac$_2$O and Et$_3$N. The solution was stirred overnight and washed with water, brine, dried (MgSO4), filtered, and concentrated under vacuum to give the title compound. MS (DCI) m/e 222 (M+H)$^+$.

EXAMPLE 227B methyl 3-[4-(acetylamino)-3-nitrophenyl]propanoate

The title compound was prepared by substituting Example 227A for Example 223A in Example 224B. MS (DCI) m/e 267 (M+H)$^+$.

EXAMPLE 227C methyl 3-(4-amino-3-nitrophenyl)propanoate

The title compound was prepared by substituting Example 227B for Example 223B in Example 223C. MS (DCI) m/e 225 (M+H)$^+$; $^1$H NMR (500 MHz, DMSO-d$_6$) δ 7.78 (d, J=2.03 Hz, 1H), 7.28-7.32 (m, 2H), 6.94 (d, J=8.11 Hz, 1H), 3.57 (s, 3H), 2.74 (d, J=7.29 Hz, 2H), 2.56-2.61 (t, J=7.29 Hz, 2H).

EXAMPLE 227D methyl 4-chloro-2-{[4-(3-methoxy-3-oxopropyl)-2-nitrophenyl]amino}benzoate The title compound was prepared by substituting Example 227C for methyl 3,4-diaminobenzoate in Example 1A. MS (DCI) m/e 393 (M+H)$^+$; $^1$H NMR (500 MHz, DMSO-d$_6$) δ 10.77 (s, 1H), 8.01 (d, J=1.69 Hz, 1H), 7.96 (d, J=8.48 Hz, 1H), 7.56-7.65 (m, 2H), 7.41 (d, J=2.03 Hz, 1H), 7.09 (dd, J=8.81, 2.03 Hz, 1H), 3.89 (s, 3H), 3.60 (s, 3H), 2.90 (t, J=7.46 Hz, 2H), 2.59 (t, J=7.29 Hz, 2H).

EXAMPLE 227E methyl 2-{[2-amino-4-(3-methoxy-3-oxopropyl)phenyl]amino}-4-chlorobenzoate The title compound was prepared by substituting Example 227D for Example 6B in Example 6C. MS (DCI) m/e 363 (M+H)$^+$; $^1$H NMR (500 MHz, DMSO-d$_6$) δ 8.79 (s, 1H), 7.84 (d, J=8.82 Hz, 1H), 6.92 (d, J=7.80 Hz, 1H), 6.69 (dd, J=8.48, 2.03 Hz, 1H), 6.66 (d, J=1.70 Hz, 1H), 6.47 (dd, J=7.97, 1.87 Hz, 1H), 6.37 (d, J=2.03 Hz, 1H), 4.94 (s, 2H), 3.85 (s, 3H), 3.60 (s, 3H), 2.76 (t, J=7.46 Hz, 2H), 2.61 (t, J=7.29 Hz, 2H).

EXAMPLE 227F methyl 3-(3-chloro-11-oxo-10,11-dihydro-5H-dibenzo[b,e][1,4]diazepin-8-yl)propanoate The title compound was prepared by substituting Example 227E for Example 6C in Example 6D. MS (DCI) m/e 331 (M+H)$^+$; $^1$H NMR (500 MHz, DMSO-d$_6$) δ 9.82 (s, 1H), 7.96 (s, 1H), 7.67 (d, J=8.42 Hz, 1H), 7.05 (d, J=2.18 Hz, 1H), 6.91 (dd, J=8.42, 1.87 Hz, 1H), 6.87-6.88 (m, 1H), 6.81-6.83 (m, 2H), 3.58 (s, 3H), 2.72 (t, J=7.49 Hz, 2H), 2.55 (t, J=7.64 Hz, 2H).

EXAMPLE 227G 3-chloro-8-(3-hydroxy-3-methylbutyl)-5,10-dihydro-11H-dibenzo[b,e][1,4]diazepin-11-one The desired product was prepared by substituting Example 227F for Example 1B in Example 189A. MS (DCI) m/e 331 (M+H)$^+$; $^1$H NMR (500 MHz, DMSO-d$_6$) δ 9.80 (s, 1H), 7.93 (s, 1H), 7.67 (d, J=8.59 Hz, 1H), 7.05 (d, J=2.15 Hz, 1H), 6.91 (dd, J=8.44, 1.99 Hz, 1H), 6.86-6.89 (m, 1H), 6.78-6.81 (m, 2H), 4.21 (s, 1H), 2.46 (m, 2H), 1.54-1.58 (m, 2H), 1.10 (s, 6H).

EXAMPLE 227H

3-[(2,6-difluoropyridin-4-yl)amino]-8-(3-hydroxy-3-methylbutyl)-5,10-dihydro-11H-dibenzo[b,e][1,4]diazepin-11-one The title compound was prepared by substituting Example 227G and Example 203A for Example 189A and 4-aminopyridine in Example 191. MS (DCI) m/e 425 (M+H)$^+$; $^1$H NMR (500 MHz, DMSO-d$_6$) δ 9.65 (s, 1H), 9.58 (s, 1H), 7.82 (s, 1H), 7.68 (d, J=8.59 Hz, 1H), 6.84-6.88 (m, 2H), 6.75-6.77 (m, 2H), 6.67 (dd, J=8.59, 1.83 Hz, 1H), 6.55 (s, 2H), 4.20 (s, 1H), 2.44-2.50 (m, 2H), 1.53-1.57 (m, 2H), 1.11 (s, 6H).

EXAMPLE 228

8-(3-hydroxy-3-methylbutyl)-3-(3-methoxy-4-nitrophenyl)-5,10-dihydro-11H-dibenzo[b,e][1,4]diazepin-11-one The title compound was prepared by substituting Example 227G and Example 266G for Example 59B and Example 56A, respectively, in Example 59C. MS (DCI) m/e 448 (M+H)$^+$; $^1$H NMR (500 MHz, DMSO-d$_6$) δ 9.80 (s, 1H), 8.01 (d, J=8.42 Hz, 1H), 7.90 (s, 1H), 7.80 (d, J=8.11 Hz, 1H), 7.52 (d, J=1.25 Hz, 1H), 7.34-7.35 (m, 2H), 7.29 (dd, J=8.11, 1.56 Hz, 1H), 6.92 (d, J=8.11 Hz, 1H), 6.79-6.81 (m, 2H), 4.21 (s, 1H), 4.03 (s, 3H), 2.48-2.50 (m, 2H), 1.56-1.59 (m, 2H), 1.12 (s, 6H).

EXAMPLE 229 methyl 3-[3-(3-methoxy-4-nitrophenyl)-11-oxo-10,11-dihydro-5H-dibenzo[b,e][1,4]diazepin-8-yl]propanoate The title compound was prepared by substituting Example 227F and Example 266G for Example 59B and Example 56A, respectively, in Example 59C. MS (DCI) m/e 448 (M+H)$^+$; $^1$H NMR (500 MHz, DMSO-d$_6$) δ 9.83 (s, 1H), 8.01 (d, J=8.42 Hz, 1H), 7.93 (s, 1H), 7.79 (d, J=8.42 Hz, 1H), 7.52 (d, J=1.56 Hz, 1H), 7.33-7.35 (m, 2H), 7.29 (dd, J=8.26, 1.72 Hz, 1H), 6.92 (d, J=8.11 Hz, 1H), 6.82-6.83 (m, 2H), 4.03 (s, 3H), 3.58 (s, 3H), 2.73 (t, J=7.49 Hz, 2H), 2.55 (t, J=7.49 Hz, 2H).

EXAMPLE 230

3-[3-(3-methoxy-4-nitrophenyl)-11-oxo-10,11-dihydro-5H-dibenzo[b,e][1,4]diazepin-8-yl]propanoic acid The desired product was prepared by substituting Example 229 for Example 12 in Example 13. MS (ESI) m/e 434 (M+H)$^+$; $^1$H NMR (300 MHz, DMSO-d$_6$) δ 12.04 (br, 1H), 9.81 (s, 1H), 8.01 (d, J=8.14 Hz, 1H), 7.94 (s, 1H), 7.79 (d, J=8.14 Hz, 1H), 7.52 (d, J=1.70 Hz, 1H), 7.30-7.34 (m, 3H), 6.93 (m, 1H), 6.83 (d, J=5.09 Hz, 2H), 4.03 (s, 3H), 2.69 (t, J=7.46 Hz, 2H), 2.45 (t, J=7.46 Hz, 2H).

EXAMPLE 231

3-[3-(3-methoxy-4-nitrophenyl)-11-oxo-10,11-dihydro-5H-dibenzo[b,e][1,4]diazepin-8-yl]-N,N-dimethylpropanamide The desired product was prepared by substituting Example 230 and N,N-dimethylamine hydrochloride for dimethylaminoacetic acid and Example 120, respectively, in Example 122. MS (ESI) m/e 461 (M+H)$^+$; $^1$H NMR (300 MHz, DMSO-d$_6$) δ 9.83 (s, 1H), 8.01 (d, J=8.14 Hz, 1H)), 7.93 (s, 1H), 7.79 (d, J=8.14 Hz, 1H), 7.5 (d, J=1.7 Hz, 1H), 7.3 (m, 3H), 6.9 (m, 1H), 6.83 (d, J=5.43 Hz, 2H), 4.03 (s, 3H), 2.92 (s, 3H), 2.80 (s, 3H), 2.67 (t, J=7.46 Hz, 2H), 2.50-2.52 (m, 2H).

EXAMPLE 232

3-[3-(3-methoxy-4-nitrophenyl)-11-oxo-10,11-dihydro-5H-dibenzo[b,e][1,4]diazepin-8-yl]N(4-morpholin-4-ylphenyl)propanamide The desired product was prepared by substituting Example 230 and 4-morpholin-4-ylphenylamine for dimethylaminoacetic acid and Example 120, respectively, in Example 122. MS (ESI) m/e 594 (M+H)$^+$; $^1$H NMR (300 MHz, DMSO-d$_6$) δ 9.78 (s, 1H), 9.7 (s, 1H), 7.93 (d, J=8.42 Hz, 1H), 7.85 (s, 1H), 7.72 (d, J=8.11 Hz, 1H), 7.45 (d, J=1.56 Hz, 1H), 7.34 (d, J=9.04 Hz, 2H), 7.27 (m, 2H), 7.22 (dd, J=8.26, 1.72 Hz, 1H), 6.86 (d, J=8.11 Hz, 1H), 6.75-6.79 (m, 4H), 3.96 (s, 3H), 3.64 (br, m, 4H), 2.95 (br, m, 4H), 2.65-2.68 (m, 2H), 2.43-2.45 (m, 2H).

EXAMPLE 233

8-(3-azetidin-1-yl-3-oxopropyl)-3-(3-methoxy-4-nitrophenyl)-5,10-dihydro-11H-dibenzo[b,e][1,4]diazepin-11-one The desired product was prepared by substituting Example 230 and azetidine for dimethylaminoacetic acid and Example 120, respectively, in Example 122. MS (ESI) m/e 473 (M+H)$^+$; $^1$H NMR (300 MHz, DMSO-d$_6$) δ 9.84 (s, 1H), 8.01 (d, J=8.48 Hz, 1H), 7.94 (s, 1H), 7.79 (d, J=8.14 Hz, 1H), 7.52 (d, J=1.70 Hz, 1H), 7.34 (m, 2H), 7.29 (dd, J=8.14, 1.7 Hz, 1H), 6.90 (m, 1H), 6.82 (m, 2H), 4.03 (s, 3H), 3.99 (d, J=7.46 Hz, 2H), 3.8 (t, J=7.80 Hz, 2H), 2.65 (t, J=7.63 Hz, 2H), 2.30 (t, J=7.80 Hz, 2H), 2.12 (m, 2H).

EXAMPLE 234

3-(3-methoxy-4-nitrophenyl)-8-(3-oxo-3-pyrrolidin-1-ylpropyl)-5,10-dihydro-11H-dibenzo[b,e][1,4]diazepin-11-one The desired product was prepared by substituting Example 230 and pyrrolidine for dimethylaminoacetic acid and Example 120, respectively, in Example 122. MS (ESI) m/e 487 (M+H)$^+$; $^1$H NMR (300 MHz, DMSO-d$_6$) δ 9.83 (s, 1H), 8.01 (d, J=8.48 Hz, 1H), 7.92 (s, 1H), 7.79 (d, J=8.14 Hz, 1H), 7.52 (d, J=1.7 Hz, 1H), 7.34 (m, 2H), 7.30 (dd, J=8.31, 1.86 Hz, 1H), 6.92 (m, 1H), 6.83 (m, 2H), 4.03 (s, 3H), 3.35-3.24 (br, 4H), 2.69 (t, J=7.63 Hz, 2H), 2.44 (d, J=7.46 Hz, 2H), 1.85-1.70 (br, 4H).

EXAMPLE 235

3-(3-methoxy-4-nitrophenyl)-8-(3-morpholin-4-yl-3-oxopropyl)-5,10-dihydro-11H-dibenzo[b,e][1,4]diazepin-11-one The desired product was prepared by substituting Example 230 and morpholine for dimethylaminoacetic acid and Example 120, respectively, in Example 122. MS (ESI) m/e 503 (M+H)$^+$; $^1$H NMR (300 MHz, DMSO-d$_6$) δ 9.83 (s, 1H), 8.01 (d, J=8.14 Hz, 1H), 7.94 (s, 1H), 7.79 (d, J=8.14 Hz, 1H), 7.52 (d, J=1.70 Hz, 1H), 7.34 (m, 1H), 7.29 (dd, J=8.31, 1.87 Hz, 2H), 6.92 (m, 2H), 6.85 (m, 2H), 4.03 (s, 3H), 3.41 (m, 8H), 2.69 (t, J=7.29 Hz, 2H), 2.55 (d, J=7.46 Hz, 2H).

EXAMPLE 236

N,N-diethyl-3-[3-(3-methoxy-4-nitrophenyl)-11-oxo-10,11-dihydro-5H-dibenzo[b,e][1,4]diazepin-8-yl]propanamide The desired product was prepared by substituting Example 230 and diethylamine for dimethylaminoacetic acid and Example 120, respectively, in Example 122. MS (ESI) m/e 489 (M+H)$^+$; $^1$H NMR (300 MHz, DMSO-d$_6$) δ 9.83 (s, 1H), 8.01 (d, J=8.48 Hz, 1H), 7.93 (s, 1H), 7.79 (d, J=8.14 Hz, 1H), 7.52 (d, J=1.7 Hz, 1H), 7.33 (m, 2H), 7.29 (dd, J=8.14, 1.70 Hz, 1H), 6.92 (m, 1H), 6.84 (d, J=5.43 Hz, 2H), 4.03 (s, 3H), 3.24 (m, 4H), 2.69 (t, J=7.63 Hz, 2H), 2.5-2.43 (m, 2H), 1.02 (br, 6H).

EXAMPLE 237

8-[3-(4-hydroxypiperidin-1-yl)-3-oxopropyl]-3-(3-methoxy-4-nitrophenyl)-5,10-dihydro-11H-dibenzo[b,e][1,4]diazepin-11-one The desired product was prepared by substituting Example 230 and 4-hydroxypiperidine for dimethylaminoacetic acid and Example 120, respectively, in Example 122. MS (ESI) m/e517 (M+H)$^+$; $^1$H NMR (300 MHz, DMSO-d$_6$) δ 9.82 (s, 1H), 8.01 (d, J=8.14 Hz, 1H), 7.93 (s, 1H), 7.79 (d, J=8.14 Hz, 1H), 7.52 (d, J=1.36 Hz, 1H), 7.34 (m, 2H), 7.29 (dd, J=8.14, 1.70 Hz, 1H), 6.92 (m, 1H), 6.84 (d, J=5.09 Hz, 2H), 4.69 (s, 1H), 4.03 (s, 3H), 3.65 (s, 2H), 3.2-2.95 (br, 4H), 2.67 (t, J=7.29 Hz, 2H), 1.65 (d, J=9.83 Hz, 2H), 1.24 (m, 2H).

EXAMPLE 238

3-[3-(3-methoxy-4-nitrophenyl)-11-oxo-10,11-dihydro-5H-dibenzo[b,e][1,4]diazepin-8-yl]N1,3-thiazol-2-ylpropanamide The desired product was prepared by substituting Example 230 and thiazol-2-ylamine for dimethylaminoacetic acid and Example 120, respectively, in Example 122. MS (ESI) m/e517 (M+H)$^+$; $^1$H NMR (300 MHz, DMSO-d$_6$) δ 12.08 (s, 1H), 9.87 (s, 1H), 8.01 (d, J=8.48 Hz, 1H), 7.94 (s, 1H), 7.79 (d, J=8.14 Hz, 1H), 7.52 (d, J=1.7 Hz, 1H), 7.43 (d, J=3.73 Hz, 1H), 7.33 (m, 2H), 7.29 (dd, J=8.14, 1.70 Hz, 1H), 7.18 (d, J=3.73 Hz, 1H), 6.93 (m, 1H), 6.83 (m, 2H), 4.03 (s, 3H), 2.79 (d, J=7.46 Hz, 2H), 2.70 (m, 2H).

EXAMPLE 239

8-(2-hydroxyethyl)-3-(3-methoxy-4-nitrophenyl)-5,10-dihydro-11H-dibenzo[b,e][1,4]diazepin-11-one The title compound was prepared by substituting Example 204A and Example 266G for Example 59B and Example 56A, respectively, in Example 59C. MS (DCI) m/e 406 (M+H)$^+$; $^1$H NMR (500 MHz, DMSO-d$_6$) δ 9.80 (s, 1H), 7.99 (d, J=8.42 Hz, 1H), 7.89 (s, 1H), 7.78 (d, J=8.11 Hz, 1H), 7.51 (d, J=1.56 Hz, 1H), 7.32-7.34 (m, 2H), 7.28 (dd, J=8.11, 1.56 Hz, 1H), 6.91 (d, J=7.80 Hz, 1H), 6.80-6.82 (m, 2H), 4.57 (t, J=5.15 Hz, 1H), 4.02 (s, 3H), 3.50-3.54 (m, 2H), 2.58 (t, J=7.52 Hz, 2H).

EXAMPLE 240

8-(3-hydroxypropyl)-3-(3-methoxy-4-nitrophenyl)-5,10-dihydro-11H-dibenzo[b,e][1,4]diazepin-11-one

EXAMPLE 240A 3-chloro-8-(3-hydroxypropyl)-5,10-dihydro-11H-dibenzo[b,e][1,4]diazepin-11-one The title compound was prepared by substituting Example 227F for Example 6D in Example 204A. MS (DCI) m/e 289 (M+H)$^+$; $^1$H NMR (500 MHz, DMSO-d$_6$) δ 9.81 (s, 1H), 7.94 (s, 1H), 7.68 (d, J=8.42 Hz, 1H), 7.06 (d, J=1.87 Hz, 1H), 6.91 (dd, J=8.42, 1.87 Hz, 1H), 6.88 (m, 1H), 6.79-6.82 (m, 2H), 4.41 (t, J=4.99 Hz, 1H), 3.37-3.41 (m, 2H), 2.46-2.49 (m, 2H), 1.62-1.67 (m, 2H).

EXAMPLE 240B 8-(3-hydroxypropyl)-3-(3-methoxy-4-nitrophenyl)-5,10-dihydro-11H-dibenzo[b,e][1,4]diazepin-11-one The title compound was prepared by substituting Example 240A and Example 266G for Example 59B and Example 56A, respectively, in Example 59C. MS (DCI) m/e 420 (M+H)$^+$; $^1$H NMR (500 MHz, DMSO-d$_6$) δ 9.81 (s, 1H), 8.01 (d, J=8.42 Hz, 1H), 7.90 (s, 1H), 7.82 (d, J=8.11 Hz, 1H), 7.52 (s, 1H), 7.34-7.35 (m, 2H), 7.29 (dd, J=8.11, 1.56 Hz, 1H), 6.93 (d, J=8.11 Hz, 1H), 6.79-6.82 (m, 2H), 4.42 (t, J=4.83 Hz, 1H), 4.04 (s, 3H), 3.40 (q, J=5.93 Hz, 2H), 2.54-2.50 (m, 2H), 1.63-1.67 (m, 2H).

EXAMPLE 241 methyl 3-[3-(4-chloro-3-methoxyphenyl)-11-oxo-10,11-dihydro-5H-dibenzo[b,e][1,4]diazepin-8-yl]propanoate

EXAMPLE 241A methyl 3-[11-oxo-3-(4,4,5,5-tetramethyl-1,3,2-dioxaborolan-2-yl)-10,11-dihydro-5H-dibenzo[b,e][1,4]diazepin-8-yl]propanoate The title compound was prepared by substituting Example 227F for Example 6D in Example 54A. MS (DCI) m/e 420 (M+H)$^+$; $^1$H NMR (500 MHz, DMSO-d$_6$) δ 9.79 (s, 1H), 7.74 (s, 1H), 7.65 (d, J=7.80 Hz, 1H), 7.38 (s, 1H), 7.13 (d, J=7.80 Hz, 1H), 6.90 (d, J=8.73 Hz, 1H), 6.79-6.80 (m, 2H), 3.57 (s, 3H), 2.71 (t, J=7.49 Hz, 2H), 2.54 (t, J=7.49 Hz, 2H), 1.92 (s, 12H).

EXAMPLE 241B methyl 3-[3-(4-chloro-3-methoxyphenyl)-11-oxo-10,11-dihydro-5H-dibenzo[b,e][1,4]diazepin-8-yl]propanoate The desired product was prepared by substituting Example 241A and 2-chloro-5-iodoanisole for 2-methoxy-4-(4,4,5,5-tetramethyl-1,3,2-dioxaborolan-2-yl)phenol and Example 1B, respectively, in Example 10. MS (DCI) m/e 437 (M+H)$^+$; $^1$H NMR (500 MHz, DMSO-d$_6$) δ 9.77 (s, 1H), 7.87 (s, 1H), 7.76 (d, J=8.11 Hz, 1H), 7.53 (d, J=8.11 Hz, 1H), 7.33 (d, J=1.87 Hz, 1H), 7.29 (d, J=1.87 Hz, 1H), 7.19-7.23 (m, 2H), 6.92 (d, J=8.42 Hz, 1H), 6.81-6.82 (m, 2H), 3.96 (s, 3H), 3.58 (s, 3H), 2.72 (t, J=7.49 Hz, 2H), 2.55 (t, J=7.49 Hz, 2H).

EXAMPLE 242

3-[3-(4-chloro-3-methoxyphenyl)-11-oxo-10,11-dihydro-5H-dibenzo[b,e][1,4]diazepin-8-yl]-N,N-dimethylpropanamide

EXAMPLE 242A

3-[3-(4-chloro-3-methoxyphenyl)-11-oxo-10,11-dihydro-5H-dibenzo[b,e][1,4]diazepin-8-yl]propanoic acid The desired product was prepared by substituting Example 241B for Example 12 in Example 13. MS (DCI) m/e 423 (M+H)$^+$; $^1$H NMR (500 MHz, DMSO-d$_6$) δ 12.08 (s, 1H), 9.76 (s, 1H), 7.87 (s, 1H), 7.77 (d, J=8.11 Hz, 1H), 7.53 (d, J=8.11 Hz, 1H), 7.34 (d, J=1.87 Hz, 1H), 7.29 (d, J=1.56 Hz, 1H), 7.19-7.23 (m, 2H), 6.93 (d, J=7.80 Hz, 1H), 6.82-6.83 (m, 2H), 3.96 (s, 3H), 2.70 (t, J=7.49 Hz, 2H), 2.46 (t, J=7.64 Hz, 2H).

EXAMPLE 242B

3-[3-(4-chloro-3-methoxyphenyl)-11-oxo-10,11-dihydro-5H-dibenzo[b,e][1,4]diazepin-8-yl]-N,N-dimethylpropanamide The title compound was prepared by substituting Example 242B and dimethylamine hydrochloride for Example 120 and dimethylaminoacetic acid, respectively, in Example 122. MS (DCI) m/e 423 (M+H)$^+$; $^1$H NMR (500 MHz, DMSO-d$_6$) δ

9.75 (s, 1H), 7.86 (s, 1H), 7.76 (d, J=7.98 Hz, 1H), 7.53 (d, J=7.98 Hz, 1H), 7.33 (d, J=1.84 Hz, 1H), 7.29 (d, J=1.53 Hz, 1H), 7.19-7.23 (m, 2H), 6.91 (d, J=7.80 Hz, 1H), 6.82-6.84 (m, 2H), 3.96 (s, 3H), 2.92 (s, 3H), 2.80 (s, 3H), 2.67 (t, J=7.36 Hz, 2H), 2.50 (t, J=7.64 Hz, 2H).

EXAMPLE 243

3-(4-chloro-3-methoxyphenyl)-8-(3-hydroxy-3-methylbutyl)-5,10-dihydro-11H-dibenzo[b,e][1,4]diazepin-11-one The title compound was prepared by substituting Example 241B for Example 1B in Example 189A. MS (DCI) m/e 437 (M+H)$^+$; $^1$H NMR (500 MHz, DMSO-d$_6$) δ 9.66 (s, 1H), 9.59 (s, 1H), 7.84 (s, 1H), 7.69 (d, J=8.42 Hz, 1H), 6.90 (d, J=1.87 Hz, 1H), 6.84-6.86 (m, 1H), 6.81 (s, 1H), 6.78 (dd, J=7.95, 1.72 Hz, 1H), 6.68 (dd, J=8.42, 2.18 Hz, 1H), 6.57 (m, 2H), 4.22 (s, 1H), 3.96 (s, 3H), 2.48-2.50 (m, 2H), 1.56-1.59 (m, 2H), 1.12 (s, 6H).

EXAMPLE 244

3-(3-methoxy-4-nitrophenyl)-8-[2-(3-methyl-1,2,4-oxadiazol-5-yl)ethyl]-5,10-dihydro-11H-dibenzo[b,e][1,4]diazepin-11-one

EXAMPLE 244A

N-({3-[3-(3-methoxy-4-nitrophenyl)-11-oxo-10,11-dihydro-5H-dibenzo[b,e][1,4]diazepin-8-yl]propanoyl}oxy)ethanimidamide A mixture of Example 230 (65 mg, 0.15 mmol), N-hydroxy-acetamidine (14 mg, 0.18 mmol) in 1 mL of DMF was treated with DIC in 1 mL of CH$_2$Cl$_2$ at 0° C. The reaction mixture was stirred overnight and partitioned between EtOAc and water. The organic layer was separated, washed with brine, dried (MgSO4), filtered, and concentrated under vacuum. The residue was purified by flash column chromatography on silica gel with 100:1 ethyl acetate/MeOH to provide the desired product. MS (DCI) m/e 490 (M+H)$^+$; $^1$H NMR (500 MHz, DMSO-d$_6$) δ 9.83 (s, 1H), 8.01 (d, J=8.29 Hz, 1H), 7.94 (s, 1H), 7.79 (d, J=8.29 Hz, 1H), 7.52 (d, J=1.23 Hz, 1H), 7.33-7.34 (m, 2H), 7.29 (m, 1H), 6.93 (m, 1H), 6.83-6.85 (m, 2H), 6.27 (s, 2H), 4.03 (s, 3H), 2.73-2.76 (m, 2H), 2.58-2.62 (m, 2H), 1.72 (s, 3H).

EXAMPLE 244B 3-(3-methoxy-4-nitrophenyl)-8-[2-(3-methyl-1,2,4-oxadiazol-5-yl)ethyl]-5,10-dihydro-1H-dibenzo[b,e][1,4]diazepin-11-one Example 244A (30 MG, 0.060 mmol) IN 2 mL OF DMF WAS HEATED AT 110° C. for 2 hours. After the reaction mixture cooled to room temperature, it was purified by preparative HPLC to give the title compound. MS (DCI) m/e 472 (M+H)$^+$; $^1$H NMR (500 MHz, DMSO-d$_6$) δ 9.82 (s, 1H), 7.99 (d, J=8.59 Hz, 1H), 7.94 (s, 1H), 7.78 (d, J=7.98 Hz, 1H), 7.51 (d, J=1.23 Hz, 1H), 7.33-7.34 (m, 2H), 7.29 (m, 1H), 6.92 (m, 1H), 6.82-6.84 (m, 2H), 4.02 (s, 3H), 2.73 (t, J=7.52 Hz, 2H), 2.59 (t, J=7.36 Hz, 2H), 1.71 (s, 3H).

EXAMPLE 245 methyl 3-[8-methoxy-3-(3-methoxy-4-nitrophenyl)-11-oxo-10,11-dihydro-5H-dibenzo[b,e][1,4]diazepin-7-yl]propanoate The title compound was prepared by substituting Example 2231 and Example 266G for Example 59B and Example 56A, respectively, in Example 59C. MS (DCI) m/e 478 (M+H)$^+$; $^1$H NMR (500 MHz, DMSO-d$_6$) δ 9.74 (s, 1H), 8.01 (d, J=8.42 Hz, 1H), 7.78 (d, J=8.11 Hz, 1H), 7.74 (s, 1H), 7.33-7.35 (m, 2H), 7.27 (dd, J=8.26, 1.72 Hz, 1H), 6.81 (s, 1H), 6.64 (s, 1H), 4.03 (s, 3H), 3.70 (s, 3H), 3.58 (s, 3H), 2.70 (t, J=7.49 Hz, 2H), 2.51 (t, J=7.49 Hz, 2H).

EXAMPLE 246

7-(2-hydroxy-2-methylpropyl)-8-methoxy-3-(3-methoxy-4-nitrophenyl)-5,10-dihydro-11H-dibenzo[b,e][1,4]diazepin-11-one

EXAMPLE 246A methyl (2-methoxy-5-nitrophenyl)acetate (2-Hydroxy-phenyl)-acetic acid (6.02 g, 39.6 mmol) was suspended in 17 mL of water at 0° C. To this solution was added 40% HNO$_3$ (prepared from 5 mL of concentrated HNO$_3$ and 3 mL of water). The reaction mixture was stirred for 2 hours at 0° C., warmed up to room temperature, and stirred for another 30 min. The reaction mixture was poured on the water/ice, extracted with EtOAc several times, dried (MgSO$_4$), filtered, and concentrated under vacuum. The residue was dissolved in 100 mL of CH$_2$Cl$_2$ and 10 mL of MeOH and treated with excess of TMSCHN$_2$ dropwise. After bubbling ceased, the solvents were removed, and the residue was purified by flash column chromatography on silica gel with 85:15 hexanes/ethyl acetate to provide 2.67 g (30%) of the desired product. MS (DCI) m/e 478 (M+H)$^+$; $^1$H NMR (500 MHz, DMSO-d$_6$) δ 8.20-8.24 (m, 2H), 7.22 (d, J=9.16 Hz, 1H), 3.91 (s, 3H), 3.76 (s, 2H), 3.61 (s, 3H).

EXAMPLE 246B methyl [5-(acetylamino)-2-methoxyphenyl]acetate

A mixture of Example 246A (3.8 g, 17 mmol), 5% Pd/C, methanol (50 mL) was equipped with a balloon of hydrogen gas and stirred at room temperature. After uptake of the hydrogen was complete, the solution was filtered through diatomaceous earth (Celite®). The filtrate was concentrated under vacuum and the residue was treated with excess of Ac$_2$O and Et$_3$N to give 3.5 g (88%) of the title compound. MS (DCI) m/e 238 (M+H)$^+$; $^1$H NMR (500 MHz, DMSO-d$_6$) δ 9.75 (s, 1H), 7.44 (dd, J=8.82, 2.71 Hz, 1H), 6.90 (d, J=8.82 Hz, 1H), 3.71 (s, 3H), 3.59 (s, 3H), 3.56 (s, 2H), 2.00 (s, 3H).

EXAMPLE 246C methyl [5-(acetylamino)-2-methoxy-4-nitrophenyl]acetate

The title compound was prepared by substituting Example 246B for Example 223A in Example 223B. MS (DCI) m/e 283 (M+H)$^+$; $^1$H NMR (500 MHz, DMSO-d$_6$) δ 10.05 (s, 1H), 7.49 (s, 1H), 7.42 (s, 1H), 3.83 (s, 3H), 3.71 (s, 2H), 3.61 (s, 3H), 2.02 (s, 3H).

EXAMPLE 246D methyl (5-amino-2-methoxy-4-nitrophenyl)acetate

The title compound was prepared by substituting Example 246C for Example 223B in Example 223C. MS (DCI) m/e 241 (M+H)+.

EXAMPLE 246E methyl 4-chloro-2-{[4-methoxy-5-(2-methoxy-2-oxoethyl)-2-nitrophenyl]amino}benzo ate The title compound was prepared by substituting Example 246D for methyl 3,4-diaminobenzoate in Example 1A. MS (DCI) m/e 409 (M+H)+; $^1$H NMR (500 MHz, DMSO-$d_6$) δ 10.58 (s, 1H), 7.94 (d, J=8.82 Hz, 1H), 7.65-7.66 (m, 2H), 7.24 (d, J=2.03 Hz, 1H), 7.02 (dd, J=8.81, 2.03 Hz, 1H), 3.89 (s, 3H), 3.87 (s, 3H), 3.76 (s, 2H), 3.62 (s, 3H).

EXAMPLE 246F methyl 2-{[2-amino-4-methoxy-5-(2-methoxy-2-oxoethyl)phenyl]amino}-4-chlorobenzoate The title compound was prepared by substituting Example 246E for Example 6B in Example 6C. MS (DCI) m/e 379 (M+H)+; $^1$H NMR (500 MHz, DMSO-$d_6$) δ 8.70 (s, 1H), 7.84 (d, J=8.48 Hz, 1H), 6.82 (s, 1H), 6.67 (dd, J=8.65, 2.20 Hz, 1H), 6.45 (s, 1H), 6.33 (d, J=2.03 Hz, 1H), 5.00 (s, 2H), 3.85 (s, 3H), 3.71 (s, 3H), 3.57 (s, 3H), 3.44 (s, 2H).

EXAMPLE 246G methyl (3-chloro-8-methoxy-11-oxo-10,11-dihydro-5H-dibenzo[b,e][1,4]diazepin-7-yl)acetate The title compound was prepared by substituting Example 246F for Example 6C in Example 6D. MS (DCI) m/e 347 (M+H)+; $^1$H NMR (500 MHz, DMSO-$d_6$) δ 9.81 (s, 1H), 7.84 (s, 1H), 7.66 (d, J=8.48 Hz, 1H), 7.04 (d, J=2.04 Hz, 1H), 6.90 (dd, J=8.48, 2.03 Hz, 1H), 6.81 (s, 1H), 6.84 (s, 1H), 3.66 (s, 3H), 3.58 (s, 3H), 3.50 (s, 2H).

EXAMPLE 246H 3-chloro-7-(2-hydroxy-2-methylpropyl)-8-methoxy-5,10-dihydro-11H-dibenzo[b,e][1,4]diazepin-11-one The title compound was prepared by substituting Example 246G for Example 1B in Example 189A. MS (DCI) m/e 347 (M+H)+; $^1$H NMR (500 MHz, DMSO-$d_6$) δ 9.75 (s, 1H), 7.82 (s, 1H), 7.66 (d, J=8.24 Hz, 1H), 7.05 (d, J=2.14 Hz, 1H), 6.88 (dd, J=8.39, 1.98 Hz, 1H), 6.85 (s, 1H), 6.60 (s, 1H), 4.25 (s, 1H), 3.65 (s, 3H), 2.56 (s, 2H), 1.03 (s, 6H).

EXAMPLE 246I 7-(2-hydroxy-2-methylpropyl)-8-methoxy-3-(3-methoxy-4-nitrophenyl)-5,10-dihydro-11H-dibenzo[b,e][1,4]diazepin-11-one The title compound was prepared by substituting Example 246H and Example 266G for Example 59B and Example 56A, respectively, in Example 59C. MS (DCI) m/e 464 (M+H)+; $^1$H NMR (500 MHz, DMSO-$d_6$) δ 9.72 (s, 1H), 8.01 (d, J=8.59 Hz, 1H), 7.78 (m, 1H), 7.51 (s, 1H), 7.32-7.35 (m, 2H), 7.26 (dd, J=7.98, 1.53 Hz, 1H), 6.89 (s, 1H), 6.63 (s, 1H), 4.22 (s, 1H), 4.03 (s, 3H), 3.67 (s, 3H), 3.67 (s, 3H), 3.65 (s, 2H), 1.04 (s, 6H).

EXAMPLE 247

7-(2-hydroxyethyl)-8-methoxy-3-(3-methoxy-4-nitrophenyl)-5,10-dihydro-11H-dibenzo[b,e][1,4]diazepin-11-one

EXAMPLE 247A 3-chloro-7-(2-hydroxyethyl)-8-methoxy-5,10-dihydro-11H-dibenzo[b,e][1,4]diazepin-11-one The title compound was prepared by substituting Example 246G for Example 6D in Example 204A. MS (DCI) m/e 319 (M+H)+; $^1$H NMR (500 MHz, DMSO-$d_6$) δ 9.72 (s, 1H), 7.77 (s, 1H), 7.66 (d, J=8.42 Hz, 1H), 7.03 (d, J=2.18 Hz, 1H), 6.88 (dd, J=8.58, 2.03 Hz, 1H), 6.78 (s, 1H), 6.61 (s, 1H), 4.56 (t, J=5.46 Hz, 1H), 3.68 (s, 3H), 3.48-3.52 (m, 2H), 2.59 (t, J=7.18 Hz, 1H).

EXAMPLE 247B 7-(2-hydroxyethyl)-8-methoxy-3-(3-methoxy-4-nitrophenyl)-5,10-dihydro-11H-dibenzo[b,e][1,4]diazepin-11-one The title compound was prepared by substituting Example 247A and Example 266G for Example 59B and Example 56A, respectively, in Example 59C. MS (DCI) m/e 436 (M+H)+; $^1$H NMR (500 MHz, DMSO-$d_6$) δ 9.76 (s, 1H), 8.01 (d, J=8.54 Hz, 1H), 7.80 (d, J=8.24 Hz, 1H), 7.75 (s, 1H), 7.52 (s, 1H), 7.33-7.35 (m, 2H), 7.27 (dd, J=8.24, 1.83 Hz, 1H), 6.83 (s, 1H), 6.63 (s, 1H), 4.59 (t, J=5.34 Hz, 1H), 4.03 (s, 3H), 3.69 (s, 3H), 3.48-3.52 (m, 2H), 2.60 (t, J=7.02 Hz, 2H).

EXAMPLE 248

8-methoxy-3-(3-methoxy-4-nitrophenyl)-7-(2-oxopropyl)-5,10-dihydro-11H-dibenzo[b,e][1,4]diazepin-11-one

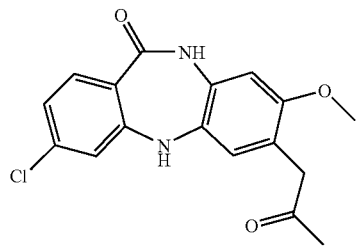

EXAMPLE 248A 3-chloro-8-methoxy-7-(2-oxopropyl)-5,10-dihydro-11H-dibenzo[b,e][1,4]diazepin-11-one The title compound was isolated as a minor product in Example 246H. MS (DCI) m/e 331 (M+H)+; $^1$H NMR (500 MHz, DMSO-$d_6$) δ 9.81 (s, 1H), 7.82 (s, 1H), 7.67 (d, J=8.54 Hz, 1H), 7.03 (d, J=1.83 Hz, 1H), 6.90 (dd, J=8.39, 1.98 Hz, 1H), 6.73 (s, 1H), 6.64 (s, 1H), 3.65 (s, 3H), 3.56 (s, 3H), 2.08 (s, 2H).

EXAMPLE 248B 8-methoxy-3-(3-methoxy-4-nitrophenyl)-7-(2-oxo-propyl)-5,10-dihydro-11H-dibenzo[b,e][1,4]diazepin-11-one The title compound was prepared by substituting Example 248A and Example 266G for Example 59B and Example 56A, respectively, in Example 59C. MS (DCI) m/e 448 (M+H)$^+$; $^1$H NMR (500 MHz, DMSO-d$_6$) δ 9.79 (s, 1H), 8.01 (d, J=8.59 Hz, 1H), 7.77-7.80 (m, 2H), 7.52 (s, 1H), 7.32-7.35 (m, 2H), 7.28 (d, J=8.29 Hz, 1H), 6.78 (s, 1H), 6.66 (s, 1H), 4.03 (s, 3H), 3.67 (s, 3H), 3.55 (s, 2H), 2.08 (s, 2H).

EXAMPLE 249

7-(2-hydroxy-11-dimethylethyl)-8-methoxy-3-(3-methoxy-4-nitrophenyl)-5,10-dihydro-11H-dibenzo[b,e][1,4]diazepin-11-one

EXAMPLE 249A methyl 2-(2-methoxy-5-nitrophenyl)-2-methylpropanoate

A mixture of Example 246A (1.5 g, 6.66 mmol), MeI (3.78 g, 26.6 mmol), and 18-crown-6 (0.301 g, 1.14 mmol) in 20 mL of anhydrous DMF was cooled to 0° C. To this solution was added 60% NaH (0.64 g, 16 mmol). The solution was stirred at 0° C. for 30 min and warmed up gradually overnight. The reaction mixture was partitioned between EtOAc and water. The aqueous layer was extracted with additional EtOAc several times. The combined organic layers were washed by brine, dried (MgSO$_4$), filtered, and concentrated under vacuum. The residue was purified by flash column chromatography on silica gel with 9:1 hexanes/ethyl acetate to provide 1.3 g (77%) of the desired product. MS (DCI) m/e 254 (M+H)$^+$; $^1$H NMR (500 MHz, DMSO-d$_6$) δ 8.22 (dd, J=8.99, 2.88 Hz, 1H), 8.12 (d, J=2.71 Hz, 1H), 7.24 (d, J=8.24 Hz, 1H), 3.88 (s, 3H), 3.55 (s, 3H), 1.55 (s, 6H).

EXAMPLE 249B methyl 2-[5-(acetylamino)-2-methoxyphenyl]-2-methylpropanoate

The title compound was prepared by substituting Example 249A for Example 246A in Example 246B. MS (DCI) m/e 266 (M+H)$^+$; $^1$H NMR (500 MHz, DMSO-d$_6$) δ 9.76, (s, 1H), 7.46-7.50 (m, 1H), 7.43 (d, J=2.71 Hz, 1H), 6.90 (d, J=8.82 Hz, 1H), 3.67 (s, 3H), 3.52 (s, 3H), 2.00 (s, 3H), 1.39 (s, 6H).

EXAMPLE 249C methyl 2-[5-(acetylamino)-2-methoxy-4-nitrophenyl]-2-methylpropanoate The title compound was prepared by substituting Example 249B for Example 223A in Example 223B. MS (DCI) m/e 311 (M+H)$^+$; $^1$H NMR (500 MHz, DMSO-d$_6$) δ 10.09 (s, 1H), 7.49 (s, 1H), 7.45 (s, 1H), 3.80 (s, 3H), 3.55 (s, 3H), 2.03 (s, 3H), 1.43 (s, 6H).

EXAMPLE 249D methyl 2-(5-amino-2-methoxy-4-nitrophenyl)-2-methylpropanoate

The title compound was prepared by substituting Example 249C for Example 223B in Example 223C. MS (DCI) m/e 269 (M+H)$^+$.

EXAMPLE 249E methyl 4-chloro-2-{[4-methoxy-5-(2-methoxy-1,1-dimethyl-2-oxoethyl)-2-nitrophenyl]amino}benzoate The title compound was prepared by substituting Example 249D for methyl 3,4-diaminobenzoate in Example 1A. MS (DCI) m/e 437 (M+H)$^+$; $^1$H NMR (500 MHz, DMSO-d$_6$) δ 10.65 (s, 1H), 7.95 (d, J=8.82 Hz, 1H), 7.66 (s, 1H), 7.60 (s, 1H), 7.29 (d, J=2.03 Hz, 1H), 7.04 (dd, J=8.48, 2.03 Hz, 1H), 3.89 (s, 3H), 3.83 (s, 3H), 3.58 (s, 3H), 1.41 (s, 6H).

EXAMPLE 249F methyl 2-{[2-amino-4-methoxy-5-(2-methoxy-1,1-dimethyl-2-oxoethyl)phenyl]amino}-4-chlorobenzoate The title compound was prepared by substituting Example 249E for Example 6B in Example 6C. MS (DCI) m/e 406 (M+H)$^+$; $^1$H NMR (500 MHz, DMSO-d$_6$) δ 8.76 (s, 1H), 7.84 (d, J=8.48 Hz, 1H), 6.84 (s, 1H), 6.67 (dd, J=8.65, 2.20 Hz, 1H), 6.44 (s, 1H), 6.31 (d, J=2.03 Hz, 1H), 4.93 (s, 2H), 3.85 (s, 3H), 3.66 (s, 3H), 3.53 (s, 3H), 1.34 (s, 6H).

EXAMPLE 249G methyl 2-(3-chloro-8-methoxy-11-oxo-10,11-dihydro-5H-dibenzo[b,e][1,4]diazepin-7-yl)-2-methylpropanoate The title compound was prepared by substituting Example 249F for Example 6C in Example 6D. MS (DCI) m/e 375 (M+H)$^+$; $^1$H NMR (500 MHz, DMSO-d$_6$) δ 9.75 (s, 1H), 7.81 (s, 1H), 7.66 (d, J=8.42 Hz, 1H), 7.03 (d, J=2.18 Hz, 1H), 6.93 (s, 1H), 6.89 (dd, J=8.42, 2.18 Hz, 1H), 6.62 (s, 1H), 3.60 (s, 3H), 3.50 (s, 3H), 1.37 (s, 6H).

EXAMPLE 249H 3-chloro-7-(2-hydroxy-11-dimethylethyl)-8-methoxy-5,10-dihydro-11H-dibenzo[b,e][1,4]diazepin-11-one The title compound was prepared by substituting Example 249G for Example 6D in Example 204A. MS (DCI) m/e 347 (M+H)$^+$; $^1$H NMR (500 MHz, DMSO-d$_6$) δ 9.72 (s, 1H), 7.80 (s, 1H), 7.66 (d, J=8.54 Hz, 1H), 7.04 (d, J=2.14 Hz, 1H), 6.87-6.89 (m, 2H), 6.61 (s, 1H), 4.43 (t, J=5.64 Hz, 1H), 3.68 (s, 3H), 3.54 (d, J=5.80 Hz, 1H), 1.21 (s, 6H).

EXAMPLE 249I 7-(2-hydroxy-11-dimethylethyl)-8-methoxy-3-(3-methoxy-4-nitrophenyl)-5,10-dihydro-11H-dibenzo[b,e][1,4]diazepin-11-one The title compound was prepared by substituting Example 249H and Example 266G for Example 59B and Example 56A, respectively, in Example 59C. MS (DCI) m/e 464

(M+H)⁺; ¹H NMR (500 MHz, DMSO-d₆) δ 9.96 (s, 1H), 7.99 (d, J=8.59 Hz, 1H), 7.74-7.78 (m, 2H), 7.51 (s, 1H), 7.33-7.35 (m, 2H), 7.24 (d, J=7.98 Hz, 1H), 6.91 (s, 1H), 6.62 (s, 1H), 4.40 (t, J=5.01 Hz, 1H), 4.02 (s, 3H), 3.86 (s, 3H), 3.54 (d, J=4.90 Hz, 1H), 1.21 (s, 6H).

EXAMPLE 250

7-(3-hydroxypropyl)-3-(3-methoxy-4-nitrophenyl)-8-(trifluoromethoxy)-5,10-dihydro-11H-dibenzo[b,e][1,4]diazepin-11-one

EXAMPLE 250A

N-[5-bromo-2-nitro-4-(trifluoromethoxy)phenyl]acetamide

The title compound was prepared by substituting N-(3-bromo-4-trifluoromethoxy-phenyl)acetamide, prepared from acetylation of the corresponding aniline, for Example 223A in Example 223B. MS (DCI) m/e 344 (M+H)⁺; ¹H NMR (500 MHz, DMSO-d₆) δ 10.45 (s, 1H), 8.15 (s, 2H), 2.10 (s, 3H).

EXAMPLE 250B 5-bromo-2-nitro-4-(trifluoromethoxy)aniline

The title compound was prepared by substituting Example 250A for Example 223B in Example 223C. MS (DCI) m/e 302 (M+H)⁺; ¹H NMR (500 MHz, DMSO-d₆) δ 8.01 (s, 1H), 7.88 (s, 2H), 7.46 (s, 1H).

EXAMPLE 250C methyl 2-{[5-bromo-2-nitro-4-(trifluoromethoxy)phenyl]amino}-4-chlorobenzoate The title compound was prepared by substituting Example 250B for methyl 3,4-diaminobenzoate in Example 1A. MS (DCI) m/e 470 (M+H)⁺; ¹H NMR (500 MHz, DMSO-d₆) δ 10.83 (s, 1H), 8.24 (s, 1H), 7.96-7.99 (m, 2H), 7.68 (d, J=2.03 Hz, 1H), 7.25 (dd, J=8.48, 2.03 Hz, 1H), 3.88 (s, 3H).

EXAMPLE 250D methyl 2-{[5-bromo-2-nitro-4-(trifluoromethoxy)phenyl]amino}-4-chlorobenzoate The title compound was prepared by substituting Example 250C for Example 6B in Example 6C. MS (DCI) m/e 440 (M+H)⁺; ¹H NMR (500 MHz, DMSO-d₆) δ 8.84 (s, 1H), 7.87 (d, J=8.42 Hz, 1H), 7.41 (s, 1H), 6.95 (s, 1H), 6.78 (dd, J=8.48, 2.18 Hz, 1H), 6.39 (d, J=2.18 Hz, 1H), 3.86 (s, 3H).

EXAMPLE 250E

2-{[2-amino-5-bromo-4-(trifluoromethoxy)phenyl]amino}-4-chlorobenzoic acid

The title compound was prepared by substituting Example 250D for Example 12 in Example 13. MS (DCI) m/e 426 (M+H)⁺.

EXAMPLE 250F 7-bromo-3-chloro-8-(trifluoromethoxy)-5,10-dihydro-11H-dibenzo[b,e][1,4]diazepin-11-one The title compound was prepared by substituting Example 250E for Example 243F in Example 243G. MS (DCI) m/e 426 (M+H)⁺; ¹H NMR (500 MHz, DMSO-d₆) δ 10.12 (s, 1H), 8.31 (s, 1H), 7.71 (d, J=8.48 Hz, 1H), 7.34 (s, 1H), 7.13 (s, 1H), 7.02 (dd, J=7.46, 2.03 Hz, 1H), 6.98 (d, J=2.37 Hz, 1H).

EXAMPLE 250G methyl 3-[3-chloro-11-oxo-8-(trifluoromethoxy)-10,11-dihydro-5H-dibenzo[b,e][1,4]diazepin-7-yl]acrylate The title compound was prepared by substituting Example 250F for Example 223G in Example 223H. MS (DCI) m/e 413 (M+H)⁺; ¹H NMR (500 MHz, DMSO-d₆) δ 10.23 (s, 1H), 8.26 (s, 1H), 7.72 (d, J=8.48 Hz, 1H), 7.60 (d, J=15.60 Hz, 1H), 7.45 (s, 1H), 7.08 (s, 1H), 7.06 (d, J=2.18 Hz, 1H), 6.98 (dd, J=8.58, 2.03 Hz, 1H), 6.42 (d, J=16.22 Hz, 1H).

EXAMPLE 250H methyl 3-[3-chloro-11-oxo-8-(trifluoromethoxy)-10,11-dihydro-5H-dibenzo[b,e][1,4]diazepin-7-yl]propanoate The title compound was prepared by substituting Example 250G for Example 6B in Example 6C. MS (DCI) m/e 415 (M+H)⁺; ¹H NMR (500 MHz, DMSO-d₆) δ 9.89 (s, 1H), 8.09 (s, 1H), 7.61 (d, J=8.48 Hz, 1H), 6.99 (d, J=1.87 Hz, 1H), 6.86-6.89 (m 3H), 3.52 (s, 3H), 2.70 (t, J=7.49 Hz, 2H), 2.49 (t, J=7.49 Hz, 2H).

EXAMPLE 250I 3-chloro-7-(3-hydroxypropyl)-8-(trifluoromethoxy)-5,10-dihydro-11H-dibenzo[b,e][1,4]diazepin-11-one The title compound was prepared by substituting Example 250H for Example 6D in Example 204A. MS (DCI) m/e 387 (M+H)⁺; ¹H NMR (500 MHz, DMSO-d₆) δ 9.98 (s, 1H), 8.17 (s, 1H), 7.59 (d, J=8.64 Hz, 1H), 7.06 (d, J=2.14 Hz, 1H), 6.95-6.97 (m 3H), 4.53 (t, J=5.19 Hz, 1H), 3.40-3.44 (m, 2H), 2.50-2.54 (m, 2H), 1.63-1.66 (m, 2H).

EXAMPLE 250

7-(3-hydroxypropyl)-3-(3-methoxy-4-nitrophenyl)-8-(trifluoromethoxy)-5,10-dihydro-11H-dibenzo[b,e][1,4]diazepin-11-one The title compound was prepared by substituting Example 250I and Example 266G for Example 59B and Example 56A, respectively, in Example 59C. MS (DCI) m/e 504 (M+H)⁺; ¹H NMR (500 MHz, DMSO-d₆) δ 9.96 (s, 1H), 8.14 (s, 1H), 8.01 (d, J=8.29 Hz, 1H), 7.82 (d, J=8.29 Hz, 1H), 7.53 (s, 1H), 7.32-7.36 (m, 3H), 7.01 (s, 1H), 6.98 (s, 1H), 4.50 (t, J=5.06 Hz, 1H), 4.04 (s, 3H), 3.41-3.45 (m, 2H), 2.52-2.56 (m, 2H), 1.64-1.68 (m, 2H).

EXAMPLE 251

7-(3-hydroxy-3-methylbutyl)-3-(3-methoxy-4-nitrophenyl)-8-(trifluoromethoxy)-5,10-dihydro-11H-dibenzo[b,e][1,4]diazepin-11-one

EXAMPLE 251A 3-chloro-7-(3-hydroxy-3-methylbutyl)-8-(trifluoromethoxy)-5,10-dihydro-11H-dibenzo[b,e][1,4]diazepin-11-one The title compound was prepared by substituting Example 250H for Example 1B in Example 189A. MS (DCI) m/e 415 (M+H)$^+$; $^1$H NMR (500 MHz, DMSO-d$_6$) δ 9.95 (s, 1H), 8.13 (s, 1H), 7.69 (d, J=8.29 Hz, 1H), 7.06 (d, J=2.15 Hz, 1H), 6.94-6.97 (m 3H), 4.29 (s, 1H), 2.50-2.56 (m, 2H), 1.53-1.57 (m, 2H), 1.13 (m, 6H).

EXAMPLE 251B 7-(3-hydroxy-3-methylbutyl)-3-(3-methoxy-4-nitrophenyl)-8-(trifluoromethoxy)-5,10-dihydro-11H-dibenzo[b,e][1,4]diazepin-11-one The title compound was prepared by substituting Example 251A and Example 266G for Example 59B and Example 56A, respectively, in Example 59C. MS (DCI) m/e 532 (M+H)$^+$; $^1$H NMR (500 MHz, DMSO-d$_6$) δ 9.96 (s, 1H), 8.12 (s, 1H), 8.01 (d, J=8.29 Hz, 1H), 7.81 (d, J=7.98 Hz, 1H), 7.54 (d, J=1.84 Hz, 1H), 7.32-7.37 (m, 3H), 7.01 (s, 1H), 6.97 (d, J=1.23 Hz, 1H), 4.30 (s, 1H), 4.04 (s, 3H), 2.49-2.56 (m, 2H), 1.54-1.58 (m, 2H), 1.14 (m, 6H).

EXAMPLE 252

7-(3-hydroxy-3-methylbutyl)-3-(3-methoxy-4-nitrophenyl)-8-methyl-5,10-dihydro-11H-dibenzo[b,e][1,4]diazepin-11-one

EXAMPLE 252A

N-(5-bromo-4-methyl-2-nitrophenyl)acetamide

The title compound was prepared by substituting N-(3-bromo-4-methylphenyl)acetamide for Example 223A in Example 223B. MS (DCI) m/e 344 (M+H)$^+$; $^1$H NMR (500 MHz, DMSO-d$_6$) δ 10.22 (s, 1H), 7.98 (s, 1H), 7.94 (s, 1H), 2.39 (s, 3H), 2.07 (s, 3H).

EXAMPLE 252B 5-bromo-4-methyl-2-nitro aniline

The title compound was prepared by substituting Example 252A for Example 223B in Example 223C. MS (DCI) m/e 302 (M+H)$^+$; $^1$H NMR (500 MHz, DMSO-d$_6$) δ 7.92 (s, 1H), 7.33 (s, 3H), 2.44 (s, 3H).

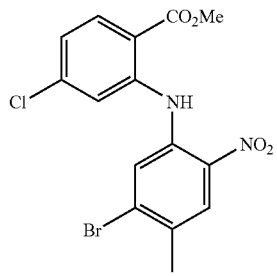

EXAMPLE 252C methyl 2-[(5-bromo-4-methyl-2-nitrophenyl)amino]-4-chlorobenzoate The title compound was prepared by substituting Example 252B for methyl 3,4-diaminobenzoate in Example 1A. MS (DCI) m/e 400 (M+H)$^+$; $^1$H NMR (500 MHz, DMSO-d$_6$) δ 10.72 (s, 1H), 8.16 (s, 1H), 7.97 (d, J=8.48 Hz, 1H), 7.85 (s, 1H), 7.51 (d, J=2.03 Hz, 1H), 7.14 (dd. J=8.82, 2.03 Hz, 1H), 3.88 (s, 3H), 2.38 (s, 3H).

EXAMPLE 252D methyl 2-[(2-amino-5-bromo-4-methylphenyl)amino]-4-chlorobenzoate The title compound was prepared by substituting Example 252C for Example 6B in Example 6C. MS (DCI) m/e 440 (M+H)$^+$; $^1$H NMR (500 MHz, DMSO-d$_6$) δ 10.72 (s, 1H), 8.16 (s, 1H), 7.96 (d, J=8.48 Hz, 1H), 7.85 (s, 1H), 7.51 (d, J=2.03 Hz, 1H), 7.14 (dd, J=8.82, 2.03 Hz, 1H), 3.88 (s, 3H), 2.38 (s, 3H).

EXAMPLE 252E

2-[(2-amino-5-bromo-4-methylphenyl)amino]-4-chlorobenzoic acid

The title compound was prepared by substituting Example 252D for Example 12 in Example 13. MS (DCI) m/e 356 (M+H)$^+$.

EXAMPLE 252F 7-bromo-3-chloro-8-methyl-5,10-dihydro-11H-dibenzo[b,e][1,4]diazepin-11-one The title compound was prepared by substituting Example 252E for Example 223F in Example 223G. MS (DCI) m/e 338 (M+H)$^+$; $^1$H NMR (500 MHz, DMSO-d$_6$) δ 9.94 (s, 1H), 8.06 (s, 1H), 7.69 (d, J=8.73 Hz, 1H), 7.20 (s, 1H), 7.02 (d, J=2.08 Hz, 1H), 6.95 (dd, J=8.42, 1.87 Hz, 1H), 6.91 (s, 1H), 2.20 (s, 3H).

EXAMPLE 252G methyl (2E)-3-(3-chloro-8-methyl-11-oxo-10,11-dihydro-5H-dibenzo[b,e][1,4]diazepin-7-yl)acrylate The title compound was prepared by substituting Example 252F for Example 223G in Example 223H. MS (DCI) m/e 343 (M+H)$^+$; $^1$H NMR (500 MHz, DMSO-d$_6$) δ 10.02 (s, 1H), 8.00 (s, 1H), 7.73 (d, J=15.59 Hz, 1H), 7.68 (d, J=8.42 Hz, 1H), 7.28 (s, 1H), 7.03 (d, J=1.87 Hz, 1H), 6.92 (dd, J=8.42, 1.87 Hz, 1H), 6.83 (s, 1H), 6.25 (d, J=15.59 Hz, 1H), 3.72 (s, 3H), 2.25 (s, 3H).

EXAMPLE 252H methyl 3-(3-chloro-8-methyl-11-oxo-10,11-dihydro-5H-dibenzo[b,e][1,4]diazepin-7-yl)propanoate The title compound was prepared by substituting Example 252G for Example 6B in Example 6C. MS (DCI) m/e 345 (M+H)$^+$; $^1$H NMR (500 MHz, DMSO-d$_6$) δ 9.76 (s, 1H), 7.89 (s, 1H), 7.66 (d, J=8.42 Hz, 1H), 7.05 (d, J=2.18 Hz, 1H), 6.89 (dd, J=8.42, 2.18 Hz, 1H), 6.74 (s, 1H), 6.73 (s, 1H), 3.59 (s, 3H), 2.72 (t, J=7.64 Hz, 2H), 2.53 (t, J=7.64 Hz, 2H), 2.13 (s, 3H).

EXAMPLE 252I 3-chloro-7-(3-hydroxy-3-methylbutyl)-8-methyl-5,10-dihydro-11H-dibenzo[b,e][1,4]diazepin-11-one The title compound was prepared by substituting Example 252H for Example 1B in Example 189A. MS (DCI) m/e 345 (M+H)$^+$; $^1$H NMR (500 MHz, DMSO-d$_6$) δ 9.73 (s, 1H), 7.85 (s, 1H), 7.66 (d, J=8.42 Hz, 1H), 7.04 (d, J=1.87 Hz, 1H), 6.75 (s, 1H), 6.72 (s, 1H), 4.22 (s, 1H), 2.45-2.50 (m, 2H), 2.12 (s, 2H), 1.49-1.53 (m, 2H), 1.15 (s, 6H).

EXAMPLE 252J 7-(3-hydroxy-3-methylbutyl)-3-(3-methoxy-4-nitrophenyl)-8-methyl-5,10-dihydro-11H-dibenzo[b,e][1,4]diazepin-11-one The title compound was prepared by substituting Example 252I and Example 266G for Example 59B and Example 56A, respectively, in Example 59C. MS (DCI) m/e 462 (M+H)$^+$; $^1$H NMR (500 MHz, DMSO-d$_6$) δ 9.74 (s, 1H), 8.01 (d, J=8.42 Hz, 1H), 7.79-7.82 (m, 2H), 7.53 (d, J=1.84 Hz, 1H), 7.34-7.35 (m, 2H), 7.28 (d, J=7.80 Hz, 1H), 6.81 (s, 1H), 6.84 (s, 1H), 4.24 (s, 1H), 4.04 (s, 3H), 2.47-2.50 (m, 2H), 2.14 (d, 3H), 1.51-1.54 (m, 2H), 1.16 (m, 6H).

EXAMPLE 253

3-(3-methoxy-4-nitrophenyl)-8-(2-pyridin-4-yl-ethyl)-5,10-dihydro-11H-dibenzo[b,e][1,4]diazepin-11-one

EXAMPLE 253A 3-chloro-8-[(E)-2-pyridin-4-ylvinyl]-5,10-dihydro-11H-dibenzo[b,e][1,4]diazepin-11-one The title compound was prepared by substituting Example 2B and 4-vinylpyridine for Example 223G and methyl acrylate, respectively, in Example 223H. MS (DCI) m/e 348 (M+H)$^+$; $^1$H NMR (500 MHz, DMSO-d$_6$) δ 9.94 (s, 1H), 8.52 (d, J=5.52 Hz, 2H), 8.26 (s 1H), 7.72 (d, J=8.59 Hz, 1H), 7.52 (d, J=6.14 Hz, 2H), 7.40 (d, J=16.57 Hz, 1H), 7.31 (dd, J=8.29, 2.15 Hz, 1H), 7.22 (d, J=1.84 Hz, 1H), 7.08 (d, J=2.15 Hz, 1H), 6.99-7.04 (m, 2H), 6.94 (dd, J=8.44, 199, Hz, 1H).

EXAMPLE 253B 3-chloro-8-(2-pyridin-4-ylethyl)-5,10-dihydro-11H-dibenzo[b,e][1,4]diazepin-11-one The title compound was prepared by substituting Example 253A for Example 6B in Example 6C. MS (DCI) m/e 351 (M+H)$^+$; $^1$H NMR (500 MHz, DMSO-d$_6$) δ 9.61 (s, 1H), 8.67 (d, J=7.93 Hz, 2H), 7.97 (s, 1H), 7.66-7.67 (m, 2H), 7.05 (d, J=2.18 Hz, 1H), 6.91 (dd, J=8.42, 2.18 Hz, 1H), 6.87-6.88 (m, 1H), 6.82-6.84 (m, 1H), 6.80 (d, J=1.87 Hz, 1H), 3.04 (t, J=7.64 Hz, 2H), 2.87 (t, J=7.80 Hz, 2H).

EXAMPLE 253C 3-(3-methoxy-4-nitrophenyl)-8-(2-pyridin-4-yl-ethyl)-5,10-dihydro-11H-dibenzo[b,e][1,4]diazepin-11-one The title compound was prepared by substituting Example 253B and Example 266G for Example 59B and Example 56A, respectively, in Example 59C. MS (DCI) m/e 467 (M+H)$^+$; $^1$H NMR (500 MHz, DMSO-d$_6$) δ 9.81 (s, 1H), 8.65 (d, J=5.93 Hz, 2H), 8.01 (d, J=8.42 Hz, 1H), 7.94 (s, 1H), 7.65 (d, J=5.61 Hz, 2H), 7.51 (d, J=1.56 Hz, 1H), 7.32-7.35 (m, 2H), 7.29 (dd, J=8.11, 1.56 Hz, 1H), 6.82 (d, J=7.80 Hz, 1H), 6.82-6.83 (m, 2H), 4.24 (s, 1H), 4.03 (s, 3H), 3.04 (t, J=7.64 Hz, 2H), 2.86 (t, J=7.64 Hz, 2H).

EXAMPLE 254

3-(3-methoxy-4-nitrophenyl)-8-(2-pyridin-2-yl-ethyl)-5,10-dihydro-11H-dibenzo[b,e][1,4]diazepin-11-one

EXAMPLE 254A 3-chloro-8-[(E)-2-pyridin-2-ylvinyl]-5,10-dihydro-11H-dibenzo[b,e][1,4]diazepin-11-one The title compound was prepared by substituting Example 2B and 2-vinylpyridine for Example 223G and methyl acrylate, respectively, in Example 223H. MS (DCI) m/e 348 (M+H)$^+$; $^1$H NMR (500 MHz, DMSO-d$_6$) δ 9.91 (s, 1H), 8.55 (d, J=4.06 Hz, 2H), 8.23 (s 1H), 7.72-7.78 (m, 2H), 7.53 (d, J=8.36 Hz, 1H), 7.51 (s, 1H), 7.30 (dd, J=8.27, 1.72 Hz, 1H), 7.22-7.24 (m, 2H), 7.07-7.10 (m, 2H), 6.99 (d, J=8.11 Hz, 1H), 6.94 (dd, J=8.42, 2.18,Hz, 1H).

EXAMPLE 254B 3-chloro-8-(2-pyridin-2-ylethyl)-5,10-dihydro-11H-dibenzo[b,e][1,4]diazepin-11-one The title compound was prepared by substituting Example 254A for Example 6B in Example 6C. MS (DCI) m/e 351 (M+H)$^+$; $^1$H NMR (500 MHz, DMSO-d$_6$) δ 9.82 (s, 1H), 8.48 (d, J=3099 Hz, 1H), 7.95 (s, 1H), 7.64-7.68 (m, 2H), 7.22 (d, J=7.98 Hz, 1H), 7.17-7.19 (m, 1H), is 7.05 (d, J=2.15 Hz, 1H), 6.91 (dd, J=8.59, 2.15 Hz, 1H), 6.80-6.87 (m, 3H), 2.92-2.98 (m, 2H), 2.84-2.89 (m, 2H).

EXAMPLE 254C 3-(3-methoxy-4-nitrophenyl)-8-(2-pyridin-2-yl-ethyl)-5,10-dihydro-11H-dibenzo[b,e][1,4]diazepin-11-one The title compound was prepared by substituting Example 254B and Example 266G for Example 59B and Example 56A, respectively, in Example 59C. MS (DCI) m/e 467 (M+H)$^+$; $^1$H NMR (500 MHz, DMSO-d$_6$) δ 9.81 (s, 1H), 8.49 (d, J=4.06 Hz, 1H), 8.01 (d, J=8.42 Hz, 1H), 7.91 (s, 1H), 7.80 (d, J=8.11 Hz, 1H), 7.64-7.68 (m, 1H), 7.52 (d, J=1.56 Hz, 1H), 7.33-7.35 (m, 2H), 7.29 (dd, J=8.11, 1.87 Hz, 1H), 7.22 (d, J=7.80 Hz, 1H), 7.17-7.20 (m, 1H), 6.90 (d, J=8.11 Hz, 1H), 6.86 (d, J=1.86 Hz, 1H), 6.81 (dd, J=7.96, 1.72 Hz, 1H), 4.03 (s, 3H), 2.95-2.98 (m, 2H), 2.86-2.88 (m, 2H).

EXAMPLE 255

3-(3-methoxy-4-nitrophenyl)-8-[2-(2-oxopyridin-1(2H)-yl)ethyl]-5,10-dihydro-11H-dibenzo[b,e][1,4]diazepin-11-one The title compound was prepared by substituting Example 239 for Example 204A in Example 221A. MS (DCI) m/e 483 (M+H)$^+$; $^1$H NMR (500 MHz, DMSO-d$_6$) δ 9.83 (s, 1H), 8.01 (d, J=8.42 Hz, 1H), 7.96 (s, 1H), 7.80 (d, J=8.42 Hz, 1H), 7.50-7.53 (m, 2H), 7.34-7.39 (m, 3H), 7.29 (d, J=8.11 Hz, 1H), 6.93 (d, J=7.80 Hz, 1H), 6.84 (s, 1H), 6.80 (d, J=8.11 Hz, 1H), 6.37 (d, J=9.04 Hz, 1H), 6.11-6.13 (m, 1H), 4.01-4.03 (m, 5H), 2.81 (t, J=7.49 Hz, 2H).

EXAMPLE 256

8-[2-(5-fluoro-2-oxopyridin-1(2H)-yl)ethyl]-3-(3-methoxy-4-nitrophenyl)-5,10-dihydro-11H-dibenzo[b,e][1,4]diazepin-11-one The title compound was prepared by substituting Example 239 and 5-fluoro-pyridin-2-ol for Example 204A and pyridin-2(1H)-one, respectively, in Example 221A. MS (DCI) m/e 501 (M+H)$^+$; $^1$H NMR (500 MHz, DMSO-d$_6$) δ 9.84 (s, 1H), 8.01 (d, J=8.42 Hz, 1H), 7.96 (s, 1H), 7.80 (d, J=8.42 Hz, 1H), 7.78-7.81 (m, 2H), 7.50-7.54 (m, 2H), 7.33-7.35 (m, 2H), 7.29 (dd, J=8.11, 1.87 Hz, 1H), 6.94 (d, J=8.11 Hz, 1H), 6.81-6.84 (m, 2H), 6.40 (dd, J=10.14, 5.46 Hz, 1H), 3.97-4.03 (m, 5H), 2.80-2.83 (m, 2H).

EXAMPLE 257

3-(3-methoxy-4-nitrophenyl)-8-[2-(6-oxopyridazin-1(6H)-yl)ethyl]-5,10-dihydro-11H-dibenzo[b,e][1,4]diazepin-11-one The title compound was prepared by substituting Example 239 and pyridazin-3-ol for Example 204A and pyridin-2(1H)-one, respectively, in Example 221A. MS (DCI) m/e 484 (M+H)$^+$; $^1$H NMR (500 MHz, DMSO-d$_6$) δ 9.83 (s, 1H), 8.01 (d, J=8.42 Hz, 1H), 7.95 (s, 1H), 7.88 (dd, J=3.90, 1.72 Hz, 1H), 7.80 (d, J=8.42 Hz, 1H), 7.52 (d, J=1.56 Hz, 1H), 7.38 (dd, J=9.36, 3.74 Hz, 2H), 7.33-7.35 (m, 2H), 6.92 (m, 1H), 6.82 (s, 1H), 6.80 (dd, J=7.95, 1.72 Hz, 1H), 4.20 (t, J=7.49 Hz, 2H), 4.03 (s, 3H), 2.88-2.83 (t, J=7.49 Hz, 2H).

EXAMPLE 258

3-(3-methoxy-4-nitrophenyl)-8-[2-(pyridin-2-yloxy)ethyl]-5,10-dihydro-11H-dibenzo[b,e][1,4]diazepin-11-one The title compound was prepared by substituting Example 239 for Example 204A in Example 221A. MS (DCI) m/e 483 (M+H)$^+$; $^1$H NMR (500 MHz, DMSO-d$_6$) δ 9.85 (s, 1H), 8.15 (dd, J=5.06, 1.99 Hz, 1H), 8.01 (d, J=8.29 Hz, 1H), 7.95 (s, 1H), 7.80 (d, J=8.29 Hz, 1H), 7.66-7.70 (m, 1H), 7.52 (d, J=1.53 Hz, 1H), 7.33-7.35 (m, 2H), 7.29 (dd, J=7.98, 1.84 Hz, 1H), 6.89-6.97 (m, 4H), 6.78 (d, J=8.59 Hz, 1H), 4.40 (t, J=6.75 Hz, 2H), 4.03 (s, 3H), 2.90 (t, J=6.75 Hz, 2H).

EXAMPLE 259

8-{2-[(5-chloropyridin-3-yl)oxy]ethyl}-3-(3-methoxy-4-nitrophenyl)-5,10-dihydro-11H-dibenzo[b,e][1,4]diazepin-11-one The title compound was prepared by substituting Example 239 and 3-chloro-5-hydroxypyridine for Example 204A and pyridin-2(1H)-one, respectively, in Example 221A. MS (DCI) m/e 517 (M+H)$^+$; $^1$H NMR (500 MHz, DMSO-d$_6$) δ 9.89 (s, 1H), 8.26 (d, J=8.44 Hz, 1H), 8.19 (d J=1.82 Hz, 1H), 8.01 (d, J=8.24 Hz, 1H), 7.98 (s, 1H), 7.80 (d, J=8.24 Hz, 1H), 7.59-7.60 (m, 1H), 7.52 (d, J=1.53 Hz, 1H), 7.33-7.35 (m, 2H), 7.30 (dd, J=8.24, 1.53 Hz, 1H), 6.92-6.97 (m, 3H), 4.24 (t, J=6.56 Hz, 2H), 4.03 (s, 3H), 2.92 (t, J=6.56 Hz, 2H).

EXAMPLE 260

8-methoxy-3-(3-methoxy-4-nitrophenyl)-7-[2-(pyridin-3-yloxy)ethyl]-5,10-dihydro-11H-dibenzo[b,e][1,4]diazepin-11-one The title compound was prepared by substituting Example 247 and 3-hydroxypyridine for Example 204A and pyridin-2(1H)-one, respectively, in Example 221A. MS (DCI) m/e 513 (M+H)$^+$; $^1$H NMR (500 MHz, DMSO-d$_6$) δ 9.72 (s, 1H), 8.33 (d, J=2.76 Hz, 1H), 8.20 (d J=4.91 Hz, 1H), 7.94 (d, J=8.29 Hz, 1H), 7.71-7.73 (m, 2H), 7.57 (m, 1H), 7.43-7.47 (m, 2H), 7.26-7.28 (m, 2H), 7.21 (dd, J=8.29, 1.84 Hz, 1H), 6.85 (s, 1H), 6.61 (s, 1H), 4.15 (t, J=6.90 Hz, 2H), 4.03 (s, 3H), 2.86 (t, J=7.06 Hz, 2H).

EXAMPLE 261 methyl (3-isoquinolin-5-yl-11-oxo-10,11-dihydro-5H-dibenzo[b,e][1,4]diazepin-8-yl)acetate The title compound was prepared by substituting 5-bromoisoquinoline and Example 54A for Example 9 and 2-methoxy-4-(4,4,5,5-tetramethyl-1,3,2-dioxaborolan-2-yl)phenol, respectively, in Example 10. MS (DCI) m/e 410 (M+H)$^+$; $^1$H NMR (500 MHz, DMSO-d$_6$) δ 9.87 (s, 1H), 9.39 (s, 1H), 8.50 (d, J=6.24 Hz, 1H), 8.19 (d J=7.80 Hz, 1H), 7.97 (s, 1H), 7.84 (d, J=7.80 Hz, 1H), 7.70-7.78 (m, 3H), 7.14 (d, J=1.56 Hz, 1H), 7.02 (dd, J=7.95, 1.72 Hz, 1H), 6.93 (d, J=7.80 Hz, 1H), 6.89 (d, J=1.56 Hz, 1H), 6.86 (dd, J=7.80, 1.87 Hz, 1H), 3.59 (s, 3H), 3.54 (s, 2H).

EXAMPLE 262 methyl [3-(8-nitroisoquinolin-5-yl)-11-oxo-10,11-dihydro-5H-dibenzo[b,e][1,4]diazepin-8-yl]acetate

EXAMPLE 262A 5-bromo-8-nitroisoquinoline

5-Bromo-isoquinoline (100 mg, 0.48 mmol) was suspended in 0.58 mL of concentrated $H_2SO_4$. To this solution was added $KNO_3$ (68 mg, 0.58 mmol) in 0.48 mL of concentrated $H_2SO_4$. The reaction mixture was stirred at room temperature for 1.5 hours, poured into water/ice, neutralized with 2.0 M $Na_2CO_3$, and extracted with EtOAc three times The combined organic layers were washed brine, dried ($MgSO_4$), filtered and concentrated under vacuum to give 121 mg (995) of the title product. MS (DCI) m/e 255 $(M+H)^+$; $^1H$ NMR (500 MHz, $CDCl_3$) δ 10.0 (s, 1H), 9.39 (s, 1H), 8.85 (d, J=5.76 Hz, 1H), 8.17-8.22 (m, 2H), 8.12 (d, J=8.14 Hz, 1H).

EXAMPLE 262B methyl [3-(8-nitroisoquinolin-5-vi)-11-oxo-10,11-dihydro-5H-dibenzo[b,e][1,4]diazepin-8-yl]acetate The title compound was prepared by substituting Example 262A and Example 54A for Example 9 and 2-methoxy-4-(4,4,5,5-tetramethyl-1,3,2-dioxaborolan-2-yl)phenol, respectively, in Example 10. MS (DCI) m/e 455 $(M+H)^+$; $^1H$ NMR (500 MHz, DMSO-$d_6$) δ 9.93 (s, 1H), 9.84 (s, 1H), 8.70 (d, J=5.83 Hz, 1H), 8.50 (d J=7.98 Hz, 1H), 8.05 (s, 1H), 7.91 (d, J=7.98 Hz, 1H), 7.87 (d, J=7.98 Hz, 1H), 7.83 (d, J=5.83 Hz, 1H), 7.14 (s, 1H), 7.05 (dd, J=7.98 Hz, 1H), 6.85-6.94 (m, 3H), 3.60 (s, 3H), 3.54 (s, 2H).

EXAMPLE 263 methyl 3-[3-(4-formyl-3-methoxyphenyl)-11-oxo-10,11-dihydro-5H-dibenzo[b,e][1,4]diazepin-8-yl]propanoate The title compound was prepared by substituting 4-chloro-2-methoxy-benzaldehyde and Example 241A for Example 59B and Example 56A, respectively, in Example 59C. MS (DCI) m/e 431 $(M+H)^+$; $^1H$ NMR (500 MHz, DMSO-$d_6$) δ 10.38 (s, 1H), 9.81 (s, 1H), 7.92 (s, 1H), 7.78-7.81 (m, 2H), 7.42 (s, 1H), 7.34 (d, J=1.87 Hz, 1H), 7.33 (d, J=8.11 Hz, 1H), 7.29 (dd, J=8.11, 1.87 Hz, 1H), 6.92-6.93 (m, 1H), 6.81-6.82 (m, 2H), 4.03 (s, 3H), 3.58 (s, 3H), 2.75 (t, J=7.49 Hz, 2H), 2.55 (t, J=7.49 Hz, 2H).

EXAMPLE 264 methyl 3-{3-[4-(hydroxymethyl)-3-methoxyphenyl]-11-oxo-10,11-dihydro-5H-dibenzo[b,e][1,4]diazepin-8-yl}propanoate The title compound was prepared by substituting (4-chloro-2-methoxy-phenyl)-methanol and Example 241A for Example 59B and Example 56A, respectively, in Example 59C. MS (DCI) m/e 433 $(M+H)^+$; $^1H$ NMR (500 MHz, DMSO-$d_6$) δ 9.74 (s, 1H), 7.85 (s, 1H), 7.75 (d, J=8.11 Hz, 1H), 7.47 (d, J=7.80 Hz, 1H), 7.29 (d, J=1.26 Hz, 1H), 7.20-7.22 (m, 2H), 7.16 (s, 1H), 6.92 (d, J=8.74 Hz, 1H), 6.80-6.82 (m, 2H), 5.03 (t, J=5.03 Hz, 1H), 3.87 (s, 3H), 3.58 (s, 3H), 2.72 (t, J=7.49 Hz, 2H), 2.55 (t, J=7.49 Hz, 2H).

EXAMPLE 265 methyl 3-[3-(3-methoxy-4-propionylphenyl)-11-oxo-10,11-dihydro-5H-dibenzo[b,e][1,4]diazepin-8-yl]propanoate

EXAMPLE 265A 1-(4-chloro-2-methoxyphenyl)propan-1-one

4-Chloro-2-methoxy-benzaldehyde (0.54 g, 3.2 mmol) in 10 mL of THF was treated with 3.0 M EtMgBr (2 mL, 6.0 mmol) at room temperature. The solution was stirred for 1 hour and quenched with MeOH. The solution was poured into water, treated 10 mL of 10% HCl, extracted with EtOAc several times. The combined organic layers were washed brine, dried ($MgSO_4$), filtered, and concentrated. The residue was diluted with $CH_2Cl_2$, treated with PCC (1.33 g, 6.4 mmol) for 2 hours. The reaction mixture was filtered through a pack of silica gel to give 0.42 g of the title compound. MS (DCI) m/e 199 $(M+H)^+$.

EXAMPLE 265B methyl 3-[3-(3-methoxy-4-propionylphenyl)-11-oxo-10,11-dihydro-5H-dibenzo[b,e][1,4]diazepin-8-yl]propanoate The title compound was prepared by substituting Example 265A and Example 241A for Example 59B and Example 56A, respectively, in Example 59C. MS (DCI) m/e 459 $(M+H)^+$; $^1H$ NMR (500 MHz, DMSO-$d_6$) δ 9.79 (s, 1H), 7.90 (s, 1H), 7.77 (d, J=8.11 Hz, 1H), 7.66 (d, J=8.11 Hz, 1H), 7.35 (d, J=1.25 Hz, 1H), 7.33 (d, J=1.87 Hz, 1H), 7.25-7.28 (m, 2H), 6.92 (d, J=8.73 Hz, 1H), 6.81-6.82 (m, 2H), 3.98 (s, 3H), 3.58 (s, 3H), 2.96 (q, J=7.18 Hz, 1H), 2.72 (t, J=7.49 Hz, 2H), 2.55 (t, J=7.49 Hz, 2H), 1.07 (t, J=7.18 Hz, 3H).

EXAMPLE 266

2-[3-(3-methoxy-4-nitrophenyl)-11-oxo-10,11-dihydro-5H-dibenzo[b,e][1,4]diazepin-8-yl]-2-methylN(4-morpholin-4-ylphenyl)propanamide

EXAMPLE 266A methyl 2-methyl-2-(4-nitrophenyl)propanoate

A solution of 4-nitrophenylacetic acid (60.0 g, 0.33 mol), iodomethane (130.0 mL, 296.4 g, 2.10 mol), and 18-crown-6 (15 g, 0.057 mol) in DMF (1.0 L) was cooled to 0° C., then 95% NaH (30.0 g, 1.19 mol) was added in portions, keeping $T_{rxn}$<25° C. The reaction was allowed to warm to room temperature overnight, then partitioned between water (2 L) and $Et_2O$ (400 mL). The aqueous layer was extracted with $Et_2O$ (2×300 mL), then the combined organic layers were washed with brine and dried over $Na_2SO_4$. After filtration and concentration, recovered 74 g (99%) product as an orange oil. MS (DCI) m/e 241 $(M+NH_4)^+$; $^1H$ NMR (300 MHz, $CDCl_3$) δ 8.19 (m, 2H), 7.50 (m, 2H), 3.67 (s, 3H), 1.62 (s, 6H).

EXAMPLE 266B methyl 2-(4-aminophenyl)-2-methylpropanoate

Dissolved the compound described in Example 266A (59.4 g, 0.27 mol) in MeOH (600 mL), then added $SnCl_2.2H_2O$ (120.0 g, 0.53 mol) and concentrated HCl (300 mL). The reaction was allowed to stir at room temperature overnight, then more SnCl$_2$.2H$_2$O (49.0 g, 0.22 mol) and concentrated HCl (100 mL) were added, and the reaction heated to 50° C. for 4 hours. After cooling the reaction was partitioned between pH=14 water and EtOAc. The aqueous layer was again extracted with EtOAc, then the combined organic layers were dried (Na$_2$SO$_4$). The residue was purified by column chromatography using 4/1, then 1/1 hexanes/EtOAc to give 38.0 g (74%) product. MS (DCI) m/e 194 (M+H)$^+$, 211 (M+NH$_4$)$^+$; $^1$H NMR (300 MHz, CDCl$_3$) δ 7.13 (m, 2H), 6.64 (m, 2H), 3.62 (s, 3H), 1.55 (s, 6H).

EXAMPLE 266C methyl 2-(4-amino-3-nitrophenyl)-2-methylpropanoate

Example 266B (38.0 g, 0.20 mol) was treated with acetic anhydride to give the acetamide, then nitrated, hydrolyzed, and subjected to a Fischer esterification by the method described in Example 6A to give the title compound (43.2 g, 0.18 mol, 90% overall). MS (DCI) m/e 239 (M+H)$^+$, 256 (M+NH$_4$)$^+$; $^1$H NMR (300 MHz, CDCl$_3$) δ 8.12 (d, J=2.4 Hz, 1H), 7.37 (dd, J=8.8, 2.4 Hz, 1H), 6.78 (d, J=8.8 Hz, 1H), 6.05 (br s, 2H), 3.66 (s, 3H), 1.57 (s, 6H).

EXAMPLE 266D methyl 4-chloro-2-{[4-(2-methoxy-1,1-dimethyl-2-oxoethyl)-2-nitrophenyl]amino}benzoate The title compound was prepared by substituting Example 266C for 4-bromo-2-nitroaniline in Example 2A. MS (DCI) m/e 407 and 409 (M+H)$^+$, 424 and 426 (M+NH$_4$)$^+$; $^1$H NMR (300 MHz, DMSO-d$_6$) δ 10.84 (s, 1H), 8.03 (d, J=2.0 Hz, 1H), 7.97 (d, J=8.5 Hz, 1H), 7.66 (m, 2H), 7.50 (d, J=2.0 Hz, 1H), 7.14 (dd, J=8.5, 2.0 Hz, 1H), 3.89 (s, 3H), 3.63 (s, 3H), 1.55 (s, 6H).

EXAMPLE 266E methyl 2-{[2-amino-4-(2-methoxy-1,1-dimethyl-2-oxoethyl)phenyl]amino}-4-chlorobenzoate The title compound was prepared by substituting Example 266D for Example 6B in Example 6C. MS (DCI) m/e 377 and 379 (M+H)$^+$; $^1$H NMR (300 MHz, DMSO-d$_6$) δ 8.82 (s, 1H), 7.85 (d, J=8.5 Hz, 1H), 6.98 (d, J=8.1 Hz, 1H), 6.78 (d, J=2.0 Hz, 1H), 6.70 (dd, J=8.5, 2.0 Hz, 1H), 6.55 (dd, J=8.1, 2.0 Hz, 1H), 6.42 (d, J=2.0 Hz, 1H), 5.01 (br s, 2H), 3.85 (s, 3H), 3.61 (s, 3H), 1.48 (s, 6H).

EXAMPLE 266F methyl 2-(3-chloro-11-oxo-10,11-dihydro-5H-dibenzo[b,e][1,4]diazepin-8-yl)-2-methylpropanoate The title compound was prepared by substituting Example 266E for Example 5B in Example 5C. MS (DCI) m/e 345 and 347 (M+H)$^+$; $^1$H NMR (300 MHz, DMSO-d$_6$) δ 9.84 (s, 1H), 8.06 (s, 1H), 7.68 (d, J=8.5 Hz, 1H), 7.06 (d, J=2.0 Hz, 1H), 6.93 (m, 4H), 3.58 (s, 3H), 1.43 (s, 6H).

EXAMPLE 266G 2-(3-methoxy-4-nitrophenyl)-4,4,5,5-tetramethyl-1,3,2-dioxaborolane The title compound was prepared by substituting 4-chloro-2-methoxy-1-nitro-benzene for Example 9 in Example 56A. MS (DCI) m/e 297 (M+NH$_4$)$^+$.

EXAMPLE 266H methyl 2-[3-(3-methoxy-4-nitrophenyl)-11-oxo-10,11-dihydro-5H-dibenzo[b,e][1,4]diazepin-8-yl]-2-methylpropanoate Example 266F (7.0 g, 20.3 mmol) was slurried in a mixture of DME (130 mL) and MeOH (65 mL). That mixture was subjected to several cycles of vacuum-N$_2$ refill, then the following compounds were added: Example 266G (8.3 g, 29.7 mmol), 2-dicyclohexylphosphino-2'-(N,N-dimethylamino)biphenyl (CyMAP ligand; 0.66 g, 1.7 mmol), palladium(II) acetate (0.24 g, 1.1 mmol), and cesium fluoride (9.2 g, 60.5 mmol). After a few more cycles of vacuum-N$_2$ refill, the reaction was heated at 70° C. under N$_2$ overnight. The reaction was then cooled, filtered through Celite®, and the filtrate was slowly diluted with water (1.2 L). The resultant solids were filtered off and dried, giving the crude material (11.6 g) as reddish-brown solids. Those solids were slurried in Et$_2$O (100 mL) overnight, giving 8.4 g solids after filtration and drying. Another Et$_2$O (40 mL) slurry for 2 hours, then filtration and drying gave the product (8.1 g, 86%) as dark red solids. MS (DCI) m/e 462 (M+H)$^+$; $^1$H NMR (300 MHz, DMSO-d$_6$) δ 9.84 (s, 1H), 8.03 (s, 1H), 8.01 (d, J=8.5 Hz, 1H), 7.80 (d, J=8.1 Hz, 1H), 7.52 (d, J=1.7 Hz, 1H), 7.30-7.35 (m, 3H), 6.90-6.98 (m, 3H), 4.03 (s, 3H), 3.58 (s, 3H), 1.44 (s, 6H).

EXAMPLE 266I

2-[3-(3-methoxy-4-nitrophenyl)-11-oxo-10,11-dihydro-5H-dibenzo[b,e][1,4]diazepin-8-yl]-2-methylpropanoic acid The title compound was prepared by substituting Example 266H for Example 12 in Example 13. MS (DCI) m/e 448 (M+H)$^+$, 465 (M+NH$_4$)$^+$; $^1$H NMR (300 MHz, DMSO-d$_6$) δ 12.25 (v br s, 1H), 9.85 (s, 1H), 8.02 (d, J=8.5 Hz, 1H), 8.01 (s, 1H), 7.80 (d, J=8.1 Hz, 1H), 7.52 (d, J=1.7 Hz, 1H), 7.30-7.35 (m, 3H), 6.96-7.02 (m, 3H), 4.03 (s, 3H), 1.41 (s, 6H).

EXAMPLE 266J

2-[3-(3-methoxy-4-nitrophenyl)-11-oxo-10,11-dihydro-5H-dibenzo[b,e][1,4]diazepin-8-yl]-2-methylN(4-morpholin-4-ylphenyl)propanamide Example 266I (5.3 g, 11.8 mmol), 4-morpholinoaniline (2.7 g, 15.3 mmol), triethylamine (2.1 mL, 1.5 g, 15.2 mmol), and O-(7-azabenzotriazol-1-yl)-N,N,N',N'-tetramethyluronium hexafluorophosphate (HATU; 5.8 g, 15.3 mmol) were dissolved in DMF (70 mL) and stirred at room temperature overnight. The reaction was slowly diluted with water (1 L), and after filtration and drying recovered 7.4 g crude material. Those solids were slurried in absolute EtOH (70 mL) for 30 minutes, then that slurry was slowly diluted with water (420 mL), giving 6.5 g solids after filtration and drying. Those solids were slurried in CH$_3$CN/MeOH 1/1 (300 mL), added conc. HCl (1.0 mL), everything dissolved, then slowly added water (1.5 L). After filtration and drying, recovered the product (5.2 g, 73%) as brown solids. MS (DCI) m/e 608 (M+H)$^+$; $^1$H NMR (300 MHz, DMSO-d$_6$) δ 9.87 (s, 1H), 8.79 (s, 1H), 8.01 (m, 2H), 7.80 (d, J=8.1 Hz, 1H), 7.52 (s, 1H), 7.42 (d, J=8.7 Hz, 2H), 7.30-7.35 (m, 3H), 7.06 (s, 1H), 7.00 (m, 1H), 6.95 (m, 1H), 6.84 (d, J=8.7 Hz, 2H), 4.03 (s, 3H), 3.71 (m, 4H), 3.00 (m, 4H), 1.49 (s, 6H).

EXAMPLE 267

2-[3-(4-cyano-3-methoxyphenyl)-11-oxo-10,11-dihydro-5H-dibenzo[b,e][1,4]diazepin-8-yl]-2-methylN(4-morpholin-4-ylphenyl)propanamide

EXAMPLE 267A 4-amino-2-methoxybenzonitrile

The title compound was prepared by substituting 4-nitro-2-methoxy-benzonitrile for Example 6B in Example 6C. MS (DCI) m/e 149 (M+H)$^+$, 166 (M+NH$_4$)$^+$; $^1$H NMR (300 MHz, CDCl$_3$) δ 7.29 (d, J=8.1 Hz, 1H), 6.22 (dd, J=8.1, 2.0 Hz, 1H), 6.16 (d, J=2.0 Hz, 1H), 4.16 (br s, 2H), 3.85 (s, 3H).

EXAMPLE 267B 4-iodo-2-methoxybenzonitrile

The title compound was prepared by substituting Example 267A for Example 57A in Example 57B. MS (DCI) m/e 277 (M+NH$_4$)$^+$; $^1$H NMR (300 MHz, CDCl$_3$) δ 7.40 (m, 1H), 7.33 (m, 1H), 7.25 (d, J=8.1 Hz, 1H), 3.93 (s, 3H).

EXAMPLE 267C 2-methoxy-4-(4,4,5,5-tetramethyl-1,3,2-dioxaborolan-2-yl)benzonitrile Example 267B (2.0 g, 7.7 mmol), bis(pinacolato)-diboron, (2.2 g, 8.7 mmol), KOAc (2.2 g, 22.4 mmol), and PdCl$_2$(dppf)-CH$_2$Cl$_2$ (315 mg, 0.39 mmol) in DMSO (40 mL) was heated at 80° C. for 2 hours. The reaction was then cooled, filtered through Celite®, then partitioned between toluene and water. The organic layer was washed with brine, dried over Na$_2$SO$_4$, filtered and concentrated to give 2.3 g crude material. That crude was stirred in 50° C. hexane (35 mL) for 1 hour, filtered, and the filtrate was allowed to cool to room temperature, then placed in the refrigerator overnight. Recovered 1.3 g (65%) grayish-brown crystals. MS (DCI) m/e 277 (M+NH$_4$)$^+$; $^1$H NMR (300 MHz, DMSO-d$_6$) δ 7.73 (d, J=7.8 Hz, 1H), 7.35 (m, 2H), 3.93 (s, 3H), 1.32 (s, 12H).

EXAMPLE 267D

2-[3-(4-cyano-3-methoxyphenyl)-11-oxo-10,11-dihydro-5H-dibenzo[b,e][1,4]diazepin-8-yl]-2-methylN(4-morpholin-4-ylphenyl)propanamide The title compound was prepared by substituting Example 267C and Example 266F for Example 56A and Example 59B, respectively, in Example 59C. MS (DCI) m/e 442 (M+H)$^+$; $^1$H NMR (300 MHz, DMSO-d$_6$) δ 9.84 (s, 1H), 8.01 (s, 1H), 7.84 (d, J=8.1 Hz, 1H), 7.79 (d, J=8.1 Hz, 1H), 7.42 (d, J=1.4 Hz, 1H), 7.27-7.34 m, 3H), 6.97 (m, 2H), 6.91 (dd, J=8.5 Hz, 2.0 Hz, 1H), 4.03 (s, 3H), 3.58 (s, 3H), 1.44 (s, 6H).

EXAMPLE 267E

2-[3-(4-cyano-3-methoxyphenyl)-11-oxo-10,11-dihydro-5H-dibenzo[b,e][1,4]diazepin-8-yl]-2-methylN(4-morpholin-4-ylphenyl)propanamide Example 267D was saponified by the method of Example 13, then that acid was converted to the final compound by the method described in Example 266J, except preparative HPLC was used for the purification. MS (ESI) m/e 588 (M+H)$^+$; $^1$H NMR (400 MHz, DMSO-d$_6$) δ 9.85 (s, 1H), 8.81 (s, 1H), 7.96 (s, 1H), 7.82 (d, J=8.0 Hz, 1H), 7.77 (d, J=8.0 Hz, 1H), 7.43 (d, J=8.9 Hz, 2H), 7.40 (s, 1H), 7.26-7.33 (m, 3H), 7.04 (d, J=1.5 Hz, 1H), 6.97 (d, J=6.0 Hz, 1H), 6.93 (dd, J=6.0, 1.5 Hz, 1H), 6.88 (d, J=8.9 Hz, 2H), 4.03 (s, 3H), 3.71 (m, 4H), 3.00 (m, 4H), 1.49 (s, 6H).

EXAMPLE 268

2-[3-(4-chloro-3-methoxyphenyl)-11-oxo-10,11-dihydro-5H-dibenzo[b,e][1,4]diazepin-8-yl]-2-methylN(4-morpholin-4-ylphenyl)propanamide

EXAMPLE 268A 2-(4-chloro-3-methoxyphenyl)-4,4,5,5-tetramethyl-1,3,2-dioxaborolane Starting with 2-methoxy-4-nitro-chlorobenzene, the title compound was prepared by the methods described in Examples 267A, 267B, and 267C. MS (DCI) m/e (M+H)$^+$ 286 and 288 (M+NH$_4$)$^+$.

EXAMPLE 268B

2-[3-(4-chloro-3-methoxyphenyl)-11-oxo-10,11-dihydro-5H-dibenzo[b,e][1,4]diazepin-8-yl]-2-methylN(4-morpholin-4-ylphenyl)propanamide Starting with the compounds described in 266F and 268A, the title compound was prepared by the methods of Examples 266H, 266I, and Example 266J, except preparative HPLC was used for the purification. MS (ESI) m/e 595 and 597 (M+H)$^+$; $^1$H NMR (400 MHz, DMSO-d$_6$) δ 9.80 (s, 1H), 8.81 (s, 1H), 7.92 (s, 1H), 7.75 (d, J=8.0 Hz, 1H), 7.51 (d, J=8.3 Hz, 1H), 7.43 (d, J=9.2 Hz, 2H), 7.32 (d, J=1.8 Hz, 1H), 7.28 (d, J=1.5 Hz, 1H), 7.03 (d, J=1.5 Hz, 1H), 6.97 (d, J=8.4 Hz, 1H), 6.93 (dd, J=8.4, 1.5 Hz, 1H), 6.88 (d, J=9.2 Hz, 2H), 3.94 (s, 3H), 3.72 (m, 4H), 3.04 (m, 4H), 1.48 (s, 6H).

EXAMPLE 269

2-[3-(3-methoxy-4-nitrophenyl)-11-oxo-10,11-dihydro-5H-dibenzo[b,e][1,4]diazepin-8-yl]-2-methylN-pyridin-2-ylpropanamide The title compound was prepared by substituting Example 266I and pyridin-2-ylamine for dimethylaminoacetic acid and Example 120, respectively, in Example 122. MS (ESI) m/e 524 (M+H)$^+$; $^1$H NMR (300 MHz, DMSO-d$_6$) δ 9.86 (s, 1H), 9.19 (s, 1H), 8.23 (m, 1H), 8.04 (s, 1H), 8.00 (d, J=8.5 Hz, 2H), 7.82 (m, 1H), 7.79 (d, J=8.1 Hz, 1H), 7.52 (d, J=1.7 Hz, 1H), 7.28-7.35 (m, 3H), 7.10 (m, 1H), 7.06 (s, 1H), 7.00 (s, 2H), 4.02 (s, 3H), 1.53 (s, 6H).

EXAMPLE 270

2-[3-(3-methoxy-4-nitrophenyl)-11-oxo-10,11-dihydro-5H-dibenzo[b,e][1,4]diazepin-8-yl]-2-methylN-pyridin-3-ylpropanamide The title compound was prepared by substituting Example 266I and pyridin-3-ylamine for dimethylaminoacetic acid and Example 120, respectively, in Example 122. MS (ESI) m/e 524 (M+H)$^+$; $^1$H NMR (300 MHz, DMSO-d$_6$) δ 9.89 (s, 1H), 9.50 (s, 1H), 8.92 (d, J=2.4 Hz, 1H), 8.35 (dd, J=4.7, 1.0

Hz, 1H), 8.20 (m, 1H), 8.04 (s, 1H), 8.01 (d, J=8.1 Hz, 1H), 7.79 (d, J=8.1 Hz, 1H), 7.54 (m, 1H), 7.51 (d, J=1.7 Hz, 1H), 7.28-7.35 (m, 3H), 7.02 (d, J=2.0 Hz, 1H), 7.00 (d, J=8.3 Hz, 1H), 6.96 (dd, J=8.3, 2.0, 1H), 4.03 (s, 3H), 1.52 (s, 6H).

EXAMPLE 271

2-[3-(3-methoxy-4-nitrophenyl)-11-oxo-10,11-dihydro-5H-dibenzo[b,e][1,4]diazepin-8-yl]-2-methylN-pyridin-4-ylpropanamide The title compound was prepared by substituting Example 266I and pyridin-4-ylamine for dimethylaminoacetic acid and Example 120, respectively, in Example 122. MS (ESI) m/e 524 (M+H)$^+$; $^1$H NMR (300 MHz, DMSO-d$_6$) δ 10.24 (s, 1H), 9.88 (s, 1H), 8.64 (d, J=7.1 Hz, 2H), 8.11 (d, J=7.1 Hz, 2H), 8.08 (s, 1H), 8.01 (d, J=8.5 Hz, 1H), 7.79 (d, J=8.1 Hz, 1H), 7.51 (d, J=1.7 Hz, 1H), 7.28-7.35 (m, 3H), 7.02 (d, J=8.1 Hz, 1H), 7.00 (d, J=2.0 Hz, 1H), 6.93 (dd, J=8.1, 2.0 Hz, 1H), 4.03 (s, 3H), 1.53 (s, 6H).

EXAMPLE 272

2-[3-(3-methoxy-4-nitrophenyl)-11-oxo-10,11-dihydro-5H-dibenzo[b,e][1,4]diazepin-8-yl]-2-methylN(pyridin-3-ylmethyl)propanamide The title compound was prepared by substituting Example 266I and 3-(aminomethyl)pyridine for dimethylaminoacetic acid and Example 120, respectively, in Example 122. MS (ESI) m/e 538 (M+H)$^+$; $^1$H NMR (300 MHz, DMSO-d$_6$) δ 9.84 (s, 1H), 8.57 (dd, J=5.8, 1.4 Hz, 1H), 8.52 (d, J=1.4 Hz, 1H), 8.02 (s, 1H), 8.01 (d, J=8.5 Hz, 1H), 7.92 (m, 1H), 7.87 (m, 1H), 7.82 (d, J=8.1 Hz, 1H), 7.58 (dd, 7.8, 5.1 Hz, 1H), 7.52 (d, J=1.7 Hz, 1H), 7.29-7.35 (m, 3H), 7.00 (d, J=2.0 Hz, 1H), 6.96 (d, J=8.3 Hz, 1H), 6.89 (dd, J=8.3, 2.0 Hz, 1H), 4.29 (d, J=5.8 Hz, 2H), 4.03 (s, 3H), 1.42 (s, 6H).

EXAMPLE 273

2-[3-(3-methoxy-4-nitrophenyl)-11-oxo-10,11-dihydro-5H-dibenzo[b,e][1,4]diazepin-8-yl]-2-methylN(pyridin-3-ylmethyl)propanamide The title compound was prepared by substituting Example 266I and 4-(aminomethyl)pyridine for dimethylaminoacetic acid and Example 120, respectively, in Example 122. MS (ESI) m/e 538 (M+H)$^+$; $^1$H NMR (300 MHz, DMSO-d$_6$) δ 9.87 (s, 1H), 8.63 (dd, J=6.1 Hz, 2H), 8.03 (s, 1H), 8.01 (d, J=8.5 Hz, 1H), 7.98 (d, J=5.8 Hz, 1H), 7.82 (d, J=8.1 Hz, 1H), 7.51 (m, 3H), 7.29-7.36 (m, 3H), 7.02 (d, J=1.7 Hz, 1H), 7.00 (d, J=8.3 Hz, 1H), 6.93 (dd, J=8.3, 1.7 Hz, 1H), 4.30 (d, J=5.8 Hz, 2H), 4.03 (s, 3H), 1.46 (s, 6H).

EXAMPLE 274

2-[3-(3-methoxy-4-nitrophenyl)-11-oxo-10,11-dihydro-5H-dibenzo[b,e][1,4]diazepin-8-yl]-2-methylN(tetrahydrofuran-3-ylmethyl)propanamide The title compound was prepared by substituting Example 266I and (±)-3-aminomethyltetrahydrofuran for dimethylaminoacetic acid and Example 120, respectively, in Example 122. MS (DCI) m/e 531 (M+H)$^+$; $^1$H NMR (500 MHz, DMSO-d$_6$) δ 9.83 (s, 1H), 8.01 (d, J=8.4 Hz, 1H), 7.97 (s, 1H), 7.80 (d, J=8.1 Hz, 1H), 7.52 (d, J=1.6 Hz, 1H), 7.30-7.35 (m, 4H), 6.98 (d, J=2.0 Hz, 1H), 6.96 (d, J=8.3 Hz, 1H), 6.86 (dd, J=8.3, 2.0 Hz, 1H), 4.03 (s, 3H), 3.63 (m, 1H), 3.54 (m, 2H), 3.29 (m, 1H), 2.99 (m, 2H), 2.34 (m, 1H), 1.79 (m, 1H), 1.44 (m, 1H), 1.38 (s, 6H).

EXAMPLE 275

2-[3-(3-methoxy-4-nitrophenyl)-11-oxo-10,11-dihydro-5H-dibenzo[b,e][1,4]diazepin-8-yl]-2-methylN1,3-thiazol-2-ylpropanamide The title compound was prepared by substituting Example 266I and 2-aminothiazole for dimethylaminoacetic acid and Example 120, respectively, in Example 122. MS (ESI) m/e 530 (M+H)$^+$; $^1$H NMR (300 MHz, DMSO-d$_6$) δ 11.54 (s, 1H), 9.87 (s, 1H), 8.02 (s, 1H), 8.01 (d, J=8.5 Hz, 1H), 7.79 (d, J=8.1 Hz, 1H), 7.52 (d, J=1.7 Hz, 1H), 7.42 (d, J=3.7 Hz, 1H), 7.28-7.35 (m, 3H), 7.19 (d, J=3.7 Hz, 1H), 6.99 (m, 2H), 6.90 (dd, J=8.1, 2.0 Hz, 1H), 4.02 (s, 3H), 1.54 (s, 6H).

EXAMPLE 276

2-[3-(3-methoxy-4-nitrophenyl)-11-oxo-10,11-dihydro-5H-dibenzo[b,e][1,4]diazepin-8-yl]-2-methylN{[6-(trifluoromethyl)pyridin-3-yl]methyl}propanamide The title compound was prepared by substituting Example 266I and 5-(aminomethyl)-2-(trifluoromethyl)-pyridine for dimethylaminoacetic acid and Example 120, respectively, in Example 122. MS (ESI) m/e 606 (M+H)$^+$; $^1$H NMR (300 MHz, DMSO-d$_6$) δ 9.87 (s, 1H), 8.55 (s, 1H), 8.02 (d, J=8.5 Hz, 1H), 8.01 (s, 1H), 7.93 (t, J=5.9 Hz, 1H), 7.81 (d, J=8.1 Hz, 1H), 7.76 (d, J=1.4 Hz, 2H), 7.52 (d, J=1.4 Hz, 1H), 7.29-7.35 (m, 3H), 7.01 (d, J=2.0 Hz, 1H), 6.97 (d, J=8.1 Hz, 1H), 6.87 (dd, J=8.1, 2.0 Hz, 1H), 4.31 (d, J=5.9 Hz, 2H), 4.03 (s, 3H), 1.42 (s, 6H).

EXAMPLE 277

N-(4-fluorophenyl)-2-[3-(3-methoxy-4-nitrophenyl)-11-oxo-10,11-dihydro-5H-dibenzo[b,e][1,4]diazepin-8-yl]-2-methylpropanamide The title compound was prepared by substituting Example 266I and 4-fluoroaniline for dimethylaminoacetic acid and Example 120, respectively, in Example 122. MS (ESI) m/e 539 (M−H)$^−$; $^1$H NMR (300 MHz, DMSO-d$_6$) δ 9.89 (s, 1H), 9.06 (s, 1H), 8.01 (s, 1H), 8.01 (d, J=8.5 Hz, 1H), 7.79 (d, J=8.1 Hz, 1H), 7.57 (m, 2), 7.51 (d, J=1.4 Hz, 1H), 7.30-7.35 (m, 3H), 7.10 (m, 2H), 7.04 (d, J=2.0 Hz, 1H), 7.00 (d, J=8.1 Hz, 1H), 6.97 (dd, J=8.1, 2.0 Hz, 1H), 4.03 (s, 3H), 1.49 (s, 6H).

EXAMPLE 278

N-(2,5-difluorobenzyl)-2-[3-(3-methoxy-4-nitrophenyl)-11-oxo-10,11-dihydro-5H-dibenzo[b,e][1,4]diazepin-8-yl]-2-methylpropanamide The title compound was prepared by substituting Example 266I and 2,5-difluoro-benzylamine for dimethylaminoacetic acid and Example 120, respectively, in Example 122. MS (ESI) m/e 571 (M−H)$^−$; $^1$H NMR (300 MHz, DMSO-d$_6$) δ 9.84 (s, 1H), 8.01 (d, J=8.5 Hz, 1H), 8.01 (s, 1H), 7.83 (t, J=5.8 Hz, 1H), 7.81 (d, J=8.1 Hz, 1H), 7.52 (d, J=1.4 Hz, 1H), 7.35, 7.32, 7.28 (all m, total 3H), 7.17 (m, 1H), 7.07 (m, 1H), 7.02 (d, J=2.0 Hz, 1H), 6.99 (d, J=8.3 Hz, 1H), 6.90 (dd, J=8.3, 2.0 Hz, 1H), 6.77 (m, 1H), 4.22 (d, J=5.8 Hz, 2H), 4.03 (s, 3H), 1.43 (s, 6H).

EXAMPLE 279

2-methyl-2-[11-oxo-3-(pyrimidin-4-ylamino)-10,11-dihydro-5H-dibenzo[b,e][1,4]diazepin-8-yl]N[3-(trifluoromethyl)benzyl]propanamide

EXAMPLE 279A methyl 2-methyl-2-[11-oxo-3-(pyrimidin-4-ylamino)-10,11-dihydro-5H-dibenzo[b,e][1,4]diazepin-8-yl]propanoate Example 266F (1.60 g, 4.64 mmol), 4-aminopyrimidine (0.76 g, 8.00 mmol), CyMAP ligand (0.34 g, 0.87 mmol), $Pd_2(dba)_3$ (0.28 g, 0.31 mmol), and $CsCO_3$ (2.60 g, 7.97 mmol) in dioxane (25 mL) were heated at 85° C. overnight. The reaction was then cooled, filtered through Celite®, and concentrated. The crude solids were slurried in $Et_2O$ (25 mL) overnight. After filtration and drying, had 1.98 g solids that were slurried in $Et_2O$ (20 mL) for 3 hours, then the solids were filtered off. Recovered the product (1.66 g, 89%) as pale green solids. MS (DCI) m/e 404 $(M+H)^+$; $^1H$ NMR (300 MHz, DMSO-$d_6$) δ 9.77 (s, 1H), 9.57 (s, 1H), 8.70 (s, 1H), 8.54 (d, 5.8, J=5.8 Hz, 1H), 7.95 (s, 1H), 7.64 (d, J=8.5 Hz, 1H), 7.51 (d, J=2.0 Hz, 1H), 7.07 (dd, J=8.5, 2.0 Hz, 1H), 6.97 (d, J=8.1 Hz, 1H), 6.91 (m, 2H), 6.88 (d, J=5.8 Hz, 1H), 3.57 (s, 3H), 1.43 (s, 6H).

EXAMPLE 279B 2-methyl-2-[11-oxo-3-(pyrimidin-4-ylamino)-10,11-dihydro-5H-dibenzo[b,e][1,4]diazepin-8-yl]N[3-(trifluoromethyl)benzyl]propanamide The title compound was prepared by substituting the acid, from hydrolysis of Example 279A, and 3-(trifluoromethyl)benzylamine for dimethylaminoacetic acid and Example 120, respectively, in Example 122. MS (DCI) m/e 547 $(M+H)^+$; $^1H$ NMR (300 MHz, DMSO-$d_6$) δ 10.50 (s, 1H), 9.66 (s, 1H), 8.85 (s, 1H), 8.39 (d, J=6.4 Hz, 1H), 7.99 (s, 1H), 7.89 (t, J=6.4 Hz, 1H), 7.69 (d, J=8.5 Hz, 1H), 7.55, 7.42, 7.30 (all m, total 5H), 7.14 (dd, J=8.5, 1.9 Hz, 1H), 6.93-7.00 (m, 3H), 6.86 (dd, J=8.1, 2.0 Hz, 1H), 4.28 (d, J=6.4 Hz, 2H), 1.42 (s, 6H).

EXAMPLE 280

2-methyl-2-[11-oxo-3-(pyrimidin-4-ylamino)-10,11-dihydro-5H-dibenzo[b,e][1,4]diazepin-8-yl]N[3-(trifluoromethoxy)benzyl]propanamide The title compound was prepared by substituting the acid, from hydrolysis of Example 279A, and 3-(trifluoromethoxy)benzylamine for dimethylaminoacetic acid and Example 120, respectively, in Example 122. MS (DCI) m/e 563 $(M+H)^+$; $^1H$ NMR (300 MHz, DMSO-$d_6$) δ 10.46 (s, 1H), 9.65 (s, 1H), 8.85 (s, 1H), 8.39 (d, J=6.1 Hz, 1H), 7.98 (s, 1H), 7.86 (t, J=6.4 Hz, 1H), 7.69 (d, J=8.8 Hz, 1H), 7.39 (d, J=2.0 Hz, 1H), 7.34 (d, J=8.1 Hz, 1H), 7.15 (m, 3H), 7.07 (br s, 1H), 6.93-7.00 (m, 3H), 6.86 (dd, J=8.3, 2.2 Hz, 1H), 4.25 (d, J=6.1 Hz, 2H), 1.42 (s, 6H).

EXAMPLE 281

1-[3-(3-methoxy-4-nitrophenyl)-11-oxo-10,11-dihydro-5H-dibenzo[b,e][1,4]diazepin-8-yl]N(4-morpholin-4-ylphenyl)cyclopropanecarboxamide

EXAMPLE 281A methyl 1-(4-nitrophenyl)cyclopropanecarboxylate

The title compound was prepared by substituting 1,2-dibromoethane for MeI in Example 266A. MS (DCI) m/e 239 $(M+NH_4)^+$; $^1H$ NMR (300 MHz, CDCl$_3$) δ 8.17 (m, 2H), 7.51 (m, 2H), 3.65 (s, 3H), 1.71 (m, 2H), 1.23 (m, 2H).

EXAMPLE 281B methyl 1-[4-(acetylamino)phenyl]cyclopropanecarboxylate

Example 281A (11.1 g, 50.2 mmol) and iron powder (325 mesh, 24.4 g, 437 mmol) in $CH_3CO_2H$ (500 mL) were heated under reflux with mechanical stirring overnight. The reaction was cooled and partitioned between water and EtOAc. The organic layer was washed with brine and dried over $Na_2SO_4$. After filtration and concentration toluene was used to azeotrope off the remaining acetic acid, giving the product (11.8 g, 100%) as off-white solids. MS (DCI) m/e 234 $(M+H)^+$, 251 $(M+NH_4)^+$; $^1H$ NMR (300 MHz, CDCl$_3$) δ 7.43 (br d, J=8.5 Hz, 2H), 7.29 (br d, J=8.5 Hz, 2H), 7.13 (br s, 1H), 3.62 (s, 3H), 1.59 (m, 2H), 1.16 (m, 2H).

EXAMPLE 281C methyl 1-(4-amino-3-nitrophenyl)cyclopropanecarboxylate

Example 281B was nitrated by the method described in the first paragraph of Example 6A, then the acetamide was hydrolyzed by the following method.

That nitro-acetamide (13.2 g, 47.5 mmol) was dissolved in MeOH (650 mL) and conc. $H_2SO_4$ (65 mL) and heated under reflux for 2 hours. The reaction was cooled, most of the MeOH stripped off, then slowly added to 0.5M $Na_2CO_3$ (1.2 L). That aqueous layer was extracted with EtOAc (1 L), then the organic layer was washed with brine and dried over $Na_2SO_4$. After filtration and concentration the product (11.2 g, 100%) was obtained as a dark syrup that slowly crystallized upon standing. MS (DCI) m/e 254 $(M+NH_4)^+$; $^1H$ NMR (300 MHz, DMSO-$d_6$) δ 7.84 (d, J=2.0 Hz, 1H), 7.43 (br s, 2H), 7.39 (dd, J=8.6, 2.0 Hz, 1H), 6.96 (d, J=8.6 Hz, 1H), 3.55 (s, 3H), 1.45 (m, 2H), 1.17 (m, 2H).

EXAMPLE 281D

1-[3-(3-methoxy-4-nitrophenyl)-11-oxo-10,11-dihydro-5H-dibenzo[b,e][1,4]diazepin-8-yl]cyclopropanecarboxylic acid The title compound was prepared from the compound described in Example 281C by the methods of Examples 1A, 281B, the second paragraph of 281C, 5C, 266H, and 13. MS (DCI) m/e 446 $(M+H)^+$, 463 $(M+NH_4)^+$; $^1H$ NMR (300 MHz, DMSO-$d_6$) δ 12.26 (v br s, 1H), 9.84 (s, 1H), 8.02 (d, J=8.5 Hz, 1H), 8.01 (s, 1H), 7.80 (d, J=8.1 Hz, 1H), 7.52 (d, J=1.7 Hz, 1H), 7.30-7.35 (m, 3H), 6.93 (m, 3H), 4.03 (s, 3H), 1.40 (m, 2H), 1.05 (m, 2H).

EXAMPLE 281E

1-[3-(3-methoxy-4-nitrophenyl)-11-oxo-10,11-dihydro-5H-dibenzo[b,e][1,4]diazepin-8-yl]N(4-morpholin-4-ylphenyl)cyclopropanecarboxamide The title compound was prepared by substituting Example 281I and 4-morpholin-4-yl-phenylamine for dimethylaminoacetic acid and Example 120, respectively, in Example 122. MS (ESI) m/e 606 (M+H)$^+$; $^1$H NMR (300 MHz, DMSO-d$_6$) δ 9.86 (s, 1H), 8.55 (s, 1H), 8.06 (s, 1H), 8.01 (d, J=8.1 Hz, 1H), 7.80 (d, J=8.1 Hz, 1H), 7.52 (d, J=1.7 Hz, 1H), 7.29-7.32 (m, 5H), 7.03 (s, 1H), 7.00 (s, 2H), 6.82 (m, 2H), 4.03 (s, 3H), 3.70 (m, 4H), 3.01 (m, 4H), 1.38 (m, 2H), 0.98 (m, 2H).

EXAMPLE 282

2-[3-(3-methoxy-4-nitrophenyl)-11-oxo-10,11-dihydro-5H-dibenzo[b,e][1,4]diazepin-7-yl]-2-methylN(4-morpholin-4-ylphenyl)propanamide

EXAMPLE 282A methyl 2-(3-fluoro-4-nitrophenyl)-2-methylpropanoate 2-(3-Fluoro-4-nitro-phenyl)-propionic acid methyl ester was prepared from 2-fluoronitrobenzene by the procedure of T. Lemek, et. al. Tetrahedron, 57, 4753 (2001) and then converted to the title compound using the method of Example 266A. MS (DCI) m/e 259 (M+NH$_4$)$^+$; $^1$H NMR (300 MHz, CDCl$_3$) δ 8.03 (m, 1H), 7.26 (m, 2H), 3.69 (s, 3H), 1.61 (s, 6H).

EXAMPLE 282B methyl 2-(3-amino-4-nitrophenyl)-2-methylpropanoate

Example 282A (14.5 g, 60.2 mmol) in 7.0N NH$_3$ in MeOH (150 mL) was heated at 70° C. in a sealed tube overnight. The reaction was cooled, concentrated, and purified by column chromatography using 85/15 hexane/EtOAc. Recovered the product (8.3 g, 58%) as bright yellow solids. MS (DCI) m/e 239 (M+H)$^+$, 256 (M+NH$_4$)$^+$; $^1$H NMR (300 MHz, DMSO-d$_6$) δ 7.79 (d, J=8.8 Hz, 1H), 7.41 (br s, 2H), 6.78 (d, J=2.0 Hz, 1H), 6.97 (dd, J=8.8, 2.0 Hz, 1H), 3.61 (s, 3H), 1.46 (s, 6H).

EXAMPLE 282C methyl 2-(3-chloro-11-oxo-10,11-dihydro-5H-dibenzo[b,e][1,4]diazepin-7-yl)-2-methylpropanoate Example 282B was converted to the title compound by the methods of Examples 1A, 266B, and 5C. MS (DCI) m/e 345 and 347 (M+H)$^+$; $^1$H NMR (300 MHz, DMSO-d$_6$) δ 9.90 (s, 1H), 8.07 (s, 1H), 7.68 (d, J=8.5 Hz, 1H), 7.06 (d, J=2.0 Hz, 1H), 6.95, 6.91 (both m, total 4H), 3.58 (s, 3H), 1.46 (s, 6H).

EXAMPLE 282D

2-[3-(3-methoxy-4-nitrophenyl)-11-oxo-10,11-dihydro-5H-dibenzo[b,e][1,4]diazepin-7-yl]-2-methylpropanoic acid The compound described in Example 282C was converted to the title compound by the methods of Examples 266H and 13. MS (DCI) m/e 448 (M+H)$^+$, 465 (M+NH$_4$)$^+$; $^1$H NMR (300 MHz, DMSO-d$_6$) δ 12.25 (v br s, 1H), 9.89 (s, 1H), 8.06 (s, 1H), 8.01 (d, J=8.5 Hz, 1H), 7.80 (d, J=8.1 Hz, 1H), 7.53 (d, J=1.7 Hz, 1H), 7.29-7.38 m, 3H), 7.06, 6.92 (both m, total 3H), 4.04 (s, 3H), 1.43 (s, 6H).

EXAMPLE 282E

2-[3-(3-methoxy-4-nitrophenyl)-11-oxo-10,11-dihydro-5H-dibenzo[b,e][1,4]diazepin-7-yl]-2-methylN(4-morpholin-4-ylphenyl)propanamide The title compound was prepared by substituting Example 282D and 4-morpholin-4-yl-phenylamine for dimethylaminoacetic acid and Example 120, respectively, in Example 122. MS (ESI) m/e 608 (M+H)$^+$; $^1$H NMR (300 MHz, DMSO-d$_6$) δ 9.89 (s, 1H), 8.85 (s, 1H), 8.06 (s, 1H), 8.01 (d, J=8.5 Hz, 1H), 7.79 (d, J=8.1 Hz, 1H), 7.52 (d, J=1.7 Hz, 1H), 7.42 (d, J=9.2 Hz, 2H), 7.29-7.38 (m, 3H), 7.04 (d, J=1.7 Hz, 1H), 6.91 (m, 2H), 6.83 (d, J=9.2 Hz, 2H), 4.03 (s, 3H), 3.71 (m, 4H), 3.00 (m, 4H), 1.49 (s, 6H).

EXAMPLE 283

2-[3-(3-methoxy-4-nitrophenyl)-11-oxo-10,11-dihydro-5H-dibenzo[b,e][1,4]diazepin-7-yl]-2-methylN(pyridin-2-ylmethyl)propanamide The title compound was prepared by substituting Example 282D and 2-(aminomethyl)pyridine for dimethylaminoacetic acid and Example 120, respectively, in Example 122. MS (ESI) m/e 538 (M+H)$^+$; $^1$H NMR (300 MHz, DMSO-d$_6$) δ 9.91 (s, 1H), 8.52 (m, 1H), 8.05 (s, 1H), 8.03 (d, J=8.5 Hz, 1H), 7.95 (t, J=5.8 Hz, 1H), 7.81 (d, J=8.1 Hz, 1H), 7.78 (m, 1H), 7.52 (d, J=1.7 Hz, 1H), 7.39 (d, J=1.7 Hz, 1H), 7.37-7.30 (m, 3H), 7.16 (br d, J=7.8 Hz, 1H), 7.06 (d, J=2.0 Hz, 1H), 6.95 (d, J=8.1 Hz, 1H), 6.90 (dd, J=8.1, 2.0 Hz, 1H), 4.35 (d, J=5.8 Hz, 1H), 4.04 (s, 3H), 1.46 (s, 6H).

EXAMPLE 284

2-[3-(3-methoxy-4-nitrophenyl)-11-oxo-10,11-dihydro-5H-dibenzo[b,e][1,4]diazepin-7-yl]-2-methylN(thien-2-ylmethyl)propanamide The title compound was prepared by substituting Example 282D and 2-(aminomethyl)thiophene for dimethylaminoacetic acid and Example 120, respectively, in Example 122. MS (ESI) m/e 543 (M+H)$^+$; $^1$H NMR (300 MHz, DMSO-d$_6$) δ 9.88 (s, 1H), 8.03 (s, 1H), 8.02 (d, J=8.5 Hz, 1H), 7.79 (d, J=8.1 Hz, 1H), 7.75 (t, J=5.8 Hz, 1H), 7.52 (d, J=1.7 Hz, 1H), 7.39 (d, J=1.7 Hz, 1H), 7.30-7.37 (m, 3H), 7.04 (m, 2H), 6.88-6.90 (m, 3H), 4.20 (d, J=5.8 Hz, 1H), 4.03 (s, 3H), 1.43 (s, 6H).

EXAMPLE 285

N-(cyclopropylmethyl)-2-[3-(3-methoxy-4-nitrophenyl)-11-oxo-10,11-dihydro-5H-dibenzo[b,e][1,4]diazepin-7-yl]-2-methylpropanamide The title compound was prepared by substituting Example 282D and (aminomethyl)cyclopropane for dimethylaminoacetic acid and Example 120, respectively, in Example 122. MS (ESI) m/e 501 (M+H)$^+$; $^1$H NMR (300 MHz, DMSO-d$_6$) δ 9.88 (s, 1H), 8.02 (s, 1H), 8.01 (d, J=8.5 Hz, 1H), 7.79 (d, J=8.1 Hz, 1H), 7.52 (d, J=1.7 Hz, 1H), 7.38 (d, J=1.7 Hz, 1H), 7.36, 7.32, 7.28 (all m, 3H total), 7.00 (d, J=1.7

Hz, 1H), 6.91 (d, J=8.3 Hz, 1H), 6.85 (dd, J=8.3, 1.7 Hz, 1H), 4.03 (s, 3H), 2.91 (m, 2H), 1.39 (s, 6H), 0.87 (m, 1H), 0.29 (m, 2H), 0.08 (m, 2H).

EXAMPLE 286

7-(3-hydroxypropyl)-3-(3-methoxy-4-nitrophenyl)-5,10-dihydro-11H-dibenzo[b,e][1,4]diazepin-11-one

EXAMPLE 286A methyl 3-[3-(acetylamino)-4-nitrophenyl]propanoate

Methyl 3-(3'-aminophenyl)propionate was treated with acetic anhydride and nitrated using the method described in the first paragraph of Example 6A. MS (DCI) m/e 267 (M+H)$^+$, 284 (M+NH$_4$)$^+$; $^1$H NMR (300 MHz, DMSO-d$_6$) δ 10.22 (s, 1H), 7.86 (d, J=8.5 Hz, 1H), 7.49 (d, J=2.0 Hz, 1H), 7.21 (dd, J=8.5, 2.0 Hz, 1H), 3.59 (s, 3H), 2.92 (t, J=7.3 Hz, 2H), 2.68 (t, J=7.3 Hz, 2H), 2.06 (s, 3H).

EXAMPLE 286B methyl 3-(3-chloro-11-oxo-10,11-dihydro-5H-dibenzo[b,e][1,4]diazepin-7-yl)propanoate The title compound was prepared from the compound described in Example 286A by the methods described in the second paragraph of Example 281C, Example 1A, Example 6C, and Example 5C. MS (DCI) m/e 331 and 333 (M+H)$^+$; $^1$H NMR (300 MHz, DMSO-d$_6$) δ 9.85 (s, 1H), 8.00 (s, 1H), 7.67 (d, J=8.5 Hz, 1H), 7.07 (d, J=2.4 Hz, 1H), 6.92 (dd, J=8.5, 2.4 Hz, 1H), 6.88 (d, J=8.3 Hz, 1H), 6.77-6.80 (m, 2H), 3.58 (s, 3H), 2.73 (t, J=7.3 Hz, 2H), 2.50 (t, J=7.3 Hz, 2H).

EXAMPLE 286C 3-chloro-7-(3-hydroxypropyl)-5,10-dihydro-11H-dibenzo[b,e][1,4]diazepin-11-one The title compound was prepared by substituting Example 286B for Example 6D in Example 204A. MS (DCI) m/e 303 and 305 (M+H)$^+$; $^1$H NMR (300 MHz, DMSO-d$_6$) δ 9.84 (s, 1H), 7.97 (s, 1H), 7.67 (d, J=8.5 Hz, 1H), 7.06 (d, J=2.0 Hz, 1H), 6.92 (dd, J=8.5, 2.0 Hz, 1H), 6.87 (d, J=8.1 Hz, 1H), 6.80 (d, J=1.7 Hz, 1H), 6.78 (dd, J=8.1, 1.7 Hz, 1H), 4.44 (t, J=5.1 Hz, 1H), 3.38 (m, 2H), 2.50 (m, 2H), 1.66 (m, 2H).

EXAMPLE 286D 7-(3-hydroxypropyl)-3-(3-methoxy-4-nitrophenyl)-5,10-dihydro-11H-dibenzo[b,e][1,4]diazepin-11-one The title compound was prepared by substituting Example 286C and Example 266G for Example 59B and Example 56A, respectively, in Example 59C. MS (DCI) m/e 420 (M+H)$^+$; $^1$H NMR (300 MHz, DMSO-d$_6$) δ 9.83 (s, 1H), 8.01 (d, J=8.5 Hz, 1H), 7.94 (s, 1H), 7.79 (d, J=8.1 Hz, 1H), 7.52 (d, J=1.7 Hz, 1H), 7.29-7.36 (m, 3H), 6.87 (d, J=8.0 Hz, 1H), 6.85 (d, J=2.0 Hz, 1H), 6.75 (dd, J=8.0, 2.0 Hz, 1H), 4.44 (t, J=5.3 Hz, 1H), 4.03 (s, 3H), 3.39 (m, 2H), 3.30 (m, 2H), 1.66 (m, 2H).

EXAMPLE 287

7-(3-hydroxy-3-methylbutyl)-3-(3-methoxy-4-nitrophenyl)-5,10-dihydro-11H-dibenzo [b,e][1,4]diazepin-11-one

EXAMPLE 287A 3-chloro-7-(3-hydroxy-3-methylbutyl)-5,10-dihydro-11H-dibenzo[b,e][1,4]diazepin-11-one The title compound was prepared by substituting Example 286B for Example 1B in Example 189A. MS (DCI) m/e 331 and 333 (M+H)$^+$; $^1$H NMR (300 MHz, DMSO-d$_6$) δ 9.84 (s, 1H), 7.95 (s, 1H), 7.67 (d, J=8.5 Hz, 1H), 7.06 (d, J=2.0 Hz, 1H), 6.92 (dd, J=8.5, 2.0 Hz, 1H), 6.85 (d, J=8.1 Hz, 1H), 6.81 (d, J=2.0 Hz, 1H), 6.75 (dd, J=8.1, 2.0 Hz, 1H), 4.24 (br s, 1H), 2.50 (m, 2H), 1.57 (m, 2H), 1.12 (s, 6H).

EXAMPLE 287B 7-(3-hydroxy-3-methylbutyl)-3-(3-methoxy-4-nitrophenyl)-5,10-dihydro-11H-dibenzo[b,e][1,4]diazepin-11-one The title compound was prepared by substituting Example 287A and Example 266G for Example 59B and Example 56A, respectively, in Example 59C. MS (DCI) m/e 448 (M+H)$^+$; $^1$H NMR (300 MHz, DMSO-d$_6$) δ 9.84 (s, 1H), 8.01 (d, J=8.5 Hz, 1H), 7.92 (s, 1H), 7.79 (d, J=8.1 Hz, 1H), 7.52 (d, J=1.4 Hz, 1H), 7.29-7.36 (m, 3H), 6.87 (d, J=8.0 Hz, 1H), 6.85 (d, J=2.0 Hz, 1H), 6.75 (dd, J=8.0, 2.0 Hz, 1H), 4.24 (s, 1H), 4.04 (s, 3H), 2.50 (m, 2H), 1.57 (m, 2H), 1.12 (s, 6H).

EXAMPLE 288

8-(2-hydroxy-11-dimethylethyl)-3-(3-methoxy-4-nitrophenyl)-5,10-dihydro-11H-dibenzo[b,e][1,4]diazepin-11-one

EXAMPLE 288A 3-chloro-8-(2-hydroxy-11-dimethylethyl)-5,10-dihydro-11H-dibenzo[b,e][1,4]diazepin-11-one The title compound was prepared by substituting Example 266F for Example 6D in Example 204A. MS (DCI) m/e 317 and 319 (M+H)$^+$; $^1$H NMR (300 MHz, DMSO-d$_6$) δ 9.77 (s, 1H), 7.97 (s, 1H), 7.67 (d, J=8.5 Hz, 1H), 7.05 (d, J=2.0 Hz, 1H), 6.88-6.99 (m, 4H), 4.61 (t, J=5.1 Hz, 1H), 3.32 (m, 2H), 1.15 (s, 6H).

EXAMPLE 288B 8-(2-hydroxy-11-dimethylethyl)-3-(3-methoxy-4-nitrophenyl)-5,10-dihydro-11H-dibenzo[b,e][1,4]diazepin-11-one The title compound was prepared by substituting Example 288A and Example 266G for Example 59B and Example 56A, respectively, in Example 59C. MS (ESI) m/e 434 (M+H)$^+$; $^1$H NMR (300 MHz, DMSO-d$_6$) δ 9.78 (s, 1H), 8.01 (d, J=8.5 Hz, 1H), 7.93 (s, 1H), 7.79 (d, J=8.1 Hz, 1H), 7.52 (d, J=1.7 Hz, 1H), 7.28-7.35 (m, 3H), 7.01 (m, 1H), 6.94 (m, 2H), 4.61 (t, J=5.1 Hz, 1H), 4.03 (s, 3H), 3.33 (m, 2H), 1.16 (s, 6H).

EXAMPLE 289

8-(2-hydroxy-1,1,2-trimethylpropyl)-3-(3-methoxy-4-nitrophenyl)-5,10-dihydro-11H-dibenzo[b,e][1,4]diazepin-11-one

EXAMPLE 289A 3-chloro-8-(2-hydroxy-1,1,2-trimethylpropyl)-5,10-dihydro-11H-dibenzo[b,e][1,4]diazepin-11-one The title compound was prepared by substituting Example 266F for Example 1B in Example 189A. MS (DCI) m/e 345 and 347 (M+H)$^+$; $^1$H NMR (300 MHz, DMSO-d$_6$) δ 9.75 (s, 1H), 7.95 (s, 1H), 7.67 (d, J=8.5 Hz, 1H), 7.07 (d, J=2.0 Hz, 1H), 7.05 (d, J=2.0 Hz, 1H), 7.01 (dd, J=8.5, 2.0 Hz, 1H), 6.89 (dd, J=8.5, 2.0 Hz, 1H), 6.83 (d, J=8.5 Hz, 1H), 4.03 (s, 1H), 1.24 (s, 6H), 0.96 (s, 6H).

EXAMPLE 289

8-(2-hydroxy-1,1,2-trimethylpropyl)-3-(3-methoxy-4-nitrophenyl)-5,10-dihydro-11H-dibenzo[b,e][1,4]diazepin-11-one The title compound was prepared by substituting Example 289A and Example 266G for Example 59B and Example 56A, respectively, in Example 59C. MS (ESI) m/e 462 (M+H)$^+$; $^1$H NMR (400 MHz, DMSO-d$_6$) δ 9.73 (s, 1H), 8.00 (d, J=8.6 Hz, 1H), 7.89 (s, 1H), 7.79 (d, J=8.3 Hz, 1H), 7.51 (d, J=1.5 Hz, 1H), 7.27-7.34 (m, 3H), 7.08 (d, J=1.8 Hz, 1H), 7.00 (dd, J=8.3, 1.8 Hz, 1H), 6.87 (d, J=8.3 Hz, 1H), 4.03, (s, 3H), 4.00 (s, 1H), 1.24 (s, 6H), 0.96 (s, 6H).

EXAMPLE 290

8-(1,1-dimethyl-2-oxopropyl)-3-(3-methoxy-4-nitrophenyl)-5,10-dihydro-11H-dibenzo[b,e][1,4]diazepin-11-one

EXAMPLE 290A 3-chloro-8-(1,1-dimethyl-2-oxopropyl)-5,10-dihydro-11H-dibenzo[b,e][1,4]diazepin-11-one The title compound was isolated as a by-product in Example 289A. MS (ESI) m/e 329 and 331 (M+H)$^+$.

EXAMPLE 290B 8-(1,1-dimethyl-2-oxopropyl)-3-(3-methoxy-4-nitrophenyl)-5,10-dihydro-11H-dibenzo[b,e][1,4]diazepin-11-one The title compound was prepared by substituting Example 290A and Example 266G for Example 59B and Example 56A, respectively, in Example 59C. MS (ESI) m/e 446 (M+H)$^+$; $^1$H NMR (500 MHz, DMSO-d$_6$) δ 9.82 (s, 1H), 8.04 (s, 1H), 8.01 (d, J=8.4 Hz, 1H), 7.80 (d, J=8.1 Hz, 1H), 7.52 (d, J=1.5 Hz, 1H), 7.30-7.35 (m, 3H), 7.01 (d, J=8.4 Hz, 1H), 6.93 (d, J=1.9 Hz, 1H), 6.88 (dd, J=8.4, 1.9 Hz, 1H), 4.03, (s, 3H), 1.89 (s, 3H), 1.35 (s, 6H).

EXAMPLE 291

7-(2-hydroxy-1,1-dimethylethyl)-3-(3-methoxy-4-nitrophenyl)-5,10-dihydro-11H-dibenzo[b,e][1,4]diazepin-11-one Example 282D (0.18 g, 0.40 mmol) in THF (2 mL) was cooled to 0° C., then 1.0M BH$_3$ in THF (8 mL) was added dropwise. The reaction was stirred at 0° C. for 1 hour, then at room temperature for 1 hour. 1.0M H$_3$PO$_4$ was carefully added, then the mixture was extracted with EtOAc. The organic layer was washed with brine and dried over Na$_2$SO$_4$. After filtration and concentration the crude material was purified by preoperative HPLC to give the product (34 mg, 19%). MS (DCI) m/e 434 (M+H)$^+$; $^1$H NMR (300 MHz, DMSO-d$_6$) δ 9.83 (s, 1H), 8.01 (d, J=8.5 Hz, 1H), 7.95 (s, 1H), 7.79 (d, J=8.1 Hz, 1H), 7.53 (d, J=1.4 Hz, 1H), 7.29-7.37 (m, 3H), 7.04 (d, J=1.7 Hz, 1H), 6.90 (m, 2H), 4.64 (t, J=5.4 Hz, 1H), 4.04 (s, 3H), 3.35 (d, J=5.4 Hz, 2H), 1.17 (s, 6H).

EXAMPLE 292

8-[1-(hydroxymethyl)cyclopropyl]-3-(3-methoxy-4-nitrophenyl)-5,10-dihydro-11H-dibenzo[b,e][1,4]diazepin-11-one The title compound was prepared by substituting Example 281D for Example 282D in Example 291. MS (DCI) m/e 432 (M+H)$^+$; $^1$H NMR (300 MHz, DMSO-d$_6$) δ 9.79 (s, 1H), 8.02 (d, J=8.5 Hz, 1H), 7.93 (s, 1H), 7.79 (d, J=8.1 Hz, 1H), 7.52 (d, J=1.7 Hz, 1H), 7.28-7.34 (m, 3H), 6.92 (m, 3H), 4.60 (t, J=5.8 Hz, 1H), 4.03 (s, 3H), 3.46 (d, J=5.8 Hz, 2H), 0.77 (m, 2H), 0.61 (m, 2H).

EXAMPLE 293

3-[(2-chloropyridin-4-yl)amino]-8-(2-hydroxy-11-dimethylethyl)-5,10-dihydro-11H-dibenzo[b,e][1,4]diazepin-11-one The title compound was prepared by substituting Example 288A and 4-amino-2-chloro-pyridine for Example 189A and 4-aminopyridine in Example 191. MS (ESI) m/e 407 (M−H)$^−$; $^1$H NMR (300 MHz, DMSO-d$_6$) δ 9.52 (s, 1H), 9.31 (s, 1H), 8.08 (m, 1H), 7.86 (s, 1H), 7.67 (d, J=8.8 Hz, 1H), 6.99 (m, 3H), 6.93 (m, 1H), 6.86 (m, 2H), 6.64 (dd, J=8.5, 2.0, 1H), 3.32 (s, 2H), 1.15 (s, 6H).

EXAMPLE 294

3-[(2,6-difluoropyridin-4-yl)amino]-8-(2-hydroxy-11-dimethylethyl)-5,10-dihydro-11H-dibenzo [b,e][1,4]diazepin-11-one The title compound was prepared by substituting Example 288A and Example 203A for Example 189A and 4-aminopyridine in Example 191. MS (DCI) m/e 411 (M+H)$^+$; $^1$H NMR (300 MHz, DMSO-d$_6$) δ 9.67 (s, 1H), 9.56 (s, 1H), 7.86 (s, 1H), 7.68 (d, J=8.5 Hz, 1H), 6.98 (d, J=1.7 Hz, 1H), 6.94 (m, 1H), 6.89 (m, 2H), 6.67 (dd, J=8.8, 2.0, 1H), 6.56 (s, 2H), 3.37 (s, 1H), 3.32 (s, 2H), 1.15 (s, 6H).

EXAMPLE 295

3-[(2,6-difluoropyridin-4-yl)amino]-8-(2-hydroxy-1,1,2-trimethylpropyl)-5,10-dihydro-11H-dibenzo[b,e][1,4]diazepin-11-one The title compound was prepared by substituting Example 289A and Example 203A for Example 189A and 4-aminopyridine in Example 191. MS (DCI) m/e 439 (M+H)$^+$; $^1$H NMR (300 MHz, DMSO-d$_6$) δ 9.67 (s, 1H), 9.54 (s, 1H), 7.85 (s, 1H), 7.68 (d, J=8.8 Hz, 1H), 7.06 (d, J=2.0 Hz, 1H), 6.99 (dd, J=8.8, 2.0 Hz, 1H), 6.89 (d, J=2.0 Hz, 1H), 6.83 (d, J=8.5 Hz, 1H), 6.66 (dd, J=8.8, 2.0, 1H), 6.57 (s, 2H), 4.01 (s, 1H), 1.24 (s, 6H), 0.97 (s, 6H).

EXAMPLE 296

3-(4-chloro-3-methoxyphenyl)-8-(2-hydroxy-11-dimethylethyl)-5,10-dihydro-11H-dibenzo[b,e][1,4]diazepin-11-one The title compound was prepared by substituting Example 288A and Example 268A for Example 59B and Example 56A, respectively, in Example 59C. MS (ESI) m/e 423 and 425 (M+H)$^+$; $^1$H NMR (300 MHz, DMSO-d$_6$) δ 9.71 (s, 1H), 7.87 (s, 1H), 7.75 (d, J=8.5 Hz, 1H), 7.53 (d, J=8.1 Hz, 1H), 7.33 (d, J=1.7 Hz, 1H), 7.29 (d, J=1.7 Hz, 1H), 7.20 (m, 2H), 7.00 (d, J=1.4 Hz, 1H), 6.94 (m, 2H), 3.96 (s, 3H), 3.32 (m, 2H), 1.15 (s, 6H).

EXAMPLE 297

3-(3-methoxy-4-nitrophenyl)-8-[2-(4-morpholin-4-ylphenoxy)ethyl]-5,10-dihydro-11H-dibenzo[b,e][1,4]diazepin-11-one

EXAMPLE 297A 3-chloro-8-[2-(4-morpholin-4-ylphenoxy)ethyl]-5,10-dihydro-11H-dibenzo[b,e][1,4]diazepin-11-one Example 204A (0.57 g, 2.0 mmol) and 4-morpholinophenol (0.45 g, 2.5 mmol; M. C. Harris, et. al., Org. Lett., 4, 2885 (2002)) were dissolved in THF (15 mL), then polymer-supported PPh$_3$ (2.0 g, 6.0 mmol PPh$_3$; Aldrich, product # 36,645-5) was added, followed by di-tert-butylazodicarboxylate (0.52 g, 2.3 mmol), then the reaction was stirred at room temperature overnight. The reaction was then filtered and concentrated to give 1.6 g crude material that was then slurried in Et$_2$O (20 mL) overnight. Filtration gave the product (0.74 g, 81%) as off-white solids. MS (DCI) m/e 450 and 452 (M+H)$^+$; $^1$H NMR (300 MHz, DMSO-d$_6$) δ 9.87 (s, 1H), 8.00 (s, 1H), 7.67 (d, J=8.5 Hz, 1H), 7.06 (d, J=2.0 Hz, 1H), 6.84-6.91 (m, 8H), 4.03 (t, J=6.6 Hz, 2H), 3.71 (m, 4H), 2.96 (m, 4H), 2.86 (t, J=6.6 Hz, 2H).

EXAMPLE 297B 3-(3-methoxy-4-nitrophenyl)-8-[2-(4-morpholin-4-ylphenoxy)ethyl]-5,10-dihydro-11H-dibenzo[b,e][1,4]diazepin-11-one The title compound was prepared by substituting Example 297A and Example 266G for Example 59B and Example 56A, respectively, in Example 59C. MS (ESI) m/e 567 (M+H)$^+$; $^1$H NMR (300 MHz, DMSO-d$_6$) δ 9.87 (s, 1H), 8.01 (d, J=8.5 Hz, 1H), 7.96 (s, 1H), 7.79 (d, J=8.1 Hz, 1H), 7.52 (d, J=1.7 Hz, 1H), 7.33-7.35 (m, 2H), 7.28 (dd, J=8.1, 1.7 Hz, 1H), 6.84-6.92, (m, 7H), 4.03 (m, 5H), 3.71 (m, 4H), 2.96 (m, 4H), 2.87 (t, J=6.6 Hz, 2H).

EXAMPLE 298

3-(4-chloro-3-methoxyphenyl)-8-[2-(4-morpholin-4-ylphenoxy)ethyl]-5,10-dihydro-11H-dibenzo[b,e][1,4]diazepin-11-one The title compound was prepared by substituting Example 297A and Example 268A for Example 59B and Example 56A, respectively, in Example 59C. MS (ESI) m/e 556 and 558 (M+H)$^+$; $^1$H NMR (300 MHz, DMSO-d$_6$) δ 9.81 (s, 1H), 7.96 (s, 1H), 7.75 (d, J=8.1 Hz, 1H), 7.53 (d, J=8.1 Hz, 1H), 7.33 (d, J=2.0 Hz, 1H), 7.29 (d, J=1.7 Hz, 1H), 7.23 (dd, J=8.1, 1.7 Hz, 1H), 7.20 (dd, J=8.1, 2.0 Hz, 1H), 6.92, 6.84 (both m, total 7H), 4.05 (t, J=6.6 Hz, 2H), 3.96 (s, 3H), 3.71 (m, 4H), 3.03 (m, 4H), 2.87 (t, J=6.6 Hz, 2H).

EXAMPLE 299

2-methoxy-4-{8-[2-(4-morpholin-4-ylphenoxy)ethyl]-11-oxo-10,11-dihydro-5H-dibenzo[b,e][1,4]diazepin-3-yl}benzonitrile The title compound was prepared by substituting Example 297A and Example 267C for Example 59B and Example 56A, respectively, in Example 59C. MS (ESI) m/e 547 (M+H)$^+$; $^1$H NMR (300 MHz, DMSO-d$_6$) δ 9.87 (s, 1H), 7.95 (s, 1H), 7.84 (d, J=7.8 Hz, 1H), 7.79 (d, J=8.1 Hz, 1H), 7.42 (d, J=1.7 Hz, 1H), 7.32 (m, 2H), 7.28 (dd, J=8.1, 1.7 Hz, 1H), 6.93, 6.84 (both m, total 7H), 4.04 (t, J=6.8 Hz, 2H), 4.02 (s, 3H), 3.71 (m, 4H), 2.96 (m, 4H), 2.86 (t, J=6.8 Hz, 2H).

EXAMPLE 300

3-(3-methoxy-4-nitrophenyl)-8-{2-[(4-morpholin-4-ylphenyl)amino]ethyl}-5,10-dihydro-11H-dibenzo[b,e][1,4]diazepin-11-one

EXAMPLE 300A 2-(3-chloro-11-oxo-10,11-dihydro-5H-dibenzo[b,e][1,4]diazepin-8-yl)ethyl 4-methylbenzenesulfonate Example 204A (2.0 g, 6.9 mmol) and p-toluenesulfonyl chloride (1.7 g, 8.9 mmol) were dissolved in dioxane (35 mL), then triethylamine (1.3 mL, 0.95 g, 9.4 mmol) and 4-(dimethylamino)pyridine (0.09 g, 0.7 mmol) were added. The reaction was stirred at room temperature for 3 days, then diluted with acetone and CHCl$_3$ and washed twice with saturated NaHCO$_3$. The organic layer was concentrated, then toluene was used to azeotrope off the last of the water. The crude material (2.8 g) was slurried in Et$_2$O (25 mL) overnight, then filtered off to give the product (2.4 g, 78%) as pale yellow solids. MS (DCI) m/e 443 and 445 (M+H)$^+$; $^1$H NMR (300 MHz, DMSO-d$_6$) δ 9.83 (s, 1H), 8.00 (s, 1H), 7.70 (d, J=8.5 Hz, 1H), 7.70 (d, J=8.1 Hz, 2H), 7.62 (d, J=8.1 Hz, 2H), 7.06 (d, J=2.0 Hz, 1H), 6.94 (dd, J=8.5, 2.0 Hz, 1H), 6.83 (m, 1H), 6.73 (m, 2H), 4.14 (t, J=6.4 Hz, 2H), 2.74 (t, J=6.4 Hz, 2H), 2.36 (s, 3H).

EXAMPLE 300B 3-chloro-8-{2-[(4-morpholin-4-ylphenyl)amino]ethyl}-5,10-dihydro-11H-dibenzo[b,e][1,4]diazepin-11-one Example 300A (0.22 g, 0.50 mmol) and 4-morpholinoaniline (0.09 g, 0.50 mmol) were dissolved in DMF (2 mL), then added K$_2$CO$_3$ (0.13 g, 0.96 mmol) and heated the reaction at 70° C. for 24 hours. The reaction was cooled, partitioned between EtOAc and 0.5M NaHCO$_3$, then the organic layer was washed with brine and dried over Na$_2$SO$_4$. After filtration and concentration the crude material was purified by column chromatography using 1/1 then 3/7 hexane/EtOAc. Recovered the product (0.10 g, 44%) as yellow solids. MS (DCI) m/e 449 and 451 (M+H)$^+$; $^1$H NMR (300 MHz, DMSO-d$_6$) δ 9.83 (s, 1H), 7.98 (s, 1H), 7.67 (d, J=8.5 Hz, 1H), 7.06 (d, J=2.0 Hz, 1H), 6.94 (dd, J=8.5, 2.0 Hz, 1H), 6.86-6.88, (m, 3H), 6.75 (d, J=8.8 Hz, 2H), 6.51 (d, J=8.8 Hz, 2H), 3.71 (m, 4H), 3.13 (m, 2H), 2.89 (m, 4H), 2.67 (m, 2H).

EXAMPLE 300C 3-(3-methoxy-4-nitrophenyl)-8-{2-[(4-morpholin-4-ylphenyl)amino]ethyl}-5,10-dihydro-11H-dibenzo[b,e][1,4]diazepin-11-one The title compound was prepared by substituting Example 300B and Example 266G for Example 59B and Example 56A, respectively, in Example 59C. MS (ESI) m/e 566 (M+H)$^+$.

EXAMPLE 301

3-(3-methoxy-4-nitrophenyl)-8-[2-(3-methyl-2-oxopyridin-1 (2H)-yl)ethyl]-5,10-dihydro-11H-dibenzo[b,e][1,4]diazepin-11-one Example 239 (100 mg, 0.25 mmol), PPh$_3$ (79 mg, 0.30 mmol), and 3-methyl-2-pyridol (33 mg, 0.30 mmole) were dissolved in DMF (1 mL), then di-tert-butylazodicarboxylate (68 mg, 0.30 mmol) was added and the reaction allowed to stir at room temperature overnight. The reaction was then diluted with MeOH (9 mL) and purified using preoperative HPLC. The HPLC purification gave not only the title pyridone (27 mg, 22%), but also the pyridyl ether (24 mg, 21%). MS (ESI) m/e 497 (M+H)$^+$; $^1$H NMR (300 MHz, DMSO-d$_6$) δ 9.87 (s, 1H), 8.01 (d, J=8.5 Hz, 1H), 7.97 (s, 1H), 7.80 (d, J=8.1 Hz, 1H), 7.52 (d, J=1.7 Hz, 1H), 7.25-7.39 (m, 5H), 6.93 (d, J=7.8 Hz, 1H), 6.82 (m, 2H), 6.05 (m, 1H), 4.03 (m, 5H), 2.80 (t, J=7.5 Hz, 2H), 2.00 (s, 3H).

EXAMPLE 302

3-(3-methoxy-4-nitrophenyl)-8-{2-[(5-methylpyridin-2-yl)oxy]ethyl}-5,10-dihydro-11H-dibenzo[b,e][1,4]diazepin-11-one The title compound was isolated as second product in Example 351. MS (ESI) m/e 497 (M+H)$^+$; $^1$H NMR (300 MHz, DMSO-d$_6$) δ 9.86 (s, 1H), 8.01 (d, J=8.5 Hz, 1H), 7.96 (m, 2H), 7.79 (d, J=8.1 Hz, 1H), 7.52 (d, J=1.4 Hz, 1H), 7.50 (dd, J=8.5, 2.0 Hz, 1H), 7.28-7.34 (m, 3H), 6.95 (d, J=7.8 Hz, 1H), 6.90 (m, 2H), 6.69 (d, J=8.5 Hz, 1H), 4.35 (t, J=6.8 Hz, 2H), 4.03 (s, 3H), 2.80 (t, J=6.8 Hz, 2H), 2.19 (s, 3H).

EXAMPLE 303

3-(3-methoxy-4-nitrophenyl)-8-[2-(4-methyl-2-oxopyridin-1 (2H)-yl)ethyl]-5,10-dihydro-11H-dibenzo[b,e][1,4]diazepin-11-one The title compound was prepared by substituting 4-methyl-2-pyridol for 3-methylpyridin-2(1H)-one in Example 301. MS (ESI) m/e 497 (M+H)$^+$; $^1$H NMR (300 MHz, DMSO-d$_6$) δ 9.86 (s, 1H), 8.01 (d, J=8.5 Hz, 1H), 7.97 (s, 1H), 7.80 (d, J=8.1 Hz, 1H), 7.52 (d, J=1.7 Hz, 1H), 7.39 (d, J=7.1 Hz, 1H), 7.28-7.34 (m, 3H), 6.93 (d, J=8.1 Hz, 1H), 6.83 (m, 1H), 6.78 (m, 1H), 6.18 (m, 1H), 5.98 (dd, J=6.9, 1.9 Hz, 1H), 4.03 (s, 3H), 3.97 (t, J=7.5 Hz, 2H), 2.78 (t, J=7.5 Hz, 2H), 2.09 (s, 3H).

EXAMPLE 304

8-[2-(isoquinolin-3-yloxy)ethyl]-3-(3-methoxy-4-nitrophenyl)-5,10-dihydro-11H-dibenzo [b,e][1,4]diazepin-11-one The title compound was prepared by substituting 3-hydroxyisoquinoline for 3-methylpyridin-2 (1H)-one in Example 301. MS (ESI) m/e 533 (M+H)$^+$; $^1$H NMR (300 MHz, DMSO-d$_6$) δ 9.88 (s, 1H), 9.04 (s, 1H), 8.01 (d, J=8.5 Hz, 2H), 7.97 (s, 1H), 7.80 (d, J=8.1 Hz, 2H), 7.65 (m, 1H), 7.52 (d, J=1.7 Hz, 1H), 7.42 (m, 1H), 7.28-7.35 (m, 3H), 7.16 (s, 1H), 6.96 (m, 3H), 4.47 (t, J=6.8 Hz, 2H), 4.03 (s, 3H), 2.96 (t, J=6.8 Hz, 2H).

EXAMPLE 305

8-[2-(5-chloro-2-oxopyridin-1 (2H)-yl)ethyl]-3-(3-methoxy-4-nitrophenyl)-5,10-dihydro-11H-dibenzo[b,e][1,4]diazepin-11-one The title compound was prepared by substituting 5-chloro-2-pyridol for 3-methylpyridin-2(1H)-one in Example 301. MS (ESI) m/e 517 and 519 (M+H)$^+$; $^1$H NMR (300 MHz, DMSO-d$_6$) δ 9.88 (s, 1H), 8.01 (d, J=8.5 Hz, 1H), 7.98 (s, 1H), 7.85 (d, J=2.7 Hz, 1H), 7.80 (d, J=8.1 Hz, 1H), 7.52 (d, J=1.7 Hz, 1H), 7.45 (dd, J=9.8, 2.7 Hz, 1H), 7.28-7.34 (m, 3H), 6.94 (d, J=8.1 Hz, 1H), 6.82 (m, 2H), 6.42 (d, J=9.8 Hz, 1H), 4.03 (s, 3H), 4.00 (t, J=7.5 Hz, 2H), 2.80 (t, J=7.5 Hz, 2H).

EXAMPLE 306

8-[1,1-dimethyl-2-(pyridin-2-yloxy)ethyl]-3-(3-methoxy-4-nitrophenyl)-5,10-dihydro-11H-dibenzo[b,e][1,4]diazepin-11-one

EXAMPLE 306A 3-chloro-8-[1,1-dimethyl-2-(pyridin-2-yloxy)ethyl]-5,10-dihydro-11H-dibenzo[b,e][1,4]diazepin-11-one Example 288A (160 mg, 0.51 mmol) and 2-fluoropyridine (43 µL, 48 mg, 0.50 mmol) were dissolved in DMF (1.2 mL), then 95% NaH (28 mg, 1.11 mmol) was added. After stirring the reaction at room temperature for 4 hours water and EtOAc were added, then the organic layer was washed with brine and dried over Na$_2$SO$_4$. After filtration and concentration the crude material was purified by column chromatography using 7/3 hexane/EtOAc, giving the product (47 mg, 24%). MS (DCI) m/e 394 and 396 (M+H)$^+$.

EXAMPLE 306B

8-[1,1-dimethyl-2-(pyridin-2-yloxy)ethyl]-3-(3-methoxy-4-nitrophenyl)-5,10-dihydro-11H-dibenzo [b,e][1,4]diazepin-11-one The title compound was prepared by substituting Example 306A and Example 266G for Example 59B and Example 56A, respectively, in Example 59C. MS (ESI) m/e 511 (M+H)$^+$; $^1$H NMR (300 MHz, DMSO-d$_6$) δ 9.81 (s, 1H), 8.11 (m, 1H), 8.01 (d, J=8.5 Hz, 1H), 7.97 (s, 1H), 7.79 (d, J=8.1 Hz, 1H), 7.65 (m, 1H), 7.52 (d, J=1.7 Hz, 1H), 7.33-7.35 (m, 2H), 7.29 (d, J=8.3, 1.7 Hz, 1H), 7.10 (d, J=2.0 Hz, 1H), 7.06 (m, 1H), 6.93-6.96 (m, 2H), 6.75 (d, J=8.5 Hz, 1H), 4.22 (s, 2H), 4.03 (s, 3H), 1.32 (s, 6H).

EXAMPLE 307

8-[1,1-dimethyl-2-(4-morpholin-4-ylphenoxy)ethyl]-3-(3-methoxy-4-nitrophenyl)-5,10-dihydro-11H-dibenzo[b,e][1,4]diazepin-11-one

EXAMPLE 307A 3-chloro-8-[1,1-dimethyl-2-(4-nitrophenoxy)ethyl]-5,10-dihydro-11H-dibenzo[b,e][1,4]diazepin-11-one The title compound was prepared by substituting 4-fluoronitrobenzene for 2-fluoropyridine in Example 306A. Starting with the compound described in Example 288A and 4-fluoronitrobenzene the title compound was prepared using the method of Example 306A. MS (DCI) m/e 438 and 440 (M+H)$^+$, 455 and 457 (M+NH$_4$)$^+$; $^1$H NMR (300 MHz, DMSO-d$_6$) δ 9.81 (s, 1H), 8.17 (m, 2H), 8.02 (s, 1H), 7.67 (d, J=8.5 Hz, 1H), 7.13 (m, 2H), 7.05-7.09 (m, 3H), 6.92, 6.90 (m, 2H), 4.08 (s, 2H), 1.34 (s, 6H).

EXAMPLE 307B

8-[2-(4-aminophenoxy)-1,1-dimethylethyl]-3-chloro-5,10-dihydro-11H-dibenzo[b,e][1,4]diazepin-11-one The title compound was prepared by substituting Example 307A for Example 6B in Example 6C. MS (DCI) m/e 408 and 410 (M+H)$^+$; $^1$H NMR (300 MHz, DMSO-d$_6$) δ 9.79 (s, 1H), 8.00 (s, 1H), 7.67 (d, J=8.5 Hz, 1H), 7.02-7.06 (m, 3H), 6.90 (m, 2H), 6.60 (m, 2H), 6.46 (m, 2H), 4.56 (s, 2H), 3.75 (s, 2H), 1.28 (s, 6H).

EXAMPLE 307C 3-chloro-8-[1,1-dimethyl-2-(4-morpholin-4-ylphenoxy)ethyl]-5,10-dihydro-11H-dibenzo[b,e][1,4]diazepin-11-one Example 307B (0.57 g, 1.4 mmol) was dissolved in DMA (2.8 mL), then 2-chloroethyl ether (0.40 g, 2.8 mmol) and K$_2$CO$_3$ (0.39 g, 2.8 mmol) were added and the reaction heated at 150° C. for 3 hours. Water and EtOAc were added, then the organic layer was washed with brine and dried over Na$_2$SO$_4$. After filtration and concentration the crude material was purified by column chromatography using 6/4 hexane/EtOAc, giving the product (0.33 g, 49%). MS (ESI) m/e 478 and 480 (M+H)$^+$.

EXAMPLE 307D

8-[1,1-dimethyl-2-(4-morpholin-4-ylphenoxy)ethyl]-3-(3-methoxy-4-nitrophenyl)-5,10-dihydro-11H-dibenzo[b,e][1,4]diazepin-11-one The title compound was prepared by substituting Example 307C and Example 266G for Example 59B and Example 56A, respectively, in Example 59C. MS (ESI) m/e 595 (M+H)$^+$; $^1$H NMR (300 MHz, DMSO-d$_6$) δ 9.87 (s, 1H), 8.00 (d, J=8.4 Hz, 1H), 7.95 (s, 1H), 7.80 (d, J=8.1 Hz, 1H), 7.52 (d, J=1.7 Hz, 1H), 7.34 (m, 2H), 7.29 (dd, J=8.4, 1.7 Hz, 1H), 7.09 (d, J=2.2 Hz, 1H), 7.04 (dd, J=8.4, 2.2 Hz, 1H), 6.96 (d, J=8.4 Hz, 1H), 6.89 (d, J=9.0 Hz, 2H), 6.82 (d, J=9.0 Hz, 2H), 4.03 (s, 3H), 3.85 (s, 2H), 3.72 (m, 4H), 3.00 (m, 4H), 1.31 (s, 6H).

EXAMPLE 308

2-[3-(3-methoxy-4-nitrophenyl)-11-oxo-10,11-dihydro-5H-dibenzo[b,e][1,4]diazepin-8-yl]-2-methylN(tetrahydrofuran-2-ylmethyl)propanamide The title compound was prepared by substituting Example 266I and (±)—C-(tetrahydro-furan-2-yl)-methylamine for dimethylaminoacetic acid and Example 120, respectively, in Example 122. MS (DCI) m/e 531 (M+H)$^+$; $^1$H NMR (500 MHz, DMSO-d$_6$) δ 9.83 (s, 1H), 8.01 (d, J=8.4 Hz, 1H), 7.97 (s, 1H), 7.80 (d, J=8.1 Hz, 1H), 7.52 (d, J=1.6 Hz, 1H), 7.30-7.35 (m, 3H), 7.07 (t, J=5.6 Hz, 1H), 6.95 (m, 2H), 6.90 (dd, J=8.3, 2.0 Hz, 1H), 4.03 (s, 3H), 3.80 (m, 1H), 3.60 (m, 1H), 3.53 (m, 1H), 3.07 (m, 2H), 1.61 (m, 3H), 1.40 (m, 1H), 1.38 (s, 6H).

EXAMPLE 309

8-(2-hydroxy-11-dimethylethyl)-3-(3-methoxy-4-nitrophenyl)-7-methyl-5,10-dihydro-11H-dibenzo[b,e][1,4]diazepin-11-one The title compound was prepared from 3-methyl-nitrobenzene by the sequential application of the following methods: Examples 282A and 6C, treatment with acetic anhydride, Examples 281C, 1A, 6C, 5C, 286C, and 266H. Instead of the Et$_2$O slurry described in Example 266H, the title compound was purified by column chromatography using 4/6 hexane/EtOAc, then an EtOAc slurry. MS (DCI) m/e 448 (M+H)$^+$; $^1$H NMR (300 MHz, DMSO-d$_6$) δ 9.69 (s, 1H), 8.00 (d, J=8.4 Hz, 1H), 7.83 (s, 1H), 7.79 (d, J=8.1 Hz, 1H), 7.52 (s, 1H), 7.34 (m, 2H), 7.27 (d, J=8.1 Hz, 1H), 6.97 (s, 1H), 6.73 (s, 1H), 4.57 (t, J=5.5 Hz, 1H), 4.03 (s, 3H), 3.50 (d, J=5.5 Hz, 2H), 2.34 (s, 3H), 1.24 (s, 6H).

EXAMPLE 310

2-[3-(3-methoxy-4-nitrophenyl)-2-methyl-11-oxo-10,11-dihydro-5H-dibenzo[b,e][1,4]diazepin-8-yl]N(4-morpholin-4-ylphenyl)acetamide

EXAMPLE 310A 5-chloro-2-iodo-4-methylaniline

3-Chloro-4-methylaniline (1.50 g, 10.6 mmol) and benzyltrimethylammonium dichloroiodate (4.60 g, 13.2 mmol) were dissolved in CH$_2$Cl$_2$ (50 mL) and MeOH (20 mL), then CaCO$_3$ (3.10 g, 31.0 mmol) was added and the reaction stirred at room temperature overnight. The reaction was diluted with Et$_2$O (200 mL), filtered through Celite®, and concentrated. The crude material was purified by column chromatography using 97.5/2.5 hexane/EtOAc, giving the product (1.80 g, 63%) as light tan solids. MS (DCI) m/e 268 and 270 (M+H)$^+$; $^1$H NMR (300 MHz, CDCl$_3$) δ 7.48 (s, 1H), 6.76 (s, 1H), 4.00 (v br s, 2H), 2.22 (s, 3H).

EXAMPLE 310B methyl 2-(acetylamino)-4-chloro-5-methylbenzoate

The compound described in 310A (1.65 g, 6.17 mmol) was dissolved in 1,2-dichloroethane (30 mL), then acetyl chloride (0.60 mL, 0.66 g, 8.41 mmol) was added. The reaction was stirred at room temperature for 3 hours, then concentrated to give the acetamide (1.91 g, 100%), which was carried on with no purification.

That acetamide was dissolved in DMF (12 mL) and MeOH (2.4 mL), then triethylamine (1.80 mL, 1.31 g, 1.30 mmol), 1,1'-bis(diphenylphosphino)ferrocene (300 mg, 0.54 mmol), and palladium(II)acetate (60 mg, 0.27 mmol) were added. The reaction was heated at 70° C. under a CO balloon overnight. The reaction was then cooled and poured into ice water. The solids were filtered off, dried, and purified by column chromatography using 9/1, then 4/1 hexane/EtOAc. The product (1.36 g, 91%) was recovered as off-white solids. MS (DCI) m/e 242 and 244 (M+H)$^+$; $^1$H NMR (300 MHz, CDCl$_3$) δ 8.79 (s, 1H), 7.87 (s, 1H), 3.92 (s, 3H), 2.34 (s, 3H), 2.22 (s, 3H).

EXAMPLE 310C methyl 4-chloro-2-iodo-5-methylbenzoate

The compound described in Example 310B was converted to the title compound by the methods found in the second paragraph of Example 281C and Example 57B. MS (DCI) m/e 328 and 330 (M+H)$^+$.

EXAMPLE 310D

2-[3-(3-methoxy-4-nitrophenyl)-2-methyl-11-oxo-10,11-dihydro-5H-dibenzo[b,e][1,4]diazepin-8-yl]N(4-morpholin-4-ylphenyl)acetamide Starting with the compounds described in Examples 6A and 310C, the title compound was prepared by the methods described in Examples 1A, 6C, 5C, 266H, 13, and 266J. The title compound was purified by preparative HPLC. MS (ESI) m/e 594 (M+H)$^+$; $^1$H NMR (300 MHz, DMSO-d$_6$) δ 9.88 (s, 1H), 9.85 (s, 1H), 7.95 (d, J=8.1 Hz, 1H), 7.77 (s, 1H), 7.61 (s, 1H), 7.45 (d, J=8.7 Hz, 2H), 7.30 (d, J=1.6 Hz, 1H), 7.06 (dd, J=8.4, 1.6 Hz, 1H), 6.91 (m, 6H), 3.95 (s, 3H), 3.73 (m, 4H), 3.46 (s, 2H), 3.05 (m, 4H), 2.13 (s, 3H).

EXAMPLE 311 methyl {3-[4-(aminomethyl)-3-methoxyphenyl]-11-oxo-10,11-dihydro-5H-dibenzo[b,e][1,4]diazepin-8-yl}acetate Example 61 (31 mg, 0.075 mmol) was dissolved in MeOH (50 mL) and triethylamine (5 mL), then Raney nickel (100 mg) was added and the reaction stirred under hydrogen at 60 psi overnight. The reaction was filtered, concentrated, and the crude material purified by column chromatography to give 18 mg (45%) of the product. MS (DCI) m/e 418 (M+H)$^+$; $^1$H NMR (300 MHz, DMSO-d$_6$) δ 9.85 (s, 1H), 8.04 (v br s, 3H), 7.96 (s, 1H), 7.77 (d, J=8.5 Hz, 1H), 7.46 (d, J=7.8 Hz, 1H), 7.32 (d, J=1.7 Hz, 1H), 7.28, 7.25, 7.23 (all m, total 3H), 6.96 (d, J=8.3 Hz, 1H), 6.87, 6.84 (both m, total 2H), 4.03 (br s, 2H), 3.94 (s, 3H), 3.60 (s, 3H), 3.54 (s, 2H).

EXAMPLE 312

2-[3-(2-methoxy-5-methylpyridin-4-yl)-11-oxo-10,11-dihydro-5H-dibenzo[b,e][1,4]diazepin-8-yl]-2-methylN(4-morpholin-4-ylphenyl)propanamide Starting with the compounds described in Examples 71C and 266F the title compound was made using the methods described in Examples 266H, 72 (except no TMSCHN$_2$ treatment), and 266J. The final compound was purified by column chromatography using EtOAc, then converted to the dihydrochloride salt. MS (ESI) m/e 578 (M+H)$^+$; $^1$H NMR (300 MHz, DMSO-d$_6$) δ 9.87 (s, 1H), 8.94 (br s, 1H), 8.09 (m, 1H), 7.97 (s, 1H), 7.74 (d, J=8.1 Hz, 1H), 7.51 (d, J=8.8 Hz, 2H), 6.89-7.08 (m, 7H), 6.66 (s, 1H), 3.85 (s, 3H), 3.91 (m, 4H), 3.16 (br m, 4H), 2.13 (s, 3H), 1.49 (s, 6H).

EXAMPLE 313

8-(2-hydroxy-11-dimethylethyl)-3-[(2-methylpyridin-4-yl)amino]-5,10-dihydro-11H-dibenzo[b,e][1,4]diazepin-11-one The title compound was prepared by substituting Example 288A and 4-amino-2-picoline for Example 189A and 4-aminopyridine in Example 191. MS (DCI) m/e 389 (M+H)$^+$; $^1$H NMR (300 MHz, DMSO-d$_6$) δ 10.40 (s, 1H), 9.69 (s, 1H), 8.25 (d, J=7.5 Hz, 1H), 7.97 (s, 1H), 7.76 (d, J=8.5 Hz, 1H), 7.07 (m, 2H), 6.88 (m, 4H), 6.81 (dd, J=8.5, 2.0, 1H), 4.60 (v br s, 1H), 3.34 (s, 2H), 2.50 (s, 3H), 1.15 (s, 6H).

EXAMPLE 314 (A799661.2)

8-(2-hydroxy-1,1,2-trimethylpropyl)-3-(pyrimidin-4-ylamino)-5,10-dihydro-11H-dibenzo[b,e][1,4]diazepin-11-one The title compound was prepared by substituting Example 289A and pyrimidin-4-ylamine for Example 189A and 4-aminopyridine in Example 191. MS (DCI) m/e 404 (M+H)$^+$; $^1$H NMR (300 MHz, DMSO-d$_6$) δ 10.48 (s, 1H), 9.58 (s, 1H), 8.85 (s, 1H), 8.38 (d, J=6.4 Hz, 1H), 7.91 (s, 1H), 7.69 (d, J=8.5 Hz, 1H), 7.39 (d, J=2.0 Hz, 1H), 7.11 (dd, J=8.5, 2.0 Hz, 1H), 7.06 (d, J=2.0 Hz, 1H), 6.99 (m, 2H), 6.87 (d, J=8.5 Hz, 1H), 1.24 (s, 6H), 0.96 (s, 6H).

EXAMPLE 315

2-[3-(3-methoxy-4-nitrophenyl)-11-oxo-10,11-dihydro-5H-dibenzo[b,e][1,4]diazepin-8-yl]NmethylN(3-pyrrolidin-1-ylpropyl)acetamide The title compound was prepared by substituting Example 73 and methyl(3-pyrrolidin-1-ylpropyl)amine (B. R. de Costa, et. al., J. Med. Chem., 33, 38 (1992)) for dimethylaminoacetic acid and Example 120, respectively, in Example 122. MS (DCI) m/e 544 (M+H)$^+$.

EXAMPLE 316

2-[3-(3-methoxy-4-nitrophenyl)-11-oxo-10,11-dihydro-5H-dibenzo[b,e][1,4]diazepin-8-yl]-2-methylN(3-pyrrolidin-1-ylpropyl)propanamide The title compound was prepared by substituting Example 266I and (3-pyrrolidin-1-yl-propyl)amine for dimethylaminoacetic acid and Example 120, respectively, in Example 122. MS (DCI) m/e 558 (M+H)$^+$.

EXAMPLE 317

2-[3-(3-methoxy-4-nitrophenyl)-11-oxo-10,11-dihydro-5H-dibenzo[b,e][1,4]diazepin-8-yl]-2-methylN-pyrimidin-4-ylpropanamide The title compound was prepared by substituting Example 266I and 4-aminopyrimidine for dimethylaminoacetic acid and Example 120, respectively, in Example 122. MS (ESI) m/e 525 (M+H)$^+$.

EXAMPLE 318

2-[3-(3-methoxy-4-nitrophenyl)-11-oxo-10,11-dihydro-5H-dibenzo[b,e][1,4]diazepin-8-yl]-2-methylN(4-methyl-1,3-thiazol-2-yl)propanamide The title compound was prepared by substituting Example 266I and 2-amino-4-methylthiazole for dimethylaminoacetic acid and Example 120, respectively, in Example 122. MS (ESI) m/e 543 (M+H)$^+$.

Examples 319 through 335 were made by the method used for Examples 80-118, substituting the acid described in Example 266I for the acid described in Example 73.

EXAMPLE 319

2-[3-(3-methoxy-4-nitrophenyl)-11-oxo-10,11-dihydro-5H-dibenzo[b,e][1,4]diazepin-8-yl]-2-methylN(2,2,2-trifluoroethyl)propanamide The desired product was prepared using 2,2,2-trifluoroethylamine. MS (ESI) m/e 529 (M+H)$^+$.

EXAMPLE 320

N-(3-fluorophenyl)-2-[3-(3-methoxy-4-nitrophenyl)-11-oxo-10,11-dihydro-5H-dibenzo[b,e][1,4]diazepin-8-yl]-2-methylpropanamide The desired product was prepared using 3-fluoroaniline. MS (ESI) m/e 539 (M−H)$^−$.

EXAMPLE 321

2-[3-(3-methoxy-4-nitrophenyl)-11-oxo-10,11-dihydro-5H-dibenzo[b,e][1,4]diazepin-8-yl]-2-methylN[4-(trifluoromethoxy)phenyl]propanamide The desired product was prepared using 4-(trifluoromethoxy)aniline. MS (ESI) m/e 605 (M−H)$^−$.

EXAMPLE 322

2-[3-(3-methoxy-4-nitrophenyl)-11-oxo-10,11-dihydro-5H-dibenzo[b,e][1,4]diazepin-8-yl]-2-methylN[3-(trifluoromethyl)phenyl]propanamide The desired product was prepared using 3-(trifluoromethyl)aniline. MS (ESI) m/e 591 (M+H)$^+$.

EXAMPLE 323

2-[3-(3-methoxy-4-nitrophenyl)-11-oxo-10,11-dihydro-5H-dibenzo[b,e][1,4]diazepin-8-yl]-2-methylN[3-(trifluoromethoxy)phenyl]propanamide The desired product was prepared using 3-(trifluoromethoxy)aniline. MS (ESI) m/e 607 (M+H)$^+$.

EXAMPLE 324

N-[3-fluoro-5-(trifluoromethyl)benzyl]-2-[3-(3-methoxy-4-nitrophenyl)-11-oxo-10,11-dihydro-5H-dibenzo[b,e][1,4]diazepin-8-yl]-2-methylpropanamide The desired product was prepared using (3-fluoro-5-trifluoromethyl)benzylamine. MS (ESI) m/e 621 (M−H)$^−$.

EXAMPLE 325

N-(2-fluorobenzyl)-2-[3-(3-methoxy-4-nitrophenyl)-11-oxo-10,11-dihydro-5H-dibenzo[b,e][1,4]diazepin-8-yl]-2-methylpropanamide The desired product was prepared using 2-fluorobenzylamine. MS (ESI) m/e 553 (M−H)$^−$.

EXAMPLE 326

N-(3-fluorobenzyl)-2-[3-(3-methoxy-4-nitrophenyl)-11-oxo-10,11-dihydro-5H-dibenzo[b,e][1,4]diazepin-8-yl]-2-methylpropanamide The desired product was prepared using 3-fluorobenzylamine. MS (ESI) m/e 553 (M−H)$^−$.

EXAMPLE 327

N-(4-fluorobenzyl)-2-[3-(3-methoxy-4-nitrophenyl)-11-oxo-10,11-dihydro-5H-dibenzo[b,e][1,4]diaz-epin-8-yl]-2-methylpropanamide The desired product was prepared using 4-fluorobenzylamine. MS (ESI) m/e 553 (M−H)$^−$.

EXAMPLE 328

2-[3-(3-methoxy-4-nitrophenyl)-11-oxo-10,11-dihydro-5H-dibenzo[b,e][1,4]diazepin-8-yl]-2-methylN[4-(trifluoromethoxy)benzyl]propanamide The desired product was prepared using 4-(trifluoromethoxy)benzylamine. MS (ESI) m/e 621 (M+H)$^+$.

EXAMPLE 329

2-[3-(3-methoxy-4-nitrophenyl)-11-oxo-10,11-dihydro-5H-dibenzo[b,e][1,4]diazepin-8-yl]-2-methylN[3-(trifluoromethyl)benzyl]propanamide The desired product was prepared using 3-(trifluoromethyl)benzylamine. MS (ESI) m/e 603 (M−H)$^−$.

EXAMPLE 330

2-[3-(3-methoxy-4-nitrophenyl)-11-oxo-10,11-dihydro-5H-dibenzo[b,e][1,4]diazepin-8-yl]-2-methylN[4-(trifluoromethyl)benzyl]propanamide The desired product was prepared using 4-(trifluoromethyl)benzylamine. MS (ESI) m/e 603 (M−H)$^−$.

EXAMPLE 331

2-[3-(3-methoxy-4-nitrophenyl)-11-oxo-10,11-dihydro-5H-dibenzo[b,e][1,4]diazepin-8-yl]-2-methylN[3-(trifluoromethoxy)benzyl]propanamide The desired product was prepared using 3-(trifluoromethoxy)benzylamine. MS (ESI) m/e 619 (M−H)$^−$.

EXAMPLE 332

N-[2-(2-fluorophenyl)ethyl]-2-[3-(3-methoxy-4-nitrophenyl)-11-oxo-10,11-dihydro-5H-dibenzo[b,e][1,4]diazepin-8-yl]-2-methylpropanamide The desired product was prepared using 2-(2-fluorophenyl)ethylamine. MS (ESI) m/e 567 (M−H)−.

EXAMPLE 333

N-[2-(3-fluorophenyl)ethyl]-2-[3-(3-methoxy-4-nitrophenyl)-11-oxo-10,11-dihydro-5H-dibenzo[b,e][1,4]diazepin-8-yl]-2-methylpropanamide The desired product was prepared using 2-(3-fluorophenyl)ethylamine. MS (ESI) m/e 567 (M−H)−.

EXAMPLE 334

N-(2,4-difluorobenzyl)-2-[3-(3-methoxy-4-nitrophenyl)-11-oxo-10,11-dihydro-5H-dibenzo[b,e][1,4]diazepin-8-yl]-2-methylpropanamide The desired product was prepared using 2,4-difluorobenzylamine. MS (ESI) m/e 571 (M−H)−.

EXAMPLE 335

N-(2,6-difluorobenzyl)-2-[3-(3-methoxy-4-nitrophenyl)-11-oxo-10,11-dihydro-5H-dibenzo[b,e][1,4]diazepin-8-yl]-2-methylpropanamide The desired product was prepared using 2,6-difluorobenzylamine. MS (ESI) m/e 571 (M−H)−.

EXAMPLE 336

N-(cyclopropylmethyl)-2-[3-(3-methoxy-4-nitrophenyl)-11-oxo-10,11-dihydro-5H-dibenzo[b,e][1,4]diazepin-8-yl]-2-methylpropanamide The title compound was prepared by substituting Example 266I and cyclopropylmethylamine for dimethylaminoacetic acid and Example 120, respectively, in Example 122. MS (DCI) m/e 501 (M+H)+.

EXAMPLE 337

N-(3-ethoxypropyl)-2-methyl-2-[11-oxo-3-(pyrimidin-4-ylamino)-10,11-dihydro-5H-dibenzo[b,e][1,4]diazepin-8-yl]propanamide

EXAMPLE 337A 2-methyl-2-[11-oxo-3-(pyrimidin-4-ylamino)-10,11-dihydro-5H-dibenzo[b,e][1,4]diazepin-8-yl]propanoic acid The title compound was prepared by substituting Example 279A for Example 12 in Example 13. MS (DCI) m/e 390 (M+H)+.

EXAMPLE 337B

N-(3-ethoxypropyl)-2-methyl-2-[11-oxo-3-(pyrimidin-4-ylamino)-10,11-dihydro-5H-dibenzo[b,e][1,4]diazepin-8-yl]propanamide The title compound was prepared by substituting Example 337A and 3-ethoxypropylamine for dimethylaminoacetic acid and Example 120, respectively, in Example 122. MS (DCI) m/e 475 (M+H)+.

EXAMPLE 338

N-(3,4-difluorobenzyl)-2-methyl-2-[11-oxo-3-(pyrimidin-4-ylamino)-10,11-dihydro-5H-dibenzo[b,e][1,4]diazepin-8-yl]propanamide The title compound was prepared by substituting Example 337A and (3,4-difluoro)benzylamine for dimethylaminoacetic acid and Example 120, respectively, in Example 122. MS (DCI) m/e 514 (M+H)+.

EXAMPLE 339

8-[11-dimethyl-2-oxo-2-(4-phenylpiperazin-1-yl)ethyl]-3-(pyrimidin-4-ylamino)-5,10-dihydro-11H-dibenzo[b,e][1,4]diazepin-11-one The title compound was prepared by substituting Example 337A and (N-phenyl)piperazine for dimethylaminoacetic acid and Example 120, respectively, in Example 122. MS (DCI) m/e 533 (M+H)+.

EXAMPLE 340

N-cyclopentyl-2-methyl-2-[11-oxo-3-(pyrimidin-4-ylamino)-10,11-dihydro-5H-dibenzo[b,e][1,4]diazepin-8-yl]propanamide The title compound was prepared by substituting Example 337A and cyclopentylamine for dimethylaminoacetic acid and Example 120, respectively, in Example 122. MS (DCI) m/e 457 (M+H)+.

EXAMPLE 341

8-(1,1-dimethyl-2-morpholin-4-yl-2-oxoethyl)-3-(pyrimidin-4-ylamino)-5,10-dihydro-11H-dibenzo[b,e][1,4]diazepin-11-one The title compound was prepared by substituting Example 337A and morpholine for dimethylaminoacetic acid and Example 120, respectively, in Example 122. MS (DCI) m/e 459 (M+H)+.

EXAMPLE 342

2-methyl-2-[11-oxo-3-(pyrimidin-4-ylamino)-10,11-dihydro-5H-dibenzo[b,e][1,4]diazepin-8-yl]N(tetrahydrofuran-3-ylmethyl)propanamide The title compound was prepared by substituting Example 337A and (±)-3-aminomethyltetrahydrofuran for dimethylaminoacetic acid and Example 120, respectively, in Example 122. MS (DCI) m/e 473 (M+H)+.

EXAMPLE 343

N-(cyclopentylmethyl)-2-methyl-2-[11-oxo-3-(pyrimidin-4-ylamino)-10,11-dihydro-5H-dibenzo[b,e][1,4]diazepin-8-yl]propanamide The title compound was prepared by substituting Example 337A and cyclopentylmethylamine for dimethylaminoacetic acid and Example 120, respectively, in Example 122. MS (DCI) m/e 471 (M+H)$^+$.

EXAMPLE 344

N-(cyclopropylmethyl)-2-methyl-2-[11-oxo-3-(pyrimidin-4-ylamino)-10,11-dihydro-5H-dibenzo[b,e][1,4]diazepin-8-yl]propanamide The title compound was prepared by substituting Example 337A and cyclopropylmethylamine for dimethylaminoacetic acid and Example 120, respectively, in Example 122. MS (DCI) m/e 443 (M+H)$^+$.

EXAMPLE 345

2-methyl-2-[11-oxo-3-(pyrimidin-4-ylamino)-10,11-dihydro-5H-dibenzo[b,e][1,4]diazepin-8-yl]N(tetrahydrofuran-2-ylmethyl)propanamide The title compound was prepared by substituting Example 337A and tetrahydrofuran-2-ylmethylamine for dimethylaminoacetic acid and Example 120, respectively, in Example 122. MS (DCI) m/e 473 (M+H)$^+$.

EXAMPLE 346

2-[3-(3-methoxy-4-nitrophenyl)-11-oxo-10,11-dihydro-5H-dibenzo[b,e][1,4]diazepin-7-yl]-2-methylN1,3-thiazol-2-ylpropanamide The title compound was prepared by substituting Example 282D and 2-aminothiazole for dimethylaminoacetic acid and Example 120, respectively, in Example 122. MS (ESI) m/e 530 (M+H)$^+$.

EXAMPLE 347

N-(2,5-difluorobenzyl)-2-[3-(3-methoxy-4-nitrophenyl)-11-oxo-10,11-dihydro-5H-dibenzo[b,e][1,4]diazepin-7-yl]-2-methylpropanamide The title compound was prepared by substituting Example 282D and (2,5-difluoro)benzylamine for dimethylaminoacetic acid and Example 120, respectively, in Example 122. MS (ESI) m/e 573 (M+H)$^+$.

EXAMPLE 348

N-(2-ethoxyethyl)-2-[3-(3-methoxy-4-nitrophenyl)-11-oxo-10,11-dihydro-5H-dibenzo[b,e][1,4]diazepin-7-yl]-2-methylpropanamide The title compound was prepared by substituting Example 282D and 2-ethoxyethylamine for dimethylaminoacetic acid and Example 120, respectively, in Example 122. MS (ESI) m/e 533 (M+H)$^+$.

EXAMPLE 349

N-(4-fluorophenyl)-2-[3-(3-methoxy-4-nitrophenyl)-11-oxo-10,11-dihydro-5H-dibenzo[b,e][1,4]diazepin-7-yl]-2-methylpropanamide The title compound was prepared by substituting Example 282D and 4-fluoroaniline for dimethylaminoacetic acid and Example 120, respectively, in Example 122. MS (ESI) m/e 541 (M+H)$^+$.

EXAMPLE 350

3-(3-methoxy-4-nitrophenyl)-8-[2-(quinolin-2-yloxy)ethyl]-5,10-dihydro-11H-dibenzo[b,e][1,4]diazepin-11-one The title compound was prepared by substituting quinolin-2 (1H)-one for 3-methylpyridin-2 (1H)-one in Example 301. MS (ESI) m/e 533 (M+H)$^+$.

EXAMPLE 351

3-(3-methoxy-4-nitrophenyl)-8-[2-(5-methyl-2-oxopyridin-1 (2H)-yl)ethyl]-5,10-dihydro-11H-dibenzo[b,e][1,4]diazepin-11-one The title compound was prepared by substituting 5-methylpyridin-2 (1H)-one for 3-methylpyridin-2 (1H)-one in Example 301. MS (ESI) m/e 497 (M+H)$^+$.

EXAMPLE 352

2-{2-[3-(3-methoxy-4-nitrophenyl)-11-oxo-10,11-dihydro-5H-dibenzo[b,e][1,4]diazepin-8-yl]ethoxy}-6-methylnicotinonitrile The title compound was prepared by substituting 6-methyl-2-oxo-1,2-dihydropyridine-3-carbonitrile for 3-methylpyridin-2 (1H)-one in Example 301. MS (ESI) m/e 522 (M+H)$^+$.

EXAMPLE 353

3-(3-methoxy-4-nitrophenyl)-8-[2-(1-oxoisoquinolin-2 (1H)-yl)ethyl]-5,10-dihydro-11H-dibenzo[b,e][1,4]diazepin-11-one The title compound was prepared by substituting isoquinolin-1 (2H)-one for 3-methylpyridin-2 (1H)-one in Example 301. MS (ESI) m/e 533 (M+H)$^+$.

EXAMPLE 354

3-(3-methoxy-4-nitrophenyl)-8-{2-[2-oxo-5-(trifluoromethyl)pyridin-1 (2H)-yl]ethyl}-5,10-dihydro-11H-dibenzo[b,e][1,4]diazepin-11-one The title compound was prepared by substituting 5-(trifluoromethyl)pyridin-2 (1H)-one for 3-methylpyridin-2 (1H)-one in Example 301. MS (ESI) m/e 551 (M+H)$^+$.

EXAMPLE 355

3-(3-methoxy-4-nitrophenyl)-8-[2-(3-methoxy-2-oxopyridin-1 (2H)-yl)ethyl]-5,10-dihydro-11H-dibenzo[b,e][1,4]diazepin-11-one The title compound was prepared by substituting 3-methoxypyridin-2 (1H)-one for 3-methylpyridin-2 (1H)-one in Example 301. MS (ESI) m/e 513 (M+H)$^+$.

EXAMPLE 356

3-(3-methoxy-4-nitrophenyl)-8-{2-[(4-methylpyridin-2-yl)oxy]ethyl}-5,10-dihydro-11H-dibenzo[b,e][1,4]diazepin-11-one The title compound was prepared by substituting 4-methylpyridin-2 (1H)-one for 3-methylpyridin-2 (1H)-one in Example 301. MS (ESI) m/e 497 (M+H)$^+$.

EXAMPLE 357

3-(3-methoxy-4-nitrophenyl)-8-{2-[(3-methoxypyridin-2-yl)oxy]ethyl}-5,10-dihydro-11H-dibenzo[b,e][1,4]diazepin-11-one The title compound was prepared by substituting 3-methoxypyridin-2 (1H)-one for 3-methylpyridin-2 (1H)-one in Example 301. MS (ESI) m/e 513 (M+H)$^+$.

EXAMPLE 358

3-(3-methoxy-4-nitrophenyl)-8-[2-(3-oxoisoquinolin-2 (3H)-yl)ethyl]-5,10-dihydro-11H-dibenzo[b,e][1,4]diazepin-11-one The title compound was prepared by substituting isoquinolin-3 (2H)-one for 3-methylpyridin-2 (1H)-one in Example 301. MS (ESI) m/e 533 (M+H)$^+$.

EXAMPLE 359

8-{2-[(6-chloropyridin-2-yl)oxy]ethyl}-3-(3-methoxy-4-nitrophenyl)-5,10-dihydro-11H-dibenzo[b,e][1,4]diazepin-11-one The title compound was prepared by substituting 6-chloropyridin-2 (1H)-one for 3-methylpyridin-2 (1H)-one in Example 301. MS (ESI) m/e 517 and 519 (M+H)$^+$.

EXAMPLE 360

8-{2-[(5-chloropyridin-2-yl)oxy]ethyl}-3-(3-methoxy-4-nitrophenyl)-5,10-dihydro-11H-dibenzo[b,e][1,4]diazepin-11-one The title compound was prepared by substituting 5-chloropyridin-2 (1H)-one for 3-methylpyridin-2 (1H)-one in Example 301. MS (ESI) m/e 515 and 517 (M–H)$^-$.

EXAMPLE 361

[[3-(4-chloro-3-methoxyphenyl)-11-oxo-10,11-dihydro-5H-dibenzo[b,e][1,4]diazepin-8-yl]acetic acid The desired product was prepared by substituting Example 54B for Example 12 in Example 13. MS (DCI) m/e 409 (M+H)$^+$.

EXAMPLE 362 methyl [3-(4-acetyl-3-methoxyphenyl)-11-oxo-10,11-dihydro-5H-dibenzo[b,e][1,4]diazepin-8-yl]acetate The desired product was prepared by substituting Example 54A for Example 56A in Example 59C. MS (DCI) m/e 431 (M+H)$^+$, $^1$H NMR (300 MHz, DMSO-d$_6$): □ 9.87 (s, 1H), 7.98 (s, 1H), 7.78 (d, J=8.14 Hz, 1H), 7.70 (d, J=8.14 Hz, 1H), 7.35 (m, 2H), 7.28 (d, J=7.80 Hz, 2H), 6.89 (m, 3H), 4.00 (s, 3H), 3.60 (s, 3H), 3.54 (s, 2H), 2.56 (s, 3H).

EXAMPLE 363

[3-(4-acetyl-3-methoxyphenyl)-11-oxo-10,11-dihydro-5H-dibenzo[b,e][1,4]diazepin-8-yl]acetic acid The desired product was prepared by substituting Example 362 for Example 12 in Example 13. MS (ESI) m/e 417 (M+H)$^+$, $^1$H NMR (300 MHz, DMSO-d$_6$): □ 12.27 (s, 1H), 9.86 (s, 1H), 7.96 (s, 1H), 7.78 (d, J=8.14 Hz, 1H), 7.70 (d, J=8.14 Hz, 1H), 7.36 (d, J=1.70 Hz, 1H), 7.34 (d, J=1.36 Hz, 1H), 7.29 (d, J=1.70 Hz, 1H), 7.26 (d, J=1.70 Hz, 1H), 6.84-6.97 (m, 3H), 4.00 (s, 3H), 3.42 (s, 2H), 2.56 (s, 3H).

EXAMPLE 364

2-[3-(4-chloro-3-methoxyphenyl)-11-oxo-10,11-dihydro-5H-dibenzo[b,e][1,4]diazepin-8-yl]-N,N-dimethylacetamide The desired product was prepared by substituting Example 361 and N,N-dimethylamine hydrochloride for Example 13 and 3-pyrrolidin-1-ylpropylamine, respectively, in Example 14. MS (APCI) m/e 436 (M+H)$^+$, $^1$H NMR (300 MHz, DMSO-d$_6$): □ 9.83 (s, 1H), 7.91 (s, 1H), 7.77 (s, 1H), 7.63 (s, 1H), 7.34 (d, J=2.03 Hz, 1H), 7.29 (d, J=1.36 Hz, 1H), 7.19-7.24 (m, 2H), 6.80-6.95 (m, 3H), 3.96 (s, 3H), 3.54 (s, 2H), 2.97 (s, 3H), 2.81 (s, 3H).

EXAMPLE 365 tert-butyl 1-{[3-(3-methoxy-4-nitrophenyl)-11-oxo-10,11-dihydro-5H-dibenzo[b,e][1,4]diazepin-8-yl]acetyl}pyrrolidin-3-ylcarbamate The desired product was prepared by substituting Example 73 and tert-butyl pyrrolidin-3-ylcarbamate for Example 13 and 3-pyrrolidin-1-ylpropylamine, respectively, in Example 14. MS (DCI) m/e 588 (M+H)$^+$, $^1$H NMR (500 MHz, DMSO-d$_6$): □ 9.87 (s, 1H), 8.01 (d, J=8.42 Hz, 1H), 7.95 (s, 1H), 7.79 (d, J=8.11 Hz, 1H), 7.52 (s, 1H), 7.34 (m, 2H), 7.30 (d, J=8.11 Hz, 1H), 7.10 (s, 1H), 6.94 (dd, J=7.96, 2.96 Hz, 1H), 6.80-6.85 (m, 2H), 4.03 (s, 3H), 3.97 (m, 1H), 3.59 (m, 1H), 3.37-3.47 (m, 4H), 3.17 (m, 1H), 1.99 (m, 1H), 1.75 (m, 1H), 1.38 (s, 4H), 1.35 (s, 5H).

EXAMPLE 366

8-[2-(3-aminopyrrolidin-1-yl)-2-oxoethyl]-3-(3-methoxy-4-nitrophenyl)-5,10-dihydro-11H-dibenzo[b,e][1,4]diazepin-11-one Trifluoroacetic acid (2 mL) was added to a solution of Example 365 (35 mg, 0.06 mmol) in CH$_2$Cl$_2$ (3 mL) and stirred at room temperature for 5 hours. Concentrated under vacuum. Residue was purified by preparative HPLC to provide 25 mg (70%) of the desired product as the trifluoroacetate salt. MS (DCI) m/e 488 (M+H)$^+$, $^1$H NMR (500 MHz, DMSO-d$_6$): ☐ 9.87 (s, 1H), 7.99-8.08 (m, 4H), 7.95 (s, 1H), 7.80 (d, J=8.42 Hz, 1H), 7.52 (s, 1H), 7.36 (s, 1H), 7.34 (dd, J=8.42, 1.56 Hz, 1H), 7.30 (dd, J=8.11, 1.25 Hz, 1H), 6.82-6.97 (m, 2H), 4.03 (s, 3H), 3.83 (m, 1H), 3.64-3.74 (m, 2H), 3.38-3.57 (m, 4H), 2.19 (m, 1H), 1.95 (m, 1H).

EXAMPLE 367

[3-(2-methoxy-5-methylpyridin-4-yl)-11-oxo-10,11-dihydro-5H-dibenzo[b,e][1,4]diazepin-8-yl]acetic acid The desired product was prepared by substituting Example 72 for Example 12 in Example 13. MS (DCI) m/e 390 (M+H)$^+$, $^1$H NMR (500 MHz, DMSO-d$_6$): ☐ 9.86 (s, 1H), 8.09 (s, 1H), 7.91 (s, 1H), 7.75 (d, J=8.11 Hz, 1H), 7.01 (d, J=1.25 Hz, 1H), 6.84-6.93 (m, 4H), 6.66 (s, 1H), 3.86 (s, 3H), 3.43 (s, 2H), 2.14 (s, 3H).

EXAMPLE 368

2-[3-(2-methoxy-5-methylpyridin-4-yl)-11-oxo-10,11-dihydro-5H-dibenzo[b,e][1,4]diazepin-8-yl]-N,N-dimethylacetamide The title compound was prepared by substituting Example 367 and N,N-dimethylamine hydrochloride for dimethylaminoacetic acid and Example 120, respectively, in Example 122. MS (DCI) m/e 417 (M+H)$^+$, $^1$H NMR (300 MHz, DMSO-d$_6$): ☐ 9.87 (s, 1H), 8.09 (s, 1H), 7.92 (s, 1H), 7.74 (d, J=8.14 Hz, 1H), 7.00 (d, J=1.70 Hz, 1H), 6.88-6.93 (m, 2H), 6.79-6.83 (m, 2H), 6.65 (s, 1H), 3.85 (s, 3H), 3.55 (s, 2H), 2.97 (s, 3H), 2.81 (s, 3H), 2.14 (s, 3H).

EXAMPLE 369

8-{2-[(2S)-2-(hydroxymethyl)pyrrolidin-1-yl]-2-oxoethyl}-3-(2-methoxy-5-methylpyridin-4-yl)-5,10-dihydro-11H-dibenzo[b,e][1,4]diazepin-11-one The desired product was prepared by substituting Example 367 and (2S)-2-pyrrolidinylmethanol for dimethylaminoacetic acid and Example 120, respectively, in Example 122. MS (DCI) m/e 473 (M+H)$^+$, $^1$H NMR (300 MHz, DMSO-d$_6$): ☐ 9.85 (s, 1H), 8.09 (s, 1H), 7.88 (d, J=4.99 Hz, 1H), 7.74 (d, J=7.80 Hz, 1H), 6.99 (s, 1H), 6.88-6.91 (m, 2H), 6.80-6.85 (m, 2H), 6.65 (s, 1H), 3.96 (m, 1H), 3.85 (s, 3H), 3.39-3.52 (m, 4H), 3.23-3.26 (m, 2H), 2.14 (s, 3H), 1.76-1.89 (m, 4H).

EXAMPLE 370 tert-butyl 1-{[3-(2-methoxy-5-methylpyridin-4-yl)-11-oxo-10,11-dihydro-5H-dibenzo[b,e][1,4]diazepin-8-yl]acetyl}pyrrolidin-3-ylcarbamate The desired product was prepared by substituting Example 367 and tert-butyl pyrrolidin-3-ylcarbamate for dimethylaminoacetic acid and Example 120, respectively, in Example 122. MS (DCI) m/e 558 (M+H)$^+$, $^1$H NMR (500 MHz, DMSO-d$_6$): ☐ 9.84 (s, 1H), 8.09 (s, 1H), 7.88 (s, 1H), 7.75 (d, J=8.11 Hz, 1H), 7.10 (s, 1H), 6.99 (s, 1H), 6.88-6.91 (m, 2H), 6.80-6.86 (m, 2H), 6.65 (d, J=2.18 Hz, 1H), 3.98 (m, 1H), 3.85 (s, 3H), 3.55-3.65 (m, 2H), 3.39-3.53 (m, 2H), 3.11-3.30 (m, 2H), 2.14 (s, 3H), 1.99 (m, 1H), 1.76 (m 1H), 1.37 (d, J=13.73 Hz, 9H).

EXAMPLE 371

N-{2-[4-(aminosulfonyl)phenyl]ethyl}-2-[3-(4-chloro-3-methoxyphenyl)-11-oxo-10,11-dihydro-5H-dibenzo[b,e][1,4]diazepin-8-yl]acetamide The desired product was prepared by substituting Example 361 and 4-(2-aminoethyl)benzenesulfonamide for dimethylaminoacetic acid and Example 120, respectively, in Example 122. MS (DCI) m/e 592 (M+H)$^+$, $^1$H NMR (500 MHz, DMSO-d$_6$): ☐ 9.83 (s, 1H), 8.05 (t, J=5.15 Hz, 1H), 7.89 (s, 1H), 7.77 (d, J=8.11 Hz, 1H), 7.73 (d, J=8.11 Hz, 1H), 7.53 (d, J=8.11 Hz, 1H), 7.34-7.37 (m, 3H), 7.30 (s, 1H), 7.20-7.26 (m, 4H), 6.93 (d, J=8.11 Hz, 1H), 6.87 (s, 1H), 6.82 (d, J=7.80 Hz, 1H), 3.96 (s, 3H), 3.27 (m, 4H), 2.77 (t, J=7.02 Hz, 1H).

EXAMPLE 372 tert-butyl 1-{[3-(4-chloro-3-methoxyphenyl)-11-oxo-10,11-dihydro-5H-dibenzo[b,e][1,4]diazepin-8-yl]acetyl}pyrrolidin-3-ylcarbamate The desired product was prepared by substituting Example 361 and tert-butyl pyrrolidin-3-ylcarbamate for dimethylaminoacetic acid and Example 120, respectively, in Example 122. MS (DCI) m/e 578 (M+H)$^+$, $^1$H NMR (500 MHz, DMSO-d$_6$): ☐ 9.79 (s, 1H), 7.89 (s, 1H), 7.76 (d, J=8.11 Hz, 1H), 7.53 (d, J=8.11 Hz, 1H), 7.33 (s, 1H), 7.29 (s, 1H), 7.19-7.23 (m, 2H), 7.10 (m, 1H), 6.93 (dd, J=8.11, 3.12 Hz, 1H), 6.79-6.84 (m, 2H), 3.91-4.02 (m, 4H), 3.59 (m, 1H), 3.37-3.49 (m, 4H), 3.18 (m, 1H), 1.96 (m, 1H), 1.75 (m, 1H), 1.37 (d, J=13.10 Hz, 9H).

EXAMPLE 373

3-(4-chloro-3-methoxyphenyl)-8-[2-(3-hydroxypiperidin-1-yl)-2-oxoethyl]-5,10-dihydro-11H-dibenzo[b,e][1,4]diazepin-11-one The desired product was prepared by substituting Example 361 and 3-piperidinol for dimethylaminoacetic acid and Example 120, respectively, in Example 122. MS (DCI) m/e 492 (M+H)$^+$, $^1$H NMR (500 MHz, DMSO-d$_6$): ☐ 9.81 (d, J=2.81 Hz, 1H), 7.89 (s, 1H), 7.76 (d, J=8.11 Hz, 1H), 7.53 (d, J=8.11 Hz, 1H), 7.34 (d, J=1.87 Hz, 1H), 7.29 (s, 1H), 7.19-7.23 (m, 2H), 6.94 (d, J=7.80 Hz, 1H), 6.79-6.82 (m, 2H), 3.96-4.16 (m, 4H), 3.49-3.65 (m, 4H), 2.93-3.06 (m, 2H), 1.78 (m, 1H), 1.61 (m, 1H), 1.18-1.41 (m, 2H).

EXAMPLE 374

3-(4-chloro-3-methoxyphenyl)-8-{2-[(2S)-2-(hydroxymethyl)pyrrolidin-1-yl]-2-oxoethyl}-5,10-dihydro-11H-dibenzo[b,e][1,4]diazepin-11-one The desired product was prepared by substituting Example 361 and (2S)-2-pyrrolidinylmethanol for dimethylaminoacetic acid and Example 120, respectively, in Example 122. MS (DCI) m/e 492 (M+H)$^+$, $^1$H NMR (500 MHz, DMSO-d$_6$): ☐ 9.80 (s, 1H), 7.89 (s, 1H), 7.76 (d, J=8.11 Hz, 1H), 7.53 (d, J=8.42 Hz, 1H), 7.34 (d, J=1.87 Hz, 1H), 7.29 (s, 1H), 7.19-7.23 (m, 2H), 6.93 (m, 1H), 6.81-6.84 (m, 2H), 3.89-3.96 (m, 4H), 3.48-3.52 (m, 2H), 3.23-3.27 (m, 4H), 1.77-1.92 (m, 4H).

EXAMPLE 375

2-[3-(4-chloro-3-methoxyphenyl)-11-oxo-10,11-dihydro-5H-dibenzo[b,e][1,4]diazepin-8-yl]N(4-morpholin-4-ylphenyl)acetamide The desired product was prepared by substituting Example 361 and 4 (4-morpholinyl)aniline for dimethylaminoacetic acid and Example 120, respectively, in Example 122. MS (DCI) m/e 570 (M+H)$^+$, $^1$H NMR (500 MHz, DMSO-d$_6$): □ 9.86 (s, 1H), 9.84 (s, 1H), 7.90 (s, 1H), 7.76 (d, J=8.11 Hz, 1H), 7.53 (d, J=8.11 Hz, 1H), 7.44 (s, 1H), 7.43 (s, 1H), 7.33 (d, J=1.87 Hz, 1H), 7.29 (d, J=1.56 Hz, 1H), 7.19-7.23 (m, 2H), 6.86-6.97 (m, 5H), 3.95 (s, 3H), 3.71 (m, 4H), 3.46 (s, 2H), 3.02 (m, 4H).

EXAMPLE 376 tert-butyl 4-{[3-(3-methoxy-4-nitrophenyl)-11-oxo-10,11-dihydro-5H-dibenzo[b,e][1,4]diazepin-8-yl]acetyl}piperazine-1-carboxylate The desired product was prepared by substituting Example 73 and tert-butyl piperazine-1-carboxylate for dimethylaminoacetic acid and Example 120, respectively, in Example 122. MS (DCI) m/e 588 (M+H)$^+$, $^1$H NMR (400 MHz, DMSO-d$_6$): □ 9.88 (s, 1H), 8.01 (d, J=8.59 Hz, 1H), 7.97 (s, 1H), 7.80 (d, J=8.29 Hz, 1H), 7.52 (d, J=1.84 Hz, 1H), 7.33-7.36 (m, 2H), 7.29-7.31 (dd, J=8.29, 1.84 Hz, 1H), 6.95 (d, J=8.59 Hz, 1H), 6.81-6.85 (m, 2H), 4.03 (s, 3H), 3.60 (s, 2H), 3.43-3.45 (m, 4H), 3.20-3.29 (m, 4H), 1.39 (s, 9H).

EXAMPLE 377

3-(3-methoxy-4-nitrophenyl)-8-(2-oxo-2-piperazin-1-ylethyl)-5,10-dihydro-11H-dibenzo[b,e][1,4]diazepin-11-one The desired product was prepared by substituting Example 376 for Example 365 in Example 366. MS (DCI) m/e 488 (M+H)$^+$, $^1$H NMR (500 MHz, DMSO-d$_6$): □ 9.89 (s, 1H), 8.78 (s, 2H), 7.99-8.02 (m, 2H), 7.80 (d, J=8.42 Hz, 1H), 7.52 (s, 1H), 7.34-7.36 (m, 2H), 7.31 (d, J=8.11 Hz, 1H), 6.97 (d, J=8.42 Hz, 1H), 6.82-6.84 (m, 2H), 4.03 (s, 3H), 3.64 (s, 2H), 3.36-3.51 (m, 2H), 3.03-3.08 (m, 4H).

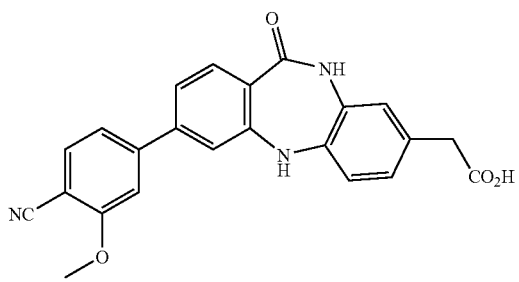

EXAMPLE 378

[3-(4-cyano-3-methoxyphenyl)-11-oxo-10,11-dihydro-5H-dibenzo[b,e][1,4]diazepin-8-yl]acetic acid The desired product was prepared by substituting Example 61 for Example 12 in Example 13. MS (DCI) m/e 400 (M+H)$^+$, $^1$H NMR (400 MHz, DMSO-d$_6$): □ 12.25 (s, 1H), 9.87 (s, 1H), 7.97 (s, 1H), 7.83 (d, J=7.98 Hz, 1H), 7.79 (d, J=8.29 Hz, 1H), 7.42 (d, J=1.23 Hz, 1H), 7.32-7.35 (m, 2H), 7.28 (dd, J=8.29, 1.53 Hz, 1H), 6.84-6.97 (m, 3H), 4.02 (s, 3H), 3.42 (s, 2H).

EXAMPLE 379

2-[3-(4-cyano-3-methoxyphenyl)-11-oxo-10,11-dihydro-5H-dibenzo[b,e][1,4]diazepin-8-yl]N(4-morpholin-4-ylphenyl)acetamide The desired product was prepared by substituting Example 378 and 4-morpholin-4-ylphenylamine for dimethylaminoacetic acid and Example 120, respectively, in Example 122. MS (DCI) m/e 560 (M+H)$^+$, $^1$H NMR (500 MHz, DMSO-d$_6$): □ 9.89 (s, 1H), 9.86 (s, 1H), 7.94 (s, 1H), 7.83 (d, J=8.11 Hz, 1H), 7.79 (d, J=8.11 Hz, 1H), 7.42-7.44 (m, 3H), 7.32-7.34 (m, 2H), 7.28 (dd, J=8.27, 1.72 Hz, 1H), 6.91-6.97 (m, 3H), 6.88 (s, 1H), 6.86 (s, 1H), 4.02 (s, 3H), 3.70-3.72 (m, 4H), 3.46 (s, 2H), 3.01-3.03 (m, 4H).

EXAMPLE 380

2-[3-(3-methoxy-4-nitrophenyl)-11-oxo-10,11-dihydro-5H-dibenzo[b,e][1,4]diazepin-8-yl]Nmethylacetamide The desired product was prepared by substituting Example 73 and methylamine hydrochloride for dimethylaminoacetic acid Example 120, respectively, in Example 122. MS (DCI) m/e 433 (M+H)$^+$, $^1$H NMR (500 MHz, DMSO-d$_6$): □ 9.86 (s, 1H), 8.01 (m, 1H), 7.95 (s, 1H), 7.82 (d, J=4.37 Hz, 1H), 7.80 (d, J=8.42 Hz, 1H), 7.52 (s, 1H), 7.29-7.35 (m, 3H), 6.84-6.95 (m, 3H), 4.03 (s, 3H), 3.26 (s, 2H), 2.56 (d, J=4.68 Hz, 3H).

EXAMPLE 381

3-(3-methoxy-4-nitrophenyl)-8-(2-morpholin-4-yl-2-oxoethyl)-5,10-dihydro-11H-dibenzo[b,e][1,4]diazepin-11-one The desired product was prepared by substituting Example 73 and morpholine for dimethylaminoacetic acid and Example 120, respectively, in Example 122. MS (DCI) m/e 489 (M+H)$^+$, $^1$H NMR (500 MHz, DMSO-d$_6$): □ 9.88 (s, 1H), 8.01 (d, J=8.42 Hz, 1H), 7.97 (s, 1H), 7.80 (d, J=8.11 Hz, 1H), 7.52 (d, J=1.25 Hz, 1H), 7.33-7.35 (m, 2H), 7.30 (dd, J=8.27, 1.72 Hz, 1H), 6.95 (d, J=7.80 Hz, 1H), 6.80-6.83 (m, 2H), 4.03 (s, 3H), 3.59 (s, 2H), 3.52 (m, 4H), 3.45 (m, 4H).

EXAMPLE 382

3-(2-methoxy-5-methylpyridin-4-yl)-8-(2-morpholin-4-yl-2-oxoethyl)-5,10-dihydro-11H-dibenzo[b,e][1,4]diazepin-11-one The desired product was prepared by substituting Example 367 and morpholine for dimethylaminoacetic acid and Example 120, respectively, in Example 122. MS (DCI) m/e 459 (M+H)$^+$, $^1$H NMR (400 MHz, DMSO-d$_6$): □ 9.87 (s, 1H), 8.09 (s, 1H), 7.90 (s, 1H), 7.75 (d, J=7.98 Hz, 1H), 6.99 (d, J=1.53 Hz, 1H), 6.88-6.92 (m, 2H), 6.82 (m, 2H), 6.66 (s, 1H), 3.85 (s, 3H), 3.59 (s, 2H), 3.49-3.55 (m, 4H), 3.43-3.46 (m, 4H), 2.14 (s, 3H).

EXAMPLE 383

[3-(2-fluoropyridin-4-yl)-11-oxo-10,11-dihydro-5H-dibenzo[b,e][1,4]diazepin-8-yl]acetic acid

EXAMPLE 383A methyl [3-(2-fluoropyridin-4-yl)-11-oxo-10,11-dihydro-5H-dibenzo[b,e][1,4]diazepin-8-yl]acetate The desired product was prepared by substituting Example 69A and Example 6D for Example 56A and Example 59B respectively, in Example 59C. MS (DCI) m/e 378 (M+H)$^+$, 396 (M+NH$_4$)+, $^1$H NMR (500 MHz, DMSO-d$_6$): ☐ 9.91 (s, 1H), 8.35 (d, J=5.30 Hz, 1H), 7.99 (s, 1H), 7.81 (d, J=8.11 Hz, 1H), 7.61 (m, 1H), 7.43 (s, 1H), 7.41 (d, J=1.56 Hz, 1H), 7.34 (dd, J=8.27, 1.72 Hz, 1H), 6.96 (d, J=7.80 Hz, 1H), 6.86-6.89 (m, 2H), 3.60 (s, 3H), 3.54 (s, 2H).

EXAMPLE 383B

[3-(2-fluoropyridin-4-yl)-11-oxo-10,11-dihydro-5H-dibenzo[b,e][1,4]diazepin-8-yl]acetic acid The desired product was prepared by substituting Example 383A for Example 69B in Example 69C. MS (DCI) m/e 364 (M+H)$^+$.

EXAMPLE 384

N,N-dimethyl-2-[11-oxo-3-(2-oxo-1,2-dihydropyridin-4-yl)-10,11-dihydro-5H-dibenzo[b,e][1,4]diazepin-8-yl]acetamide

EXAMPLE 384A

2-[3-(2-fluoropyridin-4-yl)-11-oxo-10,11-dihydro-5H-dibenzo[b,e][1,4]diazepin-8-yl]-N,N-dimethylacetamide The desired product was prepared by substituting Example 383B and N,N-dimethylamine hydrochloride for dimethylaminoacetic acid and Example 120, respectively, in Example 122. MS (DCI) m/e 391 (M+H)$^+$.

EXAMPLE 384B

N,N-dimethyl-2-[11-oxo-3-(2-oxo-1,2-dihydropyridin-4-yl)-10,11-dihydro-5H-dibenzo[b,e][1,4]diazepin-8-yl]acetamide The desired product was prepared by substituting Example 384A for Example 69D in Example 70. MS (DCI) m/e 389 (M+H)$^+$, $^1$H NMR (500 MHz, DMSO-d$_6$): ☐ 9.84 (s, 1H), 7.88 (s, 1H), 7.74 (d, J=8.42 Hz, 1H), 7.46 (d, J=6.86 Hz, 1H), 7.28 (d, J=1.56 Hz, 1H), 7.16 (dd, J=8.11, 1.56 Hz, 1H), 6.91 (d, J=8.11 Hz, 1H), 6.80-6.83 (m, 2H), 6.51 (s, 1H), 6.40 (m, 1H), 3.53 (s, 2H), 2.96 (s, 3H), 2.80 (s, 3H).

EXAMPLE 385

8-(2-morpholin-4-yl-2-oxoethyl)-3-(2-oxo-1,2-dihydropyridin-4-yl)-5,10-dihydro-11H-dibenzo[b,e][1,4]diazepin-11-one

EXAMPLE 385A 3-(2-fluoropyridin-4-yl)-8-(2-morpholin-4-yl-2-oxoethyl)-5,10-dihydro-11H-dibenzo[b,e][1,4]diazepin-11-one The desired product was prepared by substituting Example 383B and morpholine for dimethylaminoacetic acid and Example 120, respectively, in Example 122. MS (DCI) m/e 433 (M+H)$^+$.

EXAMPLE 385B 8-(2-morpholin-4-yl-2-oxoethyl)-3-(2-oxo-1,2-dihydropyridin-4-yl)-5,10-dihydro-11H-dibenzo[b,e][1,4]diazepin-11-one The desired product was prepared by substituting Example 385A for Example 69D in Example 70. MS (DCI) m/e 431 (M+H)$^+$, $^1$H NMR (500 MHz, DMSO-d$_6$): ☐ 9.86 (s, 1H), 7.89 (s, 1H), 7.74 (d, J=8.11 Hz, 1H), 7.47 (d, J=6.55 Hz, 1H), 7.28 (d, J=1.56 Hz, 1H), 7.16 (dd, J=8.26, 1.72 Hz, 1H), 6.92 (d, J=8.42 Hz, 1H), 6.80-6.82 (m, 2H), 6.52 (d, J=1.25 Hz, 1H), 6.41 (dd, J=6.86, 1.56 Hz, 1H), 3.57 (s, 2H), 3.52-3.53 (m, 2H), 3.48-3.50 (m, 2H), 3.43-3.45 (m, 4H).

EXAMPLE 386

N-(4-morpholin-4-ylphenyl)-2-[11-oxo-3-(2-oxo-1,2-dihydropyridin-4-yl)-10,11-dihydro-5H-dibenzo[b,e][1,4]diazepin-8-yl]acetamide

EXAMPLE 386A

2-[3-(2-fluoropyridin-4-yl)-11-oxo-10,11-dihydro-5H-dibenzo[b,e][1,4]diazepin-8-yl]N(4-morpholin-4-ylphenyl)acetamide The desired product was prepared by substituting Example 383B and 4 (4-morpholinyl)aniline for dimethylaminoacetic acid and Example 120, respectively, in Example 122. MS (DCI) m/e 524 (M+H)$^+$.

EXAMPLE 386B

N-(4-morpholin-4-ylphenyl)-2-[11-oxo-3-(2-oxo-1,2-dihydropyridin-4-yl)-10,11-dihydro-5H-dibenzo[b,e][1,4]diazepin-8-yl]acetamide The desired product was prepared by substituting Example 386A for Example 69D in Example 70. MS (DCI) m/e 522 (M+H)$^+$, $^1$H NMR (500 MHz, DMSO-d$_6$): ☐ 9.88 (s, 1H), 9.86 (s, 1H), 7.89 (s, 1H), 7.74 (d, J=8.11 Hz, 1H), 7.46 (d, J=6.86 Hz, 1H), 7.43 (d, J=9.04 Hz, 2H), 7.28 (d, J=1.56 Hz, 1H), 7.16 (dd, J=8.11, 1.56 Hz, 1H), 6.90-6.94 (m, 3H), 6.87 (d, J=9.04 Hz, 2H), 6.51 (d, J=1.56 Hz, 1H), 6.40 (d, J=6.86 Hz, 1H), 3.70-3.72 (m, 4H), 3.45 (s, 2H), 3.01-3.03 (m, 4H).

EXAMPLE 387 methyl [11-oxo-3-(2-oxo-1,2-dihydropyridin-4-yl)-10,11-dihydro-5H-dibenzo[b,e][1,4]diazepin-8-yl]acetate The desired product was prepared by substituting Example 383A for Example 69D in Example 70. MS (DCI) m/e 376 (M+H)$^+$, $^1$H NMR (400 MHz, DMSO-d$_6$): ☐ 11.66 (s, 1H), 9.87 (s, 1H), 7.94 (s, 1H), 7.75 (d, J=8.29 Hz, 1H), 7.48 (d, J=6.75 Hz, 1H), 7.29 (s, 1H), 7.18 (d, J=7.67 Hz, 1H), 6.96 (m, 1H), 6.85-6.87 (m, 2H), 6.53 (s, 1H), 6.41 (d, J=6.75 Hz, 1H), 3.60 (s, 3H), 3.54 (s, 2H).

EXAMPLE 388 methyl [3-(3-methoxy-4-nitrophenyl)-11-oxo-10,11-dihydro-5H-dibenzo[b,e][[4]diazepin-7-yl]acetate

EXAMPLE 388A methyl (3-amino-4-nitrophenyl)acetate

Methyl (3-aminophenyl)acetate was treated with acetic anhydride to provide methyl[3-(acetylamino)phenyl]acetate. The desired product was prepared by substituting methyl[3-(acetylamino)phenyl]acetate for N-[4-(cyanomethyl)phenyl]acetamide in Example 6A. MS (DCI) m/e 211 (M+H)$^+$.

EXAMPLE 388B methyl 4-chloro-2-{[5-(2-methoxy-2-oxoethyl)-2-nitrophenyl]amino}benzoate The desired product was prepared by substituting Example 388A for methyl 3,4-diaminobenzoate in Example 1A. MS (APCI) m/e 379 (M+H)$^+$.

EXAMPLE 388C methyl 2-{[2-amino-5-(2-methoxy-2-oxoethyl)phenyl]amino}-4-chlorobenzoate The desired product was prepared by substituting Example 388B for Example 6B in Example 6C. MS (DCI) m/e 349 (M+H)$^+$.

EXAMPLE 388D methyl (3-chloro-11-oxo-10,11-dihydro-5H-dibenzo[b,e][1,4]diazepin-7-yl)acetate The desired product was prepared by substituting Example 388C for Example 5B in Example 5C. MS (DCI) m/e 317 (M+H)$^+$, 334 (M+NH$_4$)+, $^1$H NMR (500 MHz, DMSO-d$_6$): □ 9.88 (s, 1H), 8.05 (s, 1H), 7.68 (d, J=8.42 Hz, 1H), 7.07 (d, J=1.87 Hz, 1H), 6.93 (dd, J=8.58, 2.03 Hz, 1H), 6.88-6.91 (m, 2H), 6.82 (dd, J=8.11, 1.87 Hz, 1H), 3.60 (s, 3H), 3.56 (s, 2H).

EXAMPLE 388E methyl [3-(3-methoxy-4-nitrophenyl)-11-oxo-10,11-dihydro-5H-dibenzo[b,e][1,4]diazepin-7-yl]acetate The desired product was prepared by substituting Example 388D and Example 266G for Example 59B and Example 56A, respectively, in Example 59C. MS (DCI) m/e 434 (M+H)$^+$, $^1$H NMR (500 MHz, DMSO-d$_6$) □ 9.88 (s, 1H), 8.00-8.02 (m, 2H), 7.80 (d, J=8.11 Hz, 1H), 7.52 (d, J=1.56 Hz, 1H), 7.37 (d, J=1.56 Hz, 1H), 7.35 (dd, J=8.42, 1.56 Hz, 1H), 7.31 (dd, J=8.11, 1.87 Hz, 1H), 6.91-6.93 (m, 2H), 6.81 (dd, J=8.11, 1.87 Hz, 1H), 4.03 (s, 3H), 3.60 (s, 3H), 3.56 (s, 2H).

EXAMPLE 389

[3-(3-methoxy-4-nitrophenyl)-11-oxo-10,11-dihydro-5H-dibenzo[b,e][1,4]diazepin-7-yl]acetic acid The desired product was prepared by substituting Example 388E for Example 12 in Example 13. MS (DCI) m/e 420 (M+H)$^+$, $^1$H NMR (500 MHz, DMSO-d$_6$): □ 12.29 (s, 1H), 9.87 (s, 1H), 8.00-8.02 (m, 2H), 7.80 (d, J=7.80 Hz, 1H), 7.53 (d, J=1.53 Hz, 1H), 7.38 (d, J=1.84 Hz, 1H), 7.34 (dd, J=8.44, 1.69 Hz, 1H), 7.31 (dd, J=8.29, 1.53 Hz, 1H), 6.94 (d, J=1.84 Hz, 1H), 6.91 (d, J=8.29 Hz, 1H), 6.80 (dd, J=8.13, 1.69 Hz, 1H), 4.03 (s, 3H), 3.44 (s, 2H).

EXAMPLE 390

3-(3-methoxy-4-nitrophenyl)-7-(2-morpholin-4-yl-2-oxoethyl)-5,10-dihydro-11H-dibenzo[b,e][1,4]diazepin-11-one The desired product was prepared by substituting Example 389 and morpholine for dimethylaminoacetic acid and Example 120, respectively, in Example 122. MS (DCI) m/e 489 (M+H)$^+$, 506 (M+NH$_4$)+, $^1$H NMR (500 MHz, DMSO-d$_6$): □ 9.86 (s, 1H), 8.00-8.02 (m, 2H), 7.80 (d, J=8.42 Hz, 1H), 7.52 (d, J=1.56 Hz, 1H), 7.37 (d, J=1.56 Hz, 1H), 7.34 (dd, J=8.42, 1.56 Hz, 1H), 7.32 (m, 1H), 6.90-6.92 (m, 2H), 6.73 (m, 1H), 4.03 (s, 3H), 3.60 (s, 2H), 3.53 (d, J=4.37 Hz, 2H), 3.49 (d, J=4.37 Hz, 2H), 3.45 (d, J=4.37 Hz, 4H).

EXAMPLE 391

2-[3-(3-methoxy-4-nitrophenyl)-11-oxo-10,11-dihydro-5H-dibenzo[b,e][1,4]diazepin-7-yl]Npyridin-2-ylacetamide The desired product was prepared by substituting Example 389 and 2-aminopyridine for dimethylaminoacetic acid and Example 120, respectively, in Example 122. MS (DCI) m/e 496 (M+H)$^+$, $^1$H NMR (400 MHz, DMSO-d$_6$): □ 10.59 (s, 1H), 9.80 (s, 1H), 8.24 (d, J=4.60 Hz, 1H), 7.92-7.98 (m, 3H), 7.67-7.74 (m, 2H), 7.45 (d, J=1.23 Hz, 1H), 7.31 (d, J=1.53 Hz, 1H), 7.27 (dd, J=8.29, 1.53 Hz, 1H), 7.23 (dd, J=8.29, 1.53 Hz, 1H), 7.03 (dd, J=6.90, 5.37 Hz, 1H), 6.93 (S, 1H), 6.81-6.87 (m, 2H), 3.96 (s, 3H), 3.55 (s, 2H).

EXAMPLE 392

2-[3-(3-methoxy-4-nitrophenyl)-11-oxo-10,11-dihydro-5H-dibenzo[b,e][1,4]diazepin-7-yl]Npyridin-3-ylacetamide The desired product was prepared by substituting Example 389 and 3-aminopyridine for dimethylaminoacetic acid and Example 120, respectively, in Example 122. MS (DCI) m/e 496 (M+H)$^+$, $^1$H NMR (400 MHz, DMSO-d$_6$): □ 10.46 (s, 1H), 9.81 (s, 1H), 8.80 (s, 1H), 8.28 (d, J=4.60 Hz, 1H), 8.07 (d, J=8.29 Hz, 1H), 7.97 (s, 1H), 7.94 (d, J=8.29 Hz, 1H), 7.73 (d, J=8.29 Hz, 1H), 7.42-7.45 (m, 2H), 7.30 (d, J=1.53 Hz, 1H), 7.27 (dd, J=8.29, 1.53 Hz, 1H), 7.24 (dd, J=8.29, 1.53 Hz, 1H), 6.93 (s, 1H), 6.80-6.88 (m, 2H), 3.96 (s, 3H), 3.53 (s, 2H).

EXAMPLE 393

2-[3-(3-methoxy-4-nitrophenyl)-11-oxo-10,11-dihydro-5H-dibenzo[b,e][1,4]diazepin-7-yl]Npyridin-4-ylacetamide The desired product was prepared by substituting Example 389 and 4-aminopyridine for dimethylaminoacetic acid and Example 120, respectively, in Example 122. MS (DCI) m/e 496 (M+H)$^+$, $^1$H NMR (500 MHz, DMSO-d$_6$): □ 11.21 (s, 1H), 9.83 (s, 1H), 8.57 (s, 1H), 8.55 (s, 1H), 7.98 (s, 1H), 7.94

(d, J=8.59 Hz, 1H), 7.88 (s, 1H), 7.86 (s, 1H), 7.74 (d, J=8.29 Hz, 1H), 7.45 (d, J=1.53 Hz, 1H), 7.30 (d, J=1.53 Hz, 1H), 7.23-7.28 (m, 2H), 6.92 (d, J=1.23 Hz, 1H), 6.88 (m, 1H), 6.82 (m, 1H), 3.96 (s, 3H), 3.63 (s, 2H).

EXAMPLE 394

7-[2-(4-hydroxypiperidin-1-yl)-2-oxoethyl]-3-(3-methoxy-4-nitrophenyl)-5,10-dihydro-11H-dibenzo[b,e][1,4]diazepin-11-one The desired product was prepared by substituting Example 389 and 4-piperidinol for dimethylaminoacetic acid and Example 120, respectively, in Example 122. MS (DCI) m/e 503 (M+H)$^+$, $^1$H NMR (400 MHz, DMSO-d$_6$): □ 9.78 (s, 1H), 7.93-7.95 (m, 2H), 7.73 (d, J=8.29 Hz, 1H), 7.45 (d, J=1.84 Hz, 1H), 7.30 (d, J=1.84 Hz, 1H), 7.28 (dd, J=8.59, 1.84 Hz, 1H), 7.23 (dd, J=8.29, 1.84 Hz, 1H), 6.82-6.84 (m, 2H), 6.71 (dd, J=7.98, 1.84 Hz, 1H), 3.97 (s, 3H), 3.85 (m, 1H), 3.51 (s, 2H), 3.03-3.10 (m, 2H), 2.89-2.96 (m, 2H), 1.53-1.62 (m, 2H), 1.08-1.20 (m, 2H).

EXAMPLE 395

7-[2-(3-hydroxypiperidin-1-yl)-2-oxoethyl]-3-(3-methoxy-4-nitrophenyl)-5,10-dihydro-11H-dibenzo[b,e][1,4]diazepin-11-one The desired product was prepared by substituting Example 389 and 3-piperidinol for dimethylaminoacetic acid and Example 120, respectively, in Example 120. MS (DCI) m/e 503 (M+H)$^+$, $^1$H NMR (400 MHz, DMSO-d$_6$): □ 9.85 (s, 1H), 8.00-8.02 (m, 2H), 7.80 (d, J=8.29 Hz, 1H), 7.52 (d, J=1.53 Hz, 1H), 7.37 (d, J=1.53 Hz, 1H), 7.34 (dd, J=8.44, 1.69 Hz, 1H), 7.30 (dd, J=8.29, 1.84 Hz, 1H), 6.84-6.91 (m, 2H), 6.77 (m, 1H), 4.03 (s, 3H), 3.64 (m, 1H), 3.57 (s, 2H), 3.27-3.38 (m, 2H), 2.93-3.10 (m, 2H), 1.58-1.82 (m, 2H), 1.18-1.4 (m, 2H).

EXAMPLE 396

2-[3-(3-methoxy-4-nitrophenyl)-11-oxo-10,11-dihydro-5H-dibenzo[b,e][1,4]diazepin-7-yl]N(pyridin-3-ylmethyl)acetamide The desired product was prepared by substituting Example 389 and pyridin-3-ylmethylamine for dimethylaminoacetic acid and Example 120, respectively, in Example 122. MS (DCI) m/e 510 (M+H)$^+$, $^1$H NMR (500 MHz, DMSO-d$_6$): □ 9.79 (s, 1H), 8.51-8.54 (m, 3H), 7.94-7.95 (m, 2H), 7.88 (d, J=7.80 Hz, 1H), 7.73 (d, J=8.11 Hz, 1H), 7.53 (dd, J=7.80, 5.30 Hz, 1H), 7.46 (d, J=1.56 Hz, 1H), 7.31 (d, J=1.56 Hz, 1H), 7.28 (dd, J=8.42, 1.87 Hz, 1H), 7.24 (dd, J=8.26, 1.72 Hz, 1H), 6.88 (d, J=1.56 Hz, 1H), 6.84 (d, J=8.11 Hz, 1H), 6.75 (dd, J=8.11, 1.82 Hz, 1H), 4.28 (d, J=5.93 Hz, 1H), 3.97 (s, 3H), 3.32 (s, 2H).

EXAMPLE 397

2-[3-(3-methoxy-4-nitrophenyl)-11-oxo-10,11-dihydro-5H-dibenzo[b,e][1,4]diazepin-7-yl]N(pyridin-4-ylmethyl)acetamide The desired product was prepared by substituting Example 389 and pyridin-4-ylmethylamine for dimethylaminoacetic acid and Example 120, respectively, in Example 120. MS (DCI) m/e 510 (M+H)$^+$, $^1$H NMR (500 MHz, DMSO-d$_6$): □ 9.86 (s, 1H), 8.65-8.69 (m, 3H), 7.99-8.01 (m, 2H), 7.79 (d, J=8.11 Hz, 1H), 7.57 (s, 1H), 7.56 (s, 1H), 7.51 (d, J=1.56 Hz, 1H), 7.37 (d, J=1.87 Hz, 1H), 7.33 (dd, J=8.42, 1.56 Hz, 1H), 7.30 (dd, J=8.26, 1.72 Hz, 1H), 6.96 (d, J=1.56 Hz, 1H), 6.91 (d, J=8.11 Hz, 1H), 6.84 (dd, J=8.11, 1.56 Hz, 1H), 4.42 (d, J=5.93 Hz, 1H), 4.02 (s, 3H), 3.43 (s, 2H).

EXAMPLE 398

2-[3-(3-methoxy-4-nitrophenyl)-11-oxo-10,11-dihydro-5H-dibenzo[b,e][1,4]diazepin-7-yl]N(pyridin-2-ylmethyl)acetamide The desired product was prepared by substituting Example 389 and pyridin-2-ylmethylamine for dimethylaminoacetic acid and Example 120, respectively, in Example 122. MS (DCI) m/e 510 (M+H)$^+$, $^1$H NMR (500 MHz, DMSO-d$_6$): □ 9.86 (s, 1H), 8.60 (t, J=5.93 Hz, 1H), 8.54 (d, J=4.68 Hz, 1H), 8.00-8.02 (m, 2H), 7.84 (t, J=7.80 Hz, 1H), 7.80 (d, J=8.42 Hz, 1H), 7.52 (d, J=1.56 Hz, 1H), 7.38 (d, J=1.87 Hz, 1H), 7.30-7.35 (m, 4H), 6.97 (d, J=1.56 Hz, 1H), 6.91 (m, 1H), 6.84 (dd, J=8.11, 1.87 Hz, 1H), 4.39 (d, J=5.93 Hz, 1H), 4.03 (s, 3H), 3.42 (s, 2H).

EXAMPLE 399

7-(2-azetidin-1-yl-2-oxoethyl)-3-(3-methoxy-4-nitrophenyl)-5,10-dihydro-11H-dibenzo[b,e][1,4]diazepin-11-one The desired product was prepared by substituting Example 389 and azetidine for dimethylaminoacetic acid and Example 120, respectively, in Example 122. MS (DCI) m/e 459 (M+H)$^+$, $^1$H NMR (500 MHz, DMSO-d$_6$): □ 9.88 (s, 1H), 8.01-8.03 (m, 2H), 7.80 (d, J=8.24 Hz, 1H), 7.53 (d, J=1.53 Hz, 1H), 7.37 (d, J=1.53 Hz, 1H), 7.35 (dd, J=8.39, 1.68 Hz, 1H), 7.31 (dd, J=8.24, 1.83 Hz, 1H), 6.92 (d, J=1.53 Hz, 1H), 6.89 (d, J=8.24 Hz, 1H), 6.77 (dd, J=8.09, 1.68 Hz, 1H), 4.15 (t, J=7.63 Hz, 2H), 4.04 (s, 3H), 3.82 (t, J=7.63 Hz, 2H), 3.27 (s, 2H), 2.13-2.20 (m, 2H).

EXAMPLE 400

1-{[3-(3-methoxy-4-nitrophenyl)-11-oxo-10,11-dihydro-5H-dibenzo[b,e][1,4]diazepin-7-yl]acetyl}piperidine-3-carboxamide The desired product was prepared by substituting Example 389 and piperidine-3-carboxamide for dimethylaminoacetic acid and Example 120, respectively, in Example 122. MS (DCI) m/e 530 (M+H)$^+$, $^1$H NMR (500 MHz, DMSO-d$_6$): □ 9.88 (d, J=2.44 Hz, 1H), 8.00-8.02 (m, 2H), 7.80 (d, J=8.24 Hz, 1H), 7.53 (d, J=1.53 Hz, 1H), 7.37 (s, 1H), 7.35 (dd, J=8.54, 1.22 Hz, 1H), 7.30-7.32 (m, 2H), 6.75-6.92 (m, 4H), 4.26 (m, 1H), 4.03 (s, 3H), 3.85 (m, 1H), 3.56-3.68 (m, 2H), 3.01 (m, 1H), 2.60 (m, 1H), 2.15 (m, 1H), 1.84 (m, 1H), 1.47-1.64 (m, 2H), 1.23 (m, 1H).

EXAMPLE 401

1-{[3-(3-methoxy-4-nitrophenyl)-1-oxo-10,11-dihydro-5H-dibenzo[b,e][1,4]diazepin-7-yl]acetyl}piperidine-4-carboxamide The desired product was prepared by substituting Example 389 and piperidine-4-carboxamide for dimethylaminoacetic acid and Example 120, respectively, in Example 122. MS (DCI) m/e 528 (M+H)+, 1H NMR (500 MHz, DMSO-d6): □ 9.87 (s, 1H), 8.00-8.02 (m, 2H), 7.80 (d, J=8.24 Hz, 1H), 7.53 (d, J=1.53 Hz, 1H), 7.37 (d, J=1.53 Hz, 1H), 7.35 (dd, J=8.39, 1.68 Hz, 1H), 7.30 (dd, J=8.09, 1.68 Hz, 1H), 7.25 (s, 1H), 6.90 (m, 2H), 6.77-6.79 (m, 2H), 4.33 (d, J=12.82 Hz, 1H), 4.03 (s, 3H), 3.91 (d, J=13.43, 1H), 3.55-3.62 (m, 2H), 2.98 (t, J=11.75 Hz, 1H), 2.59 (m, 1H), 2.29 (m, 1H), 1.64-1.70 (m, 2H), 1.29-1.39 (m, 2H).

EXAMPLE 402

7-{2-[(2R)-2-(hydroxymethyl)pyrrolidin-1-yl]-2-oxoethyl}-3-(3-methoxy-4-nitrophenyl)-5,10-dihydro-11H-dibenzo[b,e][1,4]diazepin-11-one The desired product was prepared by substituting Example 389 and (2R)-2-pyrrolidinylmethanol for dimethylaminoacetic acid and Example 120, respectively, in Example 122. MS (ESI) m/e 503 (M+H)+, 1H NMR (500 MHz, DMSO-d6): □ 9.85 (s, 1H), 7.99-8.02 (m, 2H), 7.80 (d, J=8.42 Hz, 1H), 7.52 (d, J=1.56 Hz, 1H), 7.37 (d, J=1.56 Hz, 1H), 7.34 (dd, J=8.42, 1.56 Hz, 1H), 7.30 (dd, J=8.42, 1.56 Hz, 1H), 6.88-6.93 (m, 2H), 6.77 (dd, J=8.11, 1.56 Hz, 1H), 4.03 (s, 3H), 3.93 (m, 1H), 3.40-3.68 (m, 6H), 1.77-1.90 (m, 4H).

EXAMPLE 403

2-[3-(3-methoxy-4-nitrophenyl)-11-oxo-10,11-dihydro-5H-dibenzo[b,e][1,4]diazepin-7-yl]-N,N-dimethylacetamide The desired product was prepared by substituting Example 389 and N,N-dimethylamine hydrochloride for dimethylaminoacetic acid and Example 120, respectively, in Example 122. MS (DCI) m/e 447 (M+H)+, 1H NMR (500 MHz, DMSO-d6): □ 9.85 (s, 1H), 8.00 (m, 2H), 7.80 (d, J=8.11 Hz, 1H), 7.52 (d, J=1.56 Hz, 1H), 7.37 (d, J=1.56 Hz, 1H), 7.34 (dd, J=8.42, 1.56 Hz, 1H), 7.30 (dd, J=8.11 Hz, 8.42, 1.56 Hz, 1H), 6.89-6.91 (m, 2H), 6.78 (dd, J=7.95, 1.72 Hz, 1H), 4.03 (s, 3H), 3.56 (s, 2H), 2.98 (s, 3H), 2.82 (s, 3H).

EXAMPLE 404

N,N-bis(2-methoxyethyl)-2-[3-(3-methoxy-4-nitrophenyl)-11-oxo-10,11-dihydro-5H-dibenzo[b,e][1,4]diazepin-7-yl]acetamide The desired product was prepared by substituting Example 389 and N,N-bis(2-methoxyethyl)amine for dimethylaminoacetic acid and Example 120, respectively, in Example 122. MS (ESI) m/e 535 (M+H)+, 1H NMR (500 MHz, DMSO-d6): □ 9.85 (s, 1H), 7.98-8.01 (m, 2H), 7.80 (d, J=8.11 Hz, 1H), 7.52 (s, 1H), 7.37 (d, J=1.56 Hz, 1H), 7.34 (dd, J=8.42, 1.56 Hz, 1H), 7.30 (dd, J=8.26, 1.72 Hz, 1H), 6.88-6.90 (m, 2H), 6.75 (d, J=8.11 Hz, 1H), 4.03 (s, 3H), 3.60 (s, 2H), 3.40-3.50 (m, 8H), 3.26 (s, 3H), 3.20 (s, 3H).

EXAMPLE 405

2-[3-(3-methoxy-4-nitrophenyl)-11-oxo-10,11-dihydro-5H-dibenzo[b,e][1,4]diazepin-7-yl]N[(2S)-tetrahydrofuran-2-ylmethyl]acetamide The desired product was prepared by substituting Example 389 and (2S)-tetrahydrofuran-2-ylmethylamine for dimethylaminoacetic acid and Example 120, respectively, in Example 122. MS (ESI) m/e 503 (M+H)+, 1H NMR (500 MHz, DMSO-d6): □ 9.84 (s, 1H),

EXAMPLE 406

2-[3-(3-methoxy-4-nitrophenyl)-11-oxo-10,11-dihydro-5H-dibenzo[b,e][1,4]diazepin-7-yl]N(2-propoxyethyl)acetamide The desired product was prepared by substituting Example 389 and 2-propoxyethylamine for dimethylaminoacetic acid and Example 120, respectively, in Example 122. MS (DCI) m/e 505 (M+H)+, 1H NMR (500 MHz, DMSO-d6): □ 9.84 (s, 1H), 7.99-8.02 (m, 3H), 7.79 (d, J=8.11 Hz, 1H), 7.52 (d, J=1.25 Hz, 1H), 7.38 (d, J=1.37 Hz, 1H), 7.34 (dd, J=8.42, 1.56 Hz, 1H), 7.30 (dd, J=8.26, 1.72 Hz, 1H), 6.93 (d, J=1.25 Hz, 2H), 6.88 (d, J=8.11 Hz, 1H), 6.80 (dd, J=8.11, 1.56 Hz, 1H), 4.03 (s, 3H), 3.28-3.37 (m, 6H), 3.18 (q, J=5.82 Hz, 2H), 1.43-1.50 (m, 2H), 0.81 (t, J=7.33 Hz, 3H).

EXAMPLE 407

7-{2-[(2S)-2-(hydroxymethyl)pyrrolidin-1-yl]-2-oxoethyl}-3-(3-methoxy-4-nitrophenyl)-5,10-dihydro-11H-dibenzo[b,e][1,4]diazepin-11-one The desired product was prepared by substituting Example 389 and (2S)-2-pyrrolidinylmethanol for dimethylaminoacetic acid and Example 120, respectively, in Example 122. MS (DCI) m/e 503 (M+H)+, 1H NMR (500 MHz, DMSO-d6): □ 9.85 (s, 1H), 7.99-8.02 (m, 2H), 7.80 (d, J=8.11 Hz, 1H), 7.52 (s, 1H), 7.33-7.37 (m, 2H), 7.30 (d, J=8.42 Hz, 1H), 6.89-6.92 (m, 2H), 6.77 (d, J=7.80 Hz, 1H), 4.03 (s, 3H), 3.93 (m, 1H), 3.40-3.68 (m, 6H), 1.77-1.87 (m, 4H).

EXAMPLE 408

7-[2-(3-aminopyrrolidin-1-yl)-2-oxoethyl]-3-(3-methoxy-4-nitrophenyl)-5,10-dihydro-11H-dibenzo[b,e][1,4]diazepin-11-one The desired product was prepared by substituting Example 389 and tert-butyl pyrrolidin-3-ylcarbamate for dimethylaminoacetic acid and Example 120, respectively, in Example 122. Isolated material was then treated with trifluoracetic acid at room temperature to provide the desired product. MS (DCI) m/e 488 (M+H)+, 1H NMR (500 MHz, DMSO-d6): □ 9.87 (d, J=4.37 Hz, 1H), 8.00-8.02 (m, 4H), 7.81 (d, J=8.11 Hz, 1H), 7.52 (s, 1H), 7.38 (s, 1H), 7.34 (dd, J=8.42, 1.25 Hz, 1H), 7.31 (dd, J=8.11, 1.56 Hz, 1H), 6.90-6.94 (m, 2H), 6.77-6.81 (m, 1H), 4.03 (s, 3H), 3.65-3.85 (m, 2H), 3.47-3.56 (m, 4H), 1.84-2.27 (m, 3H).

EXAMPLE 409

3-(3-methoxy-4-nitrophenyl)-7-(2-oxo-2-piperazin-1-ylethyl)-5,10-dihydro-11H-dibenzo[b,e][1,4]diazepin-11-one The desired product was prepared by substituting Example 389 and tert-butyl piperazine-1-carboxylate for dimethylaminoacetic acid and Example 120, respectively, in Example 122. Isolated material was then treated with trifluoracetic acid at room temperature to provide the desired product. MS (DCI) m/e 488 (M+H)+, 1H NMR (500 MHz, DMSO-d6): □ 9.88 (s, 1H), 8.77 (s, 1H), 8.00-8.02 (m, 2H), 7.81 (d, J=8.42 Hz, 1H), 7.52 (d, J=1.56 Hz, 1H), 7.37 (d, J=1.56 Hz, 1H), 7.34 (dd, J=8.42, 1.87 Hz, 1H), 7.31 (dd, J=8.26, 1.72 Hz, 1H), 6.92 (d, J=8.11 Hz, 1H), 6.89 (d, J=1.56 Hz, 1H), 6.79 (dd, J=8.11, 1.56 Hz, 1H), 4.03 (s, 3H), 3.62-3.69 (m, 6H), 3.04-3.09 (m, 4H).

Example 410 to Example 439 were prepared using the same procedure as Example 80 to Example 118 except substituting Example 389 for Example 73.

EXAMPLE 410

2-[3-(3-methoxy-4-nitrophenyl)-11-oxo-10,11-dihydro-5H-dibenzo[b,e][1,4]diazepin-7-yl]N(3-methoxypropyl)acetamide The desired product was prepared using 3-methoxypropylamine. MS (ESI) m/e 491 (M+H)⁺, ¹H NMR (500 MHz, DMSO-d₆): ☐ 9.84 (s, 1H), 7.99-8.02 (m, 2H), 7.93 (t, J=5.61 Hz, 1H), 7.80 (d, J=8.11 Hz, 1H), 7.52 (d, J=1.56 Hz, 1H), 7.38 (d, J=1.56 Hz, 1H), 7.34 (dd, J=8.42, 1.87 Hz, 1H), 7.30 (dd, J=8.11, 1.87 Hz, 1H), 6.93 (d, J=1.56 Hz, 1H), 6.89 (d, J=8.11 Hz, 1H), 6.79 (dd, J=7.95, 1.72 Hz, 1H), 4.03 (s, 3H), 3.28 (d, J=6.24 Hz, 2H), 3.18 (s, 3H), 3.05-3.09 (m, 2H), 1.58-1.64 (m, 2H).

EXAMPLE 411

N-(cyanomethyl)-2-[3-(3-methoxy-4-nitrophenyl)-11-oxo-10,11-dihydro-5H-dibenzo[b,e][1,4]diazepin-7-yl]acetamide The desired product was prepared using aminoacetonitrile. MS (ESI) m/e 458 (M+H)⁺, ¹H NMR (500 MHz, DMSO-d₆): ☐ 9.86 (s, 1H), 8.66 (t, J=5.46 Hz, 1H), 8.00-8.02 (m, 2H), 7.80 (d, J=8.42 Hz, 1H), 7.52 (d, J=1.56 Hz, 1H), 7.38 (d, J=1.56 Hz, 1H), 7.34 (dd, J=8.42, 1.56 Hz, 1H), 7.30 (dd, J=8.11, 1.56 Hz, 1H), 6.93 (d, J=1.56 Hz, 1H), 6.91 (d, J=8.11 Hz, 1H), 6.80 (dd, J=8.11, 1.56 Hz, 1H), 4.11 (d, J=5.61 Hz, 2H), 4.03 (s, 3H), 3.38 (s, 2H).

EXAMPLE 412

N-(cyclopropylmethyl)-2-[3-(3-methoxy-4-nitrophenyl)-1-oxo-10,11-dihydro-5H-dibenzo[b,e][1,4]diazepin-7-yl]acetamide The desired product was prepared using cyclopropylmethylamine. MS (ESI) m/e 473 (M+H)⁺, ¹H NMR (500 MHz, DMSO-d₆): ☐ 9.84 (s, 1H), 7.99-8.05 (m, 3H), 7.80 (d, J=8.11 Hz, 1H), 7.52 (d, J=1.56 Hz, 1H), 7.38 (d, J=1.56 Hz, 1H), 7.34 (dd, J=8.42, 1.87 Hz, 1H), 7.30 (dd, J=8.11, 1.87 Hz, 1H), 6.95 (d, J=1.56 Hz, 1H), 6.89 (d, J=7.80 Hz, 1H), 6.80 (dd, J=8.11, 1.56 Hz, 1H), 4.04 (s, 3H), 2.92-2.94 (m, 2H), 2.50 (s, 2H), 0.88 (m, 1H), 0.37-0.41 (m, 2H), 0.12-0.15 (m, 2H).

EXAMPLE 413

N-(1,3-dioxolan-2-ylmethyl)-2-[3-(3-methoxy-4-nitrophenyl)-11-oxo-10,11-dihydro-5H-dibenzo[b,e][1,4]diazepin-7-yl]Nmethylacetamide The desired product was prepared using N-(1,3-dioxolan-2-ylmethyl)Nmethylamine. MS (ESI) m/e 519 (M+H)⁺, ¹H NMR (500 MHz, DMSO-d₆): ☐ 9.85 (s, 1H), 7.99-8.02 (m, 2H), 7.80 (d, J=8.11 Hz, 1H), 7.52 (d, J=1.56 Hz, 1H), 7.37 (s, 1H), 7.34 (d, J=8.42 Hz, 1H), 7.30 (d, J=8.42 Hz, 1H), 6.88-6.91 (m, 2H), 6.76 (m, 1H), 4.92 (m, 1H), 4.03 (s, 3H), 3.86-3.93 (m, 2H), 3.75-3.83 (m, 2H), 3.59-3.62 (m, 2H), 3.52 (d, J=3.74 Hz, 1H), 3.40 (d, J=4.68 Hz, 2H), 3.03 (s, 1H), 2.88 (s, 1H).

EXAMPLE 414

3-(3-methoxy-4-nitrophenyl)-7-(2-oxo-2-thiomorpholin-4-ylethyl)-5,10-dihydro-11H-dibenzo[b,e][1,4]diazepin-11-one The desired product was prepared using thiomorpholine. MS (ESI) m/e 505 (M+H)⁺, ¹H NMR (500 MHz, DMSO-d₆): ☐ 9.86 (s, 1H), 8.00-8.02 (m, 2H), 7.80 (d, J=8.11 Hz, 1H), 7.52 (d, J=1.56 Hz, 1H), 7.30-7.37 (m, 3H), 6.90-6.93 (m, 2H), 6.79 (dd, J=8.11, 1.87 Hz, 1H), 4.03 (s, 3H), 3.67-3.76 (m, 4H), 3.61 (d, J=2.18 Hz, 2H), 2.52-2.54 (m, 2H), 2.45-2.47 (m, 2H).

EXAMPLE 415

2-[3-(3-methoxy-4-nitrophenyl)-11-oxo-10,11-dihydro-5H-dibenzo[b,e][1,4]diazepin-7-yl]N(2-pyridin-3-ylethyl)acetamide The desired product was prepared using 2-pyridin-3-yl-ethylamine. MS (ESI) m/e 524 (M+H)⁺, ¹H NMR (500 MHz, DMSO-d₆): ☐ 9.85 (s, 1H), 8.64 (s, 1H), 8.05-8.07 (m, 2H), 7.98-8.02 (m, 2H), 7.80 (d, J=8.42 Hz, 1H), 7.67 (m, 1H), 7.52 (d, J=1.56 Hz, 1H), 7.38 (d, J=1.87 Hz, 1H), 7.34 (dd, J=8.42, 1.56 Hz, 1H), 7.31 (dd, J=8.26, 1.72 Hz, 1H), 6.87-6.90 (m, 2H), 6.72 (dd, J=8.11, 1.87 Hz, 1H), 4.03 (s, 3H), 3.33-3.37 (m, 2H), 3.24 (s, 2H), 2.85 (t, J=6.71 Hz, 2H).

EXAMPLE 416

2-[3-(3-methoxy-4-nitrophenyl)-11-oxo-10,11-dihydro-5H-dibenzo[b,e][1,4]diazepin-7-yl]N(2-pyridin-4-ylethyl)acetamide The desired product was prepared using 2-pyridin-4-yl-ethylamine. MS (ESI) m/e 524 (M+H)⁺, ¹H NMR (500 MHz, DMSO-d₆): ☐ 9.85 (s, 1H), 8.68 (d, J=6.24 Hz, 2H), 8.08 (t, J=5.61 Hz, 1H), 7.99-8.02 (m, 2H), 7.80 (d, J=8.11 Hz, 1H), 7.69 (d, J=6.24 Hz, 2H), 7.52 (d, J=1.56 Hz, 1H), 7.38 (d, J=1.56 Hz, 1H), 7.34 (dd, J=8.42, 1.56 Hz, 1H), 7.31 (dd, J=8.26, 1.72 Hz, 1H), 6.88-6.91 (m, 2H), 6.74 (dd, J=7.95, 1.72 Hz, 1H), 4.03 (s, 3H), 3.38-3.41 (m, 2H), 3.25 (s, 2H), 2.93 (t, J=6.86 Hz, 2H).

EXAMPLE 417

N-[2-(2,3-dimethoxyphenyl)ethyl]-2-[3-(3-methoxy-4-nitrophenyl)-11-oxo-10,11-dihydro-5H-dibenzo[b,e][1,4]diazepin-7-yl]acetamide The desired product was prepared using 2-(2,3-dimethoxyphenyl)ethylamine. MS (ESI) m/e 581 (M+H)⁺, ¹H NMR (500 MHz, DMSO-d₆): ☐ 9.85 (s, 1H), 7.99-8.04 (m, 3H), 7.80 (d, J=8.42 Hz, 1H), 7.52 (d, J=1.56 Hz, 1H), 7.38 (d, J=1.56 Hz, 1H), 7.34 (dd, J=8.42, 1.87 Hz, 1H), 7.31 (dd, J=8.26, 1.72 Hz, 1H), 6.84-6.93 (m, 4H), 6.77 (dd, J=7.95, 1.72 Hz, 1H), 6.68 (dd, J=7.64, 1.40 Hz, 1H), 4.03 (s, 3H), 3.76 (s, 3H), 3.69 (s, 3H), 3.27 (s, 2H), 3.19-3.23 (m, 2H), 2.66-2.69 (m, 2H).

EXAMPLE 418

N-[2-(1,3-benzodioxol-5-yl)ethyl]-2-[3-(3-methoxy-4-nitrophenyl)-11-oxo-10,11-dihydro-5H-dibenzo[b,e][1,4]diazepin-7-yl]acetamide The desired product was prepared using 2-benzo[1,3]dioxol-5-yl-ethylamine. MS (ESI) m/e 567 (M+H)⁺, ¹H NMR (500 MHz, DMSO-d$_6$): ☐ 9.84 (s, 1H), 7.96-8.01 (m, 3H), 7.80 (d, J=8.11 Hz, 1H), 7.52 (d, J=1.56 Hz, 1H), 7.38 (d, J=1.56 Hz, 1H), 7.34 (dd, J=8.42, 1.87 Hz, 1H), 7.30 (dd, J=8.26, 1.72 Hz, 1H), 6.92 (d, J=1.87 Hz, 1H), 6.88 (d, J=8.11 Hz, 1H), 6.74-6.76 (m, 3H), 6.59 (dd, J=7.80, 1.56 Hz, 1H), 5.93 (s, 2H), 4.03 (s, 3H), 3.26 (s, 2H), 3.19-3.23 (m, 2H), 2.60 (t, J=7.33 Hz, 2H).

EXAMPLE 419

2-[3-(3-methoxy-4-nitrophenyl)-11-oxo-10,11-dihydro-5H-dibenzo[b,e][1,4]diazepin-7-yl]N(thien-2-ylmethyl)acetamide The desired product was prepared using thien-2-ylmethylamine. MS (ESI) m/e 515 (M+H)$^+$, $^1$H NMR (500 MHz, DMSO-d$_6$): ☐ 9.85 (s, 1H), 8.56 (t, J=5.77 Hz, 1H), 8.00-8.02 (m, 2H), 7.80 (d, J=8.42 Hz, 1H), 7.52 (d, J=1.56 Hz, 1H), 7.38 (d, J=1.87 Hz, 1H), 7.34-7.36 (m, 2H), 7.30 (dd, J=8.26, 1.72 Hz, 1H), 6.89-6.95 (m, 4H), 6.81 (dd, J=8.11, 1.87 Hz, 1H), 4.41 (d, J=5.93 Hz, 2H), 4.03 (s, 3H), 3.34 (s, 2H).

EXAMPLE 420

2-[3-(3-methoxy-4-nitrophenyl)-11-oxo-10,11-dihydro-5H-dibenzo[b,e][1,4]diazepin-7-yl]N(1,3-thiazol-5-ylmethyl)acetamide The desired product was prepared using 1,3-thiazol-5-ylmethylamine. MS (ESI) m/e 516 (M+H)$^+$, $^1$H NMR (500 MHz, DMSO-d$_6$): ☐ 9.85 (s, 1H), 9.04 (d, J=1.87 Hz, 1H), 8.51 (t, J=5.46 Hz, 1H), 8.00-8.02 (m, 2H), 7.80 (d, J=8.11 Hz, 1H), 7.52 (d, J=1.56 Hz, 1H), 7.34-7.38 (m, 3H), 7.30 (dd, J=8.26, 1.72 Hz, 1H), 6.79-6.96 (m, 2H), 4.39 (d, J=5.61 Hz, 2H), 4.03 (s, 3H), 3.38 (s, 2H).

EXAMPLE 421

N-[2-(1H-imidazol-4-yl)ethyl]-2-[3-(3-methoxy-4-nitrophenyl)-11-oxo-10,11-dihydro-5H-dibenzo[b,e][1,4]diazepin-7-yl]acetamide The desired product was prepared using 2-(1H-imidazol-4-yl)ethylamine. MS (ESI) m/e 513 (M+H)$^+$, $^1$H NMR (500 MHz, DMSO-d$_6$): ☐ 9.85 (s, 1H), 8.96 (d, J=1.25 Hz, 1H), 8.12 (t, J=5.77 Hz, 1H), 7.99-8.02 (m, 2H), 7.80 (d, J=8.11 Hz, 1H), 7.52 (d, J=1.56 Hz, 1H), 7.38-7.40 (m, 2H), 7.34 (dd, J=8.42, 1.56 Hz, 1H), 7.31 (dd, J=8.27, 1.72 Hz, 1H), 6.91 (d, J=1.56 Hz, 1H), 6.89 (d, J=8.11 Hz, 1H), 6.75 (dd, J=8.11, 1.56 Hz, 1H), 4.03 (s, 3H), 3.31-3.35 (m, 2H), 3.27 (s, 2H), 3.17 (s, 1H), 2.77 (t, J=6.86 Hz, 2H).

EXAMPLE 422

7-[2-(1,4-dioxa-8-azaspiro[4.5]dec-8-yl)-2-oxoethyl]-3-(3-methoxy-4-nitrophenyl)-5,10-dihydro-11H-dibenzo[b,e][1,4]diazepin-11-one The desired product was prepared using 1,4-dioxa-8-azaspiro[4.5]decane. MS (ESI) m/e 545 (M+H)$^+$, $^1$H NMR (500 MHz, DMSO-d$_6$): ☐ 9.84 (s, 1H), 7.99-8.01 (m, 2H), 7.80 (d, J=8.11 Hz, 1H), 7.53 (d, J=1.25 Hz, 1H), 7.37 (d, J=1.56 Hz, 1H), 7.35 (dd, J=8.42, 1.56 Hz, 1H), 7.30 (dd, J=8.11, 1.56 Hz, 1H), 6.90-6.92 (m, 2H), 6.79 (d, J=8.11 Hz, 1H), 4.06 (s, 3H), 3.89 (s, 4H), 3.62 (s, 2H), 3.53 (d, J=5.61 Hz, 4H), 1.48-1.55 (m, 4H).

EXAMPLE 423

7-{2-[2,6-dimethylmorpholin-4-yl]-2-oxoethyl}-3-(3-methoxy-4-nitrophenyl)-5,10-dihydro-1H-dibenzo[b,e][1,4]diazepin-11-one The desired product was prepared using 2,6-dimethylmorpholine. MS (ESI) m/e 545 (M+H)$^+$, $^1$H NMR (500 MHz, DMSO-d$_6$): ☐ 9.86 (s, 1H), 7.99-8.02 (m, 2H), 7.80 (d, J=8.11 Hz, 1H), 7.53 (d, J=1.56 Hz, 1H), 7.39 (d, J=1.56 Hz, 1H), 7.34 (dd, J=8.58, 1.72 Hz, 1H), 7.29 (dd, J=8.27, 1.72 Hz, 1H), 6.89-6.93 (m, 2H), 6.80 (m, 1H), 4.26 (d, J=13.10 Hz, 1H), 4.03 (s, 3H), 3.84 (d, J=13.10 Hz, 1H), 3.58 (m, 3H), 3.16 (m, 1H), 2.64 (dd, J=12.94, 10.76 Hz, 1H), 2.25 (dd, J=12.94, 11.07 Hz, 1H), 1.06 (m, 6H).

EXAMPLE 424

7-[2-(4-acetylpiperazin-1-yl)-2-oxoethyl]-3-(3-methoxy-4-nitrophenyl)-5,10-dihydro-11H-dibenzo[b,e][1,4]diazepin-11-one The desired product was prepared using 1-acetylpiperazine. MS (ESI) m/e 530 (M+H)$^+$, $^1$H NMR (500 MHz, DMSO-d$_6$): ☐ 9.83 (s, 1H), 7.99-8.02 (m, 2H), 7.81 (d, J=8.11 Hz, 1H), 7.51 (d, J=1.25 Hz, 1H), 7.37 (d, J=1.56 Hz, 1H), 7.34 (dd, J=8.42, 1.56 Hz, 1H), 7.29 (dd, J=8.11, 1.87 Hz, 1H), 6.90-6.92 (m, 2H), 6.79 (m, 1H), 4.08 (s, 3H), 3.64 (d, J=7.17 Hz, 2H), 3.35-3.51 (m, 8H), 1.97 (d, J=3.12 Hz, 3H).

EXAMPLE 425

3-(3-methoxy-4-nitrophenyl)-7-[2-oxo-2-(4-pyridin-2-ylpiperazin-1-yl)ethyl]-5,10-dihydro-11H-dibenzo[b,e][1,4]diazepin-11-one The desired product was prepared using 1-pyridin-2-ylpiperazine. MS (ESI) m/e 565 (M+H)$^+$, $^1$H NMR (500 MHz, DMSO-d$_6$): ☐ 9.87 (s, 1H), 8.06 (dd, J=5.46, 1.40 Hz, 1H), 7.99-8.01 (m, 2H), 7.81 (d, J=8.11 Hz, 1H), 7.75 (t, J=7.33 Hz, 1H), 7.52 (d, J=1.56 Hz, 1H), 7.36 (d, J=1.87 Hz, 1H), 7.33 (dd, J=8.42, 1.56 Hz, 1H), 7.30 (dd, J=8.26, 1.72 Hz, 1H), 7.05 (d, J=8.11 Hz, 1H), 6.91-6.93 (m, 2H), 6.78-6.82 (m, 2H), 4.03 (s, 3H), 3.67 (s, 2H), 3.60-3.65 (m, 4H), 3.54-3.59 (m, 4H).

EXAMPLE 426

3-({[3-(3-methoxy-4-nitrophenyl)-11-oxo-10,11-dihydro-5H-dibenzo[b,e][1,4]diazepin-7-yl]acetyl}amino)benzamide The desired product was prepared using 3-aminobenzamide. MS (ESI) m/e 537 (M+H)$^+$, $^1$H NMR (500 MHz, DMSO-d$_6$): ☐ 10.23 (s, 1H), 9.86 (s, 1H), 7.99-8.03 (m, 3H), 7.80 (d, J=8.42 Hz, 1H), 7.76 (dd, J=8.11, 1.25 Hz, 1H), 7.51-7.53 (m, 2H), 7.34-7.38 (m, 3H), 7.27-7.31 (m, 2H), 7.00 (d, J=1.25 Hz, 1H), 6.87-6.94 (m, 2H), 4.03 (s, 3H), 3.54 (s, 2H).

EXAMPLE 427

2-[3-(3-methoxy-4-nitrophenyl)-11-oxo-10,11-dihydro-5H-dibenzo[b,e][1,4]diazepin-7-yl]N(4-morpholin-4-ylphenyl)acetamide The desired product was prepared using 4-morpholin-4-ylphenylamine. MS (ESI) m/e 580 (M+H)$^+$, $^1$H NMR (500 MHz, DMSO-d$_6$): ☐ 9.89 (s, 1H), 9.86 (s, 1H), 7.99-8.02 (m, 2H), 7.80 (d, J=8.11 Hz, 1H), 7.52 (d, J=1.56 Hz, 1H), 7.45 (d, J=9.36 Hz, 2H), 7.37 (d, J=1.56 Hz, 1H), 7.34 (dd, J=8.42, 1.56 Hz, 1H), 7.30 (dd, J=8.27, 1.72 Hz, 1H), 6.99 (d, J=1.56 Hz, 1H), 6.85-6.93 (m, 4H), 4.03 (s, 3H), 3.71-3.73 (m, 4H), 3.48 (s, 2H), 3.01-3.03 (m, 4H).

EXAMPLE 428

2-[3-(3-methoxy-4-nitrophenyl)-11-oxo-10,11-dihydro-5H-dibenzo[b,e][1,4]diazepin-7-yl]Nquinolin-6-ylacetamide The desired product was prepared using quinolin-6-ylamine. MS (ESI) m/e 546 (M+H)+, 1H NMR (500 MHz, DMSO-$d_6$): □ 10.52 (s, 1H), 9.88 (s, 1H), 8.85 (m, 1H), 8.39-8.42 (m, 2H), 8.04 (s, 1H), 7.99-8.02 (m, 2H), 7.88 (dd, J=9.20, 2.03 Hz, 1H), 7.80 (d, J=8.11 Hz, 1H), 7.55-7.58 (m, 1H), 7.52 (d, J=1.56 Hz, 1H), 7.37 (d, J=1.87 Hz, 1H), 7.34 (dd, J=8.42, 1.87 Hz, 1H), 7.30 (dd, J=8.11, 1.87 Hz, 1H), 7.04 (m, 1H), 6.90-6.95 (m, 2H), 4.02 (s, 3H), 3.62 (s, 2H).

EXAMPLE 429

N-[(1S)-1-(hydroxymethyl)-2-methylpropyl]-2-[3-(3-methoxy-4-nitrophenyl)-11-oxo-10,11-dihydro-5H-dibenzo[b,e][1,4]diazepin-7-yl]acetamide The desired product was prepared using (S)-2-amino-3-methyl-1-butanol. MS (ESI) m/e 505 (M+H)+, 1H NMR (500 MHz, DMSO-$d_6$): □ 9.83 (s, 1H), 8.00-8.02 (m, 2H), 7.98 (s, 1H), 7.80 (d, J=8.11 Hz, 1H), 7.62 (d, J=9.04 Hz, 1H), 7.52 (d, J=1.25 Hz, 1H), 7.38 (d, J=1.56 Hz, 1H), 7.34 (dd, J=8.42, 1.87 Hz, 1H), 7.31 (dd, J=8.26, 1.72 Hz, 1H), 6.94 (d, J=1.56 Hz, 1H), 6.81-6.89 (m, 2H), 4.03 (s, 3H), 3.52-3.56 (m, 2H), 3.29-3.37 (m, 3H), 1.81 (m, 1H), 0.81 (dd, J=9.04, 6.86 Hz, 6H).

EXAMPLE 430

(2S)-2-({[3-(3-methoxy-4-nitrophenyl)-11-oxo-10,11-dihydro-5H-dibenzo[b,e][1,4]diazepin-7-yl]acetyl}amino)-4-methylpentanamide The desired product was prepared using L-leucine amide. MS (ESI) m/e 530 (M+H)+, 1H NMR (500 MHz, DMSO-$d_6$): □ 9.83 (s, 1H), 8.00-8.02 (m, 2H), 7.98 (s, 1H), 7.80 (d, J=8.11 Hz, 1H), 7.52 (d, J=1.56 Hz, 1H), 7.38 (d, J=1.56 Hz, 1H), 7.34 (dd, J=8.42, 1.56 Hz, 1H), 7.29-7.31 (m, 2H), 6.87-6.93 (m, 3H), 6.82 (m, 1H), 4.11 (m, 1H), 4.03 (s, 3H), 3.34-3.39 (m, 4H), 1.55 (m, 1H), 0.81 (d, J=6.85 Hz, 3H), 0.79 (d, J=6.55 Hz, 3H).

EXAMPLE 431

N-[(1S)-2-hydroxy-1-phenylethyl]-2-[3-(3-methoxy-4-nitrophenyl)-11-oxo-10,11-dihydro-5H-dibenzo[b,e][1,4]diazepin-7-yl]acetamide The desired product was prepared using (S)-phenylglycinol. MS (ESI) m/e 539 (M+H)+, 1H NMR (500 MHz, DMSO-$d_6$): □ 9.83 (s, 1H), 8.37 (d, J=8.11 Hz, 1H), 8.02 (d, J=8.42 Hz, 1H), 7.96 (s, 1H), 7.80 (d, J=8.11 Hz, 1H), 7.52 (d, J=1.56 Hz, 1H), 7.38 (d, J=1.87 Hz, 1H), 7.34 (dd, J=8.58, 1.72 Hz, 1H), 7.31 (dd, J=8.27, 1.72 Hz, 1H), 7.24-7.28 (m, 3H), 7.17 (m, 1H), 6.87-6.93 (m, 2H), 6.82 (m, 1H), 4.81 (m, 1H), 4.03 (s, 3H), 3.54-3.57 (m, 2H), 3.39 (d, J=3.12 Hz, 2H).

EXAMPLE 432

N-(2,3-dihydroxypropyl)-2-[3-(3-methoxy-4-nitrophenyl)-11-oxo-10,11-dihydro-5H-dibenzo[b,e][1,4]diazepin-7-yl]acetamide The desired product was prepared using 3-amino-propane-1,2-diol. MS (ESI) m/e 491 (M+H)+.

EXAMPLE 433

N-[3-(1H-imidazol-1-yl)propyl]-2-[3-(3-methoxy-4-nitrophenyl)-11-oxo-10,11-dihydro-5H-dibenzo[b,e][14]diazepin-7-yl]acetamide The desired product was prepared using 3-(1H-imidazol-1-yl)propylamine. MS (ESI) m/e 527 (M+H)+.

EXAMPLE 434

2-[3-(3-methoxy-4-nitrophenyl)-11-oxo-10,11-dihydro-5H-dibenzo[b,e][1,4]diazepin-7-yl]N[3-(2-oxopyrrolidin-1-yl)propyl]acetamide The desired product was prepared using 1-(3-aminopropyl)pyrrolidin-2-one. MS (ESI) m/e 544 (M+H)+.

EXAMPLE 435

N-(2,6-difluorobenzyl)-2-[3-(3-methoxy-4-nitrophenyl)-11-oxo-10,11-dihydro-5H-dibenzo[b,e][1,4]diazepin-7-yl]acetamide The desired product was prepared using 2,6-difluorobenzylamine. MS (ESI) m/e 545 (M+H)+.

EXAMPLE 436

N-{2-[4-(aminosulfonyl)phenyl]ethyl}-2-[3-(3-methoxy-4-nitrophenyl)-11-oxo-10,11-dihydro-5H-dibenzo[b,e][1,4]diazepin-7-yl]acetamide The desired product was prepared using 4-(2-aminoethyl)benzenesulfonamide. MS (ESI) m/e 602 (M+H)+.

EXAMPLE 437

N-[(1R)-1-(hydroxymethyl)-2-methylpropyl]-2-[3-(3-methoxy-4-nitrophenyl)-11-oxo-10,11-dihydro-5H-dibenzo[b,e][1,4]diazepin-7-yl]acetamide The desired product was prepared using (R)-2-amino-3-methyl-1-butanol. MS (ESI) m/e 505 (M+H)+.

EXAMPLE 438

N-[(1R)-2-hydroxy-1-phenylethyl]-2-[3-(3-methoxy-4-nitrophenyl)-11-oxo-10,11-dihydro-5H-dibenzo[b,e][1,4]diazepin-7-yl]acetamide The desired product was prepared using (R)-phenylglycinol. MS (ESI) m/e 539 (M+H)+.

EXAMPLE 439

2-[3-(3-methoxy-4-nitrophenyl)-11-oxo-10,11-dihydro-5H-dibenzo[b,e][1,4]diazepin-7-yl]N(thien-3-ylmethyl)acetamide The desired product was prepared using thien-3-ylmethylamine. MS (ESI) m/e 515 (M+H)$^+$.

EXAMPLE 440 methyl {3-[4-(aminocarbonyl)-3-methoxyphenyl]-11-oxo-10,11-dihydro-5H-dibenzo[b,e][1,4]diazepin-8-yl}acetate The desired product was prepared by substituting Example 54A and 4-chloro-2-methoxybenzamide for Example 56A and Example 59B, respectively, in Example 59C. MS (DCI) m/e 432 (M+H)$^+$, $^1$H NMR (500 MHz, DMSO-d$_6$): □ 9.84 (s, 1H), 7.96 (s, 1H), 7.90 (d, J=8.11 Hz, 1H), 7.78 (d, J=8.11 Hz, 1H), 7.66 (s, 1H), 7.54 (s, 1H), 7.34 (d, J=1.56 Hz, 1H), 7.32 (d, J=1.32 Hz, 1H), 7.26-7.29 (m, 2H), 6.96 (d, J=7.80 Hz, 1H), 6.84-6.87 (m, 2H), 3.99 (s, 3H), 3.60 (s, 3H), 3.54 (s, 2H).

EXAMPLE 441

8-hydroxy-3-(3-methoxy-4-nitrophenyl)-5,10-dihydro-11H-dibenzo[b,e][1,4]diazepin-11-one The desired product was prepared by substituting Example 8C and Example 266G for Example 59B and Example 56A, respectively, in Example 59C. MS (DCI) m/e 378 (M+H)$^+$, $^1$H NMR (500 MHz, DMSO-d$_6$): □ 9.80 (s, 1H), 9.12 (s, 1H), 8.00 (d, J=8.42 Hz, 1H), 7.77 (d, J=8.11 Hz, 1H), 7.66 (s, 1H), 7.52 (d, J=1.56 Hz, 1H), 7.34 (dd, J=8.58, 1.72 Hz, 1H), 7.32 (d, J=1.56 Hz, 1H), 7.26 (dd, J=8.27, 1.72 Hz, 1H), 6.82 (d, J=8.73 Hz, 1H), 6.45 (d, J=2.50 Hz, 1H), 6.38 (dd, J=8.58, 2.65 Hz, 1H), 4.03 (s, 3H).

EXAMPLE 442

8-methoxy-3-(3-methoxy-4-nitrophenyl)-5,10-dihydro-11H-dibenzo[b,e][1,4]diazepin-11-one

EXAMPLE 442A methyl 4-chloro-2-[(4-methoxy-2-nitrophenyl)amino]benzoate

The desired product was prepared by substituting 4-methoxy-2-nitroaniline for methyl 3,4-diaminobenzoate in Example 1A. MS (DCI) m/e 337 (M+H)$^+$, $^1$H NMR (500 MHz, DMSO-d$_6$): □ 10.46 (s, 1H), 7.93 (d, J=8.42 Hz, 1H), 7.65 (d, J=9.05 Hz, 1H), 7.62 (d, J=2.81 Hz, 1H), 7.37 (dd, J=9.20, 2.96 Hz, 1H), 7.20 (d, J=1.87 Hz, 1H), 6.99 (dd, J=8.58, 2.03 Hz, 1H), 3.89 (s, 3H), 3.86 (s, 3H).

EXAMPLE 442B methyl 2-[(2-amino-4-methoxyphenyl)amino]-4-chlorobenzoate

The desired product was prepared by substituting Example 442A for Example 6B in Example 6C. MS (DCI) m/e 307 (M+H)$^+$, $^1$H NMR (500 MHz, DMSO-d$_6$): □ 8.70 (s, 1H), 7.82 (d, J=8.73 Hz, 1H), 6.90 (d, J=8.42 Hz, 1H), 6.67 (dd, J=8.58, 2.03 Hz, 1H), 6.40 (d, J=2.81 Hz, 1H), 6.32 (d, J=2.18 Hz, 1H), 6.19 (dd, J=8.73, 2.81 Hz, 1H), 5.00 (s, 2H), 3.85 (s, 3H), 3.70 (s, 3H).

EXAMPLE 442C 3-chloro-8-methoxy-5,10-dihydro-11H-dibenzo[b,e][1,4]diazepin-11-one Example 442B was substituted for Example 12 in Example 13 to provide 2-(2-amino-4-methoxy-phenylamino)-4-chloro-benzoic acid. This material was then treated with 3 equivalents of HATU in DMF to provide the desired product. MS (DCI) m/e 275 (M+H)$^+$, $^1$H NMR (300 MHz, DMSO-d$_6$): □ 9.84 (s, 1H), 7.86 (s, 1H), 7.67 (d, J=8.48 Hz, 1H), 7.03 (d, J=2.03 Hz, 1H), 6.87-6.92 (m, 2H), 6.57-6.59 (m, 2H), 3.86 (s, 3H).

EXAMPLE 442D 8-methoxy-3-(3-methoxy-4-nitrophenyl)-5,10-dihydro-11H-dibenzo[b,e][1,4]diazepin-11-one The desired product was prepared by substituting Example 442C and Example 266G for Example 59B and Example 56A, respectively, in Example 59C. MS (DCI) m/e 392 (M+H)$^+$, $^1$H NMR (500 MHz, DMSO-d$_6$): □ 9.83 (s, 1H), 8.01 (d, J=8.29 Hz, 1H), 7.78-7.81 (m, 2H), 7.52 (d, J=1.53 Hz, 1H), 7.32-7.35 (m, 2H), 7.28 (dd, J=8.29, 1.53 Hz, 1H), 6.94 (d, J=8.29 Hz, 1H), 6.57-6.61 (m, 2H), 4.03 (s, 3H), 3.67 (s, 3H).

EXAMPLE 443

8-ethoxy-3-(3-methoxy-4-nitrophenyl)-5,10-dihydro-11H-dibenzo[b,e][1,4]diazepin-11-one The desired product was prepared in the same manner as Example 442, beginning with the substitution of 4-ethoxy-2-nitroaniline for 4-methoxy-2-nitroaniline in Example 442A. MS (DCI) m/e 405 (M+H)$^+$, $^1$H NMR (500 MHz, DMSO-d$_6$): □ 9.82 (s, 1H), 8.01 (d, J=8.42 Hz, 1H), 7.78-7.81 (m, 2H), 7.52 (s, 1H), 7.33-7.35 (m, 2H), 7.28 (d, J=8.11 Hz, 1H), 6.92 (d, J=8.42 Hz, 1H), 6.55-6.59 (m, 2H), 4.03 (s, 3H), 3.92 (d, J=8.42 Hz, 2H), 1.29 (t, J=7.02 Hz, 3H).

EXAMPLE 444

3-(3-methoxy-4-nitrophenyl)-8-[2-(4-methyl-1,3-thiazol-5-yl)ethoxy]-5,10-dihydro-11H-dibenzo[b,e][1,4]diazepin-11-one

EXAMPLE 444A

4-[2-(4-methyl-1,3-thiazol-5-yl)ethoxy]-2-nitroaniline

A mixture of 4-amino-3-nitrophenol (386 mg, 2.5 mmol), 2-(4-methyl-1,3-thiazol-5-yl)ethanol (0.299 mL, 2.5 mmol), polymer supported triphenylphosphine (1.25 g, 3 mmol/g, 3.75 mmol), and di-tert-butyl azodicarboxylate (864 mg, 3.75 mmol) in THF (10 mL) was stirred at room temperature for 16 hours. Filtered through Celite and concentrated under vacuum. The residue was purified by flash column chromatography on silica gel with 1:1 hexanes/ethyl acetate to provide 602 mg (86%) of the desired product. MS (DCI) m/e 279 (M+H)$^+$, $^1$H NMR (300 MHz, DMSO-d$_6$): □ 8.83 (s, 1H), 7.37 (d, J=3.05 Hz, 1H), 7.25 (s, 2H), 7.16 (dd, J=8.99, 2.88 Hz, 1H), 7.01 (s, 1H), 4.10 (t, J=6.27 Hz, 2H), 3.19 (t, J=6.27 Hz, 2H), 2.35 (s, 3H).

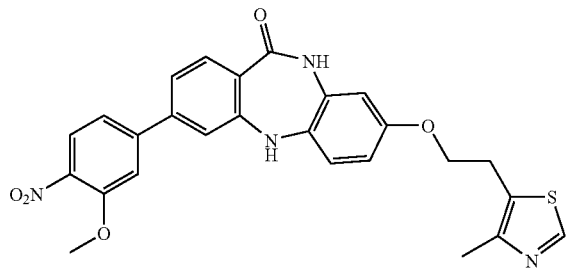

EXAMPLE 444B 3-(3-methoxy-4-nitrophenyl)-8-[2-(4-methyl-1,3-thiazol-5-yl)ethoxy]-5,10-dihydro-11H-dibenzo[b,e][1,4]diazepin-11-one The desired product was prepared in the same manner as Example 442, beginning with the substitution of Example 444A for 4-methoxy-2-nitroaniline in Example 442A. MS (ESI) m/e 503 (M+H)$^+$, $^1$H NMR (400 MHz, DMSO-d$_6$): □ 9.82 (s, 1H), 8.82 (s, 1H), 8.00 (s, J=8.59 Hz, 1H), 7.83 (s, 1H), 7.79 (d, J=7.98 Hz, 1H), 7.52 (d, J=1.23 Hz, 1H), 7.31-7.35 (m, 2H), 7.28 (dd, J=8.13, 1.38 Hz, 1H), 6.93 (d, J=8.59 Hz, 1H), 6.55-6.62 (m, 2H), 4.03-4.07 (m, 5H), 3.18 (t, J=6.14 Hz, 2H), 2.34 (s, 3H).

EXAMPLE 445

8-[3-(dimethylamino)propoxy]-3-(3-methoxy-4-nitrophenyl)-5,10-dihydro-11H-dibenzo[b,e][1,4]diazepin-11-one The desired product was prepared in the same manner as Example 444, beginning with the substitution of 3-(dimethylamino)propan-1-ol for 2-(4-methyl-1,3-thiazol-5-yl)ethanol in Example 444A. MS (DCI) m/e 463 (M+H)$^+$, $^1$H NMR (400 MHz, DMSO-d$_6$): □ 9.86 (s, 1H), 8.00 (d, J=8.59 Hz, 1H), 7.84 (s, 1H), 7.78 (d, J=8.29 Hz, 1H), 7.51 (d, J=1.53 Hz, 1H), 7.33 (m, 2H), 7.28 (dd, J=8.13, 1.69 Hz, 1H), 6.94 (d, J=9.51 Hz, 1H), 6.58-6.61 (m, 2H), 3.92-4.06 (m, 5H), 3.16 (d, J=4.60 Hz, 2H), 2.78 (s, 6H), 2.01-2.04 (m, 2H).

EXAMPLE 446

3-(3-methoxy-4-nitrophenyl)-8-(2-morpholin-4-ylethoxy)-5,10-dihydro-11H-dibenzo[b,e][1,4]diazepin-11-one The desired product was prepared in the same manner as Example 444, beginning with the substitution of 2-morpholin-4-ylethanol for 2-(4-methyl-1,3-thiazol-5-yl)ethanol in Example 444A. MS (DCI) m/e 491 (M+H)$^+$, $^1$H NMR (400 MHz, DMSO-d$_6$): □ 9.89 (s, 1H), 8.01 (d, J=8.42 Hz, 1H), 7.88 (s, 1H), 7.80 (d, J=8.42 Hz, 1H), 7.52 (d, J=1.25 Hz, 1H), 7.33-7.35 (m, 2H), 7.29 (dd, J=8.27, 1.40 Hz, 1H), 6.98 (m, 1H), 6.65-6.68 (m, 2H), 4.21-4.24 (m, 2H), 3.99-4.07 (m, 5H), 3.64-3.76 (m, 2H), 3.47-3.56 (m, 2H), 3.24-3.37 (m, 4H).

EXAMPLE 447

3-(3-methoxy-4-nitrophenyl)-8-[2-(4-morpholin-4-ylphenyl)ethoxy]-5,10-dihydro-11H-dibenzo[b,e][1,4]diazepin-11-one

EXAMPLE 447A 2-(4-morpholin-4-ylphenyl)ethanol

A mixture of 2-(4-bromophenyl)ethanol (0.70 mL, 5 mmol), morpholine (0.52 mL, 6 mmol), LHMDS (11 mL, IM solution in THF), Pd$_2$(dba)$_3$ (46 mg, 0.05 mmol), and CyMAP (24 mg, 0.06 mmol) was heated to reflux for 16 hours. Cooled to room temperature. Acidified with IM HCl, stirred for 10 minutes, and neutralized with saturated NaHCO$_3$. Partitioned between ethyl acetate and water. The organic layer was washed with brine, dried (MgSO$_4$), filtered, and concentrated under vacuum. The residue was purified by flash column chromatography on silica gel with 1:1 hexanes/ethyl acetate to provide 520 mg (50%) of the desired product. MS (ESI) m/e 208 (M+H)$^+$, $^1$H NMR (300 MHz, CDCl$_3$): □ 7.15 (d, J=8.48 Hz, 2H), 6.88 (d, J=8.48 Hz, 2H), 3.78-3.87 (m, 6H), 3.11-3.14 (m, 4H), 2.79 (t, J=6.61 Hz, 2H), 1.43 (m, 1H).

EXAMPLE 447B

4-[2-(4-morpholin-4-ylphenyl)ethoxy]-2-nitroaniline

The desired product was prepared by substituting Example 447A for 2-(4-methyl-1,3-thiazol-5-yl)ethanol in Example 444A. MS (ESI) m/e 344 (M+H)$^+$.

EXAMPLE 447C 3-(3-methoxy-4-nitrophenyl)-8-[2-(4-morpholin-4-ylphenyl)ethoxy]-5,10-dihydro-11H-dibenzo[b,e][1,4]diazepin-11-one The desired product was prepared in the same manner as Example 442, beginning with the substitution of Example 447B for 4-methoxy-2-nitroaniline in Example 442A. MS (ESI) m/e 567 (M+H)$^+$, $^1$H NMR (300 MHz, DMSO-d$_6$): □ 9.82 (s, 1H), 8.00 (m, 1H), 7.77-7.82 (m, 2H), 7.52 (d, J=2.03 Hz, 1H), 7.26-7.35 (m, 4H), 7.14-7.17 (m, 2H), 6.86-6.91 (m, 2H), 6.57-6.61 (m, 2H), 4.02-4.05 (m, 5H), 3.71-3.74 (m, 4H), 3.28-3.30 (m, 2H), 3.04-3.08 (m, 4H).

EXAMPLE 448

3-(3-methoxy-4-nitrophenyl)-7-piperidin-1-yl-5,10-dihydro-1H-dibenzo[b,e][1,4]diazepin-11-one

EXAMPLE 448A 2-nitro-5-piperidin-1-ylphenylamine

A mixture of 5-chloro-2-nitroaniline (1.73 g, 10 mmol), piperidine (1.09 mL, 11 mmol), and K$_2$CO$_3$ (1.52 g, 11 mmol) in DMF was heated to 120° C. for 24 hours. Cooled to room temperature. Partitioned between ethyl acetate and water. The organic layer was washed with brine, dried (MgSO$_4$), filtered, and concentrated under vacuum. The residue was purified by flash column chromatography on silica gel with 4:1 hexanes/ethyl acetate to provide 1.33 g (60%) of the desired product. MS (ESI) m/e 222 (M+H)$^+$, $^1$H NMR (300 MHz, DMSO-d$_6$):

7.79 (d, J=9.83 Hz, 1H), 7.22 (s, 2H), 6.37 (dd, J=9.83, 2.71 Hz, 1H), 6.19 (d, J=2.71 Hz, 1H), 3.34-3.38 (m, 4H), 1.53-1.60 (m, 6H).

EXAMPLE 448B 3-chloro-7-piperidin-1-yl-5,10-dihydro-11H-dibenzo[b,e][1,4]diazepin-11-one Example 448A was substituted for methyl 3,4-diaminobenzoate in Example 1A to provide 4-chloro-2-(2-nitro-5-piperidin-1-yl-phenylamino)-benzoic acid methyl ester. This material was then substituted for Example 6B in Example 6C to provide 2-(2-amino-5-piperidin-1-yl-phenylamino)-4-chloro-benzoic acid methyl ester. Subsequently, this material was substituted for Example 442B in Example 442C to provide the desired product. MS (ESI) m/e 328 (M+H)$^+$.

EXAMPLE 448C 3-(3-methoxy-4-nitrophenyl)-7-piperidin-1-yl-5,10-dihydro-11H-dibenzo[b,e][1,4]diazepin-11-one The desired product was prepared by substituting Example 448B and Example 266G for Example 59B and Example 56A, respectively, in Example 59C. MS (ESI) m/e 445 (M+H)$^+$, $^1$H NMR (400 MHz, DMSO-d$_6$): ☐ 9.67 (s, 1H), 8.00 (d, J=8.59 Hz, 1H), 7.77-7.80 (m, 2H), 7.52 (d, J=1.84 Hz, 1H), 7.33-7.36 (m, 2H), 7.30 (dd, J=8.13, 1.69 Hz, 1H), 6.81 (d, J=8.59 Hz, 1H), 6.62 (d, J=2.76 Hz, 1H), 6.52 (dd, J=8.59, 2.76 Hz, 1H), 4.03 (s, 3H), 3.03-3.06 (m, 4H), 1.58-1.62 (m, 4H), 1.49-1.54 (m, 2H).

EXAMPLE 449

7-[(2S)-2-(hydroxymethyl)pyrrolidin-1-yl]-3-(3-methoxy-4-nitrophenyl)-5,10-dihydro-11H-dibenzo[b,e][1,4]diazepin-11-one

EXAMPLE 449A

[(2S)-1-(3-amino-4-nitrophenyl)pyrrolidin-2-yl]methanol

The desired product was prepared by substituting (2S)-2-pyrrolidinylmethanol for piperidine in Example 448A. MS (DCI) m/e 238 (M+H)$^+$.

EXAMPLE 449B 3-chloro-7-[(2S)-2-(hydroxymethyl)pyrrolidin-1-yl]-5,10-dihydro-11H-dibenzo[b,e][1,4]diazepin-11-one The desired product was prepared by substituting Example 449A for Example 448A in Example 448B. MS (DCI) m/e 344 (M+H)$^+$.

EXAMPLE 449C

7-[(2S)-2-(hydroxymethyl)pyrrolidin-1-yl]-3-(3-methoxy-4-nitrophenyl)-5,10-dihydro-11H-dibenzo[b,e][1,4]diazepin-11-one The desired product was prepared by substituting Example 449B and Example 266G for Example 59B and Example 56A, respectively, in Example 59C. MS (ESI) m/e 461 (M+H)$^+$, $^1$H NMR (400 MHz, DMSO-d$_6$): ☐ 9.57 (s, 1H), 8.01 (d, J=8.29 Hz, 1H), 7.84 (s, 1H), 7.78 (d, J=8.29 Hz, 1H), 7.53 (d, J=1.84 Hz, 1H), 7.37 (d, J=1.53 Hz, 1H), 7.34 (dd, J=8.44, 1.69 Hz, 1H), 7.29 (dd, J=8.13, 1.38 Hz, 1H), 6.79 (d, J=8.59 Hz, 1H), 6.33 (d, J=2.15 Hz, 1H), 6.22 (dd, J=8.75, 2.30 Hz, 1H), 4.03 (s, 3H), 3.60 (m, 1H), 3.46 (dd, J=10.43, 3.38 Hz, 1H), 3.31 (m, 1H), 3.19 (dd, J=10.28, 8.44 Hz, 1H), 2.99 (m, 1H), 1.82-2.02 (m, 4H).

EXAMPLE 450

3-(3-methoxy-4-nitrophenyl)-7-morpholin-4-yl-5,10-dihydro-11H-dibenzo[b,e][1,4]diazepin-11-one

EXAMPLE 450A 5-morpholin-4-yl-2-nitrophenylamine

The desired product was prepared by substituting morpholine for piperidine in Example 448A. MS (DCI) m/e 224 (M+H)$^+$.

EXAMPLE 450B 3-chloro-7-morpholin-4-yl-5,10-dihydro-11H-dibenzo[b,e][1,4]diazepin-11-one The desired product was prepared by substituting Example 450A for Example 448A in Example 448B. MS (DCI) m/e 330 (M+H)$^+$.

EXAMPLE 450C 3-(3-methoxy-4-nitrophenyl)-7-morpholin-4-yl-5,10-dihydro-11H-dibenzo[b,e][1,4]diazepin-11-one The desired product was prepared by substituting Example 450B and Example 266G for Example 59B and Example 56A, respectively, in Example 59C. MS (ESI) m/e 447 (M+H)$^+$, $^1$H NMR (500 MHz, DMSO-d$_6$): ☐ 9.70 (s, 1H), 8.01 (d, J=8.42 Hz, 1H), 7.86 (s, 1H), 7.79 (d, J=8.42 Hz, 1H), 7.53 (d, J=1.56 Hz, 1H), 7.33-7.36 (m, 2H), 7.30 (dd, J=8.27, 1.72 Hz, 1H), 6.85 (d, J=8.73 Hz, 1H), 6.62 (d, J=2.49 Hz, 1H), 6.56 (dd, J=8.73, 2.81 Hz, 1H), 4.03 (s, 3H), 3.71-3.73 (m, 4H), 3.00-3.02 (m, 4H).

EXAMPLE 451

7-(4-hydroxypiperidin-1-yl)-3-(3-methoxy-4-nitrophenyl)-5,10-dihydro-11H-dibenzo[b,e][1,4]diazepin-11-one

EXAMPLE 451A 1-(3-amino-4-nitrophenyl)piperidin-4-ol

The desired product was prepared by substituting 4-hydroxypiperidine for piperidine in Example 448A. MS (DCI) m/e 238 (M+H)$^+$.

EXAMPLE 451B 3-chloro-7-(4-hydroxypiperidin-1-yl)-5,10-dihydro-11H-dibenzo[b,e][1,4]diazepin-11-one The desired product was prepared by substituting Example 451A for Example 448A in Example 448B. MS (DCI) m/e 344 (M+H)$^+$.

EXAMPLE 451C 7-(4-hydroxypiperidin-1-yl)-3-(3-methoxy-4-nitrophenyl)-5,10-dihydro-11H-dibenzo[b,e][1,4]diazepin-11-one The desired product was prepared by substituting Example 451B and Example 266G for Example 59B and Example 56A, respectively, in Example 59C. MS (ESI) m/e 461 (M+H)$^+$, $^1$H NMR (500 MHz, DMSO-d$_6$): □ 9.80 (s, 1H), 8.01 (d, J=8.42 Hz, 1H), 7.95 (s, 1H), 7.80 (d, J=8.42 Hz, 1H), 7.53 (d, J=1.87 Hz, 1H), 7.34-7.36 (m, 2H), 7.32 (d, J=8.42 Hz, 1H), 6.90 (d, J=8.11 Hz, 1H), 6.81 (m, 1H), 6.73 (m, 1H), 4.03 (s, 3H), 3.69 (m, 1H), 3.45-3.48 (m, 2H), 2.96-3.00 (m, 2H), 1.84-1.87 (m, 2H), 1.55-1.57 (m, 2H),

EXAMPLE 452 methyl {3-[3-methoxy-4-(3-methyl-1,2,4-oxadiazol-5-yl)phenyl]-11-oxo-10,11-dihydro-5H-dibenzo[b,e][1,4]diazepin-8-yl}acetate

EXAMPLE 452A 5-(4-iodo-2-methoxyphenyl)-3-methyl-1,2,4-oxadiazole

A mixture of 4-iodo-2-methoxy benzoic acid (83 mg, 0.3 mmol), HATU (114 mg, 0.3 mmol), DIEA (26 µL, 0.15 mmol), and HOBt (8 mg, 0.06 mmol) in DMF was stirred at room temperature for 5 minutes. Acetamide oxime (22 mg, 0.3 mmol) was added, and reaction was stirred for 30 minutes at room temperature. The reaction was then heated to 110° C. for 16 hours. Cooled to room temperature. Partitioned between ethyl acetate and water. The organic layer was washed with brine, dried (MgSO$_4$), filtered, and concentrated under vacuum. The residue was purified by HPLC to provide 37 mg (39%) of desired product. MS (ESI) m/e 317 (M+H)$^+$, $^1$H NMR (300 MHz, DMSO-d$_6$): □ 7.70 (d, J=8.14 Hz, 1H), 7.64 (d, J=1.36 Hz, 1H), 7.53 (dd, J=8.31-1.53 Hz, 1H), 3.94 (s, 3H), 2.40 (s, 3H).

EXAMPLE 452B methyl {3-[3-methoxy-4-(3-methyl-1,2,4-oxadiazol-5-yl)phenyl]-11-oxo-10,11-dihydro-5H-dibenzo[b,e][1,4]diazepin-8-yl}acetate The desired product was prepared by substituting Example 452A and Example 54A for Example 9 and 2-methoxy-4-(4,4,5,5-tetramethyl-1,3,2-diozborolan-2-yl)phenol, respectively, in Example 10. MS (ESI) m/e 471 (M+H)$^+$, $^1$H NMR (500 MHz, DMSO-d$_6$): □ 9.89 (s, 1H), 8.09 (d, J=8.24 Hz, 1H), 8.00 (s, 1H), 7.80 (d, J=7.93 Hz, 1H), 7.47 (s, 1H), 7.39-7.41 (m, 2H), 7.33 (dd, J=8.24, 1.53 Hz, 1H), 6.97 (d, J=7.93 Hz, 1H), 6.85-6.88 (m, 2H), 4.04 (s, 3H), 3.60 (s, 3H), 3.54 (s, 2H), 2.42 (s, 3H).

EXAMPLE 453

8-(2-ethyl-2-hydroxybutyl)-3-(3-methoxy-4-nitrophenyl)-5,10-dihydro-11H-dibenzo[b,e][1,4]diazepin-11-one

EXAMPLE 453A 3-chloro-8-(2-ethyl-2-hydroxybutyl)-5,10-dihydro-11H-dibenzo[b,e][1,4]diazepin-11-one The desired product was prepared by substituting Example 6D and ethylmagnesium bromide for Example 1B and methylmagnesium bromide, respectively, in Example 189A. MS (DCI) m/e 345 (M+H)$^+$.

EXAMPLE 453B 8-(2-ethyl-2-hydroxybutyl)-3-(3-methoxy-4-nitrophenyl)-5,10-dihydro-11H-dibenzo[b,e][1,4]diazepin-11-one The desired product was prepared by substituting Example 453A and Example 266G for Example 59B and Example 56A, respectively, in Example 59B. MS (DCI) m/e 461 (M+H)$^+$, $^1$H NMR (400 MHz, DMSO-d$_6$): □ 9.82 (s, 1H), 8.01 (d, J=8.29 Hz, 1H), 7.89 (s, 1H), 7.79 (d, J=8.29 Hz, 1H), 7.52 (d, J=1.84 Hz, 1H), 7.33-7.35 (m, 2H), 7.29 (dd, J=8.29, 1.84 Hz, 1H), 6.81-6.91 (m, 3H), 4.03 (s, 3H), 2.49-2.51 (m, 2H), 1.27 (q, J=7.36 Hz, 4H), 0.81 (t, J=7.36 Hz, 6H).

EXAMPLE 454

3-[(2-chloropyridin-4-yl)amino]-8-(2-ethyl-2-hydroxybutyl)-5,10-dihydro-11H-dibenzo[b,e][1,4]diazepin-11-one The title compound was prepared by substituting Example 453A and 2-chloro-4-aminopyridine for Example 189A and 4-aminopyridine, respectively, in Example 191. MS (DCI) m/e 462 (M+H)$^+$, $^1$H NMR (500 MHz, DMSO-d$_6$): □ 9.56 (s, 1H), 9.29 (s, 1H), 8.08 (d, J=6.14 Hz, 1H), 7.82 (s, 1H), 7.66 (d, J=8.59 Hz, 1H), 6.99-7.01 (m, 2H), 6.78-6.87 (m, 4H), 6.65 (dd, J=8.59, 2.15 Hz, 1H), 2.47 (s, 1H), 1.27 (q, J=7.36 Hz, 4H), 0.81 (t, J=7.36 Hz, 6H).

EXAMPLE 455

N,N-dimethyl-2-[11-oxo-3-(pyridin-4-ylamino)-10,11-dihydro-5H-dibenzo[b,e][1,4]diazepin-8-yl]acetamide

EXAMPLE 455A

[11-oxo-3-(pyridin-4-ylamino)-10,11-dihydro-5H-dibenzo[b,e][14]diazepin-8-yl]acetic acid The desired product was prepared by substituting Example 209 for Example 12 in Example 13. MS (DCI) m/e 361 (M+H)$^+$.

EXAMPLE 455B

N,N-dimethyl-2-[11-oxo-3-(pyridin-4-ylamino)-10,11-dihydro-5H-dibenzo[b,e][1,4]diazepin-8-yl]acetamide The desired product was prepared by substituting Example 455A and N,N-dimethylamine hydrochloride for dimethylaminoacetic acid and Example 120, respectively, in Example 122. MS (DCI) m/e 388 (M+H)$^+$, $^1$H NMR (500 MHz, DMSO-d$_6$): □ 10.49 (s, 1H), 9.78 (s, 1H), 8.36 (d, J=7.48 Hz, 2H), 7.99 (s, 1H), 7.77 (d, J=8.42 Hz, 1H), 7.22 (d, J=7.49 Hz, 2H), 6.94 (d, J=1.87 Hz, 1H), 6.91 (d, J=8.11 Hz, 1H), 6.80-6.84 (m, 3H), 3.54 (s, 2H), 2.98 (s, 3H), 2.82 (s, 3H).

EXAMPLE 456

N-(4-morpholin-4-ylphenyl)-2-[11-oxo-3-(pyridin-4-ylamino)-10,11-dihydro-5H-dibenzo[b,e][1,4]diazepin-8-yl]acetamide The desired product was prepared by substituting Example 455A and 4-morpholin-4-ylphenylamine for dimethylaminoacetic acid and Example 120, respectively, in Example 122. MS (DCI) m/e 520 (M+H)$^+$, $^1$H NMR (500 MHz, DMSO-d$_6$): ☐ 10.55 (s, 1H), 9.90 (s, 1H), 9.82 (s, 1H), 8.35 (d, J=7.48 Hz, 2H), 8.01 (s, 1H), 7.76 (d, J=8.42 Hz, 1H), 7.44 (d, J=9.04 Hz, 2H), 7.22 (d, J=7.48 Hz, 2H), 6.87-6.94 (m, 5H), 6.83 (dd, J=8.58, 2.03 Hz, 2H), 3.70-3.72 (m, 4H), 3.46 (s, 2H), 3.02-3.04 (m, 4H).

EXAMPLE 457

8-(2-hydroxy-2-methylpropyl)-3-(pyrimidin-4-ylamino)-5,10-dihydro-11H-dibenzo[b,e][1,4]diazepin-11-one The desired product was prepared by substituting Example 208A and 4-aminopyrimidine for Example 189A and 4-aminopyridine, respectively, in Example 191. MS (DCI) m/e 376 (M+H)$^+$, $^1$H NMR (500 MHz, DMSO-d$_6$): ☐ 10.49 (s, 1H), 9.63 (s, 1H), 8.85 (s, 1H), 8.39 (d, J=6.24 Hz, 1H), 7.89 (s, 1H), 7.69 (d, J=8.42 Hz, 1H), 7.39 (s, 1H), 7.12 (d, J=8.42 Hz, 1H), 6.98 (d, J=6.24 Hz, 1H), 6.90 (d, J=7.80 Hz, 1H), 6.77-6.81 (m, 2H), 2.50 (s, 2H), 1.03 (s, 6H).

EXAMPLE 458

8-(2-hydroxy-2-methylpropyl)-3-[(2-methylpyridin-4-yl)amino]-5,10-dihydro-11H-dibenzo[b,e][1,4]diazepin-11-one The desired product was prepared by substituting Example 208A and 4-amino-2-picoline for Example 189A and 4-aminopyridine, respectively, in Example 191. MS (DCI) m/e 389 (M+H)$^+$, $^1$H NMR (500 MHz, DMSO-d$_6$): ☐ 10.41 (s, 1H), 9.73 (s, 1H), 8.26 (d, J=7.48 Hz, 1H), 7.95 (s, 1H), 7.76 (d, J=8.73 Hz, 1H), 7.07-7.10 (m, 2H), 6.93 (d, J=1.87 Hz, 1H), 6.87 (d, J=7.80 Hz, 1H), 6.79-6.84 (m, 3H), 2.50-2.52 (m, 5H), 1.04 (s, 6H).

EXAMPLE 459

3-(3-methoxy-4-nitrophenyl)-8-(2-oxopropyl)-5,10-dihydro-11H-dibenzo[b,e][1,4]diazepin-11-one

EXAMPLE 459A 3-chloro-8-(2-oxopropyl)-5,10-dihydro-11H-dibenzo[b,e][1,4]diazepin-11-one The desired product was obtained as a side product from Example 208A. MS (DCI) m/e 301 (M+H)$^+$.

EXAMPLE 459B 3-(3-methoxy-4-nitrophenyl)-8-(2-oxopropyl)-5,10-dihydro-11H-dibenzo[b,e][1,4]diazepin-11-one The desired product was prepared by substituting Example 459A and Example 266G for Example 59B and Example 56A, respectively, in Example 59C. MS (DCI) m/e 418 (M+H)$^+$, $^1$H NMR (500 MHz, DMSO-d$_6$): ☐ 9.89 (s, 1H), 8.01 (m, 2H), 7.80 (d, J=7.93 Hz, 1H), 7.52 (s, 1H), 7.33-7.35 (m, 2H), 7.30 (d, J=8.24 Hz, 1H), 6.96 (d, J=8.54 Hz, 1H), 6.79-6.81 (m, 2H), 4.03 (s, 3H), 3.62 (s, 2H), 2.10 (s, 3H).

EXAMPLE 460

3-[(2-chloropyridin-4-yl)amino]-8-(2-oxopropyl)-5,10-dihydro-11H-dibenzo[b,e][1,4]diazepin-11-one The desired product was prepared by substituting Example 459A and 2-chloro-4-aminopyridine for Example 189A and 4-aminopyridine, respectively, in Example 191. MS (DCI) m/e 393 (M+H)$^+$, $^1$H NMR (500 MHz, DMSO-d$_6$): ☐ 9.64 (s, 1H), 9.31 (s, 1H), 8.09 (d, J=6.10 Hz, 1H), 7.92 (s, 1H), 7.67 (d, J=8.54 Hz, 1H), 7.00-7.02 (m, 2H), 6.91 (d, J=8.54 Hz, 1H), 6.86 (d, J=2.14 Hz, 1H), 6.76-6.78 (m, 2H), 6.66 (dd, J=8.70, 1.98 Hz, 1H), 3.61 (s, 2H), 2.09 (s, 3H).

EXAMPLE 461

3-({2-[(2-chloropyridin-4-yl)amino]pyridin-4-yl}amino)-8-(2-oxopropyl)-5,10-dihydro-11H-dibenzo[b,e][1,4]diazepin-11-one The desired product was obtained as a side product from Example 460. MS (DCI) m/e 485 (M+H)$^+$, $^1$H NMR (500 MHz, DMSO-d$_6$): ☐ 9.63 (s, 1H), 9.59 (s, 1H), 9.02 (s, 1H), 8.05-8.08 (m, 2H), 7.99 (d, J=1.83 Hz, 1H), 7.87 (s, 1H), 7.66 (d, J=8.24 Hz, 1H), 7.41 (dd, J=5.80, 1.83 Hz, 1H), 6.92 (d, J=8.54 Hz, 1H), 6.83 (d, J=2.14 Hz, 1H), 6.75-6.78 (m, 2H), 6.62-6.68 (m, 3H), 3.61 (s, 2H), 2.09 (s, 3H).

EXAMPLE 462 methyl 2-methyl-2-[11-oxo-3-(pyrimidin-4-ylamino)-10,11-dihydro-5H-dibenzo[b,e][1,4]diazepin-8-yl]propanoate The desired product was prepared by substituting Example 266F and 4-aminopyrimidine for Example 189A and 4-aminopyridine, respectively, in Example 191. MS (DCI) m/e 404 (M+H)$^+$, $^1$H NMR (500 MHz, DMSO-d$_6$): ☐ 10.60 (s, 1H), 9.66 (s, 1H), 8.87 (s, 1H), 8.39 (d, J=6.55 Hz, 1H), 8.02 (s, 1H), 7.70 (d, J=8.73 Hz, 1H), 7.39 (d, J=1.56 Hz, 1H), 7.14 (dd, J=8.58, 1.72 Hz, 1H), 7.00 (d, J=6.55 Hz, 1H), 6.97 (m, 1H), 6.95 (d, J=1.87 Hz, 1H), 6.89 (dd, J=8.26, 2.03 Hz, 1H), 3.58 (s, 3H), 1.44 (s, 6H).

EXAMPLE 463 methyl 2-methyl-2-{3-[(2-methylpyridin-4-yl)amino]-11-oxo-10,11-dihydro-5H-dibenzo[b,e][1,4]diazepin-8-yl}propanoate The desired product was prepared by substituting Example 266F and 4-amino-2-picoline for Example 189A and 4-aminopyridine, respectively, in Example 191. MS (DCI) m/e 417 (M+H)$^+$, $^1$H NMR (500 MHz, DMSO-d$_6$): ☐ 10.43 (s, 1H), 9.74 (s, 1H), 8.26 (d, J=7.49 Hz, 1H), 8.06 (s, 1H), 7.77 (d, J=8.42 Hz, 1H), 7.07-7.09 (m, 2H), 6.90-6.97 (m, 4H), 6.83 (dd, J=8.58, 2.03 Hz, 1H), 3.58 (s, 3H), 3.54 (s, 3H), 1.44 (s, 6H).

EXAMPLE 464

2-methylN(4-morpholin-4-ylphenyl)-2-[11-oxo-3-(pyrimidin-4-ylamino)-10,11-dihydro-5H-dibenzo[b,e][1,4]diazepin-8-yl]propanamide

EXAMPLE 464A 2-methyl-2-[11-oxo-3-(pyrimidin-4-ylamino)-10,11-dihydro-5H-dibenzo[b,e][1,4]diazepin-8-yl]propanoic acid The desired product was prepared by substituting Example 462 for Example 12 in Example 13. MS (DCI) m/e 390 (M+H)$^+$.

EXAMPLE 464B 2-methylN(4-morpholin-4-ylphenyl)-2-[11-oxo-3-(pyrimidin-4-ylamino)-10,11-dihydro-5H-dibenzo[b,e][1,4]diazepin-8-yl]propanamide The desired product was prepared by substituting Example 464A and 4-(4-morpholino)aniline for dimethylaminoacetic acid and Example 120, respectively, in Example 208. MS (DCI) m/e 510 (M+H)$^+$, $^1$H NMR (500 MHz, DMSO-d$_6$): □ 10.67 (s, 1H), 9.70 (s, 1H), 8.88 (s, 1H), 8.79 (s, 1H), 8.39 (d, J=6.55 Hz, 1H), 7.99 (s, 1H), 7.70 (d, J=8.42 Hz, 1H), 7.43 (s, 1H), 7.41 (s, 1H), 7.37 (s, 1H), 7.13 (dd, J=8.58, 1.72 Hz, 1H), 6.91-7.02 (m, 4H), 6.86 (s, 1H), 6.84 (s, 1H), 3.71-3.73 (m, 4H), 3.01-3.03 (m, 4H), 1.48 (s, 6H).

EXAMPLE 465

2-methyl-2-{3-[(2-methylpyridin-4-yl)amino]-11-oxo-10,11-dihydro-5H-dibenzo[b,e][1,4]diazepin-8-yl}N(4-morpholin-4-ylphenyl)propanamide

EXAMPLE 465A 2-methyl-2-{3-[(2-methylpyridin-4-yl)amino]-1-oxo-10,11-dihydro-5H-dibenzo[b,e][1,4]diazepin-8-yl}propanoic acid The desired product was prepared by substituting Example 463 for Example 12 in Example 13. MS (DCI) m/e 403 (M+H)$^+$.

EXAMPLE 465B 2-methyl-2-{3-[(2-methylpyridin-4-yl)amino]-1-oxo-10,11-dihydro-5H-dibenzo[b,e][1,4]diazepin-8-yl}N(4-morpholin-4-ylphenyl)propanamide The desired product was prepared by substituting Example 465A and 4-(4-morpholino)aniline for dimethylaminoacetic acid and Example 120, respectively, in Example 122. MS (ESI) m/e 563 (M+H)$^+$. $^1$H NMR (500 MHz, DMSO-d$_6$): □ 9.53 (s, 1H), 8.91 (s, 1H), 8.77 (s, 1H), 8.16 (d, J=4.99 Hz, 1H), 7.84 (s, 1H), 7.62 (d, J=8.73 Hz, 1H), 7.41 (d, J=9.04 Hz, 2H), 7.01 (d, J=1.56 Hz, 1H), 6.82-6.92 (m, 7H), 6.60 (dd, J=8.58, 2.03 Hz, 1H), 3.71 (m, 4H), 3.01 (m, 4H), 2.37 (s, 3H), 1.47 (s, 6H).

EXAMPLE 466

3-{[3-(2-hydroxyethyl)pyridin-4-yl]amino}-8-(1-hydroxy-1-methylethyl)-5,10-dihydro-11H-dibenzo[b,e][1,4]diazepin-11-one

EXAMPLE 466A 2-(4-aminopyridin-3-yl)ethanol

A solution of di-tert-butyl dicarbonate (3.274 g, 15 mmol) in CH$_2$Cl$_2$ (8 mL) was added to a solution of 4-aminopyridine (1.412 g, 15 mmol) in CH$_2$Cl$_2$ (15 mL), and was stirred at room temperature for 30 minutes. Acidified with IM HCl. Washed with CH$_2$Cl$_2$. Neutralized aqueous layer with K$_2$CO$_3$. Partitioned between CH$_2$Cl$_2$ and water. The organic layer was washed with brine, dried (MgSO$_4$), filtered, and concentrated under vacuum to provide 2.41 g (83%) of pyridin-4-yl-carbamic acid tert-butyl ester.

Solution A was prepared by combining pyridin-4-yl-carbamic acid tert-butyl ester (388 mg, 2 mmol) in THF (5 mL) and cooling to −78° C. t-BuLi (2.8 mL, 1.7M solution in pentane) was added dropwise. Once the addition was complete, the solution was stirred at −78° C. for 15 minutes, then warmed to −15° C. and stirred for 90 minutes. In a separate flask, solution B was prepared by combining bromoethanol (0.21 mL, 3 mmol) in THF (5 mL) and cooling to −78° C. n-BuLi (1.44 mL, 2.5M solution in hexanes) was added dropwise. Once the addition was complete, the solution was stirred at −78° C. for 10 minutes. Solution A was recooled to −78° C., and solution B was added to solution A via cannula. Stirred with warming to room temperature for 2 hours. The reaction was recooled, and quenched with water. Partitioned between CH$_2$Cl$_2$ and water. The organic layer was washed with brine, dried (MgSO$_4$), filtered, and concentrated under vacuum. The residue was purified by flash column chromatography on silica gel with 100% ethyl acetate to provide 91 mg (19%) of [3-(2-hydroxy-ethyl)-pyridin-4-yl]-carbamic acid tert-butyl ester.

A solution of [3-(2-hydroxy-ethyl)-pyridin-4-yl]-carbamic acid tert-butyl ester (91 mg, 0.38 mmol) in CH$_2$Cl$_2$ (3 mL) was treated with TFA (2 mL) and stirred at room temperature for 3 hours. Concentrated under vacuum to provide 21 mg (23%) of desired product. MS (DCI) m/e 139 (M+H)$^+$.

EXAMPLE 466B

3-{[3-(2-hydroxyethyl)pyridin-4-yl]amino}-8-(1-hydroxy-1-methylethyl)-5,10-dihydro-11H-dibenzo[b,e][1,4]diazepin-11-one The desired product was prepared by substituting Example 466A for 4-aminopyridine in Example 191. MS (DCI) m/e 387 (M+H)$^+$, $^1$H NMR (300 MHz, DMSO-d$_6$): □ 9.77 (s, 1H), 9.60 (s, 1H), 8.23-8.27 (m, 2H), 7.96 (s, 1H), 7.78 (d, J=8.48 Hz, 1H), 7.17 (m, 1H), 7.12 (d, J=2.03 Hz, 1H), 7.03 (m, 1H), 6.88-6.93 (m, 2H), 6.82 (dd, J=8.48, 2.03 Hz, 1H), 3.73 (t, J=5.93 Hz, 2H), 2.90 (t, J=5.76 Hz, 2H), 1.36 (s, 6H).

EXAMPLE 467

8-(2-hydroxy-2-methylpropyl)-3-[(2-methoxypyridin-4-yl)amino]-5,10-dihydro-11H-dibenzo[b,e][1,4]diazepin-11-one

EXAMPLE 467A 2-methoxypyridin-4-amine

Na (0.7 g, 30 mmol) was added to methanol (10 mL) at room temperature. Once all Na had dissolved, 2-chloro-4-aminopyridine (0.5 g, 3.9 mmol) was added. The solution was heated to reflux for 16 hours. After the reaction solution cooled to room, it was partitioned between ethyl acetate and water. The aqueous layer was extracted twice with additional ethyl acetate. The combined organic layers were washed with brine, dried (MgSO$_4$), filtered, and concentrated under vacuum to give the title product. MS (DCI) m/e 125 (M+H)$^+$.

EXAMPLE 467B 8-(2-hydroxy-2-methylpropyl)-3-[(2-methoxypyridin-4-yl)amino]-5,10-dihydro-11H-dibenzo[b,e][1,4]diazepin-11-one The desired product was prepared by substituting Example 208A and Example 467A for Example 189A and 4-aminopyridine, respectively, in Example 191. MS (DCI) m/e 404 (M+H)$^+$, $^1$H NMR (500 MHz, DMSO-d$_6$): □ 9.48 (s, 1H), 8.97 (s, 1H), 7.91 (d, J=5.83 Hz, 1H), 7.82 (s, 1H), 7.62 (d, J=8.59 Hz, 1H), 7.08 (d, J=2.15 Hz, 1H), 7.00 (m, 1H), 6.85-6.89 (m, 2H), 6.66 (dd, J=5.83, 1.84 Hz, 1H), 6.59 (dd, J=8.59, 2.15 Hz, 1H), 6.42 (d, J=1.84 Hz, 1H), 4.86 (s, 1H), 3.81 (s, 3H), 1.36 (s, 3H).

EXAMPLE 468

8-(2-hydroxy-2-methylpropyl)-3-[(2-methylpyridin-4-yl)amino]-5,10-dihydro-11H-dibenzo[b,e][1,4]diazepin-11-one The desired product was prepared by substituting Example 208A and 4-amino-2-picoline for Example 189A and 4-aminopyridine, respectively, in Example 191. MS (DCI) m/e 388 (M+H)$^+$, $^1$H NMR (300 MHz, DMSO-d$_6$): □ 9.48 (s, 1H), 8.91 (s, 1H), 8.16 (d, J=5.52 Hz, 1H), 7.78-7.80 (m, 2H), 7.63 (d, J=8.59 Hz, 1H), 7.08 (d, J=1.84 Hz, 1H), 7.00 (m, 1H), 6.83-6.89 (m, 3H), 6.61 (dd, J=8.90, 2.15 Hz, 1H), 2.37 (s, 3H), 1.36 (s, 6H).

EXAMPLE 469 methyl 11-oxo-3-(pyrimidin-4-ylamino)-10,11-dihydro-5H-dibenzo[b,e][1,4]diazepine-7-carboxylate

EXAMPLE 469A methyl 3-amino-4-nitrobenzoate

A solution of 5-chloro-2-nitro-aniline (6.902 g, 40 mmol), Zn(CN)$_2$ (2.818 g, 24 mmol), and Pd(PPh$_3$)$_4$ (2.311 g, 2 mmol) in DMF (40 mL) was heated to 120° C. for 4 days. Cooled to room temperature. Partitioned between ethyl acetate and water. The organic layer was washed with brine, dried (MgSO$_4$), filtered, and concentrated under vacuum. The residue was purified by flash column chromatography on silica gel with 4:1 hexanes/ethyl acetate to provide 1.49 g (23%) of 3-amino-4-nitro-benzonitrile.

A mixture of 3-amino-4-nitro-benzonitrile (1.2 g, 7.36 mmol), concentrated HCl (50 mL), and water (100 mL) was heated to reflux for 2 days. Cooled to room temperature and collected orange solid by filtration. Washed solid with water until wash was neutral, to provide 1.11 g (83%) of 3-amino-4-nitro-benzoic acid.

(Trimethylsilyl)diazomethane (6 mL, 2M solution in hexanes) was added to a solution of 3-amino-4-nitro-benzoic acid in CH$_2$Cl$_2$ (25 mL) and methanol (25 mL). Stirred at room temperature until bubbling ceased. Concentrated under vacuum to provide 1.2 g of desired product. MS (DCI) m/e 197 (M+H)$^+$.

EXAMPLE 469B methyl 4-chloro-2-{[5-(methoxycarbonyl)-2-nitrophenyl]amino}benzoate The desired product was prepared by substituting Example 469A for methyl 3,4-diaminobenzoate in Example 1A. MS (DCI) m/e 365 (M+H)$^+$.

EXAMPLE 469C methyl 3-chloro-11-oxo-10,11-dihydro-5H-dibenzo[b,e][1,4]diazepine-7-carboxylate The desired product was prepared by substituting Example 469B for Example 2A in Example 2B. MS (DCI) m/e 303 (M+H)$^+$.

EXAMPLE 469D methyl 11-oxo-3-(pyrimidin-4-ylamino)-10,11-dihydro-5H-dibenzo[b,e][1,4]diazepine-7-carboxylate The desired product was prepared by substituting Example 469C and 4-aminopyrimidine for Example 189A and 4-aminopyridine, respectively, in Example 191. MS (DCI) m/e 360 (M+H)$^+$, $^1$H NMR (400 MHz, DMSO-d$_6$): □ 10.43 (s, 1H), 9.94 (s, 1H), 8.80 (s, 1H), 8.34 (d, J=6.44 Hz, 1H), 8.17 (s, 1H), 7.65 (m, 2H), 7.42 (m, 2H), 7.07 (dd, J=8.75, 1.99 Hz, 1H), 6.98 (d, J=8.29 Hz, 1H), 6.93 (dd, J=6.44, 0.92 Hz, 1H), 3.75 (s, 3H).

EXAMPLE 470

7-(1-hydroxy-1-methylethyl)-3-(3-methoxy-4-nitrophenyl)-5,10-dihydro-11H-dibenzo[b,e][1,4]diazepin-11-one

EXAMPLE 470A 3-chloro-7-(1-hydroxy-1-methylethyl)-5,10-dihydro-11H-dibenzo[b,e][1,4]diazepin-11-one The desired product was prepared by substituting Example 469C for Example 1B in Example 189A. MS (DCI) m/e 303 (M+H)$^+$.

EXAMPLE 470B 7-(1-hydroxy-1-methylethyl)-3-(3-methoxy-4-nitrophenyl)-5,10-dihydro-11H-dibenzo[b,e][1,4]diazepin-11-one The desired product was prepared by substituting Example 470A and Example 266G for Example 59B and Example 56A, respectively, in Example 59C. MS (DCI) m/e 420 (M+H)$^+$, $^1$H NMR (500 MHz, DMSO-d$_6$): □ 9.82 (s, 1H), 8.01 (d, J=8.42 Hz, 1H), 7.96 (s, 1H), 7.80 (d, J=8.11 Hz, 1H), 7.52 (d, J=1.56 Hz, 1H), 7.40 (d, J=1.56 Hz, 1H), 7.35 (dd, J=8.58, 1.72 Hz, 1H), 7.30 (dd, J=8.26, 1.72 Hz, 1H), 7.19 (d, J=1.87 Hz, 1H), 6.96 (m, 1H), 6.89 (d, J=8.42 Hz, 1H), 4.04 (s, 3H), 1.38 (s, 6H).

EXAMPLE 471

7-(1-hydroxy-1-methylethyl)-3-(pyrimidin-4-ylamino)-5,10-dihydro-11H-dibenzo[b,e][1,4]diazepin-11-one The desired product was prepared by substituting Example 470A and 4-aminopyrimidine for Example 189A and 4-aminopyridine, respectively, in Example 191. MS (DCI) m/e 362 (M+H)$^+$, $^1$H NMR (500 MHz, DMSO-d$_6$): □ 10.47 (s, 1H), 9.63 (s, 1H), 8.85 (s, 1H), 8.39 (d, J=6.55 Hz, 1H), 7.95 (s, 1H), 7.69 (s, 1H), 7.43 (d, J=2.18 Hz, 1H), 7.20 (d, J=1.87 Hz, 1H), 7.12 (dd, J=8.73, 1.87 Hz, 1H), 6.98 (d, J=6.55 Hz, 1H), 6.94 (m, 1H), 6.86 (d, J=8.11 Hz, 1H), 1.38 (s, 6H).

EXAMPLE 472

2-{3-[(6-methoxypyrimidin-4-yl)amino]-11-oxo-10,11-dihydro-5H-dibenzo[b,e][1,4]diazepin-8-yl}-2-methylN(4-morpholin-4-ylphenyl)propanamide The desired product was prepared by substituting Example 202B and 6-methoxy-4-aminopyrimidine for Example 189A and 4-aminopyridine, respectively, in Example 191. MS (DCI) m/e 580 (M+H)$^+$, $^1$H NMR (500 MHz, DMSO-d$_6$): □ 9.56 (d, J=9.67 Hz, 2H), 8.79 (s, 1H), 8.44 (s, 1H), 7.88 (s, 1H), 7.61 (d, J=8.73 Hz, 1H), 7.42 (d, J=9.04 Hz, 2H), 7.37 (d, J=1.87 Hz, 1H), 6.95-7.00 (m, 3H), 6.89 (dd, J=8.26, 2.03 Hz, 1H), 6.86 (d, J=9.04 Hz, 2H), 6.20 (s, 1H), 3.87 (s, 3H), 3.72 (m, 4H), 3.03 (m, 4H), 1.47 (s, 6H).

EXAMPLE 473

3-(3-methoxy-4-nitrophenyl)-8-{2-[(6-morpholin-4-ylpyridin-3-yl)oxy]ethyl}-5,10-dihydro-11H-dibenzo[b,e][1,4]diazepin-11-one

EXAMPLE 473A 6-morpholin-4-ylpyridin-3-ol

The desired product was prepared by substituting 6-chloro-3-hydroxypyridine for 2-(4-bromo-phenyl)-ethanol in Example 447A. MS (DCI) m/e 181 (M+H)$^+$.

EXAMPLE 473B 3-(3-methoxy-4-nitrophenyl)-8-{2-[(6-morpholin-4-ylpyridin-3-yl)oxy]ethyl}-5,10-dihydro-11H-dibenzo[b,e][1,4]diazepin-11-one The desired product was prepared by substituting Example 239 and Example 473A for Example 204A and 2-hydroxypyridine, respectively, in Example 221A. MS (DCI) m/e 568 (M+H)$^+$, $^1$H NMR (500 MHz, DMSO-d$_6$): □ 9.85 (s, 1H), 8.01 (d, J=8.11 Hz, 1H), 7.95 (s, 1H), 7.87 (d, J=2.81 Hz, 1H), 7.79 (d, J=8.11 Hz, 1H), 7.52 (d, J=1.56 Hz, 1H), 7.28-7.35 (m, 4H), 6.92-6.96 (m, 3H), 6.81 (d, J=9.05 Hz, 1H), 4.10 (t, J=6.71 Hz, 2H), 4.03 (s, 3H), 3.68-3.70 (m, 4H), 3.29-3.31 (m, 4H), 2.87 (t, J=6.55 Hz, 2H).

EXAMPLE 474

3-(4-hydroxy-3-methoxyphenyl)-8-[2-(4-morpholin-4-ylphenoxy)ethyl]-5,10-dihydro-11H-dibenzo[b,e][1,4]diazepin-11-one The desired product was prepared by substituting Example 297A and 2-methoxy-4-(4,4,5,5-tetramethyl-1,3,2-dioxaborolan-2-yl)phenol for Example 59B and Example 56A, respectively, in Example 59C. MS (DCI) m/e 538 (M+H)$^+$, $^1$H NMR (300 MHz, DMSO-d$_6$): □ 9.70 (s, 1H), 9.22 (s, 1H), 7.80 (s, 1H), 7.70 (d, J=8.11 Hz, 1H), 7.22 (d, J=0.94 Hz, 1H), 7.17 (d, J=1.87 Hz, 1H), 7.14 (d, J=8.11 Hz, 1H), 7.07 (dd, J=8.27, 2.03 Hz, 1H), 6.81-6.94 (m, 8H), 4.04 (t, J=6.71 Hz, 2H), 3.85 (s, 3H), 3.70-3.72 (m, 4H), 2.96-2.98 (m, 4H), 2.86 (t, J=6.71 Hz, 2H).

EXAMPLE 475

3-[(2,6-difluoropyridin-4-yl)amino]-8-[2-(4-morpholin-4-ylphenoxy)ethyl]-5,10-dihydro-11H-dibenzo[b,e][1,4]diazepin-11-one The desired product was prepared by substituting Example 297A and Example 203A for Example 189A and 4-aminopyridine, respectively, in Example 191. MS (DCI) m/e 544 (M+H)$^+$, $^1$H NMR (300 MHz, DMSO-d$_6$): □ 9.65 (s, 1H), 9.62 (s, 1H), 7.87 (s, 1H), 7.67 (d, J=8.73 Hz, 1H), 6.80-6.88 (m, 8H), 6.66 (dd, J=8.58, 2.03 Hz, 1H), 6.55 (s, 2H), 4.02 (t, J=6.08 Hz, 2H), 3.69-3.71 (m, 4H), 2.94-2.96 (m, 4H), 2.84 (t, J=6.55 Hz, 2H).

EXAMPLE 476

7-hydroxy-8-methoxy-3-(3-methoxy-4-nitrophenyl)-5,10-dihydro-11H-dibenzo[b,e][1,4]diazepin-11-one

EXAMPLE 476A

{2-[(2-methoxy-5-nitrophenoxy)methoxy]ethyl}(trimethyl)silane

A mixture of 2-methoxy-5-nitrophenol (10 g, 59.1 mmol) in dichloromethane (150 mL) was treated with 2-(trimethylsilyl)ethoxymethyl chloride (10.5 mL, 59.3 mmol) and N,N-diisopropylethylamine (11.3 mL, 64.9 mmol) at room temperature and stirred for 1.5 hours. The reaction mixture was then concentrated under vacuum, diluted with ethyl acetate, washed with water and brine, dried (MgSO$_4$), filtered, and concentrated under vacuum to provide the desired product.

EXAMPLE 476B 4-methoxy-3-{[2-(trimethylsilyl)ethoxy]methoxy}phenylamine

A mixture Example 476A, 5% Pt/C (1 g) and ethanol (500 mL) was equipped with a balloon of hydrogen gas and stirred at room temperature. After uptake of the hydrogen was complete, the solution was filtered through diatomaceous earth (Celite®). The filtrate was concentrated under vacuum to provide the desired product.

EXAMPLE 476C

N-(4-methoxy-3-{[2-(trimethylsilyl)ethoxy]methoxy}phenyl)acetamide

A mixture of Example 476B, acetic anhydride (20 mL), and 4-(dimethylamino)pyridine (722 mg, 5.9 mmol) in dichloroethane (150 mL) was stirred at room temperature for 2 hours. The reaction mixture was then concentrated under vacuum, diluted with ethyl acetate, washed with water and brine, dried (MgSO$_4$), filtered, and concentrated under vacuum. The residue was diluted with hexanes and stirred vigorously until a solid formed. The solid was filtered, rinsed with hexane, and dried under vacuum to produce 15 g (81% over 3 steps from Examples 476A-C) of the desired product. MS (ESI) m/e 334 (M+Na)+; $^1$H NMR (300 MHz, DMSO-d$_6$) □ 9.74 (s, 1H), 7.33 (d, J=2.7 Hz, 1H), 7.18 (dd, J=2.5, 8.7 Hz, 1H), 6.89 (d, J=8.8 Hz, 1H), 5.13 (s, 2H), 3.67-3.73 (m, 2H), 3.71 (s, 3H), 1.98 (s, 3H), 0.86-0.92 (m, 2H), -0.02 (s, 9H).

EXAMPLE 476D

N-(4-methoxy-2-nitro-5-{[2-(trimethylsilyl)ethoxy]methoxy}phenyl)acetamide

The desired product was prepared by substituting Example 476C for Example 223A in Example 223B. MS (DCI) m/e 374 (M+NH$_4$)+; $^1$H NMR (300 MHz, DMSO-d$_6$) □ 10.14 (s, 1H), 7.56 (s, 1H), 7.51 (s, 1H), 5.32 (s, 2H), 3.85 (s, 3H), 3.69-3.75 (m, 2H), 2.06 (s, 3H), 0.87-0.93 (m, 2H), -0.02 (s, 9H).

EXAMPLE 476E 4-methoxy-2-nitro-5-{[2-(trimethylsilyl)ethoxy]methoxy}aniline

A mixture of Example 476D and K$_2$CO$_3$ (7.0 g, 50.6 mmol) in methanol (220 mL) was stirred at room temperature overnight, concentrated under vacuum, diluted with ethyl acetate, washed with water and brine, dried (MgSO$_4$), filtered and concentrated under vacuum to produce 9.7 g (91%) of the desired product. MS (ESI) m/e 315 (M+H)+; $^1$H NMR (300 MHz, DMSO-d$_6$) □ 7.43 (br s, 2H), 7.37 (s, 1H), 6.66 (s, 1H), 5.28 (s, 2H), 3.69-3.75 (m, 2H), 3.73 (s, 3H), 0.89-0.94 (m, 2H), -0.01 (s, 9H).

EXAMPLE 476F methyl 4-chloro-2-[(4-methoxy-2-nitro-5-{[2-(trimethylsilyl)ethoxy]methoxy}phenyl)amino]benzoate The desired product was prepared by substituting Example 476E for methyl 3,4-diaminobenzoate in Example 1A. MS (ESI) m/e 483 (M+H)+; $^1$H NMR (300 MHz, DMSO-d$_6$) □ 10.95 (s, 1H), 7.96 (d, J=8.5 Hz, 1H), 7.67 (s, 1H), 7.50 (d, J=1.7 Hz, 1H), 7.34 (s, 1H), 7.09 (dd, J=1.9, 8.7 Hz, 1H), 5.32 (s, 2H), 3.89 (s, 3H), 3.86 (s, 3H), 3.69-3.74 (m, 2H), 0.89-0.95 (m, 2H), -0.06 (s, 9H).

EXAMPLE 476G 3-chloro-8-methoxy-7-{[2-(trimethylsilyl)ethoxy]methoxy}-5,10-dihydro-11H-dibenzo[b,e][1,4]diazepin-11-one A mixture of Example 476F (11.4 g, 23.6 mmol), LiOH.H$_2$O (2.97 g, 70.8 mmol), methanol (200 mL), THF (100 mL) and water (10 mL) was heated at 65° C. for 4.25 hours. When hydrolysis was complete, triethylamine (65.8 mL, 472 mmol) was added, followed by SnCl$_2$.2H$_2$O (26.6 g, 118 mmol). The mixture was heated at 65° C. overnight, then cooled to room temperature when hydrogenation was complete. DMF (200 mL), triethylamine (16.5 mL, 118 mmol) and HATU (17.95 g, 47.2 mmol) were added and the mixture was stirred overnight, filtered through diatomaceous earth (Celite®), concentrated under vacuum, diluted with ethyl acetate, washed with water and brine, dried (MgSO$_4$), filtered, and concentrated under vacuum. Hexane was added to a solution of the concentrate in diethyl ether to invoke formation of a solid which was filtered, rinsed with hexane, and dried under vacuum to give 8.8 g (89%) of the desired product. MS (ESI) m/e 421 (M+H)+; $^1$H NMR (300 MHz, DMSO-d$_6$) □ 9.69 (s, 1H), 7.81 (s, 1H), 7.65 (d, J=8.5 Hz, 1H), 7.04 (d, J=2.0 Hz, 1H), 6.91 (dd, J=2.0, 8.5 Hz, 1H), 6.76 (s, 1H), 6.65 (s, 1H), 5.11 (s, 2H), 3.67 (s, 3H), 3.65-3.72 (m, 2H), 0.86-0.94 (m, 2H), -0.03 (s, 9H).

EXAMPLE 476H 8-methoxy-3-(3-methoxy-4-nitrophenyl)-7-{[2-(trimethylsilyl)ethoxy]methoxy}-5,10-dihydro-11H-dibenzo[b,e][1,4]diazepin-11-one A mixture of Example 476G (60 mg, 0.14 mmol), Example 266G (60 mg, 0.22 mmol), Pd(PPh$_3$)$_4$ (66 mg, 0.057 mmol), IM Na$_2$CO$_3$ solution (0.2 mL, 0.2 mmol), and a 7:2:3 mixture of ethylene glycol dimethyl ether/ethanol/water (4 mL) was placed in a microwave process vial, crimped and heated at 160° C. for 30 minutes in an Emrys Synthesizer set at 300 W. It was then removed from the instrument, cooled to room temperature, filtered through diatomaceous earth (Celite®), concentrated under vacuum, diluted with ethyl acetate, washed with water and brine, dried (MgSO$_4$), filtered, and concentrated under vacuum. The residue was purified by column chromatography to give 47 mg (62%) of the desired product. MS (ESI) m/e 538 (M+H)+; $^1$H NMR (300 MHz, DMSO-d$_6$) □ 9.68 (s, 1H), 8.01 (d, J=8.5 Hz, 1H), 7.76-7.79 (m, 2H), 7.51 (d, J=1.7 Hz, 1H), 7.27-7.35 (m, 3H), 6.82 (s, 1H), 6.67 (s, 1H), 5.11 (s, 2H), 4.03 (s, 3H), 3.68 (s, 3H), 3.67-3.72 (m, 2H), 0.86-0.92 (m, 2H), -0.04 (s, 9H).

EXAMPLE 476I 7-hydroxy-8-methoxy-3-(3-methoxy-4-nitrophenyl)-5,10-dihydro-11H-dibenzo[b,e][1,4]diazepin-11-one A mixture of Example 476H (429 mg, 0.8 mmol) in methylene chloride (20 mL) and methanol (10 mL) was treated with 4N HCl/dioxane (1 mL, 4.0 mmol) and stirred one hour at room temperature. The mixture was concentrated under vacuum to provide 325 mg (quantitative) of desired product. MS (ESI) m/e 408 (M+H)+; $^1$H NMR (300 MHz, DMSO-d$_6$) □ 9.57 (s, 1H), 8.89 (s, 1H), 8.01 (d, J=8.1 Hz, 1H), 7.76 (d, J=8.1 Hz, 1H), 7.65 (s, 1H), 7.51 (d, J=1.7 Hz, 1H), 7.26-7.35 (m, 3H), 6.59 (s, 1H), 6.52 (s, 1H), 4.03 (s, 3H), 3.67 (s, 3H).

EXAMPLE 477

8-hydroxy-7-methoxy-3-(3-methoxy-4-nitrophenyl)-5,10-dihydro-11H-dibenzo[b,e][1,4]diazepin-11-one

EXAMPLE 477A

{2-[(2-methoxy-4-nitrophenoxy)methoxy]ethyl}(trimethyl)silane

The desired product was prepared by substituting 2-methoxy-4-nitrophenol for 2-methoxy-5-nitrophenol in Example 476A. MS (ESI) m/e 317 (M+NH$_4$)$^+$; $^1$H NMR (300 MHz, DMSO-d$_6$) ☐ 7.89 (dd, J=2.7, 8.8 Hz, 1H), 7.70 (d, J=2.7 Hz, 1H), 7.27 (d, J=8.8 Hz, 1H), 5.38 (s, 2H), 3.90 (s, 3H), 3.70-3.75 (m, 2H), 0.86-0.92 (m, 2H), -0.03 (s, 9H).

EXAMPLE 477B 3-methoxy-4-{[2-(trimethylsilyl)ethoxy]methoxy}aniline

The desired product was prepared by substituting Example 477A for Example 476A in Example 476B.

EXAMPLE 477C

N-(3-methoxy-4-{[2-(trimethylsilyl)ethoxy]methoxy}phenyl)acetamide

The desired product was prepared by substituting Example 477B for Example 476B in Example 476C. $^1$H NMR (300 MHz, DMSO-d$_6$) ☐ 9.80 (s, 1H), 7.31 (d, J=2.0 Hz, 1H), 7.02 (dd, J=2.4, 8.8 Hz, 1H), 6.95 (d, J=8.8 Hz, 1H), 5.09 (s, 2H), 3.72 (s, 3H), 3.67-3.74 (m, 2H), 2.00 (s, 3H), 0.84-0.90 (m, 2H), -0.02 (s, 9H).

EXAMPLE 477D

N-(5-methoxy-2-nitro-4-{[2-(trimethylsilyl)ethoxy]methoxy}phenyl)acetamide

The desired product was prepared by substituting Example 477C for Example 223A in Example 223B. MS (ESI) m/e 357 (M+H)$^+$; $^1$H NMR (300 MHz, DMSO-d$_6$) ☐ 10.20 (s, 1H), 7.74 (s, 1H), 7.51 (s, 1H), 5.27 (s, 2H), 3.86 (s, 3H), 3.70-3.75 (m, 2H), 2.10 (s, 3H), 0.86-0.92 (m, 2H), -0.03 (s, 9H).

EXAMPLE 477E 5-methoxy-2-nitro-4-{[2-(trimethylsilyl)ethoxy]methoxy}aniline

The desired product was prepared by substituting Example 477D for Example 476D in Example 476E. MS (ESI) m/e 313 (M−H)$^−$; $^1$H NMR (300 MHz, DMSO-d$_6$) ☐ 7.59 (s, 1H), 7.43 (br s, 2H), 6.52 (s, 1H), 5.11 (s, 2H), 3.80 (s, 3H), 3.68-3.73 (m, 2H), 0.86-0.91 (m, 2H), -0.02 (s, 9H).

EXAMPLE 477F methyl 4-chloro-2-[(5-methoxy-2-nitro-4-{[2-(trimethylsilyl)ethoxy]methoxy}phenyl)amino]benzoate The desired product was prepared by substituting Example 477E for methyl 3,4-diaminobenzoate in Example 1A. MS (ESI) m/e 483 (M+H)$^+$; $^1$H NMR (300 MHz, DMSO-d$_6$) ☐ 10.96 (s, 1H), 7.96 (d, J=8.8 Hz, 1H), 7.85 (s, 1H), 7.62 (d, J=2.0 Hz, 1H), 7.19 (s, 1H), 7.11 (dd, J=2.0, 8.5 Hz, 1H), 5.27 (s, 2H), 3.89 (s, 3H), 3.83 (s, 3H), 3.72-3.78 (m, 2H), 0.89-0.94 (m, 2H), -0.01 (s, 9H).

EXAMPLE 477G 3-chloro-7-methoxy-8-{[2-(trimethylsilyl)ethoxy]methoxy}-5,10-dihydro-11H-dibenzo[b,e][1,4]diazepin-11-one The desired product was prepared by substituting Example 477F for Example 476F in Example 476G. MS (ESI) m/e 421 (M+H)$^+$; $^1$H NMR (300 MHz, DMSO-d$_6$) ☐ 9.70 (s, 1H), 7.84 (s, 1H), 7.65 (d, J=8.5 Hz, 1H), 7.03 (d, J=2.0 Hz, 1H), 6.92 (dd, J=2.0, 8.5 Hz, 1H), 6.75 (s, 1H), 6.65 (s, 1H), 5.03 (s, 2H), 3.71 (s, 3H), 3.65-3.71 (m, 2H), 0.86-0.91 (m, 2H), -0.02 (s, 9H).

EXAMPLE 477H 7-methoxy-3-(3-methoxy-4-nitrophenyl)-8-{[2-(trimethylsilyl)ethoxy]methoxy}-5,10-dihydro-11H-dibenzo[b,e][1,4]diazepin-11-one The desired product was prepared by substituting Example 477G for Example 476G in Example 476H. MS (ESI) m/e 538 (M+H)$^+$.

EXAMPLE 477I 8-hydroxy-7-methoxy-3-(3-methoxy-4-nitrophenyl)-5,10-dihydro-11H-dibenzo[b,e][1,4]diazepin-11-one The desired product was prepared by substituting Example 477H for Example 476H in Example 476I . MS (ESI) m/e 408 (M+H)$^+$; $^1$H NMR (400 MHz, DMSO-d$_6$) ☐ 9.64 (s, 1H), 8.62 (s, 1H), 8.01 (d, J=8.6 Hz, 1H), 7.76 (d, J=8.3 Hz, 1H), 7.62 (s, 1H), 7.52 (d, J=1.2 Hz, 1H), 7.26-7.35 (m, 3H), 6.64 (s, 1H), 6.48 (s, 1H), 4.03 (s, 3H), 3.70 (s, 3H).

EXAMPLE 478

8-methoxy-3-(3-methoxy-4-nitrophenyl)-7-(tetrahydro-2H-pyran-2-ylmethoxy)-5,10-dihydro-11H-dibenzo[b,e][1,4]diazepin-11-one A mixture of Example 476I (40 mg, 0.098 mmol), 2-bromomethyl-tetrahydro-2H-pyran (0.13 mL, 0.98 mmol), K$_2$CO$_3$ (136 mg, 0.98 mmol) and DMF (2 mL) was heated at 100° C. overnight, cooled to room temperature, diluted with ethyl acetate, washed with water and brine, dried (MgSO$_4$), filtered and concentrated under vacuum. The residue was purified by column chromatography on silica gel with 49:1 dichloromethane/methanol to provide 23 mg (47%) of the desired product. MS (ESI) m/e 506 (M+H)$^+$; $^1$H NMR (300 MHz, DMSO-d$_6$) ☐9.66 (s, 1H), 8.01 (d, J=8.5 Hz, 1H), 7.77 (d, J=8.8 Hz, 1H), 7.71 (s, 1H), 7.53 (d, J=1.7 Hz, 1H), 7.35 (dd, J=1.7, 8.5 Hz, 1H), 7.26-7.31 (m, 2H), 6.69 (s, 1H), 6.64 (s, 1H), 4.03 (s, 3H), 3.72-3.94 (m, 3H), 3.67 (s, 3H), 3.60 (m, 1H), 3.39 (m, 1H), 1.82 (m, 1H), 1.64 (m, 1H), 1.41-1.55 (m, 3H), 1.27 (m, 1H).

EXAMPLE 479

8-methoxy-3-(3-methoxy-4-nitrophenyl)-7-[(1-methylpiperidin-3-yl)methoxy]-5,10-dihydro-11H-dibenzo[b,e][1,4]diazepin-11-one The desired product was prepared by substituting 3-chloromethyl-1-methyl-piperidine for 2-bromomethyl-tetrahydro-2H-pyran in Example 478. MS (ESI) m/e 519 (M+H)$^+$; $^1$H NMR (300 MHz, DMSO-d$_6$) ☐ 9.66 (s, 1H), 8.02 (d, J=8.5 Hz, 1H), 7.78 (d, J=8.8 Hz, 1H), 7.72 (s, 1H), 7.53 (d, J=1.7 Hz, 1H), 7.36 (dd, J=1.7, 8.5 Hz, 1H), 7.25-7.30 (m, 2H), 6.71 (s, 1H), 6.65 (s, 1H), 4.03 (s, 3H), 3.69-3.87 (m, 2H), 3.68 (s, 3H), 3.29 (s, 3H), 2.85 (m, 1H), 2.12-2.29 (m, 2H), 2.00 (m, 1H), 1.58-1.75 (m, 2H), 1.49 (m, 1H), 1.10 (m, 1H), 0.88 (m, 1H).

EXAMPLE 480

8-methoxy-3-(3-methoxy-4-nitrophenyl)-7-(pyridin-2-ylmethoxy)-5,10-dihydro-11H-dibenzo[b,e][1,4]diazepin-11-one The desired product was prepared by substituting 2-(chloromethyl)pyridine hydrochloride for 2-bromomethyl-tetrahydro-2H-pyran in Example 478. MS (ESI) m/e 499 (M+H)$^+$; $^1$H NMR (300 MHz, DMSO-d$_6$) ☐ 9.65 (s, 1H), 8.58 (m, 1H), 8.00 (d, J=8.4 Hz, 1H), 7.85 (m, 1H), 7.78 (d, J=8.1 Hz, 1H), 7.73 (s, 1H), 7.51 (d, J=1.6 Hz, 1H), 7.49 (d, J=7.8 Hz, 1H), 7.32-7.35 (m, 2H), 7.27-7.30 (m, 2H), 6.77 (s, 1H), 6.70 (s, 1H), 5.09 (s, 2H), 4.03 (s, 3H), 3.71 (s, 3H).

EXAMPLE 481

8-methoxy-3-(3-methoxy-4-nitrophenyl)-7-(pyridin-3-ylmethoxy)-5,10-dihydro-11H-dibenzo[b,e][1,4]diazepin-11-one The desired product was prepared by substituting 3-(chloromethyl)pyridine hydrochloride for 2-bromomethyl-tetrahydro-2H-pyran in Example 478. MS (ESI) m/e 499 (M+H)$^+$; $^1$H NMR (500 MHz, DMSO-d$_6$) ☐ 9.66 (s, 1H), 8.65 (d, J=1.9 Hz, 1H), 8.54 (dd, J=1.6, 4.7 Hz, 1H), 8.01 (d, J=8.4 Hz, 1H), 7.83 (m, 1H), 7.77-7.79 (m, 2H), 7.52 (d, J=1.6 Hz, 1H), 7.43 (dd, J=5.0, 7.8 Hz, 1H), 7.35 (dd, J=1.6, 8.4 Hz, 1H), 7.32 (d, J=1.6 Hz, 1H), 7.29 (dd, J=1.6, 8.1 Hz, 1H), 6.81 (s, 1H), 6.69 (s, 1H), 5.05 (s, 2H), 4.03 (s, 3H), 3.69 (s, 3H).

EXAMPLE 482

8-methoxy-3-(3-methoxy-4-nitrophenyl)-7-(pyridin-4-ylmethoxy)-5,10-dihydro-11H-dibenzo[b,e][1,4]diazepin-11-one The desired product was prepared by substituting 4-(chloromethyl)pyridine hydrochloride for 2-bromomethyl-tetrahydro-2H-pyran in Example 478. MS (ESI) m/e 499 (M+H)$^+$; $^1$H NMR (500 MHz, DMSO-d$_6$) ☐ 9.69 (s, 1H), 8.72 (d, J=5.3 Hz, 2H), 8.01 (d, J=8.4 Hz, 1H), 7.78 (d, J=8.7 Hz, 1H), 7.75 (s, 1H), 7.66 (d, J=5.6 Hz, 2H), 7.52 (d, J=1.6 Hz, 1H), 7.33 (dd, J=1.6, 8.4 Hz, 1H), 7.28-7.30 (m, 2H), 6.75 (s, 1H), 6.72 (s, 1H), 5.19 (s, 2H), 4.03 (s, 3H), 3.73 (s, 3H).

EXAMPLE 483

8-methoxy-3-(3-methoxy-4-nitrophenyl)-7-[(5-methylisoxazol-3-yl)methoxy]-5,10-dihydro-11H-dibenzo[b,e][1,4]diazepin-11-one The desired product was prepared by substituting 3-bromomethyl-5-methyl-isoxazole for 2-bromomethyl-tetrahydro-2H-pyran in Example 478. MS (ESI) m/e 503 (M+H)$^+$; $^1$H NMR (500 MHz, DMSO-d$_6$) ☐9.69 (s, 1H), 8.01 (d, J=8.5 Hz, 1H), 7.76-7.79 (m, 2H), 7.52 (d, J=1.7 Hz, 1H), 7.27-7.36 (m, 3H), 6.77 (s, 1H), 6.68 (s, 1H), 6.30 (d, J=0.7 Hz, 1H), 5.03 (s, 2H), 4.03 (s, 3H), 3.69 (s, 3H), 2.41 (d, J=0.7 Hz, 3H).

EXAMPLE 484

8-methoxy-3-(3-methoxy-4-nitrophenyl)-7-[(1-methyl-1H-imidazol-5-yl)methoxy]-5,10-dihydro-11H-dibenzo[b,e][1,4]diazepin-11-one

EXAMPLE 484A 5-(chloromethyl)-1-methyl-1H-imidazole hydrochloride

A mixture of (1-methyl-1H-imidazol-5-yl)methanol (500 mg, 4.5 mmol) in DMF (5 mL) at −5° C. was slowly treated with thionyl chloride (0.49 mL, 6.7 mmol), stirred an additional 10 minutes at −5° C., warmed to room temperature, stirred 1.5 hours, cooled to −5° C., quenched with isopropyl alcohol and ethyl acetate, stirred 30 minutes at −5° C., concentrated under vacuum, and filtered to collect the solid. The solid was rinsed with ethyl acetate and dried under vacuum to give (212 mg, 28%) of the desired product as the hydrochloride salt. MS (DCI) m/e 131 (M+H)$^+$; $^1$H NMR (300 MHz, DMSO-d$_6$) ☐ 9.10 (s, 1H), 7.76 (s, 1H), 5.02 (s, 2H), 3.88 (s, 3H).

EXAMPLE 484B 8-methoxy-3-(3-methoxy-4-nitrophenyl)-7-[(1-methyl-1H-imidazol-5-yl)methoxy]-5,10-dihydro-11H-dibenzo[b,e][1,4]diazepin-11-one The desired product was prepared by substituting Example 484A for 2-bromomethyl-tetrahydro-2H-pyran in Example 478. MS (ESI) m/e 502 (M+H)$^+$; $^1$H NMR (300 MHz, DMSO-d$_6$) ☐10.08 (s, 1H), 8.94 (s, 1H), 9.04 (m, 1H), 8.02 (d, J=8.5 Hz, 1H), 7.71 (d, J=8.1 Hz, 1H), 7.65 (s, 2H), 7.49-7.56 (m, 2H), 7.46 (dd, J=1.7, 8.5 Hz, 1H), 6.81 (s, 1H), 6.68 (s, 1H), 5.05-5.30 (m, 2H), 4.06 (s, 3H), 3.87 (s, 3H), 3.69 (s, 3H).

EXAMPLE 485

8-methoxy-3-(3-methoxy-4-nitrophenyl)-7-[(2-methyl-1,3-thiazol-4-yl)methoxy]-5,10-dihydro-11H-dibenzo[b,e][1,4]diazepin-11-one The desired product was prepared by substituting 4-chloromethyl-2-methyl-thiazole hydrochloride for 2-bromomethyl-tetrahydro-2H-pyran in Example 478. MS (ESI) m/e 519 (M+H)$^+$; $^1$H NMR (500 MHz, DMSO-d$_6$) ☐ 9.65 (s, 1H), 8.00 (d, J=8.4 Hz, 1H), 7.78 (d, J=8.1 Hz, 1H), 7.72 (s, 1H), 7.52 (d, J=1.6 Hz, 1H), 7.46 (s, 1H), 7.27-7.35 (m, 3H), 6.79 (s, 1H), 6.67 (s, 1H), 5.00 (s, 2H), 4.03 (s, 3H), 3.68 (s, 3H), 2.65 (s, 3H)

EXAMPLE 486

8-methoxy-3-(3-methoxy-4-nitrophenyl)-7-[(2-oxo-1,3-oxazolidin-5-yl)methoxy]-5,10-dihydro-11H-dibenzo[b,e][1,4]diazepin-11-one The desired product was prepared by substituting 5-chloromethyl-2-oxazolidinone for 2-bromomethyl-tetrahydro-2H-pyran in Example 478. MS (ESI) m/e 507 (M+H)$^+$; $^1$H NMR (500 MHz, DMSO-d$_6$) □ 9.66 (s, 1H), 8.00 (d, J=8.4.0 Hz, 1H), 7.77 (d, J=7.8 Hz, 1H), 7.72 (s, 1H), 7.54 (s, 1H), 7.52 (d, J=1.3 Hz, 1H), 7.27-7.34 (m, 3H), 6.73 (s, 1H), 6.67 (s, 1H), 4.86 (m, 1H), 4.02 (s, 3H), 3.97-4.09 (m, 3H), 3.68 (s, 3H), 3.58 (t, J=8.9 Hz, 1H).

EXAMPLE 487

8-methoxy-3-(3-methoxy-4-nitrophenyl)-7-(tetrahydrofuran-2-ylmethoxy)-5,10-dihydro-11H-dibenzo[b,e][1,4]diazepin-11-one The desired product was prepared by substituting 2-bromomethyl-tetrahydro-furan for 2-bromomethyl-tetrahydro-2H-pyran in Example 478. MS (ESI) m/e 492 (M+H)$^+$; $^1$H NMR (400 MHz, DMSO-d$_6$) □ 9.63 (s, 1H), 8.00 (d, J=8.3 Hz, 1H), 7.76 (d, J=8.0 Hz, 1H), 7.69 (s, 1H), 7.51, (d, J=1.2 Hz, 1H), 7.26-7.35 (m, 3H), 6.70 (s, 1H), 6.64 (s, 1H), 4.10 (m, 1H), 3.81-3.84 (m, 2H), 3.77 (m, 1H), 4.02 (s, 3H), 3.67 (s, 3H), 3.67 (m, 1H), 1.97 (m, 1H), 1.77-1.90 (m, 2H), 1.63 (m, 1H).

EXAMPLE 488

7-[(2,2-dimethyl-1,3-dioxolan-4-yl)methoxy]-8-methoxy-3-(3-methoxy-4-nitrophenyl)-5,10-dihydro-11H-dibenzo[b,e][1,4]diazepin-11-one The desired product was prepared by substituting 4-chloromethyl-2,2-dimethyl-[1,3]dioxolane for 2-bromomethyl-tetrahydro-2H-pyran in Example 478. MS (ESI) m/e 522 (M+H)$^+$; $^1$H NMR (300 MHz, DMSO-d$_6$) □ 9.68 (s, 1H), 8.01 (d, J=8.5 Hz, 1H), 7.77 (d, J=8.5 Hz, 1H), 7.72 (s, 1H), 7.53 (d, J=1.7 Hz, 1H), 7.35 (dd, J=1.7, 8.5 Hz, 1H), 7.27-7.32 (m, 2H), 6.73 (s, 1H), 6.66 (s, 1H), 4.38 (m, 1H), 4.08 (dd, J=6.6, 8.3 Hz, 1H), 4.03 (s, 3H), 3.89 (d, J=5.4 Hz, 2H), 3.74 (dd, J=5.9, 8.3 Hz, 1H), 3.68 (s, 3H), 1.35 (s, 3H), 1.30 (s, 3H).

EXAMPLE 489

8-methoxy-3-(3-methoxy-4-nitrophenyl)-7-[(2R)-pyrrolidin-2-ylmethoxy]-5,10-dihydro-11H-dibenzo[b,e][1,4]diazepin-11-one

EXAMPLE 489A tert-butyl (2R)-2-({[(4-methylphenyl)sulfonyl]oxy}methyl)pyrrolidine-1-carboxylate A mixture of Boc-D-prolinol (201 mg, 1.0 mmol), p-toluenesulfonyl chloride (400 mg, 2.1 mmol), triethylamine (420 μL, 3.0 mmol), and 4-(dimethylamino)pyridine (12 mg, 0.1 mmol) in dichloromethane (10 mL) was heated at 40° C. for 48 hours, cooled to room temperature, concentrated under vacuum, diluted with ethyl acetate, washed with water and brine, dried (MgSO$_4$), filtered, and concentrated. The residue was purified by column chromatography on silica gel to provide 160 mg (45%) of the desired product.

EXAMPLE 489B tert-butyl (2R)-2-({[8-methoxy-3-(3-methoxy-4-nitrophenyl)-11-oxo-10,11-dihydro-5H-dibenzo[b,e][1,4]diazepin-7-yl]oxy}methyl)pyrrolidine-1-carboxylate The desired product was prepared by substituting Example 489A for 2-bromomethyl-tetrahydro-2H-pyran in Example 478.

EXAMPLE 489C 8-methoxy-3-(3-methoxy-4-nitrophenyl)-7-[(2R)-pyrrolidin-2-ylmethoxy]-5,10-dihydro-11H-dibenzo[b,e][1,4]diazepin-11-one A mixture of Example 489B in methanol (2 mL) was treated with 4.0N HCl/dioxane (0.15 mL, 0.6 mmol), stirred overnight at room temperature, concentrated under vacuum, and purified by preparative HPLC to give 3.9 mg (9%) of the desired product as the TFA salt. MS (ESI) m/e 491 (M+H)$^+$; $^1$H NMR (300 MHz, DMSO-d$_6$) □ 9.72 (s, 1H), 8.70 (s, 1H), 8.02 (d, J=8.1 Hz, 1H), 7.77-7.80 (m, 2H), 7.53 (d, J=1.4 Hz, 1H), 7.29-7.36 (m, 3H), 6.75 (s, 1H), 6.71 (s, 1H), 4.15 (m, 1H), 4.03 (s, 3H), 3.83-3.96 (m, 1H), 3.71 (s, 3H), 3.17-3.27 (m, 3H), 2.13 (m, 1H), 1.84-2.01 (m, 2H), 1.72 (m, 1H).

EXAMPLE 490

7,8-dimethoxy-3-(3-methoxy-4-nitrophenyl)-5,10-dihydro-11H-dibenzo[b,e][1,4]diazepin-11-one The desired product was obtained by substituting iodomethane for 2-bromomethyl-tetrahydro-2H-pyran in Example 478. MS (ESI) m/e 422 (M+H)$^+$; $^1$H NMR (400 MHz, DMSO-d$_6$) □ 9.61 (s, 1H), 8.00 (d, J=8.3 Hz, 1H), 7.77 (d, J=8.3 Hz, 1H), 7.73 (s, 1H), 7.52 (d, J=1.5 Hz, 1H), 7.34 (dd, J=1.8, 8.6 Hz, 1H), 7.31 (d, J=1.8 Hz, 1H), 7.28 (dd, J=1.7, 8.1 Hz, 1H), 6.69 (s, 1H), 6.64 (s, 1H), 4.02 (s, 3H), 3.69 (s, 3H), 3.66 (s, 3H).

EXAMPLE 491

8-methoxy-7-[2-(2-methoxyethoxy)ethoxy]-3-(3-methoxy-4-nitrophenyl)-5,10-dihydro-11H-dibenzo[b,e][1,4]diazepin-11-one The desired product was prepared by substituting 1-bromo-2-(2-methoxyethoxy)ethane for 2-bromomethyl-tetrahydro-2H-pyran in Example 478. MS (ESI) m/e 510 (M+H)$^+$; $^1$H NMR (500 MHz, DMSO-d$_6$) □ 9.67 (s, 1H), 8.01 (d, J=8.2 Hz, 1H), 7.77 (d, J=7.9 Hz, 1H), 7.73 (s, 1H), 7.53 (d, J=1.5 Hz, 1H), 7.35 (dd, J=1.5, 8.5 Hz, 1H), 7.28-7.30 (m, 2H), 6.70 (s, 1H), 6.65 (s, 1H), 4.03 (s, 3H), 3.98-4.00 (m, 2H), 3.70-3.72 (m, 2H), 3.68 (s, 3H) 3.57-3.59 (m, 2H), 3.44-3.46 (m, 2H), 3.23 (s, 3H).

EXAMPLE 492

7-(2,3-dihydroxypropoxy)-8-methoxy-3-(3-methoxy-4-nitrophenyl)-5,10-dihydro-11H-dibenzo[b,e][1,4]diazepin-11-one The desired product was prepared by substituting 3-chloro-1,2-propanediol for 2-bromomethyl-tetrahydro-2H-pyran in Example 478. MS (ESI) m/e 482 (M+H)$^+$; $^1$H NMR (300

MHz, DMSO-d$_6$) □ 9.65 (s, 1H), 8.01 (d, J=8.5 Hz, 1H), 7.78 (d, J=8.5 Hz, 1H), 7.72 (s, 1H), 7.53 (d, J=1.7 Hz, 1H), 7.35 (dd, J=1.5, 8.3 Hz, 1H), 7.27-7.30 (m, 2H), 6.72 (s, 1H), 6.65 (s, 1H), 4.91 (d, J=4.8 Hz, 1H), 4.63 (t, J=5.6 Hz, 1H), 4.03 (s, 3H), 3.90 (m, 1H), 3.73-3.80 (m, 2H), 3.68 (s, 3H), 3.42-3.45 (m, 2H).

EXAMPLE 493

7-[3-hydroxy-2,2-bis(hydroxymethyl)propoxy]-8-methoxy-3-(3-methoxy-4-nitrophenyl)-5,10-dihydro-11H-dibenzo[b,e][1,4]diazepin-11-one The desired product was prepared by substituting 2-(bromomethyl)-2-(hydroxymethyl)-1,3-propanediol for 2-bromomethyl-tetrahydro-2H-pyran in Example 478. MS (ESI) m/e 526 (M+H)$^+$; $^1$H NMR (300 MHz, DMSO-d$_6$) □ 9.64 (s, 1H), 8.00 (d, J=8.5 Hz, 1H), 7.77 (d, J=7.8 Hz, 1H), 7.72 (s, 1H), 7.54 (d, J=1.7 Hz, 1H), 7.36 (dd, J=1.7, 8.5 Hz, 1H), 7.27-7.30 (m, 2H), 6.74 (s, 1H), 6.63 (s, 1H), 4.34 (t, J=5.1 Hz, 3H), 4.04 (s, 3H), 3.80 (s, 2H), 3.68 (s, 3H), 3.48 (d, J=5.4 Hz, 6H).

EXAMPLE 494

2-hydroxy-3-{[8-methoxy-3-(3-methoxy-4-nitrophenyl)-11-oxo-10,11-dihydro-5H-dibenzo[b,e][1,4]diazepin-7-yl]oxy}propane-1-sulfonic acid The desired product was prepared by substituting 3-chloro-2-hydroxy-1-propanesulfonic acid, sodium salt hydrate for 2-bromomethyl-tetrahydro-2H-pyran in Example 478. MS (ESI) m/e 546 (M+H)$^+$; $^1$H NMR (400 MHz, DMSO-d$_6$) □9.62 (s, 1H), 8.00 (d, J=8.6 Hz, 1H), 7.77 (d, J=8.0 Hz, 1H), 7.73 (s, 1H), 7.53 (d, J=1.5 Hz, 1H), 7.26-7.37 (m, 3H), 6.71 (s, 1H), 6.65 (s, 1H), 4.15 (m, 1H), 4.07 (m, 1H), 4.03 (s, 3H), 3.96 (m, 1H), 3.83 (m, 1H), 3.69 (s, 3H), 2.76 (m, 1H), 2.60 (m, 1H).

EXAMPLE 495

7-(3-aminopropoxy)-8-methoxy-3-(3-methoxy-4-nitrophenyl)-5,10-dihydro-11H-dibenzo[b,e][1,4]diazepin-11-one The desired product was prepared by substituting N-(3-bromo-propyl)phthalimide for 2-bromomethyl-tetrahydro-2H-pyran in Example 478, followed by the addition of hydrazine hydrate and THF. The mixture was heated at 50° C. for 2 hours, cooled to room temperature, and concentrated under vacuum. The residue was purified by preparative HPLC to provide 6 mg (8%) of the desired product as the TFA salt. MS (ESI) m/e 465 (M+H)$^+$; $^1$H NMR (300 MHz, DMSO-d$_6$) □ 9.67 (s, 1H), 8.02 (d, J=8.1 Hz, 1H), 7.76-7.79 (m, 2H), 7.52 (d, J=1.7 Hz, 1H), 7.28-7.35 (m, 3H), 6.73 (s, 1H), 6.67 (s, 1H), 4.03 (s, 3H), 3.95-3.99 (m, 2H), 3.68 (s, 3H), 2.91-2.95 (m, 2H), 1.93-2.04 (m, 2H).

EXAMPLE 496

7-[2-(dimethylamino)ethoxy]-8-methoxy-3-(3-methoxy-4-nitrophenyl)-5,10-dihydro-11H-dibenzo[b,e][1,4]diazepin-11-one The desired product was prepared by substituting (2-chloroethyl)dimethylamine for 2-bromomethyl-tetrahydro-2H-pyran in Example 478. MS (ESI) m/e 479 (M+H)$^+$; $^1$H NMR (400 MHz, DMSO-d$_6$) □9.63 (s, 1H), 8.01 (d, J=8.6 Hz, 1H), 7.78 (d, J=8.0 Hz, 1H), 7.71 (s, 1H), 7.53 (d, J=1.5 Hz, 1H), 7.35 (dd, J=1.5, 8.3 Hz, 1H), 7.27-7.31 (m, 2H), 6.72 (s, 1H), 6.65 (s, 1H), 4.03 (s, 3H), 3.95 (t, J=6.1 Hz, 2H), 3.67 (s, 3H), 2.60 (t, J=6.1 Hz, 2H), 2.21 (s, 6H).

EXAMPLE 497

7-(2-chloroethoxy)-8-methoxy-3-(3-methoxy-4-nitrophenyl)-5,10-dihydro-11H-dibenzo[b,e][1,4]diazepin-11-one The desired product was prepared by substituting 2-chloroethyl methanesulfonate for 2-bromomethyl-tetrahydro-2H-pyran in Example 478. MS (ESI) m/e 470 (M+H)$^+$; $^1$H NMR (300 MHz, DMSO-d$_6$) □ 9.68 (s, 1H), 8.01 (d, J=8.1 Hz, 1H), 7.78 (d, J=8.8 Hz, 1H), 7.74 (s, 1H), 7.53 (d, J=1.7 Hz, 1H), 7.34 (dd, J=1.7, 8.5 Hz, 1H), 7.27-7.30 (m, 2H), 6.73 (s, 1H), 6.68 (s, 1H), 4.13-4.16 (m, 2H), 4.03 (s, 3H), 3.89-3.93 (m, 2H), 3.69 (s, 3H).

EXAMPLE 498

8-methoxy-3-(3-methoxy-4-nitrophenyl)-7-(2-pyrrolidin-1-ylethoxy)-5,10-dihydro-11H-dibenzo[b,e][1,4]diazepin-11-one A mixture of Example 497 (11 mg, 0.023 mmol), pyrrolidine (3.9 µL, 0.046 mmol), K$_2$CO$_3$ (6.5 mg, 0.046 mmol) and DMF (0.5 mL) was heated overnight at 50° C., cooled to room temperature, and filtered. The filtrate was purified by preparative HPLC to provide 6 mg (51%) of the desired product. MS (ESI) m/e 505 (M+H)$^+$; $^1$H NMR (500 MHz, DMSO-d$_6$) □9.72 (s, 1H), 8.02 (d, J=8.4 Hz, 1H), 7.78-7.80 (m, 2H), 7.53 (d, J=1.6 Hz, 1H), 7.29-7.35 (m, 3H), 6.78 (s, 1H), 6.73 (s, 1H), 4.18 (t, J=5.0 Hz, 2H), 4.03 (s, 3H), 3.71 (s, 3H), 3.44-3.68 (m, 4H), 3.11-3.17 (m, 2H), 2.00-2.07 (m, 2H), 1.95-1.93 (m, 2H).

EXAMPLE 499

8-methoxy-3-(3-methoxy-4-nitrophenyl)-7-(2-morpholin-4-ylethoxy)-5,10-dihydro-11H-dibenzo[b,e][1,4]diazepin-11-one The desired product was prepared by substituting 4-(2-chloroethyl)morpholine hydrochloride for 2-bromomethyl-tetrahydro-2H-pyran in Example 478. MS (ESI) m/e 521 (M+H)$^+$; $^1$H NMR (500 MHz, DMSO-d$_6$) □ 9.71 (s, 1H), 8.00 (d, J=8.4 Hz, 1H), 7.77-7.78 (m, 2H), 7.51 (s, 1H), 7.29-7.33 (m, 3H), 6.76 (s, 1H), 6.71 (s, 1H), 4.20-4.22 (m, 2H), 4.02 (s, 3H), 3.87-3.97 (m, 2H), 3.60-3.89 (m, 2H), 3.69 (s, 3H), 3.48-3.55 (m, 2H), 3.10-3.40 (m, 4H).

EXAMPLE 500

7-(4-hydroxybutoxy)-8-methoxy-3-(3-methoxy-4-nitrophenyl)-5,10-dihydro-11H-dibenzo[b,e][1,4]diazepin-11-one

EXAMPLE 500A

7-[4-(tert-butyl-dimethyl-silanyloxy)-butoxy]-8-methoxy-3-(3-methoxy-4-nitro-phenyl)-5,10-dihydro-dibenzo[b,e][1,4]diazepin-11-one The desired product was prepared by substituting tert-butyl (4-iodobutoxy)dimethylsilane for 2-bromomethyl-tetrahydro-2H-pyran in Example 478.

EXAMPLE 500B 7-(4-hydroxybutoxy)-8-methoxy-3-(3-methoxy-4-nitrophenyl)-5,10-dihydro-11H-dibenzo[b,e][1,4]diazepin-11-one A mixture of Example 500A, Et$_4$NF.H$_2$O (10 equiv.) and THF was heated overnight at 65° C., concentrated under vacuum, diluted with ethyl acetate, washed with water and brine, dried (MgSO$_4$), filtered and concentrated under vacuum. The residue was purified by preparative HPLC to provide 50 mg (28%) of the desired product. MS (ESI) m/e 480 (M+H)$^+$; $^1$H NMR (400 MHz, DMSO-d$_6$) ☐ 9.63 (s, 1H), 8.01 (d, J=8.6 Hz, 1H), 7.78 (d, J=8.3 Hz, 1H), 7.71 (s, 1H), 7.53 (d, J=1.2 Hz, 1H), 7.35 (dd, J=1.5, 8.6 Hz, 1H), 7.28-7.30 (m, 2H), 6.70 (s, 1H), 6.65 (s, 1H), 4.03 (s, 3H), 3.89 (t, J=6.6 Hz, 2H), 3.67 (s, 3H), 3.44 (t, J=6.4 Hz, 2H), 1.69-1.76 (m, 2H), 1.51-1.58 (m, 2H).

EXAMPLE 501

7-(4-hydroxybutoxy)-3-(4-hydroxy-3-methoxyphenyl)-8-methoxy-5,10-dihydro-11H-dibenzo[b,e][1,4]diazepin-11-one

EXAMPLE 501A 3-chloro-7-hydroxy-8-methoxy-5,10-dihydro-11H-dibenzo[b,e][1,4]diazepin-11-one The desired product was prepared by substituting Example 476G for Example 476H in Example 476I. MS (ESI) m/e 291 (M+H)$^+$; $^1$H NMR (300 MHz, DMSO-d$_6$) ☐ 9.57 (s, 1H), 8.94 (s, 1H), 7.69 (s, 1H), 7.64 (d, J=8.5 Hz, 1H), 7.02 (d, J=2.4 Hz, 1H), 6.89 (dd, J=2.0, 8.5 Hz, 1H), 6.57 (s, 1H), 6.47 (s, 1H), 3.66 (s, 3H).

EXAMPLE 501B

7-[4-(tert-butyl-dimethyl-silanyloxy)-butoxy]-3-chloro-8-methoxy-5,10-dihydro-dibenzo[b,e][1,4]diazepin-11-one The desired product was prepared by substituting Example 501A and tert-butyl(4-iodobutoxy)dimethylsilane for Example 476 and 2-bromomethyl-tetrahydro-2H-pyran, respectively, in Example 478. MS (ESI) m/e 477 (M+H)$^+$; $^1$H NMR (300 MHz, DMSO-d$_6$) ☐ 9.64 (s, 1H), 7.73 (s, 1H), 7.64 (d, J=8.5 Hz, 1H), 7.00 (d, J=2.4 Hz, 1H), 6.90 (dd, J=2.0, 8.5 Hz, 1H), 6.62 (s, 2H), 3.89 (t, J=6.4 Hz, 2H), 3.65 (s, 3H), 3.63 (t, J=6.4 Hz, 2H), 1.68-1.77 (m, 2H), 1.53-1.62 (m. 2H), 0.84 (s, 9H), 0.02 (s, 6H).

EXAMPLE 501C

7-[4-(tert-butyl-dimethyl-silanyloxy)-butoxy]-3-(4-hydroxy-3-methoxy-phenyl)-8-methoxy-5,10-dihydro-dibenzo[b,e][1,4]diazepin-11-one The desired product was prepared by substituting Example 501B and 2-methoxy-4-(4,4,5,5-tetramethyl-[1,3,2]dioxaborolan-2-yl)-phenol for Example 476G and Example 266G respectively, in Example 476H. MS (ESI) m/e 565 (M+H)$^+$.

EXAMPLE 501D 7-(4-hydroxybutoxy)-3-(4-hydroxy-3-methoxyphenyl)-8-methoxy-5,10-dihydro-11H-dibenzo [b,e][1,4]diazepin-11-one The desired product was prepared by substituting Example 501C for Example A-500A in Example 500B. MS (ESI) m/e 451 (M+H)$^+$; $^1$H NMR (300 MHz, DMSO-d$_6$) ☐9.51 (s, 1H), 9.25 (s, 1H), 7.68 (d, J=8.1 Hz, 1H), 7.58 (s, 1H), 7.04-7.20 (m, 4H), 6.86 (d, J=8.1 Hz, 1H), 6.69 (s, 1H) 6.53 (s, 1H), 4.43 (t, J=5.3 Hz, 1H), 3.88 (t, J=6.4 Hz, 2H), 3.86 (s, 3H), 3.66 (s, 3H), 3.39-3.50 (m, 2H), 1.68-1.77 (m, 2H), 1.49-1.59 (m, 2H).

EXAMPLE 502

7-(4-hydroxybutoxy)-8-methoxy-3-(pyrimidin-4-ylamino)-5,10-dihydro-11H-dibenzo[b,e][1,4]diazepin-11-one

EXAMPLE 502A

7-[4-(tert-butyl-dimethyl-silanyloxy)-butoxy]-8-methoxy-3-(pyrimidin-4-ylamino)-5,10-dihydro-dibenzo[b,e][1,4]diazepin-11-one The desired product was prepared by substituting Example 501B and 4-aminopyrimidine for Example 189A and 4-aminopyridine, respectively, in Example 191.

EXAMPLE 502B 7-(4-hydroxybutoxy)-8-methoxy-3-(pyrimidin-4-ylamino)-5,10-dihydro-11H-dibenzo[b,e][1,4]diazepin-11-one The desired product was prepared by substituting Example 502A for Example 500A in Example 500B. MS (ESI) m/e 422 (M+H)$^+$; $^1$H NMR (400 MHz, DMSO-d$_6$) ☐ 9.73 (s, 1H), 9.34 (s, 1H), 8.70 (s, 1H), 8.33 (d, J=5.5 Hz, 1H), 7.61-7.65 (m, 2H), 7.49 (s, 1H), 7.03 (dd, J=1.5, 8.6 Hz, 1H), 6.87 (d, J=5.8 Hz, 1H), 6.72 (s, 1H), 6.61 (s, 1H), 4.42 (t, J=5.1 Hz, 1H), 3.88 (t, J=6.6 Hz, 1H), 3.66 (s, 3H), 3.45 (q, J=6.1 Hz, 2H), 1.69-1.76 (m, 2H), 1.51-1.58 (m, 2H).

EXAMPLE 503

4-{[7-(4-hydroxybutoxy)-8-methoxy-11-oxo-10,11-dihydro-5H-dibenzo[b,e][1,4]diazepin-3-yl]amino}pyridine-2-carbonitrile

EXAMPLE 503A

4-{7-[4-(tert-butyl-dimethyl-silanyloxy)-butoxy]-8-methoxy-11-oxo-10,11-dihydro-5H-dibenzo[b,e][1,4]diazepin-3-ylamino}-pyridine-2-carbonitrile The desired product was prepared by substituting Example 501B and Example 193A for Example 189A and 4-aminopyridine, respectively, in Example 191.

EXAMPLE 503B

4-{[7-(4-hydroxybutoxy)-8-methoxy-11-oxo-10,11-dihydro-5H-dibenzo[b,e][1,4]diazepin-3-yl]amino}pyridine-2-carbonitrile The desired product was prepared by substituting Example 503A for Example 500A in Example 500B. MS (ESI) m/e 446 (M+H)$^+$; $^1$H NMR (500 MHz, DMSO-d$_6$) ☐9.44 (s, 1H), 9.39, (s, 1H), 8.38 (d, J=5.6 Hz, 1H), 7.66 (d, J=8.4 Hz, 1H), 7.62, (s, 1H), 7.48 (d, J=2.5 Hz, 1H), 7.24 (dd, J=2.5, 5.9 Hz, 1H), 6.84 (d, J=1.9 Hz, 1H), 6.68 (dd, J=2.0, 8.6 Hz, 1H), 6.625 (s, 1H), 6.63 (s, 1H), 4.45 (t, J=6.4 Hz, 1H), 3.87 (t, J=6.7 Hz, 2H), 3.66 (s, 3H), 3.44 (t, J=6.4 Hz, 2H), 1.69-1.75 (m, 2H), 1.52-1.55 (m, 2H).

EXAMPLE 504

3-[(2,6-difluoropyridin-4-yl)amino]-7-(4-hydroxybutoxy)-8-methoxy-5,10-dihydro-11H-dibenzo[b,e][1,4]diazepin-11-one

EXAMPLE 504A

7-[4-(tert-butyl-dimethyl-silanyloxy)-butoxy]-3-(2,6-difluoro-pyridin-4-ylamino)-8-methoxy-5,10-dihydro-dibenzo[b,e][1,4]diazepin-11-one The desired product was prepared by substituting Example 501B and Example 203A for Example 189A and 4-aminopyridine, respectively, in Example 191.

EXAMPLE 504B

3-[(2,6-difluoropyridin-4-yl)amino]-7-(4-hydroxybutoxy)-8-methoxy-5,10-dihydro-11H-dibenzo[b,e][1,4]diazepin-11-one The desired product was prepared by substituting Example 504A for Example 500A in Example 500B. MS (ESI) m/e 457 (M+H)$^+$; $^1$H NMR (300 MHz, DMSO-d$_6$) □9.66 (s, 1H), 9.42 (s, 1H), 7.65-7.68 (m, 2H), 6.86 (d, J=3.0 Hz, 1H), 6.67 (dd, J=3.0, 9.0 Hz, 1H), 6.62 (s, 2H), 6.57 (s, 2H), 4.43 (t, J=6.0 Hz, 1H), 3.87 (t, J=6.0 Hz, 2H), 3.66 (s, 3H), 3.44 (q, J=6.0 Hz, 2H), 1.67-1.75 (m, 2H), 1.50-1.58 (m, 2H).

EXAMPLE 505

7-(4-hydroxybutoxy)-8-methoxy-3-[(2,3,6-trifluoro-pyridin-4-yl)amino]-5,10-dihydro-11H-dibenzo[b,e][1,4]diazepin-11-one

EXAMPLE 505A

7-[4-(tert-butyl-dimethyl-silanyloxy)-butoxy]-8-methoxy-3-(2,3,6-trifluoro-pyridin-4-ylamino)-5,10-dihydro-dibenzo[b,e][1,4]diazepin-11-one The desired product was prepared by substituting Example 501B and Example 199A for Example 189A and 4-aminopyridine, respectively, in Example 191.

EXAMPLE 505B 7-(4-hydroxybutoxy)-8-methoxy-3-[(2,3,6-trifluoro-pyridin-4-yl)amino]-5,10-dihydro-11H-dibenzo[b,e][1,4]diazepin-11-one The desired product was prepared by substituting Example 505A for Example 500A in Example 500B. MS (ESI) m/e 475 (M+H)$^+$; $^1$H NMR (500 MHz, DMSO-d$_6$) □ 9.52 (s, 1H), 9.44 (s, 1H), 7.55-7.68 (m, 2H), 6.87 (d, J=1.5 Hz, 1H), 6.76-6.81 (m, 2H), 6.62-6.64 (m, 2H), 4.42 (t, J=6.5 Hz, 1H), 3.77-3.97 (m, 2H), 3.66 (s, 3H), 3.44 (t, J=6.5 Hz, 2H), 1.69-1.75 (m, 2H), 1.51-1.57 (m, 2H).

EXAMPLE 506

7-ethoxy-3-(3-methoxy-4-nitrophenyl)-5,10-dihydro-11H-dibenzo[b,e][1,4]diazepin-11-one

EXAMPLE 506A 5-ethoxy-2-nitroaniline

A mixture of sodium metal (1.86 g, 80.9 mmol) and ethanol (65 mL) was stirred at ambient temperature until all of the sodium metal had been consumed. 5-Chloro-2-nitroaniline (4.64 g, 26.9 mmol) was added and the mixture was heated at 80° C. for 48 hours, cooled to room temperature, quenched with water, concentrated under vacuum, diluted with ethyl acetate, washed with water and brine, dried (MgSO$_4$), filtered, and concentrated under vacuum. The residue was purified by column chromatography on silica gel with 7:3 hexane/ethyl acetate to provide 4.6 g (94%) of the desired product. MS (ESI) m/e 183 (M+H)$^+$; $^1$H NMR (300 MHz, DMSO-d$_6$) □ 7.90 (d, J=9.5 Hz, 1H), 7.46 (br s, 2H), 6.43 (d, J=2.7 Hz, 1H), 6.23 (dd, J=2.7, 9.5 Hz, 1H), 4.04 (q, J=7.1 Hz, 2H), 1.33 (t, J=7.0 Hz, 3H).

EXAMPLE 506B methyl 4-chloro-2-[(5-ethoxy-2-nitrophenyl)amino]benzoate

The desired product was prepared by substituting Example 506A for methyl 3,4-diaminobenzoate in Example 1A. MS (ESI) m/e 351 (M+H)$^+$; $^1$H NMR (300 MHz, DMSO-d$_6$) □ 11.03 (s, 1H), 8.16 (d, J=9.2 Hz, 1H), 7.97 (d, J=8.8 Hz, 1H), 7.66 (d, J=2.0 Hz, 1H), 7.18 (dd, J=2.0, 8.8 Hz, 1H), 7.00 (d, J=2.4 Hz, 1H), 6.71 (dd, J=2.5, 9.3 Hz, 1H), 4.11 (q, J=6.8 Hz, 2H), 3.88 (s, 3H), 1.33 (t, J=6.9 Hz, 3H).

EXAMPLE 506C 3-chloro-7-ethoxy-5,10-dihydro-11H-dibenzo[b,e][1,4]diazepin-11-one The desired product was prepared by substituting Example 506B for Example 476F in Example 476G. MS (ESI) m/e 289 (M+H)$^+$; $^1$H NMR (300 MHz, DMSO-d$_6$) □ 9.76 (s, 1H), 7.98 (s, 1H), 7.67 (d, J=8.5 Hz, 1H), 7.05 (d, J=2.0 Hz, 1H), 6.91 (dd, J=2.0, 8.5 Hz, 1H), 6.86 (d, J=8.5 Hz, 1H), 6.50-6.56 (m, 2H), 3.94 (q, J=7.1 Hz, 2H), 1.29 (t, J=7.0 Hz, 3H).

EXAMPLE 506D 7-ethoxy-3-(3-methoxy-4-nitrophenyl)-5,10-dihydro-11H-dibenzo[b,e][1,4]diazepin-11-one The desired product was prepared by substituting Example 506C for Example 476G in Example 476H. MS (ESI) m/e 406 (M+H)$^+$; $^1$H NMR (300 MHz, DMSO-d$_6$) □9.76 (s, 1H), 8.02 (d, J=8.5 Hz, 1H), 7.96 (s, 1H), 7.80, (d, J=8.1 Hz, 1H), 7.53 (d, J=1.4 Hz, 1H), 7.30-7.36 (m, 3H), 6.88 (d, J=8.8 Hz, 1H), 6.62 (d, J=2.7 Hz, 1H), 6.51 (dd, J=2.7, 8.5 Hz, 1H), 4.03 (s, 3H), 3.95 (q, J=7.1 Hz, 2H), 1.29 (t, J=7.1 Hz, 3H).

EXAMPLE 507

7-(4-hydroxybutoxy)-3-(3-methoxy-4-nitrophenyl)-5,10-dihydro-11H-dibenzo[b,e][1,4]diazepin-11-one

EXAMPLE 507A 3-chloro-7-hydroxy-5,10-dihydro-11H-dibenzo[b,e][1,4]diazepin-11-one A mixture of Example 506C (1.87 g, 6.5 mmol) in dichloromethane (50 mL) at −78° C. was treated dropwise with a 1.0M solution of $BBr_3$ in dichloromethane, stirred overnight and allowed to reach room temperature, quenched with a saturated solution of ammonium chloride, concentrated under vacuum, and extracted with ethyl acetate. The extracts were combined, washed with brine, dried ($MgSO_4$), filtered, and concentrated under vacuum to provide the desired product.

EXAMPLE 507B 3-chloro-7-hydroxy-5-{[2-(trimethylsilyl)ethoxy]methyl}-5,10-dihydro-11H-dibenzo[b,e][1,4]diazepin-11-one The desired product was prepared by substituting Example 507A for 2-methoxy-5-nitrophenol in Example 476A. MS (ESI) m/e 391 $(M+H)^+$; $^1H$ NMR (300 MHz, DMSO-$d_6$) □ 10.04 (s, 1H), 9.37 (br s, 1H), 7.63 (d, J=8.1 Hz, 1H), 7.54 (d, J=2.0 Hz, 1H), 7.19 (dd, J=2.0, 8.5 Hz, 1H), 6.91 (d, J=2.7 Hz, 1H), 6.84 (d, J=8.8 Hz, 1H), 6.51 (dd, J=2.5, 8.7 Hz, 1H), 4.90-5.03 (m, 2H), 3.62 (t, J=8.0 Hz, 2H), 0.93-0.98 (m, 2H), 0.01 (s, 9H).

EXAMPLE 507C

7-[4-(tert-butyl-dimethyl-silanyloxy)-butoxy]-3-chloro-5-(2-trimethylsilanyl-ethoxymethyl)-5,10-dihydro-dibenzo[b,e][1,4]diazepin-11-one The desired product was prepared by substituting Example 507B and tert-butyl(4-iodobutoxy)dimethylsilane for Example 476 and 2-bromomethyl-tetrahydro-2H-pyran, respectively, in Example 478. MS (ESI) m/e 577 $(M+H)^+$.

EXAMPLE 507D

7-[4-(tert-butyl-dimethyl-silanyloxy)-butoxy]-8-methoxy-3-(3-methoxy-4-nitro-phenyl)-5,10-dihydro-dibenzo[b,e][1,4]diazepin-11-one The desired product was prepared by substituting Example 507C for Example 476G in Example 476H.

EXAMPLE 507E 7-(4-hydroxybutoxy)-3-(3-methoxy-4-nitrophenyl)-5,10-dihydro-11H-dibenzo[b,e][1,4]diazepin-11-one The desired product was prepared by substituting Example 507D for Example 500A in Example 500B. MS (ESI) m/e 450 $(M+H)^+$; $^1H$ NMR (300 MHz, DMSO-$d_6$) □9.76 (s, 1H), 8.02 (d, J=8.5 Hz, 1H), 7.95 (s, 1H), 7.79 (d, J=8.1 Hz, 1H), 7.53 (d, J=1.7 Hz, 1H), 7.28-7.38 (m, 3H), 6.87 (d, J=8.8 Hz, 1H), 6.63 (d, J=2.7 Hz, 1H), 6.51 (dd, J=2.9, 8.7 Hz, 1H), 4.03 (s, 3H), 3.89 (t, J=6.4 Hz, 2H), 3.43 (t, J=6.4 Hz, 2H), 1.65-1.78 (m 2H), 1.46-1.59 (m, 2H).

EXAMPLE 508

7-(2-hydroxyethoxy)-3-(3-methoxy-4-nitrophenyl)-5,10-dihydro-11H-dibenzo[b,e][1,4]diazepin-11-one

EXAMPLE 508A

7-[2-(tert-butyl-dimethyl-silanyloxy)-ethoxy]-3-chloro-5-(2-trimethylsilanyl-ethoxymethyl)-5,10-dihydro-dibenzo[b,e][1,4]diazepin-11-one The desired product was prepared by substituting Example 507B and (2-bromoethoxy)-tert-butyldimethylsilane for Example 476 and 2-bromomethyl-tetrahydro-2H-pyran, respectively, in Example 478.

EXAMPLE 508B

7-[2-(tert-butyl-dimethyl-silanyloxy)-ethoxy]-3-(3-methoxy-4-nitro-phenyl)-5,10-dihydro-dibenzo[b,e][1,4]diazepin-11-one The desired product was prepared by substituting Example 508A for Example 476G in Example 476H.

EXAMPLE 508C 7-(2-hydroxyethoxy)-3-(3-methoxy-4-nitrophenyl)-5,10-dihydro-11H-dibenzo[b,e][1,4]diazepin-11-one The desired product was prepared by substituting Example 508B for Example 500A in Example 500B. MS (ESI) m/e 422 $(M+H)^+$; $^1H$ NMR (300 MHz, DMSO-$d_6$) □9.77 (s, 1H), 8.02 (d, J=8.5 Hz, 1H), 7.97 (s, 1H), 7.79 (d, J=7.8 Hz, 1H), 7.53 (d, J=1.4 Hz, 1H), 7.30-7.37 (m, 3H), 6.88 (d, J=8.8 Hz, 1H), 6.64 (d, J=2.7 Hz, 1H), 6.53 (dd, J=2.7, 8.8 Hz, 1H), 4.83 (t, J=5.6 Hz, 1H), 4.03 (s, 3H), 3.90 (t, J=4.9 Hz, 2H), 3.68 (q, J=5.2 Hz, 2H).

EXAMPLE 509

7-(2,3-dihydroxypropoxy)-3-(3-methoxy-4-nitrophenyl)-5,10-dihydro-11H-dibenzo[b,e][1,4]diazepin-11-one

EXAMPLE 509A 3-chloro-7-(2,3-dihydroxypropoxy)-5,10-dihydro-11H-dibenzo[b,e][1,4]diazepin-11-one The desired product was prepared by substituting Example 507B and 3-chloro-1,2-propanediol for Example 476 and 2-bromomethyl-tetrahydro-2H-pyran, respectively, in Example 478.

EXAMPLE 509B 7-(2,3-dihydroxypropoxy)-3-(3-methoxy-4-nitrophenyl)-5,10-dihydro-11H-dibenzo[b,e][1,4]diazepin-11-one The desired product was prepared by substituting Example 509A for Example 476G in Example 476H. MS (ESI) m/e 452 $(M+H)^+$; $^1H$ NMR (300 MHz, DMSO-$d_6$) □ 9.77 (s, 1H), 8.01 (d, J=8.1 Hz, 1H), 7.96 (s, 1H), 7.79 (d, J=8.1 Hz, 1H), 7.53 (d, J=1.7 Hz, 1H), 7.30-7.37 (m, 3H), 6.87 (d, J=8.5 Hz, 1H), 6.65 (d, J=2.4 Hz, 1H), 6.52 (dd, J=2.7, 8.8 Hz, 1H), 4.03 (s, 3H), 3.86 (m, 1H), 3.69-3.82 (m, 2H), 3.40-3.60 (m, 4H).

EXAMPLE 510

7-[2-(2-methoxyethoxy)ethoxy]-3-(3-methoxy-4-nitrophenyl)-5,10-dihydro-11H-dibenzo[b,e][1,4]diazepin-11-one

EXAMPLE 510A 3-chloro-7-[2-(2-methoxyethoxy)ethoxy]-5,10-dihydro-11H-dibenzo[b,e][1,4]diazepin-11-one The desired product was prepared by substituting Example 507B and 1-bromo-2-(2-methoxyethoxy)ethane for Example 476 and 2-bromomethyl-tetrahydro-2H-pyran, respectively, in Example 478.

EXAMPLE 510B

7-[2-(2-methoxyethoxy)ethoxy]-3-(3-methoxy-4-nitrophenyl)-5,10-dihydro-11H-dibenzo[b,e][1,4]diazepin-11-one The desired product was prepared by substituting Example 510A for Example 476G in Example 476H. MS (ESI) m/e 480 (M+H)$^+$; $^1$H NMR (300 MHz, DMSO-d$_6$) ☐ 9.78 (s, 1H), 8.02 (d, J=8.1 Hz, 1H), 7.97 (s, 1H), 7.79 (d, J=8.5 Hz, 1H), 7.53 (d, J=1.7 Hz, 1H), 7.30-7.37 (m, 3H), 6.89 (d, J=8.8 Hz, 1H), 6.64 (d, J=2.7 Hz, 1H), 6.54 (dd, J=2.7, 8.5 Hz, 1H), 4.03 (s, 3H), 4.01 (dd, J=3.7, 5.4 Hz, 2H), 3.70 (dd, J=3.9, 5.6 Hz, 2H), 3.54-3.60 (m, 2H), 3.42-3.48 (m, 2H), 3.24 (s, 3H).

EXAMPLE 511

7-(methoxymethyl)-3-(3-methoxy-4-nitrophenyl)-5,10-dihydro-11H-dibenzo[b,e][1,4]diazepin-11-one

EXAMPLE 511A methyl 4-[(tert-butoxycarbonyl)amino]-3-iodobenzoate

A mixture of methyl 4-amino-3-iodobenzoate (5.0 g, 18.0 mmol), di-tert-butyl dicarbonate (4.7 g, 21.7 mmol), triethylamine (7.6 mL, 54.2 mmol), 4-(dimethylamino)pyridine (22 mg, 0.18 mmol), and dichloromethane (150 mL) was heated overnight at 40° C., cooled to room temperature, concentrated under vacuum, diluted with ethyl acetate, washed with water and brine, dried (MgSO$_4$), filtered and concentrated under vacuum. The residue was purified by column chromatography on silica gel to give the 3.4 g (50%) of the desired product. MS (ESI) m/e 395 (M+NH$_4$)$^+$; $^1$H NMR (300 MHz, DMSO-d$_6$) ☐ 8.51 (s, 1H), 8.33 (d, J=2.0 Hz, 1H), 7.92 (dd, J=2.0, 8.5 Hz, 1H), 7.67 (d, J=8.5 Hz, 1H), 3.84 (s, 3H), 1.48 (s, 9H).

EXAMPLE 511B

4-[(tert-butoxycarbonyl)amino]-3-iodobenzoic acid

The desired product was prepared by substituting Example 511A for Example 476F in the first step of Example 476G. The mixture was then cooled to room temperature, acidified to pH 6-7 with a saturated solution of citric acid, concentrated under vacuum, diluted with ethyl acetate, washed with water and brine, dried (MgSO$_4$), filtered, and concentrated under vacuum to provide 3.27 g (quantitative) of the desired product. MS (ESI) m/e 362 (M–H)$^-$; $^1$H NMR (300 MHz, DMSO-d$_6$) ☐ 8.49 (s, 1H), 8.31 (d, J=1.7 Hz, 1H), 7.90 (d, J=1.9, 8.3 Hz, 1H), 7.61 (d, J=8.5 Hz, 1H), 1.48 (s, 9H).

EXAMPLE 511C tert-butyl 4-(hydroxymethyl)-2-iodophenylcarbamate

A mixture of Example 511B (363 mg, 1.0 mmol) in THF (2 mL) at 0° C. was slowly treated with a 1.0M solution of borane in THF (2.0 mL, 2.0 mmol), allowed to reach room temperature, slowly quenched with a saturated solution of ammonium chloride and extracted with ethyl acetate. The combined organic extracts were dried (MgSO$_4$), filtered, and concentrated under vacuum. The residue was purified by column chromatography on silica gel to provide 275 mg (79%) of the desired product. MS (ESI) m/e 350 (M+H)$^+$; $^1$H NMR (300 MHz, DMSO-d$_6$) ☐8.44 (s, 1H), 7.77 (d, J=0.7 Hz, 1H), 7.25-7.32 (m, 2H), 5.25 (t, J=5.8 Hz, 1H), 4.44 (d, J=5.4 Hz, 2H), 1.45 (s, 9H).

EXAMPLE 511D methyl 2-{[2-[(tert-butoxycarbonyl)amino]-5-(hydroxymethyl)phenyl]amino}-4-chlorobenzoate The desired product was prepared by substituting Example 511C and methyl 2-amino-4-chlorobenzoate for methyl 4-chloro-2-iodobenzoate and methyl 3,4-diaminobenzoate, respectively, in Example 1A. MS (ESI) m/e 407 (M+H)$^+$; $^1$H NMR (300 MHz, DMSO-d$_6$) ☐ 9.18 (s, 1H), 8.73 (s, 1H), 7.86 (d, J=8.5 Hz, 1H), 7.32 (d, J=8.1 Hz, 1H), 7.28 (d, J=1.7 Hz, 1H), 7.15 (dd, J=1.7, 8.1 Hz, 1H), 6.75 (dd, J=2.0, 8.5 Hz, 1H), 6.00 (d, J=2.0 Hz, 1H), 5.22 (t, J=5.8 Hz, 1H), 4.48 (d, J=5.4 Hz, 2H), 3.84 (s, 3H), 1.38 (s, 9H).

EXAMPLE 511E

2-{[2-[(tert-butoxycarbonyl)amino]-5-(hydroxymethyl)phenyl]amino}-4-chlorobenzoic acid The desired product was prepared by substituting Example 511D for Example 511A in Example 511B. $^1$H NMR (300 MHz, DMSO-d$_6$) ☐13.08 (br s, 1H), 9.44 (s, 1H), 8.66 (s, 1H), 7.85 (d, J=8.8 Hz, 1H), 7.32 (d, J=8.5 Hz, 1H), 7.27 (d, J=1.7 Hz, 1H), 7.13 (dd, J=2.0, 8.1 Hz, 1H), 6.72 (dd, J=2.0, 8.5 Hz, 1H), 6.61 (d, J=2.0 Hz, 1H), 5.21 (t, J=5.8 Hz, 1H), 4.47 (d, J=5.4 Hz, 2H), 1.38 (s, 9H).

EXAMPLE 511F

2-{[2-amino-5-(hydroxymethyl)phenyl]amino}-4-chlorobenzoic acid

The desired product was prepared by substituting Example 511E for Example 489B in Example 489C.

EXAMPLE 511 G 3-chloro-7-(methoxymethyl)-5,10-dihydro-11H-dibenzo[b,e][1,4]diazepin-11-one The desired product was prepared by substituting Example 511F for Example 224F in Example 224G. MS (ESI) m/e 289

(M+H)⁺; ¹H NMR (300 MHz, DMSO-d₆) δ 9.92 (s, 1H), 8.05 (s, 1H), 7.68 (d, J=8.5 Hz, 1H), 7.07 (d, J=2.0 Hz, 1H), 6.94 (m, 3H), 6.85 (dd, J=1.7, 8.1 Hz, 1H), 4.29 (s, 2H), 3.26 (s, 3H).

EXAMPLE 511H 7-(methoxymethyl)-3-(3-methoxy-4-nitrophenyl)-5,10-dihydro-11H-dibenzo[b,e][1,4]diazepin-11-one The desired product was prepared by substituting Example 511 G for Example 476G in Example 476H. MS (ESI) m/e 406 (M+H)⁺; ¹H NMR (300 MHz, DMSO-d₆) δ 9.92 (s, 1H), 8.02 (s, 1H), 8.01 (d, J=8.5 Hz, 1H), 7.80 (d, J=8.1 Hz, 1H), 7.53 (d, J=1.7 Hz, 1H), 7.29-7.36 (m, 3H), 7.01 (d, J=1.4 Hz, 1H), 6.95 (d, J=8.1 Hz, 1H), 6.85 (dd, J=1.7, 8.1 Hz, 1H), 4.30 (s, 2H), 4.03 (s, 3H), 3.27 (s, 3H).

EXAMPLE 512

7-(3-methoxy-4-nitrobenzyl)-3-(3-methoxy-4-nitrophenyl)-5,10-dihydro-11H-dibenzo[b,e][1,4]diazepin-11-one

EXAMPLE 512A 7-(bromomethyl)-3-chloro-5,10-dihydro-11H-dibenzo[b,e][1,4]diazepin-11-one The desired product was prepared by substituting Example 511G for Example 506C in Example 507A. MS (ESI) m/e 337 (M+H)⁺.

EXAMPLE 512B 7-(3-methoxy-4-nitrobenzyl)-3-(3-methoxy-4-nitrophenyl)-5,10-dihydro-11H-dibenzo[b,e][1,4]diazepin-11-one The desired product was prepared by substituting Example 512A for Example 476G in Example 476H. MS (ESI) m/e 527 (M+H)⁺; ¹H NMR (300 MHz, DMSO-d₆) δ 9.87 (s, 1H), 8.01 (d, J=8.5 Hz, 1H), 7.98 (s, 1H), 7.81 (t, J=8.5 Hz, 2H), 7.51 (d, J=1.7 Hz, 1H), 7.26-7.34 (m, 4H), 6.81-6.94 (m, 4H), 4.02 (s, 3H), 3.94 (s, 2H), 3.91 (s, 3H).

EXAMPLE 513

7-{[[2-(dimethylamino)ethyl](methyl)amino]methyl}-3-(3-methoxy-4-nitrophenyl)-5,10-dihydro-11H-dibenzo[b,e][1,4]diazepin-11-one

EXAMPLE 513A 3-chloro-7-{[[2-(dimethylamino)ethyl](methyl)amino]methyl}-5,10-dihydro-11H-dibenzo[b,e][1,4]diazepin-11-one A mixture of Example 512A (50 mg, 0.15 mmol) and N,N,N'-trimethylethylenediamine (300 μL, 2.3 mmol) was heated at 50° C. overnight, cooled to room temperature, diluted with ethyl acetate, washed with water and brine, dried (MgSO₄), filtered, and concentrated under vacuum to provide 31.5 mg (59%) of the desired product.

EXAMPLE 513B

7-{[[2-(dimethylamino)ethyl](methyl)amino]methyl}-3-(3-methoxy-4-nitrophenyl)-5,10-dihydro-11H-dibenzo[b,e][1,4]diazepin-11-one The desired product was prepared by substituting Example 513A for Example 476G in Example 476H. MS (ESI) m/e 476 (M+H)⁺; ¹H NMR (300 MHz, DMSO-d₆) δ 10.02 (s, 1H), 8.11 (s, 1H), 8.03 (d, J=8.5 Hz, 1H), 7.82 (d, J=8.1 Hz, 1H), 7.52 (d, J=1.7 Hz, 1H), 7.30-7.40 (m, 3H), 6.99-7.05 (m, 3H), 4.04 (s, 3H), 3.80-4.20 (m, 6H), 3.33 (br s, 3H), 2.79 (s, 6H).

EXAMPLE 514

3-(3-methoxy-4-nitrophenyl)-7-{[(2-tetrahydro-2H-pyran-4-ylethyl)amino]methyl}-5,10-dihydro-11H-dibenzo[b,e][1,4]diazepin-11-one

EXAMPLE 514A 3-chloro-7-{[(2-tetrahydro-2H-pyran-4-ylethyl)amino]methyl}-5,10-dihydro-11H-dibenzo[b,e][1,4]diazepin-11-one A mixture of Example 512A (50 mg, 0.15 mmol) and 2-(tetrahydro-pyran-4-yl)-ethylamine (38.3 mg, 0.30 mmol) in dioxane (2.0 mL) was heated 11 hours at 50° C., cooled to room temperature, and concentrated under vacuum. The residue was purified by preparative HPLC to give 30.3 mg (53%) of the desired product. ¹H NMR (300 MHz, DMSO-d₆) δ 10.05 (s, 1H), 8.56 (br s, 1H), 8.16 (s, 1H), 7.70 (d, J=8.5 Hz, 1H), 7.11 (d, J=2.0 Hz, 1H), 7.00-7.08 (m, 3H), 6.97 (dd, J=2.0, 8.5 Hz, 1H), 4.00-4.04 (m, 2H), 3.78-3.86 (m, 2H), 3.20-3.30 (m, 3H), 2.88-3.00 (m, 2H), 1.49-1.58 (m, 4H), 1.11-1.19 (m, 2H).

EXAMPLE 514B 3-(3-methoxy-4-nitrophenyl)-7-{[(2-tetrahydro-2H-pyran-4-ylethyl)amino]methyl}-5,10-dihydro-11H-dibenzo[b,e][1,4]diazepin-11-one The desired product was prepared by substituting Example 514A for Example 476G in Example 476H. MS (ESI) m/e 503 (M+H)⁺; ¹H NMR (300 MHz, DMSO-d₆) δ 10.05 (s, 1H), 8.59 (m, 1H), 8.15 (s, 1H), 8.03 (d, J=8.5 Hz, 1H), 7.82 (d, J=8.1 Hz, 1H), 7.51 (d, J=1.7 Hz, 1H), 7.40 (d, J=1.7 Hz, 1H), 7.30-7.38 (m, 2H), 7.00-7.08 (m, 3H), 4.03 (s, 3H), 3.98-4.07 (m, 2H), 3.77-3.85 (m, 2H), 3.18-3.31 (m, 3H), 2.87-3.01 (m, 2H), 1.46-1.59 (m, 4H), 1.06-1.26 (m, 2H).

EXAMPLE 515

8-ethyl-7-methoxy-3-(3-methoxy-4-nitrophenyl)-5,10-dihydro-11H-dibenzo[b,e][1,4]diazepin-11-one

EXAMPLE 515A 3-chloro-8-hydroxy-7-methoxy-5,10-dihydro-11H-dibenzo[b,e][1,4]diazepin-11-one The desired product was prepared by substituting Example 477G for Example 476H in Example 476I. ¹H NMR (300 MHz, DMSO-d₆) δ 9.65 (s, 1H), 7.69 (s, 1H), 7.63 (d, J=8.5

Hz, 1H), 7.02 (d, J=2.0 Hz, 1H), 6.89 (dd, J=2.0, 8.5 Hz, 1H), 6.58 (s, 1H), 6.46 (s, 1H), 3.70 (s, 3H).

EXAMPLE 515B 3-chloro-7-methoxy-11-oxo-10,11-dihydro-5H-dibenzo[b,e][1,4]diazepin-8-yl trifluoromethanesulfonate A mixture of Example 515A (290.3 mg, 1.0 mmol) in THF (10 mL) was treated with NaH (60% oil dispersion, 44 mg, 1.1 mmol) and stirred 10 minutes at room temperature. N-phenyltrifluoromethanesulfonimide (429 mg, 1.2 mmol) was added and the mixture was stirred overnight, quenched with water, concentrated under vacuum, diluted with ethyl acetate, washed with water and brine, dried (MgSO$_4$), filtered, and concentrated under vacuum. The residue was triturated with ethyl acetate and hexane, filtered, and dried under vacuum to provide 211 mg (50%) of the desired product. MS (ESI) m/e 423 (M+H)$^+$; $^1$H NMR (300 MHz, DMSO-d$_6$) □ 9.67 (s, 1H), 7.70 (s, 1H), 7.65 (d, J=8.5 Hz, 1H), 7.03 (d, J=2.0 Hz, 1H), 6.91 (dd, J=2.0, 8.5 Hz, 1H), 6.59 (s, 1H), 6.48 (s, 1H), 3.71 (s, 3H).

EXAMPLE 515C 3-chloro-7-methoxy-8-vinyl-5,10-dihydro-11H-dibenzo[b,e][1,4]diazepin-11-one A mixture of Example 515B (210 mg, 0.5 mmol), tributyl (vinyl)tin (175 μL, 0.6 mmol), Pd(PPh$_3$)$_2$Cl$_2$ (35 mg, 0.05 mmol), LiCl (169 mg, 4.0 mmol) and DMF was flushed with nitrogen, heated at 50° C. overnight, cooled to room temperature, diluted with a saturated potassium fluoride solution, stirred 15 minutes, diluted with ethyl acetate, washed with water and brine, dried (MgSO$_4$), filtered, and concentrated under vacuum. The residue was purified by column chromatography on silica gel with a solvent gradient of 4:1 to 1:1 hexane/ethyl acetate to give 77 mg (52%) of the desired product. MS (ESI) m/e 301 (M+H)$^+$; $^1$H NMR (300 MHz, DMSO-d$_6$) □ 9.72 (s, 1H), 8.14 (s, 1H), 7.68 (d, J=8.5 Hz, 1H), 7.11 (s, 1H), 7.05 (d, J=2.0 Hz, 1H), 6.94 (dd, J=2.0, 8.5 Hz, 1H), 6.80 (dd, J=11.2, 18.0 Hz, 1H), 6.63 (s, 1H), 5.56 (dd, J=1.5, 17.8 Hz, 1H), 5.14 (dd, J=1.7, 11.2 Hz, 1H), 3.75 (s, 3H).

EXAMPLE 515D 3-chloro-8-ethyl-7-methoxy-5,10-dihydro-11H-dibenzo[b,e][1,4]diazepin-11-one The desired product was prepared by substituting Example 515C for Example 476A in Example 476B. MS (ESI) m/e 303 (M+H)$^+$; $^1$H NMR (300 MHz, DMSO-d$_6$) □ 9.68 (s, 1H), 7.93 (s, 1H), 7.66 (d, J=8.5 Hz, 1H), 7.05 (d, J=2.0 Hz, 1H), 6.92 (dd, J=2.0, 8.5 Hz, 1H), 6.75 (s, 1H), 6.59 (s, 1H), 3.73 (s, 3H), 2.43 (q, J=7.6 Hz, 2H), 1.06 (t, J=7.5 Hz, 3H).

EXAMPLE 515E 8-ethyl-7-methoxy-3-(3-methoxy-4-nitrophenyl)-5,10-dihydro-11H-dibenzo[b,e][1,4]diazepin-11-one The desired product was prepared by substituting Example 515D for Example 476G in Example 476H. MS (ESI) m/e 420 (M+H)$^+$; $^1$H NMR (300 MHz, DMSO-d$_6$) □ 9.67 (s, 1H), 8.01 (d, J=8.5 Hz, 1H), 7.90 (s, 1H), 7.78 (d, J=8.1 Hz, 1H), 7.53 (d, J=1.7 Hz, 1H), 7.27-7.38 (m, 3H), 6.76 (s, 1H), 6.66 (s, 1H), 4.03 (s, 3H), 3.73 (s, 3H), 2.43 (q, J=7.5 Hz, 2H), 1.06 (t, J=7.6 Hz, 3H).

EXAMPLE 516

8-methoxy-3-(3-methoxy-4-nitrophenyl)-7-vinyl-5,10-dihydro-11H-dibenzo[b,e][1,4]diazepin-11-one

EXAMPLE 516A 3-chloro-8-methoxy-11-oxo-10,11-dihydro-5H-dibenzo[b,e][1,4]diazepin-7-yl trifluoromethanesulfonate The desired product was prepared by substituting Example 501A for Example 515A in Example 515B. MS (ESI) m/e 423 (M+H)$^+$; $^1$H NMR (300 MHz, DMSO-d$_6$) □ 10.03 (s, 1H), 8.05 (s, 1H), 7.69 (d, J=8.5 Hz, 1H), 7.07 (s, 1H), 7.01 (d, J=2.0 Hz, 1H), 6.98 (dd, J=2.0, 8.5 Hz, 1H), 6.92 (s, 1H), 3.79 (s, 3H).

EXAMPLE 516B 3-chloro-8-methoxy-7-vinyl-5,10-dihydro-11H-dibenzo[b,e][1,4]diazepin-11-one The desired product was prepared by substituting Example 516A for Example 515B in Example 515C. MS (ESI) m/e 301 (M+H)$^+$; $^1$H NMR (300 MHz, DMSO-d$_6$) □9.89 (s, 1H), 7.88 (s, 1H), 7.67 (d, J=8.5 Hz, 1H), 7.12 (s, 1H), 7.04 (d, J=2.0 Hz, 1H), 6.91 (dd, J=2.2, 8.6 Hz, 1H), 6.82 (dd, J=11.2, 18.0 Hz, 1H), 6.67 (s, 1H), 5.60 (dd, J=1.7, 17.6 Hz, 1H), 5.19 (dd, J=1.4, 11.2 Hz, 1H), 3.71 (s, 3H).

EXAMPLE 516C 8-methoxy-3-(3-methoxy-4-nitrophenyl)-7-vinyl-5,10-dihydro-11H-dibenzo[b,e][1,4]diazepin-11-one The desired product was prepared by substituting Example 516B for Example 476G in Example 476H. MS (ESI) m/e 418 (M+H)$^+$; $^1$H NMR (400 MHz, DMSO-d$_6$) □ 9.88 (s, 1H), 8.01 (d, J=8.3 Hz, 1H), 7.83 (s, 1H), 7.80 (d, J=8.3 Hz, 1H), 7.54 (s, 1H), 7.26-7.40 (m, 3H), 7.18 (s, 1H), 6.83 (dd, J=11.2, 17.6 Hz, 1H), 6.69 (s, 1H), 5.61 (d, J=17.8 Hz, 1H), 5.19 (d, J=11.4 Hz, 1H), 4.04 (s, 3H), 3.72 (s, 3H).

EXAMPLE 517

8-(3-hydroxypropyl)-7-methoxy-3-(3-methoxy-4-nitrophenyl)-5,10-dihydro-11H-dibenzo[b,e][1,4]diazepin-11-one

EXAMPLE 517A

N-(4-bromo-3-methoxyphenyl)acetamide

The desired product was prepared by substituting 1-bromo-2-methoxy-4-nitro-benzene for 2-bromo-1-methoxy-4-nitro-benzene in Example 223A. MS (DCI) m/e 244 (M+H)$^+$; $^1$H NMR (300 MHz, DMSO-d$_6$) □ 10.05 (s, 1H), 7.448 (d, J=2.4 Hz, 1H), 7.445 (d, J=8.5 Hz, 1H), 7.10 (dd, J=2.2, 8.6 Hz, 1H), 3.79 (s, 3H), 2.04 (s, 3H).

EXAMPLE 517B

N-(4-bromo-5-methoxy-2-nitrophenyl)acetamide

The desired product was prepared by substituting Example 517A for Example 223A in Example 223B. MS (DCI) m/e 306 (M+NH$_4$)$^+$; $^1$H NMR (300 MHz, DMSO-d$_6$) ☐ 10.37 (s, 1H), 8.25 (s, 1H), 7.63 (s, 1H), 3.94 (s, 3H), 2.13 (s, 3H).

EXAMPLE 517C 4-bromo-5-methoxy-2-nitroaniline

The desired product was prepared by substituting Example 517B for Example 223B in Example 223C. MS (DCI) m/e 247 (M+H)$^+$; $^1$H NMR (300 MHz, DMSO-d$_6$) ☐ 8.12 (s, 1H), 7.62 (s, 2H), 6.60 (s, 1H), 3.86 (s, 3H).

EXAMPLE 517D methyl 2-[(4-bromo-5-methoxy-2-nitrophenyl)amino]-4-chlorobenzoate The desired product was prepared by substituting Example 517C for methyl 3,4-diaminobenzoate in Example 1A. MS (ESI) m/e 415 (M+H)$^+$.

EXAMPLE 517E 8-bromo-3-chloro-7-methoxy-5,10-dihydro-11H-dibenzo[b,e][1,4]diazepin-11-one The desired product was prepared by substituting Example 517D for Example 476F in Example 476G. MS (ESI) m/e 353 (M+H)$^+$; $^1$H NMR (300 MHz, DMSO-d$_6$) ☐ 9.81 (s, 1H), 8.16 (s, 1H), 7.68 (d, J=8.5 Hz, 1H), 7.15 (s, 1H), 7.05 (d, J=2.0 Hz, 1H), 6.96 (dd, J=2.0, 8.5 Hz, 1H), 6.73 (s, 1H), 3.78 (s, 3H).

EXAMPLE 517F ethyl 3-(3-chloro-7-methoxy-11-oxo-10,11-dihydro-5H-dibenzo[b,e][1,4]diazepin-8-yl)acrylate The desired product was prepared by substituting Example 517E and ethyl acrylate for Example 223G and methyl acrylate, respectively, in Example 223H. MS (ESI) m/e 373 (M+H)$^+$; $^1$H NMR (300 MHz, DMSO-d$_6$) ☐ 9.75 (s, 1H), 8.41 (s, 1H), 7.72 (d, J=8.5 Hz, 1H), 7.68 (d, J=15.9 Hz, 1H), 7.23 (s, 1H), 7.06 (d, J=2.0 Hz, 1H), 6.97 (dd, J=2.0, 8.5 Hz, 1H), 6.69 (s, 1H), 6.31 (d, J=16.3 Hz, 1H), 4.16 (q, J=7.1 Hz, 2H), 3.83 (s, 3H), 1.24 (t, J=7.0 Hz, 3H).

EXAMPLE 517G ethyl 3-(3-chloro-7-methoxy-11-oxo-10,11-dihydro-5H-dibenzo[b,e][1,4]diazepin-8-yl)propanoate The desired product was prepared by substituting Example 517F and methanol for Example 476A and ethanol, respectively, in Example 476B. MS (ESI) m/e 375 (M+H)$^+$; $^1$H NMR (300 MHz, DMSO-d$_6$) ☐ 9.70 (s, 1H), 7.95 (s, 1H), 7.66 (d, J=8.5 Hz, 1H), 7.04 (d, J=2.0 Hz, 1H), 6.92 (dd, J=2.0, 8.5 Hz, 1H), 6.74 (s, 1H), 6.60 (s, 1H), 4.03 (q, J=7.1 Hz, 2H), 3.73 (s, 3H), 2.67 (t, J=7.5 Hz, 2H), 2.45 (t, J=7.3 Hz, 2H), 1.15 (t, J=7.1 Hz, 3H).

EXAMPLE 517H 3-chloro-8-(3-hydroxypropyl)-7-methoxy-5,10-dihydro-11H-dibenzo[b,e][1,4]diazepin-11-one The desired product was prepared by substituting 517G for Example 6D in Example 204A. MS (ESI) m/e 333 (M+H)$^+$; $^1$H NMR (300 MHz, DMSO-d$_6$) ☐ 9.67 (s, 1H), 7.92 (s, 1H), 7.66 (d, J=8.5 Hz, 1H), 7.04 (d, J=2.0 Hz, 1H), 6.92 (dd, J=2.0, 8.5 Hz, 1H), 6.73 (s, 1H), 6.59 (s, 1H), 4.39 (t, J=5.1 Hz, 1H), 3.72 (s, 3H), 3.35-3.41 (m, 2H), 2.40-2.45 (m, 2H), 1.54-1.64 (m, 2H).

EXAMPLE 517I 8-(3-hydroxypropyl)-7-methoxy-3-(3-methoxy-4-nitrophenyl)-5,10-dihydro-11H-dibenzo[b,e][1,4]diazepin-11-one The desired product was prepared by substituting Example 517H for Example 476G in Example 476H. MS (ESI) m/e 450 (M+H)$^+$; $^1$H NMR (300 MHz, DMSO-d$_6$) ☐ 9.68 (s, 1H), 8.02 (d, J=8.5 Hz, 1H), 7.90 (s, 1H), 7.78 (d, J=8.1 Hz, 1H), 7.53 (d, J=1.7 Hz, 1H), 7.27-7.38 (m, 3H), 6.75 (s, 1H), 6.66 (s, 1H), 4.40 (t, J=5.1 Hz, 1H), 4.04 (s, 3H), 3.72 (s, 3H), 3.34-3.43 (m, 2H), 2.39-2.47 (m, 2H), 1.57-1.64 (m, 2H).

EXAMPLE 518

7-methoxy-3-(3-methoxy-4-nitrophenyl)-8-{3-[(2-methylpyridin-3-yl)oxy]propyl}-5,10-dihydro-11H-dibenzo[b,e][1,4]diazepin-11-one

EXAMPLE 518A 3-chloro-7-methoxy-8-{3-[(2-methylpyridin-3-yl)oxy]propyl}-5,10-dihydro-11H-dibenzo[b,e][1,4]diazepin-11-one The desired product was prepared by substituting Example 517H and 2-methyl-3-hydroxypyridine for Example 204A and 4-morpholinophenol, respectively, in Example 297A. MS (ESI) m/e 424 (M+H)$^+$; $^1$H NMR (300 MHz, DMSO-d$_6$) ☐9.67 (s, 1H), 7.97 (dd, J=1.4, 4.8 Hz, 1H), 7.94 (s, 1H), 7.65 (d, J=8.5 Hz, 1H), 7.26 (m, 1H), 7.14 (m, 1H), 7.04 (d, J=2.0 Hz, 1H), 6.92 (dd, J=2.0, 8.5 Hz, 1H), 6.77 (s, 1H), 6.60 (s, 1H), 3.97 (t, J=6.3 Hz, 2H), 3.69 (s, 3H), 2.58-2.63 (m, 2H), 2.36 (s, 3H), 1.88-1.97 (m, 2H).

EXAMPLE 518B 7-methoxy-3-(3-methoxy-4-nitrophenyl)-8-{3-[(2-methylpyridin-3-yl)oxy]propyl}-5,10-dihydro-11H-dibenzo[b,e][1,4]diazepin-11-one The desired product was prepared by substituting Example 518A for Example 476G in Example 476H. MS (ESI) m/e 541 (M+H)$^+$; $^1$H NMR (300 MHz, DMSO-d$_6$) ☐ 9.67 (s, 1H), 8.17 (d, J=4.8 Hz, 1H), 8.02 (d, J=8.5 Hz, 1H), 7.93 (s, 1H), 7.78 (d, J=8.5 Hz, 1H), 7.69 (m, 1H), 7.51 (m, 1H), 7.53 (d, J=1.4 Hz, 1H), 7.29-7.36 (m, 3H), 6.78 (s, 1H), 6.67 (s, 1H), 4.08 (t, J=6.1 Hz, 2H), 4.03 (s, 3H), 3.69 (s, 3H), 2.62 (t, J=7.5 Hz, 2H), 2.47 (s, 3H), 1.90-2.02 (m, 2H).

EXAMPLE 519

8-{3-[(2-chloropyridin-3-yl)oxy]propyl}-7-methoxy-3-(3-methoxy-4-nitrophenyl)-5,10-dihydro-11H-dibenzo[b,e][1,4]diazepin-11-one The desired product was prepared by substituting Example 517I and 2-chloro-3-hydroxypyridine for Example 204A and 4-morpholinophenol, respectively, in Example 297A. MS (ESI) m/e 561 (M+H)$^+$; $^1$H NMR (300 MHz, DMSO-d$_6$) □ 9.68 (s, 1H), 8.01 (d, J=8.5 Hz, 1H), 7.96 (dd, J=1.4, 4.8 Hz, 1H), 7.92 (s, 1H), 7.78 (d, J=7.8 Hz, 1H), 7.52-7.56 (m, 2H), 7.29-7.39 (m, 4H), 6.78 (s, 1H), 6.67 (s, 1H), 4.08 (t, J=6.3 Hz, 2H), 4.03 (s, 3H), 3.69 (s, 3H), 2.58-2.65 (m, 2H), 1.90-1.98 (m, 2H).

EXAMPLE 520

7-methoxy-3-(3-methoxy-4-nitrophenyl)-8-[3-(4-morpholin-4-ylphenoxy)propyl]-5,10-dihydro-11H-dibenzo[b,e][1,4]diazepin-11-one

EXAMPLE 520A 3-chloro-7-methoxy-8-[3-(4-morpholin-4-ylphenoxy)propyl]-5,10-dihydro-11H-dibenzo[b,e][1,4]diazepin-11-one The desired product was prepared by substituting Example 517H for Example 204A in Example 297A. MS (ESI) m/e 494 (M+H)$^+$; $^1$H NMR (300 MHz, DMSO-d$_6$) □ 9.68 (s, 1H), 7.95 (s, 1H), 7.60 (d, J=8.5 Hz, 1H), 7.05 (d, J=2.0 Hz, 1H), 6.92 (dd, J=2.0, 8.5 Hz, 1H), 6.79-6.86 (m, 4H), 6.76 (s, 1H), 6.60 (s, 1H), 3.87 (t, J=6.3 Hz, 2H), 3.72 (s, 3H), 3.70-3.73 (m, 4H), 2.95-2.98 (m, 4H), 2.53-2.58 (m, 2H), 1.81-1.90 (m, 2H).

EXAMPLE 520B 7-methoxy-3-(3-methoxy-4-nitrophenyl)-8-[3-(4-morpholin-4-ylphenoxy)propyl]-5,10-dihydro-11H-dibenzo[b,e][1,4]diazepin-11-one The desired product was prepared by substituting Example 520A for Example 476G in Example 476H. MS (ESI) m/e 611 (M+H)$^+$; $^1$H NMR (300 MHz, DMSO-d$_6$) □ 9.68 (s, 1H), 8.01 (d, J=8.1 Hz, 1H), 7.92 (s, 1H), 7.78 (d, J=8.1 Hz, 1H), 7.53 (d, J=1.7 Hz, 1H), 7.29-7.37 (m, 3H), 6.87-6.95 (m, 2H), 6.80-6.86 (m, 2H), 6.77 (s, 1H), 6.67 (s, 1H), 4.03 (s, 3H), 3.88 (t, J=6.4 Hz, 2H) 3.70-3.75 (m, 4H), 3.72 (s, 3H), 2.98-3.04 (m, 4H), 2.50-2.60 (m, 2H), 1.84-1.91 (m, 2H).

EXAMPLE 521

8-[3-(isoquinolin-3-yloxy)propyl]-7-methoxy-3-(3-methoxy-4-nitrophenyl)-5,10-dihydro-11H-dibenzo[b,e][1,4]diazepin-11-one The desired product was prepared by substituting Example 517I and 2-hydroxyisoquinoline for Example 204A and 3-methyl-2-pyridol, respectively, in Example 301. MS (ESI) m/e 577 (M+H)$^+$; $^1$H NMR (500 MHz, DMSO-d$_6$) □ 9.66 (s, 1H), 9.03 (s, 1H), 8.01 (d, J=8.4 Hz, 2H), 7.91 (s, 1H), 7.76-7.81 (m, 2H), 7.64 (m, 1H), 7.53 (d, J=1.3 Hz, 1H), 7.42 (t, J=7.5 Hz, 1H), 7.33-7.37 (m, 2H), 7.30 (m, 1H), 7.15 (s, 1H), 6.81 (s, 1H), 6.68 (s, 1H), 4.30 (t, J=6.4 Hz, 2H), 4.04 (s, 3H), 3.71 (s, 3H), 2.62 (t, J=7.6 Hz, 2H), 1.93-2.00 (m, 2H).

EXAMPLE 522

7-methoxy-3-(3-methoxy-4-nitrophenyl)-8-[3-(3-oxoisoquinolin-2(3H)-yl)propyl]-5,10-dihydro-11H-dibenzo[b,e][1,4]diazepin-11-one The title compound was isolated as a second product in Example 521. MS (ESI) m/e 577 (M+H)$^+$; $^1$H NMR (500 MHz, DMSO-d$_6$) □ 9.63 (s, 1H), 8.74 (s, 1H), 8.01 (d, J=8.1 Hz, 1H), 7.91 (s, 1H), 7.78 (d, J=8.1 Hz, 1H), 7.51-7.54 (m, 2H), 7.23-7.36 (m, 5H), 6.89 (m, 1H), 6.78 (s, 1H), 6.66 (s, 1H), 6.50 (s, 1H), 4.16 (t, J=7.2 Hz, 2H), 4.03 (s, 3H), 3.70 (s, 3H), 2.46-2.54 (m, 2H), 1.91-1.98 (m, 2H).

EXAMPLE 523 methyl 7-methoxy-3-(3-methoxy-4-nitrophenyl)-11-oxo-10,11-dihydro-5H-dibenzo[b,e][1,4]diazepine-8-carboxylate

EXAMPLE 523A methyl 4-amino-2-methoxy-5-nitrobenzoate

The desired product was prepared by substituting methyl 4-acetylamino-2-methoxy-5-nitrobenzoate for Example 476D in Example 476E. MS (ESI) m/e 225 (M−H)$^−$; $^1$H NMR (300 MHz, DMSO-d$_6$) □ 8.50 (s, 1H), 7.85 (s, 2H), 6.55 (s, 1H), 3.82 (s, 3H), 3.74 (s, 3H).

EXAMPLE 523B methyl 4-{[5-chloro-2-(methoxycarbonyl)phenyl]amino}-2-methoxy-5-nitrobenzoate The desired product was prepared by substituting Example 523A for methyl 3,4-diaminobenzoate in Example 1A. MS (ESI) m/e 395 (M+H)$^+$; $^1$H NMR (300 MHz, DMSO-d$_6$) □ 11.24 (s, 1H), 8.61 (s, 1H), 8.00 (d, J=8.5 Hz, 1H), 7.91 (d, J=2.0 Hz, 1H), 7.31 (dd, J=2.0, 8.5 Hz, 1H), 7.09 (s, 1H), 3.88 (s, 3H), 3.84 (s, 3H), 3.81 (s, 3H).

EXAMPLE 523C methyl 3-chloro-7-methoxy-11-oxo-10,11-dihydro-5H-dibenzo[b,e][1,4]diazepine-8-carboxylate The desired product was prepared by substituting Example 523B for Example 476F in Example 476G. MS (ESI) m/e 333 (M+H)$^+$; $^1$H NMR (300 MHz, DMSO-d$_6$) □ 9.86 (s, 1H), 8.44 (s, 1H), 7.71 (d, J=8.5 Hz, 1H), 7.41 (s, 1H), 7.06 (d, J=1.7 Hz, 1H), 6.98 (dd, J=2.0, 8.5 Hz, 1H), 6.72 (s, 1H), 3.77 (s, 3H), 3.73 (s, 3H).

EXAMPLE 523D methyl 7-methoxy-3-(3-methoxy-4-nitrophenyl)-1-oxo-10,11-dihydro-5H-dibenzo[b,e][1,4]diazepine-8-carboxylate The desired product was prepared by substituting Example 523C for Example 476G in Example 476H. MS (ESI) m/e 450 (M+H)$^+$; $^1$H NMR (500 MHz, DMSO-d$_6$) □9.84 (s, 1H), 8.44 (s, 1H), 8.01 (d, J=8.4 Hz, 1H), 7.84 (d, J=8.7 Hz, 1H), 7.55 (d, J=1.3 Hz, 1H), 7.43 (s, 1H), 7.34-7.37 (m, 3H), 6.79 (s, 1H), 4.04 (s, 3H), 3.77 (s, 3H), 3.74 (s, 3H).

EXAMPLE 524 methyl 7-methoxy-11-oxo-3-(pyrimidin-4-ylamino)-10,11-dihydro-5H-dibenzo[b,e][1,4]diazepine-8-carboxylate The desired product was prepared by substituting Example 523C and 4-aminopyrimidine for Example 189A and 4-aminopyridine, respectively, in Example 191. MS (ESI) m/e 392 (M+H)$^+$; $^1$H NMR (500 MHz, DMSO-d$_6$) □ 10.49 (s, 1H), 9.65 (s, 1H), 8.86 (s, 1H), 8.39-8.40 (m, 2H), 7.73 (d, J=8.5 Hz, 1H), 7.50 (d, J=2.0 Hz, 1H), 7.40 (s, 1H), 7.12 (dd, J=2.0, 8.5 Hz, 1H), 7.00 (d, J=5.0 Hz, 1H), 6.80 (s, 1H), 3.76 (s, 3H), 3.73 (s, 3H).

EXAMPLE 525

3-[(2,6-difluoropyridin-4-yl)amino]-8-(1,1-dimethyl-2-morpholin-4-yl-2-oxoethyl)-5,10-dihydro-11H-dibenzo[b,e][1,4]diazepin-11-one The desired product was prepared by substituting Example 205B and morpholine for dimethylaminoacetic acid and Example 120, respectively, in Example 122. MS (ESI) m/e 494 (M+H)$^+$; $^1$H NMR (300 MHz, DMSO-d$_6$) δ 9.69 (s, 2H), 7.96 (s, 1H), 7.69 (d, J=8.48 Hz, 1H), 6.69-6.96 (m, 2H), 6.79-6.82 (m, 2H), 6.68 (dd, J=8.82, 2.03 Hz, 1H), 6.58 (s, 2H), 2.8-3.5 (br, 8H), 1.36 (s, 6H).

EXAMPLE 526

2-{3-[(2,6-difluoropyridin-4-yl)amino]-11-oxo-10,11-dihydro-5H-dibenzo[b,e][1,4]diazepin-8-yl}-N,N,2-trimethylpropanamide The desired product was prepared by substituting Example 205B and dimethylamine hydrochloride for dimethylaminoacetic acid and Example 120, respectively, in Example 122. MS (ESI) m/e 452 (M+H)$^+$; $^1$H NMR (300 MHz, DMSO-d$_6$) δ 9.68 (s, 1H), 9.62 (s, 1H), 7.95 (s, 1H), 7.69 (d, J=8.48 Hz, 1H), 6.9 (m, 2H), 6.82 (d, J=2.03 Hz, 1H), 6.77 (dd, J=8.14, 2.03 Hz, 1H), 6.68 (dd, J=8.65, 2.2 Hz, 1H), 6.58 (s, 2H), 2.51 (br, 6H), 1.36 (m, 6H).

EXAMPLE 527

2-{3-[(2,6-difluoropyridin-4-yl)amino]-11-oxo-10,11-dihydro-5H-dibenzo[b,e][1,4]diazepin-8-yl}-2-methylNpyridin-4-ylpropanamide The desired product was prepared by substituting Example 205B and 4-aminopyridine for dimethylaminoacetic acid and Example 120, respectively, in Example 122. MS (ESI) m/e 501 (M+H)$^+$; $^1$H NMR (300 MHz, DMSO-d$_6$) δ 10.3 (s, 1H), 9.67 (d, J=9.83 Hz, 2H), 8.65 (d, J=7.12 Hz, 2H), 8.14 (d, J=7.46 Hz, 2H), 7.99 (s, 1H), 7.69 (d, J=8.48 Hz, 1H), 6.93 (m, 4H), 6.67 (dd, J=8.65, 2.20 Hz, 1H), 6.57 (s, 2H), 1.53 (s, 6H).

EXAMPLE 528

2-{3-[(2,6-difluoropyridin-4-yl)amino]-11-oxo-10,11-dihydro-5H-dibenzo[b,e][1,4]diazepin-8-yl}-2-methylN1,3-thiazol-2-ylpropanamide The desired product was prepared by substituting Example 205B and 2-aminothiazole for dimethylaminoacetic acid and Example 120, respectively, in Example 122. MS (ESI) m/e 507 (M+H)$^+$; $^1$H NMR (300 MHz, DMSO-d$_6$) δ 9.67 (d, J=15.93 Hz, 2H), 7.95 (s, 1H), 7.69 (d, J=8.48 Hz, 1H), 7.50 (d, J=4.75 Hz, 1H), 7.23 (d, J=5.09 Hz, 1H), 6.89 (m, 5H), 6.68 (dd, J=8.65, 2.2 Hz, 1H), 6.57 (s, 2H), 1.51 (m, 6H).

EXAMPLE 529

3-[(2,6-difluoropyridin-4-yl)amino]-8-{2-[(3R)-3-hydroxypiperidin-1-yl]-1,1-dimethyl-2-oxoethyl}-5,10-dihydro-11H-dibenzo[b,e][1,4]diazepin-11-one The desired product was prepared by substituting Example 205B and (3R)-piperidin-3-ol hydrochloride for dimethylaminoacetic acid and Example 120, respectively, in Example 122. MS (ESI) m/e 508 (M+H)$^+$; $^1$H NMR (300 MHz, DMSO-d$_6$) δ 9.67 (d, J=8.81 Hz, 2H), 7.94 (s, 1H), 7.69 (d, J=8.81 Hz, 2H), 6.91 (m, 2H), 6.78 (d, J=8.14 Hz, 2H), 6.67 (dd, J=8.65, 2.20 Hz, 1H), 6.58 (s, 2H), 2.73 (m, 2H), 2.27 (s, 2H), 1.75 (s, 2H), 1.35 (s, 6H), 1.13 (m, 2H).

EXAMPLE 530

3-[(2,6-difluoropyridin-4-yl)amino]-8-{2-(4-hydroxypiperidin-1-yl)-1,1-dimethyl-2-oxoethyl}-5,10-dihydro-11H-dibenzo[b,e][1,4]diazepin-11-one The desired product was prepared by substituting Example 205B and 4-hydroxy-piperidine for dimethylaminoacetic acid and Example 120, respectively, in Example 122. MS (ESI) m/e 508 (M+H)$^+$; $^1$H NMR (300 MHz, DMSO-d$_6$) δ 9.66 (d, J=6.44 Hz, 2H), 7.94 (s, 1H), 7.7 (d, J=8.81 Hz, 2H), 6.9 (m, 2H), 6.79 (m, 2H), 6.67 (dd, J=8.48, 2.03 Hz, 1H), 6.58 (s, 2H), 3.16 (s, 4H), 3.0-2.0 (m, 4H), 1.35 (s, 6H).

EXAMPLE 531

3-[(2,6-difluoropyridin-4-yl)amino]-8-{2-[(2S)-2-(hydroxymethyl)pyrrolidin-1-yl]-1,1-dimethyl-2-oxoethyl}-5,10-dihydro-11H-dibenzo[b,e][1,4]diazepin-11-one The desired product was prepared by substituting Example 205B and (2S)-pyrrolidin-2-ylmethanol for dimethylaminoacetic acid and Example 120, respectively, in Example 122. MS (ESI) m/e 508 (M+H)$^+$; $^1$H NMR (300 MHz, DMSO-d$_6$) δ 9.64 (m, 2H), 7.96 (m, 1H), 7.69 (m, 1H), 6.93 (m, 3H), 6.79 (m, 2H), 6.67 (m, 1H), 6.57 (d, J=2.37 Hz, 2H), 3.96 (s, 2H), 3.55 (s, 2H), 2.89 (s, 2H), 2.71 (d, J=9.83 Hz, 2H), 1.35 (s, 6H).

EXAMPLE 532

3-[(2,6-difluoropyridin-4-yl)amino]-8-(1,1-dimethyl-2-oxo-2-pyrrolidin-1-ylethyl)-5,10-dihydro-11H-dibenzo[b,e][1,4]diazepin-11-one The desired product was prepared by substituting Example 205B and pyrrolidine for dimethylaminoacetic acid and Example 120, respectively, in Example 122. MS (ESI) m/e 478 (M+H)$^+$; $^1$H NMR (300 MHz, DMSO-d$_6$) δ 9.65 (d, J=15.26 Hz, 2H), 7.95 (s, 1H), 7.69 (d, J=8.48 Hz, 1H), 6.91 (m, 2H), 6.83 (d, J=2.03 Hz, 1H), 6.78 (dd, J=8.14, 2.37 Hz, 1H), 6.67 (dd, J=8.81, 2.03 Hz, 1H), 6.58 (s, 2H), 2.75 (d, J=11.19 Hz, 2H), 1.56 (s, 6H).

EXAMPLE 533

2-{3-[(2,6-difluoropyridin-4-yl)amino]-11-oxo-10,11-dihydro-5H-dibenzo[b,e][1,4]diazepin-8-yl}-2-methylNpyridin-2-ylpropanamide The desired product was prepared by substituting Example 205B and 2-aminopyridine for dimethylaminoacetic acid and Example 120, respectively, in Example 122. MS (ESI) m/e 501 (M+H)⁺.

EXAMPLE 534

2-{3-[(2,6-difluoropyridin-4-yl)amino]-11-oxo-10,11-dihydro-5H-dibenzo[b,e][1,4]diazepin-8-yl}-2-methylNpyridin-3-ylpropanamide The desired product was prepared by substituting Example 205B and 3-aminopyridine for dimethylaminoacetic acid and Example 120, respectively, in Example 122. MS (ESI) m/e 501 (M+H)⁺; ¹H NMR (499 MHz, DMSO-d₆) δ 9.66 (d, J=15.28 Hz, 2H), 9.55 (s, 1H), 8.97 (s, 1H), 8.39 (d, J=3.12 Hz, 1H), 8.25 (d, J=8.73 Hz, 1H), 7.96 (s, 1H), 7.69 (d, J=8.42 Hz, 1H), 7.59 (dd, J=8.42, 4.99 Hz, 1H), 7.02 (s, 1H), 6.95 (s, 2H), 6.9 (d, J=2.18 Hz, 1H), 6.68 (dd, J=8.58, 2.03, 1H), 6.57 (s, 2H), 1.52 (s, 6H).

EXAMPLE 535

2-{3-[(2,6-difluoropyridin-4-yl)amino]-11-oxo-10,11-dihydro-5H-dibenzo[b,e][1,4]diazepin-8-yl }N(4-fluorophenyl)-2-methylpropanamide The desired product was prepared by substituting Example 205B and 4-fluoroaniline for dimethylaminoacetic acid and Example 120, respectively, in Example 122. MS (ESI) m/e 518 (M+H)⁺; ¹H NMR (300 MHz, DMSO-d₆) δ 9.67 (s, 2H), 9.06 (s, 1H), 7.94 (s, 1H), 7.68 (d, J=8.48 Hz, 1H), 7.59 (m, 2H), 7.08 (m, 3H), 6.91 (m, 3H), 6.67 (dd, J=8.83, 2.03 Hz, 1H), 6.57 (s, 2H), 1.49 (s, 6H).

EXAMPLE 536

3-[(2,6-difluoropyridin-4-yl)amino]-8-{2-[(2R)-2-(hydroxymethyl)pyrrolidin-1-yl]-1,1-dimethyl-2-oxoethyl}-5,10-dihydro-11H-dibenzo[b,e][1,4]diazepin-11-one The desired product was prepared by substituting Example 205B and (2R)-pyrrolidin-2-ylmethanol for dimethylaminoacetic acid and Example 120, respectively, in Example 122. MS (ESI) m/e 508 (M+H)⁺; ¹H NMR (300 MHz, DMSO-d₆) δ 9.66 (d, J=14.58 Hz, 2H), 7.95 (s, 1H), 7.7 (d, J=8.48 Hz, 1H), 6.92 (m, 2H), 6.8 (m. 2H), 6.68 (d, J=8.82 Hz, 1H), 6.58 (s, 2H), 4.03 (s, 1H), 3.56 (d, J=6.78 Hz, 1H), 3.45-3.0 (m, 2H), 2.73 (s, 2H), 1.68 (d, J=6.44 Hz, 3H), 1.35 (s, 6H).

EXAMPLE 537

8-methoxy-3-(3-methoxy-4-nitrophenyl)-7-(3-morpholin-4-yl-3-oxopropyl)-5,10-dihydro-11H-dibenzo[b,e][1,4]diazepin-11-one

EXAMPLE 537A

3-[8-methoxy-3-(3-methoxy-4-nitrophenyl)-11-oxo-10,11-dihydro-5H-dibenzo[b,e][1,4]diazepin-7-yl] propanoic acid The desired product was prepared by substituting Example 245 for Example 12 in Example 13. MS (ESI) m/e 464 (M+H)⁺.

EXAMPLE 537B 8-methoxy-3-(3-methoxy-4-nitrophenyl)-7-(3-morpholin-4-yl-3-oxopropyl)-5,10-dihydro-11H-dibenzo[b,e][1,4]diazepin-11-one The desired product was prepared by substituting Example 537A and morpholine for dimethylaminoacetic acid and Example 120, respectively, in Example 122. MS (ESI) m/e 533 (M+H)⁺; ¹H NMR (300 MHz, DMSO-d₆) δ 9.76 (s, 1H), 8.01 (d, J=8.48 Hz, 1H), 7.76 (m, 2H), 7.51 (d, J=1.7 Hz, 1H), 7.32 (m, 2H), 7.27 (dd, J=8.48, 1.7 Hz, 1H), 6.83 (s, 1H), 6.63 (s, 1H), 4.03 (s, 3H), 3.7 (s, 3H), 3.4-3.2 (m, 10H), 2.65 (d, J=7.8 Hz, 2H).

EXAMPLE 538

3-[3-(3-methoxy-4-nitrophenyl)-11-oxo-10,11-dihydro-5H-dibenzo[b,e][1,4]diazepin-8-yl]Npyridin-3-ylpropanamide The desired product was prepared by substituting Example 230 and pyridin-3-ylamine dimethylaminoacetic acid and Example 120, respectively, in Example 122. MS (ESI) m/e 510 (M+H)⁺; ¹H NMR (300 MHz, DMSO-d₆) δ 10.33 (s, 1H), 9.87 (s, 1H), 8.86 (d, J=2.03 Hz, 1H), 8.34 (m, 1H), 8.13 (m, 1H), 8.01 (d, J=8.48, 1H), 7.95 (s, 1H), 7.79 (d, J=8.14 Hz, 1H), 7.52 (m, 2H), 7.33 (m, 2H), 7.28 (d, J=1.7 Hz, 1H), 6.93 (m, 1H), 6.85 (d, J=5.76 Hz, 2H), 4.03 (s, 3H), 3.8-3.4 (br, 1H), 2.81 (t, J=7.46 Hz, 2H), 2.62 (t, J=7.46 Hz, 2H).

EXAMPLE 539

3-[3-(3-methoxy-4-nitrophenyl)-11-oxo-10,11-dihydro-5H-dibenzo[b,e][1,4]diazepin-8-yl]Npyridin-4-ylpropanamide The desired product was prepared by substituting Example 230 and pyridin-4-ylamine for dimethylaminoacetic acid and Example 120, respectively, in Example 122. MS (ESI) m/e 510 (M+H)⁺; ¹H NMR (300 MHz, DMSO-d₆) δ 11.06 (s, 1H), 9.89 (s, 1H), 8.61 (d, J=6.78 Hz, 1H), 8.03-7.9 (m, 5H), 7.79 (d, J=8.14 Hz, 1H), 7.52 (d, J=1.36 Hz, 1H), 7.33 (m, 2H), 7.29 (dd, J=8.14, 1.7 Hz, 1H), 6.94 (m, 1H), 6.85 (dd, J=4.07, 2.37 Hz, 2H), 3.8-3.2 (m, 1H), 2.82 (t, J=6.95 Hz, 2H), 2.71 (m, 2H).

EXAMPLE 540

8-[3-(3-hydroxypiperidin-1-yl)-3-oxopropyl]-3-(3-methoxy-4-nitrophenyl)-5,10-dihydro-11H-dibenzo[b,e][1,4]diazepin-11-one The desired product was prepared by substituting Example 230 and 3-hydroxypiperidine for dimethylaminoacetic acid and Example 120, respectively, in Example 122. MS (ESI) m/e 517 (M+H)⁺; ¹H NMR (300 MHz, DMSO-d₆) δ 9.82 (s, 1H), 8.01 (d, J=8.48 Hz, 1H), 7.93 (s, 1H), 7.79 (d, J=8.14 Hz, 1H), 7.52 (d, J=1.7 Hz, 1H), 7.33 (m, 2H), 7.29 (dd, J=8.14, 1.7 Hz, 1H), 6.92 (m, 1H), 6.85 (d, J=2.37 Hz, 2H), 4.82 (m, 1H), 3.55 (m, 2H), 2.67 (t, J=7.12 Hz, 2H), 1.63 (m, 2H), 1.24 (m, 2H).

EXAMPLE 541

N-(4-fluorophenyl)-3-[3-(3-methoxy-4-nitrophenyl)-11-oxo-10,11-dihydro-5H-dibenzo[b,e][1,4]diazepin-8-yl]propanamide The desired product was prepared by substituting Example 230 and 4-fluoroaniline dimethylaminoacetic acid and Example 120, respectively, in Example 122. MS (ESI) m/e 527 (M+H)$^+$; $^1$H NMR (400 MHz, DMSO-d$_6$) δ 9.84 (d, J=21.79 Hz, 2H), 7.96 (d, J=8.29 Hz, 1H), 7.88 (s, 1H), 7.74 (d, J=7.98 Hz, 1H), 7.52 (dd, J=8.9, 4.91 Hz, 2H), 7.47 (d, J=1.23 Hz, 1H), 7.28 (m, 2H), 7.23 (m, 1H), 7.06 (t, J=8.9 Hz, 2H), 6.88 (m, 1H), 6.80 (d, J=8.29 Hz, 2H), 3.98 (s, 3H), 2.73 (t, J=7.67 Hz, 2H), 2.48 (m, 2H).

EXAMPLE 542

3-[3-(3-methoxy-4-nitrophenyl)-11-oxo-10,11-dihydro-5H-dibenzo[b,e][1,4]diazepin-8-yl]N[4-(trifluoromethyl)phenyl]propanamide The desired product was prepared by substituting Example 230 and 4-(trifluoromethyl) aniline for dimethylaminoacetic acid and Example 120, respectively, in Example 122. MS (ESI) m/e 577 (M+H)$^+$; $^1$H NMR (400 MHz, DMSO-d$_6$) δ 10.23 (s, 1H), 9.85 (s, 1H), 7.99 (d, J=8.59 Hz, 1H), 7.92 (s, 1H), 7.77 (t, J=7.67 Hz, 3H), 7.64 (s, 2H), 7.5 (s, 1H), 7.29 (m, 3H), 6.92 (d, J=7.36 Hz, 1H), 6.85 (s, 1H), 4.02 (s, 3H), 2.79 (s, 2H), 2.59 (s, 2H).

EXAMPLE 543

3-[3-(3-methoxy-4-nitrophenyl)-11-oxo-10,11-dihydro-5H-dibenzo[b,e][1,4]diazepin-8-yl]Nmethylpropanamide The desired product was prepared by substituting Example 230 and methylamine hydrochloride for dimethylaminoacetic acid and Example 120, respectively, in Example 122. MS (ESI) m/e 447 (M+H)$^+$; $^1$H NMR (300 MHz, DMSO-d$_6$) δ 9.86 (s, 1H), 8.01 (d, J=8.48 Hz, 1H), 7.93 (s, 1H), 7.79 (d, J=8.14 Hz, 1H), 7.72 (d, J=4.41 Hz, 1H), 7.52 (d, J=1.70 Hz, 1H), 7.34 (m, 2H), 7.29 (dd, J=8.14, 1.70 Hz, 1H), 6.92 (m, 1H), 6.79 (d, J=7.12 Hz, 2H), 4.03 (s, 3H), 2.67 (t, J=7.8 Hz, 2H), 2.54 (d, J=4.41 Hz, 3H), 2.28 (t, J=7.8 Hz, 2H).

EXAMPLE 544

3-[8-methoxy-3-(3-methoxy-4-nitrophenyl)-11-oxo-10,11-dihydro-5H-dibenzo[b,e][1,4]diazepin-7-yl]-N,N-dimethylpropanamide The desired product was prepared by substituting Example 537A and dimethylamine hydrochloride for dimethylaminoacetic acid and Example 120, respectively, in Example 122. MS (ESI) m/e 491 (M+H)$^+$; $^1$H NMR (300 MHz, DMSO-d$_6$) δ 9.76 (s, 1H), 8.01 (d, J=8.48 Hz, 1H), 7.79 (s, 1H), 7.76 (d, J=4.07 Hz, 1H), 7.52 (d, J=1.36 Hz, 1H), 7.34 (m, 2H), 7.27 (dd, J=8.14, 1.7 Hz, 1H), 6.83 (s, 1H), 6.63 (s, 1H), 4.03 (s, 3H), 3.7 (s, 3), 2.91 (s, 3H), 2.8 (s, 3H), 2.64 (m, 2H), 2.44 (d, J=6.78 Hz, 2H).

EXAMPLE 545

8-{2-[(6-chloropyridin-3-yl)oxy]ethyl}-3-(3-methoxy-4-nitrophenyl)-5,10-dihydro-11H-dibenzo[b,e][1,4]diazepin-11-one A mixture of Example 239 (41 mg, 0.1 mmol), 6-chloropyridin-3-ol (19 mg, 0.15 mmol), PPh$_3$ (39 mg, 0.15 mmol), and di-tert-butyl azodicarboxylate (35 mg, 0.15 mmol) in THF (2 ml) was stirred at room temperature for 16 hours. The reaction mixture was diluted with MeOH/DMSO (1:1), and purified by preparative HPLC to provide the desired product. MS (ESI) m/e 517 (M+H)$^+$; $^1$H NMR (499 MHz, DMSO-d$_6$) δ 9.86 (s, 1H), 8.11 (d, J=3.12 Hz, 1H), 8.01 (d, J=8.42 Hz, 1H), 7.96 (s, 1H), 7.80 (d, J=8.11 Hz, 1H), 7.52 (s, 1H), 7.47 (m, 1H), 7.40 (d, J=8.73 Hz, 1H), 7.34 (m, 2H), 7.30 (dd, J=8.11, 1.56 Hz, 2H), 6.95 (m, 2H), 4.21 (t, J=6.55 Hz, 2H), 4.03 (s, 3H), 2.92 (t, J=6.55 Hz, 2H).

EXAMPLE 546

8-{2-[(2-chloropyridin-3-yl)oxy]ethyl}-3-(3-methoxy-4-nitrophenyl)-5,10-dihydro-11H-dibenzo[b,e][1,4]diazepin-11-one The desired product was prepared by substituting 2-chloro-3-hydroxypyridine for 6-chloro-pyridin-3-ol in Example 545. MS (ESI) m/e 517 (M+H)$^+$; $^1$H NMR (300 MHz, DMSO-d$_6$) δ 9.88 (s, 1H), 8.01 (d, J=8.48 Hz, 1H), 7.95 (m, 2H), 7.79 (d, J=8.14 Hz, 1H), 7.57 (dd, J=8.31, 1.53 Hz, 1H), 7.52 (d, J=1.70 Hz, 1H), 7.33 (m, 4H), 6.96 (s, 3H), 4.23 (t, J=6.61 Hz, 2H), 4.03 (s, 3H), 2.96 (t, J=6.61 Hz, 2H).

EXAMPLE 547

3-(3-methoxy-4-nitrophenyl)-8-{2-[(6-methylpyridin-3-yl)oxy]ethyl}-5,10-dihydro-11H-dibenzo[b,e][1,4]diazepin-11-one The desired product was prepared by substituting 6-methyl-pyridin-3-ol for 6-chloro-pyridin-3-ol in Example 545. MS (ESI) m/e 497 (M+H)$^+$; $^1$H NMR (300 MHz, DMSO-d$_6$) δ 9.89 (s, 1H), 8.36 (d, J=3.05 Hz, 1H), 8.03 (s, 1H), 7.99 (d, J=2.71 Hz, 1H), 7.78 (m, 2H), 7.53 (m, 2H), 7.32 (m, 3H), 6.95 (m, 3H), 4.25 (t, J=6.61 Hz, 2H), 3.9-3.25 (m, 3H), 2.94 (t, J=6.61 Hz, 2H).

EXAMPLE 548

3-(3-methoxy-4-nitrophenyl)-8-{2-[(2-methylpyridin-3-yl)oxy]ethyl}-5,10-dihydro-11H-dibenzo[b,e][1,4]diazepin-11-one The desired product was prepared by substituting 2-methyl-pyridin-3-ol for 6-chloro-pyridin-3-ol in Example 545. MS (ESI) m/e 497 (M+H)$^+$; $^1$H NMR (300 MHz, DMSO-d$_6$) δ 9.91 (s, 1H), 8.23 (d, J=5.09, 1H), 8.01 (m, 2H), 7.89 (d, J=9.16 Hz, 1H), 7.79 (d, J=8.14 Hz, 1H), 7.63 (dd, J=7.97, 5.26 Hz, 1H), 7.52 (d, J=1.36 Hz, 1H), 7.32 (m, 3H), 6.96 (m, 3H), 4.30 (t, J=6.27 Hz, 2H), 4.03 (s, 3H), 2.97 (t, J=6.27 Hz, 2H), 2.47 (s, 3H).

EXAMPLE 549

3-(3-methoxy-4-nitrophenyl)-8-[2-(pyridin-3-yloxy)ethyl]-5,10-dihydro-11H-dibenzo[b,e][1,4]diazepin-11-one The desired product was prepared by substituting 3-hydroxy-pyridine for 6-chloro-pyridin-3-ol in Example 545. MS (ESI) m/e 483 (M+H)$^+$; $^1$H NMR (300 MHz, DMSO-d$_6$) δ 9.89 (s, 1H), 8.35 (d, J=2.71 Hz, 1H), 8.22 (d, J=4.75 Hz, 1H), 8.03 (s, 1H), 7.99 (d, J=6.10 Hz, 1H), 7.80 (d, J=8.14 Hz, 1H), 7.52 (m, 2H), 7.42 (dd, J=8.48, 4.75 Hz, 1H), 7.33 (m, 2H), 7.28 (d, J=1.7 Hz, 1H), 6.95 (m, 3H), 4.23 (t, J=6.61 Hz, 2H), 4.03 (s, 3H), 2.94 (t, J=6.61 Hz, 2H).

EXAMPLE 550

8-{2-[(2,6-dimethylpyridin-3-yl)oxy]ethyl}-3-(3-methoxy-4-nitrophenyl)-5,10-dihydro-11H-dibenzo[b,e][1,4]diazepin-11-one The desired product was prepared by substituting 2,6-dimethyl-pyridin-3-ol for 6-chloro-pyridin-3-ol in Example 545. MS (ESI) m/e 511 (M+H)$^+$; $^1$H NMR (300 MHz, DMSO-d$_6$) δ 9.89 (s, 1H), 8.03 (s, 1H), 7.99 (d, J=5.42 Hz, 1H), 7.80 (d, J=8.14 Hz, 2H), 7.52 (d, J=1.7 Hz, 2H), 7.33 (m, 3H), 7.28 (d, J=2.03 Hz, 1H), 6.95 (m, 2H), 6.91 (s, 1H), 4.26 (m, 2H), 4.03 (s, 3H), 2.41 (s, 3H), 1.39 (s, 3H).

EXAMPLE 551

8-[2-({2-[(dimethylamino)methyl]pyridin-3-yl}oxy)ethyl]-3-(3-methoxy-4-nitrophenyl)-5,10-dihydro-11H-dibenzo[b,e][1,4]diazepin-11-one The desired product was prepared by substituting 2-[(dimethylamino)methyl]pyridin-3-ol for 6-chloro-pyridin-3-ol in Example 545. MS (ESI) m/e 540 (M+H)$^+$; $^1$H NMR (300 MHz, DMSO-d$_6$) δ 9.89 (s, 1H), 8.23 (d, J=3.73 Hz., 1H), 8.02 (m, 2H), 7.80 (d, J=8.14 Hz, 1H), 7.61 (d, J=7.46 Hz, 1H), 7.52 (d, J=1.70 Hz, 1H), 7.47 (dd, J=8.31, 4.58 Hz, 1H), 7.32 (m, 3H), 6.96 (m, 3H), 4.35 (d, J=3.73 Hz, 2H), 4.25 (t, J=6.44 Hz, 2H), 4.03 (s, 3H), 2.97 (t, J=6.44 Hz, 2H), 2.5 (m, 6H).

EXAMPLE 552

8-[2-(isoquinolin-7-yloxy)ethyl]-3-(3-methoxy-4-nitrophenyl)-5,10-dihydro-11H-dibenzo[b,e][1,4]diazepin-11-one The desired product was prepared by substituting isoquinolin-7-ol for 6-chloro-pyridin-3-ol in Example 545. MS (ESI) m/e 533 (M+H)$^+$; $^1$H NMR (500 MHz, DMSO-d$_6$) δ 9.87 (s, 1H), 9.17 (s, 1H), 8.35 (d, J=5.6 Hz, 1H), 8.01 (d, J=8.42 Hz, 1H), 7.97 (s, 1H), 7.87 (d, J=8.73 Hz, 1H), 7.80 (d, J=8.42 Hz, 1H), 7.73 (d, J=5.62 Hz, 1H), 7.52 (s, 2H), 7.42 (dd, J=8.74, 2.5 Hz, 1H), 7.34 (m, 2H), 7.3 (dd, J=8.42, 1.56 Hz, 1H), 6.99 (m, 3H), 4.29 (t, J=6.71 Hz, 2H), 4.03 (s, 3H), 3.0 (t, J=6.71 Hz, 2H).

EXAMPLE 553

7-methoxy-3-(3-methoxy-4-nitrophenyl)-N,N-dimethyl-11-oxo-10,11-dihydro-5H-dibenzo[b,e][1,4]diazepine-8-carboxamide

EXAMPLE 553A 7-methoxy-3-(3-methoxy-4-nitrophenyl)-11-oxo-10,11-dihydro-5H-dibenzo[b,e][1,4]diazepine-8-carboxylic acid The desired product was prepared by substituting Example 523D for Example 12 in Example 13. MS (ESI) m/e 436 (M+H)$^+$.

EXAMPLE 553B 7-methoxy-3-(3-methoxy-4-nitrophenyl)-N,N-dimethyl-11-oxo-10,11-dihydro-5H-dibenzo[b,e][1,4]diazepine-8-carboxamide The desired product was prepared by substituting Example 553A and N, N-dimethylamine hydrochloride dimethylaminoacetic acid and Example 120, respectively, in Example 122. MS (ESI) m/e 463 (M+H)$^+$; $^1$H NMR (300 MHz, DMSO-d$_6$) δ 9.82 (s, 1H), 8.16 (s, 1H), 8.02 (d, J=8.14 Hz, 1H), 7.8 (d, J=8.14 Hz, 1H), 7.55 (d, J=1.70 Hz, 1H), 7.35 (m, 3H), 6.77 (d, J=7.12 Hz, 2H), 4.04 (s, 3H), 3.74 (s, 3H), 2.93 (s, 3H), 2.76 (s, 3H).

EXAMPLE 554

7-{2-[(2-chloropyridin-3-yl)oxy]ethyl}-8-methoxy-3-(3-methoxy-4-nitrophenyl)-5,10-dihydro-11H-dibenzo[b,e][1,4]diazepin-11-one The desired product was prepared by substituting Example 247 and 2-chloro-3-hydroxypyridine for Example 239 and 6-chloro-pyridin-3-ol respectively, in Example 545. MS (ESI) m/e 547 (M+H)$^+$; $^1$H NMR (400 MHz, DMSO-d$_6$) δ 9.79 (s, 1H), 8.02 (d, J=8.59 Hz, 1H), 7.93 (dd, J=4.76, 1.38 Hz, 1H), 7.77 (m, 2H), 7.57 (dd, J=8.13, 1.38 Hz, 1H), 7.52 (d, J=1.53 Hz, 1H), 7.35 (m, 3H), 7.29 (dd, J=8.29, 1.84 Hz, 1H), 6.95 (s, 1H), 6.67 (s, 1H), 4.2 (t, J=6.75 Hz, 2H), 4.04 (s, 3H), 3.72 (s, 3H), 2.94 (t, J=6.6 Hz, 2H).

EXAMPLE 555

8-[2-(isoquinolin-5-yloxy)ethyl]-3-(3-methoxy-4-nitrophenyl)-5,10-dihydro-11H-dibenzo[b,e][1,4]diazepin-11-one The desired product was prepared by substituting isoquinolin-5-ol for 6-chloro-pyridin-3-ol in Example 545. MS (ESI) m/e 533 (M+H)$^+$; $^1$H NMR (500 MHz, DMSO-d$_6$) δ 9.82 (s, 1H), 9.39 (s, 1H), 8.46 (d, J=6.24 Hz, 1H), 8.06 (d, J=5.93 Hz, 1H), 7.93 (d, J=8.42 Hz, 1H), 7.89 (s, 1H), 7.72 (m, 2H), 7.63 (t, J=7.96 Hz, 1H), 7.44 (d, J=1.56 Hz, 1H), 7.32 (d, J=7.8 Hz, 1H), 7.26 (m, 2H), 7.22 (dd, J=8.11, 1.56 Hz, 1H), 6.95 (d, J=8.11 Hz, 1H), 6.91 (d, J=7.8 Hz, 2H), 4.3 (t, J=6.4 Hz, 2H), 3.95 (s, 3H), 3.01 (t, J=6.24 Hz, 2H).

EXAMPLE 556

3-(3-methoxy-4-nitrophenyl)-8-[2-(quinolin-5-yloxy)ethyl]-5,10-dihydro-11H-dibenzo[b,e][1,4]diazepin-11-one The desired product was prepared by substituting quinolin-5-ol for 6-chloro-pyridin-3-ol in Example 545. MS (ESI) m/e 533 (M+H)$^+$; $^1$H NMR (300 MHz, DMSO-d$_6$) δ 9.86 (s, 1H), 8.01 (d, J=8.42 Hz, 1H), 7.96 (s, 1H), 7.86 (d, J=8.73 Hz, 1H), 7.8 (d, J=8.11 Hz, 1H), 7.62 (m, 2H), 7.56 (m, 1H), 7.52 (d, J=1.25 Hz, 1H), 7.45 (d, J=2.5 Hz, 1H), 7.34 (dd, J=8.74, 1.56 Hz, 2H), 7.29 (dd, J=8.11, 1.56 Hz, 1H), 7.02 (dd, J=8.89, 2.34 Hz, 1H), 6.96 (m, 3H), 4.2 (t, J=6.71 Hz, 2H), 4.03 (s, 3H), 2.94 (t, J=6.71 Hz, 2H).

EXAMPLE 557

3-(3-methoxy-4-nitrophenyl)-8-[2-(4-methoxyphenoxy)ethyl]-5,10-dihydro-11H-dibenzo[b,e][1,4]diazepin-11-one The desired product was prepared by substituting 4-methoxyphenol for 6-chloro-pyridin-3-ol in Example 545. MS (ESI) m/e 512 (M+H)$^+$; $^1$H NMR (400 MHz, DMSO-d$_6$) δ 9.85 (s, 1H), 8.01 (d, J=8.29 Hz, 1H), 7.95 (s, 1H), 7.80 (d, J=8.29 Hz, 1H), 7.52 (d, J=1.23 Hz, 1H), 7.34 (m, 2H), 7.29 (m, 1H), 6.93 (m, 4H), 6.84 (d, J=3.38 Hz, 3H), 4.05 (m, 2H), 4.03 (s, 3H), 3.68 (s, 3H), 2.87 (t, J=6.60, 2H).

EXAMPLE 558

3-(3-methoxy-4-nitrophenyl)-8-[2-(3-methoxyphenoxy)ethyl]-5,10-dihydro-11H-dibenzo[b,e][1,4]diazepin-11-one The desired product was prepared by substituting 3-methoxyphenol for 6-chloro-pyridin-3-ol in Example 545. MS (ESI) m/e 512 (M+H)$^+$; $^1$H NMR (400 MHz, DMSO-d$_6$) δ 9.86 (s, 1H), 8.01 (d, J=8.29 Hz, 1H), 7.96 (s, 1H), 7.8 (d, J=8.29 Hz, 1H), 7.52 (d, J=1.23 Hz, 1H), 7.36 (m, 2H), 7.29 (m, 1H), 7.15 (t, J=8.13 Hz, 1H), 6.94 (m, 3H), 6.49 (m, 3H), 4.10 (t, J=6.75 Hz, 2H), 4.03 (s, 3H), 2.89 (t, J=6.60 Hz, 2H).

EXAMPLE 559

3-{2-[3-(3-methoxy-4-nitrophenyl)-11-oxo-10,11-dihydro-5H-dibenzo[b,e][1,4]diazepin-8-yl]ethoxy}pyridine-2-carboxamide The desired product was prepared by substituting 3-hydroxypyridine-2-carboxamide for 6-chloro-pyridin-3-ol in Example 545. MS (ESI) m/e 526 (M+H)$^+$; $^1$H NMR (500 MHz, DMSO-d$_6$) δ 9.85 (s, 1H), 9.25 (s, 1H), 8.34 (s, 1H), 8.09 (s, 1H), 8.01 (d, J=8.42 Hz, 2H), 7.81 (d, J=8.11 Hz, 2H), 7.71 (s, 1H), 7.52 (s, 1H), 7.32 (dd, J=19.03, 7.49 Hz, 3H), 6.96 (d, J=7.8 Hz, 1H), 6.82 (m, 2H), 7.75 (t, J=7.49 Hz, 2H), 4.03 (s, 3H), 3.09 (t, J=7.33 Hz, 2H).

EXAMPLE 560

3-(3-methoxy-4-nitrophenyl)-8-[3-(4-morpholin-4-ylphenoxy)propyl]-5,10-dihydro-11H-dibenzo[b,e][1,4]diazepin-11-one The desired product was prepared by substituting Example 240 and 4-morpholin-4-ylphenol (M. C. Harris, et.al., Org. Lett., 2002, 4, 2885) for Example 239 and 6-chloro-pyridin-3-ol respectively, in Example 545. MS (ESI) m/e 581 (M+H)$^+$; $^1$H NMR (400 MHz, DMSO-d$_6$) δ 9.82 (s, 1H), 8.01 (d, J=8.29 Hz, 1H), 7.93 (s, 1H), 7.80 (d, J=8.28 Hz, 1H), 7.34 (m, 2H), 7.29 (d, J=8.29, 1H), 6.93 (d, J=7.67 Hz, 3H), 6.83 (dd, J=8.13, 6.60 Hz, 4H), 4.0 (s, 3H), 3.88 (t, J=6.29 Hz, 2H), 3.74 (m, 4H), 3.02 (s, 4H), 2.60 (t, J=7.67 Hz, 2H), 1.92 (m, 2H).

EXAMPLE 561

3-(3-methoxy-4-nitrophenyl)-8-[3-(pyridin-3-yloxy)propyl]-5,10-dihydro-11H-dibenzo[b,e][1,4]diazepin-11-one The desired product was prepared by substituting Example 240 and pyridin-3-ol for Example 239 and 6-chloro-pyridin-3-ol, respectively, in Example 545. MS (ESI) m/e 497 (M+H)$^+$; $^1$H NMR (400 MHz, DMSO-d$_6$) δ 9.83 (s, 1H), 8.35 (s, 1H), 8.20 (s, 1H), 8.01 (d, J=8.29 Hz, 1H), 7.94 (s, 1H), 7.79 (d, J=8.29 Hz, 1H), 7.52 (d, J=1.23 HZ, 1H), 7.48 (m, 1H), 7.40 (dd, J=8.29, 4.60 Hz, 1H), 7.34 (m, 2H), 7.29 (dd, J=8.13, 1.69 Hz, 1H), 6.94 (d, J=7.98 Hz, 1H), 6.84 (d, J=8.59 Hz, 2H), 4.05 (s, 3H), 2.63 (t, J=7.52, 2H), 1.98 (m, 2H), 1.39 (s, 2H).

EXAMPLE 562

8-[2-(3-aminophenoxy)ethyl]-3-(3-methoxy-4-nitrophenyl)-5,10-dihydro-11H-dibenzo[b,e][1,4]diazepin-11-one The desired product was prepared by substituting 3-aminophenol for 6-chloro-pyridin-3-ol in Example 545. MS (ESI) m/e 497 (M+H)$^+$; $^1$H NMR (400 MHz, DMSO-d$_6$) δ 9.85 (s, 1H), 8.01 (d, J=8.59 Hz, 1H), 7.95 (s, 1H), 7.8 (d, J=8.29 Hz, 1H), 7.52 (d, J=1.23 Hz, 1H), 7.34 (m, 2H), 7.29 (dd, J=8.13, 1.69 Hz, 1H), 6.97-6.85 (m, 4H), 6.13 (m, 1H), 6.07 (dd, J=7.52, 1.69 Hz, 1H), 6.97-6.85 (m, 4H), 4.97 (s, 2H), 4.03 (s, 3H), 4.0 (t, J=6.75 Hz, 2H), 2.86 (t, J=6.60 Hz, 2H).

EXAMPLE 563

3-(3-methoxy-4-nitrophenyl)-8-{2-[(2-methyl-1,3-benzothiazol-7-yl)oxy]ethyl}-5,10-dihydro-11H-dibenzo[b,e][1,4]diazepin-11-one The desired product was prepared by substituting 2-methyl-1,3-benzothiazol-7-ol for 6-chloro-pyridin-3-ol in Example 545. MS (ESI) m/e 553 (M+H)$^+$; $^1$H NMR (499 MHz, DMSO-d$_6$) δ 9.86 (s, 1H), 8.01 (d, J=8.42 Hz, 1H), 7.96 (s, 1H), 7.86 (d, J=8.74 Hz, 1H), 7.8 (d, J=8.11 Hz, 1H), 7.52 (d, J=1.56 HZ, 1H), 7.45 (d, J=2.50 Hz, 1H), 7.34 (m, 2H), 7.29 (dd, J=8.11, 1.87 Hz, 1H), 7.02 (dd, J=8.74, 2.5 Hz, 1H), 6.98 (m, 3H), 4.20 (t, J=6.71 Hz, 2H), 4.03 (s, 3H), 2.94 (t, J=6.71 Hz, 2H), 2.76 (s, 3H).

EXAMPLE 564

2-[3-(3-methoxy-4-nitrophenyl)-11-oxo-10,11-dihydro-5H-dibenzo[b,e][1,4]diazepin-8-yl]-2-methylN(pyridin-2-ylmethyl)propanamide The title compound was prepared by substituting Example 266I and pyridin-2-ylmethylamine for dimethylaminoacetic acid and Example 120, respectively, in Example 122. MS (ESI) m/e 538 (M+H)$^+$; $^1$H NMR (300 MHz, DMSO-d$_6$) δ 9.86 (s, 1H), 8.54 (m, 1H), 8.02 (s, 1H), 8.01 (d, J=8.5 Hz, 1H), 7.92 (m, 2H), 7.81 (d, J=8.5 Hz, 1H), 7.52 (d, J=1.7 Hz, 1H), 7.40 (m, 1H), 7.36, 7.32, 7.30 (all m, total 3H), 7.22 (d, J=7.8 Hz, 1H), 7.03 (d, J=1.7 Hz, 1H), 6.97 (m, 2H), 4.36 (d, J=5.8 Hz, 2H), 4.03 (s, 3H), 1.45 (s, 6H).

EXAMPLE 565

8-(2-hydroxy-2-methylpropyl)-3-(3-methoxy-4-nitrophenyl)-5,10-dihydro-11H-dibenzo[b,e][1,4]diazepin-11-one The title compound was prepared by substituting Example 208A and Example 266G for Example 59B and Example 56A, respectively, in Example 59C. MS (DCI) m/e 434 (M+H)$^+$; $^1$H NMR (500 MHz, DMSO-d$_6$) δ 9.79 (s, 1H), 7.98 (d, J=8.42 Hz, 1H), 7.87 (s, 1H), 7.76 (d, J=8.11 Hz, 1H), 7.49

(s, 1H), 7.31-7.32 (m, 2H), 7.26 (dd, J=8.26, 1.40 Hz, 1H), 6.88 (d, J=8.11 Hz, 1H), 6.77-6.81 (m, 2H), 4.21 (s, 1H), 4.00 (s, 3H), 2.49 (s, 2H), 1.02 (s, 6H).

EXAMPLE 566

3-(3-methoxy-4-nitrophenyl)-8-[(4-methylpiperazin-1-yl)methyl]-5,10-dihydro-11H-dibenzo[b,e][1,4]diazepin-11-one

EXAMPLE 566A

N-(4-formyl-2-nitrophenyl)acetamide

To fuming $HNO_3$ (30 mL) at 0° C. was added N-(4-formylphenyl)acetamide (10.3 g, 63.1 mmoles) portionwise. After two hours, the reaction mixture was poured into 4° C. water (1 L). The resulting solid was filtered, washed with water (0.5 L×3), and dried in vacuo to give the desired product (10.57 g, 80%). MS (APCI)+m/e 209 (M+H)$^+$; $^1$H NMR (300 MHz, DMSO-$d_6$) □ 10.61 (s, 1H), 10.00 (s, 1H), 8.46 (d, J=1.70 Hz, 1H), 8.17 (dd, J=8.31, 1.86 Hz, 1H), 7.91 (d, J=8.48 Hz, 1H), 2.13 (s, 3H).

EXAMPLE 566B

N-{4-[(4-methylpiperazin-1-yl)methyl]-2-nitrophenyl}acetamide

Example 566A (2.02 g, 9.71 mmoles), 1-methyl-piperazine (1.1 mL, 9.71 mmoles), NaBH(OAc)$_3$ (3.09 g, 14.57 mmoles) and 1,2-dichloroethane were mixed, and stirred under $N_2$ at room temperature for 3 hours. After the reaction, the solvent was removed. Silica gel column was used to purify and give the desired product (2.74 g, 96.5%). MS (APCI) m/e 293 (M+H)$^+$; 1H NMR (300 MHz, DMSO-$d_6$) □ 10.22 (s, 1H), 7.81 (d, J=1.70 Hz, 1H), 7.60 (m, 1H), 7.55 (d, J=8.14 Hz, 1H), 3.50 (s, 2H), 2.32 (m, 8H), 2.14 (s, 3H), 2.05 (s, 3H).

EXAMPLE 566C

4-[(4-methylpiperazin-1-yl)methyl]-2-nitrophenylamine

Example 566B (2.74 g, 9.37 mmoles) was added to concentrated hydrochloric acid (40 mL). The reaction was heated at 65° C. for 15 minutes. The solvents were removed to give a yellow solid. 2N NaOH solution was added until the solution became basic. The water was removed. Silica gel column was used to purify and give the desired product (1.88 g, 77%). MS (APCI) m/e 251 (M+H)$^+$; $^1$H NMR (300 MHz, CD$_3$OD) □ 7.98 (d, J=2.03 Hz, 1H), 7.35 (dd, J=8.82, 2.03 Hz, 1H), 6.93 (d, J=8.48 Hz, 1H), 3.43 (s, 2H) 2.49 (br. s, 8H), 2.27 (s, 3H).

EXAMPLE 566D methyl 4-chloro-2-({4-[(4-methylpiperazin-1-yl)methyl]-2-nitrophenyl}amino)benzoate The title compound was prepared by substituting Example 566C for methyl 3,4-diaminobenzoate in Example 1A. MS (APCI) m/e 419 (M+H)$^+$; 1H NMR (300 MHz, DMSO-$d_6$) □ 10.83 (s, 1H), 8.03 (d, J=2.03 Hz, 1H), 7.96 (d, J=8.48 Hz, 1H), 7.67 (d, J=8.50, 1H), 7.60 (dd, J=8.65, 1.87 Hz, 1H), 7.48 (d, J=2.03 Hz, 1H), 7.11 (dd, J=8.48, 1.83 Hz, 1H), 3.49 (s, 2H), 3.87 (s, 3H), 2.39 (m, 8H), 2.16 (m, 3H).

EXAMPLE 566E methyl 2-({2-amino-4-[(4-methylpiperazin-1-yl)methyl]phenyl}amino)-4-chlorobenzoate Example 566D (2.45 g, 5.85 mmoles), Fe (2.34 g, 42 mmoles), NH$_4$Cl (0.22 g, 4.2 mmoles), ethanol (30 mL) and water (10.5 mL) were mixed, stirred, and heated to reflux overnight. The reaction mixture was purified by silica gel column to give 1.11 g of the desired product (49%). MS (APCI) m/e 389 (M+H)$^+$; 1H NMR (300 MHz, CD$_3$OD) □ 9.00 (s, 1H), 7.89 (d, J=8.48 Hz, 1H), 7.01 (d, J=7.80 Hz, 1H), 6.88 (d, J=1.70 Hz, 1H), 6.71 (dd, J=7.80, 2.03 Hz, 1H), 6.64 (dd, J=8.48, 2.03 Hz, 1H), 6.50 (d, J=2.03 Hz, 1H), 3.90 (s, 3H), 3.48 (s, 2H), 2.53 (m, 8H), 2.28 (s, 3H).

EXAMPLE 566F 3-chloro-8-[(4-methylpiperazin-1-yl)methyl]-5,10-dihydro-11H-dibenzo[b,e][1,4]diazepin-11-one The title compound was prepared by substituting Example 566E for Example 6C in Example 6D. MS (APCI) m/e 357 (M+H)$^+$; 1H NMR (300 MHz, DMSO-$d_6$) □ 9.86 (s, 1H), 8.02 (s, 1H), 7.67 (d, J=8.48 Hz, 1H), 7.06 (d, J=2.03 Hz, 1H), 6.90 (m, 4H), 2.30 (m, 8H), 3.29 (s, 2H), 2.13 (s, 3H).

EXAMPLE 566G 3-(3-methoxy-4-nitrophenyl)-8-[(4-methylpiperazin-1-yl)methyl]-5,10-dihydro-11H-dibenzo[b,e][1,4]diazepin-11-one The title compound was prepared by substituting Example 566F and Example 266G for Example 59B and Example 56A, respectively, in Example 59C. MS (APCI) m/e 474 (M+H)$^+$; 1H NMR (500 MHz, DMSO-$d_6$) □ 9.94 (s, 1H), 8.10 (s, 1H), 8.02 (d, J=8.54 Hz, 1H), 7.80 (d, J=8.24 Hz, 1H), 7.52 (d, J=1.53 Hz, 1H), 7.37 (d, J=1.53 Hz, 1H), 7.34 (dd, J=8.54, 1.53 Hz, 1H), 7.32 (dd, J=8.09, 1.68 Hz, 1H), 7.01 (s, 1H), 6.95 (s, 2H), 4.04 (s, 3H), 3.78 (m, 4H,) 3.37 (m, 2H), 2.99 (m, 4H), 2.76 (s, 3H).

EXAMPLE 567

3-(4-chloro-3-methoxyphenyl)-8-[(4-methylpiperazin-1-yl)methyl]-5,10-dihydro-11H-dibenzo[b,e][1,4]diazepin-11-one

EXAMPLE 567A

8-[(4-methylpiperazin-1-yl)methyl]-3-(4,4,5,5-tetramethyl-1,3,2-dioxaborolan-2-yl)-5,10-dihydro-11H-dibenzo[b,e][1,4]diazepin-11-one The title compound was prepared by substituting Example 566F for Example 6D in Example 54A. MS (APCI) m/e 449 (M+H)$^+$.

EXAMPLE 567B 3-(4-chloro-3-methoxyphenyl)-8-[(4-methylpiperazin-1-yl)methyl]-5,10-dihydro-11H-dibenzo[b,e][1,4]diazepin-11-one The desired product was prepared by substituting Example 567A and 2-chloro-5-iodoanisole for 2-methoxy-4-(4,4,5,5- tetramethyl-1,3,2-dioxaborolan-2-yl)phenol and Example 1B, respectively, in Example 10. MS (APCI) m/e 464 (M+H)+; 1H NMR (400 MHz, DMSO-d6) ☐ 9.88 (s, 1H), 8.04 (s, 1H), 7.77 (d, J=8.30 Hz, 1H), 7.54 (d, J=8.29 Hz, 1H), 7.33 (d, J=2.15 Hz, 1H), 7.32 (d, J=1.84 Hz, 1H), 7.25 (dd, J=8.13, 1.69 Hz, 1H), 7.21 (dd, J=8.29, 1.84 Hz, 1H), 7.02 (d, J=8.60 Hz, 1H), 6.95 (m, 2H), 3.96 (s, 3H) 3.68 (m, 4H), 3.41 (m, 2H), 3.11 (m, 4H), 2.77 (s, 3H).

EXAMPLE 568

2-methoxy-4-{8-[(4-methylpiperazin-1-yl)methyl]-11-oxo-10,11-dihydro-5H-dibenzo[b,e][1,4]diazepin-3-yl}benzonitrile The desired product was prepared by substituting Example 567A and 4-iodo-2-methoxy-benzonitrile for 2-methoxy-4-(4,4,5,5-tetramethyl-1,3,2-dioxaborolan-2-yl)phenol and Example 1B, respectively, in Example 10. MS (APCI) m/e 454 (M+H)+; 1H NMR (400 MHz, DMSO-d6) ☐ 9.92 (s, 1H), 8.07 (s, 1H), 7.84 (d, J=7.90 Hz 1H), 7.80 (d, J=8.29 Hz, 1H), 7.42 (s, 1H), 7.36 (d, J=1.23 Hz, 1H), 7.33 (dd, J=7.98, 1.23 Hz, 1H), 7.30 (dd, J=8.29, 1.53 Hz, 1H), 7.02 (d, J=8.30 Hz 1H), 6.95 (m, 2H), 4.02 (s, 3H), 3.62 (m, 4H), 3.41 (m, 2H), 3.10 (m, 4H), 2.78 (s, 3H).

EXAMPLE 569

3-(4-hydroxy-3-methoxyphenyl)-8-(hydroxymethyl)-5,10-dihydro-11H-dibenzo[b,e][1,4]diazepin-11-one

EXAMPLE 569A (4-amino-3-nitrophenyl)methanol (4-chloro-3-nitrophenyl)methanol (7.0 g, 37.32 mmoles), liquid NH3 (100 mL) and methanol (125 mL) were mixed in a sealed reactor. The temperature was set to 160° C., and the pressure became about 600 psi. After 16 hours, the reaction was cooled down. The high pressure was released. All the solvents were removed. The solid residual was purified by silica gel column to give 4.51 g of the above intermediate (72%). MS (DCI) m/e 169 (M+H)+; 1H NMR (300 MHz, CD3OD) ☐ 8.02 (d, J=1.70 Hz, 1H), 7.36 (dd, J=8.48, 2.03 Hz, 1H), 6.95 (d, J=8.48 Hz, 1H), 4.48 (s, 2H).

EXAMPLE 569B methyl 4-chloro-2-{[4-(hydroxymethyl)-2-nitrophenyl]amino}benzoate The title compound was prepared by substituting Example 569A for methyl 3,4-diaminobenzoate in Example 1A. MS (APCI) m/e 337 (M+H)+; 1H NMR (300 MHz, DMSO-d6) ☐ 10.82 (s, 1H), 8.09 (s, 1H), 7.97 (d, J=8.48 Hz, 1H), 7.69 (m, 1H), 7.64 (d, J=1.70 Hz, 1H), 7.43 (d, J=2.03 Hz, 1H), 7.10 (dd, J=8.65, 1.87 Hz, 1H), 5.42 (t, J=5.76 Hz, 1H), 4.54 (d, J=5.76 Hz, 1H), 3.89 (s, 3H).

EXAMPLE 569C methyl 2-{[2-amino-4-(hydroxymethyl)phenyl]amino}-4-chlorobenzoate The title compound was prepared by substituting Example 569B for Example 566D in Example 566E. MS (APCI) m/e 389 (M+H)+; 1H NMR (300 MHz, CD3OD) ☐ 9.00 (s, 1H), 7.89 (d, J=8.48 Hz, 1H), 7.01 (d, J=7.80 Hz, 1H), 6.88 (d, J=1.70 Hz, 1H), 6.71 (dd, J=7.80, 2.03 Hz, 1H), 6.64 (dd, J=8.48, 2.03 Hz, 1H), 6.50 (d, J=2.03 Hz, 1H), 3.90 (s, 3H), 3.48 (s, 2H), 2.53 (m, 8H), 2.28 (s, 3H).

EXAMPLE 569D

2-{[2-amino-4-(hydroxymethyl)phenyl]amino}-4-chlorobenzoic acid

Example 569C (1.44 g, 4.69 mmole) was dissolved in DMF (45 mL). To this solution was added LiOH (1.12 g, 46.95 mmole) in water (5 mL). The mixture was stirred for 3 hours. Then the reaction mixture was poured into water (100 mL). Adjust the pH to 5 with 2N hydrochloric solution. Extract the solution with ethyl acetate (50 mL×4). The organic phases were dried (MgSO4) and concentrated to give 1.35 g of the desired product (98%). MS (APCI) m/e 293 (M+H)+; 1H NMR (300 MHz, CD3OD) ☐ 7.90 (d, J=8.48 Hz, 1H), 7.03 (d, J=7.80 Hz, 1H), 6.91 (d, J=1.70 Hz, 1H), 6.74 (dd, J=7.97, 1.86 Hz, 1H, 6.62 (dd, J=8.65, 2.20 Hz, 1H), 6.49 (d, J=2.03 Hz, 1H), 4.54 (s, 2H).

EXAMPLE 569E 3-chloro-8-(hydroxymethyl)-5,10-dihydro-11H-dibenzo[b,e][1,4]diazepin-11-one The title compound was prepared by substituting Example 569D for Example 233F in Example 233G. MS (APCI)+m/e 275 (M+H)+; 1H NMR (300 MHz, DMSO-d6) ☐ 9.90 (s, 1H), 8.00 (s, 1H), 7.68 (d, J=8.48 Hz, 1H), 7.06 (d, J=2.03 Hz, 1H,) 6.92 (m, 4H), 5.09 (t, J=5.76 Hz, 1H), 4.35 (d, J=5.09 Hz, 2H).

EXAMPLE 569F 3-(4-hydroxy-3-methoxyphenyl)-8-(hydroxymethyl)-5,10-dihydro-11H-dibenzo[b,e][1,4]diazepin-11-one The title compound was prepared by substituting Example 569E and 2-methoxy-4-(4,4,5,5-tetramethyl-[1,3,2]dioxaborolan-2-yl)-phenol for Example 59B and Example 56A, respectively, in Example 59C. MS (APCI) m/e 363 (M+H)+; 1H NMR (300 MHz, DMSO-d6) ☐ 9.76 (s, 1H), 9.25 (s, 1H), 7.83 (s, 1H), 7.71 (d, J=8.14 Hz, 1H), 7.22 (d, J=1.70 Hz, 1H), 7.17 (d, J=2.03 Hz, 1H), 7.14 (dd, J=8.14, 1.70 Hz, 1H), 7.07 (dd, J=8.14, 2.03 Hz, 1H), 6.88 (m, 2H), 6.94 (m, 2H), 5.07 (t, J=5.59 Hz, 1H), 4.35 (d, J=5.76 Hz, 2H), 3.86 (s, 3H).

EXAMPLE 570

3-(3-methoxy-4-nitrophenyl)-8-(morpholin-4-ylmethyl)-5,10-dihydro-11H-dibenzo[b,e][1,4]diazepin-11-one

EXAMPLE 570A methyl 2-{[4-(bromomethyl)-2-nitrophenyl]amino}-4-chlorobenzoate A mixture of Example 569B (0.336 g, 1.0 mmol) and LiBr (0.1 g) in 3 mL of DMF was treated with PBr3 (0.1 mL) at 0° C. The solution was stirred for additional two hours, and partitioned between water and ethyl acetate. The organic layer was washed with brine, dried (MgSO4), filtered, and concentrated under vacuum to give 0.38 g of the title compound (97%). MS (DCI) m/e 401 (M+H)⁺; ¹H NMR (300 MHz, DMSO-d₆) □ 10.94 (s, 1H), 8.29 (d, J=2.03 Hz, 1H), 7.98 (d, J=8.82 Hz, 1H,) 7.70-7.75 (m, 2H), 7.54 (d, J=2.03 Hz, 1H), 7.18 (dd, J=8.48, 2.03 Hz, 1H), 4.80 (s, 2H), 3.89 (s, 3H).

EXAMPLE 570B methyl 4-chloro-2-{[4-(morpholin-4-ylmethyl)-2-nitrophenyl]amino}benzoate A mixture of Example 570A (80 mg, 0.2 mmol) and morpholine (35 mg, 0.4 mmol) in 4 mL of toluene was heated under reflux for two hours. After the reaction mixture was cooled to room temperature, it was loaded onto silica gel for purification that yielded 76 mg of the desired product (94%). MS (DCI) m/e 406 (M+H)⁺; ¹H NMR (300 MHz, DMSO-d₆) □ 10.61 (s, 1H), 8.04 (d, J=1.87 Hz, 1H), 7.95 (d, J=8.73 Hz, 1H,) 7.65-7.66 (m, 1H), 7.61 (dd, J=8.73, 1.87 Hz, 1H), 7.46 (d, J=1.87 Hz, 1H), 7.10 (dd, J=8.58, 2.03 Hz, 1H), 3.88 (s, 3H), 3.57-3.59 (m, 4H), 3.39 (s, 2H), 2.28-2.90 (m, 4H).

EXAMPLE 570C methyl 2-{[2-amino-4-(morpholin-4-ylmethyl)phenyl]amino}-4-chlorobenzoate The title compound was prepared by substituting Example 570B for Example 6B in Example 6C. MS (DCI) m/e 376 (M+H)⁺; ¹H NMR (300 MHz, DMSO-d₆) □ 8.81 (s, 1H), 7.85 (d, J=8.73 Hz, 1H), 6.96 (d, J=7.80 Hz, 1H,) 6.80 (d, J=1.56 Hz, 1H), 6.69 (dd, J=8.73, 2.18 Hz, 1H), 6.55 (dd, J=7.95, 1.72 Hz, 1H), 6.41 (d, J=2.08 Hz, 1H), 4.95 (s, 2H), 3.66 (s, 3H), 3.58-3.60 (m, 4H), 3.35 (s, 2H), 2.35-2.37 (m, 4H).

EXAMPLE 570D

2-{[2-amino-4-(morpholin-4-ylmethyl)phenyl]amino}-4-chlorobenzoic acid

The title compound was prepared by substituting Example 570C for Example 12 in Example 13. MS (DCI) m/e 362 (M+H)⁺.

EXAMPLE 570E 3-chloro-8-(morpholin-4-ylmethyl)-5,10-dihydro-11H-dibenzo[b,e][1,4]diazepin-11-one The title compound was prepared by substituting Example 570D for Example 233F in Example 233G. MS (APCI) m/e 344 (M+H)⁺; 1H NMR (300 MHz, DMSO-d₆) □ 10.02 (s, 1H), 8.29 (s, 1H), 7.86 (d, J=8.73 Hz, 1H), 7.24 (d, J=1.87 Hz, 1H,) 7.04-7.12 (m, 4H), 3.72-3.74 (m, 4H), 3.37 (s, 2H), 2.47-2.49 (m, 2H).

EXAMPLE 570F 3-(3-methoxy-4-nitrophenyl)-8-(morpholin-4-ylmethyl)-5,10-dihydro-11H-dibenzo[b,e][1,4]diazepin-11-one The title compound was prepared by substituting Example 570E and Example 266G for Example 59B and Example 56A, respectively, in Example 59C. MS (APCI) m/e 474 (M+H)⁺; 1H NMR (500 MHz, DMSO-d₆) □ 9.84 (s, 1H), 8.00 (d, J=8.54 Hz, 1H), 7.97 (s, 1H), 7.89 (d, J=8.24 Hz, 1H), 7.51 (d, J=1.56 Hz, 1H), 7.32-7.34 (m, 2H), 7.29 (dd, J=8.11, 1.56 Hz, 1H), 6.87-6.97 (m 4H), 4.02 (s, 3H), 3.55 (br, s, 4H,) 3.40-3.44 (m, 2H), 2.31 (br, s, 4H).

EXAMPLE 571

8-{[(2R)-2-(hydroxymethyl)pyrrolidin-1-yl]methyl}-3-(3-methoxy-4-nitrophenyl)-5,10-dihydro-11H-dibenzo[b,e][1,4]diazepin-11-one The title compound was prepared by substituting (2R)-pyrrolidin-2-ylmethanol for morpholine in Example 570B, 570C, 570D, 570E, and 570F. MS (APCI) m/e 478 (M+H)⁺.

EXAMPLE 572

7-(2-hydroxyethoxy)-8-methoxy-3-(3-methoxy-4-nitrophenyl)-5,10-dihydro-11H-dibenzo[b,e][1,4]diazepin-11-one

EXAMPLE 572A

7-[2-(tert-butyl-dimethyl-silanyloxy)-ethoxy]-8-methoxy-3-(3-methoxy-4-nitro-phenyl)-5,10-dihydro-dibenzo[b,e][1,4]diazepin-11-one The desired product was prepared by substituting (2-bromoethoxy)-tert-butyldimethylsilane for 2-bromomethyl-tetrahydro-2H-pyran in Example 478.

EXAMPLE 572B 7-(2-hydroxyethoxy)-8-methoxy-3-(3-methoxy-4-nitrophenyl)-5,10-dihydro-11H-dibenzo[b,e][1,4]diazepin-11-one The desired product was prepared by substituting Example 572A for Example 500A in Example 500B. MS (ESI) m/e 450 (M−H)⁻; ¹H NMR (500 MHz, DMSO-d₆) □ 9.63 (s, 1H), 8.01 (d, J=8.0 Hz, 1H), 7.78 (d, J=8.0 Hz, 1H), 7.72 (s, 1H), 7.53 (s, 1H), 7.28-7.36 (m, 3H), 6.71 (s, 1H), 6.65 (s, 1H), 4.81 (t, J=5.3 Hz, 1H), 4.03 (s, 3H), 3.90 (t, J=4.7 Hz, 2H), 3.68-3.70 (m, 2H), 3.68 (s, 3H).

EXAMPLE 573

8-{3-[2-(hydroxymethyl)pyrrolidin-1-yl]-3-oxopropyl}-3-(3-methoxy-4-nitrophenyl)-5,10-dihydro-11H-dibenzo[b,e][1,4]diazepin-11-one The desired product was prepared by substituting Example 230 and pyrrolidin-2-ylmethanol for dimethylaminoacetic acid and Example 120, respectively, in Example 122. MS (ESI) m/e517 (M+H)⁺; ¹H NMR (300 MHz, DMSO-d₆) δ 9.83 (s, 1H), 8.01 (d, J=8.48 Hz, 1H), 7.93 (s, 1H), 7.79 (d, J=8.14 Hz, 1H), 7.52 (d, J=1.36 Hz, 1H), 7.34 (m, 2H), 7.29 (dd, J=8.14, 1.7 Hz, 1H), 6.92 (m, 1H), 6.84 (dd, J=4.07, 2.37 Hz, 2H), 4.03 (s, 3H), 3.78 (s, 1H), 3.48 (dd, J=10.51, 4.07 Hz, 1H), 3.21 (m, 2H), 2.86 (d, J=35.6 Hz, 2H), 2.7 (m, 2H), 1.79 (m, 3H).

EXAMPLE 574

(cis) 4-hydroxyN[3-(3-methoxy-4-nitrophenyl)-11-oxo-10,11-dihydro-5H-dibenzo[b,e][1,4]diazepin-7-yl]cyclohexanecarboxamide The title compound was prepared by substituting Example 179 and (cis) 4-hydroxycyclohexanecarboxylic acid for Example 120 and dimethylaminoacetic acid, respectively, in Example 122. MS (DCI) m/e 503 (M+H)$^+$; $^1$H NMR (500 MHz, DMSO-d$_6$) δ 9.78 (s, 1H), 9.66 (s, 1H), 8.00-8.02 (m, 2H), 7.79 (d, J=8.11 Hz, 1H), 7.62 (d, J=1.87 Hz, 1H), 7.52 (d, J=1.56 Hz, 1H), 7.42 (d, J=1.56 Hz, 1H), 7.35 (dd, J=8.42, 1.56 Hz, 1H), 7.31 (dd, J=8.26, 1.72 Hz, 1H), 6.91-6.93 (m, 1H), 6.87 (d, J=8.42 Hz, 1H), 4.04 (s, 3H), 3.79 (s, 1H), 2.29 (m, 1H), 1.80-1.86 (m 2H), 1.67-1.70 (m, 2H), 1.42-1.49 (m, 4H).

EXAMPLE 575

3-(4-chloro-3-methoxyphenyl)-8-{2-[(2-methylpyridin-3-yl)oxy]ethyl}-5,10-dihydro-11H-dibenzo[b,e][1,4]diazepin-11-one

EXAMPLE 575A 3-(4-chloro-3-methoxyphenyl)-8-(2-hydroxyethyl)-5,10-dihydro-11H-dibenzo[b,e][1,4]diazepin-11-one The title compound was prepared by substituting Example 54B for Example 6D in Example 204A. MS (DCI) m/e 395 (M+H)$^+$; $^1$H NMR (500 MHz, DMSO-d$_6$) δ 9.83 (s, 1H), 7.94 (s, 1H), 7.77 (d, J=8.0 Hz, 1H), 7.53 (d, J=8.3 Hz, 1H), 7.29 (d, J=1.7 Hz, 1H), 7.34 (d, J=1.8 Hz, 1H), 7.30 (d, J=1.8 Hz, 1H), 7.19-7.24 (m, 2H), 6.96 (d, J=8.0 Hz, 1H), 6.86 (m, 1H), 4.58 (t, J=5.15 Hz, 1H), 3.52-3.56 (m, 2H), 2.60 (t, J=7.02 Hz, 2H).

EXAMPLE 575B 3-(4-chloro-3-methoxyphenyl)-8-{2-[(2-methylpyridin-3-yl)oxy]ethyl}-5,10-dihydro-11H-dibenzo[b,e][1,4]diazepin-11-one The title compound was prepared by substituting Example 575A and 2-methyl-pyridin-3-ol for Example 204A and 4-morpholinophenol, respectively, in Example 297A. MS (APCI) m/e 486 (M+H)$^+$, $^1$H NMR (500 MHz, DMSO-d$_6$): □ 9.92 (s, 1H), 9.19 (d, J=4.99 Hz, 1H), 7.91 (s, 1H), 7.75-7.79 (m, 2H), 7.52-7.56 (m, 2H), 7.33 (d, J=1.87 Hz, 1H), 7.29 (d, J=1.56 Hz, 1H), 7.19-7.22 (m, 2H), 6.93-9.97 (m, 3H), 4.27 (t, J=6.4 Hz, 2H), 3.96 (s, 3H), 2.96 (t, J=6.4 Hz, 2H), 2.43 (s, 3H).

EXAMPLE 576

4-[8-(2-hydroxyethyl)-11-oxo-10,11-dihydro-5H-dibenzo[b,e][1,4]diazepin-3-yl]-2-methoxybenzamide

EXAMPLE 576A 8-(2-Hydroxy-ethyl)-3-(4,4,5,5-tetramethyl-[1,3,2]dioxaborolan-2-yl)-5,10-dihydro-dibenzo[b,e][1,4]diazepin-11-one The title compound was prepared by substituting Example 204A for Example 6D in Example 54A. MS (DCI) m/e 381 (M+H)$^+$.

EXAMPLE 576B

4-[8-(2-hydroxyethyl)-11-oxo-10,11-dihydro-5H-dibenzo[b,e][1,4]diazepin-3-yl]-2-methoxybenzamide The title compound was prepared by substituting 4-chloro-2-methoxybenzamide and Example 576A for Example 59B and Example 56A, respectively, in Example 59C. MS (APCI) m/e 404 (M+H)$^+$, $^1$H NMR (500 MHz, DMSO-d$_6$): □ 9.80 (s, 1H), 7.89-7.91 (m, 2H), 7.77 (d, J=8.24 Hz, 1H), 7.67 (s, 1H), 7.57 (s, 1H), 7.25-7.33 (m, 4H), 6.92 (d, J=7.63 Hz, 1H), 6.80-6.82 (m, 2H), 4.60 (t, J=5.19 Hz, 1H), 3.99 (s, 3H), 3.50-3.54 (m, 2H), 2.59 (t, J=7.02 Hz, 2H).

EXAMPLE 577

8-(2-hydroxyethyl)-3-[4-(1H-imidazol-1-yl)-3-methoxyphenyl]-5,10-dihydro-11H-dibenzo[b,e][1,4]diazepin-11-one

EXAMPLE 577A 1-(4-chloro-2-methoxyphenyl)-1H-imidazole

A mixture of 4-chloro-1-iodo-2-methoxy-benzene (0.268 g, 1 mmol), imidazole (0.082 g, 1.2 mmol), 1,0-phenanthroline (0.018 g, 0.1 mmol), CuI (0.01 g, 0.05 mmol), and Cs$_2$CO$_3$ (0.684 g, 2.1 mmol) in dioxane (1.5 mL) was heated at 110° C. for 24 hours. After the reaction mixture cooled to room temperature, it was partitioned between H$_2$O and EtOAc. The aqueous layer was extracted with additional EtOAc. The combined organic layers were washed with water, brine, dried over MgSO$_4$ and concentrated under reduced pressure. The residue was purified by silica gel column chromatography, eluting with EtOAc to give 0.095 g of the title compound (46%). MS (APCI) m/e 209 (M+H)$^+$, $^1$H NMR (500 MHz, DMSO-d$_6$): □ 7.44 (s, 1H), 7.43 (s, 1H), 7.35 (d, J=2.14 Hz, 2H), 7.15 (d, J=2.14 Hz, 1H), 7.13 (d, J=2.14 Hz, 1H), 3.86 (s, 3H).

EXAMPLE 577B 8-(2-hydroxyethyl)-3-[4-(1H-imidazol-1-yl)-3-methoxyphenyl]-5,10-dihydro-11H-dibenzo[b,e][1,4]diazepin-11-one The title compound was prepared by substituting Example 577A and Example 576A for Example 59B and Example 56A, respectively, in Example 59C. MS (APCI) m/e 427 (M+H)$^+$, $^1$H NMR (500 MHz, DMSO-d$_6$): □ 9.80 (s, 1H), 7.96 (s, 1H), 7.89 (s, 1H), 7.77 (d, J=8.24 Hz, 1H), 7.53 (d, J=8.24 Hz, 1H), 7.49 (s, 1H), 7.44 (d, J=1.53 Hz, 1H), 7.33-7.34 (m, 2H), 7.27 (dd, J=8.42, 1.53 Hz, 1H), 7.08 (s, 1H), 6.93 (d, J=7.93 Hz, 1H), 6.81-6.83 (m, 2H), 4.61 (t, J=5.34 Hz, 1H), 3.94 (s, 3H), 3.51-3.55 (m, 2H), 2.59 (t, J=7.02 Hz, 2H).

EXAMPLE 578

2-methoxy-4-{8-[2-(4-morpholin-4-ylphenoxy)ethyl]-11-oxo-10,11-dihydro-5H-dibenzo[b,e][1,4]diazepin-3-yl}benzamide

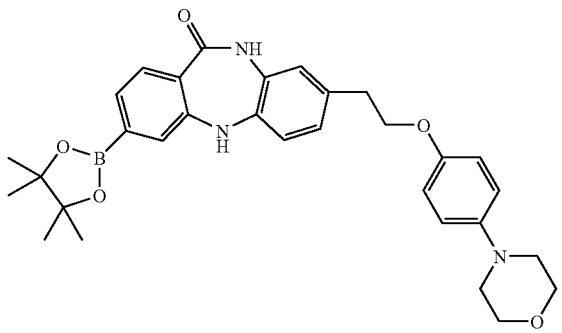

EXAMPLE 578A

8-[2-(4-Morpholin-4-yl-phenoxy)-ethyl]-3-(4,4,5,5-tetramethyl-[1,3,2]dioxaborolan-2-yl)-5,10-dihydro-dibenzo[b,e][1,4]diazepin-11-one The title compound was prepared by substituting Example 297A for Example 6D in Example 54A. MS (ESI) m/e 542 (M+H)$^+$, $^1$H NMR (300 MHz, DMSO-d$_6$): □ 9.84 (s, 1H), 7.71 (s, 1H), 7.65 (d, J=7.80 Hz, 1H), 7.38 (s, 1H), 7.13 (dd, J=7.63, 0.85 Hz, 1H), 6.80-6.95 (m, 7H), 4.03 (t, J=6.78 Hz, 2H), 3.69-3.72 (m, 4H), 2.95-2.98 (m, 4H), 2.85 (t, J=6.61 Hz, 2H), 1.29 (s, 12H).

EXAMPLE 578B 2-methoxy-4-{8-[2-(4-morpholin-4-ylphenoxy)ethyl]-11-oxo-10,11-dihydro-5H-dibenzo[b,e][1,4]diazepin-3-yl}benzamide The title compound was prepared by substituting 4-chloro-2-methoxybenzamide and
Example 578A for Example 59B and Example 56A, respectively, in Example 59C. MS (APCI) m/e 565 (M+H)$^+$, $^1$H NMR (500 MHz, DMSO-d$_6$): □ 9.80 (s, 1H), 7.90-7.91 (m, 2H), 7.77 (d, J=8.11 Hz, 1H), 7.65 (s, 1H), 7.53 (s, 1H), 7.33 (dd, J=7.96, 1.4 Hz, 2H), 7.26-7.29 (m, 2H), 6.91-6.69 (m, 3H), 6.81-6.87 (m, 4H), 4.04 (t, J=7.18 Hz, 2H), 3.99 (s, 3H), 3.70-3.72 (m, 4H), 2.96-2.97 (m, 4H), 2.86 (t, J=6.55 Hz, 2H).

EXAMPLE 579

3-(4-Imidazol-1-yl-3-methoxy-phenyl)-8-[2-(4-morpholin-4-yl-phenoxy)-ethyl]-5,10-dihydro-dibenzo[b,e][1,4]diazepin-11-one The title compound was prepared by substituting Example 577A and Example 578A for Example 59B and Example 56A, respectively, in Example 59C. MS (APCI) m/e 588 (M+H)$^+$, $^1$H NMR (500 MHz, DMSO-d$_6$): □ 9.80 (s, 1H), 7.95 (s, 1H), 7.91 (s, 1H), 7.78 (d, J=8.11 Hz, 1H), 7.52 (d, J=8.11 Hz, 1H), 7.48 (s, 1H), 7.44 (d, J=1.25 Hz, 1H), 7.31-7.34 (m, 2H), 7.27 (dd, J=8.11, 1.56 Hz, 1H), 7.07 (s, 1H), 6.90-6.67 (m, 3H), 6.81-6.87 (m, 4H), 4.07 (t, J=6.71 Hz, 2H), 3.94 (s, 3H), 3.70-3.72 (m, 4H), 2.96-2.97 (m, 4H), 2.86 (t, J=6.71 Hz, 2H).

EXAMPLE 580

2-methoxy-4-(11-oxo-8-{2-[4-(1,2,3-thiadiazol-5-yl)phenoxy]ethyl}-10,11-dihydro-5H-dibenzo[b,e][1,4]diazepin-3-yl)benzamide The title compound was prepared by substituting Example 576 and 4-[1,2,3]thiadiazol-4-yl-phenol for Example 204A and pyridin-2(1H)-one, respectively, in Example 221A. MS (APCI) m/e 564 (M+H)$^+$, $^1$H NMR (500 MHz, DMSO-d$_6$): □ 9.82 (s, 1H), 9.45 (s, 1H), 8.04 (d, J=8.59 Hz, 2H), 7.88-7.92 (m, 2H), 7.77 (d, J=8.29 Hz, 1H), 7.65 (s, 1H), 7.53 (s, 1H), 7.24-7.33 (m, 4H), 7.09 (d, J=8.59 Hz, 2H), 6.94-6.68 (m, 3H), 4.20 (t, J=6.75 Hz, 2H), 3.98 (s, 3H), 2.94 (t, J=6.29 Hz, 2H).

EXAMPLE 581

8-(2-hydroxyethyl)-3-[3-methoxy-4-(1,3,4-oxadiazol-2-yl)phenyl]-5,10-dihydro-11H-dibenzo[b,e][1,4]diazepin-11-one The title compound was prepared by substituting Example 204A and Example 689D for Example 59B and Example 56A, respectively, in Example 59C. MS (APCI) m/e 429 (M+H)$^+$, $^1$H NMR (500 MHz, DMSO-d$_6$): □ 9.79 (s, 1H), 9.34 (s, 1H), 7.98 (d, J=8.11 Hz, 1H), 7.89 (s, 1H), 7.80 (d, J=8.11 Hz, 1H), 7.46 (d, J=1.56 Hz, 1H), 7.36-7.40 (m, 2H), 7.31 (dd, J=8.27, 1.72 Hz, 1H), 6.93 (d, J=8.11 Hz, 1H), 6.81-6.83 (m, 2H), 4.57 (t, J=5.3 Hz, 2H), 4.01 (s, 3H), 3.51-3.55 (m, 2H), 2.59 (t, J=7.02 Hz, 2H).

EXAMPLE 582

2-methoxy-4-(8-{2-[(2-methylpyridin-3-yl)oxy]ethyl}-11-oxo-10,11-dihydro-5H-dibenzo[b,e][1,4]diazepin-3-yl)benzamide The title compound was prepared by substituting Example 576 and 2-methyl-pyridin-3-ol for Example 204A and pyridin-2(1H)-one, respectively, in Example 221A. MS (APCI) m/e 495 (M+H)$^+$, $^1$H NMR (500 MHz, DMSO-d$_6$): □ 9.83 (s, 1H), 8.22 (d, J=4.68 Hz, 1H), 7.95 (s, 1H), 7.91 (d, J=8.11 Hz, 1H), 7.85 (d, J=8.45 Hz, 1H), 7.78 (d, J=8.11 Hz, 1H), 7.66 (s, 1H), 7.60 (dd, J=8.27, 5.46 Hz, 1H), 7.54 (s, 1H), 7.35 (d, J=1.56 Hz, 1H), 7.32 (s, 1H), 7.26-7.28 (m, 2H), 6.93-6.98 (m, 3H), 4.29 (t, J=6.4 Hz, 2H), 4.00 (s, 3H), 2.97 (t, J=6.4 Hz, 2H), 2.46 (s, 3H).

EXAMPLE 583

3-[4-(1H-imidazol-1-ylmethyl)-3-methoxyphenyl]-8-[2-(4-morpholin-4-ylphenoxy)ethyl]-5,10-dihydro-11H-dibenzo[b,e][1,4]diazepin-11-one

EXAMPLE 583A 1-(bromomethyl)-4-chloro-2-methoxybenzene

The title compound was prepared by substituting (4-chloro-2-methoxy-phenyl)-methanol for Example 569B in Example 570A. MS (DCI) m/e 236 (M+H)$^+$.

EXAMPLE 583B

1-(4-Chloro-2-methoxy-benzyl)-1H-imidazole

Imidazole (0.163 g, 2.4 mmol) in 5 mL of DMF was treated with 60% NaH (0.192 g, 4.8 mmol) at 0° C. After bubbling stopped, Example 583A in 2 mL of DMF was added to the solution. The solution continued to stir at 0° C. for 1 hour and then was partitioned between water and EtOAc. The aqueous layer was extracted with additional EtOAc. The combined organic layers were washed with water, brine, dried over $MgSO_4$, and concentrated under reduced pressure. The residue was purified by silica gel column chromatography eluting with 1% MeOH in EtOAc to give 0.35 g of the title compound (80%). MS (APCI) m/e 223 (M+H)+

Example 583C 3-[4-(1H-imidazol-1-ylmethyl)-3-methoxyphenyl]-8-[2-(4-morpholin-4-ylphenoxy)ethyl]-5,10-dihydro-11H-dibenzo[b,e][1,4]diazepin-11-one The title compound was prepared by substituting Example 583B and Example 578A for Example 59B and Example 56A, respectively, in Example 59C. MS (APCI) m/e 602 (M+H)+, $^1$H NMR (500 MHz, DMSO-$d_6$): ☐ 9.77 (s, 1H), 7.89 (s, 1H), 7.75 (d, J=8.11 Hz, 1H), 7.70 (s, 1H), 7.29 (d, J=1.25 Hz, 1H), 7.24 (s, 1H), 7.12-7.21 (m, 4H), 6.81-6.95 (m, 8H), 5.17 (s, 2H), 4.03 (t, J=6.71 Hz, 2H), 3.94 (s, 3H), 3.70-3.72 (m, 4H), 2.95-2.97 (m, 4H), 2.86 (t, J=6.71 Hz, 2H).

EXAMPLE 584

3-[3-methoxy-4-(1,3,4-oxadiazol-2-yl)phenyl]-8-{2-[(2-methylpyridin-3-yl)oxy]ethyl}-5,10-dihydro-11H-dibenzo[b,e][1,4]diazepin-11-one The title compound was prepared by substituting Example 581 and 2-methyl-pyridin-3-ol for Example 204A and pyridin-2(1H)-one, respectively, in Example 221A. MS (APCI) m/e 520 (M+H)+, $^1$H NMR (500 MHz, DMSO-$d_6$): ☐ 9.86 (s, 1H), 9.33 (s, 1H), 8.19 (d, J=4.68 Hz, 1H), 7.98 (d, J=8.11 Hz, 1H), 7.96 (s, 1H), 7.81 (s, 1H), 7.80 (s, 1H), 7.56 (dd, J=8.42, 5.3 Hz, 1H), 7.45 (s, 1H), 7.38-7.41 (m, 2H), 7.32 (dd, J=8.11, 1.56 Hz, 1H), 6.93-9.98 (m, 3H), 4.28 (t, J=6.4 Hz, 2H), 4.01 (s, 3H), 2.97 (t, J=6.4 Hz, 2H), 2.44 (s, 3H).

EXAMPLE 585 methyl {3-[4-(1H-imidazol-1-ylmethyl)-3-methoxyphenyl]-11-oxo-10,11-dihydro-5H-dibenzo[b,e][1,4]diazepin-8-yl}acetate The title compound was prepared by substituting Example 583B and Example 54A for Example 59B and Example 56A, respectively, in Example 59C. MS (APCI) m/e 469 (M+H)+, $^1$H NMR (500 MHz, DMSO-$d_6$): ☐ 9.79 (s, 1H), 7.92 (s, 1H), 7.74 (d, J=8.11 Hz, 1H), 7.69 (s, 1H), 7.27 (d, J=1.56 Hz, 1H), 7.22 (s, 1H), 7.12-7.21 (m, 4H), 6.94 (d, J=8.11 Hz, 1H), 6.83-6.89 (m, 3H), 5.16 (s, 2H), 3.93 (s, 3H), 3.58 (s, 3H), 3.52 (s, 2H).

EXAMPLE 586

8-(2-hydroxyethyl)-3-[4-(1H-imidazol-1-ylmethyl)-3-methoxyphenyl]-5,10-dihydro-11H-dibenzo[b,e][1,4]diazepin-11-one The title compound was prepared by substituting Example 585 for Example 6D in Example 204A. MS (APCI) m/e 441 (M+H)+, $^1$H NMR (500 MHz, DMSO-$d_6$): ☐ 9.74 (s, 1H), 7.84 (s, 1H), 7.74 (d, J=8.29 Hz, 1H), 7.70 (s, 1H), 7.27 (d, J=1.84 Hz, 1H), 7.24 (d, J=1.54 Hz, 1H), 7.12-7.21 (m, 4H), 6.89-6.92 (m, 2H), 6.79-6.82 (m, 2H), 5.17 (s, 2H), 4.57 (t, J=5.22 Hz, 1H), 3.94 (s, 3H), 3.50-3.55 (m, 2H), 2.58 (t, J=7.06 Hz, 2H).

EXAMPLE 587

[3-(4-Cyanomethyl-3-methoxy-phenyl)-11-oxo-10,11-dihydro-5H-dibenzo[b,e][1,4]diazepin-8-yl]-acetic acid methyl ester

EXAMPLE 587A

(4-chloro-2-methoxyphenyl)acetonitrile

A mixture of Example 585A (0.92 g, 3.9 mmol), KCN (0.508 g, 7.8 mmol), and 18-Crown-6 in 10 mL of $CH_3CN$ was heated under reflux overnight. The reaction mixture was partitioned between water and EtOAc. The organic layer was washed with water, then brine, and dried over $MgSO_4$, and concentrated under reduced pressure. The residue was purified by silica gel column chromatography eluting with 9:1 Hexanes/EtOAc to give 0.69 g of the title compound (97%). MS (APCI) m/e 182 (M+H)+, $^1$H NMR (500 MHz, DMSO-$d_6$): ☐ 7.35 (d, J=8.14 Hz, 1H), 7.15 (d, J=2.03 Hz, 1H), 7.05 (dd, J=8.14, 2.03 Hz, 1H), 3.87 (s, 3H), 3.83 (s, 2H).

EXAMPLE 587B methyl {3-[4-(cyanomethyl)-3-methoxyphenyl]-11-oxo-10,11-dihydro-5H-dibenzo[b,e][1,4]diazepin-8-yl}acetate The title compound was prepared by substituting Example 587A and Example 54A for Example 59B and Example 56A, respectively, in Example 59C. MS (APCI) m/e 428 (M+H)+, $^1$H NMR (500 MHz, DMSO-$d_6$): ☐ 9.82 (s, 1H), 7.94 (s, 1H), 7.77 (d, J=8.29 Hz, 1H), 7.44 (d, J=7.98 Hz, 1H), 7.30 (d, J=1.53 Hz, 1H), 7.21-7.27 (m, 3H), 6.96 (d, J=7.98 Hz, 1H), 6.85-6.87 (m, 2H), 3.95 (s, 3H), 3.89 (s, 2H), 3.60 (s, 3H), 3.54 (s, 2H).

EXAMPLE 588 methyl {3-[3-methoxy-4-(1H-pyrazol-1-ylmethyl)phenyl]-11-oxo-10,11-dihydro-5H-dibenzo[b,e][1,4]diazepin-8-yl}acetate

EXAMPLE 588A

1-(4-chloro-2-methoxybenzyl)-1H-pyrazole

The title compound was prepared by substituting pyrazole for imidazole in Example 583B. MS (APCI) m/e 223 (M+H)+, $^1$H NMR (500 MHz, DMSO-$d_6$): ☐ 7.73 (d, J=2.37 Hz, 1H), 7.45 (d, J=1.7 Hz, 1H), 7.10 (d, J=1.7 Hz, 1H), 6.96 (m, 1H), 6.82 (d, J=8.14 Hz, 1H), 6.26 (m, 1H), 5.25 (s, 2H), 3.85 (s, 3H).

EXAMPLE 588B methyl {3-[3-methoxy-4-(1H-pyrazol-1-ylmethyl)phenyl]-11-oxo-10,11-dihydro-5H-dibenzo[b,e][1,4]diazepin-8-yl}acetate The title compound was prepared by substituting Example 588A and Example 54A for Example 59B and Example 56A, respectively, in Example 59C. MS (APCI) m/e 469 (M+H)+, $^1$H NMR (500 MHz, DMSO-$d_6$): ☐ 9.81 (s, 1H), 7.93 (s, 1H), 7.74-7.76 (m, 2H), 7.47 (s, 1H), 7.28 (d, J=1.53 Hz, 1H), 7.14-7.24 (m, 3H), 6.93-6.97 (m, 2H), 6.84-6.87 (m, 2H), 6.27 (t, J=1.99 Hz, 1H), 5.33 (s, 2H), 3.93 (s, 3H), 3.60 (s, 3H), 3.53 (s, 2H).

EXAMPLE 589

3-[3-methoxy-4-(1H-pyrazol-1-ylmethyl)phenyl]-8-[2-(4-morpholin-4-ylphenoxy)ethyl]-5,10-dihydro-11H-dibenzo[b,e][1,4]diazepin-11-one The title compound was prepared by substituting Example 588A and Example 578A for Example 59B and Example 56A, respectively, in Example 59C. MS (APCI) m/e 602 (M+H)$^+$, $^1$H NMR (500 MHz, DMSO-d$_6$): ☐ 9.77 (s, 1H), 7.87 (s, 1H), 7.73-7.75 (m, 2H), 7.45 (d, J=1.53 Hz, 1H), 7.26 (d, J=1.23 Hz, 1H), 7.22 (s, 1H), 7.18 (dd, J=8.29, 1.53 Hz, 1H), 7.14 (d, J=7.94 Hz, 1H), 6.80-6.94 (m, 8H), 6.26 (m, 1H), 5.31 (s, 2H), 4.02 (t, J=6.6 Hz, 2H), 3.91 (s, 3H), 3.69-3.71 (m, 4H), 2.94-2.96 (m, 4H), 2.85 (d, J=6.6 Hz, 2H).

EXAMPLE 590

(2-Methoxy-4-{8-[2-(4-morpholin-4-yl-phenoxy)-ethyl]-11-oxo-10,11-dihydro-5H-dibenzo[b,e][1,4]diazepin-3-yl}-phenyl)-acetonitrile The title compound was prepared by substituting Example 587A and Example 578A for Example 59B and Example 56A, respectively, in Example 59C. MS (APCI) m/e 561 (M+H)$^+$, $^1$H NMR (500 MHz, DMSO-d$_6$): ☐ 9.78 (s, 1H), 7.89 (s, 1H), 7.75 (d, J=7.98 Hz, 1H), 7.43 (d, J=7.98 Hz, 1H), 7.29 (s, 1H), 7.20-7.25 (m, 3H), 6.80-6.95 (m, 7H), 4.03 (t, J=6.6 Hz, 2H), 3.93 (s, 3H), 3.88 (s, 2H), 3.69-3.71 (m, 4H), 2.94-2.96 (m, 4H), 2.85 (d, J=6.6 Hz, 2H).

EXAMPLE 591

3-[4-(2-aminoethyl)-3-methoxyphenyl]-8-[2-(4-morpholin-4-ylphenoxy)ethyl]-5,10-dihydro-11H-dibenzo[b,e][1,4]diazepin-11-one The title compound was prepared by substituting Example 590 for Example 6D in Example 204A. MS (APCI) m/e 563 (M-H), $^1$H NMR (500 MHz, DMSO-d$_6$): ☐ 9.76 (s, 1H), 7.87 (s, 1H), 7.75 (d, J=8.11 Hz, 1H), 7.47 (d, J=7.8 Hz, 1H), 7.30 (d, J=1.56 Hz, 1H), 7.20-7.22 (m, 2H), 7.16 (s, 1H), 6.85-6.96 (m, 7H), 4.53 (s, 2H), 4.05 (t, J=6.71 Hz, 2H), 3.87 (s, 3H), 3.73-3.75 (m, 4H), 3.03-3.04 (m, 4H), 2.87 (d, J=6.55 Hz, 2H).

EXAMPLE 592

3-[4-(2-hydroxyethyl)-3-methoxyphenyl]-8-[2-(4-morpholin-4-ylphenoxy)ethyl]-5,10-dihydro-11H-dibenzo[b,e][1,4]diazepin-11-one

EXAMPLE 592A methyl (4-chloro-2-methoxyphenyl)acetate

Example 587A (0.5 g) in 30 mL of water and 25 mL of 37% HCl was heated under reflux for 3 days. After the reaction mixture cooled to room temperature, it was extracted with EtOAc three times. The combined organic layers were washed with water, brine, dried, and concentrated. The residue was diluted with CH$_2$Cl$_2$ (10 mL) and MeOH (11 mL), and treated with excess of TMSCHN$_2$. The solvents were removed and the residue was purified by silica gel column chromatography eluting with 9:1 Hexanes/EtOAc to give 0.5 g of the title compound (85%). MS (APCI) m/e 215 (M+H)$^+$, $^1$H NMR (500 MHz, DMSO-d$_6$): ☐ 7.22 (d, J=8.14 Hz, 1H), 7.03 (d, J=2.14 Hz, 1H), 6.96 (dd, J=8.14, 2.03 Hz, 1H), 3.78 (s, 3H), 3.59 (s, 5H).

EXAMPLE 592B methyl (2-methoxy-4-{8-[2-(4-morpholin-4-ylphenoxy)ethyl]-11-oxo-10,11-dihydro-5H-dibenzo[b,e][1,4]diazepin-3-yl}phenyl The title compound was prepared by substituting Example 592A and Example 578A for Example 59B and Example 56A, respectively, in Example 59C. MS (APCI) m/e 594 (M+H)$^+$, $^1$H NMR (500 MHz, DMSO-d$_6$): ☐ 9.77 (s, 1H), 7.88 (s, 1H), 7.25 (d, J=8.29 Hz, 1H), 7.29-7.31 (m, 2H), 7.16-7.22 (m, 3H), 6.81-6.96 (m, 7H), 4.04 (t, J=6.6 Hz, 2H), 3.86 (s, 3H), 3.70-3.72 (m, 4H), 3.65 (s, 2H), 3.61 (s, 3H), 2.95-2.98 (m, 4H), 2.86 (t, J=6.6 Hz, 2H).

EXAMPLE 592C

3-[4-(2-hydroxyethyl)-3-methoxyphenyl]-8-[2-(4-morpholin-4-ylphenoxy)ethyl]-5,10-dihydro-11H-dibenzo[b,e][1,4]diazepin-11-one The title compound was prepared by substituting Example 592B for Example 6D in Example 204A. MS (APCI) m/e 566 (M+H)$^+$, $^1$H NMR (500 MHz, DMSO-d$_6$): ☐ 9.50 (s, 1H), 7.60 (s, 1H), 7.48 (d, J=8.29 Hz, 1H), 6.97-7.01 (m, 2H), 6.85-6.94 (m, 3H), 6.54-6.70 (m, 7H), 4.34 (d, J=4.76 Hz, 1H), 3.77 (t, J=6.14 Hz, 2H), 3.61 (s, 3H), 3.41-3.43 (m, 4H), 3.31-3.34 (m, 2H), 2.68-2.70 (m, 4H), 2.58-2.61 (m, 2H), 2.49 (t, J=6.6 Hz, 2H).

EXAMPLE 593

{4-[8-(2-hydroxyethyl)-11-oxo-10,11-dihydro-5H-dibenzo[b,e][1,4]diazepin-3-yl]-2-methoxyphenyl}acetonitrile The title compound was prepared by substituting Example 587A and Example 576A for Example 59B and Example 56A, respectively, in Example 59C. MS (APCI) m/e 400 (M+H)$^+$, $^1$H NMR (500 MHz, DMSO-d$_6$): ☐ 9.76 (s, 1H), 7.85 (s, 1H), 7.76 (d, J=8.11 Hz, 1H), 7.44 (d, J=7.8 Hz, 1H), 7.30 (s, 1H), 7.21-7.26 (m, 2H), 6.92 (d, J=8.11, Hz, 1H), 6.80-6.82 (m, 2H), 4.57 (t, J=5.3 Hz, 1H), 3.94 (s, 3H), 3.89 (s, 2H), 3.51-3.55 (m, 2H), 2.59 (d, J=7.02 Hz, 2H).

EXAMPLE 594

3-(2-{3-[4-(cyanomethyl)-3-methoxyphenyl]-11-oxo-10,11-dihydro-5H-dibenzo[b,e][1,4]diazepin-8-yl}ethoxy)pyridine-2-carbonitrile The title compound was prepared by substituting Example 593 and 2-cyano-pyridin-3-ol for Example 204A and 4-morpholinophenol, respectively, in Example 297A. MS (APCI) m/e 502 (M+H)$^+$, $^1$H NMR (500 MHz, DMSO-d$_6$): ☐ 9.76 (s, 1H), 8.27 (d, J=4.6 Hz, 1H), 7.90 (s, 1H), 7.74-7.78 (m, 2H), 7.66 (m, 1H), 7.43 (d, J=7.67 Hz, 1H), 7.29 (s, 1H), 7.21-7.25 (m, 3H), 6.92-6.95 (m, 3H), 4.33 (t, J=6.44 Hz, 2H), 3.93 (s, 3H), 3.88 (s, 2H), 2.96 (d, J=6.6 Hz, 2H).

EXAMPLE 595

[2-methoxy-4-(8-{2-[(2-methylpyridin-3-yl)oxy]ethyl}-11-oxo-10,11-dihydro-5H-dibenzo[b,e][1,4]diazepin-3-yl)phenyl]acetonitrile The title compound was prepared by substituting Example 593 and 2-methyl-pyridin-3-ol for Example 204A and 4-morpholinophenol, respectively, in Example 297A. MS (APCI) m/e 491 (M+H)$^+$, $^1$H NMR (500 MHz, DMSO-d$_6$): □ 9.82 (s, 1H), 8.20 (d, J=4.91 Hz, 1H), 7.92 (s, 1H), 7.80 (d, J=8.5 Hz, 1H), 7.76 (d, J=8.29 Hz, 1H), 7.56 (m, 1H), 7.44 (d, J=7.67 Hz, 1H), 7.30 (d, J=1.53 Hz, 1H), 7.26 (s, 1H), 7.22-7.25 (m, 2H), 6.92-6.98 (m, 3H), 4.28 (t, J=6.29 Hz, 2H), 3.94 (s, 3H), 3.89 (s, 2H), 2.96 (d, J=6.29 Hz, 2H), 2.44 (s, 3H).

EXAMPLE 596

3-[3-(benzyloxy)-5-methoxyphenyl]-8-[2-(4-morpholin-4-ylphenoxy)ethyl]-5,10-dihydro-11H-dibenzo[b,e][1,4]diazepin-11-one

EXAMPLE 596A 3-chloro-5-methoxyphenol

1-Chloro-3,5-dimethoxy-benzene (1.72 g, 10 mmol) in 10 mL of CH$_2$Cl$_2$ was cooled to −78° C., followed by 1.0 M BBr$_3$ in toluene (10 mL, 10 mmol) added dropwise. The solution was stirred at −78° C. for 1 hour, and then allowed to warmed to room temperature over 2 hours. The reaction was quenched with water, and the aqueous layer was extracted with additional CH$_2$Cl$_2$. The combined organic layers were washed with brine, dried, and concentrated under pressure. The residue was purified by silica gel column chromatography eluting with 1:1 EtOAc/Hexanes to give 0.51 g of the title compound. MS (APCI) m/e 159 (M+H)$^+$, $^1$H NMR (500 MHz, DMSO-d$_6$): □ 9.88 (s, 1H), 6.43 (m, 1H), 6.39 (m, 1H), 6.28 (m, 1H), 3.70 (s, 3H).

EXAMPLE 596B 1-(benzyloxy)-3-chloro-5-methoxybenzene

The title compound was prepared by substituting Example 596A and benzyl bromide for Example imidazole and Example 583A, respectively, in Example 583B. MS (APCI) m/e 249 (M+H)$^+$, $^1$H NMR (500 MHz, DMSO-d$_6$): □ 7.33-7.45 (m, 5H), 6.69 (m, 1H), 6.61 (m, 1H), 6.56 (m, 1H), 5.11 (s, 2H), 3.74 (s, 3H).

EXAMPLE 596C

3-[3-(benzyloxy)-5-methoxyphenyl]-8-[2-(4-morpholin-4-ylphenoxy)ethyl]-5,10-dihydro-11H-dibenzo[b,e][1,4]diazepin-11-one The title compound was prepared by substituting Example 596B and Example 578A for Example 59B and Example 56A, respectively, in Example 59C. MS (APCI) m/e 628 (M+H)$^+$, $^1$H NMR (500 MHz, DMSO-d$_6$): □ 9.78 (s, 1H), 7.84 (s, 1H), 7.74 (d, J=8.29 Hz, 1H), 7.47-7.49 (m, 2H), 7.39-7.43 (m, 2H), 7.35 (d, J=7.06 Hz, 1H), 7.29 (d, J=1.23 Hz, 1H), 7.18 (dd, J=8.29, 1.53 Hz, 1H), 6.81-6.95 (m, 8H), 6.77 (s, 1H), 6.65 (m, 1H), 5.17 (s, 2H), 4.04 (t, J=6.76 Hz, 2H), 3.81 (s, 3H), 3.70-3.72 (m, 4H), 2.95-2.97 (m, 4H), 2.86 (t, J=6.6 Hz, 2H).

EXAMPLE 597

3-(3-hydroxy-5-methoxyphenyl)-8-[2-(4-morpholin-4-ylphenoxy)ethyl]-5,10-dihydro-11H-dibenzo[b,e][1,4]diazepin-11-one The title compound was prepared by substituting Example 596A and Example 578A for Example 59B and Example 56A, respectively, in Example 59C. MS (APCI) m/e 538 (M+H)$^+$, $^1$H NMR (500 MHz, DMSO-d$_6$): □ 9.79 (s, 1H), 9.64 (s, 1H), 7.87 (s, 1H), 7.72 (d, J=8.24 Hz, 1H), 7.22 (d, J=1.53 Hz, 1H), 7.10 (dd, J=8.24, 1.93 Hz, 1H), 6.89-6.95 (m, 3H), 6.81-6.87 (m, 4H), 6.60 (d, J=2.14 Hz, 2H), 6.38 (t, J=2.12, 1H), 4.03 (t, J=6.71 Hz, 2H), 3.76 (s, 3H), 3.70-3.72 (m, 4H), 2.95-2.97 (m, 4H), 2.86 (t, J=6.56 Hz, 2H).

EXAMPLE 598

[2-methoxy-4-(11-oxo-10,11-dihydro-5H-dibenzo[b,e][1,4]diazepin-3-yl)phenyl]

EXAMPLE 598A 3-(4,4,5,5-tetramethyl-1,3,2-dioxaborolan-2-yl)-5,10-dihydro-11H-dibenzo[b,e][1,4]diazepin-11-one The title compound was prepared by substituting Example 9 for Example 6D in Example 54A. MS (APCI) m/e 337 (M+H)$^+$.

EXAMPLE 598B

[2-methoxy-4-(11-oxo-10,11-dihydro-5H-dibenzo[b,e][1,4]diazepin-3-yl)phenyl]

The title compound was prepared by substituting Example 587A and Example 598A for Example 59B and Example 56A, respectively, in Example 59C. MS (APCI) m/e 356 (M+H)$^+$, $^1$H NMR (500 MHz, DMSO-d$_6$): □ 9.85 (s, 1H), 7.97 (s, 1H), 7.78 (d, J=8.24 Hz, 1H), 7.45 (d, J=7.63 Hz, 1H), 7.32 (s, 1H), 7.24-7.27 (m, 3H), 6.90-7.03 (m, 4H), 3.95 (s, 3H), 3.90 (s, 2H).

EXAMPLE 599

3-[3-methoxy-5-(1,3-thiazol-5-ylmethoxy)phenyl]-8-[2-(4-morpholin-4-ylphenoxy)ethyl]-5,10-dihydro-11H-dibenzo[b,e][1,4]diazepin-11-one

EXAMPLE 599A

5-[(3-chloro-5-methoxyphenoxy)methyl]-1,3-thiazole

The title compound was prepared by substituting Example 596A and 5-bromomethyl-thiazole hydrobromide for imidazole and Example 583A, respectively, in Example 583B. MS (DCI) m/e 256 (M+H)$^+$.

EXAMPLE 599B

3-[3-methoxy-5-(1,3-thiazol-5-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting Example 599A and Example 578A for Example 59B and Example 56A, respectively, in Example 59C. MS (DCI) m/e 635

(M+H)⁺, ¹H NMR (500 MHz, DMSO-d₆): □ 9.80 (s, 1H), 9.13 (s, 1H), 8.03 (s, 1H), 7.85 (s, 1H), 7.73 (d, J=8.24 Hz, 1H), 7.28 (d, J=1.53 Hz, 1H), 7.19 (dd, J=8.24, 1.83 Hz, 1H), 6.79-6.95 (m, 9H), 6.67 (t, J=2.14 Hz, 1H), 5.47 (s, 2H), 4.04 (t, J=6.71 Hz, 2H), 3.81 (s, 3H), 3.71-3.73 (m, 4H), 2.99-3.00 (m, 4H), 2.86 (t, J=6.56 Hz, 2H).

EXAMPLE 600

3-[3-methoxy-5-(pyridin-2-ylmethoxy)phenyl]-8-[2-(4-morpholin-4-ylphenoxy)ethyl]-5,10-dihydro-11H-dibenzo[b,e][1,4]diazepin-11-one

EXAMPLE 600A

2-[(3-chloro-5-methoxyphenoxy)methyl]pyridine

The title compound was prepared by substituting Example 596A and 2-bromomethyl-pyridine hydrobromide for imidazole and Example 583A, respectively, in Example 583B. MS (DCI) m/e 250 (M+H)⁺.

EXAMPLE 600B

3-[3-methoxy-5-(pyridin-2-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting Example 600A and Example 578A for Example 59B and Example 56A, respectively, in Example 59C. MS (DCI) m/e 629 (M+H)⁺, ¹H NMR (500 MHz, DMSO-d₆): □ 9.81 (s, 1H), 8.64 (d, J=4.88 Hz, 1H), 7.96 (m, 1H), 7.87 (s, 1H), 7.74 (d, J=8.24 Hz, 1H), 7.63 (d, J=7.63 Hz, 1H), 7.44 (dd, J=7.02, 5.19 Hz, 1H), 7.29 (d, J=1.53 Hz, 1H), 7.18 (dd, J=8.24, 1.53 Hz, 1H), 6.87-7.00 (m, 8H), 6.79 (s, 1H), 6.68 (t, J=2.12 Hz, 1H), 5.29 (s, 2H), 4.05 (t, J=6.71 Hz, 2H), 3.81 (s, 3H), 3.74-3.76 (m, 4H), 3.06-3.08 (m, 4H), 2.87 (t, J=6.71 Hz, 2H).

EXAMPLE 601

3-[3-methoxy-5-(pyridin-4-ylmethoxy)phenyl]-8-[2-(4-morpholin-4-ylphenoxy)ethyl]-5,10-dihydro-11H-dibenzo[b,e][1,4]diazepin-11-one

EXAMPLE 601A

4-[(3-chloro-5-methoxyphenoxy)methyl]pyridine

The title compound was prepared by substituting Example 596A and 4-bromomethyl-pyridine hydrobromide for imidazole and Example 583A, respectively, in Example 583B. MS (DCI) m/e 250 (M+H)⁺.

EXAMPLE 601B

3-[3-methoxy-5-(pyridin-4-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting Example 601A and Example 578A for Example 59B and Example 56A, respectively, in Example 59C. MS (DCI) m/e 629 (M+H)⁺, ¹H NMR (500 MHz, DMSO-d₆): □ 9.79 (s, 1H), 8.78 (d, J=5.52 Hz, 2H), 7.86 (s, 1H), 7.81 (d, J=6.14 Hz, 2H), 7.75 (d, J=8.29 Hz, 1H), 7.29 (s, 1H), 7.18 (dd, J=8.29, 1.53 Hz, 1H), 6.81-6.95 (m, 9H), 6.69 (m, 1H), 5.43 (s, 2H), 4.05 (t, J=6.75 Hz, 2H), 3.82 (s, 3H), 3.72-3.74 (m, 4H), 3.01-3.03 (m, 4H), 2.87 (t, J=6.6 Hz, 2H).

EXAMPLE 602

5-chloro-2-{8-[2-(4-morpholin-4-ylphenoxy)ethyl]-11-oxo-10,11-dihydro-5H-dibenzo[b,e][1,4]diazepin-3-yl}benzamide

EXAMPLE 602A methyl 5-chloro-2-{8-[2-(4-morpholin-4-ylphenoxy)ethyl]-11-oxo-10,11-dihydro-5H-dibenzo[b,e][1,4]diazepin-3-yl}benzoate The title compound was prepared by substituting 2-bromo-5-chloro-benzoic acid methyl ester and Example 578A for Example 59B and Example 56A, respectively, in Example 59C. MS (DCI) m/e 585 (M+H)⁺.

EXAMPLE 602B 5-chloro-2-{8-[2-(4-morpholin-4-ylphenoxy)ethyl]-11-oxo-10,11-dihydro-5H-dibenzo[b,e][1,4]diazepin-3-yl}benzamide Example 602A (30 mg) in 10 mL of 7 N NH₃ in MeOH was heated in a sealed tube at 90° C. for 3 days. The solvent was removed and the residue was purified by reverse phase preparative HPLC to give the title compound. MS (DCI) m/e 569 (M+H)⁺, ¹H NMR (500 MHz, DMSO-d₆): □ 9.80 (s, 1H), 7.90 (s, 1H), 7.80 (s, 1H), 7.65 (d, J=8.24 Hz, 1H), 7.57 (dd, J=8.39, 2.39 Hz, 1H), 7.50 (d, J=2.44 Hz, 1H), 7.45 (s, 1H), 7.37 (d, J=8.24 Hz, 1H), 7.00 (d, J=1.53 Hz, 1H), 6.85-6.95 (m, 8H), 4.04 (t, J=6.87 Hz, 2H), 3.73-3.75 (m, 4H), 3.02-3.05 (m, 4H), 2.86 (t, J=6.87 Hz, 2H).

EXAMPLE 603

3-[3-methoxy-5-(pyridin-3-ylmethoxy)phenyl]-8-[2-(4-morpholin-4-ylphenoxy)ethyl]-5,10-dihydro-11H-dibenzo[b,e][1,4]diazepin-11-one

EXAMPLE 603A

3-[(3-chloro-5-methoxyphenoxy)methyl]pyridine

The title compound was prepared by substituting Example 696A and 3-bromomethyl-pyridine hydrobromide for imidazole and Example 583A, respectively, in Example 583B. MS (DCI) m/e 250 (M+H)⁺.

EXAMPLE 603B

3-[3-methoxy-5-(pyridin-3-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting Example 603A and Example 578A for Example 59B and Example 56A, respectively, in Example 59C. MS (DCI) m/e 629 (M+H)⁺, ¹H NMR (500 MHz, DMSO-d₆): □ 9.90 (s, 1H), 8.93 (s, 1H), 8.80 (d, J=4.88 Hz, 1H), 8.30 (d, J=7.63 Hz, 1H), 7.96 (s, 1H), 7.80-7.84 (m, 2H), 7.38 (s, 1H), 7.28 (dd, J=8.09, 1.37 Hz, 1H), 6.94-7.05 (m, 8H), 6.89 (s, 1H), 6.77 (m, 1H), 5.39 (s, 2H), 4.14 (t, J=6.71 Hz, 2H), 3.91 (s, 3H), 3.82-3.84 (m, 4H), 3.12-3.14 (m, 4H), 2.96 (t, J=6.71 Hz, 2H).

EXAMPLE 604

5-methoxy-2-{8-[2-(4-morpholin-4-ylphenoxy)ethyl]-11-oxo-10,11-dihydro-5H-dibenzo[b,e][1,4]diazepin-3-yl}benzamide

EXAMPLE 604A methyl 5-methoxy-2-{8-[2-(4-morpholin-4-ylphenoxy)ethyl]-11-oxo-10,11-dihydro-5H-dibenzo[b,e][1,4]diazepin-3-yl}benzoate The title compound was prepared by substituting 2-bromo-5-methoxy-benzoic acid methyl ester and Example 578A for Example 59B and Example 56A, respectively, in Example 59C. MS (DCI) m/e 580 (M+H)$^+$.

EXAMPLE 604B 5-methoxy-2-{8-[2-(4-morpholin-4-ylphenoxy)ethyl]-11-oxo-10,11-dihydro-5H-dibenzo[b,e][1,4]diazepin-3-yl}benzoic acid The title compound was obtained from hydrolysis of Example 604A in MeOH/H$_2$O with LiOH. MS (DCI) m/e 566 (M+H)$^+$.

EXAMPLE 604C 5-methoxy-2-{8-[2-(4-morpholin-4-ylphenoxy)ethyl]-11-oxo-10,11-dihydro-5H-dibenzo[b,e][1,4]diazepin-3-yl}benzamide A mixture of Example 604B (27 mg, 0.05 mmol), PyBOP (52 mg, 0.1 mmol), HOBt (13.5 mg, 0.2 mmol), DIEPA (26 mg, 0.2 mmol), and NH$_4$Cl (5.3 mg, 0.1 mmol) in DMF (0.5 mL) was stirred overnight. The reaction mixture was partitioned between water and EtOAc. The organic layer was washed with brine, dried over MgSO$_4$, and concentrated under reduced pressure. The residue was purified by reverse phase prep HPLC to give the title compound. MS (DCI) m/e 565 (M+H)$^+$, $^1$H NMR (500 MHz, DMSO-d$_6$): □ 9.75 (s, 1H), 7.84 (s, 1H), 7.64 (s, 1H), 7.62 (d, J=8.24 Hz, 1H), 7.33 (s, 1H), 7.27 (d, J=8.24 Hz, 1H), 7.06 (dd, J=8.54, 2.75 Hz, 1H), 6.84-7.00 (m, 10H), 4.05 (t, J=6.71 Hz, 2H), 3.82 (s, 3H), 3.74-3.76 (m, 4H), 3.05-3.07 (m, 4H), 2.87 (t, J=6.56 Hz, 2H).

EXAMPLE 605

3-(3,4-dimethoxyphenyl)-8-[2-(4-morpholin-4-ylphenoxy)ethyl]-5,10-dihydro-11H-dibenzo[b,e][1,4]diazepin-11-one Example 605 was obtained by substituting 3,4-dimethoxychlorobenzene and Example 578A for Example 59B and Example 56A, respectively, in Example 59C. MS (ESI) m/e 552 (M+H)$^+$; $^1$H NMR (400 MHz, DMSO-d$_6$) □9.73 (s, 1H), 7.84 (s, 1H), 7.72 (d, J=8.3 Hz, 1H), 7.25 (d, J=1.8 Hz, 1H), 7.16-7.20 (m, 3H), 7.05-7.07 (m, 2H), 6.84-6.98 (m, 6H), 4.06 (t, J=6.6 Hz, 2H), 3.85 (s, 3H), 3.80 (s, 3H), 3.73-3.76 (m, 4H), 3.05-3.07 (m, 4H), 2.85-2.88 (t, J=6.6 Hz, 2H).

EXAMPLE 606

3-[3-methoxy-4-(pyridin-4-ylmethoxy)phenyl]-8-[2-(4-morpholin-4-ylphenoxy)ethyl]-5,10-dihydro-11H-dibenzo[b,e][1,4]diazepin-11-one A mixture of Example 474 (26.9 mg, 0.05 mmol) and 4-chloromethylpyridine hydrochloride (24.6 mg, 0.15 mmol) in DMF (1 mL) was treated with K$_2$CO$_3$ (34.6 mg, 0.25 mmol) and heated at 80° C. for 7 hours. The reaction mixture was then cooled to room temperature, diluted with ethyl acetate, washed with water and brine, dried (MgSO$_4$), filtered, and concentrated under vacuum. The residue was purified by preparative HPLC to provide the title compound as the di-TFA salt. MS (ESI) m/e 629 (M+H)$^+$; $^1$H NMR (300 MHz, DMSO-d$_6$) □9.77 (s, 1H), 8.79 (br s, 2H), 7.85 (s, 1H), 7.8 (d, J=4.1 Hz, 2H), 7.73 (d, J=8.5 Hz, 1H), 7.26 (dd, J=3.6, 1.9 Hz, 2H), 7.08-7.20 (m, 3H), 6.82-6.95 (m, 7H), 5.38 (s, 2H), 4.04 (t, J=6.8 Hz, 2H), 3.91 (s, 3H), 3.71-3.74 (m, 4H), 2.99-3.02 (m, 4H), 2.86 (t, J=6.8 Hz, 2H).

EXAMPLE 607

3-[3-methoxy-4-(pyridin-3-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting 3-chloromethylpyridine hydrochloride for 4-chloromethylpyridine hydrochloride in Example 606. MS (ESI) m/e 629 (M+H)$^+$; $^1$H NMR (400 MHz, DMSO-d$_6$) □9.74 (s, 1H), 8.78 (d, J=1.2 Hz, 1H), 8.67 (dd, J=5.0, 1.2 Hz, 1H), 8.12 (m, 1H), 7.84 (s, 1H), 7.73 (d, J=8.0 Hz, 1H), 7.65 (dd, J=4.9, 8.0 Hz, 1H), 7.26 (d, J=1.8 Hz, 1H), 7.24 (s, 1H), 7.17=7.19 (m, 3H), 6.82-6.95 (m, 7H), 5.25 (s, 2H), 4.05 (t, J=6.8 Hz, 2H), 3.87 (s, 3H), 3.69-3.74 (m, 4H), 3.00-3.03 (m, 4H), 2.86 (t, J=6.6 Hz, 2H).

EXAMPLE 608

3-{3-methoxy-4-[(2-methyl-1,3-thiazol-4-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting 4-chloromethyl-2-methyl-thiazole hydrochloride for 4-chloromethylpyridine hydrochloride in Example 607. MS (ESI) m/e 649 (M+H)$^+$; $^1$H NMR (500 MHz, DMSO-d$_6$) □9.73 (s, 1H), 7.83 (s, 1H), 7.72 (d, J=8.1 Hz, 1H), 7.54 (s, 1H), 7.26 (d, J=1.9 Hz, 1H), 7.16-7.22 (m, 4H), 7.87-7.95 (m, 5H), 6.82-6.85 (m, 2H), 5.13 (m, 2H), 4.04 (t, J=6.7 Hz, 2H), 3.86 (s, 3H), 3.71-3.73 (m, 4H), 2.98-2.99 (m, 4H), 2.86 (t, J=6.7 Hz, 2H), 2.67 (s, 3H).

EXAMPLE 609

3-[4-(2-hydroxyethoxy)-3-methoxyphenyl]-8-[2-(4-morpholin-4-ylphenoxy)ethyl]-5,10-dihydro-11H-dibenzo[b,e][1,4]diazepin-11-one

EXAMPLE 609A

3-[4-(2-{[tert-butyl(dimethyl)silyl]oxy}ethoxy)-3-methoxyphenyl]-8-[2-(4-morpholin-4-ylphenoxy)ethyl]-5,10-dihydro-11H-dibenzo[b,e][1,4]diazepin-11-one The title compound was prepared by substituting (2-bromo-ethoxy)-tert-butyl-dimethylsilane for 4-chloromethylpyridine hydrochloride in Example 607. MS (ESI) m/e 696 (M+H)+; 1H NMR (400 MHz, DMSO-d6) □9.73 (s, 1H), 7.83 (s, 1H), 7.72 (d, J=8.3 Hz, 1H), 7.25 (d, J=1.8 Hz, 1H), 7.15-7.20 (m, 3H), 7.07 (d, J=8.6 Hz, 1H), 6.81-6.95 (m, 7H), 4.02-4.07 (m, 4H), 3.92-3.95 (m, 2H), 3.85 (s, 3H), 3.70-3.72 (m, 4H), 2.95-2.98 (m, 4H), 2.84-2.89 (m, 2H), 0.88 (s, 9H), 0.08 (s, 6H).

EXAMPLE 609B

3-[4-(2-hydroxyethoxy)-3-methoxyphenyl]-8-[2-(4-morpholin-4-ylphenoxy)ethyl]-5,10-dihydro-11H-dibenzo[b,e][1,4]diazepin-11-one A mixture of Example 609A (23 mg, 0.033 mmol) in 1:1 MeOH:dioxane (2 mL) was treated with tetraethylammonium fluoride hydrate (49.4 mg, 0.33 mmol) at 50° C. for 24 hours. The reaction was then cooled to room temperature, concentrated, diluted with ethyl acetate, washed with water and brine, dried (MgSO4), filtered and concentrated. The residue was purified by preparative HPLC to provide the title compound. MS (ESI) m/e 582 (M+H)+; 1H NMR (300 MHz, DMSO-d6) □ 9.75 (s, 1H), 7.84 (s, 1H), 7.72 (d, J=8.1 Hz, 1H), 7.25 (d, J=1.4 Hz, 1H), 7.15-7.20 (m, 3H), 7.07 (m, 1H), 6.80-6.96 (m, 7H), 4.00-4.06 (m, 4H), 3.85 (s, 3H), 3.70-3.75 (m, 6H), 2.96-2.99 (m, 4H), 2.86 (t, J=6.4 Hz, 2H).

EXAMPLE 610

3-[4-(2,3-dihydroxypropoxy)-3-methoxyphenyl]-8-[2-(4-morpholin-4-ylphenoxy)ethyl]-5,10-dihydro-11H-dibenzo[b,e][1,4]diazepin-11-one The title compound was prepared by substituting 3-chloropropane-1,2-diol for 4-chloromethylpyridine hydrochloride in Example 607. MS (ESI) m/e 612 (M+H)+; 1H NMR (400 MHz, DMSO-d6) □9.73 (s, 1H), 7.83 (s, 1H), 7.72 (d, J=8.3 Hz, 1H), 7.25 (d, J=1.2 Hz, 1H), 7.16-7.20 (m, 3H), 7.07 (d, J=8.6 Hz, 1H), 6.81-6.95 (m, 7H), 4.92 (d, J=4.9 Hz, 1H), 4.63 (t, J=5.5 Hz, 1H), 4.00-4.05 (m, 3H), 3.92 (m, 1H), 3.86 (s, 3H), 3.82 (m, 1H), 3.70-3.72 (m, 4H), 3.45-3.48 (m, 2H), 2.95-2.98 (m, 4H), 2.86 (t, J=6.5 Hz, 2H).

EXAMPLE 611

3-{3-methoxy-4-[(5-methylisoxazol-3-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting 3-bromomethyl-5-methylisoxazole for 4-chloromethylpyridine hydrochloride in Example 607. MS (ESI) m/e 633 (M+H)+; 1H NMR (500 MHz, DMSO-d6) □ 9.74 (s, 1H), 7.83 (s, 1H), 7.73 (d, J=8.1 Hz, 1H), 7.26 (d, J=1.6 Hz, 1H), 7.23 (s, 1H), 7.16-7.18 (m, 3H), 6.88-6.95 (m, 5H), 6.83-6.86 (m, 2H), 6.33 (s, 1H), 5.17 (s, 2H), 4.05 (t, J=6.7 Hz, 2H), 3.86 (s, 3H), 3.72-3.74 (m, 4H), 3.00-3.02 (m, 4H), 2.86 (t, J=6.7 Hz, 2H), 2.42 (s, 3H).

EXAMPLE 612

3-{4-[(3,5-dimethylisoxazol-4-yl)methoxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting 4-chloromethyl-3,5-dimethyl-isoxazole for 4-chloromethylpyridine hydrochloride in Example 607. MS (ESI) m/e 647 (M+H)+; 1H NMR (400 MHz, DMSO-d6) □ 9.74 (s, 1H), 7.84 (s, 1H), 7.73 (d, J=8.3 Hz, 1H), 7.26 (d, J=1.2 Hz, 1H), 7.16-7.21 (m, 4H), 6.85-6.98 (m, 7H), 4.94 (s, 2H), 4.06 (t, J=6.8 Hz, 2H), 3.85 (s, 3H), 3.73-3.76 (m, 4H), 3.04-3.06 (m, 4H), 2.87 (t, J=6.8 Hz, 2H), 2.39 (s, 3H), 2.23 (s, 3H).

EXAMPLE 613

3-[3-methoxy-4-(1,3-thiazol-4-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting 4-chloromethylthiazole hydrochloride for 4-chloromethylpyridine hydrochloride in Example 607. MS (ESI) m/e 635 (M+H)+; 1H NMR (500 MHz, DMSO-d6) □ 9.73 (s, 1H), 9.13 (d, J=1.9 Hz, 1H), 7.83 (s, 1H), 7.78 (d, J=1.9 Hz, 1H), 7.26 (d, J=8.1 Hz, 1H), 7.26 (d, J=1.6 Hz, 1H), 7.21-7.23 (m, 2H), 7.16-7.19 (m, 2H), 6.81-6.95 (m, 7H), 5.25 (s, 2H), 4.04 (t, J=6.7 Hz, 2H), 3.86 (s, 3H), 3.70-3.72 (m, 4H), 2.96-2.98 (m, 4H), 2.86 (d, J=6.7 Hz, 2H).

EXAMPLE 614

(2-methoxy-4-{8-[2-(4-morpholin-4-ylphenoxy)ethyl]-11-oxo-10,11-dihydro-5H-dibenzo[b,e][1,4]diazepin-3-yl}phenoxy)acetonitrile The title compound was prepared by substituting bromoacetonitrile for 4-chloromethylpyridine hydrochloride in Example 607. MS (ESI) m/e 577 (M+H)+; 1H NMR (500 MHz, DMSO-d6) □9.76 (s, 1H), 7.86 (s, 1H), 7.74 (d, J=8.1 Hz, 1H), 7.28 (d, J=2.8 Hz, 1H), 7.19-7.22 (m, 4H), 6.85-6.96 (m, 7H), 5.17 (s, 2H), 4.05 (t, J=6.6 Hz, 2H), 3.89 (s, 3H), 3.73-3.75 (m, 4H), 3.02-3.04 (m, 4H), 2.87 (t, J=6.6 Hz, 2H).

EXAMPLE 615

3-{4-[(5-cyclopropyl-1,3,4-thiadiazol-2-yl)methoxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting 2-chloromethyl-5-cyclopropyl-[1,3,4]thiadiazole for 4-chloromethylpyridine hydrochloride in Example 607. MS (ESI) m/e 676 (M+H)+; 1H NMR (500 MHz, DMSO-d6) □ 9.74 (s, 1H), 7.83 (s, 1H), 7.73 (d, J=8.4 Hz, 1H), 7.25 (dd, J=4.5, 1.7 Hz, 2H), 7.16-7.22 (m, 3H), 6.81-6.95 (m, 7H), 5.52 (s, 2H), 4.04 (t, J=6.7 Hz, 2H), 3.88 (s, 3H), 3.70-3.72 (m, 4H), 2.96-2.97 (m, 4H), 2.86 (t, J=6.7 Hz, 2H), 2.54 (m, 1H), 1.20-1.24 (m, 2H), 1.04 (ddd, J=7.2, 4.5, 4.2 Hz, 2H).

EXAMPLE 616

3-[4-(2-hydroxy-3-methoxypropoxy)-3-methoxyphenyl]-8-[2-(4-morpholin-4-ylphenoxy)ethyl]-5,10-dihydro-1H-dibenzo[b,e][1,4]diazepin-11-one The title compound was prepared by substituting 1-chloro-3-methoxy-propan-2-ol for 4-chloromethylpyridine hydrochloride in Example 607. MS (ESI) m/e 626 (M+H)+; 1H NMR (500 MHz, DMSO-d6) □ 9.73 (s, 1H), 7.83 (s, 1H), 7.73 (d, J=8.1 Hz, 1H), 7.26 (d, J=1.6 Hz, 1H), 7.20 (d, J=2.2 Hz, 1H), 7.17 (d, J=8.7 Hz, 2H), 7.07 (d, J=8.4 Hz, 1H), 6.81-6.95 (m, 7H), 5.07 (d, J=5.0 Hz, 1H), 4.04 (t, J=6.7 Hz, 2H), 3.90-3.99 (m, 3H), 3.86 (s, 3H), 3.70-3.72 (m, 4H), 3.38-3.46 (m, 2H), 3.29 (s, 3H), 2.95-2.97 (m, 4H), 2.86 (t, J=6.7 Hz, 2H).

EXAMPLE 617

3-[3-methoxy-4-(2-methyl-thiazol-4-ylmethoxy)-phenyl]-8-[2-(2-methyl-pyridin-3-yloxy)-ethyl]-5,10-dihydro-dibenzo[b,e][1,4]diazepin-11-one The title compound was prepared by substituting 4-chloromethyl-2-methyl-thiazole hydrochloride and Example 664B for 4-chloromethylpyridine hydrochloride and Example 474, respectively, in Example 607. MS (ESI) m/e 626 (M+H)$^+$; $^1$H NMR (500 MHz, DMSO-d$_6$) ☐ 9.77 (s, 1H), 8.23 (d, J=5.2 Hz, 1H), 7.86-7.88 (m, 2H), 7.73 (d, J=8.3 Hz, 1H), 7.62 (dd, J=8.0, 5.5 Hz, 1H), 7.54 (s, 1H), 7.26 (d, J=1.5 Hz, 1H), 7.15-7.21 (m, 4H), 6.92-6.97 (m, 3H), 5.13 (s, 2H), 4.29 (t, J=6.4 Hz, 2H), 3.85 (s, 3H), 2.97 (t, J=6.1 Hz, 2H), 2.67 (s, 3H), 2.46 (s, 3H).

EXAMPLE 618

3-{3-methoxy-4-[(2-oxo-1,3-oxazolidin-5-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting 5-chloromethyl-oxazolidin-2-one for 4-chloromethylpyridine hydrochloride in Example 607. MS (ESI) m/e 626 (M+H)$^+$; $^1$H NMR (400 MHz, DMSO-d$_6$) ☐ 9.79 (s, 1H), 7.87 (s, 1H), 7.73 (d, J=8.3 Hz, 1H), 7.62 (s, 1H), 7.25 (dd, J=14.4, 1.5 Hz, 2H), 7.11-7.20 (m, 3H), 6.81-6.96 (m, 7H), 4.93 (m, 1H), 4.12-4.22 (m, 2H), 4.00-4.05 (m, 2H), 3.87 (s, 3H), 3.70-3.72 (m, 4H), 3.62 (t, J=8.9 Hz, 1H), 3.36 (m, 1H), 2.95-2.97 (m, 4H), 2.86 (t, J=6.6 Hz, 2H).

EXAMPLE 619

3-[3-methoxy-4-(2-morpholin-4-ylethoxy)phenyl]-8-[2-(4-morpholin-4-ylphenoxy)ethyl]-5,10-dihydro-11H-dibenzo[b,e][1,4]diazepin-11-one The title compound was prepared by substituting 4-(2-chloro-ethyl)-morpholine for 4-chloromethylpyridine hydrochloride in Example 607. MS (ESI) m/e 651 (M+H)$^+$; $^1$H NMR (400 MHz, DMSO-d$_6$) ☐☐9.79 (s, 1H), 7.87 (s, 1H), 7.72, (d, J=8.3 Hz, 1H), 7.26 (d, J=1.2 Hz, 1H), 7.16-7.20 (m, 3H), 7.09 (m, 1H), 6.81-6.96 (m, 7H), 4.12 (t, J=6.0 Hz, 2H), 4.03 (t, J=6.8 Hz, 2H), 3.85 (s, 3H), 3.70-3.72 (m, 4H), 3.57-3.59 (m, 4H), 2.95-2.97 (m, 4H), 2.86 (t, J=6.6 Hz, 2H), 2.71 (t, J=6.0 Hz, 2H), 2.48-2.52 (m, 4H).

EXAMPLE 620

3-(4-{2-[2-(2-hydroxyethoxy)ethoxy]ethoxy}-3-methoxyphenyl)-8-[2-(4-morpholin-4-ylphenoxy)ethyl]-5,10-dihydro-11H-dibenzo[b,e][1,4]diazepin-11-one The title compound was prepared by substituting 2-[2-(2-chloro-ethoxy)-ethoxy]-ethanol for 4-chloromethylpyridine hydrochloride in Example 607. MS (ESI) m/e 670 (M+H)$^+$; $^1$H NMR (400 MHz, DMSO-d$_6$) ☐9.79 (s, 1H), 7.87 (s, 1H), 7.72 (d, J=8.3 Hz, 1H), 7.26 (d, J=1.2 Hz, 1H), 7.16-7.21 (m, 3H), 7.08 (d, J=8.6 Hz, 1H), 6.81-6.96 (m, 7H), 4.61 (t, J=5.4 Hz, 1H), 4.11-4.14 (m, 2H), 4.03 (t, J=6.8 Hz, 2H), 3.86 (s, 3H), 3.75-3.77 (m, 2H), 3.70-3.72 (m, 4H), 3.60-3.62 (m, 2H), 3.54-3.56 (m, 2H), 3.47-3.52 (m, 2H), 3.42-3.44 (m, 2H), 2.95-2.97 (m, 4H), 2.86 (t, J=6.6 Hz, 2H).

EXAMPLE 621

3-[4-(1,3-dioxolan-2-ylmethoxy)-3-methoxyphenyl]-8-[2-(4-morpholin-4-ylphenoxy)ethyl]-5,10-dihydro-11H-dibenzo[b,e][1,4]diazepin-11-one The title compound was prepared by substituting 2-bromomethyl-[1,3]dioxolane for 4-chloromethylpyridine hydrochloride in Example 607. MS (ESI) m/e 624 (M+H)$^+$; $^1$H NMR (400 MHz, DMSO-d$_6$) ☐ 9.73 (s, 1H), 7.82 (s, 1H), 7.72 (d, J=8.3 Hz, 1H), 7.25 (d, J=1.2 Hz, 1H), 7.14-7.20 (m, 3H), 7.08 (d, J=8.3 Hz, 1H), 6.80-6.94 (m, 7H), 5.22 (t, J=4.0 Hz, 1H), 4.00-4.04 (m, 4H), 3.95-3.98 (m, 2H), 3.83-3.87 (m, 2H), 3.85 (s, 3H), 3.69-3.71 (m, 4H), 2.94-2.96 (m, 4H), 2.85 (t, J=6.8 Hz, 2H).

EXAMPLE 622

3-{4-[(2,2-dimethyl-1,3-dioxolan-4-yl)methoxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting 4-chloromethyl-2,2-dimethyl-[1,3]dioxolane for 4-chloromethylpyridine hydrochloride in Example 607. MS (ESI) m/e 652 (M+H)$^+$; $^1$H NMR (400 MHz, DMSO-d$_6$) ☐ 9.73 (s, 1H), 7.82 (s, 1H), 7.71 (d, J=8.3 Hz, 1H), 7.25 (d, J=1.2 Hz, 1H), 7.15-7.20 (m, 3H), 7.08 (d, J=8.6 Hz, 1H), 6.80-6.94 (m, 7H), 4.42 (m, 1H), 4.10 (dd, J=6.8, 8.3 Hz, 1H), 3.99-4.04 (m, 4H), 3.85 (s, 3H), 3.77 (dd, J=6.4, 8.3 Hz, 1H), 3.69-3.71 (m, 4H), 2.94-2.97 (m, 4H), 2.85 (t, J=6.5 Hz, 2H), 1.36 (s, 3H), 1.31 (s, 3H).

EXAMPLE 623

3-[4-(4-hydroxybutoxy)-3-methoxyphenyl]-8-[2-(4-morpholin-4-ylphenoxy)ethyl]-5,10-dihydro-11H-dibenzo[b,e][1,4]diazepin-11-one

EXAMPLE 623A

3-[4-(4-{[tert-butyl(dimethyl)silyl]oxy}butoxy)-3-methoxyphenyl]-8-[2-(4-morpholin-4-ylphenoxy)ethyl]-5,10-dihydro-11H-dibenzo[b,e][1,4]diazepin-11-one The title compound was prepared by substituting tert-butyl-(4-iodo-butoxy)-dimethylsilane for 4-chloromethylpyridine hydrochloride in Example 607.

EXAMPLE 623B

3-[4-(4-hydroxybutoxy)-3-methoxyphenyl]-8-[2-(4-morpholin-4-ylphenoxy)ethyl]-5,10-dihydro-11H-dibenzo[b,e][1,4]diazepin-11-one The title compound was prepared by substituting Example 623A for Example 609A in Example 609B. MS (ESI) m/e 610 (M+H)$^+$; $^1$H NMR (500 MHz, DMSO-d$_6$) ☐ 9.73 (s, 1H), 7.83 (s, 1H), 7.72 (d, J=8.4 Hz, 1H), 7.25 (d, J=1.3 Hz, 1H), 7.20 (t, J=2.3 Hz, 1H), 7.17 (d, J=8.1 Hz, 2H), 7.06 (dd, J=8.4, 3.1 Hz, 1H), 6.85-6.95 (m, 7H), 4.48 (t, J=6.4 Hz, 1H), 4.00-

4.07 (m, 5H), 3.85 (s, 3H), 3.73-3.75 (m, 4H), 3.46 (t, J=6.6 Hz, 1H), 3.02-3.05 (m, 4H), 2.87 (t, J=6.7 Hz, 2H), 1.74-1.92 (m, 3H), 1.58 (m, 1H).

EXAMPLE 624

3-[3-methoxy-4-(tetrahydrofuran-2-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting 2-bromomethyl-tetrahydrofuran for 4-chloromethylpyridine hydrochloride in Example 607. MS (ESI) m/e 622 (M+H)$^+$; $^1$H NMR (500 MHz, DMSO-d$_6$) ☐ 9.73 (s, 1H), 7.83 (s, 1H), 7.72 (d, J=8.1 Hz, 1H), 7.25 (d, J=1.6 Hz, 1H), 7.20 (d, J=1.9 Hz, 1H), 7.17 (ddd, J=8.4, 3.0, 2.0 Hz, 2H), 7.07 (d, J=8.4 Hz, 1H), 6.86-6.99 (m, 7H), 4.18 (m, 1H), 4.06 (t, J=6.7 Hz, 2H), 3.93-4.00 (m, 2H), 3.85 (s, 3H), 3.80 (m, 1H), 3.74-3.76 (m, 4H), 3.68 (m, 1H), 3.03-3.09 (m, 4H), 2.87 (t, J=6.7 Hz, 2H), 2.01 (m, 1H), 1.79-1.93 (m, 2H), 1.69 (m, 1H).

EXAMPLE 625

3-[3-methoxy-4-(1,3-oxazol-2-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting 2-chloromethyl-oxazole for 4-chloromethylpyridine hydrochloride in Example 607. MS (ESI) m/e 619 (M+H)$^+$; $^1$H NMR (400 MHz, DMSO-d$_6$) ☐ 9.75 (s, 1H), 8.18 (s, 1H), 7.84 (s, 1H), 7.73 (d, J=8.3 Hz, 1H), 7.23-7.28 (m, 3H), 7.15-7.20 (m, 3H), 7.02 (d, J=8.6 Hz, 2H), 6.88-6.96 (m, 5H), 5.25 (s, 2H), 4.07 (t, J=6.6 Hz, 2H), 3.86 (s, 3H), 3.75-3.78 (m, 4H), 3.05-3.15 (m, 4H), 2.87 (t, J=6.6 Hz, 2H).

EXAMPLE 626

3-{3-methoxy-4-[2-(1H-pyrrol-1-yl)ethoxy]phenyl}-8-[2-(4-morpholin-4-ylphenoxy)ethyl]-5,10-dihydro-11H-dibenzo[b,e][1,4]diazepin-11-one The title compound was prepared by substituting 1-(2-chloroethyl)-1H-pyrrole for 4-chloromethylpyridine hydrochloride in Example 607. MS (ESI) m/e 631 (M+H)$^+$; $^1$H NMR (400 MHz, DMSO-d$_6$) ☐ 9.72 (s, 1H), 7.82 (s, 1H), 7.71 (d, J=8.1 Hz, 1H), 7.24 (d, J=1.6 Hz, 1H), 7.20 (d, J=1.9 Hz, 1H), 7.15 (ddd, J=8.2, 6.2, 1.9 Hz, 2H), 7.01 (d, J=8.4 Hz, 1H), 6.84-6.95 (m, 9H), 5.99 (t, J=2.0 Hz, 2H), 4.26 (ddd, J=16.5, 7.3, 3.6 Hz, 4H), 4.04 (t, J=6.7 Hz, 2H), 3.84 (s, 3H), 3.72-3.74 (m, 4H), 3.02-3.04 (m, 4H), 2.85 (t, J=6.7 Hz, 2H).

EXAMPLE 627

3-[3-methoxy-4-(1,3-thiazol-5-ylmethoxy)phenyl]-8-[2-(4-morpholin-4-ylphenoxy)ethyl]-5,10-dihydro-11H-dibenzo[b,e][1,4]diazepin-11-one

EXAMPLE 627A 5-(chloromethyl)-1,3-thiazole

To a mixture of thiazol-5-yl-methanol (115 mg, 1 mmol) in dichloromethane (5 mL) at 0° C. was added thionyl chloride (219 μL, 3 mmol) dropwise. After stirring for 30 minutes at 0° C., the reaction mixture was concentrated to give the title compound as the hydrochloride salt. MS (DCI) m/e 134 (M+H)$^+$; $^1$H NMR (300 MHz, DMSO-d$_6$) ☐9.14 (s, 1H), 7.97 (s, 1H), 5.13 (s, 2H).

EXAMPLE 627B

3-[3-methoxy-4-(1,3-thiazol-5-ylmethoxy)phenyl]-8-[2-(4-morpholin-4-ylphenoxy)ethyl]-5,10-dihydro-11H-dibenzo[b,e][1,4]diazepin-11-one To a solution of Example 474 (26.9 mg, 0.05 mmol) in DMF (1 mL) was added NaH (5.0 mg, 0.125 mmol). The mixture was stirred for 20 minutes at room temperature and Example 627A was added. The reaction was stirred overnight, quenched with saturated ammonium chloride solution and partitioned between ethyl acetate and water. The organic layer was washed with water and brine, dried (MgSO$_4$), filtered and concentrated. The concentrate was purified by preparative HPLC to give the title compound as the TFA salt (18.5 mg, 49% yield). MS (ESI) m/e 635 (M+H)$^+$; 1H NMR (400 MHz, DMSO-d$_6$) ☐ 9.74 (s, 1H), 9.12 (s, 1H), 8.00 (s, 1H), 7.84 (s, 1H), 7.73 (d, J=8.3 Hz, 1H), 7.26 (d, J=1.5 Hz, 1H), 7.23 (d, J=1.5 Hz, 1H), 7.16-7.20 (m, 3H), 6.86-7.00 (m, 7H), 5.42 (s, 2H), 4.06 (t, J=6.8 Hz, 2H), 3.86 (s, 3H), 3.74-3.76 (m, 4H), 3.05-3.09 (m, 4H), 2.87 (t, J=6.6 Hz, 2H).

EXAMPLE 628

3-{4-[(2,4-dimethyl-1,3-thiazol-5-yl)methoxy]-3-methoxyphenyl}-8-[2-(4-morpholin-4-ylphenoxy)ethyl]-5,10-dihydro-11H-dibenzo[b,e][1,4]diazepin-11-one

EXAMPLE 628A 5-(chloromethyl)-2,4-dimethyl-1,3-thiazole hydrochloride

The title compound was prepared by substituting (2,4-dimethyl-thiazol-5-yl)-methanol for thiazol-5-yl-methanol in Example 627A. MS (DCI) m/e 162 (M+H)$^+$; $^1$H NMR (300 MHz, DMSO-d$_6$) ☐5.01 (s, 2H), 2.61 (s, 3H), 2.32 (s, 3H).

EXAMPLE 628B

3-{4-[(2,4-dimethyl-1,3-thiazol-5-yl)methoxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting Example 627A for 4-chloromethylpyridine hydrochloride in Example 607. MS (ESI) m/e 663 (M+H)$^+$; $^1$H NMR (400 MHz, DMSO-d$_6$) ☐ 9.75 (s, 1H), 7.84 (s, 1H), 7.73 (d, J=8.3 Hz, 1H), 7.26 (d, J=0.9 Hz, 1H), 7.14-7.22 (m, 4H), 6.86-7.01 (m, 7H), 5.23 (s, 2H), 4.06 (t, J=6.8 Hz, 2H), 3.85 (s, 3H), 3.74-3.77 (m, 4H), 3.06-3.09 (m, 4H), 2.87 (t, J=6.6 Hz, 2H), 2.59 (s, 3H), 2.32 (s, 3H).

EXAMPLE 629

3-[4-(3,4-dihydroxybutoxy)-3-methoxyphenyl]-8-[2-(4-morpholin-4-ylphenoxy)ethyl]-5,10-dihydro-11H-dibenzo[b,e][1,4]diazepin-11-one

EXAMPLE 629A 4-(2-bromoethyl)-2,2-dimethyl-1,3-dioxolane

To a solution of 2-(2,2-dimethyl-[1,3]dioxolan-4-yl)-ethanol (292 mg, 2 mmol) in dichloromethane (20 mL) at 0° C. was added carbon tetrabromide (796 mg, 2.4 mmol) and polymer-supported triphenyl phosphine (1 g, 3 mmol). After stirring for 1.75 hours and slowly warming to room temperature, the reaction mixture was filtered through Celite and rinsed with additional dichloromethane. The filtrate was concentrated to give the product as a mixture of product and bromoform (2:1). MS (DCI) m/e 208 (M+NH$_4$—H$_2$O)+; $^1$H NMR (300 MHz, DMSO-d$_6$) □ 4.15 (m, 1H), 4.02 (dd, J=8.1, 6.1 Hz, 1H), 3.47-3.62 (m, 3H), 1.94-2.09 (m, 2H), 1.32 (s, 3H), 1.26 (s, 3H).

EXAMPLE 629B

3-{4-[2-(2,2-dimethyl-1,3-dioxolan-4-yl)ethoxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting Example 629A for 4-chloromethylpyridine hydrochloride in Example 607. MS (ESI) m/e 666 (M+H)$^+$; $^1$H NMR (500 MHz, DMSO-d$_6$) δ9.76 (s, 1H), 7.85 (s, 1H), 7.72 (d, J=8. Hz, 1H), 7.25 (d, J=1.2 Hz, 1H), 7.20 (d, J=2.1 Hz, 1H), 7.14-7.19 (m, 2H), 7.07 (d, J=8.4 Hz, 1H), 6.81-6.95 (m, 7H), 4.22 (dq, J=6.6, 6.4 Hz, 1H), 4.02-4.13 (m, 5H), 3.86 (s, 3H), 3.70-3.72 (m, 4H), 3.61 (m, 1H), 2.95-2.97 (m, 4H), 2.86 (t, J=6.6 Hz, 2H), 1.92-2.03 (m, 2H), 1.34 (s, 3H), 1.28 (s, 3H).

EXAMPLE 629C

3-[4-(3,4-dihydroxybutoxy)-3-methoxyphenyl]-8-[2-(4-morpholin-4-ylphenoxy)ethyl]-5,10-dihydro-11H-dibenzo[b,e][1,4]diazepin-11-one A solution of Example 629B (12 mg, 0.018 mmol) in THF (1 mL) was treated with 5 drops of 1 N aqueous HCl and stirred at room temperature for 4 days. The solution was concentrated and purified by preparative HPLC to give the title compound as the TFA salt (8.4 mg, 63% yield). MS (ESI) m/e 626 (M+H)$^+$; $^1$H NMR (500 MHz, DMSO-d$_6$) δ 9.73 (s, 1H), 7.84 (s, 1H), 7.72 (d, J=8.3 Hz, 1H), 7.25 (s, 1H), 7.16-7.19 (m, 3H), 7.07 (m, 1H), 6.85-6.96 (m, 7H), 4.39 (m, 1H), 4.00-4.15 (m, 6H), 3.85 (s, 3H), 3.73-3.75 (m, 4H), 3.66 (qd, J=8.8, 3.8 Hz, 1H), 3.24 (m, 1H), 3.02-3.06 (m, 4H), 2.87 (t, J=6.4 Hz, 2H), 1.61-2.08 (m, 2H).

EXAMPLE 630

3-{3-methoxy-4-[2-(4-methyl-1,3-thiazol-5-yl)ethoxy]phenyl}-8-[2-(4-morpholin-4-ylphenoxy)ethyl]-5,10-dihydro-11H-dibenzo[b,e][1,4]diazepin-11-one

EXAMPLE 630A

5-[2-(4-bromo-2-methoxyphenoxy)ethyl]-4-methyl-1,3-thiazole

A mixture of 4-bromo-2-methoxy-phenol (50.8 mg, 0.25 mmol), 2-(4-methyl-thiazol-5-yl)-ethanol (49.5 mg, 0.25 mmol) and polymer-supported triphenyl phosphine (250 mg, 0.75 mmol) in THF (2.5 mL) was stirred at room temperature for 20 minutes. DBAD (86.3 mg, 0.375 mmol) was added and the mixture was stirred overnight at room temperature. The reaction mixture was filtered through Celite®, rinsing with THF and methanol. The filtrate was concentrated, diluted with ethyl acetate, washed with water and brine, dried (MgSO$_4$), filtered and concentrated. The concentrate was purified by column chromatography on silica gel (10 to 20% ethyl acetate in hexane) to give the title compound. MS (ESI) m/e 329 (M+H)$^+$; $^1$H NMR (300 MHz, DMSO-d$_6$) □ 8.82 (s, 1H), 7.12 (d, J=2.4 Hz, 1H), 7.03 (dd, J=8.5, 2.4 Hz, 1H), 6.91 (d, J=8.5 Hz, 1H), 4.10 (t, J=6.4 Hz, 2H), 3.77 (s, 3H), 3.20 (t, J=6.4 Hz, 2H), 2.35 (s, 3H).

EXAMPLE 630B

3-{3-methoxy-4-[2-(4-methyl-1,3-thiazol-5-yl)ethoxy]phenyl}-8-[2-(4-morpholin-4-ylphenoxy)ethyl]-5,10-dihydro-11H-dibenzo[b,e][1,4]diazepin-11-one Example 578A (27.1 mg, 0.05 mmol), Example 630A (24.6 mg, 0.075 mmol), Pd(PPh$_3$)$_4$ (11.6 mg, 0.01 mmol), and cesium fluoride (22.8 mg, 0.15 mmol) were combined in a mixture of 1,2-dimethoxyethane and methanol (2:1, 1.5 mL) and heated at 85° C. for 4 hours. The reaction mixture was then cooled to room temperature, diluted with ethyl acetate, washed with water and brine, dried (MgSO$_4$), filtered and concentrated. The concentrate was purified by column chromatography on silica gel (0 to 2% methanol in dichloromethane). The material obtained from column chromatography was further purified by preparative HPLC to give the title compound as the TFA salt (12.5 mg, 32%). MS (ESI) m/e 329 (M+H)$^+$; $^1$H NMR (300 MHz, DMSO-d$_6$) □ 9.73 (s, 1H), 8.87 (s, 1H), 7.83 (s, 1H), 7.72 (d, J=8.3 Hz, 1H), 7.25 (d, J=1.2 Hz, 1H), 7.21 (d, J=1.8 Hz, 1H), 7.14-7.18 (m, 2H), 7.06 (d, J=8.3 Hz, 1H), 6.85-6.96 (m, 7H), 4.18 (t, J=6.1 Hz, 2H), 4.05 (t, J=6.4 Hz, 2H), 3.85 (s, 3H), 3.73-3.75 (m, 4H), 3.25 (t, J=6.1 Hz, 2H), 3.02-3.06 (m, 4H), 2.86 (t, J=6.4 Hz, 2H), 2.38 (s, 3H).

EXAMPLE 631

3-{3-methoxy-4-[(1-methyl-1H-imidazol-2-yl)methoxy]phenyl}-8-[2-(4-morpholin-4-ylphenoxy)ethyl]-5,10-dihydro-11H-dibenzo[b,e][1,4]diazepin-11-one

EXAMPLE 631A

2-[(4-bromo-2-methoxyphenoxy)methyl]-1-methyl-1H-imidazole

The title compound was prepared by substituting 2-chloromethyl-1-methyl-1H-imidazole hydrochloride and 4-bromo-2-methoxyphenol for Example 627A and Example 474, respectively, in Example 627B. MS (ESI) m/e 329 (M+H)$^+$; $^1$H NMR (300 MHz, DMSO-d$_6$) □ 7.17 (d, J=1.2 Hz, 1H), 7.11-7.15 (m, 2H), 7.05 (dd, J=8.5, 2.0 Hz, 1H), 6.85 (d. J=1.0 Hz, 1H), 5.09 (s, 2H), 3.77 (s, 3H), 3.67 (s, 3H).

EXAMPLE 631B

3-{3-methoxy-4-[(1-methyl-1H-imidazol-2-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting Example 631A for Example 630A in Example 630B. MS (ESI) m/e 632 (M+H)$^+$; $^1$H NMR (400 MHz, DMSO-d$_6$) □ 9.77 (s, 1H), 7.86 (s, 1H), 7.73-7.75 (m, 2H), 7.66 (d, J=1.5 Hz, 1H), 7.18-7.27 (m, 5H), 6.82-6.95 (m, 7H), 5.42 (s, 2H), 4.04 (t, J=6.6 Hz, 2H), 3.90 (s, 3H), 3.87 (s, 3H), 3.71-3.73 (m, 4H), 2.98-3.00 (m, 4H), 2.86 (t, J=6.7 Hz, 2H).

EXAMPLE 632

3-{4-[(3-fluorobenzyl)oxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting 1-bromomethyl-3-fluorobenzene for 4-chloromethylpyridine hydrochloride in Example 607. MS (ESI) m/e 646 (M+H)$^+$; $^1$H NMR (400 MHz, DMSO-d$_6$) ☐ 9.74 (s, 1H), 7.83 (s, 1H), 7.72 (d, J=8.3 Hz, 1H), 7.45 (m, 1H), 7.23-7.31 (m, 4H), 7.12-7.18 (m, 4H), 6.83-6.95 (m, 7H), 5.17 (s, 2H), 4.04 (t, J=6.8 Hz, 2H), 3.88 (s, 3H), 3.71-3.73 (m, 4H), 2.99-3.01 (m, 4H), 2.86 (t, J=6.8 Hz, 2H).

EXAMPLE 633

3-{4-[(2-fluorobenzyl)oxy]-3-methoxyphenyl}-8-[2-(4-morpholin-4-ylphenoxy)ethyl]-5,10-dihydro-11H-dibenzo[b,e][1,4]diazepin-11-one The title compound was prepared by substituting 1-bromomethyl-2-fluorobenzene for 4-chloromethylpyridine hydrochloride in Example 607. MS (ESI) m/e 646 (M+H)$^+$; $^1$H NMR (400 MHz, DMSO-d$_6$) ☐ 9.74 (s, 1H), 7.84 (s, 1H), 7.73 (d, J=8.3 Hz, 1H), 7.57 (td, J=7.6, 1.4 Hz, 1H), 7.44 (m, 1H), 7.17-7.28 (m, 7H), 6.85-6.97 (m, 7H), 5.17 (s, 2H), 4.05 (t, J=6.8 Hz, 2H), 3.85 (s, 3H), 3.73-3.75 (m, 4H), 3.01-3.06 (m, 4H), 2.87 (t, J=6.6 Hz, 2H).

EXAMPLE 634

3-[3-methoxy-4-(1,3-thiazol-2-ylmethoxy)phenyl]-8-[2-(4-morpholin-4-ylphenoxy)ethyl]-5,10-dihydro-11H-dibenzo[b,e][1,4]diazepin-11-one

EXAMPLE 634A 1,3-thiazol-2-ylmethanol1

Sodium borohydride (114 mg, 3 mmol) was added in portions to a solution of thiazole-2-carbaldehyde (226 mg, 2 mmol) in methanol (10 mL) at 0° C. The reaction mixture was stirred for 2 hours while allowing the temperature to slowly rise to room temperature. It was then quenched with 1 N sodium hydroxide solution, concentrated to remove methanol, and partitioned between ethyl acetate and water. The organic layer was further washed with water and brine, dried (MgSO$_4$), filtered, and concentrated to give the title compound. MS (DCI) m/e 116 (M+H)+; 1H NMR (300 MHz, DMSO-d$_6$) ☐ 7.73 (d, J=3.0 Hz, 1H), 7.63 (d, J=3.0 Hz, 1H), 6.02 (t, J=5.8 Hz, 1H), 4.73 (d, J=6.1 Hz, 2H).

EXAMPLE 634B

2-[(4-bromo-2-methoxyphenoxy)methyl]-1,3-thiazole

The title compound was prepared by substituting Example 642A for 2-(4-methyl-thiazol-5-yl)-ethanol in Example 630A. MS (DCI) m/e 301 (M+H)$^+$; $^1$H NMR (300 MHz, DMSO-d$_6$) ☐ 7.84 (d, J=3.4 Hz, 1H), 7.78 (d, J=3.4 Hz, 1H), 7.17 (m, 1H), 7.04-7.06 (m, 2H), 5.40 (s, 2H), 3.81 (s, 3H).

EXAMPLE 634C

3-[3-methoxy-4-(1,3-thiazol-2-ylmethoxy)phenyl]-8-[2-(4-morpholin-4-ylphenoxy)ethyl]-5,10-dihydro-11H-dibenzo[b,e][1,4]diazepin-11-one The title compound was prepared by substituting Example 634B for Example 630A in Example 630B. MS (ESI) m/e 635 (M+H)$^+$; $^1$H NMR (400 MHz, DMSO-d$_6$) ☐ 9.74 (s, 1H), 7.82-7.86 (m, 2H), 7.79 (d, J=3.4 Hz, 1H), 7.73 (d, J=8.3 Hz, 1H), 7.16-7.25 (m, 5H), 6.83-6.95 (m, 7H), 5.47 (s, 2H), 4.04 (t, J=6.6 Hz, 2H), 3.89 (s, 3H), 3.71-3.73 (m, 4H), 2.98-3.01 (m, 4H), 2.86 (t, J=6.6 Hz, 2H).

EXAMPLE 635

3-{3-methoxy-4-[(1-methyl-1H-imidazol-5-yl)methoxy]phenyl}-8-[2-(4-morpholin-4-ylphenoxy)ethyl]-5,10-dihydro-11H-dibenzo[b,e][1,4]diazepin-11-one

EXAMPLE 635A

5-[(4-bromo-2-methoxyphenoxy)methyl]-1-methyl-1H-imidazole

The title compound was prepared by substituting (3-methyl-3H-imidazol-4-yl)-methanol for 2-(4-methyl-thiazol-5-yl)-ethanol in Example 630A. MS (DCI) m/e 297 (M+H)$^+$; $^1$H NMR (300 MHz, DMSO-d$_6$) ☐ 7.63 (s, 1H), 7.13 (s, 1H), 7.05-7.07 (m, 2H), 6.97 (d, J=0.7 Hz, 1H), 5.05 (s, 2H), 3.76 (s, 3H), 3.63 (s, 3H).

EXAMPLE 635B

3-{3-methoxy-4-[(1-methyl-1H-imidazol-5-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting Example 635A for Example 630A in Example 630B. MS (ESI) m/e 632 (M+H)$^+$; $^1$H NMR (400 MHz, DMSO-d$_6$) ☐9.75 (s, 1H), 9.09 (s, 1H), 7.84 (s, 1H), 7.80 (s, 1H), 7.72 (d, J=8.3 Hz, 1H), 7.23-7.27 (m, 3H), 7.16-7.20 (m, 2H), 6.81-6.94 (m, 7H), 5.27 (s, 2H), 4.03 (t, J=6.6 Hz, 2H), 3.91 (s, 3H), 3.85 (s, 3H), 3.70-3.72 (m, 4H), 2.97-2.99 (m, 4H), 2.85 (t, J=6.6 Hz, 2H).

EXAMPLE 636

3-{4-[(1,3-dimethyl-1H-pyrazol-5-yl)methoxy]-3-methoxyphenyl}-8-[2-(4-morpholin-4-ylphenoxy)ethyl]-5,10-dihydro-11H-dibenzo[b,e][1,4]diazepin-11-one

EXAMPLE 636A

5-[(4-bromo-2-methoxyphenoxy)methyl]-1,3-dimethyl-1H-pyrazole

The title compound was prepared by substituting (2,5-dimethyl-2H-pyrazol-3-yl)-methanol for 2-(4-methyl-thiazol-5-yl)-ethanol in Example 630A. MS (DCI) m/e 311 (M+H) $^1$H NMR (300 MHz, DMSO-d$_6$) ☐ 7.13 (m, 1H), 7.04-7.06 (m, 2H), 6.10 (s, 1H), 5.06 (s, 2H), 3.77 (s, 3H), 3.73 (s, 3H), 2.10 (s, 3H).

EXAMPLE 636B

3-{4-[(1,3-dimethyl-1H-pyrazol-5-yl)methoxy]-3-methoxyphenyl}-8-[2-(4-morpholin-4-ylphenoxy)ethyl]-5,10-dihydro-11H-dibenzo[b,e][1,4]diazepin-11-one Example 644B was prepared by substituting Example 636A for Example 630A in Example 630B. MS (ESI) m/e 646 (M+H)$^+$; $^1$H NMR (400 MHz, DMSO-d$_6$) □9.77 (s, 1H), 7.86 (s, 1H), 7.72 (d, J=8.2 Hz, 1H), 7.26 (d, J=1.5 Hz, 1H), 7.17-7.22 (m, 4H), 6.86-6.99 (m, 7H), 6.14 (s, 1H), 5.13 (s, 2H), 4.06 (t, J=6.9 Hz, 2H), 3.85 (s, 3H), 3.76 (s, 3H), 3.74-3.76 (m, 4H), 3.06-3.08 (m, 4H), 2.87 (t, J=6.7 Hz, 2H), 2.12 (s, 3H).

Example 6373-[4-(1H-imidazol-4-ylmethoxy)-3-methoxyphenyl]-8-[2-(4-morpholin-4-ylphenoxy)ethyl]-5,10-dihydro-11H-dibenzo[b,e][1,4]diazepin-11-one

EXAMPLE 637A

4-[(4-bromo-2-methoxyphenoxy)methyl]-1-trityl-1H-imidazole

The title compound was prepared by substituting (1-trityl-1H-imidazol-4-yl)-methanol for 2-(4-methyl-thiazol-5-yl)-ethanol in Example 630A. MS (ESI) m/e 523 (M−H)$^-$; $^1$H NMR (300 MHz, DMSO-d$_6$) □7.35-7.44 (m, 10H), 7.05-7.10 (m, 7H), 7.01 (d, J=1.4 Hz, 2H), 6.97 (d, J=1.4 Hz, 1H), 4.90 (s, 2H), 3.71 (s, 3H).

EXAMPLE 637B

3-{3-methoxy-4-[(1-trityl-1H-imidazol-4-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting Example 637A for Example 630A in Example 630B. MS (ESI) m/e 861 (M+H)$^+$; $^1$H NMR (400 MHz, DMSO-d$_6$) □9.76 (s, 1H), 7.85 (s, 1H), 7.73 (d, J=8.2 Hz, 1H), 7.35-7.42 (m, 10H), 7.25 (d, J=1.2 Hz, 1H), 7.13-7.19 (m, 4H), 7.07-7.09 (m, 6H), 7.02 (d, J=0.9 Hz, 1H), 6.81-6.95 (m, 8H), 4.97 (s, 2H), 4.03 (t, J=6.7 Hz, 2H), 3.80 (s, 3H), 3.70-3.72 (m, 4H), 2.95-2.97 (m, 4H), 2.92 (t, J=6.7 Hz, 2H).

EXAMPLE 637C

3-[4-(1H-imidazol-4-ylmethoxy)-3-methoxyphenyl]-8-[2-(4-morpholin-4-ylphenoxy)ethyl]-5,10-dihydro-11H-dibenzo[b,e][1,4]diazepin-11-one A mixture of Example 637B in methanol (2 mL) was treated with acetic acid (5 mL) and stirred at room temperature overnight. It was then heated for 7 hours at 45° C., cooled to room temperature and concentrated. Additional water was added and a precipitate formed. The precipitate was filtered and then purified by preparative HPLC to give the title compound as the TFA salt (6.0 mg, 14% yield over two steps). MS (ESI) m/e 619 (M+H)$^+$; $^1$H NMR (400 MHz, DMSO-d$_6$) □14.3 (br s, 1H), 9.75 (s, 1H), 9.10 (s, 1H), 7.85 (s, 1H), 7.81 (s, 1H), 7.74 (d, J=8.3 Hz, 1H), 7.17-7.28 (m, 5H), 6.82-6.95 (m, 7H), 5.19 (s, 2H), 4.04 (d, J=6.6 Hz, 2H), 3.85 (s, 3H), 3.71-3.73 (m, 4H), 2.98-3.00 (m, 4H), 2.86 (t, J=6.6 Hz, 2H).

EXAMPLE 638

3-{3-methoxy-4-[(2R)-pyrrolidin-2-ylmethoxy]phenyl}-8-[2-(4-morpholin-4-ylphenoxy)ethyl]-5,10-dihydro-11H-dibenzo[b,e][1,4]diazepin-11-one

EXAMPLE 638A tert-butyl (2R)-2-[(4-bromo-2-methoxyphenoxy)methyl]pyrrolidine-1-carboxylate The title compound was prepared by substituting N-tert-butoxycarbonyl-(R)-2-hydroxymethylpyrrolidine for 2-(4-methyl-thiazol-5-yl)-ethanol in Example 630A. MS (ESI) m/e 311 (M+H)$^+$; $^1$H NMR (300 MHz, DMSO-d$_6$) □ 7.12 (m, 1H), 7.02 (dd, J=8.5, 2.1 Hz, 1H), 6.96 (m, 1H), 3.97-4.05 (m, 2H), 3.88 (m, 1H), 3.78 (s, 3H), 3.21-3.29 (m, 2H), 1.89-1.97 (m, 3H), 1.78 (m, 1H), 1.39 (d, J=7.0 Hz, 9H).

EXAMPLE 638B tert-butyl (2R)-2-[(2-methoxy-4-{8-[2-(4-morpholin-4-ylphenoxy)ethyl]-11-oxo-10,11-dihydro-5H-dibenzo[b,e][1,4]diazepin-3-yl}phenoxy)methyl]pyrrolidine-1-carboxylate The title compound was prepared by substituting Example 638A for Example 630A in Example 630B. MS (ESI) m/e 721 (M+H)$^+$;

EXAMPLE 638C

3-{3-methoxy-4-[2R)-pyrrolidin-2-ylmethoxy]phenyl}-8-[2-(4-morpholin-4-ylphenoxy)ethyl]-5,10-dihydro-11H-dibenzo[b,e][1,4]diazepin-11-one A mixture of Example 638B in dichloromethane was treated with trifluoroacetic acid (100 μL) and stirred at ambient temperature for several hours, heated at 40° C. for 1 day and then heated at 60° C. for 2 days. When the reaction had reached 80% completion, heating was discontinued and the reaction mixture was cooled to room temperature. The reaction mixture was concentrated to remove dichloromethane and purified by preparative HPLC to give the title compound as the TFA salt. MS (ESI) m/e 619 (M+H)$^+$; $^1$H NMR (400 MHz, DMSO-d$_6$) □9.75 (s, 1H), 7.85 (s, 1H), 7.74 (d, J=8.3 Hz, 1H), 7.27 (dd, J=4.3, 1.8 Hz, 2H), 7.13-7.22 (m, 3H), 6.82-6.95 (m, 7H), 4.29 (dd, J=10.7, 3.4 Hz, 1H), 4.14 (m, 1H), 4.05 (t, J=6.8 Hz, 2H), 3.91-4.00 (m, 2H), 3.89 (s, 3H), 3.71-3.74 (m, 4H), 3.19-3.29 (m, 2H), 2.98-3.01 (m, 4H), 2.86 (t, J=6.8 Hz, 2H), 2.15 (m, 1H), 1.88-2.06 (m, 2H), 1.77 (m, 1H).

EXAMPLE 639

3-[4-(3-aminopropoxy)-3-methoxyphenyl]-8-[2-(4-morpholin-4-ylphenoxy)ethyl]-5,10-dihydro-11H-dibenzo[b,e][1,4]diazepin-11-one

EXAMPLE 639A

2-[3-(2-methoxy-4-{8-[2-(4-morpholin-4-ylphenoxy)ethyl]-11-oxo-10,11-dihydro-5H-dibenzo[b,e][1,4]diazepin-3-yl}phenoxy)propyl]-1H-isoindole-1,3(2H)-dione A mixture of Example 474 (26.9 mg, 0.05 mmol) and N-(3-bromopropyl)phthalimide (16.1 mg, 0.06 mmol) was treated with KOH (3.4 mg, 0.06 mmol) and stirred at room temperature for 5 hours. The reaction mixture was then diluted with ethyl acetate, washed with water and brine, dried (MgSO$_4$), filtered and concentrated. The concentrate was purified by silica gel column chromatography (0 to 60% ethyl acetate in dichloromethane) to give the title compound. MS (ESI) m/e 725 (M+H)$^+$; $^1$H NMR (300 MHz, DMSO-d$_6$) □ 9.76 (s, 1H), 7.70-7.88 (m, 5H), 7.71 (d, J=8.1 Hz, 1H), 7.23 (d, J=1.7 Hz, 1H), 7.10-7.16 (m, 3H), 7.00 (d, J=8.5 Hz, 1H), 6.80-6.95 (m, 7H), 3.99-4.08 (m, 4H), 3.78 (t, J=6.4 Hz, 2H), 3.69-3.73 (m, 4H), 3.62 (s, 3H), 2.95-2.98 (m, 4H), 2.86 (t, J=6.8 Hz, 2H), 2.06-2.12 (m, 2H).

EXAMPLE 639B

3-[4-(3-aminopropoxy)-3-methoxyphenyl]-8-[2-(4-morpholin-4-ylphenoxy)ethyl]-5,10-dihydro-11H-dibenzo[b,e][1,4]diazepin-11-one A mixture of Example 639A in ethanol (5 mL) was treated with hydrazine hydrate (100 µL) and heated at 60° C. for 5 hours. A second portion of hydrazine hydrate (100 µL) was added and heating was continued for an additional 3 hours. The reaction was then cooled to room temperature, diluted with ethyl acetate, washed with a 10% aqueous citric acid solution, water, and brine, dried (MgSO$_4$), filtered, and concentrated. The residue was purified by preparative HPLC to give the title compound as the TFA salt (12.0 mg, 34% yield over two steps). MS (ESI) m/e 595 (M+H)$^+$; $^1$H NMR (400 MHz, DMSO-d$_6$) □ 9.74 (s, 1H), 7.85 (s, 1H), 7.72-7.74 (m, 3H), 7.26 (d, J=1.2 Hz, 1H), 7.23 (d, J=1.8 Hz, 1H), 7.16-7.20 (m, 2H), 7.08 (d, J=8.3 Hz, 1H), 6.83-6.95 (m, 7H), 4.11 (t, J=6.0 Hz, 2H), 4.05 (t, J=6.8 Hz, 2H), 3.86 (s, 3H), 3.71-3.74 (m, 4H), 2.99-3.01 (m, 6H), 2.86 (t, J=6.8 Hz, 2H), 2.03 (qd, J=6.7, 6.4 Hz, 2H).

EXAMPLE 640

3-(3-methoxy-4-{[(2S)-5-oxotetrahydrofuran-2-yl]methoxy}phenyl)-8-[2-(4-morpholin-4-ylphenoxy)ethyl]-5,10-dihydro-11H-dibenzo[b,e][14]diazepin-11-one

EXAMPLE 640A (5S)-5-[(4-bromo-2-methoxyphenoxy)methyl]dihydrofuran-2(3H)-one The title compound was prepared by substituting 5-hydroxymethyl-dihydro-furan-2-one for 2-(4-methyl-thiazol-5-yl)-ethanol in Example 630A. MS (ESI) m/e 301 (M+H)$^+$; $^1$H NMR (300 MHz, DMSO-d$_6$) □ 7.14 (d, J=2.4 Hz, 1H), 7.06 (dd, J=8.5, 2.4 Hz, 1H), 6.93 (d, J=8.5 Hz, 1H), 4.85 (m, 1H), 4.17 (dd, J=11.2, 2.9 Hz, 1H), 4.06 (dd, J=11.2, 5.4 Hz, 1H), 3.78 (s, 3H), 2.46-2.67 (m, 2H), 2.31 (m, 1H), 2.05 (m, 1H).

EXAMPLE 640B 3-(3-methoxy-4-{[(2S)-5-oxotetrahydrofuran-2-yl]methoxy}phenyl)-8-[2-(4-morpholin-4-ylphenoxy)ethyl]-5,10-dihydro-11H-dibenzo[b,e][1,4]diazepin-11-one The title compound was prepared by substituting Example 640A for Example 630A in Example 630B. MS (ESI) m/e 636 (M+H)$^+$; $^1$H NMR (300 MHz, DMSO-d$_6$) □ 9.74, (s, 1H), 7.84 (s, 1H), 7.73 (d, J=8.3 Hz, 1H), 7.26 (d, J=1.2 Hz, 1H), 7.22 (d, J=2.2 Hz, 1H), 7.15-7.19 (m, 2H), 7.09 (d, J=8.3 Hz, 1H), 6.84-6.95 (m, 7H), 4.89 (m, 1H), 4.24 (dd, J=10.9, 2.6 Hz, 1H), 4.13 (dd, J=11.0, 5.5 Hz, 1H), 4.05 (t, J=6.8 Hz, 2H), 3.86 (s, 3H), 3.72-2.74 (m, 4H), 3.01-3.03 (m, 4H), 2.86 (t, J=6.8 Hz, 2H), 2.52-2.69 (m, 2H), 2.34 (m, 1H), 2.10 (m, 1H).

EXAMPLE 641

3-[3-methoxy-4-(1,3-thiazol-4-ylmethoxy)phenyl]-8-(2-morpholin-4-ylethyl)-5,10-dihydro-11H-dibenzo[b,e][1,4]diazepin-11-one

EXAMPLE 641A 2-(3-chloro-11-oxo-10,11-dihydro-5H-dibenzo[b,e][1,4]diazepin-8-yl)ethyl methanesulfonate A mixture of Example 204A (1.8 g, 5.58 mmol) in DME (30 mL) was treated with triethylamine (2.33 mL, 16.7 mmol), followed by methanesulfonyl chloride (648 µL, 8.4 mmol) and stirred at ambient temperature for one hour. The reaction mixture was then diluted with ethyl acetate, washed with water and brine, dried (MgSO$_4$), filtered, and concentrated to give the title compound (2 g, 98% yield). MS (ESI) m/e 367 (M+H)$^+$; $^1$H NMR (300 MHz, DMSO-d$_6$) □ 9.89 (s, 1H), 8.03 (s, 1H), 7.68 (d, J=8.5 Hz, 1H). 7.06 (d, J=2.0 Hz, 1H), 6.85-6.94 (m, 4H), 4.33 (t, J=6.6 Hz, 2H), 3.11 (s, 3H), 2.86 (t, J=6.6 Hz, 2H).

EXAMPLE 641B 3-chloro-8-(2-morpholin-4-ylethyl)-5,10-dihydro-11H-dibenzo[b,e][1,4]diazepin-11-one A mixture of Example 641A (360 mg, 0.98 mmol) in DMF (5 mL) was treated with morpholine (200 µL) and heated at 50° C. for 24 hours. The mixture was then cooled to room temperature, diluted with ethyl acetate, washed with water and brine, dried (MgSO$_4$), filtered and concentrated. The concentrate was purified by column chromatography on silica gel to provide the title compound. MS (ESI) m/e 358 (M+H)$^+$; $^1$H NMR (300 MHz, DMSO-d$_6$) □ 9.84 (s, 1H), 7.97 (s, 1H), 7.67 (d, J=8.5 Hz, 1H), 7.05 (d, J=2.0 Hz, 1H), 6.91 (dd, J=8.5, 2.0 Hz, 1H), 6.81-6.89 (m, 3H), 3.55-3.58 (m, 4H), 2.57-2.62 (m, 2H), 2.37-2.45 (m, 6H).

EXAMPLE 641C

4-{[2-methoxy-4-(4,4,5,5-tetramethyl-1,3,2-dioxaborolan-2-yl)phenoxy]methyl}-1,3-thiazole The title compound was prepared by substituting 4-chloromethylthiazole for 4-chloromethylpyridine hydrochloride and 2-methoxy-4-(4,4,5,5-tetramethyl-[1,3,2]dioxaborolan-2-yl)-phenol for Example 474, respectively, in Example 607. MS (ESI) m/e 348 (M+H)$^+$, $^1$H NMR (300 MHz, DMSO-d$_6$) δ 9.12 (d, J=2 Hz, 1H), 7.77 (d, J=2 Hz, 1H), 7.25 (dd, J=1.4, 8.1 Hz, 1H), 7.11-7.15 (m, 2H), 5.22 (s, 2H), 3.76 (s, 3H), 1.28 (s, 12H).

EXAMPLE 641D

3-[3-methoxy-4-(1,3-thiazol-4-ylmethoxy)phenyl]-8-(2-morpholin-4-ylethyl)-5,10-dihydro-11H-dibenzo[b,e][1,4]diazepin-11-one A mixture of Example 641B (71.6 mg, 0.2 mmol), Example 641C (76.4 mg, 0.22 mmol), palladium acetate (9.0 mg, 0.04 mmol), Cy-MAP ligand (31.5 mg, 0.08 mmol) and cesium fluoride (91.1 mg, 0.6 mmol) in DME (4 mL) and methanol (2 mL) was heated at 85° C. for 2 hours. It was then cooled to room temperature and filtered through Celite rinsing with DME and methanol. The concentrate was purified by column chromatography on silica gel (0 to 3% methanol in dichloromethane). The material was further purified by preparative HPLC to give the title compound. MS (ESI) m/e (M+H)$^+$; $^1$H NMR (400 MHz, DMSO-d$_6$) ⃞9.81 (s, 2H), 9.14 (d, J=1.8 Hz, 1H), 7.91 (s, 1H), 7.79 (d, J=2.2 Hz, 1H), 7.73 (d, J=8.3 Hz, 1H), 7.27 (d, J=1.5 Hz, 1H), 7.16-7.24 (m, 3H), 6.99 (d, J=7.7 Hz, 1H), 6.85-6.89 (m, 2H), 5.25 (s, 2H), 3.94-4.04 (m, 2H), 3.83 (s, 3H), 3.59-3.71 (m, 2H), 3.41-3.54 (m, 2H), 3.21-3.30 (m, 2H), 3.02-3.17 (m, 2H), 2.84-2.88 (m, 2H).

EXAMPLE 642

3-(4-{[(2R,3S,4R)-3,4-dihydroxy-5-oxotetrahydrofuran-2-yl]methoxy}-3-methoxyphenyl)-8-[2-(4-morpholin-4-ylphenoxy)ethyl]-5,10-dihydro-11H-dibenzo[b,e][1,4]diazepin-11-one

EXAMPLE 642A (3aR,6R,6aR)-6-[(4-bromo-2-methoxyphenoxy)methyl]-2,2-dimethyldihydrofuro[3,4-d][1,3]dioxol-4(3aH)-one The title compound was prepared by substituting (R,R,R)-6-hydroxymethyl-2,2-dimethyl-dihydro-furo[3,4-d][1,3]dioxol-4-one for 2-(4-methyl-thiazol-5-yl)-ethanol in Example 630A. MS (ESI) m/e 405 (M+MeOH+H)$^+$; $^1$H NMR (300 MHz, DMSO-d$_6$) ⃞ 7.15 (d, J=2.4 Hz, 1H), 7.07 (dd, J=2.4 8.5 Hz, 1H), 6.91 (d, J=8.5 Hz, 1H), 4.95-5.00 (m, 3H), 4.24 (qd, J=10.9, 2.5 Hz, 2H), 3.78 (s, 3H), 1.39 (s, 3H), 1.34 (s, 3H).

EXAMPLE 642B 3-(4-{[(3 aR,4R,6aR)-2,2-dimethyl-6-oxotetrahydrofuro[3,4-d][1,3]dioxol-4-yl]methoxy}-3-methoxyphenyl)-8-[2-(4-morpholin-4-ylphenoxy)ethyl]-5,10-dihydro-11H-dibenzo[b,e][1,4]diazepin-11-one The title compound was prepared by substituting Example 642A for Example 630A in Example 630B. MS (ESI) m/e 708 (M+H)$^+$; $^1$H NMR (400 MHz, DMSO-d$_6$) ⃞9.74 (s, 1H), 7.84 (s, 1H), 7.73 (d, J=8.3 Hz, 1H), 7.25 (d, J=1.2 Hz, 1H), 7.22 (d, J=1.5 Hz, 1H), 7.15-1.19 (m, 2H), 7.06 (d, J=8.3 Hz, 1H), 6.81-6.95 (m, 7H), 5.05 (d, J=5.5 Hz, 1H), 4.96-4.99 (m, 2H), 4.25-4.36 (m, 2H), 4.04 (t, J=6.8 Hz, 2H), 3.86 (s, 3H), 3.70-3.72 (m, 4H), 2.95-2.98 (m, 4H), 2.86 (t, J=6.6 Hz, 2H), 1.40 (s, 3H), 1.36 (s, 3H).

EXAMPLE 642C 3-(4-{[(2R,3S,4R)-3,4-dihydroxy-5-oxotetrahydrofuran-2-yl]methoxy}-3-methoxyphenyl)-8-[2-(4-morpholin-4-ylphenoxy)ethyl]-5,10-dihydro-11H-dibenzo[b,e][1,4]diazepin-11-one A mixture of Example 642B (11.2 mg, 0.016 mmol) in dichloromethane (1 mL) was treated with trifluoroacetic acid (50 μL, 0.65 mmol) and stirred at room temperature. The reaction mixture was then concentrated and purified by preparative HPLC. MS (ESI) m/e 668 (M+H)$^+$; $^1$H NMR (300 MHz, DMSO-d$_6$) ⃞9.74 (s, 1H), 7.84 (s, 1H), 7.73 (d, J=8.3 Hz, 1H), 7.25 (d, J=1.5 Hz, 1H), 7.22 (d, J=1.8 Hz, 1H), 7.15-1.19 (m, 2H), 7.07 (d, J=8.3 Hz, 1H), 6.85-6.96 (m, 7H), 4.73 (d, J=5.5 Hz, 1H), 4.59 (t, J=3.4 Hz, 1H), 4.25-4.29 (m, 3H), 4.05 (t, J=6.8 Hz, 2H), 3.86 (s, 3H), 3.75-3.85 (m, 2H), 3.73-3.75 (m, 4H), 3.03-3.05 (m, 4H), 2.87 (t, J=6.6 Hz, 2H).

EXAMPLE 643

N-{4-[(2-methoxy-4-{8-[2-(4-morpholin-4-ylphenoxy)ethyl]-11-oxo-10,11-dihydro-5H-dibenzo[b,e][1,4]diazepin-3-yl}phenoxy)methyl]-1,3-thiazol-2-yl}acetamide

EXAMPLE 643A

N-[4-(chloromethyl)-1,3-thiazol-2-yl]acetamide

A mixture of acetylthiourea (591 mg, 5 mmol) and 1,3-dichloroacetone (667 mg, 5.25 mmol) in acetone (15 mL) was heated at reflux for 7 hours, cooled to room temperature, diluted with ethyl acetate, washed with water and brine, dried (MgSO$_4$), filtered and concentrated. The concentrate was purified by column chromatography to give the title compound. MS (DCI) m/e 191 (M+H)$^+$; $^1$H NMR (300 MHz, DMSO-d$_6$) ⃞12.21 (s, 1H), 7.22 (s, 1H), 4.70 (s, 2H), 2.13 (s, 3H).

EXAMPLE 643B

N-14-[{4-bromo-2-methoxyphenoxy)methyl]-1,3-thiazol-2-yl}acetamide

The title compound was prepared by substituting Example 643A and 4-bromo-2-methoxyphenol for N-(3-bromopropyl)phthalimide and Example 474, respectively, in Example 639A. MS (ESI) m/e 357 (M+H)$^+$; $^1$H NMR (300 MHz, DMSO-d$_6$) ⃞12.15 (s, 1H), 7.17 (s, 1H), 7.12 (d, J=1.7 Hz, 1H), 7.02-7.03 (m, 2H), 5.01 (s, 2H), 3.77 (s, 3H), 2.13 (s, 3H).

EXAMPLE 643C

N-{4-[(2-methoxy-4-{8-[2-(4-morpholin-4-ylphenoxy)ethyl]-11-oxo-10,11-dihydro-5H-dibenzo[b,e][1,4]diazepin-3-yl}phenoxy)methyl]-1,3-thiazol-2-yl}acetamide The title compound was prepared by substituting Example 643B for Example 630A in Example 630B. MS (ESI) m/e 668 (M+H)$^+$; $^1$H NMR (300 MHz, DMSO-d$_6$) ⃞12.13 (s, 1H), 9.73 (s, 1H), 7.82 (s, 1H), 7.71 (d, J=8.3 Hz, 1H), 7.24 (d, J=1.5 Hz, 1H), 7.13-7.20 (m, 5H), 6.82-6.94 (m, 7H), 5.07 (s, 2H), 4.04 (t, J=6.8 Hz, 2H), 3.84 (s, 3H), 3.71-3.73 (m, 4H), 2.99-3.02 (m, 4H), 2.85 (t, J=6.8 Hz, 2H), 2.13 (s, 3H).

EXAMPLE 644

3-[3-methoxy-4-(tetrahydrofuran-3-yloxy)phenyl]-8-[2-(4-morpholin-4-ylphenoxy)ethyl]-5,10-dihydro-11H-dibenzo[b,e][1,4]diazepin-11-one

EXAMPLE 644A 3-(4-bromo-2-methoxyphenoxy)tetrahydrofuran

The title compound was prepared by substituting 3-hydroxytetrahydrofuran for 2-(4-methyl-thiazol-5-yl)-ethanol in Example 630A. MS (DCI) m/e 273 (M+H)$^+$; $^1$H NMR (300 MHz, DMSO-d$_6$) ⃞7.13 (d, J=2.4 Hz, 1H), 7.04 (dd, J=8.5, 2.4 Hz, 1H), 6.89 (d, J=8.8 Hz, 1H), 4.96 (m, 1H), 3.77 (s, 3H), 3.70-3.87 (m, 4H), 2.16 (m, 1H), 1.93 (m, 1H).

EXAMPLE 644B

3-[3-methoxy-4-(tetrahydrofuran-3-yloxy)phenyl]-8-[2-(4-morpholin-4-ylphenoxy)ethyl]-5,10-dihydro-11H-dibenzo[b,e][1,4]diazepin-11-one The title compound was prepared by substituting Example 644A for Example 630A in Example 630B. MS (ESI) m/e 608 (M+H)$^+$; $^1$H NMR (300 MHz, DMSO-d$_6$) □9.77 (s, 1H), 7.86 (s, 1H), 7.72 (d, J=8.2 Hz, 1H), 7.25 (s, 1H), 7.21 (d, J=1.8 Hz, 1H), 7.15-7.19 (m, 2H), 7.04 (d, J=8.5 Hz, 1H), 6.86-6.98 (m, 7H), 5.04 (m, 1H), 4.05 (t, J=6.7 Hz, 2H), 3.81-3.90 (m, 6H), 3.74-3.78 (m, 5H), 3.04-3.08 (m, 4H), 2.87 (t, J=6.7 Hz, 2H), 2.21 (m, 1H), 1.99 (m, 1H).

EXAMPLE 645 tert-butyl 4-(2-{3-[3-methoxy-4-(1,3-thiazol-4-ylmethoxy)phenyl]-1-oxo-10,11-dihydro-5H-dibenzo[b,e][1,4]diazepin-8-yl}ethyl)piperazine-1-carboxylate

EXAMPLE 645A tert-butyl 4-[2-(3-chloro-11-oxo-10,11-dihydro-5H-dibenzo[b,e][1,4]diazepin-8-yl)ethyl]piperazine-1-carboxylate The title compound was prepared by substituting piperazine-1-carboxylic acid tert-butyl ester for morpholine in Example 641B. MS (ESI) m/e 457 (M+H)$^+$.

EXAMPLE 645B tert-butyl 4-(2-{3-[3-methoxy-4-(1,3-thiazol-4-ylmethoxy)phenyl]-1-oxo-10,11-dihydro-5H-dibenzo[b,e][1,4]diazepin-8-yl}ethyl)piperazine-1-carboxylate The title compound was prepared by substituting Example 645A for Example 641B in Example 641D. MS (ESI) m/e 642 (M+H)$^+$; $^1$H NMR (300 MHz, DMSO-d$_6$) □9.83 (s, 1H), 9.13 (d, J=1.8 Hz, 1H), 7.91 (s, 1H), 7.79 (d, J=1.5 Hz, 1H), 7.72 (d, J=8.2 Hz, 1H), 7.25 (s, 1H), 7.15-7.22 (m, 4H), 6.97 (d, J=7.9 Hz, 1H), 6.84-6.86 (m, 2H), 5.24 (s, 2H), 3.97-4.05 (m, 2H), 3.84 (s, 3H), 3.40-3.60 (m, 2H), 3.25-3.28 (m, 2H), 2.94-3.17 (m, 4H), 2.83-2.86 (m, 2H), 1.41 (s, 9H).

EXAMPLE 646 tert-butyl (3 S)-3-(2-methoxy-4-{8-[2-(4-morpholin-4-ylphenoxy)ethyl]-11-oxo-10,11-dihydro-5H-dibenzo[b,e][1,4]diazepin-3-yl}phenoxy)pyrrolidine-1-carboxylate

EXAMPLE 646A tert-butyl (3 S)-3-(4-bromo-2-methoxyphenoxy)pyrrolidine-1-carboxylate Example 654A was prepared by substituting N-tert-butoxycarbonyl-(S)-3-pyrrolidinol for 2-(4-methyl-thiazol-5-yl)-ethanol in Example 630A. MS (ESI) m/e 394 (M+Na)+; $^1$H NMR (300 MHz, DMSO-d$_6$) □7.15 (d, J=2.4 Hz, 1H), 7.05 (dd, J=2.4, 8.8 Hz, 1H), 6.94 (d, J=8.5 Hz, 1H), 4.92 (m, 1H), 3.77 (s, 3H), 3.35-3.52 (m, 4H), 1.99-2.06 (m, 2H), 1.39 (s, 9H).

EXAMPLE 646B tert-butyl (3 S)-3-(2-methoxy-4-{8-[2-(4-morpholin-4-ylphenoxy)ethyl]-11-oxo-10,11-dihydro-5H-dibenzo[b,e][1,4]diazepin-3-yl}phenoxy)pyrrolidine-1-carboxylate A mixture of Example 578A (108 mg, 0.2 mmol), Example 646A (149 mg, 0.4 mmol), palladium acetate (4.5 mg, 0.02 mmol), biphenyl-2-yl-dicyclohexyl-phosphane (14 mg, 0.04 mmol) and cesium fluoride (91 mg, 0.6 mmol) in DME (4 mL) and methanol (2 mL) was heated at 85° C. for 2 hours, cooled to room temperature, filtered through Celite rinsing with DME and methanol and concentrated. The concentrate was purified by column chromatography on silica gel (0 to 3% methanol in dichloromethane). The product was further purified by preparative HPLC to give the title compound as the TFA salt. MS (ESI) m/e 707 (M+H)$^+$; $^1$H NMR (300 MHz, DMSO-d$_6$) □9.77 (s, 1H), 7.86 (s, 1H), 7.73 (d, J=8.3 Hz, 1H), 7.16-7.26 (m, 4H), 7.09 (d, J=8.5 Hz, 1H), 6.81-6.96 (m, 7H), 5.00 (m, 1H), 4.04 (t, J=6.8 Hz, 2H), 3.85 (s, 3H), 3.30-3.90 (m, 10H), 2.98-3.01 (m, 4H), 2.84-2.89 (m, 2H), 1.41 (d, J=3.7 Hz, 9H).

EXAMPLE 647

4-(2-{3-[3-methoxy-4-(1,3-thiazol-4-ylmethoxy)phenyl]-11-oxo-10,11-dihydro-5H-dibenzo[b,e][1,4]diazepin-8-yl}ethoxy)benzonitrile

EXAMPLE 647A

4-[2-(3-chloro-11-oxo-10,11-dihydro-5H-dibenzo[b,e][1,4]diazepin-8-yl)ethoxy]benzonitrile The title compound was prepared by substituting 4-hydroxybenzonitrile for 4-bromo-2-methoxyphenol and Example 204A for 2-(4-methyl-thiazol-5-yl)-ethanol in Example 630A. MS (ESI) m/e 390 (M+H)$^+$; $^1$H NMR (300 MHz, DMSO-d$_6$) □9.88 (s, 1H), 8.00 (s, 1H), 7.72-7.77 (m, 2H), 7.67 (d, J=8.5 Hz, 1H), 7.08-7.12 (m, 2H), 7.06 (d, J=2.0 Hz, 1H), 6.89-6.95 (m. 4H), 4.21 (t, J=6.6 Hz, 2H), 2.92 (t, J=6.6 Hz, 2H).

EXAMPLE 647B 4-(2-{3-[3-methoxy-4-(1,3-thiazol-4-ylmethoxy)phenyl]-11-oxo-10,11-dihydro-5H-dibenzo[b,e][1,4]diazepin-8-yl}ethoxy)benzonitrile The title compound was prepared by substituting Example 647A for Example 646A and Example 641C for Example 578A in Example 646B. MS (ESI) m/e 575 (M+H)$^+$; $^1$H NMR (300 MHz, DMSO-d$_6$) □9.77 (s, 1H), 9.14 (d, J=1.7 Hz, 1H), 7.86 (s, 1H), 7.80 (d, J=1.7 Hz, 1H), 7.70-7.77 (m, 3H), 7.08-7.26 (m, 7H), 6.89-6.97 (m, 3H), 5.25 (s, 2H), 4.21 (t, J=6.6 Hz, 2H), 3.85 (s, 3H), 2.92 (t, J=6.4 Hz, 2H).

EXAMPLE 648 tert-butyl 4-[2-(3-{4-[(2,2-dimethyl-1,3-dioxolan-4-yl)methoxy]-3-methoxyphenyl}-11-oxo-10,11-dihydro-5H-dibenzo[b,e][1,4]diazepin-8-yl)ethyl]piperazine-1-carboxylate

EXAMPLE 648A

4-{2-[3-(4-hydroxy-3-methoxy-phenyl)-11-oxo-10,11-dihydro-5H-dibenzo[b,e][1,4]diazepin-8-yl]-ethyl}-piperazine-1-carboxylic acid tert-butyl ester Example 648B was obtained as a side product from Example 645B.

EXAMPLE 648B tert-butyl 4-[2-(3-{4-[(2,2-dimethyl-1,3-dioxolan-4-yl)methoxy]-3-methoxyphenyl}-11-oxo-10,11-dihydro-5H-dibenzo[b,e][1,4]diazepin-8-yl)ethyl]piperazine-1-carboxylate The title compound was obtained by substituting Example 648A for Example 474 and 4-chloromethyl-2,2-dimethyl-[1,3]dioxolane for 4-chloromethylpyridine hydrochloride in Example 607. MS (ESI) m/e 659 (M+H)$^+$; $^1$H NMR (400 MHz, DMSO-d$_6$) ☐9.70 (s, 1H), 7.80 (s, 1H), 7.72 (d, J=8.3 Hz, 1H), 7.25 (s, 1H), 7.20 (s, 1H), 7.17 (d, J=8.6 Hz, 2H), 7.09 (d, J=8.3 Hz, 1H), 6.91 (d, J=8.0 Hz, 1H), 6.80-6.83 (m, 2H), 4.43 (dq, J=6.0, 5.8 Hz, 1H), 4.11 (dd, J=8.1, 6.9 Hz, 1H), 4.00-4.05 (m, 2H), 3.86 (s, 3H), 3.78 (dd, J=8.3, 6.4 Hz, 1H), 3.25-3.35 (m, 4H), 2.58-2.62 (m, 2H), 2.43-2.47 (m, 2H), 2.34-2.36 (m, 4H), 1.39 (s, 9H), 1.37 (s, 3H), 1.32 (s, 3H).

EXAMPLE 649

3-[3-methoxy-4-(1,3-thiazol-4-ylmethoxy)phenyl]-8-[2-(4-methylpiperazin-1-yl)ethyl]-5,10-dihydro-11H-dibenzo[b,e][1,4]diazepin-11-one

EXAMPLE 649A 3-chloro-8-[2-(4-methylpiperazin-1-yl)ethyl]-5,10-dihydro-11H-dibenzo[b,e][1,4]diazepin-11-one The title compound was prepared by substituting 1-methylpiperazine for morpholine in Example 641B. MS (ESI) m/e 371 (M+H)$^+$; $^1$H NMR (300 MHz, DMSO-d$_6$) ☐9.83 (s, 1H), 7.96 (s, 1H), 7.67 (d, J=8.5 Hz, 1H), 7.05 (d, J=2.0 Hz, 1H), 6.91 (dd, J=8.5, 2.0 Hz, 1H), 6.80-6.88 (m, 3H), 2.55-2.60 (m, 2H), 2.20-2.43 (m, 10H), 2.13 (s, 3H).

EXAMPLE 649B

3-[3-methoxy-4-(1,3-thiazol-4-ylmethoxy)phenyl]-8-[2-(4-methylpiperazin-1-yl)ethyl]-5,10-dihydro-11H-dibenzo[b,e][1,4]diazepin-11-one The title compound was prepared by substituting Example 649A and Example 641C for Example 646A and Example 578A, respectively, in Example 646B. MS (ESI) m/e 556 (M+H)$^+$; $^1$H NMR (300 MHz, DMSO-d$_6$) ☐9.73 (s, 1H), 9.14 (d, J=1.8 Hz, 1H), 7.84 (s, 1H), 7.79 (d, J=1.8 Hz, 1H), 7.73 (d, J=8.3 Hz, 1H), 7.26 (d, J=1.2 Hz, 1H), 7.16-7.23 (m, 4H), 6.94 (d, J=8.0 Hz, 1H), 6.80-6.85 (m, 2H), 5.25 (s, 2H), 3.86 (s, 3H), 2.22-3.35 (m, 15H).

EXAMPLE 650

8-{2-[[2-(dimethylamino)ethyl](methyl)amino]ethyl}-3-[3-methoxy-4-(1,3-thiazol-4-ylmethoxy)phenyl]-5,10-dihydro-11H-dibenzo[b,e][1,4]diazepin-11-one

EXAMPLE 650A 3-chloro-8-{2-[[2-(dimethylamino)ethyl](methyl)amino]ethyl}-5,10-dihydro-11H-dibenzo[b,e][1,4]diazepin-11-one The title compound was prepared by substituting N,N,N'-trimethylethane-1,2-diamine for morpholine in Example 641B. MS (ESI) m/e 373 (M+H)$^+$; $^1$H NMR (300 MHz, DMSO-d$_6$) ☐9.82 (s, 1H), 7.96 (s, 1H), 7.67 (d, J=2.0 Hz, 1H), 7.05 (d, J=2.0 Hz, 1H), 6.91 (dd, J=8.8, 2.0 Hz, 1H), 6.81-6.88 (m, 3H), 2.52-2.60 (m, 2H), 2.39-2.50 (m, 4H), 2.25-2.29 (m, 2H), 2.19 (s, 3H), 2.10 (s, 6H).

EXAMPLE 650B

8-{2-[[2-(dimethylamino)ethyl](methyl)amino]ethyl}-3-[3-methoxy-4-(1,3-thiazol-4-ylmethoxy)phenyl]-5,10-dihydro-11H-dibenzo[b,e][1,4]diazepin-11-one The title compound was prepared by substituting Example 641C for Example 578A and
Example 650A for Example 646A in Example 646B. MS (ESI) m/e 558 (M+H)$^+$; $^1$H NMR (300 MHz, DMSO-d$_6$) ☐9.84, (s, 1H), 9.14 (d, J=2.0 Hz, 1H), 7.91 (s, 1H), 7.80 (d, J=2.0 Hz, 1H), 7.73 (d, J=8.5 Hz, 1H), 7.15-7.27 (m, 5H), 6.99 (d, J=7.8 Hz, 1H), 6.84-6.90 (m, 2H), 5.25 (s, 2H), 3.86 (s, 3H), 3.20-3.80 (m, 8H), 2.80 (s, 9H).

EXAMPLE 651

[4-(2-{3-[3-methoxy-4-(1,3-thiazol-4-ylmethoxy)phenyl]-11-oxo-10,11-dihydro-5H-dibenzo[b,e][1,4]diazepin-8-yl}ethoxy)phenyl]acetonitrile

EXAMPLE 651A

{4-[2-(3-chloro-11-oxo-10,11-dihydro-5H-dibenzo[b,e][1,4]diazepin-8-yl)ethoxy]phenyl}acetonitrile The title compound was prepared by substituting Example 204A for 2-(4-methyl-thiazol-5-yl)-ethanol and (4-hydroxy-phenyl)-acetonitrile for 4-bromo-2-methoxy-phenol in Example 630A. MS (ESI) m/e 404 (M+H)$^+$; $^1$H NMR (300 MHz, DMSO-d$_6$) ☐9.88 (s, 1H), 8.00 (s, 1H), 7.67 (d, J=8.5 Hz, 1H), 7.21-7.26 (m, 2H), 7.06 (d, J=2.0 Hz, 1H), 6.88-6.97 (m, 6H), 4.10 (t, J=6.8 Hz, 2H), 3.92 (s, 2H), 2.89 (t, J=6.6 Hz, 2H).

EXAMPLE 651B

[4-(2-{3-[3-methoxy-4-(1,3-thiazol-4-ylmethoxy)phenyl]-11-oxo-10,11-dihydro-5H-dibenzo[b,e][1,4]diazepin-8-yl}ethoxy)phenyl]acetonitrile The title compound was prepared by substituting Example 641C for Example 578A and
Example 651A for Example 646A in Example 646B. MS (ESI) m/e 589 (M+H)$^+$; $^1$H NMR (300 MHz, DMSO-d$_6$)

☐9.77 (s, 1H), 9.14 (d, J=1.7 Hz, 1H), 7.85 (s, 1H), 7.80 (d, J=2.0 Hz, 1H), 7.67 (d, J=8.1 Hz, 1H), 7.21-7.25 (m, 7H), 6.89-6.97 (m, 5H), 5.25 (s, 2H), 4.10 (t, J=6.8 Hz, 2H), 3.92 (s, 2H), 3.85 (s, 3H), 2.89 (t, J=6.6 Hz, 2H).

EXAMPLE 652

3-{3-methoxy-4-[(2-methoxy-1,3-thiazol-4-yl)methoxy]phenyl}-8-[2-(4-morpholin-4-ylphenoxy)ethyl]-5,10-dihydro-11H-dibenzo[b,e][1,4]diazepin-11-one

EXAMPLE 652A (2-bromo-1,3-thiazol-4-yl)methanol

The title compound was prepared by substituting ethyl-2-bromothiazole-4-carboxylate for thiazole-2-carbaldehyde and ethanol for methanol in Example 634A. MS (DCI) m/e 194 (M+H)$^+$; $^1$H NMR (300 MHz, DMSO-d$_6$) ☐ 7.48 (t, J=1.0 Hz, 1H), 5.42 (t, J=5.9 Hz, 1H), 5.42 (dd, J=5.8, 1.0 Hz, 2H).

EXAMPLE 652B 2-bromo-4-{[2-methoxy-4-(4,4,5,5-tetramethyl-1,3,2-dioxaborolan-2-yl)phenoxy]methyl}-1,3-thiazole The title compound was prepared by substituting Example 652A for 2-(4-methylthiazol-5-yl)-ethanol and 2-methoxy-4-(4,4,5,5-tetramethyl-[1,3,2]dioxaborolan-2-yl)-phenol for 4-bromo-2-methoxyphenol, respectively, in Example 630A. MS (ESI) m/e 426 (M+H)$^+$; $^1$H NMR (300 MHz, DMSO-d$_6$) ☐ 7.77 (s, 1H), 7.25 (dd, J=8.1, 1.4 Hz, 1H), 7.15 (d, J=1.4 Hz, 1H), 7.09 (d, J=8.1 Hz, 1H), 5.15 (s, 2H), 3.77 (s, 3H), 1.28 (s, 12H).

EXAMPLE 652C 2-methoxy-4-{[2-methoxy-4-(4,4,5,5-tetramethyl-1,3,2-dioxaborolan-2-yl)phenoxy]methyl}-1,3-thiazole A mixture of sodium metal (34.5 mg, 1.5 mmol) in methanol (1 mL) was stirred at ambient temperature for 15 minutes. Example 652B (128 mg, 0.3 mmol) was added and the mixture was stirred for 3.5 hours. The mixture was then heated at 50° C. overnight, cooled to room temperature, quenched with water, diluted with ethyl acetate, washed with water and brine, dried (MgSO$_4$), filtered and concentrated. The concentrate was purified by column chromatography on silica gel using a gradient of 0 to 1% methanol in dichloromethane to give the title compound (55 mg, 49% yield). MS (ESI) m/e 378 (M+H)$^+$; $^1$H NMR (300 MHz, DMSO-d$_6$ ☐ 7.24 (dd, J=7.8, 1.4 Hz, 1H), 7.15 (d, J=1.4 Hz, 1H), 7.09 (d, J=8.1 Hz, 1H), 7.06 (s, 1H), 4.96 (s, 2H), 4.02 (s, 3H), 3.77 (s, 3H), 1.28 (s, 12H).

EXAMPLE 652D

3-{3-methoxy-4-[(2-methoxy-1,3-thiazol-4-yl)methoxy]phenyl}-8-[2-(4-morpholin-4-ylphenoxy)ethyl]-5,10-dihydro-11H-dibenzo[b,e][1,4]diazepin-11-one The title compound was prepared by substituting Example 652C, Example 297A and an aqueous 2M solution of sodium carbonate for Example 578A, Example 654A and cesium fluoride, respectively, in Example 654B. MS (ESI) m/e 665 (M+H)$^+$; $^1$H NMR (500 MHz, DMSO-d$_6$ ☐ 9.76 (s, 1H), 7.85 (s, 1H), 7.72 (d, J=8.2 Hz, 1H), 7.26 (s, 1H), 7.22 (s, 1H), 7.16-7.20 (m, 3H), 7.08 (s, 1H), 6.81-6.95 (m, 7H), 4.99 (s, 2H), 4.02-4.05 (m, 5H), 3.86 (s, 3H), 3.70-3.72 (m, 4H), 2.95-2.97 (m, 4H), 2.86 (t, J=6.6 Hz, 2H).

EXAMPLE 653 methyl [3-(3-methoxy-4-pyridin-4-ylphenyl)-11-oxo-10,11-dihydro-5H-dibenzo[b,e][1,4]diazepin-8-yl]acetate The title compound was prepared by substituting Example 54B and pyridine-4-boronic acid for Example 641B and Example 641C, respectively, in Example 641D. MS (ESI) m/e 466 (M+H)$^+$; $^1$H NMR (300 MHz, DMSO-d$_6$) ☐ 9.87 (s, 1H), 8.78 (d, J=5.8 Hz, 2H), 7.99 (s, 1H), 7.93 (d, J=6.1 Hz, 2H), 7.80 (d, J=8.1 Hz, 1H), 7.64 (d, J=7.8 Hz, 1H), 7.36-7.42 (m, 3H), 7.32 (dd, J=8.1, 1.7 Hz, 1H), 6.98 (d, J=8.1 Hz, 1H), 6.85-6.88 (m, 2H), 3.95 (s, 3H), 3.60 (s, 3H), 3.55 (s, 2H).

EXAMPLE 654

8-methoxy-3-(3-methoxy-4-nitrophenyl)-7-[1-(2-oxopyrrolidin-1-yl)ethyl]-5,10-dihydro-11H-dibenzo[b,e][1,4]diazepin-11-one

Example 654A 3-chloro-8-methoxy-7-[1-(2-oxopyrrolidin-1-yl)vinyl]-5,10-dihydro-11H-dibenzo[b,e][1,4]diazepin-11-one A mixture of Example 516A, 1-vinyl-2-pyrrolidinone, Pd(dppf)Cl$_2$-CH$_2$Cl$_2$, and triethylamine in DMF was heated at 110° C. overnight, cooled to room temperature, diluted with ethyl acetate, washed with water and brine, dried (MgSO$_4$), filtered and concentrated. The concentrate was purified by column chromatography on silica gel using a solvent gradient that increased from 1 to 4% methanol in dichloromethane to give the title compound. MS (ESI) m/e 384 (M+H)$^+$.

EXAMPLE 654B 3-chloro-8-methoxy-7-[1-(2-oxopyrrolidin-1-yl)ethyl]-5,10-dihydro-11H-dibenzo[b,e][1,4]diazepin-11-one A mixture Example 654A (130 mg, 0.34 mmol), 5% Pt/C (130 mg), methanol (5 mL) and DMF (12 mL) was equipped with a balloon of hydrogen gas and stirred at room temperature. After uptake of the hydrogen was complete, the solution was filtered through diatomaceous earth (Celite®). The filtrate was concentrated under vacuum and purified by column chromatography on silica gel to provide the title compound. MS (ESI) m/e 386 (M+H)$^+$; $^1$H NMR (300 MHz, DMSO-d$_6$) ☐9.80 (s, 1H), 7.87 (d, 1H), 7.67 (d, J=8.5 Hz, 1H), 7.02 (d, J=2.0 Hz, 1H), 6.85-6.92 (m, 2H), 6.64 (s, 1H), 5.20 (q, J=7.0 Hz, 1H), 3.67 (s, 3H), 3.34 (m, 1H), 3.07 (m, 1H), 2.19-2.24 (m, 2H), 1.90 (qd, J=7.5, 7.3 Hz, 2H), 1.35 (d, J=7.1 Hz, 3H).

EXAMPLE 654C 8-methoxy-3-(3-methoxy-4-nitrophenyl)-7-[1-(2-oxopyrrolidin-1-yl)ethyl]-5,10-dihydro-11H-dibenzo[b,e][1,4]diazepin-11-one The title compound was prepared by substituting Example 654B for Example 641B and
Example 266G for Example 641C in Example 641D. MS (ESI) m/e 503 (M+H)$^+$; $^1$H NMR (400 MHz, DMSO-d$_6$)

☐9.78 (s, 1H), 8.01 (d, J=8.3 Hz, 1H), 7.84 (s, 1H), 7.79 (d, J=8.3 Hz, 1H), 7.53 (d, J=1.8 Hz, 1H), 7.35 (dd, J=8.3, 1.8 Hz, 1H), 7.30 (d, J=1.5 Hz, 1H), 7.27 (dd, J=8.3, 1.8 Hz, 1H), 6.93 (s, 1H), 6.66 (s, 1H), 5.22 (q, J=7.1 Hz, 1H), 4.03 (s, 3H), 3.68 (s, 3H), 3.31 (m, 1H), 3.08 (m, 1H), 2.19-2.23 (m, 2H), 1.89 (qd, J=7.6, 7.4 Hz, 2H), 1.35 (d, J=7.1 Hz, 3H).

EXAMPLE 655

8-methoxy-3-(3-methoxy-4-nitrophenyl)-7-(2-pyridin-4-ylethyl)-5,10-dihydro-11H-dibenzo[b,e][1,4]diazepin-11-one

EXAMPLE 655A 3-chloro-8-methoxy-7-[(E)-2-pyridin-4-ylvinyl]-5,10-dihydro-11H-dibenzo[b,e][1,4]diazepin-11-one The title compound was prepared by substituting 4-vinylpyridine for 1-vinyl-2-pyrrolidinone in Example 654A. MS (ESI) m/e 378 (M+H)$^+$; $^1$H NMR (300 MHz, DMSO-d$_6$) ☐9.99 (s, 1H), 8.52 (d, J=5.8 Hz, 2H), 7.96 (s, 1H), 7.69 (d, J=8.5 Hz, 1H), 7.48-7.56 (m, 3H), 7.28 (s, 1H), 7.06 (d, J=2.0 Hz, 1H), 7.00 (d, J=16.6 Hz, 1H), 6.93 (dd, J=8.5, 2.0 Hz, 1H), 6.74 (s, 1H), 3.79 (s, 3H).

EXAMPLE 655B 3-chloro-8-methoxy-7-(2-pyridin-4-ylethyl)-5,10-dihydro-11H-dibenzo[b,e][1,4]diazepin-11-one The title compound was prepared by substituting Example 655A for Example 654A in Example 654B. MS (ESI) m/e 380 (M+H)$^+$; $^1$H NMR (300 MHz, DMSO-d$_6$) ☐9.76 (s, 1H), 8.43-8.45 (m, 2H), 7.76 (s, 1H), 7.66 (d, J=8.5 Hz, 1H), 7.18-7.20 (m, 2H), 7.01 (d, J=2.0 Hz, 1H), 6.89 (dd, J=8.5, 2.0 Hz, 1H), 6.73 (s, 1H), 6.62 (s, 1H), 3.68 (s, 3H), 2.70-2.83 (m, 4H).

EXAMPLE 655C 8-methoxy-3-(3-methoxy-4-nitrophenyl)-7-(2-pyridin-4-ylethyl)-5,10-dihydro-11H-dibenzo[b,e][1,4]diazepin-11-one The title compound was prepared by substituting Example 655B for Example 641B and
Example 266G for Example 641C in Example 641D. MS (ESI) m/e 497 (M+H)$^+$; $^1$H NMR (400 MHz, DMSO-d$_6$) ☐9.75 (s, 1H), 8.43-8.44 (m, 2H), 8.01 (d, J=8.3 Hz, 1H), 7.78 (d, J=8.0 Hz, 1H), 7.70 (s, 1H), 7.52 (d, J=1.8 Hz, 1H), 7.34 (dd, J=8.4, 1.7 Hz, 1H), 7.31 (d, J=1.7 Hz, 1H), 7.27 (dd, J=8.3, 1.8, 1H), 7.18-7.20 (m, 2H), 6.77 (s, 1H), 6.65 (s, 1H), 4.03 (s, 3H), 3.69 (s, 3H), 2.72-2.83 (m, 4H).

EXAMPLE 656 methyl {3-[3-methoxy-4-(6-oxo-1,6-dihydropyridin-3-yl)phenyl]-11-oxo-10,11-dihydro-5H-dibenzo[b,e][1,4]diazepin-8-yl}acetate

EXAMPLE 656A methyl {3-[4-(6-fluoropyridin-3-yl)-3-methoxyphenyl]-11-oxo-10,11-dihydro-5H-dibenzo[b,e][1,4]diazepin-8-yl}acetate The title compound was prepared by substituting Example 54B for Example 641B and 2-fluoropyridine-5-boronic acid for Example 641C in Example 641D. MS (ESI) m/e 484 (M+H)$^+$; $^1$H NMR (400 MHz, DMSO-d$_6$) ☐9.83 (s, 1H), 8.39 (d, J=2.5 Hz, 1H), 8.16 (m, 1H), 7.96 (s, 1H), 7.79 (d, J=8.0 Hz, 1H), 7.50 (d, J=8.0 Hz, 1H), 7.37 (d, J=1.5 Hz, 2H), 7.33 (dd, J=7.8, 1.7 Hz, 1H), 7.29 (d, J=8.3, 1.5 Hz, 1H), 7.26 (dd, J=8.6, 2.8 Hz, 1H), 6.97 (d, J=8.0 Hz, 1H), 6.85-6.88 (m, 2H), 3.91 (s, 3H), 3.60 (s, 3H), 3.54 (s, 2H).

EXAMPLE 656B methyl {3-[3-methoxy-4-(6-oxo-1,6-dihydropyridin-3-yl)phenyl]-11-oxo-10,11-dihydro-5H-dibenzo[b,e][1,4]diazepin-8-yl}acetate A mixture of Example 656A (20 mg, 0.04 mmol) in acetic acid (1 mL) and water (200 µL) was heated at 100° C. overnight, cooled to room temperature, diluted with ethyl acetate, washed with water and brine, dried (MgSO$_4$), filtered and concentrated. The concentrate was purified by preparative HPLC (2.5 mg, 13% yield). MS (ESI) m/e 482 (M+H)$^+$; $^1$H NMR (400 MHz, DMSO-d$_6$) ☐ 11.67 (br s, 1H), 9.83 (s, 1H), 7.95 (s, 1H), 7.77 (d, J=8.1 Hz, 1H), 7.69 (dd, J=9.7, 2.5 Hz, 1H), 7.56 (m, 1H), 7.24-7.43 (m, 5H), 6.96 (d, J=8.1 Hz, 1H), 6.82-6.87 (m, 2H), 6.39 (d, J=9.2 Hz, 1H), 3.90 (s, 3H), 3.60 (s, 3H), 3.54 (s, 2H).

EXAMPLE 657 methyl {3-[4-(3-fluoropyridin-4-yl)-3-methoxyphenyl]-11-oxo-10,11-dihydro-5H-dibenzo[b,e][1,4]diazepin-8-yl}acetate The title compound was prepared by substituting Example 54 for Example 641B and 3-fluoro-4-pyridineboronic acid hydrate for Example 641C in Example 641D. MS (ESI) m/e 484 (M+H)$^+$; $^1$H NMR (400 MHz, DMSO-d$_6$ ☐ 9.83 (s, 1H), 8.61 (d, J=1.5 Hz, 1H), 8.48 (d, J=4.9 Hz, 1H), 7.95 (s, 1H), 7.78 (d, J=8.3 Hz, 1H), 7.49 (m, 1H), 7.43 (d, J=7.7 Hz, 1H), 7.28-7.37 (m, 4H), 6.96 (d, J=8.0 Hz, 1H), 6.85-6.87 (m, 2H), 3.88 (s, 3H), 3.59 (s, 3H), 3.53 (s, 2H).

EXAMPLE 658 methyl {3-[4'-(acetylamino)-2-methoxy-1,1'-biphenyl-4-yl]-11-oxo-10,11-dihydro-5H-dibenzo[b,e][1,4]diazepin-8-yl}acetate The title compound was prepared by substituting Example 54B for Example 641B and 4-acetamidophenylboronic acid for Example 641C in Example 641D. MS (ESI) m/e 522 (M+H)$^+$; $^1$H NMR (400 MHz, DMSO-d$_6$ ☐ 9.98 (s, 1H), 9.81 (s, 1H), 7.95 (s, 1H), 7.78 (d, J=8.0 Hz, 1H), 7.61-7.63 (m, 2H), 7.46-7.48 (m, 2H), 7.40 (d, J=8.0 Hz, 1H), 7.35 (d, J=1.5 Hz, 1H), 7.26-7.36 (m, 3H), 6.97 (d, J=7.7 Hz, 1H), 6.85-6.88 (m, 2H), 3.87 (s, 3H), 3.60 (s, 3H), 3.54 (s, 2H), 2.07 (s, 3H).

EXAMPLE 659

N-(2'-methoxy-4'-{8-[2-(4-morpholin-4-ylphenoxy)ethyl]-11-oxo-10,11-dihydro-5H-dibenzo[b,e][1,4]diazepin-3-yl}-1,1'-biphenyl-4-yl)acetamide Example 667 was prepared by substituting Example 298 for Example 641B and 4-acetamidophenylboronic acid for Example 641C in Example 641D. MS (ESI) m/e 599 (M+H)$^+$; $^1$H NMR (400 MHz, DMSO-d$_6$ ☐ 9.98 (s, 1H), 9.78 (s, 1H), 7.90 (s, 1H), 7.77 (d, J=8.3 Hz, 1H), 7.62 (d, J=8.6 Hz, 2H), 7.47 (d, J=8.6 Hz, 2H), 7.40 (d, J=7.7 Hz, 1H), 7.35 (s, 1H), 7.25-7.30 (m, 3H), 6.81-6.97 (m, 7H), 4.04 (t, J=6.9 Hz, 2H), 3.87 (s, 3H), 3.70-3.72 (m, 4H), 2.95-2.98 (m, 4H), 2.87 (t, J=6.6 Hz, 2H), 2.06 (s, 3H).

EXAMPLE 660

3-(3-methoxy-4-pyridin-4-ylphenyl)-8-[2-(4-morpholin-4-ylphenoxy)ethyl]-5,10-dihydro-11H-dibenzo[b,e][1,4]diazepin-11-one Example 668 was prepared by substituting Example 298 for Example 641B and pyridine-4-boronic acid for Example 641C in Example 641D. MS (ESI) m/e 655 (M+H)$^+$; $^1$H NMR (300 MHz, DMSO-d$_6$ □ 9.83, (s, 1H), 8.90 (d, J=6.8 Hz, 2H), 8.22 (d, J=6.8 Hz, 2H), 8.01 (s, 1H), 7.80 (d, J=8.3 Hz, 1H), 7.73 (d, J=8.0 Hz, 1H), 7.41-7.47 (m, 3H), 7.33 (dd, J=8.3, 1.8 Hz, 1H), 7.17 (m, 1H), 6.99 (d, J=8.0 Hz, 1H), 6.91-6.95 (m, 5H), 4.09 (t, J=6.6 Hz, 2H), 3.98 (s, 3H), 3.82-3.85 (m, 4H), 3.15-3.19 (m, 4H), 2.89 (t, J=6.6 Hz, 2H).

EXAMPLE 661

3-(3-methoxyphenyl)-8-[2-(4-morpholin-4-ylphenoxy)ethyl]-5,10-dihydro-11H-dibenzo[b,e][1,4]diazepin-11-one The title compound was obtained from the reaction in which Example 298 and 3,5-difluoropyridine-4-boronic acid hydrate were substituted for Example 641B and Example 641C, respectively, in Example 641D. MS (ESI) m/e 628 (M+H)$^+$; $^1$H NMR (400 MHz, DMSO-d$_6$ □ 9.77 (s, 1H), 7.86 (s, 1H), 7.74 (d, J=8.0 Hz, 1H), 7.40 (t, J=8.0 Hz, 1H), 7.28 (d, J=1.5 Hz, 1H), 7.15-7.21 (m, 3H), 6.99 (dd, J=8.3, 2.2 Hz, 1H), 6.81-7.00 (m, 7H), 4.04 (t, J=6.6 Hz, 2H), 3.83 (s, 3H), 3.70-3.72 (m, 4H), 2.95-2.98 (m, 4H), 2.86 (t, J=6.6 Hz, 2H).

EXAMPLE 662

3-(2,4'-dimethoxy-1,1'-biphenyl-4-yl)-8-[2-(4-morpholin-4-ylphenoxy)ethyl]-5,10-dihydro-11H-dibenzo[b,e][1,4]diazepin-11-one

EXAMPLE 662A 2-methoxy-4-{8-[2-(4-morpholin-4-ylphenoxy)ethyl]-11-oxo-10,11-dihydro-5H-dibenzo[b,e][1,4]diazepin-3-yl}phenyl trifluoromethanesulfonate The title compound was prepared by substituting Example 474 for Example 515A in Example 515B. MS (ESI) m/e 628 (M+H)$^+$; $^1$H NMR (400 MHz, DMSO-d$_6$ □ 9.82 (s, 1H), 7.91 (s, 1H), 7.78 (d, J=8.3 Hz, 1H), 7.55 (d, J=8.3 Hz, 1H), 7.50 (d, J=1.8 Hz, 1H), 7.23-7.28 (m, 3H), 6.81-6.96 (m, 7H), 4.00 (s, 3H), 4.04 (t, J=6.8 Hz, 2H), 3.70-3.72 (m, 4H), 2.95-2.98 (m, 4H), 2.87 (t, J=6.6 Hz, 2H).

EXAMPLE 662B 3-(2,4'-dimethoxy-1,1'-biphenyl-4-yl)-8-[2-(4-morpholin-4-ylphenoxy)ethyl]-5,10-dihydro-11H-dibenzo[b,e][1,4]diazepin-11-one The title compound was prepared by substituting 4-methoxyphenylboronic acid and
Example 298 for Example 578A and Example 630A, respectively, in Example 630B. MS (ESI) m/e 628 (M+H)$^+$; $^1$H NMR (400 MHz, DMSO-d$_6$ □ 9.78 (s, 1H), 7.90 (s, 1H), 7.77 (d, J=8.3 Hz, 1H), 7.45-7.49 (m, 2H), 7.38 (d, J=8.0 Hz, 1H), 7.35 (d, J=1.5 Hz, 1H), 7.25-7.30 (m, 3H), 6.85-7.00 (m, 9H), 4.06 (t, J=6.8 Hz, 2H), 3.87 (s, 3H), 3.80 (s, 3H), 3.73-3.76 (m, 4H), 3.04-3.06 (m, 4H), 2.87 (d, J=6.8 Hz, 2H).

EXAMPLE 663

3-[4-(3-chloropyridin-4-yl)-3-methoxyphenyl]-8-[2-(4-morpholin-4-ylphenoxy)ethyl]-5,10-dihydro-11H-dibenzo[b,e][1,4]diazepin-11-one A mixture of Example 662A (33.5 mg (0.05 mmol), 3-chloro-4-pyridineboronic acid (11.8 mg, 0.075 mmol), palladium acetate (1.1 mg, 0.005 mmol), tricyclohexyl phosphine (2.8 mg, 0.01 mmol), and potassium fluoride (8.7 mg, 0.15 mmol) in dioxane (1.5 mL) was heated at 85° C. overnight. Additional amounts of 3-chloro-4-pyridineboronic acid (7.9 mg, 0.05 mmol), palladium acetate (2.2 mg, 0.01 mmol), tricyclohexyl phosphine (5.6 mg, 0.02 mmol), and potassium fluoride (8.7 mg, 0.15 mmol) were added and the reaction mixture was heated at 85° C. for a second night. The reaction mixture was then cooled to room temperature, diluted with ethyl acetate, washed with water and brine, dried (MgSO$_4$), filtered and concentrated. The concentrate was purified by preparative HPLC to give the title compound as the TFA salt. MS (ESI) m/e 633 (M+H)$^+$; $^1$□ NMR (300 MHz, DMSO-d$_6$ □ 9.81 (s, 1H), 8.72 (s, 1H), 8.57 (d, J=4.9 Hz, 1H), 7.91 (s, 1H), 7.79 (d, J=8.0 Hz, 1H), 7.45 (d, J=4.9 Hz, 1H), 7.32-7.35 (m, 4H), 7.29 (dd, J=8.1, 1.7 Hz, 1H), 6.86-6.97 (m, 7H), 4.06 (t, J=6.8 Hz, 2H), 3.85 (s, 3H), 3.73-3.76 (m, 4H), 3.04-3.06 (m, 4H), 2.87 (t, J=6.6 Hz, 2H).

EXAMPLE 664

3-(4-hydroxy-3-methoxyphenyl)-8-{2-[(2-methylpyridin-3-yl)oxy]ethyl}-5,10-dihydro-11H-dibenzo[b,e][1,4]diazepin-11-one

EXAMPLE 664A 3-chloro-8-{2-[(2-methylpyridin-3-yl)oxy]ethyl}-5,10-dihydro-11H-dibenzo[b,e][1,4]diazepin-11-one The title compound was prepared by substituting 2-methyl-pyridin-3-ol for 4-morpholinophenol in Example 297A. MS (ESI) m/e 380 (M+H)$^+$.

EXAMPLE 664B 3-(4-hydroxy-3-methoxyphenyl)-8-{2-[(2-methylpyridin-3-yl)oxy]ethyl}-5,10-dihydro-11H-dibenzo[b,e][1,4]diazepin-11-one The title compound was prepared by substituting 2-methoxy-4-(4,4,5,5-tetramethyl-[1,3,2]dioxaborolan-2-yl)-phenol and Example 664A for Example 56A and Example 59B, respectively, in Example 59C. MS (ESI) m/e 468 (M+H)$^+$, $^1$H NMR (DMSO-d$_6$,500 MHz): □ 9.73 (s, 1H), 8.16 (d, J=5.3 Hz, 1H), 7.82 (s, 1H), 7.70-7.73 (m, 2H), 7.50 (m, 1H), 7.22 (d, J=1.56 Hz, 1H), 7.16 (d, J=1.87 Hz, 1H), 7.14 (dd, J=8.27, 1.72 Hz, 1H), 7.07 (dd, J=8.11, 2.18 Hz, 1H), 6.88-6.95 (m, 4H), 6.75 (m, 1H), 4.25 (t, J=6.40 Hz, 2H), 3.85 (s, 3H), 2.95 (t, J=6.40 Hz, 2H), 2.42 (s, 3H).

EXAMPLE 665

8-(2-hydroxy-1-methylethyl)-3-(3-methoxy-4-nitrophenyl)-5,10-dihydro-11H-dibenzo[b,e][1,4]diazepin-11-one Example 665A methyl 2-(4-nitrophenyl)propanoate A mixture of (4-nitro-phenyl)-acetic acid methyl ester (3.0 g, 15 mmol), 18-crown-6 (396 mg, 1.5 mmol), and methyl iodide (3.74 mL, 60 mmol) were combined in DMF (50 mL) and cooled to 0° C. Sodium hydride (660 mg, 16.5 mmol) was added. The solution was stirred with warming to room temperature overnight. The solution was partitioned between ethyl acetate and water. The combined organic layers were washed with brine, dried (MgSO$_4$), filtered, and concentrated under vacuum to provide 2.19 g (70%) of the title compound. MS (DCI) m/e 210 (M+H)$^+$.

EXAMPLE 665B methyl 2-(4-amino-3-nitrophenyl)propanoate

Example 665A was substituted for Example 6B in Example 6C to provide 2-(4-amino-phenyl)-propionic acid methyl ester. The title compound was prepared by substituting 2-(4-amino-phenyl)-propionic acid methyl ester for (3-amino-phenyl)-acetic acid methyl ester in Example 388A. MS (ESI) m/e 225 (M+H)$^+$.

EXAMPLE 665C methyl 4-chloro-2-{[4-(2-methoxy-1-methyl-2-oxoethyl)-2-nitrophenyl]amino}benzoate The title compound was prepared by substituting Example 665B for methyl 3,4-diaminobenzoate in Example 1A. MS (ESI) m/e 393 (M+H)$^+$.

EXAMPLE 665D methyl 2-{[2-amino-4-(2-methoxy-1-methyl-2-oxoethyl)phenyl]amino}-4-chlorobenzoate The title compound was prepared by substituting Example 665C for Example 6B in Example 6C. MS (ESI) m/e 363 (M+H)$^+$.

EXAMPLE 665E methyl 2-(3-chloro-11-oxo-10,11-dihydro-5H-dibenzo[b,e][1,4]diazepin-8-yl)propanoate The title compound was prepared by substituting Example 665D for Example 5B in Example 5C. MS (ESI) m/e 331 (M+H)$^+$.

EXAMPLE 665F 3-chloro-8-(2-hydroxy-1-methylethyl)-5,10-dihydro-11H-dibenzo[b,e][1,4]diazepin-11-one The title compound was prepared by substituting Example 665E for Example 6D in Example 204A. MS (ESI) m/e 303 (M+H)$^+$.

EXAMPLE 665G 8-(2-hydroxy-1-methylethyl)-3-(3-methoxy-4-nitrophenyl)-5,10-dihydro-11H-dibenzo[b,e][1,4]diazepin-11-one The title compound was prepared by substituting Example 665F and Example 266G for Example 59B and Example 56A, respectively, in Example 59C. MS (ESI) m/e 421 (M+H)$^+$, $^1$H NMR (DMSO-d$_6$, 500 MHz): ☐ 9.78 (s, 1H), 8.01 (d, J=8.42 Hz, 1H), 7.90 (s, 1H), 7.80 (d, J=8.11 Hz, 1H), 7.52 (d, J=1.56 Hz, 1H), 7.33-7.35 (m, 2H), 7.29 (dd, J=8.11, 1.56 Hz, 1H), 6.93 (d, J=7.80 Hz, 1H), 6.81-6.84 (m, 2H), 4.57 (t, J=5.3 Hz, 1H), 4.03 (s, 3H), 3.43 (m, 1H), 3.34 (m, 1H), 2.66 (m, 1H), 1.13 (d, J=6.86 Hz, 3H).

EXAMPLE 666

3-(3-methoxy-4-nitrophenyl)-8-[1-methyl-2-(4-morpholin-4-ylphenoxy)ethyl]-5,10-dihydro-11H-dibenzo[b,e][1,4]diazepin-11-one The title compound was prepared by substituting Example 665G for Example 204 in Example 297A. MS (ESI) m/e 581 (M+H)$^+$, $^1$H NMR (DMSO-d$_6$, 500 MHz): ☐ 9.84 (s, 1H), 8.01 (d, J=8.54 Hz, 1H), 7.97 (s, 1H), 7.80 (d, J=8.24 Hz, 1H), 7.52 (s, 1H), 7.33-7.36 (m, 2H), 7.30 (m, 1H), 6.92-6.97 (m, 3H), 6.79-6.86 (m, 4H), 4.03 (s, 3H), 3.85-3.94 (m, 2H), 3.69-3.71 (m, 4H), 3.38 (m, 1H), 2.94-2.97 (m, 4H), 1.24 (d, J=6.71 Hz, 3H).

EXAMPLE 667

3-(4-hydroxy-3-methoxyphenyl)-7-piperidin-1-yl-5,10-dihydro-11H-dibenzo[b,e][1,4]diazepin-11-one The title compound was prepared by substituting 2-methoxy-4-(4,4,5,5-tetramethyl-[1,3,2]dioxaborolan-2-yl)-phenol and Example 448B for Example 56A and Example 59B, respectively, in Example 59C. MS (ESI) m/e 416 (M+H)$^+$, $^1$H NMR (DMSO-d$_6$, 500 MHz): ☐ 9.51 (s, 1H), 7.64-7.68 (m, 2H), 7.19 (d, J=1.84 Hz, 1H), 7.15 (d, J=2.15 Hz, 1H), 7.12 (dd, J=8.29, 1.84 Hz, 1H), 7.06 (dd, J=8.13, 1.99 Hz, 1H), 6.84 (d, J=8.29 Hz, 1H), 6.78 (d, J=8.59 Hz, 1H), 6.60 (d, J=2.56 Hz, 1H), 6.49 (dd, J=8.75, 2.61 Hz, 1H), 3.84 (s, 3H), 3.01-3.04 (m, 4H), 1.56-1.59 (m, 4H), 1.48-1.51 (m, 2H).

EXAMPLE 668

3-(4-hydroxy-3-methoxyphenyl)-8-(2-pyridin-3-ylethoxy)-5,10-dihydro-11H-dibenzo[b,e][1,4]diazepin-11-one

EXAMPLE 668A 2-nitro-4-(2-pyridin-3-ylethoxy)aniline

The title compound was prepared by substituting 2-pyridin-3-yl-ethanol for 2-(4-methyl-1,3-thiazol-5-yl)ethanol in Example 444A. MS (ESI) m/e 260 (M+H)$^+$.

EXAMPLE 668B 3-chloro-8-(2-pyridin-3-ylethoxy)-5,10-dihydro-11H-dibenzo[b,e][1,4]diazepin-11-one The title compound was prepared in the same manner as Example 442, beginning with the substitution of Example 668A for 4-methoxy-2-nitroaniline in Example 442A. MS (ESI) m/e 366 (M+H)$^+$.

EXAMPLE 668C 3-(4-hydroxy-3-methoxyphenyl)-8-(2-pyridin-3-ylethoxy)-5,10-dihydro-11H-dibenzo[b,e][1,4]diazepin-11-one The title compound was prepared by substituting 2-methoxy-4-(4,4,5,5-tetramethyl-[1,3,2]dioxaborolan-2-yl)-phenol and Example 668B for Example 56A and Example 59B, respectively, in Example 59C. MS (ESI) m/e 454 (M+H)$^+$, $^1$H NMR (DMSO-d$_6$, 400 MHz): □ 9.66 (s, 1H), 9.23 (s, 1H), 8.51 (s, 1H), 8.42 (s, 1H), 7.72 (d, J=7.98 Hz, 1H), 7.68 (d, J=8.29 Hz, 1H), 7.66 (s, 1H), 7.31 (dd, J=7.67, 4.91 Hz, 1H), 7.18 (s, 1H), 7.15 (d, J=1.84 Hz, 1H), 7.11 (dd, J=8.29, 1.53 Hz, 1H), 7.07 (dd, J=8.29, 2.15 Hz, 1H), 6.91 (d, J=8.59 Hz, 1H), 6.85 (d, J=7.98 Hz, 1H), 6.55-6.59 (m, 2H), 4.09 (t, J=6.60 Hz, 2H), 3.84 (s, 3H), 3.00 (t, J=6.75 Hz, 2H).

EXAMPLE 669

3-(4-hydroxy-3-methoxyphenyl)-7-(1H-imidazol-1-yl)-5,10-dihydro-11H-dibenzo[b,e][1,4]diazepin-11-one

EXAMPLE 669A 3-chloro-7-(1H-imidazol-1-yl)-5,10-dihydro-11H-dibenzo[b,e][1,4]diazepin-11-one The title compound was prepared in the same manner as Example 448B, beginning with the substitution of imidazole for piperidine in Example 448A. MS (ESI) m/e 311 (M+H)$^+$.

EXAMPLE 669B 3-(4-hydroxy-3-methoxyphenyl)-7-(1H-imidazol-1-yl)-5,10-dihydro-11H-dibenzo[b,e][1,4]diazepin-11-one The title compound was prepared by substituting 2-methoxy-4-(4,4,5,5-tetramethyl-[1,3,2]dioxaborolan-2-yl)-phenol and Example 669A for Example 56A and Example 59B, respectively, in Example 59C. MS (ESI) m/e 399 (M+H)$^+$, $^1$H NMR (DMSO-d$_6$, 400 MHz): □ 10.00 (s, 1H), 9.27 (s, 1H), 8.94 (br s, 1H), 8.16 (s, 1H), 7.89 (m, 1H), 7.75 (d, J=8.29 Hz, 1H), 7.57 (m, 1H), 7.20-7.28 (m, 4H), 7.19 (d, J=2.45 Hz, 1H), 7.13 (d, J=8.29 Hz, 1H), 7.09 (dd, J=7.98, 2.15 Hz, 1H), 6.88 (d, J=8.29 Hz, 1H), 3.86 (s, 3H).

EXAMPLE 670

3-(4-hydroxy-3-methoxyphenyl)-8-[2-(2-oxopyridin-1(2H)-yl)ethyl]-5,10-dihydro-11H-dibenzo[b,e][1,4]diazepin-11-one

EXAMPLE 670A 3-chloro-8-[2-(2-oxopyridin-1(2H)-yl)ethyl]-5,10-dihydro-11H-dibenzo[b,e][1,4]diazepin-11-one The title compound was prepared by substituting pyridin-2-ol for 4-morpholinophenol in Example 297A. MS (ESI) m/e 366 (M+H)$^+$.

EXAMPLE 670B 3-(4-hydroxy-3-methoxyphenyl)-8-[2-(2-oxopyridin-1(2H)-yl)ethyl]-5,10-dihydro-11H-dibenzo[b,e][1,4]diazepin-11-one The title compound was prepared by substituting 2-methoxy-4-(4,4,5,5-tetramethyl-[1,3,2]dioxaborolan-2-yl)-phenol and Example 670A for Example 56A and Example 59B, respectively, in Example 59C. MS (ESI) m/e 454 (M+H)$^+$, $^1$H NMR (DMSO-d$_6$, 400 MHz): □ 9.72 (s, 1H), 9.25 (s, 1H), 7.83 (s, 1H), 7.70 (d, J=8.14 Hz, 1H), 7.50 (dd, J=7.12, 2.03 Hz, 1H), 7.37 (m, 1H), 7.21 (d, J=2.03 Hz, 1H), 7.12-7.17 (m, 2H), 7.07 (dd, J=8.31, 2.20 Hz, 1H), 6.91 (m, 1H), 6.87 (d, J=8.14 Hz, 1H), 6.76-6.83 (m, 2H), 6.37 (m, 1H), 6.12 (m, 1H), 3.98-4.02 (m, 2H), 3.85 (s, 3H), 2.79 (t, J=7.29 Hz, 2H).

EXAMPLE 671

3-(4-acetyl-3-methoxyphenyl)-8-[2-(4-morpholin-4-ylphenoxy)ethyl]-5,10-dihydro-11H-dibenzo[b,e][1,4]diazepin-11-one The title compound was prepared by substituting Example 578A for Example 56A in Example 59C. MS (ESI) m/e 564 (M+H)$^+$, $^1$H NMR (DMSO-d$_6$, 400 MHz): □ 9.82 (s, 1H), 7.92 (s, 1H), 7.78 (d, J=7.98 Hz, 1H), 7.70 (d, J=7.98 Hz, 1H), 7.35 (dd, J=7.52, 1.69 Hz, 2H), 7.28 (dd, J=2.92, 1.69 Hz, 1H), 7.26 (dd, J=2.92, 1.69 Hz, 1H), 6.81-6.96 (m, 7H), 4.03-4.06 (m, 2H), 4.00 (s, 3H), 3.70-3.72 (m, 4H), 2.95-2.98 (m, 4H), 2.86 (d, J=6.60 Hz, 2H), 2.56 (s, 3H).

EXAMPLE 672

3-(2-{3-[4-(1H-imidazol-1-ylmethyl)-3-methoxyphenyl]-11-oxo-10,11-dihydro-5H-dibenzo[b,e][1,4]diazepin-8-yl}ethoxy)pyridine-2-carbonitrile The title compound was prepared by substituting Example 586 and 3-hydroxy-pyridine-2-carbonitrile for Example 204A and 4-morpholinophenol, respectively, in Example 297A. MS (ESI) m/e 543 (M+H)$^+$, $^1$H NMR (DMSO-d$_6$, 400 MHz): □ 9.77 (s, 1H), 9.06 (s, 1H), 8.27 (dd, J=4.45, 1.07 Hz, 1H), 7.90 (s, 1H), 7.74-7.78 (m, 2H), 7.65-7.68 (m, 2H), 7.61 (m, 1H), 7.41 (d, J=7.98 Hz, 1H), 7.19-7.28 (m, 4H), 6.92-6.95 (m, 3H), 5.38 (s, 2H), 4.33 (t, J=6.60 Hz, 2H), 3.92 (s, 3H), 2.96 (t, J=6.60 Hz, 2H).

EXAMPLE 673

3-[4-(1H-imidazol-1-ylmethyl)-3-methoxyphenyl]-8-{2-[(2-methylpyridin-3-yl)oxy]ethyl}-5,10-dihydro-11H-dibenzo[b,e][1,4]diazepin-11-one The title compound was prepared by substituting Example 586 and 2-methyl-pyridin-3-ol for Example 204A and 4-morpholinophenol, respectively, in Example 297A. MS (ESI) m/e 532 (M+H)$^+$, $^1$H NMR (DMSO-d$_6$, 400 MHz): □ 9.82 (s, 1H), 9.15 (s, 1H), 8.09 (d, J=4.60 Hz, 1H), 7.90 (s, 1H), 7.75 (d, J=7.98 Hz, 1H), 7.70 (m, 1H), 7.66 (m, 1H), 7.57 (d, J=8.59 Hz, 1H), 7.43 (d, J=7.98 Hz, 1H), 7.37 (m, 1H), 7.19-7.28 (m, 4H), 6.91-6.96 (m, 3H), 5.39 (s, 2H), 4.20 (t, J=6.29 Hz, 2H), 3.92 (s, 3H), 2.93 (t, J=6.29 Hz, 2H), 2.37 (s, 3H).

EXAMPLE 674

8-{2-[(2-bromopyridin-3-yl)oxy]ethyl}-3-[4-(1H-imidazol-1-ylmethyl)-3-methoxyphenyl]-5,10-dihydro-11H-dibenzo[b,e][1,4]diazepin-11-one The title compound was prepared by substituting Example 586 and 2-bromo-pyridin-3-ol for Example 204A and 4-morpholinophenol, respectively, in Example 297A. MS (ESI) m/e 598 (M+H)$^+$, $^1$H NMR (DMSO-d$_6$, 400 MHz): ☐ 9.79 (s, 1H), 9.14 (s, 1H), 7.93 (dd, J=4.6, 1.53 Hz, 1H), 7.89 (s, 1H), 7.75 (d, J=8.29 Hz, 1H), 7.70 (m, 1H), 7.65 (m, 1H), 7.49 (dd, J=8.29, 1.23 Hz, 1H), 7.43 (d, J=7.98 Hz, 1H), 7.36 (dd, J=7.98, 4.60 Hz, 1H), 7.19-7.29 (m, 4H), 6.92-6.95 (m, 3H), 5.39 (s, 2H), 4.21 (t, J=6.60 Hz, 2H), 3.91 (s, 3H), 2.94 (t, J=6.60 Hz, 2H).

EXAMPLE 675

3-[3-methoxy-4-(pyridin-4-ylmethyl)phenyl]-8-[2-(4-morpholin-4-ylphenoxy)ethyl]-5,10-dihydro-11H-dibenzo[b,e][1,4]diazepin-11-one

EXAMPLE 675A 4-(4-chloro-2-methoxybenzyl)pyridine

A mixture of 1-bromomethyl-4-chloro-2-methoxy-benzene (50 mg, 0.21 mmol), 4-pyridyl boronic acid (39 mg, 0.32 mmol), Pd(PPh$_3$)$_4$ (24 mg, 0.021 mmol) and 2M Na$_2$CO$_3$ were combined in DME (2 mL), purged with N$_2$, and heated to reflux for 3 hours. The mixture was then partitioned between ethyl acetate and water. The organic layer was washed with brine, dried (MgSO$_4$), filtered, and concentrated under vacuum. The residue was purified by flash column chromatography on silica gel with 1:1 hexanes/ethyl acetate to provide 17 mg (33%) of the title compound. MS (ESI) m/e 234 (M+H)$^+$.

EXAMPLE 675B

3-[3-methoxy-4-(pyridin-4-ylmethyl)phenyl]-8-[2-(4-morpholin-4-ylphenoxy)ethyl]-5,10-dihydro-11H-dibenzo[b,e][1,4]diazepin-11-one The desired compound was prepared by substituting Example 578A and Example 675A for Example 56A and Example 59B, respectively, in Example 59C. MS (ESI) m/e 613 (M+H)$^+$, $^1$H NMR (DMSO-d$_6$, 400 MHz): ☐ 9.88 (s, 1H), 8.86 (d, J=6.14 Hz, 2H), 7.87 (s, 1H), 7.75 (d, J=7.98 Hz, 1H), 7.67 (d, J=6.14 Hz, 2H), 7.39 (d, J=7.67 Hz, 1H), 7.29 (d, J=1.53 Hz, 1H), 7.20-7.23 (m, 3H), 6.87-6.93 (m, 5H), 6.82-6.84 (m, 2H), 4.16 (s, 2H), 4.04 (t, J=6.60 Hz, 2H), 3.86 (s, 3H), 3.71-3.74 (m, 4H), 2.97-3.00 (m, 4H), 2.86 (t, J=6.75 Hz, 2H).

EXAMPLE 676

2-{3-[4-(cyanomethyl)-3-methoxyphenyl]-11-oxo-10,11-dihydro-5H-dibenzo[b,e][1,4]diazepin-8-yl}-2-methyl-N-(4-morpholin-4-ylphenyl)propanamide

EXAMPLE 676A 2-methyl-N-(4-morpholin-4-ylphenyl)-2-[11-oxo-3-(4,4,5,5-tetramethyl-1,3,2-dioxaborolan-2-yl)-10,11-dihydro-5H-dibenzo[b,e][1,4]diazepin-8-yl]propanamide The title compound was prepared by substituting Example 202B for Example 6D in Example 54A. MS (ESI) m/e 583 (M+H)$^+$.

EXAMPLE 676B

2-{3-[4-(cyanomethyl)-3-methoxyphenyl]-11-oxo-10,11-dihydro-5H-dibenzo[b,e][1,4]diazepin-8-yl}-2-methyl-N-(4-morpholin-4-ylphenyl)propanamide The title compound was prepared by substituting Example 676A and Example 587A for Example 56A and Example 59B, respectively, in Example 59C. MS (ESI) m/e 602 (M+H)$^+$, $^1$H NMR (DMSO-d$_6$, 500 MHz): ☐ 9.82 (s, 1H), 8.81 (s, 1H), 7.95 (s, 1H), 7.75 (d, J=8.24 Hz, 1H), 7.41-7.44 (m, 3H), 7.30 (d, J=1.53 Hz, 1H), 7.21-7.26 (m, 3H), 7.04 (d, J=1.83 Hz, 1H), 6.92-6.98 (m, 2H), 6.84-6.86 (m, 2H), 3.94 (s, 3H), 3.89 (s, 2H), 3.70-3.72 (m, 4H), 3.01-3.03 (m, 4H), 1.48 (s, 6H).

EXAMPLE 677

3-(4-benzyl-3-methoxyphenyl)-8-[2-(4-morpholin-4-ylphenoxy)ethyl]-5,10-dihydro-11H-dibenzo[b,e][1,4]diazepin-11-one

EXAMPLE 677A 1-benzyl-4-chloro-2-methoxybenzene

1-Bromomethyl-4-chloro-2-methoxy-benzene (50 mg, 0.21 mmol), phenyl boronic acid (28 mg, 0.23 mmol), Pd(PPh$_3$)$_4$ (24 mg, 0.021 mmol) and K$_2$CO$_3$ (87 mg, 0.63 mmol) were combined in dioxane, purged with N$_2$, and heated to reflux for 16 hours. The mixture was then partitioned between ethyl acetate and water. The organic layer was washed with brine, dried (MgSO$_4$), filtered, and concentrated under vacuum. The residue was purified by flash column chromatography on silica gel eluting with 4:1 hexanes/ethyl acetate to provide 9 mg (18%) of the title compound. MS (ESI) m/e 233 (M+H)$^+$.

EXAMPLE 677B 3-(4-benzyl-3-methoxyphenyl)-8-[2-(4-morpholin-4-ylphenoxy)ethyl]-5,10-dihydro-11H-dibenzo[b,e][1,4]diazepin-11-one The title compound was prepared by substituting Example 677A and Example 578A for Example 56A and Example 59B, respectively, in Example 59C. MS (ESI) m/e 612 (M+H)$^+$, $^1$H NMR (DMSO-d$_6$, 500 MHz): ☐ 9.75 (s, 1H), 7.86 (s, 1H), 7.74 (d, J=8.42 Hz, 1H), 7.26-7.29 (m, 3H), 7.17-7.23 (m, 6H), 7.14 (m, 1H), 6.88-6.95 (m, 5H), 6.85-6.86 (m, 2H), 4.04 (t, J=6.71 Hz, 2H), 3.93 (s, 2H), 3.88 (s, 3H), 3.72-3.74 (m, 4H), 3.01-3.03 (m, 4H), 2.86 (t, J=6.71 Hz, 2H).

EXAMPLE 678

3-{3-methoxy-4-[(2-methyl-1H-imidazol-1-yl)methyl]phenyl}-8-[2-(4-morpholin-4-ylphenoxy)ethyl]-5,10-dihydro-11H-dibenzo[b,e][1,4]diazepin-11-one

EXAMPLE 678A 1-(4-chloro-2-methoxybenzyl)-2-methyl-1H-imidazole

2-Methyl imidazole (45 mg, 0.55 mmol) was dissolved in DMF. Sodium hydride (60 mg, 1.5 mmol) was added slowly. The mixture was stirred at room temperature until bubbling ceased. 1-Bromomethyl-4-chloro-2-methoxy-benzene (117 mg, 0.5 mmol) was added and the mixture was heated to 100° C. for 16 hours. The mixture was cooled to room temperature, diluted with ethyl acetate, and washed with water and with brine. The organic layer was dried (MgSO$_4$), filtered, and concentrated under vacuum. The residue was purified by flash column chromatography on silica gel (1:1 hexanes/ethyl acetate) to provide 47 mg (40%) of the title compound. MS (ESI) m/e 237 (M+H)$^+$.

EXAMPLE 678B

3-{3-methoxy-4-[(2-methyl-1H-imidazol-1-yl)methyl]phenyl}-8-[2-(4-morpholin-4-ylphenoxy)ethyl]-5,10-dihydro-11H-dibenzo[b,e][1,4]diazepin-11-one The title compound was prepared by substituting Example 678A and Example 578A for Example 56A and Example 59B, respectively, in Example 59C. MS (ESI) m/e 616 (M+H)$^+$, $^1$H NMR (DMSO-d$_6$, 400 MHz): □ 9.79 (s, 1H), 7.89 (s, 1H), 7.76 (d, J=8.11 Hz, 1H), 7.55-7.56 (m, 2H), 7.39 (d, J=8.11 Hz, 1H), 7.29 (dd, J=7.96, 1.40 Hz, 2H), 7.24 (dd, J=7.95, 1.40 Hz, 1H), 7.21 (dd, J=8.11, 1.56 Hz, 1H), 6.82-6.95 (m, 7H), 5.31 (s, 2H), 4.04 (t, J=6.71 Hz, 2H), 3.92 (s, 3H), 3.70-3.72 (m, 4H), 2.97-2.99 (m, 4H), 2.86 (t, J=6.71 Hz, 2H), 2.64 (s, 3H).

EXAMPLE 679

3-[3-methoxy-4-(1,3-thiazol-5-ylmethyl)phenyl]-8-[2-(4-morpholin-4-ylphenoxy)ethyl]-5,10-dihydro-11H-dibenzo[b,e][1,4]diazepin-11-one

EXAMPLE 679A (4-chloro-2-methoxyphenyl)(1,3-thiazol-5-yl)methanol

A solution of 4-bromo-2-trimethylsilanyl-thiazole (1.0 g, 4.23 mmol) in THF (8 mL) was cooled to −78° C. n-BuLi (1.68 mL, 2.5M in hexanes, 4.65 mmol) was added dropwise and the resulting solution was stirred at −78° C. for 30 minutes. A solution of 4-chloro-2-methoxy-benzaldehyde in THF (2 mL) was added to the reaction, followed by 30 minutes of stirring at −78° C. The reaction was then allowed to warm slowly to room temperature. 3M HCl (10 mL) was added and the reaction was stirred for 16 hours. The solution was then neutralized with Na$_2$CO$_3$ solution and partitioned between ethyl acetate and water. The combined organic layers were dried (MgSO$_4$), filtered, and concentrated under vacuum. The residue was then purified by flash column chromatography on silica gel with 7:3 hexanes/ethyl acetate to provide 204 mg (19%) of the title compound. MS (ESI) m/e 256 (M+H)$^+$, $^1$H NMR (DMSO-d$_6$, 300 MHz): □ 8.92 (s, 1H), 7.61 (s, 1H), 7.51 (d, J=7.80 Hz, 1H), 7.03-7.07 (m, 2H), 6.30 (d, J=4.75 Hz, 1H), 6.19 (d, J=4.41 Hz, 1H), 3.81 (s, 3H).

EXAMPLE 679B 5-(4-chloro-2-methoxybenzyl)-1,3-thiazole

A mixture of Example 679A (204 mg, 0.8 mmol), trifluoroacetic acid (0.87 mL, 8 mmol), and triethylsilane (1.27 mL, 8 mmol) in methylene chloride was stirred at room temperature for 5 days. The solution was concentrated under vacuum, diluted with methylene chloride, and poured into 2M NaOH. The organic layer was washed with brine, dried (MgSO$_4$), filtered, and concentrated under vacuum. The residue was then purified by flash column chromatography on silica gel with 1:1 hexanes/methylene chloride to provide 108 mg (57%) of the title compound. MS (ESI) m/e 240 (M+H)$^+$, $^1$H NMR (DMSO-d$_6$, 300 MHz): □ 8.88 (s, 1H), 7.67 (s, 1H), 7.21 (d, J=7.80 Hz, 1H), 7.07 (d, J=2.03 Hz, 1H), 6.96 (dd, J=7.80, 2.03 Hz, 1H), 4.10 (s, 2H), 3.84 (s, 3H).

EXAMPLE 679C

3-[3-methoxy-4-(1,3-thiazol-5-ylmethyl)phenyl]-8-[2-(4-morpholin-4-ylphenoxy)ethyl]-5,10-dihydro-11H-dibenzo[b,e][1,4]diazepin-11-one The title compound was prepared by substituting Example 679B and Example 578A for Example 56A and Example 59B, respectively, in Example 59C. MS (ESI) m/e 619 (M+H)$^+$, $^1$H NMR (DMSO-d$_6$, 400 MHz): □ 9.80 (s, 1H), 8.90 (s, 1H), 7.89 (s, 1H), 7.74 (d, J=8.24 Hz, 1H), 7.71 (s, 1H), 7.28-7.31 (m, 2H), 7.16-7.21 (m, 3H), 6.81-6.95 (m, 7H), 4.17 (s, 2H), 4.03 (t, J=6.56 Hz, 2H), 3.92 (s, 3H), 3.70-3.72 (m, 4H), 2.95-2.97 (m, 4H), 2.86 (t, J=6.56 Hz, 2H).

EXAMPLE 680

3-[3-methoxy-4-(morpholin-4-ylmethyl)phenyl]-8-[2-(4-morpholin-4-ylphenoxy)ethyl]-5,10-dihydro-11H-dibenzo[b,e][1,4]diazepin-11-one

EXAMPLE 680A 4-(4-chloro-2-methoxybenzyl)morpholine

A mixture of 1-bromomethyl-4-chloro-2-methoxy-benzene (705 mg), morpholine (0.52 mL, 6 mmol) in toluene (15 mL) was heated to 110° C. for 2 hours. The solution was then partitioned between ethyl acetate and water. The organic layer was washed with brine, dried (MgSO$_4$), filtered, and concentrated under vacuum to provide 675 mg (93%) of the title compound. MS (ESI) m/e 242 (M+H)$^+$.

EXAMPLE 680B

3-[3-methoxy-4-(morpholin-4-ylmethyl)phenyl]-8-[2-(4-morpholin-4-ylphenoxy)ethyl]-5,10-dihydro-11H-dibenzo[b,e][1,4]diazepin-11-one The title compound was prepared by substituting Example 680A and Example 578A for Example 476G and Example 266G, respectively, in Example 476H. MS (ESI) m/e 613 (M+H)$^+$, $^1$H NMR (DMSO-d$_6$, 400 MHz): □ 9.80 (s, 1H), 8.00 (s, 1H), 7.76 (d, J=8.29 Hz, 1H), 7.66 (d, J=7.67 z, 1H), 7.21-7.39 (m, 6H), 6.89-6.99 (m, 5H), 4.30-4.32 (m, 2H), 4.10 (t, J=6.60 Hz, 2H), 3.95 (s, 3H), 3.87-3.92 (m, 4H), 3.75-3.81 (m, 4H), 3.22-3.30 (m, 4H), 3.07-3.16 (m, 4H), 2.88 (t, J=6.75 Hz, 2H).

EXAMPLE 681

3-{3-methoxy-4-[(4-oxopyridin-1(4H)-yl)methyl]phenyl}-8-[2-(4-morpholin-4-ylphenoxy)ethyl]-5,10-dihydro-11H-dibenzo[b,e][1,4]diazepin-11-one

EXAMPLE 681A 1-(4-chloro-2-methoxybenzyl)pyridin-4(1H)-one

The title compound was prepared by substituting (4-chloro-2-methoxy-phenyl)-methanol and pyridin-4-ol for

EXAMPLE 681B

3-{3-methoxy-4-[(4-oxopyridin-1(4H)-yl)methyl]phenyl}-8-[2-(4-morpholin-4-ylphenoxy)ethyl]-5,10-dihydro-11H-dibenzo[b,e][1,4]diazepin-11-one The title compound was prepared by substituting Example 681A and Example 578A for Example 476G and Example 266G, respectively, in Example 476H. MS (ESI) m/e 629 (M+H)$^+$, $^1$H NMR (DMSO-d$_6$, 400 MHz): □ 9.80 (s, 1H), 8.58 (d, J=7.36 Hz, 2H), 7.90 (s, 1H), 7.76 (d, J=7.98 Hz, 1H), 7.51 (d, J=8.29 Hz, 1H), 7.26-7.29 (m, 3H), 7.21 (dd, J=8.29, 1.53 Hz, 1H), 7.17 (d, J=7.36 Hz, 2H), 6.82-6.95 (m, 7H), 5.51 (s, 2H), 4.04 (t, J=6.75 Hz, 2H), 3.90 (s, 3H), 3.71-3.73 (m, 4H), 2.97-3.00 (m, 4H), 2.86 (t, J=6.60 Hz, 2H).

EXAMPLE 682

3-(5-methoxy-2-nitrophenyl)-8-[2-(4-morpholin-4-ylphenoxy)ethyl]-5,10-dihydro-11H-dibenzo[b,e][1,4]diazepin-11-one The title compound was prepared by substituting 2-bromo-4-methoxy-1-nitro-benzene and Example 578A for Example 476G and Example 266G, respectively, in Example 476H. MS (ESI) m/e 567 (M+H)$^+$, $^1$H NMR (DMSO-d$_6$, 400 MHz): □ 9.82 (s, 1H), 8.05 (d, J=9.21 Hz, 1H), 7.87 (s, 1H), 7.70 (d, J=8.29 Hz, 1H), 7.15 (dd, J=8.90, 2.76 Hz, 1H), 6.96 (d, J=2.76 Hz, 1H), 6.88-6.92 (m, 6H), 6.81-6.84 (m, 3H), 4.04 (t, J=6.60 Hz, 2H), 3.88 (s, 3H), 3.70-3.73 (m, 4H), 2.99-3.01 (m, 4H), 2.86 (t, J=6.60 Hz, 2H).

EXAMPLE 683

3-{4-[hydroxy(pyridin-3-yl)methyl]-3-methoxyphenyl}-8-[2-(4-morpholin-4-ylphenoxy)ethyl]-5,10-dihydro-1H-dibenzo[b,e][1,4]diazepin-11-one

EXAMPLE 683A (4-chloro-2-methoxyphenyl)(pyridin-3-yl)methanol

Toluene (3.5 mL) was added to a 3-necked flask and cooled to −60° C. n-BuLi (1.3 mL, 2.5M in hexanes) was added. A solution of 3-bromopyridine (0.3 mL, 3 mmol) in toluene (1.2 mL) was added dropwise to maintain internal temperature <−50° C. The resulting slurry was then stirred for 30 minutes at −60° C. THF (1.2 mL) was added dropwise, and the mixture was stirred for an additional 15 minutes. 4-Chloro-2-methoxy-benzaldehyde (561 mg, 3.3 mmol) was added and the mixture was allowed to warm to room temperature. The reaction was partitioned between ethyl acetate and water. The organic layer was washed with brine, dried (MgSO$_4$), filtered, and concentrated under vacuum. The residue was purified by flash column chromatography on silica gel with 7:3 hexanes/ethyl acetate to provide 201 mg (27%) of the title compound. MS (ESI) m/e 250 (M+H)$^+$.

EXAMPLE 683B

3-{4-[hydroxy(pyridin-3-yl)methyl]-3-methoxyphenyl}-8-[2-(4-morpholin-4-ylphenoxy)ethyl]-5,10-dihydro-1H-dibenzo[b,e][1,4]diazepin-11-one The title compound was prepared by substituting Example 683A and Example 578A for Example 476G and Example 266G, respectively, in Example 476H. MS (ESI) m/e 629 (M+H)$^+$, $^1$H NMR (DMSO-d$_6$, 500 MHz): □ 9.80 (s, 1H), 8.76 (s, 1H), 8.63 (d, J=4.88 Hz, 1H), 8.14 (d, J=7.93 Hz, 1H), 7.89 (s, 1H), 7.74 (d, J=8.24 Hz, 1H), 7.71 (m, 1H), 7.64 (d, J=7.93 Hz, 1H), 7.19-7.28 (m, 4H), 6.83-6.95 (m, 7H), 6.11 (s, 1H), 4.04 (t, J=6.71 Hz, 2H), 3.86 (s, 3H), 3.78 (br s, 1H), 3.72-3.74 (m, 4H), 3.00-3.02 (m, 4H), 2.86 (t, J=6.56 Hz, 2H).

EXAMPLE 684

N-(2-methoxy-4-{8-[2-(4-morpholin-4-ylphenoxy)ethyl]-11-oxo-10,11-dihydro-5H-dibenzo[b,e][1,4]diazepin-3-yl}phenyl)thiophene-2-sulfonamide

EXAMPLE 684A

N-(4-chloro-2-methoxyphenyl)thiophene-2-sulfonamide

A mixture of 2-amino-5-chloroanisole (157 mg, 1 mmol), thiophene-2-sulfonyl chloride (183 mg, 1 mmol), and pyridine (0.25 mL, 3 mmol) in methylene chloride (3 mL) was stirred at room temperature for 16 hours. The mixture was then partitioned between methylene chloride and water. The organic layer was washed with brine, dried (MgSO$_4$), filtered, and concentrated under vacuum to provide 290 mg (96%) of the title compound. MS (ESI) m/e 304 (M+H)$^+$.

EXAMPLE 684B

N-(2-methoxy-4-{8-[2-(4-morpholin-4-ylphenoxy)ethyl]-11-oxo-10,11-dihydro-5H-dibenzo[b,e][1,4]diazepin-3-yl}phenyl)thiophene-2-sulfonamide A mixture of Example 684A (108 mg, 0.2 mmol), Example 579A (73 mg, 0.24 mmol), Pd(OAc)$_2$ (9 mg, 0.04 mmol), CyMAP (31 mg, 0.08 mmol), CsF (91 mg, 0.6 mmol), and a 2:1 mixture of ethylene glycol dimethyl ether/methanol (6 mL) was placed in a microwave process vial, capped and heated at 180° C. for 15 minutes in a CEM Explorer set at 300 W. Aqueous work-up. MS (ESI) m/e 683 (M+H)$^+$, $^1$H NMR (DMSO-d$_6$, 500 MHz): □ 9.79 (s, 1H), 9.77 (s, 1H), 7.89 (d, J=4.88 Hz, 1H), 7.87 (s, 1H), 7.73 (d, J=8.24 Hz, 1H), 7.49 (d, J=3.05 Hz, 1H), 7.37 (d, J=7.93 Hz, 1H), 7.25 (s, 1H), 7.17-7.19 (m, 3H), 7.12 (m, 1H), 6.83-6.94 (m, 7H), 4.04 (t, J=6.56 Hz, 2H), 3.72-3.74 (m, 4H), 3.67 (s, 3H), 3.00-3.02 (m, 4H), 2.86 (t, J=6.71 Hz, 2H).

EXAMPLE 685

3-{4-[hydroxy(1,3-thiazol-2-yl)methyl]-3-methoxyphenyl}-8-[2-(4-morpholin-4-ylphenoxy)ethyl]-5,10-dihydro-11H-dibenzo[b,e][1,4]diazepin-11-one

EXAMPLE 685A (4-chloro-2-methoxyphenyl)[4-(trimethylsilyl)-1,3-thiazol-2-yl]methanol The title compound was obtained during the preparation described in Example 679A. MS (ESI) m/e 328 (M+H)$^+$.

EXAMPLE 685B (4-chloro-2-methoxyphenyl)(1,3-thiazol-2-yl)methanol

Tetrabutylammonium fluoride (0.58 mL, 1M solution in THF) was added to a solution of Example 685A (96 mg, 0.29 mmol) in THF (2 mL). The resulting solution was stirred at room temperature for 1 hour. The reaction was partitioned between ethyl acetate and water. The organic layer was washed with brine, dried (MgSO$_4$), filtered, and concentrated under vacuum. The residue was purified by preparative HPLC to provide 65 mg (88%) of the title compound. MS (ESI) m/e 256 (M+H)$^+$.

EXAMPLE 685C

3-{4-[hydroxy(1,3-thiazol-2-yl)methyl]-3-methoxyphenyl}-8-[2-(4-morpholin-4-ylphenoxy)ethyl]-5,10-dihydro-11H-dibenzo[b,e][1,4]diazepin-11-one The title compound was prepared by substituting Example 685B for Example 684A in Example 684B. MS (ESI) m/e 635 (M+H)$^+$, $^1$H NMR (DMSO-d$_6$, 300 MHz): □ 9.79 (s, 1H), 7.90 (s, 1H), 7.75 (d, J=8.14 Hz, 1H), 7.68 (m, 1H), 7.61 (d, J=3.39 Hz, 1H), 7.44 (d, J=8.14 Hz, 1H), 7.29 (d, J=1.70 Hz, 1H), 7.19-7.22 (m, 3H), 6.83-6.96 (m, 7H), 6.25 (s, 1H), 4.05 (t, J=6.78 Hz, 2H), 3.87 (s, 3H), 3.81 (br s, 1H), 3.72-3.75 (m, 4H), 3.01-3.03 (m, 4H), 2.87 (t, J=6.61 Hz, 2H).

EXAMPLE 686

3-[3-methoxy-4-(pyridin-3-ylamino)phenyl]-8-[2-(4-morpholin-4-ylphenoxy)ethyl]-5,10-dihydro-11H-dibenzo[b,e][1,4]diazepin-11-one

EXAMPLE 686A

N-(4-chloro-2-methoxyphenyl)pyridin-3-amine

The title compound was prepared by substituting 4-bromopyridine and 2-amino-5-chloroanisole for Example 189A and 4-aminopyridine, respectively, in Example 191. MS (ESI) m/e 235 (M+H)$^+$.

EXAMPLE 686B

3-[3-methoxy-4-(pyridin-3-ylamino)phenyl]-8-[2-(4-morpholin-4-ylphenoxy)ethyl]-5,10-dihydro-11H-dibenzo[b,e][1,4]diazepin-11-one The title compound was prepared by substituting Example 686B for Example 684A in Example 684B. MS (ESI) m/e 614 (M+H)$^+$, $^1$H NMR (DMSO-d$_6$, 500 MHz): □ 9.81 (s, 1H), 8.77 (s, 1H), 8.31 (d, J=2.44 Hz, 1H), 8.19 (d, J=4.88 Hz, 1H), 7.90 (s, 1H), 7.84 (dd, J=8.54, 1.83 Hz, 1H), 7.76 (d, J=8.24 Hz, 1H), 7.71 (dd, J=8.54, 5.49 Hz, 1H), 7.40 (d, J=8.24 Hz, 1H), 7.36 (d, J=1.83 Hz, 1H), 7.32 (d, J=1.53 Hz, 1H), 7.23-7.26 (m, 2H), 6.83-6.96 (m, 7H), 4.04 (t, J=6.71 Hz, 2H), 3.93 (s, 3H), 3.71-3.73 (m, 4H), 2.98-3.00 (m, 4H), 2.87 (t, J=6.71 Hz, 2H).

EXAMPLE 687

3-[3-methoxy-4-(pyridin-3-ylmethyl)phenyl]-8-[2-(4-morpholin-4-ylphenoxy)ethyl]-5,10-dihydro-11H-dibenzo[b,e][1,4]diazepin-11-one

EXAMPLE 687A 3-(4-chloro-2-methoxybenzyl)pyridine

The title compound was prepared by substituting 1-bromomethyl-4-chloro-2-methoxy-benzene and 3-[1,3,2]dioxaborinan-2-yl-pyridine for 1-bromomethyl-4-chloro-2-methoxy-benzene and 4-pyridyl boronic acid, respectively, in Example 700A. MS (ESI) m/e 234 (M+H)$^+$.

EXAMPLE 687B

3-[3-methoxy-4-(pyridin-3-ylmethyl)phenyl]-8-[2-(4-morpholin-4-ylphenoxy)ethyl]-5,10-dihydro-11H-dibenzo[b,e][1,4]diazepin-11-one The title compound was prepared by substituting Example 712A for Example 709A in Example 709B. MS (ESI) m/e 613 (M+H)$^+$, $^1$H NMR (DMSO-d$_6$, 400 MHz): □ 9.77 (s, 1H), 8.70 (s, 1H), 8.62 (d, J=4.91 Hz, 1H), 8.09 (d, J=7.98 Hz, 1H), 7.87 (s, 1H), 7.74 (d, J=7.98 Hz, 1H), 7.71 (dd, J=7.83, 5.37 Hz, 1H), 7.35 (d, J=7.67 Hz, 1H), 7.28 (d, J=1.23 Hz, 1H), 7.18-7.22 (m, 3H), 6.83-6.96 (m, 7H), 4.08 (s, 2H), 4.04 (t, J=6.75 Hz, 2H), 3.88 (s, 3H), 3.71-3.74 (m, 4H), 2.99-3.01 (m, 4H), 2.86 (t, J=6.60 Hz, 2H).

EXAMPLE 688

3-(4-anilino-3-methoxyphenyl)-8-[2-(4-morpholin-4-ylphenoxy)ethyl]-5,10-dihydro-11H-dibenzo[b,e][1,4]diazepin-11-one

EXAMPLE 688A

N-(4-chloro-2-methoxyphenyl)-N-phenylamine

The title compound was prepared by substituting bromobenzene and 2-amino-5-chloroanisole for Example 189A and 4-aminopyridine, respectively, in Example 191. MS (ESI) m/e 234 (M+H)$^+$.

EXAMPLE 688B 3-(4-anilino-3-methoxyphenyl)-8-[2-(4-morpholin-4-ylphenoxy)ethyl]-5,10-dihydro-11H-dibenzo[b,e][1,4]diazepin-11-one The title compound was prepared by substituting Example 688A for Example 684A in Example 684B. MS (ESI) m/e 613 (M+H)$^+$, $^1$H NMR (DMSO-d$_6$, 400 MHz): □ 9.72 (s, 1H), 7.84 (s, 1H), 7.72 (d, J=8.29 Hz, 1H), 7.22-7.29 (m, 5H), 7.19 (dd, J=8.29, 1.53 Hz, 1H), 7.14-7.17 (m, 3H), 6.84-6.96 (m, 9H), 4.05 (t, J=6.75 Hz, 2H), 3.93 (s, 3H), 3.72-3.75 (m, 4H), 3.02-3.04 (m, 4H), 2.87 (m, t, J=6.60 Hz, 2H).

EXAMPLE 689

3-[3-methoxy-4-(1,3,4-oxadiazol-2-yl)phenyl]-8-[2-(4-morpholin-4-ylphenoxy)ethyl]-5,10-dihydro-11H-dibenzo[b,e][1,4]diazepin-11-one

EXAMPLE 689A tert-butyl 2-(4-chloro-2-methoxybenzoyl)hydrazinecarboxylate

A solution of 4-chloro-2-methoxybenzoic acid (4.3 g, 23.1 mmol), tert-butyl carbazate (3.5 g, 26.5 mmol), EDCI.HCl (5.0 g, 26.1 mmol), and triethylamine (3.5 mL, 2.6 g, 25.3 mmol) in $CH_2Cl_2$ (50 mL) was stirred at room temperature overnight. The next day the reaction was diluted with EtOAc (200 mL), then washed with 1M $H_3PO_4$, saturated $NaHCO_3$, and brine. The organic layer was dried ($Na_2SO_4$), filtered, and concentrated under vacuum, giving the product (6.0 g, 87%). MS (DCI) m/e 301 & 303 (M+H)$^+$, 318 & 320 (M+$NH_4$)$^+$; $^1$H NMR (300 MHz, CDCl$_3$) δ 9.40 (br s, 1H), 8.15 (d, J=8.2 Hz, 1H), 7.08 (dd, J=8.2, 1.7 Hz, 1H), 6.98 (d, J=1.7 Hz, 1H), 6.67 (v br s, 1H), 4.00 (s, 3H), 1.50 (s, 9H).

EXAMPLE 689B 4-chloro-2-methoxybenzohydrazide

The title compound in Example 689A (6.0 g, 20.0 mmol) was dissolved in 4N HCl in dioxane (90 mL) and stirred at room temperature for 1 hour. The reaction was concentrated, diluted with EtOAc, then washed with saturated $NaHCO_3$ and brine. The organic layer was dried ($Na_2SO_4$), filtered, and concentrated under vacuum, giving the product (3.6 g, 90%) as white solids. MS (DCI) m/e 201 & 203 (M+H)$^+$.

EXAMPLE 689C 2-(4-chloro-2-methoxyphenyl)-1,3,4-oxadiazole

The title compound in Example 689B (1.0 g, 5.0 mmol) was dissolved in triethyl orthoformate (10 mL) and stirred at 140° C. for 4 hours. The reaction was concentrated under vacuum, and the residue was purified by chromatography on silica gel with 6/4 hexanes/EtOAc, giving the product (0.66 g, 63%). MS (DCI) m/e 211 & 213 (M+H)$^+$. $^1$H NMR (300 MHz, CDCl$_3$) δ 8.48 (s, 1H), 7.90 (d, J=8.5 Hz, 1H), 7.08 (dd, J=8.5, 1.7 Hz, 1H), 7.07 (d, J=1.7 Hz, 1H), 3.98 (s, 3H).

EXAMPLE 689D

2-[2-methoxy-4-(4,4,5,5-tetramethyl-1,3,2-dioxaborolan-2-yl)phenyl]-1,3,4-oxadiazole The title compound was prepared by substituting Example 689C for Example 6D in Example 54A. MS (DCI) m/e 303 (M+H)$^+$.

EXAMPLE 689E

3-[3-methoxy-4-(1,3,4-oxadiazol-2-yl)phenyl]-8-[2-(4-morpholin-4-ylphenoxy)ethyl]-5,10-dihydro-11H-dibenzo[b,e][1,4]diazepin-11-one The title compound was prepared by substituting Example 689D and Example 297A for Example 56A and Example 59B, respectively, in Example 59C. MS (ESI) m/e 590 (M+H)$^+$. $^1$H NMR (500 MHz, DMSO-d$_6$) δ 9.82 (s, 1H), 9.34 (s, 1H), 7.98 (d, J=7.8 Hz, 1H), 7.94 (s, 1H), 7.80 (d, J=8.0 Hz, 1H), 7.46 (d, J=1.6 Hz, 1H) 7.40 (dd, J=7.8, 1.6 Hz, 1H), 7.39 (d, J=1.6 Hz, 1H), 7.31 (dd, J=8.0, 1.6 Hz, 1H), 6.94 (m, 5H), 6.86 (d, J=9.0 Hz, 2H), 4.06 (t, J=6.5 Hz, 2H), 4.00 (s, 3H), 3.74 (m, 4H), 3.04 (m, 4H), 2.87 (t, J=6.5 Hz, 2H).

EXAMPLE 690

3-[3-methoxy-4-(5-methyl-1,3,4-oxadiazol-2-yl)phenyl]-8-[2-(4-morpholin-4-ylphenoxy)ethyl]-5,10-dihydro-1H-dibenzo[b,e][1,4]diazepin-11-one

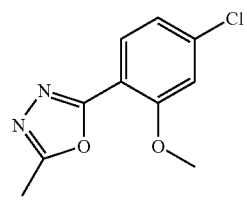

EXAMPLE 690A 2-(4-chloro-2-methoxyphenyl)-5-methyl-1,3,4-oxadiazole

The title compound was prepared by substituting triethyl orthoacetate for triethyl orthoformate in Example 689C. MS (DCI) m/e 225 & 227 (M+H)$^+$. $^1$H NMR (300 MHz, CDCl$_3$) δ 7.84 (d, J=8.1 Hz, 1H), 7.06 (dd, J=8.1, 2.0 Hz, 1H), 7.05 (d, J=2.0 Hz, 1H), 3.96 (s, 3H), 2.61 (s, 3H).

EXAMPLE 690B

2-[2-methoxy-4-(4,4,5,5-tetramethyl-1,3,2-dioxaborolan-2-yl)phenyl]-5-methyl-1,3,4-oxadiazole The title compound was prepared by substituting Example 690A for Example 6D in Example 54A. MS (DCI) m/e 317 (M+H)$^+$.

EXAMPLE 690C

3-[3-methoxy-4-(5-methyl-1,3,4-oxadiazol-2-yl)phenyl]-8-[2-(4-morpholin-4-ylphenoxy)ethyl]-5,10-dihydro-11H-dibenzo[b,e][1,4]diazepin-11-one The title compound was prepared by substituting Example 690B and Example 297A for Example 56A and Example 59B, respectively, in Example 59C. MS (ESI) m/e 604 (M+H)$^+$. $^1$H NMR (500 MHz, DMSO-d$_6$) δ 9.82 (s, 1H), 7.93 (s, 1H), 7.92 (d, J=8.1 Hz, 1H), 7.80 (d, J=8.1 Hz, 1H), 7.44 (s, 1H) 7.38 (m, 2H), 7.30 (d, J=8.1 Hz, 1H), 6.94 (m, 3H), 6.84 (m, 4H), 4.04 (t, J=6.5 Hz, 2H), 4.00 (s, 3H), 3.71 (m, 4H), 2.97 (m, 4H), 2.87 (t, J=6.5 Hz, 2H), 2.58 (s, 3H).

EXAMPLE 691

8-[2-(isoquinolin-3-yloxy)ethyl]-3-[3-methoxy-4-(1,3,4-oxadiazol-2-yl)phenyl]-5,10-dihydro-11H-dibenzo[b,e][1,4]diazepin-11-one The title compound was prepared by substituting Example 581 and 3-hydroxyisoquinoline for Example 204A and 4-morpholinophenol, respectively, in Example 297A, except here the purification was done by preparative HPLC. MS (ESI) m/e 556 (M+H)+. $^1$H NMR (500 MHz, DMSO-d$_6$) δ 9.93 (s, 1H), 9.41 (s, 1H), 9.11 (s, 1H), 8.08 (d, J=8.2 Hz, 1H), 8.04 (m, 2H), 7.85 (m, 2H), 7.70 (m, 1H), 7.52 (s, 1H), 7.48 (m, 2H), 7.45 (s, 1H), 7.37 (d, J=8.2 Hz, 1H), 7.23 (s, 1H), 7.02 (m, 3H), 4.53 (t, J=6.7 Hz, 2H), 4.07 (s, 3H), 3.03 (t, J=6.7 Hz, 2H).

EXAMPLE 692

N-(2-methoxy-4-{8-[2-(4-morpholin-4-ylphenoxy) ethyl]-11-oxo-10,11-dihydro-5H-dibenzo[b,e][1,4] diazepin-3-yl}phenyl)acetamide

EXAMPLE 692A 4-chloro-2-methoxyaniline

4-Chloro-2-methoxynitrobenzene (2.8 g, 14.9 mmol) was dissolved in MeOH (110 mL), then 5% platinum on carbon (0.61 g) was added and the reaction stirred under a H$_2$ balloon for 4 hours. The reaction was then filtered through diatomaceous earth (Celite®) and concentrated under vacuum, giving the product (2.3 g, 100%) as syrup that slowly solidified. MS (DCI) m/e 158 & 160 (M+H)+; $^1$H NMR (300 MHz, DMSO-d$_6$) δ 6.83 (d, J=2.4 Hz, 1H), 6.71 (dd, J=8.5, 2.4 Hz, 1H), 6.63 (d, J=8.5 Hz, 1H), 5.27 (v br s, 2H), 3.77 (s, 3H).

EXAMPLE 692B

N-(4-chloro-2-methoxyphenyl)acetamide

The title compound in Example 691A (2.3 g, 14.9 mmol) was dissolved in acetic anhydride (75 mL) and stirred at room temperature overnight. The reaction was poured into water and extracted with Et$_2$O. The organic layer was dried (Na$_2$SO$_4$), filtered, and concentrated under vacuum. After using toluene to azeotrope off the residual Ac$_2$O and AcOH, the product was recovered as brown solids (2.5 g, 84%). MS (DCI) m/e 200 & 202 (M+H)+; $^1$H NMR (300 MHz, DMSO-d$_6$) δ 9.20 (br s, 1H), 7.95 (d, J=8.5 Hz, 1H), 7.10 (d, J=2.4 Hz, 1H), 6.95 (dd, J=8.5, 2.4 Hz, 1H), 3.85 (s, 3H), 2.08 (s, 3H).

EXAMPLE 692C

N-(2-methoxy-4-{8-[2-(4-morpholin-4-ylphenoxy) ethyl]-11-oxo-10,11-dihydro-5H-dibenzo[b,e][1,4] diazepin-3-yl}phenyl)acetamide The title compound was prepared by substituting Example 578A and Example 692B for Example 56A and Example 59B, respectively, in Example 59C, with the exception of preparative HPLC used for purification. MS (ESI) m/e 579 (M+H)+. $^1$H NMR (400 MHz, DMSO-d$_6$) δ 9.76 (s, 1H), 9.20 (s, 1H), 8.09 (br d, J=8.0 Hz, 1H), 7.87 (s, 1H), 7.74 (d, J=8.3 Hz, 1H), 7.28 (d, J=1.5 Hz, 1H), 7.25 (d, J=1.5 Hz, 1H), 7.20 (m, 2H), 6.96 (m, 3H), 6.88 (m, 4H), 4.06 (t, J=6.7 Hz, 2H), 3.93 (s, 3H), 3.75 (m, 4H), 3.06 (m, 4H), 2.87 (t, J=6.7 Hz, 2H), 2.11 (s, 3H).

EXAMPLE 693

3-{3-methoxy-4-[(5-methyl-1,3,4-oxadiazol-2-yl) methoxy]phenyl}-8-[2-(4-morpholin-4-ylphenoxy) ethyl]-5,10-dihydro-11H-dibenzo[b,e][1,4]diazepin-11-one The title compound was prepared by substituting 2-methyl-5-chloromethyl-1,3,4-oxadiazole [prepared by the methods found in Helv. Chim. Acta, 55, 1979 (1972)] for 4-chloromethylpyridine hydrochloride in Example 607 MS (ESI) m/e 634 (M+H)+. $^1$H NMR (400 MHz, DMSO-d$_6$) δ 9.75 (s, 1H), 7.85 (s, 1H), 7.73 (d, J=8.0 Hz, 1H), 7.25, 7.19 (both m, total 5H), 6.94 (m, 5H), 6.85 (m, 2H), 5.86 (s, 2H), 4.05 (t, J=6.5 Hz, 2H), 3.86 (s, 3H), 3.74 (m, 4H), 3.05 (m, 4H), 2.87 (t, J=6.5 Hz, 2H), 2.54 (s, 3H).

EXAMPLE 694

8-{2-[4-(4-acetylpiperazin-1-yl)phenoxy]ethyl}-3-[3-methoxy-4-(1,3-thiazol-4-ylmethoxy)phenyl]-5,10-dihydro-11H-dibenzo[b,e][1,4]diazepin-11-one

EXAMPLE 694A

8-{2-[4-(4-acetylpiperazin-1-yl)phenoxy]ethyl}-3-chloro-5,10-dihydro-11H-dibenzo[b,e][1,4]diazepin-11-one A solution of 1-[4-(4-hydroxy-phenyl)-piperazin-1-yl]-ethanone (62 mg, 0.17 mmol) and potassium hydroxide (56 mg, 0.26 mmol) in DMF (10 mL) at 25° C. was treated with Example 641A (510 mg, 3 mmol). The resultant mixture was allowed to stir overnight. The suspension was then cooled to room temperature, diluted with water and extracted with ethyl acetate several times. The combined organic layers were dried and concentrated. It was then used for next reaction without further purification.

EXAMPLE 694B

8-{2-[4-(4-acetylpiperazin-1-yl)phenoxy]ethyl}-3-[3-methoxy-4-(1,3-thiazol-4-ylmethoxy)phenyl]-5,10-dihydro-11H-dibenzo[b,e][1,4]diazepin-11-one The title compound was prepared by substituting Example 641C and Example 694A for Example 56A and Example 59B, respectively, in Example 59C. MS (ESI) m/z 675 (M+H)+; $^1$H NMR (DMSO-d$_6$, 300 MHz) □ 9.76 (s, 1H), 9.14 (d, J=2 Hz, 1H), 7.85 (s, 1H), 7.80 (d, J=1.5 Hz, 1H), 7.73 (d, J=8.3 Hz, 1H), 7.26 (s, 1H), 7.13-7.23 (m, 3H), 6.86-6.94 (m, 5H), 6.76-6.85 (m, 2H), 5.25 (s, 2H), 4.04 (t, J=7 Hz, 2H), 3.86 (s, 3H), 5.51-3.56 (m, 4H), 2.99 (t, J=5 Hz, 2H), 2.93 (t, J=5.2 Hz, 2H), 2.86 (t, J=7 Hz, 2H).

EXAMPLE 695

8-[2-(4-Morpholin-4-yl-phenoxy)-ethyl]-3-(1H-pyrrolo[2,3-c]pyridin-3-yl)-5,10-dihydro-dibenzo[b,e] [1,4]diazepin-11-one

EXAMPLE 695A methyl (4-amino-3-nitrophenyl)acetate

Concentrated nitric acid (10 mL, >69% pure) was added to acetic anhydride (100 mL) cooled to −10° C. The solution was treated portionwise with N-[4-(cyanomethyl)phenyl]acetamide (5.0 g, 28.7 mmol) at a rate which maintained an internal temperature below −5° C. The solution was stirred for 1 hour while warming to room temperature. The solution was poured into an ice/water mixture and extracted several times with ethyl acetate. The combined extracts were washed with 10% Na$_2$CO$_3$ and brine, dried (MgSO$_4$), filtered, and concentrated under vacuum. The residue was purified by flash column chromatography on silica gel with 1:1 hexanes/ethyl acetate to provide 4.82 g (77%) of N-[4-(cyanomethyl)-2-nitrophenyl]acetamide.

A mixture of N-[4-(cyanomethyl)-2-nitrophenyl]acetamide (4.8 g), concentrated HCl (100 mL), and water (300 mL) was heated to reflux for two days, cooled to room temperature, and concentrated to near dryness under vacuum. The concentrate was treated with methanol (300 mL) and concentrated $H_2SO_4$ (30 mL), heated to reflux overnight, and concentrated under vacuum to remove the methanol. The residue was partitioned between ethyl acetate and water and the organic layers were combined, washed with saturated $NaHCO_3$ and brine, dried ($MgSO_4$), and concentrated under vacuum. The residue was purified by flash column chromatography on silica gel with 7:3 hexanes/ethyl acetate to provide 4.1 g (89%) of the desired product. MS (DCI) m/e 211 $(M+H)^+$, 228 $(M+NH_4)^+$; $^1H$ NMR (300 MHz, DMSO-$d_6$) δ 7.88 (d, J=2 Hz, 1H), 7.39 (s, 2H), 7.30 (dd, J=8.5, 2 Hz, 1H), 6.97 (d, J=8.4 Hz, 1H), 3.61 (s, 3H).

EXAMPLE 695B methyl 4-chloro-2-{[4-(2-methoxy-2-oxoethyl)-2-nitrophenyl]amino}benzoate A mixture of methyl 4-chloro-2-iodobenzoate (20.4 g, 69 mmol), Example 695A (14.8 g, 69 mmol), copper (4.4 g, 69 mmol), and $K_2CO_3$ (9.5 g, 69 mmol) in chlorobenzene (700 mL) was heated to reflux for 2 days, cooled to room temperature, diluted with ethyl acetate, and filtered through diatomaceous earth (Celite®). The solution was washed with water and brine, dried ($MgSO_4$), filtered, and concentrated under vacuum. The residue was purified by flash column chromatography on silica gel with 9:1 hexanes/ethyl acetate to provide 16.7 g (64%) of the desired product. MS (DCI) m/e 379 $(M+H)^+$, 396 $(M+NH_4)^+$; $^1H$ NMR (300 MHz, DMSO-$d_6$) δ 10.84 (s, 1H), 8.10 (d, J=2.1 Hz, 1H), 7.96 (d, J=8.5, Hz, 1H), 7.67 (d, J=8.5 Hz, 1H), 7.60 (dd, J=8.8, 2.0 Hz, 1H), 7.46 (d, J=2.1 Hz, 1H), 7.11 (dd, J=8.5, 2 Hz, 1H), 3.69 (s, 3H), 3.81 (s, 2H), 3.65 (s, 3H).

EXAMPLE 695C methyl 2-{[2-amino-4-(2-methoxy-2-oxoethyl)phenyl]amino}-4-chlorobenzoate A mixture of Example 695B (0.73 g, 1.93 mmol), 5% Pt/C, methanol (15 mL) and ethyl acetate (15 mL) was equipped with a balloon of hydrogen gas and stirred at room temperature. After uptake of the hydrogen was complete, the solution was filtered through diatomaceous earth (Celite®). The filtrate was concentrated under vacuum and the residue was purified by flash column chromatography on silica gel with 7:3 hexanes/ethyl acetate to provide 0.64 g (95%) of the desired product. MS (DCI) m/e 349 $(M+H)^+$, 366 $(M+NH_4)^+$; $^1H$ NMR (500 MHz, DMSO-$d_6$) δ 8.81 (s, 1H), 7.85 (d, J=8.5 Hz, 1H), 6.96 (d, J=8.1 Hz, 1H), 6.69-6.72 (m, 2H), 6.50 (dd, J=7.8, 1.8 Hz, 1H), 6.40 (d, J=2.1 Hz, 1H), 5.00 (s, 2H), 3.86 (s, 3H), 3.63 (s, 3H), 3.55 (s, 2H).

EXAMPLE 695D methyl (3-chloro-11-oxo-10,11-dihydro-5H-dibenzo[b,e][1,4]diazepin-8-yl)acetate A mixture of Example 695C (0.3 g, 0.91 mmol) and TsOH.$H_2O$ (0.35 g, 1.82 mmol) in toluene (50 mL) was heated to reflux for 20 hours using a Dean-Stark trap to remove water. The reaction was cooled to room temperature, concentrated under vacuum, diluted with ethyl acetate, washed with saturated $NaHCO_3$ and brine, dried ($MgSO_4$), filtered, and concentrated under vacuum. The residue was purified by flash column chromatography on silica gel with 7:3 hexanes/ethyl acetate to provide 0.21 g (81%) of the desired product. MS (DCI) m/e 317 $(M+H)^+$, 334 $(M+NH_4)^+$; $^1H$ NMR (500 MHz, DMSO-$d_6$) δ 9.88 (s, 1H), 8.03 (s, 1H), 7.68 (d, J=8.7 Hz, 1H), 7.06 (d, J=2.2 Hz, 1H), 6.91-6.93 (m, 2H), 6.86-6.87 (m, 2H), 3.60 (s, 3H), 3.54 (s, 2H).

EXAMPLE 695E 3-chloro-8-(2-hydroxyethyl)-5,10-dihydro-11H-dibenzo[b,e][1,4]diazepin-11-one A mixture of Example 695D (6.32 g, 20 mmol) in 100 mL of THF was treated with 1.0 M $LiAlH_4$ in THF (35 mL, 35 mmol) at 0° C. The reaction mixture was stirred for additional 30 minutes, quenched with MeOH, and concentrated under vacuum. The residue was partitioned between ethyl acetate and pH=3 water. The aqueous layer was extracted with additional ethyl acetate twice. The combined organic layers were washed with brine, dried ($MgSO_4$), filtered, and concentrated under vacuum. The residue was purified by flash column chromatography on silica gel with 1:9 hexanes/ethyl acetate to provide 5.18 g (90%) of the desired product. MS (DCI) m/e 289 and 291 $(M+H)^+$; $^1H$ NMR (300 MHz, DMSO-$d_6$) δ 9.83 (s, 1H), 7.96 (s, 1H), 7.67 (d, J=8.5 Hz, 1H), 7.06 (d, J=2.0 Hz, 1H), 6.91 (dd, J=8.5, 2.0 Hz, 1H), 6.81-6.84 (m, 3H), 4.59 (t, J=6.0 Hz, 1H), 3.51-3.53 (m, 2H), 2.58 (t, J=6.9 Hz, 2H).

EXAMPLE 695F 3-chloro-8-[2-(4-morpholin-4-ylphenoxy)ethyl]-5,10-dihydro-11H-dibenzo[b,e][1,4]diazepin-11-one Example 695E (0.57 g, 2.0 mmol) and 4-morpholinophenol (0.45 g, 2.5 mmol; M. C. Harris, et. al., Org. Lett., 4, 2885 (2002)) were dissolved in THF (15 mL), then polymer-supported $PPh_3$ (2.0 g, 6.0 mmol $PPh_3$; Aldrich, product # 36,645-5) was added, followed by di-tert-butylazodicarboxylate (0.52 g, 2.3 mmol), then the reaction was stirred at room temperature overnight. The reaction was then filtered and concentrated to give 1.6 g crude material that was then slurried in $Et_2O$ (20 mL) overnight. Filtration gave the product (0.74 g, 81%) as off-white solids. MS (DCI) m/e 450 and 452 $(M+H)^+$; $^1H$ NMR (300 MHz, DMSO-$d_6$) δ 9.87 (s, 1H), 8.00 (s, 1H), 7.67 (d, J=8.5 Hz, 1H), 7.06 (d, J=2.0 Hz, 1H), 6.84-6.91 (m, 8H), 4.03 (t, J=6.6 Hz, 2H), 3.71 (m, 4H), 2.96 (m, 4H), 2.86 (t, J=6.6 Hz, 2H).

EXAMPLE 695G

8-[2-(4-Morpholin-4-yl-phenoxy)-ethyl]-3-(4,4,5,5-tetramethyl-[1,3,2]dioxaborolan-2-yl)-5,10-dihydro-dibenzo[b,e][1,4]diazepin-11-one A mixture of CyMAP ligand (1.91 g, 4.85 mmol) and $Pd_2(dba)_3$ (0.92 g, 1.01 mmol) in dioxane (300 mL) purged with nitrogen was stirred at room temperature under nitrogen for 30 minutes, treated with Example 695F (11.1 g, 24.5 mmol), bis(pinacolato)diboron (6.9 g, 27.2 mmol), and potassium acetate (3.7 g, 37.8 mmol), stirred at 85° C. under nitrogen overnight, cooled to room temperature, concentrated to about one quarter of the original volume, then partitioned between water and EtOAc. The organic layer was washed with water and brine, dried ($Na_2SO_4$), filtered, and concentrated under vacuum. The residue was slurried in hexanes/$Et_2O$ 2/1 (150 mL) for 4 hours, then the solids were filtered off, giving the product (10.4 g, 78%). MS (ESI) m/e 542 $(M+H)^+$, $^1H$ NMR (300 MHz, DMSO-$d_6$): □ 9.84 (s, 1H), 7.71 (s, 1H), 7.65 (d, J=7.80 Hz, 1H), 7.38 (s, 1H), 7.13 (dd, J=7.63, 0.85 Hz, 1H), 6.80-6.95 (m, 7H), 4.03 (t, J=6.78 Hz, 2H), 3.69-3.72 (m, 4H), 2.95-2.98 (m, 4H), 2.85 (t, J=6.61 Hz, 2H).

EXAMPLE 695H

7-Chloro-1H-pyrrolo[2,3-c]pyridine

2-Chloro-3-nitropyridine (10 g, 63 mmol) in THF (200 mL) was cooled to −60° C. or lower. The solution was treated with vinyl magnesium bromide (200 mL, 1.0 M) at such a rate that the internal temperature was kept below −40° C. After the addition was complete, the solution was stirred for another 4-6 hours at −40° C. or less, and let warm up to room temperature gradually overnight. The reaction mixture was quenched with saturated $NH_4Cl$. The organic layer was separated, and the aqueous layer was extracted with EtOAc three times. The combined organic layers were washed with $H_2O$, brine, and dried over $MgSO_4$. The solvents were removed under reduced pressure. The residue was suspended in $CH_2Cl_2$, loaded onto a silica gel column, and eluted with 1:4 EtOAc:hexanes to give 3.6 g (37%) of the desired product. MS (DCI) m/e 153 & 155 $(M+H)^+$, $^1H$ NMR (300 MHz, DMSO-$d_6$): □ 12.0 (br s, 1H), 7.89 (d, J=5.4 Hz, 1H), 7.67 (m, 1H), 7.57 (d, J=5.4 Hz, 1H), 6.64 (m, 1H).

EXAMPLE 695I

1H-Pyrrolo[2,3-c]pyridine

A mixture of Example 695H (3.6 g, 23.6 mmol), Pd/C (0.5 g, 5%), and $Et_3N$ (2.3 g, 23.6 mmol) in MeOH (100 mL) was stirred under a balloon of hydrogen at room temperature overnight. The reaction mixture was filtered through diatomaceous earth (Celite®), and the solid was washed with additional MeOH. The solvent was removed to near dryness, and the semi-solid was treated with 300 mL of EtOAc. The precipitate was removed right away by filtration, and the filtrate was concentrated. The residue was re-dissolved in $CH_2Cl_2$, and loaded onto a silica gel column eluted with 100/5:0/5 (EtOAc/MeOH/$NH_4OH$) to give 2.7 g (100%) of the desired product. MS (DCI) m/e 119 $(M+H)^+$, $^1H$ NMR (300 MHz, DMSO-$d_6$): □ 11.6 (br s, 1H), 8.76 (dd, J=1.0, 1.0 Hz, 1H), 8.08 (d, J=5.4 Hz, 1H), 7.60 (d, J=3.0 Hz, 1H), 7.53 (dd, J=5.4, 1.0 Hz, 1H), 6.50 (dd, J=3.0, 1.0 Hz, 1H).

EXAMPLE 695J

3-Bromo-1H-pyrrolo[2,3-c]pyridine

Example 695I (3.73 g, 31.5 mmol) in $CHCl_3$ (200 mL) was treated with $Br_2$ (5.03 g, 31.5 mmol) in $CCl_4$ (50 mL) dropwise at 0° C. After the addition was complete, the solvents were removed under reduced pressure, and the residue was partitioned between water and EtOAc. The mixed layers were treated with saturated $NaHCO_3$ (100 mL), and the organic layer was separated. The aqueous layer (pH ca. 7-8) along with some yellow solid was extracted with additional EtOAc, and the combined organic layers were washed with brine, and dried over $MgSO_4$. The solvent was removed, and the residue was purified with a silica gel column eluted with 100/2/0.2 (EtOAc/MeOH/$NH_4OH$) to give 4.9 g (78%) of the desired product. MS (DCI) m/e 197 & 199 $(M+H)^+$, $^1H$ NMR (300 MHz, DMSO-$d_6$): □ 12.0 (br s, 1H), 8.78 (d, J=1.0 Hz, 1H), 8.20 (d, J=5.4 Hz, 1H), 7.81 (s, 1H), 7.40 (dd, J=5.4, 1.0 Hz, 1H).

EXAMPLE 695K

3-Bromo-pyrrolo[2,3-c]pyridine-1-carboxylic acid tert-butyl ester

A mixture of Example 695J (0.32 g, 1.62 mmol), $(BOC)_2O$ (0.43 g, 1.94 mmol) and DMAP (50 mg) in 10 mL of dioxane was stirred overnight at room temperature. The reaction mixture was partitioned between water and EtOAc. The aqueous layer was extracted with additional EtOAc. The combined organic layers were washed with water, brine, dried over $MgSO_4$, filtered, and concentrated under reduced pressure. The residue was purified by flash column chromatography on silica gel eluting with 7:3 hexanes/ethyl acetate to provide 0.36 g (75%) of the desired product. MS (APCI) m/e 298 $(M+H)^+$, $^1H$ NMR (500 MHz, DMSO-$d_6$): □ 9.29 (s, 1H), 8.28 (d, J=5.09 Hz, 1H), 8.16 (s, 1H), 7.55 (d, J=5.43 Hz, 1H), 1.65 (s, 9H).

EXAMPLE 695L

8-[2-(4-Morpholin-4-yl-phenoxy)-ethyl]-3-(1H-pyrrolo[2,3-c]pyridin-3-yl)-5,10-dihydro-dibenzo[b,e][1,4]diazepin-11-one A mixture of Example 695G (53 mg, 0.1 mmol), Example 695K (30 mg, 0.1 mmol), $Pd(PPh_3)_4$ (11 mg, 0.01 mmol), and CsF (46 mg, 0.3 mmol) in DME (4 mL) and MeOH (2 mL) was heated under reflux overnight. After the reaction mixture cooled to room temperature, it was partitioned between EtOAc and water. The organic layer was separated, and the aqueous layer was extracted with additional EtOAc. The combined organic layers were washed with brine, dried ($MgSO_4$), filtered, and concentrated under vacuum. The residue was purified flash column chromatography on silica gel with 100:5:0.5 ethyl acetate/methanol/$NH_4OH$. The desired fractions were collected and concentrated under vacuum, and the residue was further purified by preparative reverse phase HPLC to provide 8 mg of the title compound as a diTFA salt. MS (APCI) m/e 530 (M−H)+, $^1H$ NMR (500 MHz, DMSO-$d_6$): □ 13.30 (s, 1H), 9.78 (s, 1H), 9.26 (s, 1H), 8.71 (d, J=1.87 Hz, 1H), 8.38-8.45 (m, 2H), 7.96 (s, 1H), 7.80 (d, J=8.11 Hz, 1H), 7.47 (d, J=1.56 Hz, 1H), 7.30 (dd, J=8.11, 1.56 Hz, 1H), 6.82-6.96 (m, 7H), 4.05 (t, J=6.86 Hz, 2H), 3.71-3.73 (m, 4H), 2.97-2.99 (m, 4H), 2.87 (t, J=6.55 Hz, 2H).

EXAMPLE 696

3-(1-Benzyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 696A

1-Benzyl-3-bromo-1H-pyrrolo[2,3-c]pyridine

Example 695J (1.0 g, 5.1 mmol) was dissolved in DMF (10 mL), cooled to 0° C., then 95% NaH (0.16 g, 6.3 mmol) was added. After stirring at 0° C. for 10 minutes a solution of benzyl bromide (0.60 mL, 0.86 g, 5.1 mmol) in DMF (2.5 mL) was added. After stirring at 0° C. for another 10 minutes the reaction was quenched by the addition of water and extracted with EtOAc. The organic layer was washed with water and brine, dried (Na$_2$SO$_4$), filtered, and concentrated under vacuum. Purification by column chromatography using EtOAc as the eluent gave the product (0.71 g, 48%) as white solids. MS (DCI) m/e 287 & 289 (M+H)$^+$, $^1$H NMR (300 MHz, DMSO-d$_6$): □ 8.93 (d, J=1.0 Hz, 1H), 8.23 (d, J=5.4 Hz, 1H), 8.03 (s, 1H), 7.41 (dd, J=5.4, 1.0 Hz, 1H), 7.32 (m, 5H), 5.55 (s, 2H).

EXAMPLE 696B 3-(1-Benzyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one A mixture of Example 696A (57 mg, 0.2 mmol), Example 695G (108 mg, 0.2 mmol), Pd(OAc)$_2$ (4.5 mg, 0.02 mmol), dppf (22 mg, 0.04 mmol), CsF (91 mg, 0.6 mmol), and a 2:1 mixture of ethylene glycol dimethyl ether/methanol (6 mL) was placed in a microwave process vial, capped and heated at 180° C. for 15 minutes in a CEM Explorer set at 200 W. After reaction mixture cooled to room temperature, it was partitioned between water and ethyl acetate. The aqueous layer was extracted with additional EtOAc. The combined organic layers were washed with water and brine, dried (MgSO$_4$), filtered, and concentrated under vacuum. The residue was purified by column chromatography on silica gel eluted with (100:1) ethyl acetate: methanol. The desired fractions were collected and concentrated. The residue was further purified by reverse phase preparative HPLC to give 30 mg of the desired product as a diTFA salt. MS (APCI) m/e 622 (M+H)$^+$, $^1$H NMR (500 MHz, DMSO-d$_6$): □ 9.76 (s, 1H), 9.53 (s, 1H), 8.86 (s, 1H), 8.48 (d, J=6.44 Hz, 1H), 8.39 (d, J=6.44 Hz, 1H), 7.97 (s, 1H), 7.79 (d, J=8.29 Hz, 1H), 7.33-7.42 (m, 6H), 7.26 (dd, J=8.29, 1.53 Hz, 1H), 6.61-6.95 (m, 7H), 5.76 (s, 2H), 4.04 (t, J=6.75 Hz, 2H), 3.70-3.72 (m, 4H), 2.97-2.99 (m, 4H), 2.86 (t, J=6.44 Hz, 2H).

EXAMPLE 697

(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-acetonitrile

EXAMPLE 697A (3-Bromo-pyrrolo[2,3-c]pyridin-1-yl)-acetonitrile

The title compound was prepared by substituting bromoacetonitrile for benzyl bromide in Example 696A, except the longer reaction time was employed. MS (DCI) m/e 237 (M+H)$^+$, $^1$H NMR (500 MHz, DMSO-d$_6$): □ 9.06 (s, 1H), 8.35 (d, J=5.22 Hz, 1H), 7.95 (s, 1H), 7.49 (d, J=5.2 Hz, 1H), 5.68 (s, 2H).

EXAMPLE 697B (3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-acetonitrile The title compound was prepared by substituting Example 697A for Example 696A in Example 696B. MS (APCI) m/e 571 (M+H)$^+$, $^1$H NMR (500 MHz, DMSO-d$_6$): □ 9.84 (s, 1H), 9.61 (s, 1H), 8.76 (s, 1H), 8.60 (d, J=6.71 Hz, 1H), 8.42 (d, J=6.71 Hz, 1H), 8.02 (s, 1H), 7.82 (d, J=8.24 Hz, 1H), 7.44 (d, J=1.22 Hz, 1H), 7.26 (dd, J=8.24, 1.53 Hz, 1H), 6.84-6.96 (m, 7H), 5.86 (s, 2H), 4.05 (t, J=6.71 Hz, 2H), 3.72-3.74 (m, 4H), 2.99-3.01 (m, 4H), 2.88 (t, J=6.71 Hz, 2H).

EXAMPLE 698

3-(1-Methyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 698A

3-Bromo-1-methyl-1H-pyrrolo[2,3-c]pyridine

The title compound was prepared by substituting methyl iodide for benzyl bromide in Example 696A, except the longer reaction time was employed. MS (DCI) m/e 210 (M-H)+, $^1$H NMR (500 MHz, DMSO-d$_6$): □ 8.90 (s, 1H), 8.24 (d, J=5.52 Hz, 1H), 7.81 (s, 1H), 7.40 (d, J=5.52 Hz, 1H), 3.92 (s, 3H).

EXAMPLE 698B 3-(1-Methyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one The title compound was prepared by substituting Example 698A for Example 696A in Example 696B. MS (ESI) m/e 546 (M+H)$^+$, $^1$H NMR (500 MHz, DMSO-d$_6$): □ 9.82 (s, 1H), 9.47 (s, 1H), 8.73 (s, 1H), 8.49 (d, J=6.41 Hz, 1H), 8.39 (d, J=6.41 Hz, 1H), 8.00 (s, 1H), 7.80 (d, J=8.24 Hz, 1H), 7.44 (d, J=1.22 Hz, 1H), 7.25 (dd, J=8.24, 1.53 Hz, 1H), 6.84-6.96 (m, 7H), 4.13 (s, 3H), 4.05 (t, J=6.71 Hz, 2H), 3.72-3.74 (m, 4H), 3.00-3.02 (m, 4H), 2.88 (t, J=6.56 Hz, 2H).

EXAMPLE 699

3-(1-Ethyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 699A

3-Bromo-1-ethyl-1H-pyrrolo[2,3-c]pyridine

The title compound was prepared by substituting ethyl iodide for benzyl bromide in Example 696A, except the longer reaction time was employed. MS (DCI) m/e 226 (M+H)$^+$, $^1$H NMR (500 MHz, DMSO-d$_6$): □ 8.93 (s, 1H), 8.22 (d, J=5.52 Hz, 1H), 7.87 (s, 1H), 7.38 (d, J=5.52 Hz, 1H), 4.33 (q, J=7.06 Hz, 2H), 1.40 (t, J=7.21 Hz, 3H).

EXAMPLE 699B 3-(3-Ethyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one The title compound was prepared by substituting Example 699A for Example 696A in Example 696B. MS (APCI) m/e 560 (M+H)$^+$, $^1$H NMR (500 MHz, DMSO-d$_6$): □ 9.78 (s, 1H), 9.52 (s, 1H), 8.80 (s, 1H), 8.47 (d, J=6.75 Hz, 1H), 8.38 (d, J=6.75 Hz, 1H), 7.97 (s, 1H), 7.79 (d, J=8.29 Hz, 1H), 7.45 (s, 1H), 7.27 (d, J=7.98 Hz, 1H), 6.82-6.96 (m, 7H), 4.54 (q, J=7.36 Hz, 2H), 4.04 (t, J=6.6 Hz, 2H), 3.70-3.73 (m, 4H), 2.98-3.00 (m, 4H), 2.86 (t, J=6.6 Hz, 2H), 1.52 (t, J=7.21 Hz, 3H).

EXAMPLE 700

3-[1-(3,5-Difluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 700A

3-Bromo-1-(3,5-difluoro-benzyl)-1H-pyrrolo[2,3-c]pyridine

The title compound was prepared by substituting 3,5-diflurorbenzyl bromide for benzyl bromide in Example 696A. MS (DCI) m/e 324 (M+H)$^+$, $^1$H NMR (500 MHz, DMSO-d$_6$): □ 8.97 (s, 1H), 8.25 (d, J=5.52 Hz, 1H), 8.05 (s, 1H), 7.43 (d, J=5.52 Hz, 1H), 7.17 (m, 1H), 7.05-7.10 (m, 2H), 5.57 (s, 2H).

EXAMPLE 700B

3-[1-(3,5-Difluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 700A for Example 696A in Example 696B. MS (APCI) m/e 658 (M+H)$^+$, $^1$H NMR (500 MHz, DMSO-d$_6$): □ 9.79 (s, 1H), 9.55 (s, 1H), 8.86 (s, 1H), 8.50 (d, J=6.44 Hz, 1H), 8.40 (d, J=6.44 Hz, 1H), 7.98 (s, 1H), 7.80 (d, J=7.98 Hz, 1H), 7.44 (s, 1H), 7.20-7.28 (m, 4H), 6.82-6.96 (m, 7H), 5.76 (s, 2H), 4.04 (t, J=6.6 Hz, 2H), 3.70-3.72 (m, 4H), 2.97-3.00 (m, 4H), 2.86 (t, J=6.6 Hz, 2H).

EXAMPLE 701

3-[1-(3-Fluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 701A

3-Bromo-1-(3,5-difluoro-benzyl)-1H-pyrrolo[2,3-c]pyridine

The title compound was prepared by substituting 3-flurorbenzyl bromide for benzyl bromide in Example 696A. MS (DCI) m/e 306 (M+H)$^+$, $^1$H NMR (500 MHz, DMSO-d$_6$): □ 8.93 (s, 1H), 8.23 (d, J=5.52 Hz, 1H), 8.02 (s, 1H), 7.41 (d, J=5.52 Hz, 1H), 7.36 (m, 1H), 7.18 (d, J=9.82 Hz, 1H), 7.08-7.12 (m, 2H), 5.55 (s, 2H).

EXAMPLE 701B

3-[1-(3-Fluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 701A for Example 696A in Example 696B. MS (APCI) m/e 640 (M+H)$^+$, $^1$H NMR (500 MHz, DMSO-d$_6$): □ 9.78 (s, 1H), 9.54 (s, 1H), 8.86 (s, 1H), 8.49 (d, J=6.44 Hz, 1H), 8.39 (d, J=6.44 Hz, 1H), 7.97 (s, 1H), 7.80 (d, J=7.98 Hz, 1H), 7.15-7.45 (m, 6H), 6.81-6.95 (m, 7H), 5.77 (s, 2H), 4.04 (t, J=6.75 Hz, 2H), 3.70-3.72 (m, 4H), 2.96-2.99 (m, 4H), 2.86 (t, J=6.44 Hz, 2H).

EXAMPLE 702

3-[1-(2-Methyl-thiazol-5-ylmethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 702A

3-Bromo-1-(2-methyl-thiazol-5-ylmethyl)-1H-pyrrolo[2,3-c]pyridine

The title compound was prepared by substituting 5-chloromethyl-2-methyl-thiazole hydrochloride for benzyl bromide in Example 696A. MS (DCI) m/e 309 (M+H)$^+$, $^1$H NMR (500 MHz, DMSO-d$_6$): □ 8.99 (s, 1H), 8.23 (d, J=5.52 Hz, 1H), 7.91 (s, 1H), 7.50 (s, 1H), 7.40 (d, J=5.52 Hz, 1H), 5.56 (s, 2H), 2.58 (s, 3H).

EXAMPLE 702B

3-[1-(2-Methyl-thiazol-5-ylmethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 702A for Example 696A in Example 696B. MS (APCI) m/e 643 (M+H)$^+$, $^1$H NMR (500 MHz, DMSO-d$_6$): □ 9.82 (s, 1H), 9.58 (s, 1H), 8.80 (s, 1H), 8.50 (d, J=6.41 Hz, 1H), 8.40 (d, J=6.41 Hz, 1H), 7.99 (s, 1H), 7.81 (d, J=7.93 Hz, 1H), 7.62 (s, 1H), 7.44 (d, J=1.53 Hz, 1H), 7.26 (dd, J=8.24, 1.53 Hz, 1H), 6.83-6.96 (m, 7H), 5.80 (s, 2H), 4.05 (t, J=6.71 Hz, 2H), 3.71-3.73 (m, 4H), 2.97-2.99 (m, 4H), 2.87 (t, J=6.44 Hz, 2H), 2.59 (s, 3H).

EXAMPLE 703

3-[1-(2-Fluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 703A

3-Bromo-1-(2-fluoro-benzyl)-1H-pyrrolo[2,3-c]pyridine

The title compound was prepared by substituting 2-fluorobenzyl bromide for benzyl bromide in Example 696A. MS (DCI) m/e 306 (M+H)$^+$, $^1$H NMR (500 MHz, DMSO-d$_6$): □ 8.93 (s, 1H), 8.24 (d, J=5.52 Hz, 1H), 7.92 (s, 1H), 7.36-7.44 (m, 2H), 7.15-7.28 (m, 3H), 5.62 (s, 2H).

EXAMPLE 703B

3-[1-(2-Fluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 703A for Example 696A in Example 696B. MS (APCI) m/e 640 (M+H)$^+$, $^1$H NMR (500 MHz, DMSO-d$_6$): □ 9.82 (s, 1H), 9.50 (s, 1H), 8.74 (s, 1H), 8.51 (d, J=6.71 Hz, 1H), 8.40

(d, J=6.40 Hz, 1H), 7.99 (s, 1H), 7.80 (d, J=8.24 Hz, 1H), 7.20-7.43 (m, 6H), 6.82-6.95 (m, 7H), 5.85 (s, 2H), 4.04 (t, J=6.71 Hz, 2H), 3.71-3.73 (m, 4H), 2.97-2.99 (m, 4H), 2.87 (t, J=6.71 Hz, 2H).

EXAMPLE 704

8-[2-(4-Morpholin-4-yl-phenoxy)-ethyl]-3-(1-propyl-1H-pyrrolo[2,3-c]pyridin-3-yl)-5,10-dihydro-dibenzo[b,e][1,4]diazepin-11-one

EXAMPLE 704A

3-Bromo-1-propyl-1H-pyrrolo[2,3-c]pyridine

The title compound was prepared by substituting 1-iodopropane for benzyl bromide in Example 696A, except the longer reaction time was employed. MS (DCI) m/e 240 (M+H)$^+$, $^1$H NMR (500 MHz, DMSO-d$_6$): □ 8.94 (s, 1H), 8.21 (d, J=5.52 Hz, 1H), 7.85 (s, 1H), 7.38 (d, J=5.52 Hz, 1H), 4.26 (t, J=7.06 Hz, 2H), 1.78-1.83 (m 2H), 0.82 (t, J=7.36 Hz, 3H).

EXAMPLE 704B

8-[2-(4-Morpholin-4-yl-phenoxy)-ethyl]-3-(1-propyl-1H-pyrrolo[2,3-c]pyridin-3-yl)-5,10-dihydro-dibenzo[b,e][1,4]diazepin-11-one The title compound was prepared by substituting Example 704A for Example 696A in Example 696B. MS (APCI) m/e 574 (M+H)$^+$, $^1$H NMR (500 MHz, DMSO-d$_6$): □ 9.82 (s, 1H), 9.56 (s, 1H), 8.81 (s, 1H), 8.48 (d, J=6.41 Hz, 1H), 8.39 (d, J=6.41 Hz, 1H), 8.00 (s, 1H), 7.81 (d, J=8.24 Hz, 1H), 7.46 (s, 1H), 7.27 (d, J=8.24 Hz, 1H), 6.83-6.96 (m, 7H), 4.48 (t, J=7.02 Hz, 2H), 4.05 (t, J=6.71 Hz, 2H), 3.71-3.73 (m, 4H), 2.98-3.00 (m, 4H), 2.87 (t, J=6.6 Hz, 2H), 1.91-1.95 (m, 2H), 0.90 (t, J=7.32 Hz, 3H).

EXAMPLE 705

3-[1-(4-Fluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 705A

3-Bromo-1-(4-fluoro-benzyl)-1H-pyrrolo[2,3-c]pyridine

The title compound was prepared by substituting 4-fluorobenzyl bromide for benzyl bromide in Example 696A. MS (DCI) m/e 306 (M+H)$^+$, $^1$H NMR (500 MHz, DMSO-d$_6$): □ 8.95 (s, 1H), 8.23 (d, J=5.22 Hz, 1H), 8.02 (s, 1H), 7.38-7.42 (m, 3H), 7.17 (d, J=8.9 Hz, 2H), 5.53 (s, 2H).

EXAMPLE 705B

3-[1-(4-Fluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 705A for Example 696A in Example 696B. MS (APCI) m/e 640 (M+H)$^+$, $^1$H NMR (500 MHz, DMSO-d$_6$): □ 9.79 (s, 1H), 9.56 (s, 1H), 8.86 (s, 1H), 8.50 (d, J=6.44 Hz, 1H), 8.40 (d, J=6.44 Hz, 1H), 7.98 (s, 1H), 7.81 (d, J=7.98 Hz, 1H), 7.51 (dd, J=8.59, 5.52 Hz, 2H), 7.44 (s, 1H), 7.20-7.28 (m, 3H), 6.82-6.96 (m, 7H), 5.75 (s, 2H), 4.05 (t, J=6.6 Hz, 2H), 3.71-3.73 (m, 4H), 2.98-3.00 (m, 4H), 2.87 (t, J=6.6 Hz, 2H).

EXAMPLE 706

8-[2-(4-Morpholin-4-yl-phenoxy)-ethyl]-3-(1-pyridin-3-ylmethyl-1H-pyrrolo[2,3-c]pyridin-3-yl)-5,10-dihydro-dibenzo[b,e][1,4]diazepin-11-one

EXAMPLE 706A

3-Bromo-1-pyridin-3-ylmethyl-1H-pyrrolo[2,3-c]pyridine

The title compound was prepared by substituting 3-bromomethyl pyridine hydrobromide for benzyl bromide in Example 696A. MS (DCI) m/e 289 (M+H)$^+$, $^1$H NMR (500 MHz, DMSO-d$_6$): □ 9.01 (s, 1H), 8.65 (d, J=1.53 Hz, 1H), 8.50 (dd, J=4.88, 1.53 Hz, 1H), 8.25 (d, J=5.49 Hz, 1H), 8.07 (s, 1H), 7.71 (d, J=7.93 Hz, 1H), 7.43 (d, J=5.49 Hz, 1H), 7.36 (dd, J=7.78, 4.73 Hz, 1H), 5.61 (s, 2H).

EXAMPLE 706B

8-[2-(4-Morpholin-4-yl-phenoxy)-ethyl]-3-(1-pyridin-3-ylmethyl-1H-pyrrolo[2,3-c]pyridin-3-yl)-5,10-dihydro-dibenzo[b,e][1,4]diazepin-11-one The title compound was prepared by substituting Example 706A for Example 696A in Example 696B. MS (APCI) m/e 623 (M+H)$^+$, $^1$H NMR (500 MHz, DMSO-d$_6$): □ 9.80 (s, 1H), 9.63 (s, 1H), 8.90 (s, 1H), 8.80 (s, 1H), 8.61 (d, J=3.99 Hz, 1H), 8.52 (d, J=6.44 Hz, 1H), 8.42 (d, J=6.75 Hz, 1H), 7.99 (s, 1H), 7.94 (d, J=7.98 Hz, 1H), 7.81 (d, J=8.29 Hz, 1H), 7.50 (dd, J=7.83, 5.06 Hz, 1H), 7.45 (s, 1H), 7.28 (d, J=7.98 Hz, 1H), 6.84-6.96 (m, 7H), 5.85 (s, 2H), 4.06 (t, J=6.6 Hz, 2H), 3.72-3.75 (m, 4H), 3.01-3.04 (m, 4H), 2.88 (t, J=6.44 Hz, 2H).

EXAMPLE 707

8-[2-(4-Morpholin-4-yl-phenoxy)-ethyl]-3-[1-(3,4,5-trifluoro-benzyl)-1H-pyrrolo[2,3-c]pyridin-3-yl]-5,10-dihydro-dibenzo[b,e][1,4]diazepin-11-one

EXAMPLE 707A

3-Bromo-1-(3,4,5-trifluoro-benzyl)-1H-pyrrolo[2,3-c]pyridine

The desired product was prepared by substituting 3,4,5-trifluorobenzyl bromide for benzyl bromide in Example 696A. MS (ESI) m/e 341 (M+H)$^+$, $^1$H NMR (300 MHz, DMSO-d$_6$): □ 9.00 (s, 1H), 8.25 (d, J=5.43 Hz, 1H), 8.04 (s, 1H), 7.36-7.43 (m, 3H), 5.52 (s, 2H).

EXAMPLE 707B

8-[2-(4-Morpholin-4-yl-phenoxy)-ethyl]-3-[1-(3,4,5-trifluoro-benzyl)-1H-pyrrolo[2,3-c]pyridin-3-yl]-5,10-dihydro-dibenzo[b,e][1,4]diazepin-11-one The desired product was prepared by substituting Example 707A for Example 696A in Example 696B. MS (ESI) m/e 676 (M+H)$^+$, $^1$H NMR (500 MHz, DMSO-d$_6$): □ 9.83 (s, 1H), 9.56 (s, 1H), 8.85 (s, 1H), 8.52 (d, J=6.41 Hz, 1H), 8.39

(d, J=6.41 Hz, 1H), 7.99 (s, 1H), 7.81 (d, J=8.24 Hz, 1H), 7.52 (dd, J=8.29, 6.87 Hz, 2H), 7.44 (d, J=1.53 Hz, 1H), 7.28 (dd, J=8.24, 1.53 Hz, 1H), 6.82-6.95 (m, 7H), 5.72 (s, 2H), 4.04 (t, J=6.71 Hz, 2H), 3.70-3.73 (m, 4H), 2.97-2.99 (m, 4H), 2.87 (t, J=6.56 Hz, 2H).

EXAMPLE 708

4-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile

EXAMPLE 708A 4-(3-Bromo-pyrrolo[2,3-c]pyridin-1-ylmethyl)-benzonitrile

The desired product was prepared by substituting 4-cyanobenzyl bromide for benzyl bromide in Example 696A. MS (ESI) m/e 312 (M+H)+, 1H NMR (300 MHz, DMSO-d6): □ 8.91 (s, 1H), 8.24 (d, J=5.49 Hz, 1H), 8.05 (s, 1H), 7.81 (d, J=8.24 Hz, 2H), 7.42-7.45 (m, 3H), 5.67 (s, 2H).

EXAMPLE 708B 4-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile The desired product was prepared by substituting Example 708A for Example 696A in Example 696B. MS (ESI) m/e 647 (M+H)+, 1H NMR (500 MHz, DMSO-d6): □ 9.82 (s, 1H), 9.51 (s, 1H), 8.87 (s, 1H), 8.51 (d, J=6.71 Hz, 1H), 8.40 (d, J=6.41 Hz, 1H), 7.99 (s, 1H), 7.86 (d, J=8.24 Hz, 2H), 7.81 (d, J=8.24 Hz, 1H), 7.55 (d, J=8.24 Hz, 2H), 7.44 (d, J=1.22 Hz, 1H), 7.27 (dd, J=8.24, 1.53 Hz, 1H), 6.82-6.95 (m, 7H), 5.87 (s, 2H), 4.04 (t, J=6.71 Hz, 2H), 3.70-3.73 (m, 4H), 2.97-2.99 (m, 4H), 2.87 (t, J=6.56 Hz, 2H

EXAMPLE 709

8-[2-(4-Morpholin-4-yl-phenoxy)-ethyl]-3-(1-pyridin-2-ylmethyl-1H-pyrrolo[2,3-c]pyridin-3-yl)-5,10-dihydro-dibenzo[b,e][1,4]diazepin-11-one

EXAMPLE 709A

3-Bromo-1-pyridin-2-ylmethyl-1H-pyrrolo[2,3-c]pyridine

The title compound was prepared by substituting 2-bromomethyl pyridine hydrobromide for benzyl bromide in Example 696A. MS (DCI) m/e 289 (M+H)+, 1H NMR (500 MHz, DMSO-d6): □ 9.01 (s, 1H), 8.65 (d, J=1.53 Hz, 1H), 8.50 (dd, J=4.88, 1.53 Hz, 1H), 8.25 (d, J=5.49 Hz, 1H), 8.07 (s, 1H), 7.71 (d, J=7.93 Hz, 1H), 7.43 (d, J=5.49 Hz, 1H), 7.36 (dd, J=7.78, 4.73 Hz, 1H), 5.61 (s, 2H).

EXAMPLE 709B

8-[2-(4-Morpholin-4-yl-phenoxy)-ethyl]-3-(1-pyridin-2-ylmethyl-1H-pyrrolo[2,3-c]pyridin-3-yl)-5,10-dihydro-dibenzo[b,e][1,4]diazepin-11-one The title compound was prepared by substituting Example 709A for Example 696A in Example 696B. MS (APCI) m/e 623 (M+H)+, 1H NMR (500 MHz, DMSO-d6): □ 9.82 (s, 1H), 9.53 (s, 1H), 8.85 (s, 1H), 8.49-8.51 (m, 2H), 8.43 (d, J=6.71 Hz, 1H), 8.01 (s, 1H), 7.86 (m, 1H), 7.81 (d, J=8.24 Hz, 1H), 7.50 (d, J=7.63 Hz, 1H), 7.46 (d, J=1.53 Hz, 1H), 7.35 (dd, J=7.02, 5.19 Hz, 1H), 7.27 (dd, J=8.09, 1.68 Hz, 1H), 6.85-6.96 (m, 7H), 5.91 (s, 2H), 4.06 (t, J=6.71 Hz, 2H), 3.72-3.74 (m, 4H), 3.01-3.03 (m, 4H), 2.88 (t, J=6.71 Hz, 2H).

EXAMPLE 710

3-[1-(3,5-Dimethyl-isoxazol-4-ylmethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 710A

3-Bromo-1-(3,5-dimethyl-isoxazol-4-ylmethyl)-1H-pyrrolo[2,3-c]pyridine

The title compound was prepared by substituting 4-chloromethyl-3,5-dimethyl-isoxazole for benzyl bromide in Example 696A. MS (DCI) m/e 307 (M+H)+, 1H NMR (500 MHz, DMSO-d6): □ 8.92 (s, 1H), 8.26 (d, J=5.49 Hz, 1H), 7.81 (s, 1H), 7.43 (d, J=5.49 Hz, 1H), 5.39 (s, 2H), 2.43 (s, 3H), 1.98 (s, 3H).

EXAMPLE 710B

3-[1-(3,5-Dimethyl-isoxazol-4-ylmethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one c]pyridin-3-yl)-5,10-dihydro-dibenzo[b,e][1,4]diazepin-11-one The title compound was prepared by substituting Example 710A for Example 696A in Example 696B. MS (APCI) m/e 641 (M+H)+, 1H NMR (500 MHz, DMSO-d6): □ 9.81 (s, 1H), 9.46 (s, 1H), 8.85 (s, 1H), 8.53 (d, J=6.71 Hz, 1H), 8.40 (d, J=6.71 Hz, 1H), 7.97 (s, 1H), 7.79 (d, J=8.24 Hz, 1H), 7.41 (d, J=1.53 Hz, 1H), 7.29 (dd, J=8.24, 1.53 Hz, 1H), 6.82-6.95 (m, 7H), 5.58 (s, 2H), 4.04 (t, J=6.71 Hz, 2H), 3.71-3.73 (m, 4H), 2.97-2.99 (m, 4H), 2.87 (t, J=6.71 Hz, 2H), 2.47 (s, 3H), 2.04 (s, 3H).

EXAMPLE 711

3-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile

EXAMPLE 711A 3-(3-Bromo-pyrrolo[2,3-c]pyridin-1-ylmethyl)-benzonitrile

The desired product was prepared by substituting 3-bromomethyl-benzonitrile for benzyl bromide in Example 696A. MS (ESI) m/e 312 (M+H)+, 1H NMR (300 MHz, DMSO-d6): □ 8.97 (s, 1H), 8.24 (d, J=5.76 Hz, 1H), 8.06 (s, 1H), 7.89 (m, 1H), 7.77 (m, 1H), 7.52-7.63 (m, 2H), 7.42 (dd, J=5.42, 1.02 Hz, 1H), 5.60 (s, 2H).

EXAMPLE 711B 3-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile The desired product was prepared by substituting Example 711A for Example 696A in Example 696B. MS (ESI) m/e 647 (M+H)$^+$, $^1$H NMR (400 MHz, DMSO-d$_6$): ☐ 9.79 (s, 1H), 9.55 (s, 1H), 8.86 (s, 1H), 8.50 (d, J=6.44 Hz, 1H), 8.39 (d, J=6.44 Hz, 1H), 7.97 (s, 1H), 7.81 (m, 2H), 7.74 (d, J=7.98 Hz, 1H), 7.58 (t, J=7.67 Hz, 1H), 7.43 (s, 1H), 7.27 (m, 1H), 6.82-6.95 (m, 7H), 5.80 (s, 2H), 4.04 (t, J=6.75 Hz, 2H), 3.71-3.73 (m, 4H), 2.97-2.99 (m, 4H), 2.86 (t, J=6.75 Hz, 2H).

EXAMPLE 712

8-[2-(4-Morpholin-4-yl-phenoxy)-ethyl]-3-(1-pentafluorophenylmethyl-1H-pyrrolo[2,3-c]pyridin-3-yl)-5,10-dihydro-dibenzo[b,e][1,4]diazepin-11-one

EXAMPLE 712A

3-Bromo-1-pentafluorophenylmethyl-1H-pyrrolo[2,3-c]pyridine

The desired product was prepared by substituting 2,3,4,5,6-pentafluorobenzyl bromide for benzyl bromide in Example 696A. MS (ESI) m/e 377 (M+H)$^+$, $^1$H NMR (300 MHz, DMSO-d$_6$): ☐ 8.96 (s, 1H), 8.28 (d, J=5.42 Hz, 1H), 7.84 (s, 1H), 7.43 (m, 1H), 5.74 (s, 2H).

EXAMPLE 712B

8-[2-(4-Morpholin-4-yl-phenoxy)-ethyl]-3-(1-pentafluorophenylmethyl-1H-pyrrolo[2,3-c]pyridin-3-yl)-5,10-dihydro-dibenzo[b,e][1,4]diazepin-11-one The desired product was prepared by substituting Example 712A for Example 696A in Example 696B. MS (ESI) m/e 712 (M+H)$^+$, $^1$H NMR (500 MHz, DMSO-d$_6$): ☐ 9.82 (s, 1H), 9.46 (s, 1H), 8.61 (s, 1H), 8.55 (d, J=6.71 Hz, 1H), 8.39 (d, J=6.41 Hz, 1H), 7.99 (s, 1H), 7.79 (d, J=8.24 Hz, 1H), 7.41 (d, J=1.53 Hz, 1H), 7.25 (dd, J=8.24, 1.53 Hz, 1H), 6.82-6.95 (m, 7H), 5.96 (s, 2H), 4.04 (t, J=6.71 Hz, 2H), 3.70-3.72 (m, 4H), 2.97-2.99 (m, 4H), 2.87 (t, J=6.71 Hz, 2H).

EXAMPLE 713

8-[2-(4-Morpholin-4-yl-phenoxy)-ethyl]-3-[1-(2,3,5,6-tetrafluoro-benzyl)-1H-pyrrolo[2,3-c]pyridin-3-yl]-5,10-dihydro-dibenzo[b,e][1,4]diazepin-11-one

EXAMPLE 713A

3-Bromo-1-(2,3,5,6-tetrafluoro-benzyl)-1H-pyrrolo[2,3-c]pyridine

The desired product was prepared by substituting 2,3,5,6-tetrafluorobenzyl bromide for benzyl bromide in Example 696A. MS (ESI) m/e 359 (M+H)$^+$, $^1$H NMR (300 MHz, DMSO-d$_6$): ☐ 8.94 (s, 1H), 8.27 (d, J=5.43 Hz, 1H), 7.94 (m, 1H), 7.87 (s, 1H), 7.43 (d, J=5.43 Hz, 1H), 5.75 (s, 2H).

EXAMPLE 713B

8-[2-(4-Morpholin-4-yl-phenoxy)-ethyl]-3-[1-(2,3,5,6-tetrafluoro-benzyl)-1H-pyrrolo[2,3-c]pyridin-3-yl]-5,10-dihydro-dibenzo[b,e][1,4]diazepin-11-one The desired product was prepared by substituting Example 713A for Example 696A in Example 696B. MS (ESI) m/e 694 (M+H)$^+$, $^1$H NMR (500 MHz, DMSO-d$_6$): ☐ 9.82 (s, 1H), 9.47 (s, 1H), 8.66 (s, 1H), 8.55 (d, J=6.71 Hz, 1H), 8.41 (d, J=6.41 Hz, 1H), 8.00 (m, 2H), 7.79 (d, J=8.24 Hz, 1H), 7.42 (d, J=1.53 Hz, 1H), 7.26 (dd, J=8.09, 1.68 Hz, 1H), 6.82-6.95 (m, 7H), 5.97 (s, 2H), 4.05 (t, J=6.71 Hz, 2H), 3.71-3.73 (m, 4H), 2.98-3.00 (m, 4H), 2.87 (t, J=6.71 Hz, 2H).

EXAMPLE 714

8-[2-(4-Morpholin-4-yl-phenoxy)-ethyl]-3-[1-(3-trifluoromethoxy-benzyl)-1H-pyrrolo[2,3-c]pyridin-3-yl]-5,10-dihydro-dibenzo[b,e][1,4]diazepin-11-one

EXAMPLE 714A

3-Bromo-1-(3-trifluoromethoxy-benzyl)-1H-pyrrolo[2,3-c]pyridine

The desired product was prepared by substituting 3-trifluoromethoxybenzyl bromide for benzyl bromide in Example 696A. MS (ESI) m/e 371 (M+H)$^+$, $^1$H NMR (300 MHz, DMSO-d$_6$): ☐ 8.96 (s, 1H), 8.24 (d, J=5.43 Hz, 1H), 8.06 (s, 1H), 7.47 (m, 1H), 7.42 (dd, J=5.42, 1.02 Hz, 1H), 7.39 (m, 1H), 7.27-7.31 (m, 2H), 5.61 (s, 2H).

EXAMPLE 714B

8-[2-(4-Morpholin-4-yl-phenoxy)-ethyl]-3-[1-(3-trifluoromethoxy-benzyl)-1H-pyrrolo[2,3-c]pyridin-3-yl]-5,10-dihydro-dibenzo[b,e][1,4]diazepin-11-one The desired product was prepared by substituting Example 714A for Example 696A in Example 696B. MS (ESI) m/e 706 (M+H)$^+$, $^1$H NMR (400 MHz, DMSO-d$_6$): ☐ 9.79 (s, 1H), 9.53 (s, 1H), 8.87 (s, 1H), 8.50 (d, J=6.44 Hz, 1H), 8.39 (d, J=6.44 Hz, 1H), 7.98 (s, 1H), 7.81 (d, J=7.98 Hz, 1H), 7.51 (m, 2H), 7.44 (d, J=1.23 Hz, 1H), 7.39 (d, J=7.98 Hz, 1H), 7.34 (m, 1H), 7.27 (dd, J=8.29, 1.23 Hz, 1H), 6.82-6.95 (m, 7H), 5.81 (s, 2H), 4.04 (t, J=6.60 Hz, 2H), 3.70-3.72 (m, 4H), 2.97-2.99 (m, 4H), 2.87 (t, J=6.60 Hz, 2H).

EXAMPLE 715

3-[1-(3,4-Dihydroxy-butyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 715A

3-Bromo-1-[2-(2,2-dimethyl-[1,3]dioxolan-4-yl)-ethyl]-1H-pyrrolo[2,3-c]pyridine

A mixture of Example 695J (118 mg, 0.6 mmol), 3-(2,2-dimethyl-[1,3]dioxolan-4-yl)-propan-1-ol (131.6 mg, 0.9 mmol), polymer-supported PPh$_3$ (400 mg, 1.2 mmol), and DBAD (0.268 mg, 1.2 mmol) in THF (3 mL) was stirred at room temperature for 8 hours. The reaction mixture was loaded onto the silica gel column and eluted with 100% EtOAc to give 0.39 g of the desired product (67%). MS (DCI) m/e 326 (M+H)$^+$, $^1$H NMR (500 MHz, DMSO-d$_6$): ☐ 8.94 (s, 1H), 8.23 (d, J=5.49 Hz, 1H), 7.88 (s, 1H), 7.41 (d, J=5.49 Hz, 1H), 4.37-4.40 (m, 2H), 3.91-3.97 (m, 2H), 3.47 (dd, J=7.63, 6.41 Hz, 1H), 2.07 (m, 1H), 1.98 (m, 1H), 1.34 (s, 3H), 1.24 (s, 3H).

EXAMPLE 715B

3-[1-(3,4-Dihydroxy-butyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 715A for Example 696A in Example 696B. MS (APCI) m/e 620 (M+H)+, 1H NMR (500 MHz, DMSO-d6): ☐ 9.82 (s, 1H), 9.48 (s, 1H), 8.77 (s, 1H), 8.48 (d, J=6.71 Hz, 1H), 8.40 (d, J=6.71 Hz, 1H), 8.00 (s, 1H), 7.81 (d, J=8.24 Hz, 1H), 7.47 (s, 1H), 7.29 (dd, J=8.24, 1.53 Hz, 1H), 6.82-6.95 (m, 7H), 4.60-4.63 (m, 2H), 4.05-4.07 (m, 2H), 3.73-3.75 (m, 4H), 3.24-3.26 (m, 3H), 3.03-3.05 (m, 4H), 2.88 (t, J=6.56 Hz, 2H), 2.12 (m, 1H), 1.82 (m, 1H).

EXAMPLE 716

3-(1-Butyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 716A

3-Bromo-1-butyl-1H-pyrrolo[2,3-c]pyridine

The desired product was prepared by substituting bromobutane for benzyl bromide in Example 696A, except the longer reaction time was employed. MS (ESI) m/e 253 (M+H)+, 1H NMR (300 MHz, DMSO-d6): ☐ 8.95 (s, 1H), 8.22 (d, J=5.43 Hz, 1H), 7.84 (s, 1H), 7.40 (d, J=5.43 Hz, 1H), 4.31 (t, J=6.95 Hz, 2H), 1.73-1.82 (m, 2H), 1.17-1.28 (m, 2H), 0.88 (t, J=7.29 Hz, 3H).

EXAMPLE 716B 3-(1-Butyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one The desired product was prepared by substituting Example 716A for Example 696A in Example 696B. MS (ESI) m/e 588 (M+H)+, 1H NMR (500 MHz, DMSO-d6): ☐ 9.81 (s, 1H), 9.52 (s, 1H), 8.78 (s, 1H), 8.47 (d, J=6.41 Hz, 1H), 8.37 (d, J=6.41 Hz, 1H), 7.98 (s, 1H), 7.81 (d, J=8.24 Hz, 1H), 7.45 (d, J=1.53 Hz, 1H), 7.25 (dd, J=8.24, 1.53 Hz, 1H), 6.82-6.95 (m, 7H), 4.50 (t, J=7.17 Hz, 2H), 4.04 (t, J=6.71 Hz, 2H), 3.70-3.72 (m, 4H), 2.97-2.99 (m, 4H), 2.87 (t, J=6.56 Hz, 2H), 1.86-1.92 (m, 2H), 1.27-1.34 (m, 2H), 0.92 (t, J=7.48 Hz, 3H).

EXAMPLE 717

8-[2-(4-Morpholin-4-yl-phenoxy)-ethyl]-3-(1-pyridin-4-ylmethyl-1H-pyrrolo[2,3-c]pyridin-3-yl)-5,10-dihydro-dibenzo[b,e][1,4]diazepin-11-one

EXAMPLE 717A

3-Iodo-1H-pyrrolo[2,3-c]pyridine

A mixture of Example 695I (1.18 g, 10 mmol) and powder KOH (1.68 g, 30 mmol) in DMF (20 mL) was treated with 12 (2.67 g, 10.5 mmol) in DMF (20 mL) dropwise. After the addition was complete, the reaction was stirred for another 30 minutes The reaction mixture was poured into water, and the pH of the solution was brought down to 7. The mixture was extracted with EtOAc three times (3×100 mL). The combined organic layers were washed with brine, dried (MgSO4), filtered, and concentrated under vacuum. The residue was purified by flash column chromatography on silica gel eluting with 100:1 EtOAc/MeOH to give 2.1 g of the title compound (86%). MS (DCI) m/e 245 (M+H)+, 1H NMR (500 MHz, DMSO-d6): ☐ 12.03 (s, 1H), 8.73 (s, 1H), 8.20 (d, J=5.49 Hz, 1H), 7.81 (s, 1H), 7.26 (d, J=5.19 Hz, 1H).

EXAMPLE 717B

3-Iodo-1-pyridin-4-ylmethyl-1H-pyrrolo[2,3-c]pyridine

The title compound was prepared by substituting 4-bromomethyl pyridine hydrobromide and Example 717A for benzyl bromide and Example 695J, respectively, in Example 696A. MS (DCI) m/e 289 (M+H)+, 1H NMR (500 MHz, DMSO-d6): ☐ 8.41 (s, 1H), 8.51 (dd, J=4.42, 1.68 Hz, 2H), 8.24 (d, J=5.49 Hz, 1H), 8.01 (s, 1H), 7.29 (d, J=5.49 Hz, 1H), 7.17 (d, J=5.8 Hz, 2H), 5.63 (s, 2H).

EXAMPLE 717C

8-[2-(4-Morpholin-4-yl-phenoxy)-ethyl]-3-(1-pyridin-4-ylmethyl-1H-pyrrolo[2,3-c]pyridin-3-yl)-5,10-dihydro-dibenzo[b,e][1,4]diazepin-11-one The title compound was prepared by substituting Example 717B for Example 696A in Example 696B. MS (APCI) m/e 623 (M+H)+, 1H NMR (500 MHz, DMSO-d6): ☐ 9.83 (s, 1H), 9.53 (s, 1H), 8.88 (s, 1H), 8.64 (d, J=6.1 Hz, 2H), 8.54 (d, J=6.71 Hz, 1H), 8.45 (d, J=6.41 Hz, 1H), 8.02 (s, 1H), 7.82 (d, J=8.24 Hz, 1H), 7.47 (s, 1H), 7.42 (d, J=6.1 Hz, 2H), 7.28 (dd, J=8.24, 1.53 Hz, 1H), 6.84-6.96 (m, 7H), 5.92 (s, 2H), 4.05 (t, J=6.71 Hz, 2H), 3.72-3.74 (m, 4H), 3.01-3.23 (m, 3H), 2.88 (t, J=6.56 Hz, 2H).

EXAMPLE 718

8-[2-(4-Morpholin-4-yl-phenoxy)-ethyl]-3-(1-phenethyl-1H-pyrrolo[2,3-c]pyridin-3-yl)-5,10-dihydro-dibenzo[b,e][1,4]diazepin-11-one

EXAMPLE 718A

3-Iodo-1-phenethyl-1H-pyrrolo[2,3-c]pyridine

The title compound was prepared by substituting 2-phenylethanol and Example 717A for 3-(2,2-dimethyl-[1,3]dioxolan-4-yl)-propan-1-ol and Example 695J, respectively, in Example 715A. MS (DCI) m/e 349 (M+H)+, 1H NMR (500 MHz, DMSO-d6): ☐ 8.81 (s, 1H), 8.19 (d, J=5.19 Hz, 1H), 7.76 (s, 1H), 7.18-7.26 (m, 6H), 4.56 (t, J=7.48 Hz, 2H), 3.11 (t, J=7.48 Hz, 2H).

EXAMPLE 718B

8-[2-(4-Morpholin-4-yl-phenoxy)-ethyl]-3-(1-phenethyl-1H-pyrrolo[2,3-c]pyridin-3-yl)-5,10-dihydro-dibenzo[b,e][1,4]diazepin-11-one The title compound was prepared by substituting Example 718A for Example 696A in Example 696B. MS (APCI) m/e 636 (M+H)+, 1H NMR (500 MHz, DMSO-d6): ☐ 9.73 (s, 1H), 9.39 (s, 1H), 8.70 (s, 1H), 8.44 (d, J=6.44 Hz, 1H), 8.35 (d, J=6.44 Hz, 1H), 7.97 (s, 1H), 7.80 (d, J=8.29 Hz, 1H), 7.43 (s, 1H), 7.19-7.26 (m, 6H), 6.83-6.96 (m, 7H), 4.77 (t, J=7.21 Hz, 2H), 4.05 (t, J=6.75 Hz, 2H), 3.71-3.73 (m, 4H), 3.23 (t, J=7.36 Hz, 2H), 2.98-3.00 (m, 4H), 2.88 (t, J=6.75 Hz, 2H).

EXAMPLE 719

3-(1-Phenethyl-1H-pyrrolo[2,3-c]pyridin-3-yl)-5,10-dihydro-dibenzo[b,e][1,4]diazepin-11-one

EXAMPLE 719A 2-(2-Amino-phenylamino)-4-chloro-benzoic acid methyl ester

The title compound was prepared by substituting benzene-1,2-diamine for Example 695A in Example 695B. MS (DCI) m/e 277 (M+H)+, $^1$H NMR (500 MHz, DMSO-$d_6$): ☐ 8.86 (s, 1H), 7.86 (d, J=8.54 Hz, 1H), 7.02-7.05 (m, 2H), 6.82 (d, J=7.93 Hz, 1H), 6.71 (dd, J=8.7, 1.98 Hz, 1H), 6.61 (m, 1H), 6.41 (d, J=2.14 Hz, 1H), 4.99 (s, 2H), 3.86 (s, 3H).

EXAMPLE 719B

3-Chloro-5,10-dihydro-dibenzo[b,e][1,4]diazepin-11-one

The title compound was prepared by substituting Example 719A for Example 695C in Example 695D. MS (DCI) m/e 245 (M+H)+, $^1$H NMR (500 MHz, DMSO-$d_6$): ☐ 9.93 (s, 1H), 8.07 (s, 1H), 7.71 (d, J=8.54 Hz, 1H), 7.10 (d, J=1.83 Hz, 1H), 6.93-6.99 (m, 5H).

EXAMPLE 719C 3-(4,4,5,5-Tetramethyl-[1,3,2]dioxaborolan-2-yl)-5,10-dihydro-dibenzo[b,e][1,4]diazepin-11-one The title compound was prepared by substituting Example 719B for Example 695F in Example 695G. MS (APCI) m/e 337 (M+H)+,

EXAMPLE 719D 3-(1-Phenethyl-1H-pyrrolo[2,3-c]pyridin-3-yl)-5,10-dihydro-dibenzo[b,e][1,4]diazepin-11-one The title compound was prepared by substituting Example 718A and Example 719C for Example 696A and Example 695G, respectively, in Example 696B. MS (APCI) m/e 431 (M+H)+, $^1$H NMR (500 MHz, DMSO-$d_6$): ☐ 9.85 (s, 1H), 9.37 (s, 1H), 8.67 (s, 1H), 8.44 (d, J=6.41 Hz, 1H), 8.33 (d, J=6.44 Hz, 1H), 8.04 (s, 1H), 7.81 (d, J=8.24 Hz, 1H), 7.45 (d, J=1.53 Hz, 1H), 7.17-7.26 (m, 6H), 6.91-7.03 (m, 4H), 4.76 (t, J=7.17 Hz, 2H), 3.22 (t, J=7.32 Hz, 2H).

EXAMPLE 720

3-[1-(3-Methoxy-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 720A

3-Bromo-1-(3-methoxy-benzyl)-1H-pyrrolo[2,3-c]pyridine

The desired product was prepared by substituting 3-methoxybenzyl bromide for benzyl bromide in Example 696A. MS (ESI) m/e 317 (M+H)+, $^1$H NMR (300 MHz, DMSO-$d_6$): ☐ 8.94 (s, 1H), 8.22 (d, J=5.43 Hz, 1H), 8.02 (s, 1H), 7.41 (dd, J=5.76, 1.02 Hz, 1H), 7.24 (m, 1H), 6.92 (m, 1H), 6.82-6.87 (m, 2H), 5.50 (s, 2H), 3.72 (s, 3H).

EXAMPLE 720B

3-[1-(3-Methoxy-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 720A for Example 696A in Example 696B. MS (ESI) m/e 652 (M+H)+, $^1$H NMR (500 MHz, DMSO-$d_6$): ☐ 9.81 (s, 1H), 9.52 (s, 1H), 8.86 (s, 1H), 8.48 (d, J=6.71 Hz, 1H), 8.37 (d, J=6.41 Hz, 1H), 7.98 (s, 1H), 7.80 (d, J=8.24 Hz, 1H), 7.43 (d, J=1.22 Hz, 1H), 7.26-7.30 (m, 2H), 7.05 (m, 1H), 6.82-6.95 (m, 9H), 5.71 (s, 2H), 4.04 (t, J=6.71 Hz, 2H), 3.74 (s, 3H), 3.71-3.73 (m, 4H), 2.97-2.99 (m, 4H), 2.87 (t, J=6.71 Hz, 2H).

EXAMPLE 721

2-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile

EXAMPLE 721A 2-(3-Iodo-pyrrolo[2,3-c]pyridin-1-ylmethyl)-benzonitrile

The desired product was prepared by substituting 2-cyanobenzyl bromide and Example 717A for benzyl bromide and Example 695J, respectively, in Example 696A. MS (ESI) m/e 360 (M+H)+, $^1$H NMR (300 MHz, DMSO-$d_6$): ☐ 8.82 (s, 1H), 8.25 (d, J=5.42 Hz, 1H), 7.90-7.94 (m, 2H), 7.64 (m, 1H), 7.51 (m, 1H), 7.31 (d, J=5.42 Hz, 1H), 7.02 (d, J=7.46 Hz, 1H), 5.82 (s, 2H).

EXAMPLE 721B 2-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile The desired product was prepared by substituting Example 721A for Example 696A in Example 696B. MS (ESI) m/e 647 (M+H)+, $^1$H NMR (500 MHz, DMSO-$d_6$): ☐ 9.80 (s, 1H), 9.52 (s, 1H), 8.71 (s, 1H), 8.54 (d, J=6.75 Hz, 1H), 8.44 (d, J=6.44 Hz, 1H), 7.95-7.98 (m, 2H), 7.81 (d, J=8.29 Hz, 1H), 7.68 (t, J=7.83 Hz, 1H), 7.56 (d, J=7.67 Hz, 1H), 7.44 (d, J=1.23 Hz, 1H), 7.25 (dd, J=8.29, 1.53 Hz, 1H), 7.10 (d, J=7.98 Hz, 1H), 6.82-6.95 (m, 7H), 6.05 (s, 2H), 4.04 (t, J=6.60 Hz, 2H), 3.71-3.73 (m, 4H), 2.97-2.99 (m, 4H), 2.87 (t, J=6.60 Hz, 2H).

EXAMPLE 722

3-[1-(2-Morpholin-4-yl-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 722A

3-Bromo-1-(2-morpholin-4-yl-ethyl)-1H-pyrrolo[2,3-c]pyridine

The title compound was prepared by substituting 2-morpholin-4-yl-ethanol and Example 717A for 3-(2,2-dimethyl-

[1,3]dioxolan-4-yl)-propan-1-ol and Example 695J, respectively, in Example 715A. MS (DCI) m/e 358 (M+H)⁺, ¹H NMR (500 MHz, DMSO-d$_6$): ☐ 8.89 (s, 1H), 8.21 (d, J=5.19 Hz, 1H), 7.84 (s, 1H), 7.24 (d, J=5.49 Hz, 1H), 4.42 (t, J=6.41 Hz, 2H), 5.50-5.52 (m, 4H), 2.69 (t, J=6.26 Hz, 2H), 2.38-2.44 (m, 4H).

EXAMPLE 722B

3-[1-(2-Morpholin-4-yl-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 722A for Example 696A in Example 696B. MS (APCI) m/e 645 (M+H)⁺, ¹H NMR (500 MHz, DMSO-d$_6$): ☐ 9.83 (s, 1H), 9.55 (s, 1H), 8.79 (s, 1H), 8.55 (d, J=6.41 Hz, 1H), 8.42 (d, J=6.41 Hz, 1H), 8.05 (s, 1H), 7.83 (d, J=8.24 Hz, 1H), 7.48 (s, 1H), 7.25 (dd, J=8.24, 1.53 Hz, 1H), 6.84-6.97 (m, 7H), 4.89 (t, J=7.21 Hz, 2H), 4.05 (t, J=6.71 Hz, 2H), 3.79 (br, 6H), 3.71-3.73 (m, 4H), 3.24 (br, 4H), 2.99-3.01 (m, 4H), 2.88 (t, J=6.56 Hz, 2H).

EXAMPLE 723

8-[2-(4-Morpholin-4-yl-phenoxy)-ethyl]-3-[1-(4-trifluoromethoxy-benzyl)-1H-pyrrolo[2,3-c]pyridin-3-yl]-5,10-dihydro-dibenzo[b,e][1,4]diazepin-11-one

EXAMPLE 723A

3-Iodo-1-(4-trifluoromethoxy-benzyl)-1H-pyrrolo[2,3-c]pyridine

The desired product was prepared by substituting 1-bromomethyl-4-trifluoromethoxy-benzene and Example 717A for benzyl bromide and Example 695J, respectively, in Example 696A. MS (ESI) m/e 419 (M+H)⁺, ¹H NMR (300 MHz, DMSO-d$_6$): ☐ 8.88 (s, 1H), 8.23 (d, J=5.76 Hz, 1H), 8.02 (s, 1H), 7.32-7.44 (m, 4H), 7.27 (dd, J=5.43, 1.02 Hz, 1H), 5.60 (s, 2H).

EXAMPLE 723B

8-[2-(4-Morpholin-4-yl-phenoxy)-ethyl]-3-[1-(4-trifluoromethoxy-benzyl)-1H-pyrrolo[2,3-c]pyridin-3-yl]-5,10-dihydro-dibenzo[b,e][1,4]diazepin-11-one The desired product was prepared by substituting Example 723A for Example 696A in Example 696B. MS (ESI) m/e 706 (M+H)⁺, ¹H NMR (500 MHz, DMSO-d$_6$): ☐ 9.91 (s, 1H), 9.64 (s, 1H), 8.98 (s, 1H), 8.60 (d, J=6.71 Hz, 1H), 8.49 (d, J=6.41 Hz, 1H), 8.08 (s, 1H), 7.90 (d, J=8.24 Hz, 1H), 7.63 (d, J=8.85 Hz, 2H), 7.53 (d, J=1.53 Hz, 1H), 7.48 (d, J=8.24 Hz, 2H), 7.36 (dd, J=8.24, 1.53 Hz, 1H), 6.91-7.04 (m, 7H), 5.90 (s, 2H), 4.14 (t, J=6.71 Hz, 2H), 3.80-3.82 (m, 4H), 3.06-3.08 (m, 4H), 2.96 (t, J=6.71 Hz, 2H).

EXAMPLE 724

8-[2-(4-Morpholin-4-yl-phenoxy)-ethyl]-3-[1-(4-trifluoromethyl-benzyl)-1H-pyrrolo[2,3-c]pyridin-3-yl]-5,10-dihydro-dibenzo[b,e][1,4]diazepin-11-one

EXAMPLE 724A

3-Iodo-1-(4-trifluoromethyl-benzyl)-1H-pyrrolo[2,3-c]pyridine

The desired product was prepared by substituting 1-bromomethyl-4-trifluoromethyl-benzene and Example 717A for benzyl bromide and Example 695J, respectively, in Example 696A. MS (ESI) m/e 403 (M+H)⁺, ¹H NMR (300 MHz, DMSO-d$_6$): ☐ 8.85 (s, 1H), 8.23 (d, J=5.43 Hz, 1H), 8.03 (s, 1H), 7.71 (d, J=8.14 Hz, 2H), 7.47 (d, J=8.14 Hz, 2H), 7.28 (dd, J=5.26, 0.85 Hz, 1H), 5.68 (s, 2H).

EXAMPLE 724B

8-[2-(4-Morpholin-4-yl-phenoxy)-ethyl]-3-[1-(4-trifluoromethyl-benzyl)-1H-pyrrolo[2,3-c]pyridin-3-yl]-5,10-dihydro-dibenzo[b,e][1,4]diazepin-11-one The desired product was prepared by substituting Example 724A for Example 696A in Example 696B. MS (ESI) m/e 690 (M+H)⁺, ¹H NMR (500 MHz, DMSO-d$_6$): ☐ 9.82 (s, 1H), 9.53 (s, 1H), 8.89 (s, 1H), 8.51 (d, J=6.71 Hz, 1H), 8.41 (d, J=6.71 Hz, 1H), 7.99 (s, 1H), 7.81 (d, J=8.24 Hz, 1H), 7.76 (d, J=8.24 Hz, 2H), 7.58 (d, J=8.24 Hz, 2H), 7.45 (s, 1H), 7.28 (dd, J=8.24, 1.22 Hz, 1H), 6.81-6.95 (m, 7H), 5.89 (s, 2H), 4.04 (t, J=6.71 Hz, 2H), 3.70-3.73 (m, 4H), 2.97-2.99 (m, 4H), 2.87 (t, J=6.56 Hz, 2H).

EXAMPLE 725

3-(1-Cyclopentyl-1H-pyrrolo[2,3-c]pyridin-3-yl)-5,10-dihydro-dibenzo[b,e][1,4]diazepin-11-one

EXAMPLE 725A

3-Iodo-1-cyclopentyl-1H-pyrrolo[2,3-c]pyridine

The title compound was prepared by substituting cyclopentanol and Example 717A for 3-(2,2-dimethyl-[1,3]dioxolan-4-yl)-propan-1-ol and Example 695J, respectively, in Example 715A. MS (DCI) m/e 313 (M+H)⁺, ¹H NMR (500 MHz, DMSO-d$_6$): ☐ 8.91 (s, 1H), 8.22 (d, J=5.22 Hz, 1H), 7.91 (s, 1H), 7.24 (d, J=5.52 Hz, 1H), 5.05 (q, J=7.26 Hz, 1H), 2.17-2.23 (m, 2H), 1.82-1.92 (m, 4H), 1.70-1.72 (m, 2H).

EXAMPLE 725B 3-(1-Cyclopentyl-1H-pyrrolo[2,3-c]pyridin-3-yl)-5,10-dihydro-dibenzo[b,e][1,4]diazepin-11-one The title compound was prepared by substituting Example 725A and Example 719C for Example 696A and Example 695G, respectively, in Example 696B. MS (APCI) m/e 395 (M+H)⁺, ¹H NMR (500 MHz, DMSO-d$_6$): ☐ 9.82 (s, 1H), 9.53 (s, 1H), 8.84 (s, 1H), 8.47 (d, J=6.75 Hz, 1H), 8.37 (d, J=6.75 Hz, 1H), 8.02 (s, 1H), 7.82 (d, J=8.29 Hz, 1H), 7.49 (s, 1H), 7.35 (d, J=9.29 Hz, 1H), 6.90-7.04 (m, 4H), 5.23 (q, J=7.47 Hz, 1H), 2.27-2.31 (m, 2H), 1.93-2.06 (m, 4H), 1.75-1.78 (m, 2H).

EXAMPLE 726

3-[1-(2-Ethoxy-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 726A

3-Bromo-1-(2-ethoxy-ethyl)-1H-pyrrolo[2,3-c]pyridine

The title compound was prepared by substituting 2-ethoxyethanol for 3-(2,2-dimethyl-[1,3]dioxolan-4-yl)-propan-1-ol in Example 715A. MS (DCI) m/e 270 (M+H)+, 1H NMR (500 MHz, DMSO-d6): □ 8.94 (s, 1H), 8.22 (d, J=5.22 Hz, 1H), 7.81 (s, 1H), 7.39 (d, J=5.22 Hz, 1H), 4.46 (t, J=5.22 Hz, 2H), 3.72 (t, J=5.22 Hz, 2H), 3.40 (q, J=6.85 Hz, 2H), 1.01 (t, J=6.9 Hz, 3H).

EXAMPLE 726B

3-[1-(2-Ethoxy-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 726A for Example 696A in Example 696B. MS (APCI) m/e 604 (M+H)+, 1H NMR (500 MHz, DMSO-d6): □ 9.79 (s, 1H), 9.46 (s, 1H), 8.70 (s, 1H), 8.48 (d, J=6.45 Hz, 1H), 8.38 (d, J=6.44 Hz, 1H), 7.98 (s, 1H), 7.81 (d, J=8.29 Hz, 1H), 7.45 (s, 1H), 7.25 (dd, J=8.25, 1.53 Hz, 1H), 6.82-6.97 (m, 7H), 4.69 (t, J=4.91 Hz, 2H), 4.05 (t, J=6.75 Hz, 2H), 3.82 (t, J=4.91 Hz, 2H), 3.70-3.73 (m, 4H), 3.43 (q, J=7.06 Hz, 2H), 2.97-2.99 (m, 4H), 2.88 (t, J=6.6 Hz, 2H), 1.01 (t, J=7.06 Hz, 3H).

EXAMPLE 727

3-[1-(2-Ethoxy-ethyl)-1H-pyrrolo[2,3-c]pyridin-3-yl]-5,10-dihydro-dibenzo[b,e][1,4]diazepin-11-one The title compound was prepared by substituting Example 726A and Example 719C for Example 696A and Example 695G, respectively, in Example 696B. MS (APCI) m/e 604 (M+H)+, 1H NMR (500 MHz, DMSO-d6): □ 9.82 (s, 1H), 9.42 (s, 1H), 8.66 (s, 1H), 8.47 (d, J=6.44 Hz, 1H), 8.35 (d, J=6.44 Hz, 1H), 8.03 (s, 1H), 7.82 (d, J=8.29 Hz, 1H), 7.47 (s, 1H), 7.26 (dd, J=8.25, 1.53 Hz, 1H), 6.91-7.03 (m, 4H), 4.68 (t, J=4.91 Hz, 2H), 3.82 (t, J=5.06 Hz, 2H), 3.40-3.46 (m, 2H), 1.02 (t, J=6.9 Hz, 3H).

EXAMPLE 728

3-[1-(4-Methyl-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 728A

3-Iodo-1-(4-methyl-benzyl)-1H-pyrrolo[2,3-c]pyridine

The desired product was prepared by substituting 4-methylbenzyl bromide and Example 717A for benzyl bromide and Example 695J, respectively, in Example 696A. MS (ESI) m/e 349 (M+H)+, 1H NMR (300 MHz, DMSO-d6): □ 8.85 (s, 1H), 8.21 (d, J=5.43 Hz, 1H), 7.96 (s, 1H), 7.20-7.26 (m, 3H), 7.12-7.15 (m, 2H), 5.49 (s, 2H), 2.24 (s, 3H).

EXAMPLE 728B

3-[1-(4-Methyl-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 728A for Example 696A in Example 696B. MS (ESI) m/e 636 (M+H)+, 1H NMR (500 MHz, DMSO-d6): □ 9.82 (s, 1H), 9.53 (s, 1H), 8.86 (s, 1H), 8.49 (d, J=6.71 Hz, 1H), 8.39 (d, J=6.41 Hz, 1H), 7.98 (s, 1H), 7.80 (d, J=8.24 Hz, 1H), 7.43 (d, J=1.53 Hz, 1H), 7.34 (d, J=7.93 Hz, 2H), 7.27 (dd, J=8.24, 1.83 Hz, 1H), 7.19 (d, J=7.93 Hz, 2H), 6.82-6.95 (m, 7H), 5.71 (s, 2H), 4.04 (t, J=6.71 Hz, 2H), 3.71-3.73 (m, 4H), 2.98-3.00 (m, 4H), 2.87 (t, J=6.56 Hz, 2H), 2.27 (s, 3H).

EXAMPLE 729

3-(1-Cyclopentyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one The title compound was prepared by substituting Example 725A for Example 696A in Example 696B. MS (APCI) m/e 600 (M+H)+, 1H NMR (500 MHz, DMSO-d6): □ 9.81 (s, 1H), 9.55 (s, 1H), 8.87 (s, 1H), 8.48 (d, J=6.41 Hz, 1H), 8.38 (d, J=6.41 Hz, 1H), 7.98 (s, 1H), 7.80 (d, J=8.24 Hz, 1H), 7.47 (d, J=1.53 Hz, 1H), 7.34 (dd, J=8.24, 1.53 Hz, 1H), 6.83-6.96 (m, 7H), 5.26 (q, J=8.24 Hz, 1H), 4.05 (t, J=6.71 Hz, 2H), 3.71-3.73 (m, 4H), 2.97-2.99 (m, 4H), 2.86 (t, J=6.71 Hz, 2H), 2.27-2.32 (m, 2H), 1.94-2.06 (m, 4H), 1.74-1.77 (m, 2H).

EXAMPLE 730

4-[2-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-ethyl]-benzonitrile

EXAMPLE 730A

4-[2-(3-Bromo-pyrrolo[2,3-c]pyridin-1-yl)-ethyl]-benzonitrile

The desired product was prepared by substituting 4-(2-hydroxy-ethyl)-benzonitrile for 2-(2,2-dimethyl-[1,3]dioxolan-4-yl)-ethanol in Example 715A. MS (ESI) m/e 326 (M+H)+, 1H NMR (300 MHz, DMSO-d6): □ 8.87 (s, 1H), 8.20 (d, J=5.76 Hz, 1H), 7.80 (s, 1H), 7.71 (d, J=8.48 Hz, 2H), 7.40 (d, J=8.48 Hz, 2H), 7.36 (dd, J=5.76, 1.02 Hz, 1H), 4.59 (t, J=7.12 Hz, 2H), 3.22 (t, J=7.29 Hz, 2H).

EXAMPLE 730B

4-[2-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-ethyl]-benzonitrile The desired product was prepared by substituting Example 730A for Example 696A in Example 696B. MS (ESI) m/e 661 (M+H)+, 1H NMR (500 MHz, DMSO-d6): □ 9.82 (s, 1H), 9.43 (s, 1H), 8.70 (s, 1H), 8.47 (d, J=6.71 Hz, 1H), 8.35 (d, J=6.71 Hz, 1H), 7.99 (s, 1H), 7.80 (d, J=8.24 Hz, 1H), 7.75 (d, J=8.24 Hz, 2H), 7.43-7.46 (m, 3H), 7.20 (dd, J=8.24, 1.53 Hz, 1H), 6.82-6.95 (m, 7H), 4.79 (t, J=7.32 Hz, 2H), 4.05 (t, J=6.71 Hz, 2H), 3.70-3.72 (m, 4H), 3.33 (t, J=7.32 Hz, 2H) 2.96-2.98 (m, 4H), 2.87 (t, J=6.56 Hz, 2H).

EXAMPLE 731

3-[1-(4-Hydroxy-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 731A 4-(3-Iodo-pyrrolo[2,3-c]pyridin-1-ylmethyl)-phenol

Acetic acid 4-(3-iodo-pyrrolo[2,3-c]pyridin-1-ylmethyl)-phenyl ester was prepared by substituting acetic acid 4-chloromethyl-phenyl ester and Example 717A for benzyl bromide and Example 695J, respectively, in Example 696A. Acetic acid 4-(3-iodo-pyrrolo[2,3-c]pyridin-1-ylmethyl)-phenyl ester was then slurried in a mixture of THF and water, and treated with LiOH to provide the desired product. MS (ESI) m/e 351 (M+H)$^+$, $^1$H NMR (300 MHz, DMSO-d$_6$): □ 9.44 (s, 1H), 8.87 (s, 1H), 8.20 (d, J=5.43 Hz, 1H), 7.93 (s, 1H), 7.24 (dd, J=5.43, 1.02 Hz, 1H), 7.18 (d, J=8.48 Hz, 2H), 6.68-6.72 (m, 2H), 5.40 (s, 2H).

EXAMPLE 731B

3-[1-(4-Hydroxy-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 731A for Example 696A in Example 696B. MS (ESI) m/e 638 (M+H)$^+$, $^1$H NMR (400 MHz, DMSO-d$_6$): □ 9.79 (s, 1H), 9.51 (s, 1H), 8.80 (s, 1H), 8.47 (d, J=6.44 Hz, 1H), 8.37 (d, J=6.44 Hz, 1H), 7.96 (s, 1H), 7.80 (d, J=8.29 Hz, 1H), 7.41 (d, J=1.23 Hz, 1H), 7.30 (d, J=8.59 Hz, 2H), 7.26 (dd, J=8.13, 1.07 Hz, 1H), 6.82-6.95 (m, 8H), 6.75 (d, J=8.29 Hz, 2H), 5.61 (s, 2H), 4.05 (t, J=6.75 Hz, 2H), 3.71-3.73 (m, 4H), 2.97-2.99 (m, 4H), 2.87 (t, J=6.45 Hz, 2H).

EXAMPLE 732

3-{1-[2-(4-Methyl-thiazol-5-yl)-ethyl]-1H-pyrrolo[2,3-c]pyridin-3-yl}-8-[2-(4-morpholin-4-yl-phenoxy)-ethyl]-5,10-dihydro-dibenzo[b,e][1,4]diazepin-11-one

EXAMPLE 732A

3-Iodo-1-[2-(4-methyl-thiazol-5-yl)-ethyl]-1H-pyrrolo[2,3-c]pyridine

The desired product was prepared by substituting 2-(4-methyl-thiazol-5-yl)-ethanol and
Example 717A for 2-(2,2-dimethyl-[1,3]dioxolan-4-yl)-ethanol and Example 695J, respectively, in Example 715A. MS (ESI) m/e 370 (M+H)$^+$, $^1$H NMR (300 MHz, DMSO-d$_6$): □ 8.75 (s, 1H), 8.72 (d, J=1.02 Hz, 1H), 8.19 (d, J=5.43 Hz, 1H), 7.73 (s, 1H), 7.23 (dd, J=5.76, 1.02 Hz, 1H), 4.52 (t, J=6.61 Hz, 2H), 3.27-3.29 (m, 2H), 2.02 (s, 3H).

EXAMPLE 732B

3-{1-[2-(4-Methyl-thiazol-5-yl)-ethyl]-1H-pyrrolo[2,3-c]pyridin-3-yl}-8-[2-(4-morpholin-4-yl-phenoxy)-ethyl]-5,10-dihydro-dibenzo[b,e][1,4]diazepin-11-one The desired product was prepared by substituting Example 732A for Example 696A in Example 696B. MS (ESI) m/e 657 (M+H)$^+$, $^1$H NMR (500 MHz, DMSO-d$_6$): □ 9.82 (s, 1H), 9.36 (s, 1H), 8.78 (s, 1H), 8.67 (s, 1H), 8.47 (d, J=6.41 Hz, 1H), 8.37 (d, J=6.41 Hz, 1H), 7.99 (s, 1H), 7.80 (d, J=8.24 Hz, 1H), 7.42 (d, J=1.22 Hz, 1H), 7.20 (dd, J=8.24, 1.53 Hz, 1H), 6.82-6.96 (m, 7H), 4.73 (t, J=6.56 Hz, 2H), 4.05 (t, J=6.56 Hz, 2H), 3.71-3.73 (m, 4H), 3.43-3.46 (m, 2H), 2.97-2.99 (m, 4H), 2.87 (t, J=6.56 Hz, 2H), 2.09 (s, 3H).

EXAMPLE 733

8-[2-(4-Morpholin-4-yl-phenoxy)-ethyl]-3-[1-(2-pyridin-2-yl-ethyl)-1H-pyrrolo[2,3-c]pyridin-3-yl]-5,10-dihydro-dibenzo[b,e][1,4]diazepin-11-one

EXAMPLE 733A

3-Bromo-1-(2-pyridin-2-yl-ethyl)-1H-pyrrolo[2,3-c]pyridine

The desired product was prepared by substituting 2-pyridin-2-yl-ethanol for 2-(2,2-dimethyl-[1,3]dioxolan-4-yl)-ethanol in Example 715A. MS (ESI) m/e 302 (M+H)$^+$, $^1$H NMR (300 MHz, DMSO-d$_6$): □ 8.81 (s, 1H), 8.50 (m, 1H), 8.18 (d, J=5.43 Hz, 1H), 7.77 (s, 1H), 7.63 (m, 1H), 7.34 (dd, J=5.43, 1.02 Hz, 1H), 7.17-7.22 (m, 2H), 4.71 (t, J=6.95 Hz, 2H), 3.26-3.29 (m, 2H).

EXAMPLE 733B

8-[2-(4-Morpholin-4-yl-phenoxy)-ethyl]-3-[1-(2-pyridin-2-yl-ethyl)-1H-pyrrolo[2,3-c]pyridin-3-yl]-5,10-dihydro-dibenzo[b,e][1,4]diazepin-11-one The desired product was prepared by substituting Example 733A for Example 696A in Example 696B. MS (ESI) m/e 637 (M+H)$^+$, $^1$H NMR (500 MHz, DMSO-d$_6$): □ 9.82 (s, 1H), 9.44 (s, 1H), 8.69 (s, 1H), 8.50 (d, J=4.58 Hz, 1H), 8.46 (d, J=6.41 Hz, 1H), 8.35 (d, J=6.41 Hz, 1H), 7.98 (s, 1H), 7.79 (d, J=8.24 Hz, 1H), 7.74 (m, 1H), 7.41 (s, 1H), 7.30 (d, J=8.54 Hz, 1H), 7.27 (m, 1H), 7.19 (dd, J=8.24, 1.53 Hz, 1H), 6.89-6.95 (m, 5H), 6.83-6.85 (m, 2H), 4.93 (t, J=7.02 Hz, 2H), 4.05 (t, J=6.71 Hz, 2H), 3.71-3.73 (m, 4H), 3.42-3.44 (m, 2H), 2.98-3.00 (m, 4H), 2.87 (t, J=6.71 Hz, 2H).

EXAMPLE 734

8-[2-(4-Morpholin-4-yl-phenoxy)-ethyl]-3-(1-pyrazin-2-ylmethyl-1H-pyrrolo[2,3-c]pyridin-3-yl)-5,10-dihydro-dibenzo[b,e][1,4]diazepin-11-one

EXAMPLE 734A

3-Bromo-1-pyrazin-2-ylmethyl-1H-pyrrolo[2,3-c]pyridine

The title compound was prepared by substituting pyrazin-2-yl-methanol for 3-(2,2-dimethyl-[1,3]dioxolan-4-yl)-propan-1-ol in Example 715A. MS (DCI) m/e 290 (M+H)$^+$, $^1$H NMR (500 MHz, DMSO-d$_6$): □ 8.96 (s, 1H), 8.73 (s, 1H), 8.56-8.59 (m, 2H), 8.24 (d, J=5.52 Hz, 1H), 7.98 (s, 1H), 7.42 (d, J=4.2 Hz, 1H), 5.75 (s, 2H).

EXAMPLE 734B

8-[2-(4-Morpholin-4-yl-phenoxy)-ethyl]-3-(1-pyrazin-2-ylmethyl-1H-pyrrolo[2,3-c]pyridin-3-yl)-5,10-dihydro-dibenzo[b,e][1,4]diazepin-11-one The title compound was prepared by substituting Example 734A for Example 696A in Example 696B. MS (APCI) m/e 624 (M+H)$^+$, $^1$H NMR (500 MHz, DMSO-d$_6$): □ 9.82 (s, 1H), 9.55 (s, 1H), 8.87 (s, 1H), 8.84 (s, 1H), 8.63 (d, J=2.44 Hz, 1H), 8.55 (s, 1H), 8.51 (d, J=6.71 Hz, 1H), 8.41 (d, J=6.41 Hz, 1H), 7.99 (s, 1H), 7.81 (d, J=8.24 Hz, 1H), 7.45 (s, 1H), 7.26 (dd, J=8.24, 1.53 Hz, 1H), 6.83-6.95 (m, 7H), 6.00 (s, 1H), 4.05 (t, J=6.71 Hz, 2H), 3.71-3.73 (m, 4H), 2.98-3.00 (m, 4H), 2.87 (t, J=6.56 Hz, 2H).

EXAMPLE 735

3-(1-Cyclopentylmethyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 735A

3-Bromo-1-cyclopentylmethyl-1H-pyrrolo[2,3-c]pyridine

The title compound was prepared by substituting cyclopentyl-methanol for 3-(2,2-dimethyl-[1,3]dioxolan-4-yl)-propan-1-ol in Example 715A. MS (DCI) m/e 280 (M+H)$^+$, $^1$H NMR (500 MHz, DMSO-d$_6$): □ 8.97 (s, 1H), 8.22 (d, J=5.49 Hz, 1H), 7.90 (s, 1H), 7.39 (d, J=5.49 Hz, 1H), 4.22 (d J=7.63 Hz, 2H), 2.41 (m, 1H), 1.48-1.65 (m, 6H), 1.21-1.35 (m, 2H).

EXAMPLE 735B 3-(1-Cyclopentylmethyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one The title compound was prepared by substituting Example 735A for Example 696A in Example 696B. MS (APCI) m/e 614 (M+H)$^+$, $^1$H NMR (500 MHz, DMSO-d$_6$): □ 9.82 (s, 1H), 9.59 (s, 1H), 8.83 (s, 1H), 8.48 (d, J=6.41 Hz, 1H), 8.39 (d, J=6.41 Hz, 1H), 8.00 (s, 1H), 7.81 (d, J=8.24 Hz, 1H), 7.45 (s, 1H), 7.28 (dd, J=8.24, 1.53 Hz, 1H), 6.83-6.95 (m, 7H), 4.45 (t, J=7.93 Hz, 2H), 4.05 (d, J=6.71 Hz, 2H), 3.71-3.73 (m, 4H), 2.98-3.00 (m, 4H), 2.88 (t, J=6.56 Hz, 2H), 2.52 (m, 1H), 1.52-1.68 (m, 6H), 1.28-1.32 (m, 2H).

EXAMPLE 736

3-(1-Benzyl-1H-pyrrolo[2,3-c]pyridin-3-yl)-8-[2-(2-methyl-pyridin-3-yloxy)-ethyl]-5,10-dihydro-dibenzo[b,e][1,4]diazepin-11-one

EXAMPLE 736A

3-Chloro-8-[2-(2-methyl-pyridin-3-yloxy)-ethyl]-5,10-dihydro-dibenzo[b,e][1,4]diazepin-11-one The title compound was prepared by substituting 2-methyl-pyridin-3-ol for 4-morpholinophenol in Example 695F. MS (DCI) m/e 380 (M+H)$^+$, $^1$H NMR (500 MHz, DMSO-d$_6$): □ 9.89 (s, 1H), 8.00 (s, 1H), 7.98 (d, J=4.6 Hz, 1H), 7.69 (d, J=8.59 Hz, 1H), 7.29 (d, J=8.29 Hz, 1H), 7.14 (dd, J=8.20, 4.6 Hz, 1H), 7.08 (m, 1H), 6.90-6.94 (m, 4H), 4.14 (d, J=6.6 Hz, 2H), 2.93 (d, J=6.44 Hz, 2H), 2.32 (s, 3H).

EXAMPLE 736B

8-[2-(2-Methyl-pyridin-3-yloxy)-ethyl]-3-(4,4,5,5-tetramethyl-[1,3,2]dioxaborolan-2-yl)-5,10-dihydro-dibenzo[b,e][1,4]diazepin-11-one The title compound was prepared by substituting Example 736A for Example 695F in Example 695G. MS (DCI) m/e 472 (M+H)$^+$.

EXAMPLE 736C 3-(1-Benzyl-1H-pyrrolo[2,3-c]pyridin-3-yl)-8-[2-(2-methyl-pyridin-3-yloxy)-ethyl]-5,10-dihydro-dibenzo[b,e][1,4]diazepin-11-one The title compound was prepared by substituting Example 736B for Example 695G in Example 696B. MS (APCI) m/e 552 (M+H)$^+$, $^1$H NMR (500 MHz, DMSO-d$_6$): □ 10.01 (s, 1H), 9.72 (s, 1H), 9.04 (s, 1H), 8.66 (d, J=6.71 Hz, 1H), 8.56 (d, J=6.41 Hz, 1H), 8.34 (d, J=5.19 Hz, 1H), 8.18 (s, 1H), 7.97 (d, J=8.24 Hz, 1H), 7.92 (d, J=7.93 Hz, 1H), 7.69 (dd, J=7.93, 5.19 Hz, 1H), 7.43-7.60 (m, 7H), 7.10-7.12 (m, 3H), 5.93 (s, 2H), 4.43 (t, J=6.41 Hz, 2H), 3.63 (t, J=6.41 Hz, 2H), 2.59 (s, 3H).

EXAMPLE 737

8-[2-(4-Morpholin-4-yl-phenoxy)-ethyl]-3-[1-(2-piperidin-1-yl-ethyl)-1H-pyrrolo[2,3-c]pyridin-3-yl]-5,10-dihydro-dibenzo[b,e][1,4]diazepin-11-one

EXAMPLE 737A

3-Bromo-1-(2-piperidin-1-yl-ethyl)-1H-pyrrolo[2,3-c]pyridine

The title compound was prepared by substituting 2-piperidin-1-yl-ethanol for 3-(2,2-dimethyl-[1,3]dioxolan-4-yl)-propan-1-ol in Example 715A. MS (DCI) m/e 309 (M+H)$^+$, $^1$H NMR (500 MHz, DMSO-d$_6$): □ 8.93 (s, 1H), 8.22 (d, J=5.52 Hz, 1H), 7.80 (s, 1H), 7.38 (d, J=5.42 Hz, 1H), 4.39 (d, J=6.29 Hz, 2H), 2.64 (d, J=6.29 Hz, 2H), 2.36-2.37 (m, 4H), 1.34-1.45 (m, 6H).

EXAMPLE 737B

8-[2-(4-Morpholin-4-yl-phenoxy)-ethyl]-3-[1-(2-piperidin-1-yl-ethyl)-1H-pyrrolo[2,3-c]pyridin-3-yl]-5,10-dihydro-dibenzo[b,e][1,4]diazepin-11-one The title compound was prepared by substituting Example 737A for Example 696A in Example 696B. MS (APCI) m/e 643 (M+H)$^+$, $^1$H NMR (500 MHz, DMSO-d$_6$): □ 9.93 (s, 1H), 9.51 (s, 1H), 8.76 (s, 1H), 8.55 (d, J=6.41 Hz, 1H), 8.40 (d, J=6.41 Hz, 1H), 8.03 (s, 1H), 7.83 (d, J=8.24 Hz, 1H), 7.47 (s, 1H), 7.25 (dd, J=8.24, 1.53 Hz, 1H), 6.82-6.97 (m, 7H), 4.90 (t, J=6.71 Hz, 2H), 4.05 (d, J=6.71 Hz, 2H), 3.71-3.73 (m, 4H), 2.97-2.99 (m, 4H), 2.88 (t, J=6.56 Hz, 2H), 1.43-1.65 (m, 7H).

EXAMPLE 738

3-[1-(2-Imidazol-1-yl-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 738A

3-Bromo-1-(2-imidazol-1-yl-ethyl)-1H-pyrrolo[2,3-c]pyridine

The desired product was prepared by substituting 2-imidazol-1-yl-ethanol for 2-(2,2-dimethyl-[1,3]dioxolan-4-yl)-ethanol in Example 715A. MS (ESI) m/e 291 (M+H)$^+$, $^1$H NMR (300 MHz, DMSO-d$_6$): □ 8.77 (s, 1H), 8.20 (d, J=5.43 Hz, 1H), 7.61 (s, 1H), 7.36 (dd, J=5.43, 1.02 Hz, 1H), 7.33 (m, 1H), 7.05 (m, 1H), 6.79 (m, 1H), 4.67 (t, J=6.10 Hz, 2H), 4.43 (t, J=5.93 Hz, 2H).

EXAMPLE 738B

3-[1-(2-Imidazol-1-yl-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 738A for Example 696A in Example 696B. MS (ESI) m/e 626 (M+H)$^+$, $^1$H NMR (500 MHz, DMSO-d$_6$): ☐ 9.83 (s, 1H), 9.48 (s, 1H), 8.83 (s, 1H), 8.55 (d, J=6.41 Hz, 1H), 8.40 (s, 1H), 8.38 (d, J=6.41 Hz, 1H), 8.00 (s, 1H), 7.79 (d, J=8.24 Hz, 1H), 7.61 (s, 1H), 7.56 (s, 1H), 7.42 (d, J=1.22 Hz, 1H), 7.12 (dd, J=8.09, 1.68 Hz, 1H), 6.82-6.95 (m, 7H), 4.99 (t, J=5.64 Hz, 2H), 4.77 (t, J=5.64 Hz, 2H), 4.05 (t, J=6.71 Hz, 2H), 3.71-3.73 (m, 4H), 2.97-2.99 (m, 4H), 2.87 (t, J=6.56 Hz, 2H).

EXAMPLE 739

3-[1-(4-Chloro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 739A

3-Bromo-1-(4-chloro-benzyl)-1H-pyrrolo[2,3-c]pyridine

The desired product was prepared by substituting 4-chlorobenzyl bromide for benzyl bromide in Example 696A. MS (ESI) m/e 321 (M+H)$^+$, $^1$H NMR (300 MHz, DMSO-d$_6$): ☐ 8.93 (s, 1H), 8.23 (d, J=5.43 Hz, 1H), 8.03 (s, 1H), 7.38-7.42 (m, 3H), 7.32-7.35 (m, 2H), 5.55 (s, 2H).

EXAMPLE 739B

3-[1-(4-Chloro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 739A for Example 696A in Example 696B. MS (ESI) m/e 656 (M+H)$^+$, $^1$H NMR (500 MHz, DMSO-d$_6$): ☐ 9.82 (s, 1H), 9.52 (s, 1H), 8.85 (s, 1H), 8.50 (d, J=6.71 Hz, 1H), 8.39 (d, J=6.41 Hz, 1H), 7.98 (s, 1H), 7.80 (d, J=8.24 Hz, 1H), 7.45 (s, 4H), 7.43 (d, J=1.22 Hz, 1H), 7.27 (dd, J=8.24, 1.53 Hz, 1H), 6.82-6.95 (m, 7H), 5.76 (s, 2H), 4.04 (t, J=6.71 Hz, 2H), 3.70-3.72 (m, 4H), 2.96-2.98 (m, 4H), 2.87 (t, J=6.56 Hz, 2H).

EXAMPLE 740

8-[2-(4-Morpholin-4-yl-phenoxy)-ethyl]-3-{1-[2-(2-oxo-pyrrolidin-1-yl)-ethyl]-1H-pyrrolo[2,3-c]pyridin-3-yl}-5,10-dihydro-dibenzo[b,e][1,4]diazepin-11-one

EXAMPLE 740A

1-[2-(3-Bromo-pyrrolo[2,3-c]pyridin-1-yl)-ethyl]-pyrrolidin-2-one

The title compound was prepared by substituting 1-(2-hydroxy-ethyl)-pyrrolidin-2-one for 3-(2,2-dimethyl-[1,3]dioxolan-4-yl)-propan-1-ol in Example 715A. MS (DCI) m/e 309 (M+H)$^+$, $^1$H NMR (500 MHz, DMSO-d$_6$): ☐ 8.92 (s, 1H), 8.23 (d, J=5.49 Hz, 1H), 7.84 (s, 1H), 7.39 (d, J=5.49 Hz, 1H), 4.44 (d, J=5.95 Hz, 2H), 3.58 (d, J=5.95 Hz, 2H), 3.14 (d, J=7.02 Hz, 2H), 2.05 (d, J=8.09 Hz, 2H), 1.73-1.77 (m, 2H).

EXAMPLE 740B

8-[2-(4-Morpholin-4-yl-phenoxy)-ethyl]-3-{1-[2-(2-oxo-pyrrolidin-1-yl)-ethyl]-1H-pyrrolo[2,3-c]pyridin-3-yl}-5,10-dihydro-dibenzo[b,e][1,4]diazepin-11-one The title compound was prepared by substituting Example 740A for Example 696A in Example 696B. MS (APCI) m/e 643 (M+H)$^+$, $^1$H NMR (500 MHz, DMSO-d$_6$): ☐ 9.79 (s, 1H), 9.54 (s, 1H), 8.71 (s, 1H), 8.50 (d, J=6.75 Hz, 1H), 8.39 (d, J=6.44 Hz, 1H), 7.99 (s, 1H), 7.81 (d, J=8.29 Hz, 1H), 7.44 (d, J=1.23 Hz, 1H), 7.23 (dd, J=8.29, 1.53 Hz, 1H), 6.83-6.97 (m, 7H), 4.66 (t, J=5.68 Hz, 2H), 4.05 (d, J=6.75 Hz, 2H), 3.68-3.73 (m, 6H), 3.36 (d, J=6.9 Hz, 2H), 2.98-3.00 (m, 4H), 2.88 (t, J=6.6 Hz, 2H), 2.01 (t, J=7.83 Hz, 2H), 1.82-1.88 (m, 2H).

EXAMPLE 741

3-{2-[3-(1-Benzyl-1H-pyrrolo[2,3-c]pyridin-3-yl)-11-oxo-10,11-dihydro-5H-dibenzo[b,e][1,4]diazepin-8-yl]-ethoxy}-pyridine-2-carbonitrile

EXAMPLE 741A

3-[2-(3-Chloro-11-oxo-10,11-dihydro-5H-dibenzo[b,e][1,4]diazepin-8-yl)-ethoxy]-pyridine-2-carbonitrile The title compound was prepared by substituting 3-hydroxy-pyridine-2-carbonitrile for 4-morpholinophenol in Example 695F. MS (DCI) m/e 391 (M+H)$^+$, $^1$H NMR (500 MHz, DMSO-d$_6$): ☐ 9.83 (s, 1H), 8.28 (d, J=3.99 Hz, 1H), 8.00 (s, 1H), 7.78 (d, J=8.29 Hz, 1H), 7.65-7.69 (m, 2H), 7.06 (d, J=1.84 Hz, 1H), 6.91-6.98 (m, 4H), 4.33 (d, J=6.75 Hz, 2H), 2.97 (d, J=6.75 Hz, 2H).

EXAMPLE 741B

3-{2-[11-Oxo-3-(4,4,5,5-tetramethyl-[1,3,2]dioxaborolan-2-yl)-10,11-dihydro-5H-dibenzo[b,e][1,4]diazepin-8-yl]-ethoxy}-pyridine-2-carbonitrile The title compound was prepared by substituting Example 741A for Example 695F in Example 695G. MS (DCI) m/e 483 (M+H)$^+$.

EXAMPLE 741C

3-{2-[3-(1-Benzyl-1H-pyrrolo[2,3-c]pyridin-3-yl)-11-oxo-10,11-dihydro-5H-dibenzo[b,e][1,4]diazepin-8-yl]-ethoxy}-pyridine-2-carbonitrile The title compound was prepared by substituting Example 741B for Example 695G in Example 696B. MS (APCI) m/e 563 (M+H)$^+$, $^1$H NMR (500 MHz, DMSO-d$_6$): ☐ 9.77 (s, 1H), 9.52 (s, 1H), 8.84 (s, 1H), 8.49 (d, J=6.14 Hz, 1H), 8.38 (d, J=6.14 Hz, 1H), 8.28 (d, J=3.99 Hz, 1H), 8.01 (s, 1H), 7.78-7.82 (m, 2H), 7.67 (dd, J=8.59, 4.3 Hz, 1H), 7.27-7.45 (m, 7H), 6.95-6.97 (m, 3H), 5.77 (s, 2H), 4.35 (t, J=6.14 Hz, 2H), 2.98 (t, J=6.14 Hz, 2H).

EXAMPLE 742

8-[2-(4-Morpholin-4-yl-phenoxy)-ethyl]-3-[1-(3-phenyl-propyl)-1H-pyrrolo[2,3-c]pyridin-3-yl]-5,10-dihydro-dibenzo[b,e][1,4]diazepin-11-one

EXAMPLE 742A

3-Bromo-1-(3-phenyl-propyl)-1H-pyrrolo[2,3-c]pyridine

The desired product was prepared by substituting 3-phenyl-propan-1-ol for 2-(2,2-dimethyl-[1,3]dioxolan-4-yl)-ethanol in Example 715A. MS (ESI) m/e 316 (M+H)$^+$, $^1$H NMR (300 MHz, DMSO-d$_6$): ☐ 8.90 (s, 1H), 8.23 (d, J=5.43 Hz, 1H), 7.90 (s, 1H), 7.40 (dd, J=5.43, 1.02 Hz, 1H), 7.25-7.29 (m, 2H), 7.16-7.19 (m, 3H), 4.34 (t, J=7.12 Hz, 2H), 2.55-2.60 (m, 2H), 2.08-2.18 (m, 2H).

EXAMPLE 742B

8-[2-(4-Morpholin-4-yl-phenoxy)-ethyl]-3-[1-(3-phenyl-propyl)-1H-pyrrolo[2,3-c]pyridin-3-yl]-5,10-dihydro-dibenzo[b,e][1,4]diazepin-11-one The desired product was prepared by substituting Example 742A for Example 696A in Example 696B. MS (ESI) m/e 650 (M+H)$^+$, $^1$H NMR (500 MHz, DMSO-d$_6$): ☐ 9.82 (s, 1H), 9.51 (s, 1H), 8.80 (s, 1H), 8.48 (d, J=6.71 Hz, 1H), 8.37 (d, J=6.71 Hz, 1H), 7.99 (s, 1H), 7.80 (d, J=8.24 Hz, 1H), 7.45 (d, J=1.53 Hz, 1H), 7.15-7.28 (m, 6H), 6.83-6.96 (m, 7H), 4.56 (t, J=7.02 Hz, 2H), 4.05 (t, J=6.71 Hz, 2H), 3.71-3.73 (m, 4H), 2.97-2.99 (m, 4H), 2.87 (t, J=6.71 Hz, 2H), 2.65-2.68 (m, 2H), 2.25-2.29 (m, 2H).

EXAMPLE 743

3-(1-But-2-ynyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 743A

3-Bromo-1-but-2-ynyl-1H-pyrrolo[2,3-c]pyridine

The desired product was prepared by substituting but-1-yn-1-ol for 2-(2,2-dimethyl-[1,3]dioxolan-4-yl)-ethanol in Example 715A. MS (ESI) m/e 249 (M+H)$^+$, $^1$H NMR (300 MHz, DMSO-d$_6$): ☐ 8.95 (d, J=1.02 Hz, 1H), 8.27 (d, J=5.42 Hz, 1H), 7.87 (s, 1H), 7.43 (dd, J=5.42, 1.02 Hz, 1H), 5.18 (q, J=2.37 Hz, 2H), 1.81 (t, J=2.54 Hz, 3H).

EXAMPLE 743B 3-(1-But-2-ynyl-1H-pyrrolo[2,3-c]pyridin-3-yl)-8-[2-(4-morpholin-4-yl-phenoxy)-ethyl]-5,10-dihydro-dibenzo[b,e][1,4]diazepin-11-one The desired product was prepared by substituting Example 743A for Example 696A in Example 696B. MS (ESI) m/e 584 (M+H)$^+$, $^1$H NMR (500 MHz, DMSO-d$_6$): ☐ 9.82 (s, 1H), 9.47 (s, 1H), 8.72 (s, 1H), 8.52 (d, J=6.41 Hz, 1H), 8.38 (d, J=6.41 Hz, 1H), 7.99 (s, 1H), 7.81 (d, J=8.24 Hz, 1H), 7.44 (d, J=1.53 Hz, 1H), 7.27 (dd, J=8.24, 1.53 Hz, 1H), 6.82-6.95 (m, 7H), 5.40 (d, J=2.44 Hz, 2H), 4.04 (t, J=6.71 Hz, 2H), 3.70-3.72 (m, 4H), 2.96-2.98 (m, 4H), 2.87 (t, J=6.56 Hz, 2H), 1.86 (t, J=2.44 Hz, 3H).

EXAMPLE 744

3-(1-Benzyl-1H-pyrrolo[2,3-c]pyridin-3-yl)-5,10-dihydro-dibenzo[b,e][1,4]diazepin-11-one The title compound was prepared by substituting Example 719C for Example 695G in Example 696B. MS (APCI) m/e 417 (M+H)$^+$, $^1$H NMR (500 MHz, DMSO-d$_6$): ☐ 9.83 (s, 1H), 9.52 (s, 1H), 8.85 (s, 1H), 8.49 (d, J=6.44 Hz, 1H), 8.39 (d, J=6.44 Hz, 1H), 8.04 (s, 1H), 7.82 (d, J=8.29 Hz, 1H), 7.27-7.45 (m, 7H), 6.90-7.03 (m, 4H), 5.77 (s, 2H).

EXAMPLE 745

8-[2-(4-Morpholin-4-yl-phenoxy)-ethyl]-3-[1-(2-phenoxy-ethyl)-1H-pyrrolo[2,3-c]pyridin-3-yl]-5,10-dihydro-dibenzo[b,e][1,4]diazepin-11-one

EXAMPLE 745A

3-Bromo-1-(2-phenoxy-ethyl)-1H-pyrrolo[2,3-c]pyridine

The title compound was prepared by substituting 2-phenoxy-ethanol for 3-(2,2-dimethyl-[1,3]dioxolan-4-yl)-propan-1-ol in Example 715A. MS (DCI) m/e 318 (M+H)$^+$, $^1$H NMR (500 MHz, DMSO-d$_6$): ☐ 9.01 (s, 1H), 8.23 (d, J=5.52 Hz, 1H), 7.90 (s, 1H), 7.40 (m, 1H), 7.23-7.27 (m, 2H), 6.85-6.93 (m, 3H), 4.71 (d, J=5.22 Hz, 2H), 4.34 (d, J=5.06 Hz, 2H).

EXAMPLE 745B

8-[2-(4-Morpholin-4-yl-phenoxy)-ethyl]-3-[1-(2-phenoxy-ethyl)-1H-pyrrolo[2,3-c]pyridin-3-yl]-5,10-dihydro-dibenzo[b,e][1,4]diazepin-11-one The title compound was prepared by substituting Example 745A for Example 696A in Example 696B. MS (APCI) m/e 652 (M+H)$^+$, $^1$H NMR (500 MHz, DMSO-d$_6$): ☐ 9.79 (s, 1H), 9.56 (s, 1H), 8.80 (s, 1H), 8.50 (d, J=6.44 Hz, 1H), 8.37 (d, J=6.44 Hz, 1H), 7.99 (s, 1H), 7.81 (d, J=8.29 Hz, 1H), 7.45 (d, J=1.23 Hz, 1H), 7.23-7.27 (m, 3H), 6.83-6.96 (m, 10H), 4.95 (t, J=5.06 Hz, 2H), 4.45 (d, J=4.91 Hz, 2H), 4.05 (d, J=6.6 Hz, 2H), 3.71-3.73 (m, 4H), 2.98-3.00 (m, 4H), 2.87 (t, J=6.6 Hz, 2H).

EXAMPLE 746

3-[1-(2-Phenoxy-ethyl)-1H-pyrrolo[2,3-c]pyridin-3-yl]-5,10-dihydro-dibenzo[b,e][1,4]diazepin-11-one The title compound was prepared by substituting Example 745A and Example 719C for Example 696A and Example 695G, respectively, in Example 696B. MS (APCI) m/e 447 (M+H)$^+$, $^1$H NMR (500 MHz, DMSO-d$_6$): ☐ 9.73 (s, 1H), 9.05 (s, 1H), 8.29 (d, J=5.52 Hz, 1H), 8.15 (s, 1H), 7.98 (s, 1H), 7.95 (d, J=5.52 Hz, 1H), 7.75 (d, J=8.29 Hz, 1H), 7.46 (s, 1H), 7.22-7.27 (m, 3H), 6.88-7.04 (m, 7H), 4.76 (t, J=5.06 Hz, 2H), 4.40 (t, J=5.06 Hz, 2H).

EXAMPLE 747

3-(1-Benzyl-1H-pyrrolo[2,3-c]pyridin-3-yl)-8-(2-hydroxy-1,1-dimethyl-ethyl)-5,10-dihydro-dibenzo[b,e][1,4]diazepin-11-one

EXAMPLE 747A methyl 2-methyl-2-(4-nitrophenyl)propanoate

A solution of 4-nitrophenylacetic acid (60.0 g, 0.33 mol), iodomethane (130.0 mL, 296.4 g, 2.10 mol), and 18-crown-6 (15 g, 0.057 mol) in DMF (1.0 L) was cooled to 0° C., then 95% NaH (30.0 g, 1.19 mol) was added in portions, keeping $T_{rxn}$<25° C. The reaction was allowed to warm to room temperature overnight, then partitioned between water (2 L) and $Et_2O$ (400 mL). The aqueous layer was extracted with $Et_2O$ (2×300 mL), then the combined organic layers were washed with brine and dried over $Na_2SO_4$. After filtration and concentration, recovered 74 g (99%) product as an orange oil. MS (DCI) m/e 241 $(M+NH_4)^+$; $^1$H NMR (300 MHz, $CDCl_3$) δ 8.19 (m, 2H), 7.50 (m, 2H), 3.67 (s, 3H), 1.62 (s, 6H).

EXAMPLE 747B methyl 2-(4-aminophenyl)-2-methylpropanoate

Dissolved the compound described in Example 747A (59.4 g, 0.27 mol) in MeOH (600 mL), then added $SnCl_2.2H_2O$ (120.0 g, 0.53 mol) and concentrated HCl (300 mL). The reaction was allowed to stir at room temperature overnight, then more $SnCl_2.2H_2O$ (49.0 g, 0.22 mol) and concentrated HCl (100 mL) were added, and the reaction heated to 50° C. for 4 hours. After cooling the reaction was partitioned between pH=14 water and EtOAc. The aqueous layer was again extracted with EtOAc, then the combined organic layers were dried ($Na_2SO_4$). The residue was purified by column chromatography using 4/1, then 1/1 hexanes/EtOAc to give 38.0 g (74%) product. MS (DCI) m/e 194 $(M+H)^+$, 211 $(M+NH_4)^+$; $^1$H NMR (300 MHz, $CDCl_3$) δ 7.13 (m, 2H), 6.64 (m, 2H), 3.62 (s, 3H), 1.55 (s, 6H).

EXAMPLE 747C methyl 2-(4-amino-3-nitrophenyl)-2-methylpropanoate

Example 747B (38.0 g, 0.20 mol) was treated with acetic anhydride to give the acetamide, then nitrated, hydrolyzed, and subjected to a Fischer esterification by the method described in Example 695A to give the title compound (43.2 g, 0.18 mol, 90% overall). MS (DCI) m/e 239 $(M+H)^+$, 256 $(M+NH_4)^+$; $^1$H NMR (300 MHz, $CDCl_3$) δ 8.12 (d, J=2.4 Hz, 1H), 7.37 (dd, J=8.8, 2.4 Hz, 1H), 6.78 (d, J=8.8 Hz, 1H), 6.05 (br s, 2H), 3.66 (s, 3H), 1.57 (s, 6H).

EXAMPLE 747D methyl 4-chloro-2-{[4-(2-methoxy-1,1-dimethyl-2-oxoethyl)-2-nitrophenyl]amino}benzoate The title compound was prepared by substituting Example 747C for Example 695A in Example 695B. MS (DCI) m/e 407 and 409 $(M+H)^+$, 424 and 426 $(M+NH_4)^+$; $^1$H NMR (300 MHz, DMSO-$d_6$) δ 10.84 (s, 1H), 8.03 (d, J=2.0 Hz, 1H), 7.97 (d, J=8.5 Hz, 1H), 7.66 (m, 2H), 7.50 (d, J=2.0 Hz, 1H), 7.14 (dd, J=8.5, 2.0 Hz, 1H), 3.89 (s, 3H), 3.63 (s, 3H), 1.55 (s, 6H).

EXAMPLE 747E methyl 2-{[2-amino-4-(2-methoxy-1,1-dimethyl-2-oxoethyl)phenyl]amino}-4-chlorobenzoate The title compound was prepared by substituting Example 747D for Example 695B in Example 695C. MS (DCI) m/e 377 and 379 $(M+H)^+$; $^1$H NMR (300 MHz, DMSO-$d_6$) δ 8.82 (s, 1H), 7.85 (d, J=8.5 Hz, 1H), 6.98 (d, J=8.1 Hz, 1H), 6.78 (d, J=2.0 Hz, 1H), 6.70 (dd, J=8.5, 2.0 Hz, 1H), 6.55 (dd, J=8.1, 2.0 Hz, 1H), 6.42 (d, J=2.0 Hz, 1H), 5.01 (br s, 2H), 3.85 (s, 3H), 3.61 (s, 3H), 1.48 (s, 6H).

EXAMPLE 747F methyl 2-(3-chloro-11-oxo-10,11-dihydro-5H-dibenzo[b,e][1,4]diazepin-8-yl)-2-methylpropanoate The title compound was prepared by substituting Example 747E for Example 695C in Example 695D. MS (DCI) m/e 345 and 347 $(M+H)^+$; $^1$H NMR (300 MHz, DMSO-$d_6$) δ 9.84 (s, 1H), 8.06 (s, 1H), 7.68 (d, J=8.5 Hz, 1H), 7.06 (d, J=2.0 Hz, 1H), 6.93 (m, 4H), 3.58 (s, 3H), 1.43 (s, 6H).

EXAMPLE 747G 3-chloro-8-(2-hydroxy-1,1-dimethylethyl)-5,10-dihydro-11H-dibenzo[b,e][1,4]diazepin-11-one The title compound was prepared by substituting Example 747F for Example 695D in Example 695E. MS (DCI) m/e 317 and 319 $(M+H)^+$; $^1$H NMR (300 MHz, DMSO-$d_6$) δ 9.77 (s, 1H), 7.97 (s, 1H), 7.67 (d, J=8.5 Hz, 1H), 7.05 (d, J=2.0 Hz, 1H), 6.88-6.99 (m, 4H), 4.61 (t, J=5.1 Hz, 1H), 3.32 (m, 2H), 1.15 (s, 6H).

EXAMPLE 747H 8-(2-Hydroxy-11-dimethyl-ethyl)-3-(4,4,5,5-tetramethyl-[1,3,2]dioxaborolan-2-yl)-5,10-dihydro-dibenzo[b,e][1,4]diazepin-11-one The title product was prepared by substituting Example 747G for Example 695F in Example 695G. MS (DCI) m/e 409 $(M+H)^+$; $^1$H NMR (300 MHz, DMSO-$d_6$) δ 9.74 (s, 1H), 7.74 (s, 1H), 7.65 (d, J=7.5 Hz, 1H), 7.37 (s, 1H), 7.12 (dd, J=7.5, 1.0 Hz, 1H), 6.97 (m, 1H), 6.92 (m, 2H), 4.69 (t, J=5.1 Hz, 1H), 3.32 (m, 2H), 1.29 (s, 12H), 1.14 (s, 6H).

EXAMPLE 747I 3-(1-Benzyl-1H-pyrrolo[2,3-c]pyridin-3-yl)-8-(2-hydroxy-11-dimethyl-ethyl)-5,10-dihydro-dibenzo[b,e][1,4]diazepin-11-one The title compound was prepared by substituting Example 747H for Example 695G in Example 696B, except here the purification was done by column chromatography using EtOAc, then 95/5 EtOAc/EtOH, followed by conversion to the hydrochloride salt. MS (ESI) m/e 489 $(M+H)^+$; $^1$H NMR (300 MHz, DMSO-$d_6$) δ 9.71 (s, 1H), 9.67 (s, 1H), 8.89 (s, 1H), 8.49 (d, J=6.4 Hz, 1H), 8.42 (d, J=6.4 Hz, 1H), 8.02 (s, 1H), 7.80 (d, J=8.1 Hz, 1H), 7.48 (s, 1H), 7.46-7.32 (m, 6H), 7.26 (d, J=8.1 Hz, 1H), 7.01 (s, 1H), 6.95 (m, 2H), 5.78 (s, 2H), 3.33 (m, 2H), 1.16 (s, 6H).

EXAMPLE 748

2-Methoxy-4-(3-{8-[2-(4-morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile

EXAMPLE 748A 4-(3-Bromo-pyrrolo[2,3-c]pyridin-1-ylmethyl)-2-methoxy-benzonitrile The desired product was prepared by substituting 4-bromomethyl-2-methoxy-benzonitrile for benzyl bromide in Example 696A. MS (ESI) m/e 342 (M+H)$^+$, $^1$H NMR (500 MHz, DMSO-d$_6$): □ 8.96 (s, 1H), 8.25 (d, J=5.76 Hz, 1H), 8.05 (s, 1H), 7.66 (d, J=8.14 Hz, 1H), 7.43 (d, J=5.43 Hz, 1H), 7.37 (d, J=1.02 Hz, 1H), 6.82 (dd, J=8.14, 1.36 Hz, 1H), 5.61 (s, 2H), 3.91 (s, 3H).

EXAMPLE 748B

2-Methoxy-4-(3-{8-[2-(4-morpholin-4-yl-phenoxy)-ethyl]-11-oxo-10,11-dihydro-5H-dibenzo[b,e][1,4]diazepin-3-yl}-pyrrolo[2,3-c]pyridin-1-ylmethyl)-benzonitrile The desired product was prepared by substituting Example 748A for Example 696A in Example 696B. MS (ESI) m/e 677 (M+H)$^+$, $^1$H NMR (500 MHz, DMSO-d$_6$): □ 9.79 (s, 1H), 9.52 (s, 1H), 8.85 (s, 1H), 8.50 (d, J=6.44 Hz, 1H), 8.38 (d, J=6.44 Hz, 1H), 7.97 (s, 1H), 7.81 (d, J=8.29 Hz, 1H), 7.71 (d, J=7.98 Hz, 1H), 7.44 (s, 2H), 7.27 (dd, J=8.29, 1.53 Hz, 1H), 6.82-6.98 (m, 8H), 5.81 (s, 2H), 4.05 (t, J=6.75 Hz, 2H), 3.94 (s, 3H), 3.70-3.72 (m, 4H), 2.97-2.99 (m, 4H), 2.87 (t, J=6.60 Hz, 2H).

EXAMPLE 749

8-[2-(4-Morpholin-4-yl-phenoxy)-ethyl]-3-(1-pyridin-2-yl-1H-pyrrolo[2,3-c]pyridin-3-yl)-5,10-dihydro-dibenzo[b,e][1,4]diazepin-11-one

EXAMPLE 749A

3-Bromo-1-pyridin-2-yl-1H-pyrrolo[2,3-c]pyridine

The title compound was prepared by substituting 2-fluoropyridine for benzyl bromide in Example 696A, except here the reaction was done at 90° C. for 3 days. MS (DCI) m/e 274 & 276 (M+H)$^+$, $^1$H NMR (300 MHz, DMSO-d$_6$): □ 9.80 (d, J=1.0 Hz, 1H), 8.63 (m, 1H), 8.62 (s, 1H), 8.41 (d, J=5.4 Hz, 1H), 8.05 (m, 1H), 7.90 (m, 1H), 7.55 (dd, J=5.4, 1.0 Hz, 1H), 7.40 (m, 1H).

EXAMPLE 749B

8-[2-(4-Morpholin-4-yl-phenoxy)-ethyl]-3-(1-pyridin-2-yl-1H-pyrrolo[2,3-c]pyridin-3-yl)-5,10-dihydro-dibenzo[b,e][1,4]diazepin-11-one The title compound was prepared by substituting Example 749A for Example 696A in Example 696B, except here the purification was done by column chromatography using EtOAc, then 95/5 EtOAc/EtOH, followed by conversion to the hydrochloride salt. MS (ESI) m/e 609 (M+H)$^+$; $^1$H NMR (400 MHz, DMSO-d$_6$) δ 10.07 (s, 1H), 9.83 (s, 1H), 9.40 (s, 1H), 8.72 (d, J=7.5 Hz, 1H), 8.66 (d, J=6.4 Hz, 1H), 8.58 (d, J=6.4 Hz, 1H), 8.20 (m, 3H), 7.85 (d, J=8.3 Hz, 1H), 7.65 (s, 1H), 7.55 (m, 1H), 7.42 (d, J=8.3 Hz, 1H), 7.03 (m, 4H), 6.95 (m, 3H), 4.14 (t, J=6.4 Hz, 2H), 3.96 (br m, 4H), 3.35 (br m, 4H), 2.91 (t, J=6.4 Hz, 2H).

EXAMPLE 750

4-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-benzonitrile

EXAMPLE 750A 4-(3-Bromo-pyrrolo[2,3-c]pyridin-1-yl)-benzonitrile

The title compound was prepared by substituting 4-fluorobenzonitrile for benzyl bromide in Example 696A, except here the reaction was done at 90° C. for 1 hour. MS (DCI) m/e 298 & 300 (M+H)$^+$, $^1$H NMR (300 MHz, DMSO-d$_6$): □ 9.04 (d, J=1.0 Hz, 1H), 8.42 (d, J=5.4 Hz, 1H), 8.35 (s, 1H), 8.09 (m, 2H), 7.96 (m, 2H), 7.57 (dd, J=5.4, 1.0 Hz, 1H).

EXAMPLE 750B 4-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-benzonitrile The title compound was prepared by substituting Example 750A for Example 696A in Example 696B, except here the purification was done by column chromatography using EtOAc, then 95/5 EtOAc/EtOH, followed by conversion to the hydrochloride salt. MS (ESI) m/e 633 (M+H)$^+$; $^1$H NMR (400 MHz, DMSO-d$_6$) δ 9.82 (s, 1H), 9.40 (s, 1H), 9.07 (s, 1H), 8.61 (d, J=6.4 Hz, 1H), 8.56 (d, J=6.4 Hz, 1H), 8.21 (d, J=8.6 Hz, 2H), 8.17 (s, 1H), 8.12 (d, J=8.6 Hz, 2H), 7.83 (d, J=8.3 Hz, 1H), 7.63 (s, 1H), 7.38 (d, J=8.3 Hz, 1H), 7.02 (d, J=8.0 Hz, 1H), 6.94 (m, 6H), 4.11 (t, J=6.4 Hz, 2H), 3.87 (br m, 4H), 3.22 (br m, 4H), 2.90 (t, J=6.4 Hz, 2H).

EXAMPLE 751

3-{1-[2-(4-Fluoro-phenyl)-ethyl]-1H-pyrrolo[2,3-c]pyridin-3-yl}-8-[2-(4-morpholin-4-yl-phenoxy)-ethyl]-5,10-dihydro-dibenzo[b,e][1,4]diazepin-11-one

EXAMPLE 751A

3-Bromo-1-[2-(4-fluoro-phenyl)-ethyl]-1H-pyrrolo[2,3-c]pyridine

The desired product was prepared by substituting 2-(4-fluoro-phenyl)-ethanol for 2-(2,2-dimethyl-[1,3]dioxolan-4-yl)-ethanol in Example 715A. MS (ESI) m/e 319 (M+H)$^+$, $^1$H NMR (500 MHz, DMSO-d$_6$): □ 8.86 (s, 1H), 8.19 (d, J=5.76 Hz, 1H), 7.79 (s, 1H), 7.36 (d, J=5.43 Hz, 1H), 7.21 (dd, J=8.65, 5.60 Hz, 2H), 7.06 (t, J=8.82 Hz, 2H), 4.53 (t, J=7.29 Hz, 2H), 3.11 (t, J=7.12 Hz, 2H).

EXAMPLE 751B

3-{1-[2-(4-Fluoro-phenyl)-ethyl]-1H-pyrrolo[2,3-c]pyridin-3-yl}-8-[2-(4-morpholin-4-yl-phenoxy)-ethyl]-5,10-dihydro-dibenzo[b,e][1,4]diazepin-11-one The desired product was prepared by substituting Example 751A for Example 696A in Example 696B. MS (ESI) m/e 654 (M+H)$^+$, $^1$H NMR (500 MHz, DMSO-d$_6$): □ 9.79 (s, 1H), 9.39 (s, 1H), 8.71 (s, 1H), 8.45 (d, J=6.75 Hz, 1H), 8.35 (d, J=6.75 Hz, 1H), 7.97 (s, 1H), 7.80 (d, J=8.29 Hz, 1H), 7.43 (d, J=1.53 Hz, 2H), 7.20-7.26 (m, 3H), 7.07 (t, J=8.90 Hz, 2H), 6.82-6.96 (m, 7H), 4.75 (t, J=7.21 Hz, 2H), 4.05 (t, J=6.75 Hz, 2H), 3.71-3.73 (m, 4H), 3.22 (t, J=7.21 Hz, 2H), 2.97-2.99 (m, 4H), 2.87 (t, J=6.75 Hz, 2H).

EXAMPLE 752

8-[2-(4-Morpholin-4-yl-phenoxy)-ethyl]-3-[1-(2-thiophen-2-yl-ethyl)-1H-pyrrolo[2,3-c]pyridin-3-yl]-5,10-dihydro-dibenzo[b,e][1,4]diazepin-11-one

EXAMPLE 752A

3-Bromo-1-(2-thiophen-2-yl-ethyl)-1H-pyrrolo[2,3-c]pyridine

The desired product was prepared by substituting 2-thiophen-2-yl-ethanol for 2-(2,2-dimethyl-[1,3]dioxolan-4-yl)-ethanol in Example 715A. MS (ESI) m/e 307 (M+H)$^+$, $^1$H NMR (500 MHz, DMSO-d$_6$): □ 8.87 (s, 1H), 8.19 (d, J=5.43 Hz, 1H), 7.81 (s, 1H), 7.37 (d, J=5.43 Hz, 1H), 7.29 (dd, J=5.09, 1.02 Hz, 2H), 6.89 (m, 1H), 6.83 (m, 1H), 4.56 (t, J=6.95 Hz, 2H), 3.36 (t, J=7.12 Hz, 2H).

EXAMPLE 752B

8-[2-(4-Morpholin-4-yl-phenoxy)-ethyl]-3-[1-(2-thiophen-2-yl-ethyl)-1H-pyrrolo[2,3-c]pyridin-3-yl]-5,10-dihydro-dibenzo[b,e][1,4]diazepin-11-one The desired product was prepared by substituting Example 752A for Example 696A in Example 696B. MS (ESI) m/e 642 (M+H)$^+$, $^1$H NMR (400 MHz, DMSO-d$_6$): □ 9.79 (s, 1H), 9.42 (s, 1H), 8.70 (s, 1H), 8.45 (d, J=6.44 Hz, 1H), 8.36 (d, J=6.44 Hz, 1H), 7.97 (s, 1H), 7.80 (d, J=8.29 Hz, 1H), 7.43 (d, J=1.53 Hz, 1H), 7.30 (dd, J=5.06, 1.07 Hz, 1H), 7.21 (dd, J=7.98, 1.53 Hz, 1H), 6.82-6.96 (m, 9H), 4.78 (t, J=6.90 Hz, 2H), 4.05 (t, J=6.60 Hz, 2H), 3.71-3.73 (m, 4H), 3.46-3.49 (m, 2H), 2.97-2.99 (m, 4H), 2.87 (t, J=6.75 Hz, 2H).

EXAMPLE 753

4-[2-(3-{8-[2-(2-Methyl-pyridin-3-yloxy)-ethyl]-11-oxo-10,11-dihydro-5H-dibenzo[b,e][1,4]diazepin-3-yl}-pyrrolo[2,3-c]pyridin-1-yl)-ethyl]-benzonitrile The desired product was prepared by substituting Example 730A for Example 696A in Example 696B. MS (ESI) m/e 591 (M+H)$^+$, $^1$H NMR (400 MHz, DMSO-d$_6$): □ 9.82 (s, 1H), 9.42 (s, 1H), 8.69 (s, 1H), 8.46 (d, J=6.44 Hz, 1H), 8.35 (d, J=6.44 Hz, 1H), 8.12 (d, J=4.60 Hz, 1H), 7.99 (s, 1H), 7.81 (d, J=8.29 Hz, 1H), 7.74 (d, J=8.29 Hz, 2H), 7.62 (d, J=7.98 Hz, 1H), 7.43 (m, 4H), 7.20 (dd, J=8.29, 1.53 Hz, 1H), 6.94-6.96 (m, 3H), 4.80 (t, J=7.21 Hz, 2H), 4.23 (t, J=6.44 Hz, 2H), 3.32-3.35 (m, 2H), 2.97 (t, J=6.44 Hz, 2H), 2.40 (s, 3H).

EXAMPLE 754

3-[2-(3-{1-[2-(4-Cyano-phenyl)-ethyl]-1H-pyrrolo[2,3-c]pyridin-3-yl}-11-oxo-10,11-dihydro-5H-dibenzo[b,e][1,4]diazepin-8-yl)-ethoxy]pyridine-2-carbonitrile The desired product was prepared by substituting Example 730A and Example 736B for Example 696A and Example 695G, respectively, in Example 696B. MS (ESI) m/e 602 (M+H)$^+$, $^1$H NMR (400 MHz, DMSO-d$_6$): □ 9.77 (s, 1H), 9.40 (s, 1H), 8.68 (s, 1H), 8.45 (d, J=6.44 Hz, 1H), 8.34 (d, J=6.44 Hz, 1H), 8.28 (d, J=4.30 Hz, 1H), 7.98 (s, 1H), 7.78-7.82 (m, 2H), 7.74 (d, J=8.29 Hz, 2H), 7.68 (dd, J=8.75, 4.45 Hz, 1H), 7.45 (d, J=8.29 Hz, 2H), 7.42 (d, J=1.23 Hz, 1H), 7.20 (dd, J=8.29, 1.23 Hz, 1H), 6.94-6.98 (m, 3H), 4.79 (t, J=7.21 Hz, 2H), 4.35 (t, J=6.60 Hz, 2H), 3.32-3.35 (m, 2H), 2.98 (t, J=6.44 Hz, 2H).

EXAMPLE 755

3-[1-(Tetrahydro-furan-3-yl)-1H-pyrrolo[2,3-c]pyridin-3-yl]-5,10-dihydro-dibenzo[b,e][1,4]diazepin-11-one

EXAMPLE 755A

3-Bromo-1-(tetrahydro-furan-3-yl)-1H-pyrrolo[2,3-c]pyridine

The title compound was prepared by substituting tetrahydro-furan-3-ol for 3-(2,2-dimethyl-[1,3]dioxolan-4-yl)-propan-1-ol in Example 715A. MS (DCI) m/e 268 (M+H)$^+$, $^1$H NMR (500 MHz, DMSO-d$_6$): □ 9.01 (s, 1H), 8.26 (d, J=5.52 Hz, 1H), 7.85 (s, 1H), 7.14 (d, J=5.52 Hz, 1H), 5.43 (m, 1H), 4.12 (m, 1H), 3.95-3.97 (m, 2H), 3.82 (m, 1H), 2.54 (m, 1H), 2.19 (m, 1H).

EXAMPLE 755B

3-[1-(Tetrahydro-furan-3-yl)-1H-pyrrolo[2,3-c]pyridin-3-yl]-5,10-dihydro-dibenzo[b,e][1,4]diazepin-11-one The title compound was prepared by substituting Example 755A and Example 719C for Example 696A and Example 695G, respectively, in Example 696B. MS (APCI) m/e 397 (M+H)$^+$, $^1$H NMR (500 MHz, DMSO-d$_6$): □ 9.82 (s, 1H), 9.49 (s, 1H), 8.62 (s, 1H), 8.49 (d, J=6.44 Hz, 1H), 8.36 (d, J=6.14 Hz, 1H), 8.02 (s, 1H), 7.81 (d, J=8.29 Hz, 1H), 7.47 (d, J=1.53 Hz, 1H), 7.34 (dd, J=8.13, 1.69 Hz, 1H), 6.90-7.04 (m, 4H), 5.60 (m, H), 4.21 (m, 1H), 4.11 (m, 1H), 4.10 (m, 1H), 3.88 (m, 1H), 2.64 (m, 1H), 2.35 (m, 1H).

EXAMPLE 756

8-[2-(4-Morpholin-4-yl-phenoxy)-ethyl]-3-[1-(tetrahydro-furan-3-yl)-1H-pyrrolo[2,3-c]pyridin-3-yl]-5,10-dihydro-dibenzo[b,e][1,4]diazepin-11-one The title compound was prepared by substituting Example 755A for Example 696A in Example 696B. MS (APCI) m/e 602 (M+H)$^+$, $^1$H NMR (500 MHz, DMSO-d$_6$): □ 9.79 (s, 1H), 9.53 (s, 1H), 8.67 (s, 1H), 8.50 (d, J=6.44 Hz, 1H), 8.40 (d, J=6.44 Hz, 1H), 7.99 (s, 1H), 7.81 (d, J=7.98 Hz, 1H), 7.46 (d, J=1.53 Hz, 1H), 7.33 (dd, J=8.13, 1.69 Hz, 1H), 6.82-6.97 (m, 7H), 5.62 (m, 1H), 4.22 (m, 1H), 3.99-4.13 (m, 6H), 3.88 (m, 1H), 3.71-3.73 (m, 4H), 2.97-3.00 (m, 4H), 2.87 (t, J=6.6 Hz, 2H), 2.64 (m, 1H), 2.35 (m, 1H).

EXAMPLE 757

3-{1-[2-(3,5-Difluoro-phenyl)-ethyl]-1H-pyrrolo[2,3-c]pyridin-3-yl}-8-[2-(4-morpholin-4-yl-phenoxy)-ethyl]-5,10-dihydro-dibenzo[b,e][1,4]diazepin-11-one

EXAMPLE 757A

3-Bromo-1-[2-(3,5-difluoro-phenyl)-ethyl]-1H-pyrrolo[2,3-c]pyridine

The title compound was prepared by substituting 2-(3,5-difluoro-phenyl)-ethanol for 3-(2,2-dimethyl-[1,3]dioxolan-4-yl)-propan-1-ol in Example 715A. MS (DCI) m/e 338 (M+H)$^+$, $^1$H NMR (500 MHz, DMSO-d$_6$): ☐ 8.92 (s, 1H), 8.21 (d, J=5.52 Hz, 1H), 7.80 (s, 1H), 7.32 (d, J=4.6 Hz, 1H), 6.69-7.03 (m, 3H), 4.57 (d, J=7.21 Hz, 2H), 3.15 (d, J=7.21 Hz, 2H).

EXAMPLE 757B

3-{1-[2-(3,5-Difluoro-phenyl)-ethyl]-1H-pyrrolo[2,3-c]pyridin-3-yl}-8-[2-(4-morpholin-4-yl-phenoxy)-ethyl]-5,10-dihydro-dibenzo[b,e][1,4]diazepin-11-one The title compound was prepared by substituting Example 757A for Example 696A in Example 696B. MS (APCI) m/e 672 (M+H)$^+$, $^1$H NMR (500 MHz, DMSO-d$_6$): ☐ 9.78 (s, 1H), 9.48 (s, 1H), 8.69 (s, 1H), 8.46 (d, J=6.44 Hz, 1H), 8.37 (d, J=6.44 Hz, 1H), 7.99 (s, 1H), 7.80 (d, J=7.98 Hz, 1H), 7.43 (s, 1H), 7.19 (dd, J=7.98, 1.53 Hz, 1H), 6.82-7.08 (m, 10H), 4.77 (t, J=7.36 Hz, 2H), 4.04 (t, J=7.36 Hz, 2H), 3.70-3.73 (m, 4H), 3.25 (t, J=7.21 Hz, 2H), 2.98-3.00 (m, 4H), 2.87 (t, J=6.6 Hz, 2H), 2.86 (t, J=6.6 Hz, 2H).

EXAMPLE 758

3-[2-(3-{1-[2-(3,5-Difluoro-phenyl)-ethyl]-1H-pyrrolo[2,3-c]pyridin-3-yl}-11-oxo-10,11-dihydro-5H-dibenzo[b,e][1,4]diazepin-8-yl)-ethoxy]-pyridine-2-carbonitrile The title compound was prepared by substituting Example 757A and Example 741B for Example 696A and Example 695G, respectively, in Example 696B. MS (APCI) m/e 613 (M+H)$^+$, $^1$H NMR (500 MHz, DMSO-d$_6$): ☐ 9.76 (s, 1H), 9.47 (s, 1H), 8.66 (s, 1H), 8.46 (d, J=6.75 Hz, 1H), 8.35 (d, J=6.44 Hz, 1H), 8.27 (d, J=3.38 Hz, 1H), 7.99 (s, 1H), 7.77-7.80 (m, 2H), 7.67 (dd, J=8.9, 4.6 Hz, 2H), 7.42 (d, J=1.53 Hz, 1H), 7.19 (dd, J=8.29, 1.53 Hz, 1H), 6.93-7.07 (m, 6H), 4.76 (t, J=7.52 Hz, 2H), 4.33 (t, J=6.6 Hz, 2H), 3.25 (t, J=7.36 Hz, 2H), 2.97 (t, J=6.44 Hz, 2H).

EXAMPLE 759

3-{1-[2-(4-Morpholin-4-yl-phenoxy)-ethyl]-1H-pyrrolo[2,3-c]pyridin-3-yl}-5,10-dihydro-dibenzo[b,e][1,4]diazepin-11-one

EXAMPLE 759A

4-{4-[2-(Tetrahydro-pyran-2-yloxy)-ethoxy]-phenyl}-morpholine 4-morpholinophenol (0.358 g, 2 mmol) in DMF (5 mL) was cooled to 0° C. To this solution was added 60% NaH (0.192 g, 4.8 mmol). After the bubbling ceased, 2-(2-bromo-ethoxy)-tetrahydro-pyran (0.501 g, 2.4 mmol) in DMF (2 mL) was added to the above solution. The solution was stirred at room temperature for 2 hours, and partitioned between EtOAc and water. The aqueous layer was extracted with additional EtOAc, and the combined organic layers were washed with brine, dried over MgSO$_4$, filtered, and concentrated under vacuum. The residue was purified by flash column chromatography on silica gel eluting with 7:3 hexanes/EtOAc to give 0.48 g of the title compound (78%).

EXAMPLE 759B 2-(4-Morpholin-4-yl-phenoxy)-ethanol

Example 759A (0.48 g, 1.56 mmol) and Dex-50W-200 resin (2.00 g) in MeOH (30 mL) was heated at 50° C. for 2 hours. The solution was neutralized with excess NH$_4$OH. The resin was filtered off and the solvents were removed under vacuum. The residue was re-dissolved in EtOAc, and washed with water, brine, dried (MgSO$_4$), filtered, and concentrated under vacuum. The residue was purified by flash column chromatography on silica gel eluting with 1:1 hexanes/EtOAc to give 0.26 g of the title compound (75%). MS (DCI) m/e 224 (M+H)$^+$, $^1$H NMR (500 MHz, DMSO-d$_6$): ☐ 6.81-6.87 (m, 4H), 4.77 (t, J=5.52 Hz, 1H), 3.89 (t, J=5.06 Hz, 2H), 3.65-3.72 (m, 6H), 2.95-2.97 (m, 4H).

EXAMPLE 759C

3-Bromo-1-[2-(4-morpholin-4-yl-phenoxy)-ethyl]-1H-pyrrolo[2,3-c]pyridine

The title compound was prepared by substituting Example 759B for 3-(2,2-dimethyl-[1,3]dioxolan-4-yl)-propan-1-ol in Example 715A. MS (DCI) m/e 403 (M+H)$^+$, $^1$H NMR (500 MHz, DMSO-d$_6$): ☐ 8.99 (s, 1H), 8.23 (d, J=5.52 Hz, 1H), 7.88 (s, 1H), 7.39 (d, J=5.52 Hz, 1H), 6.82-8.65 (m, 2H), 6.74-6.76 (m, 2H), 4.67 (d, J=5.06 Hz, 2H), 4.27 (d, J=5.06 Hz, 2H), 3.69-3.71 (m, 4H), 2.94-2.96 (m, 4H).

EXAMPLE 759D

3-{1-[2-(4-Morpholin-4-yl-phenoxy)-ethyl]-1H-pyrrolo[2,3-c]pyridin-3-yl}-5,10-dihydro-dibenzo[b,e][1,4]diazepin-11-one The title compound was prepared by substituting Example 759C and Example 719C for Example 696A and Example 695G, respectively, in Example 696B. MS (APCI) m/e 532 (M+H)$^+$, $^1$H NMR (500 MHz, DMSO-d$_6$): ☐ 9.83 (s, 1H), 9.55 (s, 1H), 8.79 (s, 1H), 8.50 (d, J=6.44 Hz, 1H), 8.40 (d, J=6.75 Hz, 1H), 8.04 (s, 1H), 7.82 (d, J=8.29 Hz, 1H), 7.47 (s, 1H), 7.27 (d, J=7.98 Hz, 1H), 6.76-7.03 (m, 8H), 4.92 (t, J=4.76 Hz, 2H), 4.39 (t, J=4.76 Hz, 2H), 3.68-3.71 (m, 4H), 2.94-2.96 (m, 4H).

EXAMPLE 760

3-[2-(3-{1-[2-(4-Morpholin-4-yl-phenoxy)-ethyl]-1H-pyrrolo[2,3-c]pyridin-3-yl}-11-oxo-10,11-dihydro-5H-dibenzo[b,e][1,4]diazepin-8-yl)-ethoxy]-pyridine-2-carbonitrile The title compound was prepared by substituting Example 759C and Example 741B for Example 696A and Example 695G, respectively, in Example 696B. MS (APCI) m/e 678

(M+H)⁺, ¹H NMR (500 MHz, DMSO-d₆): □ 9.77 (s, 1H), 9.54 (s, 1H), 8.78 (s, 1H), 8.50 (d, J=6.44 Hz, 1H), 8.39 (d, J=6.75 Hz, 1H), 8.28 (d, J=4.6 Hz, 1H), 8.00 (s, 1H), 7.77-7.82 (m, 2H), 7.68 (dd, J=8.75, 4.45 Hz, 1H), 7.44 (d, J=1.53 Hz, 1H), 7.26 (dd, J=8.29, 1.53 Hz, 1H), 6.76-6.97 (m, 7H), 4.91 (t, J=4.76 Hz, 2H), 4.33-4.40 (m, 4H), 3.68-3.70 (m, 4H), 2.93-2.96 (m, 6H).

EXAMPLE 761

8-(2-Hydroxy-1,1-dimethyl-ethyl)-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared by substituting Example 747H and Example 707A for Example 695G and Example 696A, respectively, in Example 696B, except here the purification was done by column chromatography using EtOAc, then 95/5 EtOAc/EtOH, followed by conversion to the hydrochloride salt. MS (ESI) m/e 543 (M+H)⁺; ¹H NMR (400 MHz, DMSO-d₆) δ 9.69 (s, 1H), 9.62 (s, 1H), 8.86 (s, 1H), 8.50 (d, J=6.4 Hz, 1H), 8.43 (d, J=6.4 Hz, 1H), 8.04 (s, 1H), 7.81 (d, J=8.0 Hz, 1H), 7.56 (d, J=6.7 Hz, 1H), 7.53 (d, J=6.7 Hz, 1H), 7.50 (d, J=1.2 Hz, 1H), 7.27 (dd, J=8.0, 1.2 Hz, 1H), 7.02 (s, 1H), 6.96 (s, 2H), 5.75 (s, 2H), 3.33 (s, 2H), 1.16 (s, 6H).

EXAMPLE 762

7-(2-Hydroxy-11-dimethyl-ethyl)-3-[1-(3,4,5-trifluoro-benzyl)-1H-pyrrolo[2,3-c]pyridin-3-yl]-5,10-dihydro-dibenzo[b,e][1,4]diazepin-11-one Example 762A methyl 2-(3-fluoro-4-nitrophenyl)-2-methylpropanoate 2-(3-Fluoro-4-nitro-phenyl)-propionic acid methyl ester was prepared from 2-fluoronitrobenzene by the procedure of T. Lemek, et. al. Tetrahedron, 57, 4753 (2001) and then converted to the title compound using the method of Example 747A. MS (DCI) m/e 259 (M+NH₄)⁺; ¹H NMR (300 MHz, CDCl₃) δ 8.03 (m, 1H), 7.26 (m, 2H), 3.69 (s, 3H), 1.61 (s, 6H).

EXAMPLE 762B methyl 2-(3-amino-4-nitrophenyl)-2-methylpropanoate

Example 762A (14.5 g, 60.2 mmol) in 7.0N NH₃ in MeOH (150 mL) was heated at 70° C. in a sealed tube overnight. The reaction was cooled, concentrated, and purified by column chromatography using 85/15 hexane/EtOAc. Recovered the product (8.3 g, 58%) as bright yellow solids. MS (DCI) m/e 239 (M+H)⁺, 256 (M+NH₄)⁺; ¹H NMR (300 MHz, DMSO-d₆) δ 7.79 (d, J=8.8 Hz, 1H), 7.41 (br s, 2H), 6.78 (d, J=2.0 Hz, 1H), 6.97 (dd, J=8.8, 2.0 Hz, 1H), 3.61 (s, 3H), 1.46 (s, 6H).

EXAMPLE 762C methyl 2-(3-chloro-11-oxo-10,11-dihydro-5H-dibenzo[b,e][1,4]diazepin-7-yl)-2-methylpropanoate Example 762B was converted to the title compound by the methods of Examples 695B, 695C, and 695D. MS (DCI) m/e 345 and 347 (M+H)⁺; ¹H NMR (300 MHz, DMSO-d₆) δ 9.90 (s, 1H), 8.07 (s, 1H), 7.68 (d, J=8.5 Hz, 1H), 7.06 (d, J=2.0 Hz, 1H), 6.95, 6.91 (both m, total 4H), 3.58 (s, 3H), 1.46 (s, 6H).

EXAMPLE 762D

3-Chloro-7-(2-hydroxy-11-dimethyl-ethyl)-5,10-dihydro-dibenzo[b,e][1,4]diazepin-11-one The title compound was prepared by substituting Example 762C for Example 695D in Example 695E. MS (DCI) m/e 317 and 319 (M+H)⁺; ¹H NMR (300 MHz, DMSO-d₆) δ 9.83 (s, 1H), 7.98 (s, 1H), 7.67 (d, J=8.5 Hz, 1H), 7.07 (d, J=2.0 Hz, 1H), 6.98 (d, J=2.0 Hz, 1H), 6.91 (m, 2H), 6.86 (d, J=8.5 Hz, 1H), 4.63 (t, J=5.4 Hz, 1H), 3.34 (t, J=5.4 Hz, 2H), 1.17 (s, 6H).

EXAMPLE 762E 7-(2-Hydroxy-11-dimethyl-ethyl)-3-(4,4,5,5-tetramethyl-[1,3,2]dioxaborolan-2-yl)-5,10-dihydro-dibenzo[b,e][1,4]diazepin-11-one The title product was prepared by substituting Example 762D for Example 695F in Example 695G. MS (DCI) m/e 409 (M+H)⁺.

EXAMPLE 762F 7-(2-Hydroxy-11-dimethyl-ethyl)-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared by substituting Example 762E and Example 707A for Example 695G and Example 696A, respectively, in Example 696B, except here the purification was done by column chromatography using EtOAc, then 95/5 EtOAc/EtOH, followed by conversion to the hydrochloride salt. MS (ESI) m/e 543 (M+H)⁺; ¹H NMR (400 MHz, DMSO-d₆) δ 9.75 (s, 1H), 9.60 (s, 1H), 8.85 (s, 1H), 8.50 (d, J=6.4 Hz, 1H), 8.42 (d, J=6.4 Hz, 1H), 8.05 (s, 1H), 7.81 (d, J=8.3 Hz, 1H), 7.55 (d, J=7.1 Hz, 1H), 7.53 (d, J=7.1 Hz, 1H), 7.50 (s, 1H), 7.27 (d, J=8.3 Hz, 1H), 7.05 (s, 1H), 6.90 (s, 2H), 5.74 (s, 2H), 3.36 (s, 2H), 1.18 (s, 6H).

EXAMPLE 763

8-[2-(2-Methyl-pyridin-3-yloxy)-ethyl]-3-[1-(3,4,5-trifluoro-benzyl)-1H-pyrrolo[2,3-c]pyridin-3-yl]-5,10-dihydro-dibenzo[b,e][1,4]diazepin-11-one The desired product was prepared by substituting Example 707A and Example 736B for Example 696A and Example 695G, respectively, in Example 696B. MS (ESI) m/e 606 (M+H)⁺, ¹H NMR (400 MHz, DMSO-d₆): □ 9.82 (s, 1H), 9.54 (s, 1H), 8.83 (s, 1H), 8.51 (d, J=6.44 Hz, 1H), 8.38 (d, J=6.44 Hz, 1H), 8.14 (d, J=4.60 Hz, 1H), 8.00 (s, 1H), 7.81 (d, J=7.98 Hz, 1H), 7.66 (d, J=7.98 Hz, 1H), 7.51 (dd, J=8.44, 6.90 Hz, 2H), 7.44 (d, J=1.53 Hz, 2H), 7.27 (dd, J=8.29, 1.84 Hz, 1H), 6.94 (m, 3H), 5.72 (s, 2H), 4.24 (t, J=6.44 Hz, 2H), 2.96 (t, J=6.29 Hz, 2H), 2.40 (s, 3H).

EXAMPLE 764

3-(2-{11-Oxo-3-[1-(3,4,5-trifluoro-benzyl)-1H-pyrrolo[2,3-c]pyridin-3-yl]-10,11-dihydro-5H-dibenzo[b,e][1,4]diazepin-8-yl}-ethoxy)-pyridine-2-carbonitrile The desired product was prepared by substituting Example 707A and Example 741B for Example 696A and Example 695G, respectively, in Example 696B. MS (ESI) m/e 617 (M+H)$^+$; $^1$H NMR (400 MHz, DMSO-d$_6$): □ 9.77 (s, 1H), 9.52 (s, 1H), 8.81 (s, 1H), 8.49 (d, J=6.75 Hz, 1H), 8.37 (d, J=6.44 Hz, 1H), 8.28 (dd, J=4.45, 1.07 Hz, 1H), 7.99 (s, 1H), 7.80 (t, J=8.29 Hz, 2H), 7.68 (dd, J=8.59, 4.60 Hz, 1H), 7.51 (dd, J=8.59, 6.75 Hz, 2H), 7.43 (d, J=1.23 Hz, 1H), 7.27 (dd, J=8.13, 1.69 Hz, 1H), 6.94-6.97 (m, 3H), 5.72 (s, 2H), 4.35 (t, J=6.60 Hz, 2H), 2.98 (t, J=6.44 Hz, 2H).

EXAMPLE 765

8-(2-Hydroxy-ethyl)-3-[1-(3,4,5-trifluoro-benzyl)-1H-pyrrolo[2,3-c]pyridin-3-yl]-5,10-dihydro-dibenzo[b,e][1,4]diazepin-11-one

EXAMPLE 765A 8-(2-Hydroxy-ethyl)-3-(4,4,5,5-tetramethyl-[1,3,2]dioxaborolan-2-yl)-5,10-dihydro-dibenzo[b,e][1,4]diazepin-11-one The title compound was prepared by substituting Example 695E for Example 695F in Example 695G. MS (DCI) m/e 381 (M+H)$^+$; $^1$H NMR (300 MHz, DMSO-d$_6$) δ 9.80 (s, 1H), 7.73 (s, 1H), 7.64 (d, J=7.8 Hz, 1H), 7.37 (d, J=1.0 Hz, 1H), 7.12 (dd, J=7.8, 1.0 Hz, 1H), 6.89 (d, J=8.5 Hz, 1H), 6.79 (m, 2H), 4.59 (br s, 1H), 3.51 (t, J=6.8 Hz, 2H), 2.57 (t, J=6.8 Hz, 2H), 1.29 (s, 12H).

EXAMPLE 765B 8-(2-Hydroxy-ethyl)-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared by substituting Example 765A and Example 707A for Example 695G and Example 696A, respectively, in Example 696B, except here the purification was done by column chromatography using EtOAc, then 95/5 EtOAc/EtOH, followed by conversion to the hydrochloride salt. MS (ESI) m/e 515 (M+H)$^+$; $^1$H NMR (500 MHz, DMSO-d$_6$) δ 9.44 (s, 1H), 8.79 (s, 1H), 8.44 (d, J=6.4 Hz, 1H), 8.42 (d, J=6.4 Hz, 1H), 7.82 (d, J=8.2 Hz, 1H), 7.44 (m, 3H), 7.32 (d, J=8.2 Hz, 1H), 6.96 (d, J=7.9 Hz, 1H), 6.86 (m, 2H), 5.73 (s, 2H), 3.56 (t, J=7.0 Hz, 2H), 2.63 (t, J=7.0 Hz, 2H).

EXAMPLE 766

8-[2-(Isoquinolin-3-yloxy)-ethyl]-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared by substituting Example 765B and 3-hydroxyisoquinoline for Example 695E and 4-morpholinophenol, respectively, in Example 695F, except here preoperative HPLC was used for the purification. MS (ESI) m/e 642 (M+H)$^+$; $^1$H NMR (400 MHz, DMSO-d$_6$) δ 9.80 (s, 1H), 9.48 (s, 1H), 9.04 (s, 1H), 8.77 (s, 1H), 8.49 (d, J=6.4 Hz, 1H), 8.34 (d, J=6.4 Hz, 1H), 8.02 (d, J=8.0 Hz, 1H), 7.98 (s, 1H), 7.81 (d, J=8.0 Hz, 1H), 7.79 (d, J=8.0 Hz, 1H), 7.64 (m, 1H), 7.51 (m, 2H), 7.44 (m, 2H), 7.27 (dd, J=8.0, 1.0 Hz, 1H), 7.16 (s, 1H), 6.96 (m, 3H), 5.71 (s, 2H), 4.48 (t, J=6.7 Hz, 2H), 2.97 (t, J=6.7 Hz, 2H).

EXAMPLE 767

8-(2-Morpholin-4-yl-ethyl)-3-[1-(3,4,5-trifluoro-benzyl)-1H-pyrrolo[2,3-c]pyridin-3-yl]-5,10-dihydro-dibenzo[b,e][1,4]diazepin-11-one

EXAMPLE 767A methanesulfonic acid 2-(3-chloro-11-oxo-10,11-dihydro-5H-dibenzo[b,e][1,4]diazepin-8-yl)-ethyl ester A mixture of Example 695E-0.4 CH$_2$Cl$_2$ (1.8 g, 5.58 mmol) in DME (30 mL) was treated with triethylamine (2.33 mL, 16.7 mmol), followed by methanesulfonyl chloride (648 µL, 8.4 mmol) and stirred at ambient temperature for one hour. The reaction mixture was then diluted with ethyl acetate, washed with water and brine, dried (MgSO$_4$), filtered, concentrated and pumped dry to give the desired product (2 g, 98% yield). MS (ESI) m/e 367 (M+H)$^+$; $^1$H NMR (300 MHz, DMSO-d$_6$) □ 9.89 (s, 1H), 8.03 (s, 1H), 7.68 (d, J=8.5 Hz, 1H). 7.06 (d, J=2.0 Hz, 1H), 6.85-6.94 (m, 4H), 4.33 (t, J=6.6 Hz, 2H), 3.11 (s, 3H), 2.86 (t, J=6.6 Hz, 2H).

EXAMPLE 767B 3-chloro-8-(2-morpholin-4-yl-ethyl)-5,10-dihydro-dibenzo[b,e][1,4]diazepin-11-one A mixture of Example 767A (360 mg, 0.98 mmol) in DMF (5 mL) was treated with morpholine (200 µL) and heated at 50° C. for 24 hours. The mixture was then cooled to room temperature, diluted with ethyl acetate, washed with water and brine, dried (MgSO$_4$), filtered and concentrated. The concentrate was purified by column chromatography on silica gel to provide the desired product. MS (ESI) m/e 358 (M+H)$^+$; $^1$H NMR (300 MHz, DMSO-d$_6$) □ 9.84 (s, 1H), 7.97 (s, 1H), 7.67 (d, J=8.5 Hz, 1H), 7.05 (d, J=2.0 Hz, 1H), 6.91 (dd, J=8.5, 2.0 Hz, 1H), 6.81-6.89 (m, 3H), 3.55-3.58 (m, 4H), 2.57-2.62 (m, 2H), 2.37-2.45 (m, 6H).

EXAMPLE 767C 8-(2-Morpholin-4-yl-ethyl)-3-(4,4,5,5-tetramethyl-[1,3,2]dioxaborolan-2-yl)-5,10-dihydro-dibenzo[b,e][1,4]diazepin-11-one The desired product was prepared by substituting Example 767B for Example 695F in Example 695G. MS (ESI) m/e 450 (M+H)$^+$; $^1$H NMR (300 MHz, DMSO-d$_6$) □ 9.80 (s, 1H), 7.73 (s, 1H), 7.65 (d, J=7.80 Hz, 1H), 7.38 (s, 1H), 7.13 (d, J=7.80 Hz, 1H), 6.79-6.91 (m, 3H), 3.55-3.58 (m, 4H), 2.57-2.62 (m, 2H), 2.37-2.45 (m, 6H), 1.29 (s, 12H).

EXAMPLE 767D 8-(2-Morpholin-4-yl-ethyl)-3-[1-(3,4,5-trifluoro-benzyl)-1H-pyrrolo[2,3-c]pyridin-3-yl]-5,10-dihydro-dibenzo[b,e][1,4]diazepin-11-one The desired product was prepared by substituting Example 707A and Example 767C for Example 696A and Example 695G, respectively, in Example 696B. MS (ESI) m/e 584 (M+H)+, $^1$H NMR (300 MHz, DMSO-d$_6$): □ 9.88 (s, 1H), 9.45 (s, 1H), 8.73 (s, 1H), 8.48 (d, J=6.44 Hz, 1H), 8.29 (d, J=5.76 Hz, 1H), 8.05 (s, 1H), 7.80 (d, J=8.14 Hz, 1H), 7.51 (dd, J=8.48, 6.78 Hz, 2H), 7.43 (d, J=1.36 Hz, 1H), 7.28 (dd, J=8.14, 1.70 Hz, 1H), 6.87-7.00 (m, 3H), 5.70 (s, 2H), 3.98-4.03 (m, 2H), 3.60-3.68 (m, 2H), 3.04-3.16 (m, 4H), 2.84-2.89 (m, 4H).

EXAMPLE 768

3-[1-(2,6-Difluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 768A

3-Bromo-1-(2,6-difluoro-benzyl)-1H-pyrrolo[2,3-c]pyridine

The desired product was prepared by substituting 2,6-difluorobenzyl bromide for benzyl bromide in Example 696A. MS (ESI) m/e 323 (M+H)+, $^1$H NMR (300 MHz, DMSO-d$_6$): □ 8.90 (s, 1H), 8.25 (d, J=5.43 Hz, 1H), 7.82 (s, 1H), 7.40-7.53 (m, 2H), 7.13-7.22 (m, 2H), 5.64 (s, 2H).

EXAMPLE 768B

3-[1-(2,6-Difluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 768A for Example 696A in Example 696B. MS (ESI) m/e 658 (M+H)+, $^1$H NMR (500 MHz, DMSO-d$_6$): □ 9.82 (s, 1H), 9.43 (s, 1H), 8.61 (s, 1H), 8.53 (d, J=6.41 Hz, 1H), 8.40 (d, J=6.41 Hz, 1H), 7.97 (s, 1H), 7.79 (d, J=8.24 Hz, 1H), 7.53 (m, 1H), 7.40 (d, J=1.53 Hz, 1H), 7.26 (dd, J=8.24, 1.53 Hz, 1H), 7.20-7.24 (m, 2H), 6.88-6.95 (m, 5H), 6.83-6.85 (m, 2H), 5.88 (s, 2H), 4.04 (t, J=6.71 Hz, 2H), 3.71-3.73 (m, 4H), 2.98-3.00 (m, 4H), 2.87 (t, J=6.56 Hz, 2H).

EXAMPLE 769

8-[2-(4-Morpholin-4-yl-phenoxy)-ethyl]-3-[1-(2,3,6-trifluoro-benzyl)-1H-pyrrolo[2,3-c]pyridin-3-yl]-5,10-dihydro-dibenzo[b,e][1,4]diazepin-11-one

EXAMPLE 769A

3-Bromo-1-(2,3,6-trifluoro-benzyl)-1H-pyrrolo[2,3-c]pyridine

The desired product was prepared by substituting 2,3,6-trifluorobenzyl bromide for benzyl bromide in Example 696A. MS (ESI) m/e 323 (M+H)+, $^1$H NMR (300 MHz, DMSO-d$_6$): □ 8.92 (s, 1H), 8.26 (d, J=5.76 Hz, 1H), 7.85 (s, 1H), 7.55 (m, 1H), 7.42 (dd, J=5.43, 1.02 Hz, 1H), 7.22 (m, 1H), 5.69 (s, 2H).

EXAMPLE 769B

8-[2-(4-Morpholin-4-yl-phenoxy)-ethyl]-3-[1-(2,3,6-trifluoro-benzyl)-1H-pyrrolo[2,3-c]pyridin-3-yl]-5,10-dihydro-dibenzo[b,e][1,4]diazepin-11-one The desired product was prepared by substituting Example 769A for Example 696A in Example 696B. MS (ESI) m/e 676 (M+H)+, $^1$H NMR (500 MHz, DMSO-d$_6$): □ 9.82 (s, 1H), 9.44 (s, 1H), 8.64 (s, 1H), 8.53 (d, J=6.41 Hz, 1H), 8.39 (d, J=6.41 Hz, 1H), 7.98 (s, 1H), 7.79 (d, J=8.24 Hz, 1H), 7.60 (m, 1H), 7.41 (d, J=1.53 Hz, 1H), 7.26 (m, 2H), 6.89 (m, 7H), 5.91 (s, 2H), 4.04 (t, J=6.71 Hz, 2H), 3.71-3.73 (m, 4H), 2.97-2.99 (m, 4H), 2.87 (t, J=6.56 Hz, 2H).

EXAMPLE 770

3-[1-(2-Methanesulfonyl-ethyl)-1H-pyrrolo[2,3-c]pyridin-3-yl]-5,10-dihydro-dibenzo[b,e][1,4]diazepin-11-one

EXAMPLE 770A

3-Bromo-1-(2-methanesulfonyl-ethyl)-1H-pyrrolo[2,3-c]pyridine

The title compound was prepared by substituting 2-methanesulfonyl-ethanol for 3-(2,2-dimethyl-[1,3]dioxolan-4-yl)-propan-1-ol in Example 715A. MS (DCI) m/e 304 (M+H)+, $^1$H NMR (500 MHz, DMSO-d$_6$): □ 8.99 (s, 1H), 8.26 (d, J=5.49 Hz, 1H), 7.90 (s, 1H), 7.41 (d, J=5.58 Hz, 1H), 4.75 (d, J=6.87 Hz, 2H), 3.77 (d, J=6.87 Hz, 2H), 2.98 (s, 3H).

EXAMPLE 770B

3-[1-(2-Methanesulfonyl-ethyl)-1H-pyrrolo[2,3-c]pyridin-3-yl]-5,10-dihydro-dibenzo[b,e][1,4]diazepin-11-one The title compound was prepared by substituting Example 770B and Example 719C for Example 696A and Example 695G, respectively, in Example 696B. MS (APCI) m/e 433 (M+H)+, $^1$H NMR (500 MHz, DMSO-d$_6$): □ 9.81 (s, 1H), 9.23 (s, 1H), 8.67 (s, 1H), 8.44 (d, J=6.44 Hz, 1H), 8.36 (d, J=6.75 Hz, 1H), 8.02 (s, 1H), 7.81 (m, 1H), 7.26 (dd, J=8.29, 1.53 Hz, 1H), 6.90-7.04 (m, 5H), 4.76 (d, J=6.87 Hz, 2H), 3.77 (d, J=6.87 Hz, 2H), 3.06 (s, 3H).

EXAMPLE 771

3-(2-{3-[1-(2-Methanesulfonyl-ethyl)-1H-pyrrolo[2,3-c]pyridin-3-yl]-11-oxo-10,11-dihydro-5H-dibenzo[b,e][1,4]diazepin-8-yl}-ethoxy)-pyridine-2-carbonitrile The title compound was prepared by substituting Example 770A and Example 741B for Example 696A and Example 695G, respectively, in Example 696B. MS (APCI) m/e 579 (M+H)+, $^1$H NMR (500 MHz, DMSO-d$_6$): □ 9.75 (s, 1H), 9.21 (s, 1H), 8.64 (s, 1H), 8.42 (d, J=6.44 Hz, 1H), 8.34 (d, J=6.75 Hz, 1H), 8.28 (m, 1H), 7.98 (s, 1H), 7.78-7.80 (m, 2H), 7.68 (dd, J=8.9, 4.6 Hz, 1H), 7.47 (d, J=1.53 Hz, 1H), 7.30 (dd, J=8.13, 1.69 Hz, 1H), 6.94-6.97 (m, 3H), 4.95 (d, J=6.87 Hz, 2H), 4.35 (d, J=6.6 Hz, 2H), 3.87 (d, J=6.87 Hz, 2H), 3.05 (s, 3H), 2.98 (d, J=6.6 Hz, 2H).

EXAMPLE 772

3-[1-(2-Methanesulfonyl-ethyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The title compound was prepared by substituting Example 770A for Example 696A in Example 696B. MS (APCI) m/e 638 (M+H)$^+$, $^1$H NMR (500 MHz, DMSO-d$_6$): ☐ 9.80 (s, 1H), 9.27 (s, 1H), 8.72 (d, J=2.45 Hz, 1H), 8.45 (d, J=6.44 Hz, 1H), 8.39 (d, J=6.44 Hz, 1H), 7.97 (s, 1H), 7.80 (d, J=8.29 Hz, 1H), 7.47 (d, J=1.53 Hz, 1H), 7.30 (dd, J=8.13, 1.69 Hz, 1H), 6.83-6.97 (m, 7H), 4.98 (t, J=6.75 Hz, 2H), 4.05 (t, J=6.75 Hz, 2H), 3.77 (d, J=6.87 Hz, 2H), 3.71-3.74 (m, 4H), 3.07 (s, 3H), 2.99-3.01 (m, 4H), 2.88 (t, J=6.6 Hz, 2H).

EXAMPLE 773

8-[2-(4-Morpholin-4-yl-phenoxy)-ethyl]-3-[1-(tetrahydro-pyran-4-yl)-1H-pyrrolo[2,3-c]pyridin-3-yl]-5,10-dihydro-dibenzo[b,e][1,4]diazepin-11-one

EXAMPLE 773A

3-Bromo-1-(tetrahydro-pyran-4-yl)-1H-pyrrolo[2,3-c]pyridine

The title compound was prepared by substituting tetrahydro-pyran-4-ol for 3-(2,2-dimethyl-[1,3]dioxolan-4-yl)-propan-1-ol in Example 715A. MS (DCI) m/e 282 (M+H)$^+$, $^1$H NMR (500 MHz, DMSO-d$_6$): ☐ 9.05 (s, 1H), 8.23 (d, J=5.52 Hz, 1H), 8.03 (s, 1H), 7.40 (d, J=5.52 Hz, 1H), 4.86 (m, 1H), 3.98-4.02 (m, 2H), 3.53-3.60 (m, 2H), 1.93-2.09 (m, 4H).

EXAMPLE 773B

8-[2-(4-Morpholin-4-yl-phenoxy)-ethyl]-3-[1-(tetrahydro-pyran-4-yl)-1H-pyrrolo[2,3-c]pyridin-3-yl]-5,10-dihydro-dibenzo[b,e][1,4]diazepin-11-one The title compound was prepared by substituting Example 773A for Example 696A in Example 696B. MS (APCI) m/e 616 (M+H)$^+$, $^1$H NMR (500 MHz, DMSO-d$_6$): ☐ 9.79 (s, 1H), 9.63 (s, 1H), 8.96 (s, 1H), 8.50 (d, J=6.75 Hz, 1H), 8.39 (d, J=6.44 Hz, 1H), 7.97 (s, 1H), 7.81 (d, J=8.29 Hz, 1H), 7.47 (d, J=1.23 Hz, 1H), 7.33 (dd, J=8.29, 1.53 Hz, 1H), 6.82-6.97 (m, 7H), 5.08 (m, 1H), 4.03-4.09 (m, 4H), 3.71-3.73 (m, 4H), 3.72-3.76 (m, 2H), 2.97-3.00 (m, 4H), 2.87 (t, J=6.75 Hz, 2H), 2.15-2.24 (m, 2H), 2.04-2.07 (m, 2H).

EXAMPLE 774

3-(2-{11-Oxo-3-[1-(tetrahydro-furan-3-yl)-1H-pyrrolo[2,3-c]pyridin-3-yl]-10,11-dihydro-5H-dibenzo[b,e][1,4]diazepin-8-yl}-ethoxy)-pyridine-2-carbonitrile The title compound was prepared by substituting Example 755A and Example 741B for Example 696A and Example 695G, respectively, in Example 696B. MS (APCI) m/e 543 (M+H)$^+$, $^1$H NMR (500 MHz, DMSO-d$_6$): ☐ 9.80 (s, 1H), 9.52 (s, 1H), 8.66 (s, 1H), 8.50 (d, J=6.41 Hz, 1H), 8.38 (d, J=6.71 Hz, 1H), 8.28 (d, J=3.66 Hz, 1H), 8.00 (s, 1H), 7.78-7.81 (m, 2H), 7.68 (dd, J=8.85, 4.58 Hz, 1H), 7.45 (s, 1H), 7.33 (dd, J=8.24, 1.53 Hz, 1H), 6.94-6.97 (m, 3H), 5.61 (m, 1H), 4.34 (t, J=6.56 Hz, 2H), 4.22 (m, 1H), 4.11 (d, J=9.92, 2.29 Hz, 1H), 4.01 (m, 1H), 3.87 (m, 1H), 2.98 (d, J=6.56 Hz, 2H), 2.63 (m, 1H), 2.35 (m, 1H).

EXAMPLE 775

8-[2-(4-Morpholin-4-yl-phenoxy)-ethyl]-3-[1-(tetrahydro-furan-3-ylmethyl)-1H-pyrrolo[2,3-c]pyridin-3-yl]-5,10-dihydro-dibenzo[b,e][1,4]diazepin-11-one

EXAMPLE 775A

3-Bromo-1-(tetrahydro-furan-3-ylmethyl)-1H-pyrrolo[2,3-c]pyridine

The title compound was prepared by substituting (tetrahydro-furan-3-yl)-methanol for 3-(2,2-dimethyl-[1,3]dioxolan-4-yl)-propan-1-ol in Example 715A. MS (DCI) m/e 282 (M+H)$^+$, $^1$H NMR (500 MHz, DMSO-d$_6$): ☐ 8.99 (s, 1H), 8.24 (d, J=5.52 Hz, 1H), 7.92 (s, 1H), 7.41 (d, J=5.52 Hz, 1H), 4.25-4.36 (m, 2H), 3.82 (m, 1H), 3.60-3.66 (m, 2H), 3.44 (dd, J=8.52, 5.22 Hz, 1H), 2.08 (m, 1H), 1.83-1.89 (m, 1H), 1.56-1.63 (m, 1H).

EXAMPLE 775B

8-[2-(4-Morpholin-4-yl-phenoxy)-ethyl]-3-[1-(tetrahydro-furan-3-ylmethyl)-1H-pyrrolo[2,3-c]pyridin-3-yl]-5,10-dihydro-dibenzo[b,e][1,4]diazepin-11-one The title compound was prepared by substituting Example 775A for Example 696A in Example 696B. MS (APCI) m/e 616 (M+H)$^+$, $^1$H NMR (500 MHz, DMSO-d$_6$): ☐ 9.82 (s, 1H), 9.60 (s, 1H), 8.85 (s, 1H), 8.50 (d, J=6.41 Hz, 1H), 8.40 (d, J=6.41 Hz, 1H), 8.00 (s, 1H), 7.81 (d, J=8.24 Hz, 1H), 7.46 (d, J=1.53 Hz, 1H), 7.28 (dd, J=8.24, 1.53 Hz, 1H), 6.83-6.97 (m, 7H), 4.47-4.56 (m, 3H), 4.03-4.06 (m, 2H), 3.85 (m, 1H), 3.71-3.73 (m, 4H), 3.64-3.70 (m, 2H), 2.98-3.00 (m, 4H), 2.86-2.95 (m, 3H), 1.92 (m, 1H), 1.67 (m, 1H).

EXAMPLE 776

3-(2-{11-Oxo-3-[1-(tetrahydro-furan-3-ylmethyl)-1H-pyrrolo[2,3-c]pyridin-3-yl]-10,11-dihydro-5H-dibenzo[b,e][1,4]diazepin-8-yl}-ethoxy)-pyridine-2-carbonitrile The title compound was prepared by substituting Example 775A and Example 741B for Example 696A and Example 695G, respectively, in Example 696B. MS (APCI) m/e 557 (M+H)$^+$, $^1$H NMR (500 MHz, DMSO-d$_6$): ☐ 9.80 (s, 1H), 9.58 (s, 1H), 8.82 (s, 1H), 8.49 (d, J=6.41 Hz, 1H), 8.38 (d, J=6.41 Hz, 1H), 8.28 (d, J=4.27 Hz, 1H), 8.02 (s, 1H), 7.78-7.81 (m, 2H), 7.68 (dd, J=8.7, 4.42 Hz, 1H), 7.45 (s, 1H), 7.28 (d, J=7.93 Hz, 1H), 6.94-6.97 (m, 3H), 4.48-4.55 (m, 2H), 4.35 (t, J=6.41 Hz, 2H), 3.86 (m, 1H), 3.68 (m, 1H), 3.48 (m, 1H), 3.87 (m, 1H), 2.98 (d, J=6.41 Hz, 2H), 2.92 (m, 1H), 1.92 (m, 1H), 1.67 (m, 1H).

EXAMPLE 777

3-[1-(2,3-Difluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one

EXAMPLE 777A

3-Bromo-1-(2,3-difluoro-benzyl)-1H-pyrrolo[2,3-c]pyridine

The desired product was prepared by substituting 2,3-difluorobenzyl bromide for benzyl bromide in Example 696A. MS (ESI) m/e 323 (M+H)$^+$, $^1$H NMR (300 MHz, DMSO-d$_6$):

☐ 8.94 (s, 1H), 8.26 (d, J=5.42 Hz, 1H), 7.95 (s, 1H), 7.35-7.44 (m, 2H), 7.18 (m, 1H), 7.00 (m, 1H), 5.69 (s, 2H).

EXAMPLE 777B

3-[1-(2,3-Difluoro-benzyl)-1H-pyrrolo[2,3-c]pyridin-3-yl]-8-[2-(4-morpholin-4-yl-phenoxy)-ethyl]-5,10-dihydro-dibenzo[b,e][1,4]diazepin-11-one The desired product was prepared by substituting Example 777A for Example 696A in Example 696B. MS (ESI) m/e 658 (M+H)$^+$, $^1$H NMR (400 MHz, DMSO-d$_6$): ☐ 9.80 (s, 1H), 9.51 (s, 1H), 8.76 (s, 1H), 8.52 (d, J=6.44 Hz, 1H), 8.41 (d, J=6.75 Hz, 1H), 7.98 (s, 1H), 7.81 (d, J=7.98 Hz, 1H), 7.44 (m, 2H), 7.26 (dd, J=8.29, 1.53 Hz, 1H), 7.21 (m, 1H), 7.11 (t, J=7.21 Hz, 1H), 6.88 (m, 7H), 5.91 (s, 2H), 4.05 (t, J=6.75 Hz, 2H), 3.72 (m, 4H), 2.99 (m, 4H), 2.87 (t, J=6.60 Hz, 2H).

EXAMPLE 778

8-[2-(4-Morpholin-4-yl-phenoxy)-ethyl]-3-[1-(2,3,5-trifluoro-benzyl)-1H-pyrrolo[2,3-c]pyridin-3-yl]-5,10-dihydro-dibenzo[b,e][1,4]diazepin-11-one

EXAMPLE 778A

3-Bromo-1-(2,3,5-trifluoro-benzyl)-1H-pyrrolo[2,3-c]pyridine

The desired product was prepared by substituting 2,3,5-trifluorobenzyl bromide for benzyl bromide in Example 696A. MS (ESI) m/e 323 (M+H)$^+$, $^1$H NMR (300 MHz, DMSO-d$_6$): ☐ 8.97 (s, 1H), 8.27 (d, J=5.43 Hz, 1H), 7.96 (s, 1H), 7.53 (m, 1H), 7.44 (dd, J=5.59, 1.19 Hz, 1H), 7.02 (m, 1H), 5.67 (s, 2H).

EXAMPLE 778B

8-[2-(4-Morpholin-4-yl-phenoxy)-ethyl]-3-[1-(2,3,5-trifluoro-benzyl)-1H-pyrrolo[2,3-c]pyridin-3-yl]-5,10-dihydro-dibenzo[b,e][1,4]diazepin-11-one The desired product was prepared by substituting Example 778A for Example 696A in Example 696B. MS (ESI) m/e 676 (M+H)$^+$, $^1$H NMR (400 MHz, DMSO-d$_6$): ☐ 9.80 (s, 1H), 9.52 (s, 1H), 8.76 (s, 1H), 8.53 (d, J=6.44 Hz, 1H), 8.42 (d, J=6.44 Hz, 1H), 7.99 (s, 1H), 7.81 (d, J=8.29 Hz, 1H), 7.58 (m, 1H), 7.44 (d, J=1.53 Hz, 1H), 7.26 (dd, J=8.29, 1.53 Hz, 1H), 7.15 (m, 1H), 6.83-6.96 (m, 7H), 5.89 (s, 2H), 4.05 (t, J=6.75 Hz, 2H), 3.71-3.73 (m, 4H), 2.99-3.01 (m, 4H), 2.87 (t, J=6.60 Hz, 2H).

EXAMPLE 779

8-[2-(4-Morpholin-4-yl-phenoxy)-ethyl]-3-{1-[2-(3,4,5-trifluoro-phenyl)-ethyl]-1H-pyrrolo[2,3-c]pyridin-3-yl}-5,10-dihydro-dibenzo[b,e][1,4]diazepin-11-one

EXAMPLE 779A

3-Bromo-1-[2-(3,4,5-trifluoro-phenyl)-ethyl]-1H-pyrrolo[2,3-c]pyridine

The desired product was prepared by substituting 2-(3,4,5-trifluoro-phenyl)-ethanol for 2-(2,2-dimethyl-[1,3]dioxolan-4-yl)-ethanol in Example 715A. MS (ESI) m/e 355 (M+H)$^+$, $^1$H NMR (300 MHz, DMSO-d$_6$): ☐ 8.92 (s, 1H), 8.21 (d, J=5.76 Hz, 1H), 7.80 (s, 1H), 7.38 (m, 1H), 7.18-7.23 (m, 2H), 4.55 (t, J=7.29 Hz, 2H), 3.11 (t, J=7.29 Hz, 2H).

EXAMPLE 779B

8-[2-(4-Morpholin-4-yl-phenoxy)-ethyl]-3-{1-[2-(3,4,5-trifluoro-phenyl)-ethyl]-1H-pyrrolo[2,3-c]pyridin-3-yl}-5,10-dihydro-dibenzo[b,e][1,4]diazepin-11-one The desired product was prepared by substituting Example 779A for Example 696A in Example 696B. MS (ESI) m/e 690 (M+H)$^+$, $^1$H NMR (500 MHz, DMSO-d$_6$): ☐ 9.80 (s, 1H), 9.47 (s, 1H), 8.67 (s, 1H), 8.48 (d, J=6.44 Hz, 1H), 8.37 (d, J=6.44 Hz, 1H), 7.98 (s, 1H), 7.81 (d, J=8.29 Hz, 1H), 7.43 (d, J=1.53 Hz, 1H), 7.19-7.23 (m, 3H), 6.82-6.96 (m, 7H), 4.75 (t, J=7.21 Hz, 2H), 4.05 (t, J=6.75 Hz, 2H), 3.71-3.73 (m, 4H), 3.22 (t, J=7.21 Hz, 2H), 2.97-2.99 (m, 4H), 2.87 (t, J=6.44 Hz, 2H).

EXAMPLE 780

3-[1-(Tetrahydro-furan-3-ylmethyl)-1H-pyrrolo[2,3-c]pyridin-3-yl]-5,10-dihydro-dibenzo[b,e][1,4]diazepin-11-one The title compound was prepared by substituting Example 775A and Example 719C for Example 696A and Example 695G, respectively, in Example 696B. MS (APCI) m/e 411 (M+H)$^+$, $^1$H NMR (500 MHz, DMSO-d$_6$): ☐ 9.82 (s, 1H), 9.56 (s, 1H), 8.78 (s, 1H), 8.48 (d, J=6.44 Hz, 1H), 8.37 (d, J=6.75 Hz, 1H), 8.04 (s, 1H), 7.82 (d, J=8.29 Hz, 1H), 7.47 (s, 1H), 7.29 (dd, J=8.29, 1.23 Hz, 1H), 6.90-7.03 (m, 4H), 4.07-4.54 (m, 2H), 3.86 (m, 1H), 3.64-3.72 (m, 2H), 3.52 (m, 1H), 2.93 (m, 1H), 1.92 (m, 1H), 1.67 (m, 1H).

EXAMPLE 781

3-(1-Butyl-1H-pyrrolo[2,3-c]pyridin-3-yl)-8-(2-hydroxy-11-dimethyl-ethyl)-5,10-dihydro-dibenzo[b,e][1,4]diazepin-11-one The title compound was prepared by substituting Example 747H and Example 716A for Example 695G and Example 696A, respectively, in Example 696B, except here the purification was done by column chromatography using EtOAc, then 95/5 EtOAc/EtOH, followed by conversion to the hydrochloride salt. MS (ESI) m/e 455 (M+H)$^+$; $^1$H NMR (400 MHz, DMSO-d$_6$) δ 9.68 (s, 1H), 9.54 (s, 1H), 8.77 (s, 1H), 8.45 (d, J=6.4 Hz, 1H), 8.41 (d, J=6.4 Hz, 1H), 8.03 (s, 1H), 7.80 (d, J=8.3 Hz, 1H), 7.51 (s, 1H), 7.26 (d, J=8.3 Hz, 1H), 7.02 (s, 1H), 6.96 (s, 2H), 4.51 (t, J=7.0 Hz, 2H), 3.34 (s, 2H), 1.89 (m, 2H), 1.31 (m, 2H), 1.16 (s, 6H), 0.92 (t, J=7.4 Hz, 3H).

EXAMPLE 782

8-(2-Hydroxy-1,1-dimethyl-ethyl)-7-methyl-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared from 3-methyl-nitrobenzene by the sequential application of the following methods: Examples 762A and 695C, treatment with acetic anhydride, Examples 695A, 695B, 695C, 695D, 695E, 695G and 696B. Here the purification was done by column chromatography using EtOAc, then 95/5 EtOAc/EtOH, followed by conversion to the hydrochloride salt. MS (ESI) m/e 557 (M+H)+; 1H NMR (400 MHz, DMSO-d6) δ 9.63 (s, 1H), 9.59 (s, 1H), 8.84 (s, 1H), 8.49 (d, J=6.4 Hz, 1H), 8.41 (d, J=6.4 Hz, 1H), 7.94 (s, 1H), 7.80 (d, J=8.0 Hz, 1H), 7.56 (d, J=7.7 Hz, 1H), 7.53 (d, J=7.7 Hz, 1H), 7.46 (s, 1H), 7.27 (d, J=8.0 Hz, 1H), 6.98 (s, 1H), 6.74 (s, 1H), 5.74 (s, 2H), 3.33 (s, 2H), 2.34 (s, 3H), 1.25 (s, 6H).

EXAMPLE 783

8-(2-Hydroxy-1,1,2-trimethyl-propyl)-3-[1-(3,4,5-trifluoro-benzyl-1H-pyrrolo[2,3-c]pyridin-3-yl]-5,10-dihydro-dibenzo[b,e][1,4]diazepin-11-one

EXAMPLE 783A

3-Chloro-8-(2-hydroxy-1,1,2-trimethyl-propyl)-5,10-dihydro-dibenzo[b,e][1,4]diazepin-11-one Example 747F (1.05 G, 3.0 mmol) IN THF (100 mL) WAS TREATED DROPWISE WITH 3.0M MeMgBr (25 mL, 75 mmol) at room temperature. The reaction mixture was stirred overnight. The reaction was quenched carefully with MeOH, and the mixture was poured into water. To this solution was added 5 mL of concentrated HCl solution, and the mixture was extracted by ethyl acetate several times. The combined organic layers were washed with brine, dried (MgSO4), filtered, and concentrated under vacuum. The residue was purified by flash column chromatography on silica gel eluting with 7/3, then 1/1 hexanes/EtOAc, giving the product (0.52 g, 50%) as tan solids. MS (DCI) m/e 345 and 347 (M+H)+; 1H NMR (300 MHz, DMSO-d6) δ 9.75 (s, 1H), 7.95 (s, 1H), 7.67 (d, J=8.5 Hz, 1H), 7.07 (d, J=2.0 Hz, 1H), 7.05 (d, J=2.0 Hz, 1H), 7.01 (dd, J=8.5, 2.0 Hz, 1H), 6.90 (dd, J=8.5, 2.0 Hz, 1H), 6.83 (d, J=8.5 Hz, 1H), 4.03 (s, 1H), 1.24 (s, 6H), 0.96 (s, 6H).

EXAMPLE 783B 8-(2-Hydroxy-1,1,2-trimethyl-propyl)-3-(4,4,5,5-tetramethyl-[1,3,2]dioxaborolan-2-yl)-5,10-dihydro-dibenzo[b,e][1,4]diazepin-11-one The title compound was prepared by substituting Example 783A for Example 695F in Example 695G. MS (DCI) m/e 437 (M+H)+.

EXAMPLE 783C 8-(2-Hydroxy-1,1,2-trimethyl-propyl)-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared by substituting Example 783B and Example 707A for Example 695G and Example 696A, respectively, in Example 696B, except here the purification was done by column chromatography using EtOAc, then 95/5 EtOAc/EtOH, followed by conversion to the hydrochloride salt. MS (ESI) m/e 571 (M+H)+; 1H NMR (400 MHz, DMSO-d6) δ 9.68 (s, 1H), 9.59 (s, 1H), 8.84 (s, 1H), 8.50 (d, J=6.4 Hz, 1H), 8.42 (d, J=6.4 Hz, 1H), 8.00 (s, 1H), 7.81 (d, J=8.3 Hz, 1H), 7.56 (d, J=7.5 Hz, 1H), 7.53 (d, J=7.5 Hz, 1H), 7.48 (s, 1H), 7.27 (d, J=8.3 Hz, 1H), 7.10 (d, J=1.8 Hz, 1H), 7.01 (dd, J=8.6, 1.8 Hz, 1H), 6.90 (d, J=8.6 Hz, 1H), 5.74 (s, 2H), 1.25 (s, 6H), 0.98 (s, 6H).

EXAMPLE 784

7-(3-Hydroxy-propyl)-3-[1-(3,4,5-trifluoro-benzyl)-1H-pyrrolo[2,3-c]pyridin-3-yl]-5,10-dihydro-dibenzo[b,e][1,4]diazepin-11-one The title compound was prepared from methyl 3-(3'-aminophenyl)propionate by the sequential application of the following methods: Examples 695A, 695B, 695C, 695D, 695E, 695G and 696B. Here the final purification was done by column chromatography using EtOAc, then 95/5 EtOAc/EtOH, followed by conversion to the hydrochloride salt. MS (ESI) m/e 529 (M+H)+; 1H NMR (400 MHz, DMSO-d6) δ 9.75 (s, 1H), 9.62 (s, 1H), 8.87 (s, 1H), 8.50 (d, J=6.4 Hz, 1H), 8.44 (d, J=6.4 Hz, 1H), 8.06 (s, 1H), 7.81 (d, J=8.0 Hz, 1H), 7.56 (d, J=7.1 Hz, 1H), 7.54 (d, J=7.1 Hz, 1H), 7.51 (d, J=1.2 Hz, 1H), 7.28 (dd, J=8.0, 1.2 Hz, 1H), 6.89 (m, 2H), 6.75 (m, 1H), 5.75 (s, 2H), 3.40 (t, J=6.4 Hz, 2H), 2.50 (t, J=7.0 Hz, 2H), 1.67 (m, 2H).

EXAMPLE 785

8-[2-(4-Morpholin-4-yl-phenoxy)-ethyl]-3-thieno[2,3-c]pyridin-3-yl-5,10-dihydro-dibenzo[b,e][1,4]diazepin-11-one The title compound was prepared by substituting 3-bromothieno[2,3-c]pyridine [prepared by the methods described in Gronowitz, S. and Sandberg, E., Arkiv för Kemi, 32 (19 & 21), 217 & 249 (1970)] for Example 696A in Example 696B, except here the purification was done by column chromatography using EtOAc, then 95/5 EtOAc/EtOH, followed by conversion to the dihydrochloride salt. MS (ESI) m/e 549 (M+H)+; 1H NMR (400 MHz, DMSO-d6) δ 9.88 (s, 1H), 9.86 (s, 1H), 8.86 (s, 1H), 8.76 (d, J=6.4 Hz, 1H), 8.36 (d, J=6.4 Hz, 1H), 8.20 (s, 1H), 7.86 (d, J=8.3 Hz, 1H), 7.40 (s, 1H), 7.18 (d, J=8.3 Hz, 1H), 7.07 (m, 4H), 6.94 (m, 3H), 4.14 (t, J=6.4 Hz, 2H), 3.98 (m, 4H), 3.37 (m, 4H), 2.91 (t, J=6.4 Hz, 2H).

EXAMPLE 786

4-[2-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-ethoxy]-benzonitrile

EXAMPLE 786A 4-(2-Bromo-ethoxy)-benzonitrile

The title compound was prepared by substituting 2-bromoethanol and 4-cyanophenol for 3-(2,2-dimethyl-[1,3]dioxolan-4-yl)-propan-1-ol and 4-morpholinophenol, respectively, in Example 715A. MS (DCI) m/e 227 (M+H)+, 1H NMR (500 MHz, DMSO-d6): ☐ 7.77-7.79 (m, 2H), 7.13-7.15 (m, 2H), 4.41-4.44 (m, 2H), 3.81-3.84 (m, 2H).

EXAMPLE 786B

4-[2-(3-Bromo-pyrrolo[2,3-c]pyridin-1-yl)-ethoxy]-benzonitrile

The title compound was prepared by substituting Example 786A for benzyl bromide in Example 696A, except the longer reaction time was employed. MS (DCI) m/e 343 (M+H)+, 1H NMR (500 MHz, DMSO-d6): ☐ 9.02 (s, 1H), 8.25 (d, J=5.52 Hz, 1H), 7.91 (s, 1H), 7.73 (d, J=8.9 Hz, 2H), 7.39 (d, J=5.52 Hz, 1H), 7.04 (d, J=8.9 Hz, 2H), 4.75 (d, J=5.06 Hz, 2H), 4.47 (d, J=5.06 Hz, 2H).

EXAMPLE 786C

4-[2-(3-{8-[2-(4-Morpholin-4-yl-phenoxy)-ethyl]-11-oxo-10,11-dihydro-5H-dibenzo[b,e][1,4]diazepin-3-yl}-pyrrolo[2,3-c]pyridin-1-yl)-ethoxy]-benzonitrile The title compound was prepared by substituting Example 786B for Example 696A in Example 696B. MS (ESI) m/e 677 (M+H)$^+$, $^1$H NMR (500 MHz, DMSO-d$_6$): □ 9.79 (s, 1H), 9.55 (s, 1H), 8.78 (s, 1H), 8.50 (d, J=6.44 Hz, 1H), 8.38 (d, J=6.41 Hz, 1H), 7.98 (s, 1H), 7.81 (d, J=8.29 Hz, 1H), 7.74 (d, J=8.9 Hz, 2H), 7.44 (s, 1H), 7.25 (dd, J=8.13, 1.38 Hz, 1H), 7.07 (d, J=8.9 Hz, 2H), 6.83-6.97 (m, 7H), 4.97 (t, J=4.76 Hz, 2H), 4.57 (t, J=4.57 Hz, 2H), 4.05 (t, J=6.6 Hz, 2H), 3.71-3.73 (m, 4H), 3.64-3.70 (m, 2H), 2.97-2.99 (m, 4H), 2.87 (t, J=6.44 Hz, 2H).

EXAMPLE 787

3-[2-(3-{1-[2-(4-Cyano-phenoxy)-ethyl]-1H-pyrrolo[2,3-c]pyridin-3-yl}-11-oxo-10,11-dihydro-5H-dibenzo[b,e][1,4]diazepin-8-yl)-ethoxy]-pyridine-2-carbonitrile The title compound was prepared by substituting Example 786B and Example 741B for Example 696A and Example 695G, respectively, in Example 696B. MS (ESI) m/e 618 (M+H)$^+$, $^1$H NMR (500 MHz, DMSO-d$_6$): □ 9.77 (s, 1H), 9.52 (s, 1H), 8.75 (s, 1H), 8.49 (d, J=6.44 Hz, 1H), 8.35 (d, J=6.44 Hz, 1H), 8.29 (dd, J=4.6, 1.23 Hz, 1H), 8.00 (s, 1H), 7.78-7.82 (m, 2H), 7.74 (d, J=8.9 Hz, 2H), 7.68 (dd, J=8.75, 4.45 Hz, 1H), 7.44 (d, J=1.53 Hz, 1H), 7.25 (dd, J=8.29, 1.53 Hz, 1H), 7.07 (d, J=9.21 Hz, 2H), 6.95-6.97 (m, 3H), 4.96 (t, J=4.91 Hz, 2H), 4.56 (t, J=5.06 Hz, 2H), 3.35 (t, J=6.6 Hz, 1H), 2.98 (t, J=6.6 Hz, 2H).

EXAMPLE 788

4-{2-[3-(11-Oxo-10,11-dihydro-5H-dibenzo[b,e][1,4]diazepin-3-yl)-pyrrolo[2,3-c]pyridin-1-yl]-ethoxy}-benzonitrile The title compound was prepared by substituting Example 786B and Example 719C for Example 696A and Example 695G, respectively, in Example 696B. MS (APCI) m/e 472 (M+H)$^+$, $^1$H NMR (500 MHz, DMSO-d$_6$): □ 9.82 (s, 1H), 9.52 (s, 1H), 8.75 (s, 1H), 8.49 (d, J=6.44 Hz, 1H), 8.36 (d, J=6.44 Hz, 1H), 8.03 (s, 1H), 7.81 (d, J=7.98 Hz, 1H), 7.73 (d, J=9.21 Hz, 2H), 7.46 (d, J=1.23 Hz, 1H), 7.26 (dd, J=7.98, 1.53 Hz, 1H), 7.07 (d, J=9.21 Hz, 2H), 6.90-7.03 (m, 4H), 4.96 (t, J=4.76 Hz, 2H), 4.57 (t, J=5.06 Hz, 2H).

EXAMPLE 789

3-[2-(11-Oxo-3-{1-[2-(3,4,5-trifluoro-phenyl)-ethyl]-1H-pyrrolo[2,3-c]pyridin-3-yl}-10,11-dihydro-5H-dibenzo[b,e][1,4]diazepin-8-yl)-ethoxy]pyridine-2-carbonitrile The desired product was prepared by substituting Example 779A and Example 741B for Example 696A and Example 695G, respectively, in Example 696B. MS (ESI) m/e 631 (M+H)$^+$, $^1$H NMR (500 MHz, DMSO-d$_6$): □ 9.80 (s, 1H), 9.44 (s, 1H), 8.64 (s, 1H), 8.48 (d, J=6.41 Hz, 1H), 8.34 (d, J=6.41 Hz, 1H), 8.28 (d, J=3.66 Hz, 1H), 8.00 (s, 1H), 7.78-7.81 (m, 2H), 7.68 (dd, J=8.85, 4.58 Hz, 1H), 7.43 (d, J=1.22 Hz, 1H), 7.20-7.25 (m, 3H), 6.94-6.96 (m, 3H), 4.74 (t, J=7.17 Hz, 2H), 4.34 (t, J=6.71 Hz, 2H), 3.22 (t, J=7.32 Hz, 2H), 2.98 (t, J=6.56 Hz, 2H).

EXAMPLE 790

3-{1-[2-(3,4,5-Trifluoro-phenyl)-ethyl]-1H-pyrrolo[2,3-c]pyridin-3-yl}-5,10-dihydro-dibenzo [b,e][1,4]diazepin-11-one The desired product was prepared by substituting Example 779A and Example 719B for Example 696A and Example 695G, respectively, in Example 696B. MS (ESI) m/e 485 (M+H)$^+$, $^1$H NMR (500 MHz, DMSO-d$_6$): □ 9.85 (s, 1H), 9.42 (s, 1H), 8.62 (s, 1H), 8.47 (d, J=6.71 Hz, 1H), 8.33 (d, J=6.41 Hz, 1H), 8.04 (s, 1H), 7.81 (d, J=8.24 Hz, 1H), 7.45 (s, 1H), 7.21-7.25 (m, 3H), 6.91-7.02 (m, 4H), 4.74 (t, J=7.32 Hz, 2H), 3.22 (t, J=7.17 Hz, 2H).

EXAMPLE 791

8-(2-Hydroxy-ethyl)-3-isoquinolin-5-yl-5,10-dihydro-dibenzo[b,e][1,4]diazepin-11-one The title compound was prepared by substituting Example 765A and 5-iodo isoquinoline for Example 695G and Example 695K, respectively, in Example 695L. MS (APCI) m/e 382 (M+H)$^+$, $^1$H NMR (500 MHz, DMSO-d$_6$): □ 9.81 (s, 1H), 9.40 (s, 1H), 8.52 (d, J=5.39 Hz, 1H), 8.20 (d, J=7.8 Hz, 1H), 7.89 (s, 1H), 7.83 (d, J=8.11 Hz, 1H), 7.71-7.78 (m, 3H), 7.14 (d, J=1.56 Hz, 1H), 7.02 (dd, J=7.8, 1.56 Hz, 1H), 6.90 (d, J=8.11 Hz, 1H), 6.85 (s, 1H), 6.81 (m, 1H), 4.58 (t, J=5.15 Hz, 1H), 3.52-3.56 (m, 2H), 2.60 (t, J=7.02 Hz, 2H).

EXAMPLE 792

3-Isoquinolin-5-yl-8-[2-(4-morpholin-4-yl-phenoxy)-ethyl]-5,10-dihydro-dibenzo[b,e][1,4]diazepin-11-one The title compound was prepared by substituting 5-iodo isoquinoline for Example 695K in Example 695L. MS (APCI) m/e 543 (M+H)$^+$, $^1$H NMR (500 MHz, DMSO-d$_6$): □ 9.87 (s, 1H), 9.66 (s, 1H), 8.58 (d, J=6.24 Hz, 1H), 8.37 (dd, J=7.02, 1.72 Hz, 1H), 7.92-7.97 (m, 4H), 7.86 (d, J=8.11 Hz, 1H), 7.15 (d, J=1.56 Hz, 1H), 7.03 (dd, J=7.96, 1.72 Hz, 1H), 6.92-6.96 (m, 5H), 6.85-6.88 (m, 2H), 4.06 (t, J=6.71 Hz, 2H), 3.73-3.75 (m, 4H), 3.03-3.05 (m, 4H), 2.88 (t, J=6.55 Hz, 2H).

EXAMPLE 793

2-(3-Isoquinolin-5-yl-11-oxo-10,11-dihydro-5H-dibenzo[b,e][1,4]diazepin-7-yl)-2-methyl-propionic acid methyl ester

EXAMPLE 793A

2-Methyl-2-[11-oxo-3-(4,4,5,5-tetramethyl-[1,3,2]dioxaborolan-2-yl)-10,11-dihydro-5H-dibenzo[b,e][1,4]diazepin-7-yl]-propionic acid methyl ester The title compound was prepared by substituting Example 762C for Example 695F in Example 695G. MS (DCI) m/e 437 (M+H)$^+$.

EXAMPLE 793B 2-(3-Isoquinolin-5-yl-11-oxo-10,11-dihydro-5H-dibenzo[b,e][1,4]diazepin-7-yl)-2-methyl-propionic acid methyl ester The title compound was prepared by substituting Example 793A and 5-iodo isoquinoline for Example 695G and Example 695K, respectively, in Example 695L. MS (APCI) m/e 438 (M+H)$^+$, $^1$H NMR (500 MHz, DMSO-d$_6$): ☐ 9.86 (s, 1H), 9.41 (s, 1H), 8.52 (d, J=5.8 Hz, 1H), 8.20 (d, J=7.63 Hz, 1H), 8.02 (s, 1H), 7.85 (d, J=7.93 Hz, 1H), 7.72-7.80 (m, 3H), 7.14 (s, 1H), 7.03 (dd, J=8.09, 1.37 Hz, 1H), 6.99 (d, J=1.83 Hz, 1H), 6.91-6.96 (m, 2H), 3.59 (s, 3H), 1.45 (s, 6H).

EXAMPLE 794

7-(2-Hydroxy-1,1-dimethyl-ethyl)-3-isoquinolin-5-yl-5,10-dihydro-dibenzo[b,e][1,4]diazepin-11-one The title compound was prepared by substituting Example 762E and 5-iodo isoquinoline for Example 695G and Example 695K, respectively, in Example 695L. MS (APCI) m/e 410 (M+H)$^+$, $^1$H NMR (500 MHz, DMSO-d$_6$): ☐ 9.75 (s, 1H), 9.39 (s, 1H), 8.50 (d, J=6.14 Hz, 1H), 8.18 (d, J=7.67 Hz, 1H), 7.89 (s, 1H), 7.83 (d, J=7.98 Hz, 1H), 7.69-7.75 (m, 3H), 7.12 (d, J=1.23 Hz, 1H), 6.89-7.02 (m, 4H), 4.59 (t, J=5.37 Hz, 1H), 3.37-3.40 (m, 2H), 1.17 (s, 6H).

EXAMPLE 795

[3-(1-Cyano-isoquinolin-5-yl)-11-oxo-10,11-dihydro-5H-dibenzo[b,e][1,4]diazepin-8-yl]-acetic acid methyl ester

EXAMPLE 795A

5-Bromo-isoquinoline N-oxide

A mixture of 5-bromoisoquinoline (0.83 g, 3.0 mmol), MCPBA (1.84 g, 8 mmol) and NaHCO$_3$ (0.672 g, 8 mmol) in CH$_2$Cl$_2$ (10 mL) and H$_2$O (5 mL) was stirred overnight. The solvents were removed, and the residue was purified by silica gel column chromatography eluting with EtOAc to give 0.51 g of the title compound. MS (APCI) m/e 225 (M+H)$^+$.

EXAMPLE 795B

5-Bromo-isoquinoline-1-carbonitrile

A mixture of Example 795A (0.30 g, 1.34 mmol), Et$_3$N (0.270 g, 2.68 mmol) and TMSCN (0.18 g, 2 mmol) in CH$_3$CN (10 mL) was heated under reflux overnight. More Et$_3$N (0.27 g, 2.68 mmol) and TMSCN (0.18 g, 2 mmol) were added, and the reaction mixture was heated under reflux for another 16 hours. The reaction mixture was partitioned between water and EtOAc. The aqueous layer was extracted with additional EtOAc. The combined organic layers were washed with brine, dried over MgSO$_4$, and concentrated under reduced pressure. The residue was purified by silica gel column chromatography eluting with 4:1 Hexanes/EtOAc to give 0.28 g of the title compound (90%). MS (APCI) m/e 234 (M+H)$^+$, $^1$H NMR (500 MHz, DMSO-d$_6$): ☐ 8.85 (d, J=5.62 Hz, 1H), 8.35 (d, J=7.49 Hz, 1H), 8.29-8.33 (m, 2H), 7.85 (m, 1H).

EXAMPLE 795C

The title compound was prepared by substituting Example 695D for Example 695F in Example 695G. MS (APCI) m/e 409 (M+H)$^+$.

EXAMPLE 795D

[3-(1-Cyano-isoquinolin-5-yl)-11-oxo-10,11-dihydro-5H-dibenzo[b,e][1,4]diazepin-8-yl]-acetic acid methyl ester The title compound was prepared by substituting Example 795B and Example 795C for Example 695G and Example 695K, respectively, in Example 695L. MS (APCI) m/e 435 (M+H)$^+$, $^1$H NMR (500 MHz, DMSO-d$_6$): ☐ 9.91 (s, 1H), 8.71 (d, J=5.83 Hz, 1H), 8.34 (d, J=8.59 Hz, 1H), 8.08 (d, J=6.75 Hz, 1H), 8.01-8.03 (m, 2H), 7.94 (m, 1H), 7.86 (d, J=7.98 Hz, 1H), 7.14 (d, J=1.53 Hz, 1H), 7.04 (dd, J=8.13, 1.69 Hz, 1H), 6.85-6.95 (m, 3H), 3.61 (s, 3H), 3.55 (s, 2H).

EXAMPLE 796

5-{8-[2-(4-Morpholin-4-yl-phenoxy)-ethyl]-11-oxo-10,11-dihydro-5H-dibenzo[b,e][1,4]diazepin-3-yl}-isoquinoline-1-carbonitrile The title compound was prepared by substituting Example 795B for Example 695K in Example 695L. MS (APCI) m/e 568 (M+H)$^+$, $^1$H NMR (500 MHz, DMSO-d$_6$): ☐ 9.89 (s, 1H), 8.71 (d, J=5.83 Hz, 1H), 8.34 (d, J=8.29 Hz, 1H), 8.08 (d, J=5.83 Hz, 1H), 7.93-8.02 (m, 3H), 7.86 (d, J=7.98 Hz, 1H), 7.13 (s, 1H), 7.03 (dd, J=8.13, 1.38 Hz, 1H), 6.81-6.95 (m, 7H), 4.05 (t, J=6.75 Hz, 2H), 3.70-3.72 (m, 4H), 2.96-2.98 (m, 4H), 2.88 (d, J=6.6 Hz, 2H).

EXAMPLE 797

3-Imidazo[1,5-a]pyridin-8-yl-8-[2-(4-morpholin-4-yl-phenoxy)-ethyl]-5,10-dihydro-dibenzo[b,e][1,4]diazepin-11-one

EXAMPLE 797A

N-(3-Chloro-pyridin-2-ylmethyl)-formamide

3-Chloro-pyridine-2-carbonitrile (0.4 g) was reduced by hydrogenation in the presence of RaNi (0.1 g) in THF/20% NH$_3$ (5 mL) at 30 psi. The solvent was removed and the residue was treated with 88% formic acid (10 mL) and heated at 90° C. overnight. The solvent was removed under reduced pressure, and the residue was re-dissolved in EtOAc. The organic layer was washed with Na$_2$CO$_3$, brine, dried, and concentrated. The residue was purified by silica gel column chromatography eluting with 100% EtOAc to give 0.3 g of the title compound. MS (APCI) m/e 171 (M+H)$^+$, $^1$H NMR (500 MHz, DMSO-d$_6$): ☐ 9.8.51-8.53 (m, 2H), 8.15 (s, 1H), 7.93 (d, J=7.98 Hz, 1H), 7.38 (dd, J=8.13, 4.16 Hz, 1H), 4.53 (d, J=5.52 Hz, 1H).

EXAMPLE 797B

8-Chloro-imidazo[1,5-a]pyridine

A mixture of Example 797A (0.09 g, 0.53 mmol) and POCl$_3$ (0.244 g, 1.6 mmol) in toluene (5 mL) was heated under reflux for 3 hours. After reaction mixture cooled to room temperature, it was poured onto water and separated. The organic layer was dried over MgSO₄ and concentrated. The residue was purified by silica gel column chromatography eluting with 100% EtOAc to give 0.072 g of the title compound (90%). MS (APCI) m/e 153 (M+H)⁺, ¹H NMR (500 MHz, DMSO-d₆): □ 8.51 (s, 1H), 8.36 (d, J=7.06 Hz, 1H), 7.45 (s, 1H), 6.97 (d, J=7.06 Hz, 1H), 6.67 (m, 1H).

EXAMPLE 797C

3-Imidazo[1,5-a]pyridin-8-yl-8-[2-(4-morpholin-4-yl-phenoxy)-ethyl]-5,10-dihydro-dibenzo[b,e][1,4]diazepin-11-one A mixture of Example 695G (53 mg, 0.1 mmol), Example 797B (16 mg, 0.1 mmol), Pd(OAc)2 (5.3 mg, 0.0024 mmol), CyMAP (18.7 mg, 0.048 mmol), and CsF (46 mg, 0.3 mmol) in DME (2 mL) and MeOH (1 mL) was heated under reflux for 16 hours. After the reaction mixture was cooled to room temperature, it was partitioned between water and EtOAc. The organic layer was washed with brine, dried (MgSO4), filtered, and concentrated under vacuum. The residue was purified by silica gel column chromatography eluting with 100:3:0.3 EtOAc:MeOH:NH₄OH to give 0.022 g of the title compound. MS (APCI) m/e 531 (M+H)⁺, ¹H NMR (500 MHz, DMSO-d₆): □ 9.81 (s, 1H), 8.49 (s, 1H), 8.39 (d, J=6.86 Hz, 1H), 7.96 (s, 1H), 7.80 (d, J=8.11 Hz, 1H), 7.53 (s, 1H), 7.45 (d, J=1.56 Hz, 1H), 7.22 (dd, J=8.11, 1.87 Hz, 1H), 6.90-6.95 (m, 4H), 6.76-6.87 (m, 5H), 4.04 (d, J=6.71 Hz, 2H), 3.70-3.72 (m, 4H), 2.96-2.98 (m, 4H), 2.87 (t, J=6.71 Hz, 2H).

EXAMPLE 798

3-Isoquinolin-5-yl-8-[2-(2-methyl-pyridin-3-yloxy)-ethyl]-5,10-dihydro-dibenzo[b,e][1,4]diazepin-11-one The desired product was prepared by substituting Example 791 and 2-methyl-pyridin-3-ol for Example 695E and 4-morpholinophenol, respectively, in Example 695F. MS (ESI) m/e 473 (M+H)⁺, ¹H NMR (DMSO-d₆, 500 MHz): □ 9.94 (s, 1H), 9.62 (s, 1H), 8.57 (d, J=6.10 Hz, 1H), 8.35 (m, 1H), 8.27 (d, J=4.88 Hz, 1H), 8.02 (s, 1H), 7.95 (d, J=8.54 Hz, 1H), 7.90-7.92 (m, 3H), 7.86 (d, J=8.24 Hz, 1H), 7.69 (dd, J=8.54, 5.49 Hz, 1H), 7.15 (d, J=1.22 Hz, 1H), 7.04 (dd, J=8.24, 1.53 Hz, 1H), 6.95-6.97 (m, 3H), 4.32 (t, J=6.26 Hz, 2H), 2.99 (t, J=6.41 Hz, 2H), 2.49 (s, 3H).

EXAMPLE 799

3-[2-(3-Isoquinolin-5-yl-11-oxo-10,11-dihydro-5H-dibenzo[b,e][1,4]diazepin-8-yl)-ethoxy]-pyridine-2-carbonitrile The desired product was prepared by substituting Example 791 and 3-hydroxy-pyridine-2-carbonitrile for Example 695E and 4-morpholinophenol, respectively, in Example 695F. MS (ESI) m/e 484 (M+H)⁺, ¹H NMR (DMSO-d₆, 500 MHz): □ 9.97 (s, 1H), 9.67 (s, 1H), 8.65 (d, J=6.41 Hz, 1H), 8.41 (dd, J=5.80, 3.66 Hz, 1H), 8.38 (m, 1H), 8.08 (s, 1H), 7.97-7.99 (m, 3H), 7.94 (d, J=7.93 Hz, 1H), 7.88 (d, J=7.93 Hz, 1H), 7.78 (dd, J=8.70, 4.42 Hz, 1H), 7.23 (d, J=1.53 Hz, 1H), 7.13 (dd, J=7.93, 1.53 Hz, 1H), 7.02-7.07 (m, 3H), 4.43 (t, J=6.56 Hz, 2H), 3.07 (t, J=6.56 Hz, 2H).

EXAMPLE 800

8-[2-(2-Chloro-pyridin-3-yloxy)-ethyl]-3-isoquinolin-5-yl-5,10-dihydro-dibenzo[b,e][1,4]diazepin-11-one The desired product was prepared by substituting Example 791 and 2-chloro-pyridin-3-ol for Example 695E and 4-morpholinophenol, respectively, in Example 695F. MS (ESI) m/e 493 (M+H)⁺, ¹H NMR (DMSO-d₆, 500 MHz): □ 9.91 (s, 1H), 9.58 (s, 1H), 8.55 (d, J=6.10 Hz, 1H), 8.32 (m, 1H), 7.98 (s, 1H), 7.96 (dd, J=4.73, 1.37 Hz, 1H), 7.87-7.90 (m, 3H), 7.85 (d, J=8.24 Hz, 1H), 7.58 (dd, J=8.24, 1.22 Hz, 1H), 7.37 (dd, J=8.09, 4.73 Hz, 1H), 7.14 (d, J=1.53 Hz, 1H), 7.03 (dd, J=8.09, 1.37 Hz, 1H), 6.93-6.98 (m, 3H), 4.24 (t, J=6.71 Hz, 2H), 2.97 (t, J=6.56 Hz, 2H).

EXAMPLE 801

3-(8-Amino-isoquinolin-5-yl)-8-[2-(4-morpholin-4-yl-phenoxy)-ethyl]-5,10-dihydro-dibenzo[b,e][1,4]diazepin-11-one

EXAMPLE 801A 5-bromo-8-nitroisoquinoline

5-Bromo-isoquinoline (100 mg, 0.48 mmol) was suspended in 0.58 mL of concentrated H₂SO₄. To this solution was added KNO₃ (68 mg, 0.58 mmol) in 0.48 mL of concentrated H₂SO₄. The reaction mixture was stirred at room temperature for 1.5 hours, poured into water/ice, neutralized with 2.0 M Na₂CO₃, and extracted with EtOAc three times The combined organic layers were washed brine, dried (MgSO₄), filtered and concentrated under vacuum to give 121 mg of the title product. MS (DCI) m/e 255 (M+H)⁺; ¹H NMR (500 MHz, CDCl₃) δ 10.0 (s, 1H), 9.39 (s, 1H), 8.85 (d, J=5.76 Hz, 1H), 8.17-8.22 (m, 2H), 8.12 (d, J=8.14 Hz, 1H).

EXAMPLE 801B

5-Bromo-isoquinolin-8-ylamine

A mixture of Example 801A (500 mg, 2 mmol), 5% Pt/C and acetic acid (50 mL) was equipped with a balloon of hydrogen gas and stirred at room temperature. When the reaction was complete, the solution was filtered through Celite. The mixture was treated with 50% sodium hydroxide solution until pH reached 10. Filtration provided 267 mg (60%) of the desired product as a yellow solid. MS (ESI) m/e 223 (M+H)⁺.

EXAMPLE 801C 3-(8-Amino-isoquinolin-5-yl)-8-[2-(4-morpholin-4-yl-phenoxy)-ethyl]-5,10-dihydro-dibenzo[b,e][1,4]diazepin-11-one The desired product was prepared by substituting Example 801B for Example 695K in Example 695L. MS (ESI) m/e 558 (M+H)⁺, ¹H NMR (DMSO-d₆, 500 MHz): □ 9.84 (s, 1H), 9.75 (s, 1H), 8.37 (d, J=6.71 Hz, 1H), 7.92-7.95 (m, 2H), 7.80 (d, J=7.93 Hz, 1H), 7.77 (d, J=8.24 Hz, 1H), 7.25 (br s, 2H), 7.03-7.06 (m, 2H), 6.87-6.94 (m, 6H), 6.82-6.85 (m, 2H), 4.04 (t, J=6.56 Hz, 2H), 3.71-3.73 (m, 4H), 2.97-2.99 (m, 4H), 2.87 (t, J=6.71 Hz, 2H).

EXAMPLE 802

8-[2-(2-Bromo-pyridin-3-yloxy)-ethyl]-3-isoquinolin-5-yl-5,10-dihydro-dibenzo[b,e][1,4]diazepin-11-one The desired product was prepared by substituting Example 791 and 2-bromo-pyridin-3-ol for Example 695E and 4-morpholinophenol, respectively, in Example 695F. MS (ESI) m/e 537 (M+H)$^+$, $^1$H NMR (DMSO-d$_6$, 400 MHz): ☐ 9.86 (s, 1H), 9.40 (s, 1H), 8.51 (d, J=5.83 Hz, 1H), 8.20 (d, J=7.06 Hz, 1H), 7.94 (br s, 2H), 7.84 (d, J=8.29 Hz, 1H), 7.74-7.79 (m, 2H), 7.71 (d, J=5.83 Hz, 1H), 7.51 (d, J=8.59 Hz, 1H), 7.37 (dd, J=8.29, 4.60 Hz, 1H), 7.14 (d, J=1.23 Hz, 1H), 7.02 (dd, J=8.13, 1.07 Hz, 1H), 6.92-6.99 (m, 3H), 4.23 (t, J=6.44 Hz, 2H), 2.96 (t, J=6.44 Hz, 2H).

EXAMPLE 803

3-Isoquinolin-5-yl-8-[2-(4-[1,2,3]thiadiazol-4-yl-phenoxy)-ethyl]-5,10-dihydro-dibenzo[b,e][1,4]diazepin-11-one The desired product was prepared by substituting Example 791 and 4-[1,2,3]thiadiazol-4-yl-phenol for Example 695E and 4-morpholinophenol, respectively, in Example 695F. MS (ESI) m/e 542 (M+H)$^+$, $^1$H NMR (DMSO-d$_6$, 400 MHz): ☐ 9.88 (s, 1H), 9.51 (s, 1H), 9.47 (s, 1H), 8.54 (d, J=6.24 Hz, 1H), 8.27 (dd, J=6.08, 3.28 Hz, 1H), 8.04-8.07 (m, 2H), 7.96 (s, 1H), 7.82-7.86 (m, 4H), 7.15 (d, J=1.56 Hz, 1H), 7.12 (m, 1H), 7.10 (m, 1H), 7.03 (dd, J=7.96, 1.72 Hz, 1H), 6.99 (s, 1H), 6.94-6.96 (br s, 2H), 4.22 (t, J=6.71 Hz, 2H), 2.96 (t, J=6.55 Hz, 2H).

EXAMPLE 804

3-Isoquinolin-5-yl-8-[2-(2-oxo-2H-pyridin-1-yl)-ethyl]-5,10-dihydro-dibenzo[b,e][1,4]diazepin-11-one The desired product was prepared by substituting Example 791 and pyridin-2-ol for Example 695E and 4-morpholinophenol, respectively, in Example 695F. MS (ESI) m/e 459 (M+H)$^+$, $^1$H NMR (DMSO-d$_6$, 400 MHz): ☐ 9.86 (s, 1H), 9.65 (s, 1H), 8.56 (d, J=6.14 Hz, 1H), 8.30 (m, 1H), 7.97 (s, 1H), 7.85-7.87 (m, 4H), 7.54 (dd, J=6.75, 1.84 Hz, 1H), 7.38 (m, 1H), 7.14 (d, J=1.53 Hz, 1H), 7.03 (dd, J=8.13, 1.38 Hz, 1H), 6.87-6.91 (m, 2H), 6.80 (dd, J=7.83, 1.99 Hz, 1H), 6.38 (d, J=8.59 Hz, 1H), 6.14 (m, 1H), 4.03 (t, J=7.52 Hz, 2H), 2.82 (t, J=7.67 Hz, 2H).

EXAMPLE 805

3-Isoquinolin-5-yl-8-[2-(pyridin-2-yloxy)-ethyl]-5,10-dihydro-dibenzo[b,e][1,4]diazepin-11-one The desired product was obtained as a side product from Example 804. MS (ESI) m/e 459 (M+H)$^+$, $^1$H NMR (DMSO-d$_6$, 400 MHz): ☐ 9.88 (s, 1H), 9.65 (s, 1H), 8.58 (d, J=6.44 Hz, 1H), 8.37 (dd, J=6.75, 2.46 Hz, 1H), 8.15 (dd, J=5.06, 1.99 Hz, 1H), 7.90-7.97 (m, 4H), 7.86 (d, J=7.98 Hz, 1H), 7.69 (m, 1H), 7.14 (d, J=1.53 Hz, 1H), 7.03 (dd, J=7.98, 1.53 Hz, 1H), 6.95-6.98 (m, 2H), 6.89-6.92 (m, 2H), 6.79 (m, 1H), 4.40 (t, J=6.90 Hz, 2H), 2.91 (t, J=6.75 Hz, 2H).

EXAMPLE 806

2-(3-Isoquinolin-5-yl-11-oxo-10,11-dihydro-5H-dibenzo[b,e][1,4]diazepin-8-yl)-2-methyl-propionic acid methyl ester The desired product was prepared by substituting 5-bromo-isoquinoline and Example 747F for Example 695K and Example 695G, respectively, in Example 695L. MS (ESI) m/e 438 (M+H)$^+$, $^1$H NMR (DMSO-d$_6$, 400 MHz): ☐ 9.84 (s, 1H), 9.40 (s, 1H), 8.52 (d, J=5.83 Hz, 1H), 8.20 (d, J=7.36 Hz, 1H), 8.00 (s, 1H), 7.84 (d, J=7.98 Hz, 1H), 7.75-7.80 (m, 2H), 7.72 (d, J=5.83 Hz, 1H), 7.14 (d, J=1.53 Hz, 1H), 7.03 (dd, J=8.13, 1.69 Hz, 1H), 6.99 (d, J=1.84 Hz, 1H), 6.92-6.96 (m, 2H), 3.59 (s, 3H), 1.45 (s, 6H).

EXAMPLE 807

[3-(8-Chloro-isoquinolin-5-yl)-11-oxo-10,11-dihydro-5H-dibenzo[b,e][1,4]diazepin-8-yl]-acetic acid methyl ester

EXAMPLE 807A

5-Bromo-8-chloro-isoquinoline

Example 801B (238 mg, 1.07 mmol) was dissolved in concentrated HCl (1 mL) and water (1 mL). This solution was diazotized at 0° C. with sodium nitrite (90 mg, 1.3 mmol) dissolved in water (1 mL). The resulting solution was slowly added to a solution of cuprous chloride (167 mg, 1.69 mmol) in HCl (2 mL) at 75° C. The resulting mixture was stirred at room temperature for 18 hours, and then made basic by addition of 50% NaOH solution. Partitioned between ethyl acetate and water. Combined organic layers were washed with water and brine, dried (MgSO$_4$), and concentrated under vacuum. The residue was purified by flash column chromatography on silica gel with 3:2 hexanes/ethyl acetate to provide 57 mg (22%) of the desired product. MS (ESI) m/e 242 (M+H)$^+$.

EXAMPLE 807B

[3-(8-Chloro-isoquinolin-5-yl)-11-oxo-10,11-dihydro-5H-dibenzo[b,e][1,4]diazepin-8-yl]-acetic acid methyl ester The desired product was prepared by substituting Example 807A and Example 795C for Example 695K and Example 695G, respectively, in Example 695L. MS (ESI) m/e 444 (M+H)$^+$, $^1$H NMR (DMSO-d$_6$, 400 MHz): ☐ 9.90 (s, 1H), 9.65 (s, 1H), 8.66 (d, J=5.83 Hz, 1H), 8.01 (s, 1H), 7.92 (d, J=7.67 Hz, 1H), 7.85 (d, J=7.98 Hz, 1H), 7.76 (d, J=5.83 Hz, 1H), 7.73 (d, J=7.67 Hz, 1H), 7.13 (d, J=1.53 Hz, 1H), 7.02 (dd, J=7.98, 1.53 Hz, 1H), 6.90-6.95 (m, 2H), 6.86 (m, 1H), 3.61 (s, 3H), 3.55 (s, 2H).

EXAMPLE 808

2-(3-Isoquinolin-5-yl-11-oxo-10,11-dihydro-5H-dibenzo[b,e][1,4]diazepin-8-yl)-2-methyl-propionic acid A mixture of Example 806 (85 mg, 0.2 mmol) and LiOH.H$_2$O (42 mg, 1 mmol) in THF (3 mL) and water (5 mL) was heated under reflux for 6 hours. After the reaction mixture cooled to room temperature, it was neutralized to pH=6. The solution was extracted with EtOAc three times, and combined organic layers were washed with brine, dried (MgSO4), filtered, and concentrated under vacuum to give the title compound. MS (ESI) m/e 424 (M+H)$^+$, $^1$H NMR (DMSO-d$_6$, 500 MHz): □ 9.85 (s, 1H), 9.56 (s, 1H), 8.55 (br s, 1H), 8.30 (dd, J=6.08, 3.28 Hz, 1H), 7.99 (s, 1H), 7.85-7.88 (m, 4H), 7.14 (d, J=1.87 Hz, 1H), 7.05 (s, 1H), 7.03 (dd, J=7.96, 1.72 Hz, 1H), 6.95 (d, J=1.25 Hz, 2H), 1.42 (s, 6H).

EXAMPLE 809

8-(2-Hydroxy-1,1-dimethyl-ethyl)-3-isoquinolin-5-yl-5,10-dihydro-dibenzo[b,e][1,4]diazepin-11-one The desired product was prepared by substituting Example 806 for Example 695D in Example 695E. MS (ESI) m/e 410 (M+H)$^+$, $^1$H NMR (DMSO-d$_6$, 500 MHz): □ 9.77 (s, 1H), 9.58 (s, 1H), 8.56 (d, J=6.24 Hz, 1H), 8.32 (m, 1H), 7.92 (s, 1H), 7.87-7.89 (m, 3H), 7.85 (d, J=8.11 Hz, 1H), 7.13 (d, J=1.56 Hz, 1H), 7.01-7.04 (m, 2H), 6.90-6.97 (m, 2H), 4.01 (br s, 1H), 3.34 (s, 2H), 1.17 (s, 6H).

EXAMPLE 810

2-(3-Isoquinolin-5-yl-11-oxo-10,11-dihydro-5H-dibenzo[b,e][1,4]diazepin-8-yl)-N-(4-morpholin-4-yl-phenyl)-isobutyramide Example 808 (85 mg, 0.2 mmol), 4-morpholinoaniline (47 mg, 0.26 mmol), triethylamine (27 mg, 0.26 mmol), and O-(7-azabenzotriazol-1-yl)-N,N,N',N'-tetramethyluronium hexafluorophosphate (HATU; 99 mg, 0.26 mmol) were dissolved in DMF (2 mL) and stirred at room temperature overnight. The reaction was partitioned between water and EtOAc. The aqueous layer was extracted with additional EtOAc. The combined organic layers were washed with brine, dried (MgSO4), filtered, and concentrated under vacuum. The residue was purified by silica gel column chromatography eluting with 100:3:0.3 EtOAc:MeOH:NH$_4$OH to give 0.052 g of the title compound. MS (ESI) m/e 584 (M+H)$^+$, $^1$H NMR (DMSO-d$_6$, 400 MHz): □ 9.89 (s, 1H), 9.60 (s, 1H), 8.80 (s, 1H), 8.56 (d, J=6.44 Hz, 1H), 8.33 (t, J=4.91 Hz, 1H), 7.99 (s, 1H), 7.88 (d, J=5.22 Hz, 2H), 7.85 (d, J=7.98 Hz, 1H), 7.40-7.44 (m, 2H), 7.14 (d, J=1.84 Hz, 1H), 7.07 (m, 1H), 7.02 (dd, J=7.98, 1.84 Hz, 1H), 6.95 (br s, 2H), 6.84-6.90 (m, 3H), 3.71-3.73 (m, 4H), 3.02-3.04 (m, 4H), 1.50 (s, 6H).

EXAMPLE 811

3-(8-Fluoro-isoquinolin-5-yl)-8-[2-(4-morpholin-4-yl-phenoxy)-ethyl]-5,10-dihydro-dibenzo[b,e][1,4]diazepin-11-one

EXAMPLE 811A

5-Bromo-8-fluoro-isoquinoline

A mixture of 5-bromo-2-fluorobenzaldehyde (15 g, 74 mmol) and 2,2-dimethoxy-ethylamine (7.77 g, 74 mmol) in toluene (142 mL) was heated to reflux for 30 minutes using a Dean-Stark trap to remove water. The solution was then concentrated under vacuum to provide 5-bromo-2-fluorobenzylidene-2,2-dimethoxyethylamine. 5-Bromo-2-fluorobenzylidene-2,2-dimethoxyethylamine and cold concentrated sulfuric acid (28 mL) were added separately, dropwise, over a period of 20 minutes to concentrated sulfuric acid (83 mL) at 140° C. The mixture was stirred at 135° C. for 30 minutes, allowed to cool, and carefully poured onto ice. Filtered to remove solids and the mixture was washed with dichloromethane. The aqueous layer was made basic by cautious addition of 50% sodium hydroxide solution, and extracted with diethyl ether. Combined ether layers were dried (MgSO$_4$), filtered and concentrated under vacuum to provide 310 mg (2%) of the desired product. MS (ESI) m/e 226 (M+H)$^+$.

EXAMPLE 811B 3-(8-Fluoro-isoquinolin-5-yl)-8-[2-(4-morpholin-4-yl-phenoxy)-ethyl]-5,10-dihydro-dibenzo[b,e][1,4]diazepin-11-one The desired product was obtained by substituting Example 811A for Example 695K in Example 695L. MS (ESI) m/e 561 (M+H)$^+$, $^1$H NMR (DMSO-d$_6$, 500 MHz): □ 9.85 (s, 1H), 9.58 (s, 1H), 8.694 (d, J=6.24 Hz, 1H), 7.93 (s, 1H), 7.83 (d, 8.11 Hz, 1H), 7.77-7.79 (m, 2H), 7.60 (m, 1H), 7.11 (d, J=1.56 Hz, 1H), 6.99 (dd, J=7.95, 1.72 Hz, 1H), 6.85-6.96 (m, 7H), 4.05 (t, J=6.71 Hz, 2H), 3.73-3.75 (m, 4H), 3.03-3.05 (m, 4H), 2.87 (t, J=6.71 Hz, 2H).

EXAMPLE 812

3-Isoquinolin-5-yl-8-[2-(4-[1,2,4]triazol-1-yl-phenoxy)-ethyl]-5,10-dihydro-dibenzo[b,e][1,4]diazepin-11-one The desired product was prepared by substituting Example 791 and 4-[1,2,4]triazol-1-yl-phenol for Example 695E and 4-morpholinophenol, respectively, in Example 695F. MS (ESI) m/e 525 (M+H)$^+$, $^1$H NMR (DMSO-d$_6$, 500 MHz): □ 9.90 (s, 1H), 9.65 (s, 1H), 9.15 (s, 1H), 8.58 (d, J=6.14 Hz, 1H), 8.37 (dd, J=6.60, 2.61 Hz, 1H), 8.18 (d, 1H), 7.99 (s, 1H), 7.91-7.95 (m, 3H), 7.86 (d, J=7.98 Hz, 1H), 7.74 (d, J=8.90 Hz, 2H), 7.15 (d, J=1.23 Hz, 1H), 7.12 (m, 1H), 7.10 (m, 1H), 7.03 (dd, J=7.98, 1.53 Hz, 1H), 6.99 (m, 1H), 6.95 (br, s, 2H), 4.19 (t, J=6.60 Hz, 2H), 2.95 (t, J=6.60 Hz, 2H).

EXAMPLE 813

8-[2-(2-Fluoro-phenoxy)-ethyl]-3-isoquinolin-5-yl-5,10-dihydro-dibenzo[b,e][1,4]diazepin-11-one The desired product was prepared by substituting Example 791 and 2-fluoro-phenol for Example 695E and 4-morpholinophenol, respectively, in Example 695F. MS (ESI) m/e 476 (M+H)$^+$, $^1$H NMR (DMSO-d$_6$, 500 MHz): □ 9.88 (s, 1H), 9.42 (s, 1H), 8.52 (d, J=6.10 Hz, 1H), 8.21 (d, J=7.63 Hz, 1H), 7.96 (s, 1H), 7.84 (d, J=7.93 Hz, 1H), 7.76-7.80 (m, 2H), 7.73 (d, J=6.10 Hz, 1H), 7.14-7.21 (m, 3H), 7.11 (m, 1H), 7.03 (dd, J=7.93, 1.53 Hz, 1H), 6.91-6.97 (m, 4H), 4.19 (t, J=6.87 Hz, 2H), 2.94 (t, J=6.87 Hz, 2H).

EXAMPLE 814

2-[2-(3-Isoquinolin-5-yl-11-oxo-10,11-dihydro-5H-dibenzo[b,e][1,4]diazepin-8-yl)-ethoxy]-benzonitrile The desired product was prepared by substituting Example 791 and 2-hydroxy-benzonitrile for Example 695E and 4-morpholinophenol, respectively, in Example 695F. MS (ESI) m/e 483 (M+H)$^+$, $^1$H NMR (DMSO-d$_6$, 500 MHz): □ 9.86 (s, 1H), 9.58 (s, 1H), 8.59 (d, J=6.24 Hz, 1H), 8.33 (t, J=4.84 Hz, 1H), 8.00 (s, 1H), 7.88-7.91 (m, 4H), 7.75 (dd, J=7.64, 1.72 Hz, 1H), 7.68 (m, 1H), 7.29 (d, J=8.42 Hz, 1H), 7.18 (d, J=1.56 Hz, 1H), 7.12 (m, 1H), 7.07 (dd, J=7.96, 1.72 Hz, 1H), 6.97-7.03 (m, 3H), 4.31 (t, J=6.71 Hz, 2H), 3.01 (t, J=6.55 Hz, 2H).

EXAMPLE 815

3-(3H-Benzoimidazol-4-yl)-8-[2-(4-morpholin-4-yl-phenoxy)-ethyl]-5,10-dihydro-dibenzo[b,e][1,4]diazepin-11-one

EXAMPLE 815A

1-Bromo-2-methoxy-3-nitro-benzene

2-Bromo-6-nitrophenol (5.1 g, 23.4 mmol) was dissolved in DMF (60 mL), then 95% NaH (900 mg, 35.6 mmol) was added in a few portions, followed by the addition of iodomethane (3.0 mL, 6.8 g, 48.5 mmol). The reaction was stirred at room temperature overnight, then heated at 50° C. for 3 hours. The reaction was cooled, poured into water, and the solids filtered off and dried. The product (5.5 g, 100%) was recovered as tan solids. $^1$H NMR (300 MHz, DMSO-$d_6$) δ 8.02 (dd, J=8.1, 1.7 Hz, 1H), 7.96 (dd, J=8.1, 1.7 Hz, 1H), 7.83 (dd, 8.1, 8.1 Hz, 1H), 3.92 (s, 3H).

EXAMPLE 815B

2-Bromo-6-nitro-phenylamine

The compound described in Example 815A (1.1 g, 4.7 mmol) was slurried in 7.0N $NH_3$ in MeOH (45 mL), then heated at 120° C. in a sealed tube overnight. The reaction was then cooled, concentrated under vacuum, and the residue partitioned between $Et_2O$ and 2M $Na_2CO_3$ The organic layer was washed with brine, dried ($Na_2SO_4$), filtered, and concentrated under vacuum to give the product (0.49 g, 48%) as bright orange solids. MS (DCI) m/e 216 & 218 (M+H)$^+$; $^1$H NMR (300 MHz, DMSO-$d_6$) δ 8.06 (dd, J=8.5, 1.4 Hz, 1H), 7.86 (dd, J=7.8, 1.4 Hz, 1H), 7.15 (br s, 2H), 6.66 (dd, J=8.5, 7.8 Hz, 1H).

EXAMPLE 815C

3-Bromo-benzene-1,2-diamine

The title compound was prepared by substituting Example 815B for Example 695B in Example 695C. MS (DCI) m/e 187 & 189 (M+H)$^+$; $^1$H NMR (300 MHz, DMSO-$d_6$) δ 6.66 (dd, J=7.8, 1.4 Hz, 1H), 6.51 (dd, J=7.8, 1.4 Hz, 1H), 6.31 (dd, 7.8, 7.8 Hz, 1H), 4.76 (v br s, 4H)

EXAMPLE 815D

1-Benzyl-4-bromo-1H-benzoimidazole

The compound described in Example 815C was coverted to the benzimidazole by the method found in J. Med. Chem., 35, 847 (1992), then treated with NaH and benzyl bromide in THF to give the title compound as a mix of regioisomers. MS (DCI) m/e 287 & 289 (M+H)$^+$.

EXAMPLE 815E 3-(3H-Benzimidazol-4-yl)-8-[2-(4-morpholin-4-yl-phenoxy)-ethyl]-5,10-dihydro-dibenzo[b,e][1,4]diaz-epin-11-one Substituting Example 815D for Example 695K in Example 695L, the crude biaryl compound was prepared and the benzyl group was removed using ammonium formate and palladium on carbon in MeOH at reflux for 3 hours. Purification was done using preparative HPLC. MS (ESI) m/e 532 (M+H)$^+$. $^1$H NMR (400 MHz, DMSO-$d_6$) δ 9.83 (s, 1H), 9.11 (br s, 1H), 7.93 (s, 1H), 7.83 (d, J=8.0 Hz, 1H), 7.78 (d, J=7.4 Hz, 1H), 7.53 (m, 2H), 7.41 (s, 1H), 7.29 (d, J=8.0 Hz, 1H), 6.94 (m, 5H), 6.84 (d, J=9.2 Hz, 2H), 4.05 (t, J=6.7 Hz, 2H), 3.73 (m, 4H), 3.00 (m, 4H), 2.87 (t, J=6.7 Hz, 2H).

EXAMPLE 816

3-(6-Benzyl-6H-pyrrolo[2,3-c]pyridin-3-yl)-8-[2-(4-morpholin-4-yl-phenoxy)-ethyl]-5,10-dihydro-dibenzo[b,e][1,4]diazepin-11-one

EXAMPLE 816A

6-Benzyl-3-bromo-6H-pyrrolo[2,3-c]pyridine

The title compound was isolated as a by-product from Example 696A. MS (DCI) m/e 287 & 289 (M+H)$^+$, $^1$H NMR (300 MHz, DMSO-$d_6$): □ 8.98 (s, 1H), 8.01 (s, 1H), 7.90 (dd, J=6.71, 1.22 Hz, 1H), 7.46 (d, J=6.41 Hz, 1H), 7.34-7.42 (m, 5H), 5.60 (s, 2H).

EXAMPLE 816B 3-(6-Benzyl-6H-pyrrolo[2,3-c]pyridin-3-yl)-8-[2-(4-morpholin-4-yl-phenoxy)-ethyl]-5,10-dihydro-dibenzo[b,e][1,4]diazepin-11-one The title compound was prepared by substituting Example 816A for Example 696A in Example 696B. MS (APCI) m/e 622 (M+H)$^+$, $^1$H NMR (500 MHz, DMSO-$d_6$): □ 9.81 (s, 1H), 9.52 (s, 1H), 8.77 (d, J=2.75, 1H), 8.64 (m, 1H), 8.42 (d, J=6.71 Hz, 1H), 7.94 (s, 1H), 7.79 (d, J=8.24 Hz, 1H), 7.39-7.51 (m, 6H), 7.30 (dd, J=8.24, 1.53 Hz, 1H), 6.81-6.94 (m, 7H), 5.91 (s, 2H), 4.04 (t, J=6.71 Hz, 2H), 3.70-3.72 (m, 4H), 2.96-2.98 (m, 4H), 2.87 (t, J=6.56 Hz, 2H).

EXAMPLE 817

4-{8-[2-(4-Morpholin-4-yl-phenoxy)-ethyl]-11-oxo-10,11-dihydro-5H-dibenzo[b,e][1,4]diazepin-3-yl}-nicotinamide

EXAMPLE 817A

4-{8-[2-(4-Morpholin-4-yl-phenoxy)-ethyl]-11-oxo-10,11-dihydro-5H-dibenzo[b,e][1,4]diazepin-3-yl}-nicotinic acid methyl ester The title compound was prepared by substituting 4-chloro-nicotinic acid methyl ester for Example 695K in Example 695L. MS (DCI) m/e 551 (M+H)$^+$.

EXAMPLE 817B

4-{8-[2-(4-Morpholin-4-yl-phenoxy)-ethyl]-11-oxo-10,11-dihydro-5H-dibenzo[b,e][1,4]diazepin-3-yl}-nicotinamide Example 817A (30 mg) in 10 mL of 7 N $NH_3$ in MeOH was heated in a sealed tube at 90° C. for 24 h. The solvent was removed and the residue was purified by reverse phase prep HPLC to give the desired product. MS (DCI) m/e 536 (M+H)$^+$, $^1$H NMR (500 MHz, DMSO-$d_6$): □ 9.87 (s, 1H), 8.68-8.71 (m, 2H), 7.98 (s, 1H), 7.95 (s, 1H), 7.71 (d, J=7.93 Hz, 1H), 7.61 (s, 1H), 7.50 (d, J=2.44 Hz, 1H), 7.46 (m, 1H), 7.08 (d, J=1.53 Hz, 1H), 6.87-7.00 (m, 7H), 4.05 (t, J=6.71 Hz, 2H), 3.75-3.77 (m, 4H), 3.07-3.09 (m, 4H), 2.87 (t, J=6.71 Hz, 2H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

For example, the following compounds can be prepared using the synthetic methodology described herein or by using synthetic methodology known to those of skill in the art.

8-[2-(1H-imidazol-1-yl)ethyl]-3-[3-methoxy-4-(1,3-thiazol-4-ylmethoxy)phenyl]-5,10-dihydro-1H-dibenzo[b,e][1,4]diazepin-11-one;

8-[2-(4-bromo-1H-imidazol-1-yl)ethyl]-3-[3-methoxy-4-(1,3-thiazol-4-ylmethoxy)phenyl]-5,10-dihydro-11H-dibenzo[b,e][1,4]diazepin-11-one;

4-[1-(2-{3-[3-methoxy-4-(1,3-thiazol-4-ylmethoxy)phenyl]-11-oxo-10,11-dihydro-5H-dibenzo[b,e][1,4]diazepin-8-yl}ethyl)-1H-imidazol-4-yl]benzonitrile;

3-[3-methoxy-4-(1,3-thiazol-4-ylmethoxy)phenyl]-8-[2-(4-phenyl-1H-imidazol-1-yl)ethyl]-5,10-dihydro-11H-dibenzo[b,e][1,4]diazepin-11-one;

[1-(2-{3-[3-methoxy-4-(1,3-thiazol-4-ylmethoxy)phenyl]-11-oxo-10,11-dihydro-5H-dibenzo[b,e][1,4]diazepin-8-yl}ethyl)-1H-imidazol-4-yl]acetonitrile;

8-{2-[4-(4-methoxyphenyl)-1H-imidazol-1-yl]ethyl}-3-[3-methoxy-4-(1,3-thiazol-4-ylmethoxy)phenyl]-5,10-dihydro-11H-dibenzo[b,e][1,4]diazepin-11-one;

8-[2-(5-bromo-1H-imidazol-1-yl)ethyl]-3-[3-methoxy-4-(1,3-thiazol-4-ylmethoxy)phenyl]-5,10-dihydro-11H-dibenzo[b,e][1,4]diazepin-11-one;

4-[1-(2-{3-[3-methoxy-4-(1,3-thiazol-4-ylmethoxy)phenyl]-11-oxo-10,11-dihydro-5H-dibenzo[b,e][1,4]diazepin-8-yl}ethyl)-1H-imidazol-5-yl]benzonitrile;

8-[2-(2-bromo-1H-imidazol-1-yl)ethyl]-3-[3-methoxy-4-(1,3-thiazol-4-ylmethoxy)phenyl]-5,10-dihydro-11H-dibenzo[b,e][1,4]diazepin-11-one;

3-[3-methoxy-4-(1,3-thiazol-4-ylmethoxy)phenyl]-8-[2-(2-methyl-1H-imidazol-1-yl)ethyl]-5,10-dihydro-11H-dibenzo[b,e][1,4]diazepin-11-one;

3-[3-methoxy-4-(1,3-thiazol-4-ylmethoxy)phenyl]-8-[2-(2-phenyl-1H-imidazol-1-yl)ethyl]-5,10-dihydro-11H-dibenzo[b,e][1,4]diazepin-11-one;

8-[2-(4-bromo-1H-pyrazol-1-yl)ethyl]-3-[3-methoxy-4-(1,3-thiazol-4-ylmethoxy)phenyl]-5,10-dihydro-11H-dibenzo[b,e][1,4]diazepin-11-one;

4-[1-(2-{3-[3-methoxy-4-(1,3-thiazol-4-ylmethoxy)phenyl]-11-oxo-10,11-dihydro-5H-dibenzo[b,e][1,4]diazepin-8-yl}ethyl)-1H-pyrazol-4-yl]benzonitrile;

3-[3-methoxy-4-(1,3-thiazol-4-ylmethoxy)phenyl]-8-[2-(4-methyl-1H-pyrazol-1-yl)ethyl]-5,10-dihydro-11H-dibenzo[b,e][1,4]diazepin-11-one;

3-[3-methoxy-4-(1,3-thiazol-4-ylmethoxy)phenyl]-8-[2-(1H-pyrazol-1-yl)ethyl]-5,10-dihydro-1H-dibenzo[b,e][1,4]diazepin-11-one;

3-[3-methoxy-4-(1,3-thiazol-4-ylmethoxy)phenyl]-8-[2-(1H-pyrrol-1-yl)ethyl]-5,10-dihydro-1H-dibenzo[b,e][1,4]diazepin-11-one;

8-[2-(4-bromo-3,5-dimethyl-1H-pyrazol-1-yl)ethyl]-3-[3-methoxy-4-(1,3-thiazol-4-ylmethoxy)phenyl]-5,10-dihydro-11H-dibenzo[b,e][1,4]diazepin-11-one;

8-{2-[4-(4-fluorophenyl)-1H-imidazol-1-yl]ethyl}-3-[3-methoxy-4-(1,3-thiazol-4-ylmethoxy)phenyl]-5,10-dihydro-11H-dibenzo[b,e][1,4]diazepin-11-one;

3-[3-methoxy-4-(1,3-thiazol-4-ylmethoxy)phenyl]-8-(2-{4-[4-(trifluoromethyl)phenyl]-1H-imidazol-1-yl}ethyl)-5,10-dihydro-11H-dibenzo[b,e][1,4]diazepin-11-one;

3-[3-methoxy-4-(1,3-thiazol-4-ylmethoxy)phenyl]-8-[2-(4-nitro-1H-imidazol-1-yl)ethyl]-5,10-dihydro-1H-dibenzo[b,e][1,4]diazepin-11-one;

3-[3-methoxy-4-(1,3-thiazol-4-ylmethoxy)phenyl]-8-{2-[4-(4-methylphenyl)-1H-imidazol-1-yl]ethyl}-5,10-dihydro-11H-dibenzo[b,e][1,4]diazepin-11-one;

3-[3-methoxy-4-(1,3-thiazol-4-ylmethoxy)phenyl]-8-(2-{4-[4-(trifluoromethoxy)phenyl]-1H-imidazol-1-yl}ethyl)-5,10-dihydro-11H-dibenzo[b,e][1,4]diazepin-11-one;

8-[2-(4-bromo-3-methyl-1H-pyrazol-1-yl)ethyl]-3-[3-methoxy-4-(1,3-thiazol-4-ylmethoxy)phenyl]-5,10-dihydro-11H-dibenzo[b,e][1,4]diazepin-11-one;

8-[2-(4-iodo-1H-pyrazol-1-yl)ethyl]-3-[3-methoxy-4-(1,3-thiazol-4-ylmethoxy)phenyl]-5,10-dihydro-11H-dibenzo[b,e][1,4]diazepin-11-one;

ethyl 1-(2-{3-[3-methoxy-4-(1,3-thiazol-4-ylmethoxy)phenyl]-1-oxo-10,11-dihydro-5H-dibenzo[b,e][1,4]diazepin-8-yl}ethyl)-1H-pyrazole-4-carboxylate;

8-{2-[4-(hydroxymethyl)-1H-imidazol-1-yl]ethyl}-3-[3-methoxy-4-(1,3-thiazol-4-ylmethoxy)phenyl]-5,10-dihydro-11H-dibenzo[b,e][1,4]diazepin-11-one;

8-[2-(2,4-dimethyl-1H-pyrrol-1-yl)ethyl]-3-[3-methoxy-4-(1,3-thiazol-4-ylmethoxy)phenyl]-5,10-dihydro-11H-dibenzo[b,e][1,4]diazepin-11-one;

3-[3-methoxy-4-(1,3-thiazol-4-ylmethoxy)phenyl]-8-[2-(4-pyridin-4-yl-1H-imidazol-1-yl)ethyl]-5,10-dihydro-11H-dibenzo[b,e][1,4]diazepin-11-one;

3-[3-methoxy-4-(1,3-thiazol-4-ylmethoxy)phenyl]-8-[2-(4-pyrimidin-2-yl-1H-imidazol-1-yl)ethyl]-5,10-dihydro-11H-dibenzo[b,e][1,4]diazepin-11-one;

3-[3-methoxy-4-(1,3-thiazol-4-ylmethoxy)phenyl]-8-{2-[4-(4-methylphenyl)piperazin-1-yl]ethyl}-5,10-dihydro-11H-dibenzo[b,e][1,4]diazepin-11-one;

3-[3-methoxy-4-(1,3-thiazol-4-ylmethoxy)phenyl]-8-{2-[4-(4-nitrophenyl)piperazin-1-yl]ethyl}-5,10-dihydro-11H-dibenzo[b,e][1,4]diazepin-11-one;

4-[4-(2-{3-[3-methoxy-4-(1,3-thiazol-4-ylmethoxy)phenyl]-11-oxo-10,11-dihydro-5H-dibenzo[b,e][1,4]diazepin-8-yl}ethyl)piperazin-1-yl]benzonitrile;

3-[3-methoxy-4-(1,3-thiazol-4-ylmethoxy)phenyl]-8-[2-(4-pyrimidin-2-ylpiperazin-1-yl)ethyl]-5,10-dihydro-11H-dibenzo[b,e][1,4]diazepin-11-one;

3-[3-methoxy-4-(1,3-thiazol-4-ylmethoxy)phenyl]-8-[2-(4-pyridin-4-ylpiperazin-1-yl)ethyl]-5,10-dihydro-11H-dibenzo[b,e][1,4]diazepin-11-one;

8-{2-[4-(4-chlorobenzyl)piperazin-1-yl]ethyl}-3-[3-methoxy-4-(1,3-thiazol-4-ylmethoxy)phenyl]-5,10-dihydro-11H-dibenzo[b,e][1,4]diazepin-11-one;

4-[4-(2-{3-[3-methoxy-4-(1,3-thiazol-4-ylmethoxy)phenyl]-11-oxo-10,11-dihydro-5H-dibenzo[b,e][1,4]diazepin-8-yl}ethyl)piperazin-1-yl]benzonitrile;

8-[2-(4-benzoylpiperazin-1-yl)ethyl]-3-[3-methoxy-4-(1,3-thiazol-4-ylmethoxy)phenyl]-5,10-dihydro-11H-dibenzo[b,e][1,4]diazepin-11-one;

8-[2-(4-benzylpiperazin-1-yl)ethyl]-3-[3-methoxy-4-(1,3-thiazol-4-ylmethoxy)phenyl]-5,10-dihydro-1H-dibenzo[b,e][1,4]diazepin-11-one;

8-{2-[4-(cyclohexylmethyl)piperazin-1-yl]ethyl}-3-[3-methoxy-4-(1,3-thiazol-4-ylmethoxy)phenyl]-5,10-dihydro-11H-dibenzo[b,e][1,4]diazepin-11-one;

8-{2-[4-(4-methoxybenzyl)piperazin-1-yl]ethyl}-3-[3-methoxy-4-(1,3-thiazol-4-ylmethoxy)phenyl]-5,10-dihydro-11H-dibenzo[b,e][1,4]diazepin-11-one; and 8-{2-[4-(2-ethoxyethyl)piperazin-1-yl]ethyl}-3-[3-methoxy-4-(1,3-thiazol-4ylmethoxy)phenyl]-5,10-dihydro-11H-dibenzo[b,e][1,4]diazepin-11-one.

What is claimed is:

1. A pharmaceutical composition comprising 2-[3-(3-methoxy-4-nitrophenyl)-11-oxo-10,11-dihydro-5H-dibenzo[b,e][1,4]diazepin-8-yl]-2-methyl-N-(4-morpholin-4-ylphenyl)propanamide, or a therapeutically acceptable salt thereof in combination with a therapeutically acceptable carrier.

2. The compound 2-[3-(3-methoxy-4-nitrophenyl)-11-oxo-10,11-dihydro-5H-dibenzo[b,e][1,4]diazepin-8-yl]-2-methyl-N-(4-morpholin-4-ylphenyl)propanamide, or a therapeutically acceptable salt thereof.

* * * * *

UNITED STATES PATENT AND TRADEMARK OFFICE
CERTIFICATE OF CORRECTION

| | |
|---|---|
| PATENT NO. | : 7,456,169 B2 |
| APPLICATION NO. | : 11/466638 |
| DATED | : November 25, 2008 |
| INVENTOR(S) | : Lisa A. Hasvold et al. |

It is certified that error appears in the above-identified patent and that said Letters Patent is hereby corrected as shown below:

Column 1, line 44, "In its principle embodiment" to read as --In its principal embodiment--

Column 180, line 55, "bucally, as an oral or nasal spray" to read as --buccally, as an oral or nasal spray--

Column 181, line 1, "bucally, as an oral or nasal spray" to read as --buccally, as an oral or nasal spray--

Column 182, line 21, "5□M ATP" to read as --5µM ATP-- and "5□M" to read as --5µM--

Column 182, line 26, "40 □L" to read as --40 µl--

Column 182, line 28, "160 □L" to read as --160 µl--

Column 277, line 25, "methyl [3-(8-nitroisoquinolin-5-vi)-11-oxo-diazepin-8-yl]acetate" to read as --methyl [3-(8-nitroisoquinolin-5-yl)-11-oxo-diazepin-8-yl]acetate--

Signed and Sealed this

Twenty-eighth Day of September, 2010

David J. Kappos
*Director of the United States Patent and Trademark Office*